US012485118B2

(12) United States Patent
Jones et al.

(10) Patent No.: US 12,485,118 B2
(45) **Date of Patent: *Dec. 2, 2025**

(54) COMBINATIONS OF GLP-1R AND THRβ AGONISTS AND METHODS OF USE THEREOF

(71) Applicant: Terns Pharmaceuticals, Inc., Foster City, CA (US)

(72) Inventors: Christopher T. Jones, Walnut Creek, CA (US); Jeffrey R. Jasper, Mountain View, CA (US); Olivia D. Teal, Cardiff, CA (US); Kevin P. Quinn, San Mateo, CA (US)

(73) Assignee: Terns Pharmaceuticals, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/072,846

(22) Filed: Mar. 6, 2025

(65) Prior Publication Data

US 2025/0195512 A1 Jun. 19, 2025

Related U.S. Application Data

(63) Continuation of application No. 18/629,151, filed on Apr. 8, 2024.

(60) Provisional application No. 63/615,985, filed on Dec. 29, 2023, provisional application No. 63/526,362, filed on Jul. 12, 2023, provisional application No. 63/495,049, filed on Apr. 7, 2023.

(51) Int. Cl.

| | |
|---|---|
| ***A61K 31/501*** | (2006.01) |
| ***A61K 31/437*** | (2006.01) |
| ***A61K 31/444*** | (2006.01) |
| ***A61K 38/26*** | (2006.01) |
| ***A61P 3/04*** | (2006.01) |

(52) U.S. Cl.

CPC .......... *A61K 31/501* (2013.01); *A61K 31/437* (2013.01); *A61K 31/444* (2013.01); *A61K 38/26* (2013.01); *A61P 3/04* (2018.01)

(58) Field of Classification Search

CPC .................................................... A61K 31/501

USPC .................................................... 514/252.02

See application file for complete search history.

(56) References Cited

U.S. PATENT DOCUMENTS

| | | | |
|---|---|---|---|
| 4,197,307 | A | 4/1980 | Gallay et al. |
| 5,114,938 | A | 5/1992 | Lindner et al. |
| 5,665,732 | A | 9/1997 | Baker et al. |
| 5,714,498 | A | 2/1998 | Kulagowski et al. |
| 5,763,263 | A | 6/1998 | Dehlinger |
| 5,780,475 | A | 7/1998 | Baker et al. |
| 6,787,652 | B1 | 9/2004 | Dow et al. |
| 7,807,674 | B2 | 10/2010 | Haynes et al. |
| 8,153,624 | B2 | 4/2012 | Genin et al. |
| 8,791,266 | B2 | 7/2014 | Kawata et al. |
| 9,764,003 | B2 | 9/2017 | Jensen |
| 10,208,019 | B2 | 2/2019 | Aspnes et al. |
| 10,335,462 | B2 | 7/2019 | Jensen |
| 10,669,259 | B2 | 6/2020 | Aspnes et al. |
| 10,800,767 | B2 | 10/2020 | Kirschberg et al. |
| 10,844,049 | B2 | 11/2020 | Zhong |
| 10,851,081 | B2 | 12/2020 | Aspnes et al. |
| 11,034,676 | B2 | 6/2021 | Yu et al. |
| 11,084,802 | B2 | 8/2021 | Yu et al. |
| 11,168,079 | B2 | 11/2021 | Carpenter et al. |
| 11,203,587 | B2 | 12/2021 | Kirschberg et al. |
| 11,512,070 | B2 | 11/2022 | Aspnes et al. |
| 11,584,751 | B1 | 2/2023 | Ren et al. |
| 11,918,623 | B2 | 3/2024 | Corvari et al. |
| 11,964,964 | B2 | 4/2024 | Jin et al. |
| 12,024,507 | B2 | 7/2024 | Reeves et al. |
| 12,338,232 | B2 | 6/2025 | Yu et al. |
| 12,365,669 | B2 | 7/2025 | Yu et al. |
| 12,378,236 | B2 | 8/2025 | Reeves et al. |
| 12,378,237 | B2 | 8/2025 | Reeves et al. |
| 12,378,238 | B2 | 8/2025 | Reeves et al. |
| 12,378,239 | B2 | 8/2025 | Reeves et al. |
| 12,410,163 | B2 | 9/2025 | Reeves et al. |
| 2003/0078288 | A1 | 4/2003 | Haning et al. |
| 2003/0162790 | A1 | 8/2003 | Cowart et al. |
| 2003/0176438 | A1 | 9/2003 | Arienti et al. |
| 2004/0127504 | A1 | 7/2004 | Cowart et al. |
| 2004/0157844 | A1 | 8/2004 | Dow et al. |
| 2005/0004114 | A1 | 1/2005 | Whitehouse et al. |
| 2005/0085541 | A1 | 4/2005 | Shiohara et al. |
| 2007/0244126 | A1 | 10/2007 | Edwards et al. |
| 2008/0167313 | A1 | 7/2008 | Dupont-Passelaigue et al. |

(Continued)

FOREIGN PATENT DOCUMENTS

| | | | |
|---|---|---|---|
| CN | 101228135 | A | 7/2008 |
| CN | 102898377 | A | 1/2013 |

(Continued)

OTHER PUBLICATIONS

1H-Benzimidazole-6-carboxylic acid, 2-[[4-[(2S)-2-(5-chloro-2-pyridinyl)-2-methyl-1,3-benzodioxol-4-yl]-1-piperidinyl]methyl]-1-[(2S)-2-oxetanylmethyl]-, Chemical Book, 2017, 2 pages.

"Safety, Pharmacokinetics and Pharmacodynamics of CT-996, an Oral Small-Molecule, Signal-Biased GLP-1 Receptor Agonist Over 4 Weeks in Adults with Obesity," Presented at the 60th European Association for the Study of Diabetes Annual Meeting, Sep. 11, 2024, 37 pages.

Ahmad, I., et al., "Xanthine oxidase/tyrosinase inhibiting, antioxidant, and antifungal oxindole alkaloids from Isatis costata," Pharmaceutical Biology, 2010, 48(6), pp. 716-721.

(Continued)

*Primary Examiner* — Niloofar Rahmani

(74) *Attorney, Agent, or Firm* — Cooley LLP

(57) ABSTRACT

Provided herein are combinations comprising a glucagon-like peptide-1 receptor (GLP-1R) agonist and a thyroid hormone receptor beta (THRβ) agonist and methods comprising administering to a subject in need thereof such combinations.

30 Claims, 28 Drawing Sheets

(56) References Cited

U.S. PATENT DOCUMENTS

2008/0280933 A1 11/2008 Efremov et al.
2009/0247539 A1 10/2009 Bell et al.
2010/0004271 A1 1/2010 Garcia Collazo et al.
2010/0152166 A1 6/2010 Genin et al.
2010/0286182 A1 11/2010 Samuels et al.
2012/0028959 A1 2/2012 Thunuguntla et al.
2012/0129812 A1 5/2012 Kawata et al.
2014/0275077 A1 9/2014 Dandu et al.
2015/0051211 A1 2/2015 Ji et al.
2015/0368205 A1 12/2015 Ji et al.
2017/0050949 A1 2/2017 Dandu et al.
2017/0334883 A1 11/2017 Albrecht et al.
2018/0170908 A1 6/2018 Aspnes et al.
2019/0119255 A1 4/2019 Aspnes et al.
2019/0352286 A1 11/2019 Claremon et al.
2019/0382384 A1 12/2019 Aspnes et al.
2020/0062742 A1 2/2020 Kirschberg et al.
2020/0071306 A1 3/2020 Esler et al.
2020/0115362 A1 4/2020 Kirschberg et al.
2020/0190064 A1 6/2020 Yu et al.
2020/0354345 A1 11/2020 Vandyck et al.
2020/0399249 A1 12/2020 Yu et al.
2021/0047298 A1 2/2021 Aspnes et al.
2021/0379040 A1 12/2021 Fenaux et al.
2021/0379043 A1 12/2021 Fenaux et al.
2022/0016136 A1 1/2022 Lian et al.
2022/0089578 A1 3/2022 Romero et al.
2022/0135540 A1 5/2022 Sweetana et al.
2022/0281849 A1 9/2022 Kirschberg et al.
2022/0332707 A1 10/2022 Du et al.
2022/0348561 A1 11/2022 Kirschberg et al.
2022/0348564 A1 11/2022 Ren et al.
2022/0356177 A1 11/2022 Kirschberg et al.
2023/0124938 A1 4/2023 Aspnes et al.
2023/0150998 A1 5/2023 Reeves et al.
2023/0159512 A1 5/2023 Reeves et al.
2023/0278988 A1 9/2023 Yu et al.
2023/0322744 A1 10/2023 Romero et al.
2023/0322758 A1 10/2023 Reeves et al.
2024/0051925 A1 2/2024 Confalone et al.
2024/0059682 A1 2/2024 Kirschberg et al.
2024/0156826 A1 5/2024 Taub
2024/0239761 A1 7/2024 Zhang et al.
2024/0293416 A1 9/2024 Jones et al.
2024/0360122 A1 10/2024 Bian et al.
2024/0368120 A1 11/2024 Luehr et al.
2024/0391910 A1 11/2024 Reeves et al.
2024/0398794 A1* 12/2024 Jones ..................... A61K 31/53
2025/0145612 A1 5/2025 Reeves et al.
2025/0145613 A1 5/2025 Reeves et al.
2025/0145614 A1 5/2025 Reeves et al.
2025/0145615 A1 5/2025 Reeves et al.
2025/0145616 A1 5/2025 Reeves et al.
2025/0179053 A1 6/2025 Yu et al.
2025/0179054 A1 6/2025 Yu et al.
2025/0236615 A1 7/2025 Kirschberg et al.

FOREIGN PATENT DOCUMENTS

CN 105477636 A 4/2016
CN 110325530 A 10/2019
CN 111484481 A 8/2020
CN 111909137 A 11/2020
CN 113480534 A 10/2021
CN 113493447 A 10/2021
CN 114430743 A 5/2022
CN 114437034 A 5/2022
EP 1471049 A1 10/2004
EP 3807267 A1 4/2021
EP 3555064 B1 11/2022
JP 2001114768 A 4/2001
JP 2007512314 A 5/2007
JP 2009500305 A 1/2009
JP 2009501759 A 1/2009
JP 2011528007 A 11/2011
JP 2015500212 A 1/2015
JP 2019099571 A 6/2019
JP 2020511411 A 4/2020
JP 2024516291 A 4/2024
JP 2024525900 A 7/2024
RU 2668960 C2 10/2018
TW 202128659 A 8/2021
WO WO-0198256 A1 12/2001
WO WO-03064369 A1 8/2003
WO WO-03094845 A2 11/2003
WO WO-2005049616 A1 6/2005
WO WO-2007003419 A1 1/2007
WO WO-2007009913 A1 1/2007
WO WO-2007128492 A1 11/2007
WO WO-2007132475 A1 11/2007
WO WO-2007134864 A1 11/2007
WO WO-2009012125 A1 1/2009
WO WO-2009037172 A1 3/2009
WO WO-2010006962 A1 1/2010
WO WO-2010114957 A1 10/2010
WO WO-2010122980 A1 10/2010
WO WO-2011038207 A1 3/2011
WO WO-2011143365 A1 11/2011
WO WO-2014043706 A1 3/2014
WO WO-2015166398 A1 11/2015
WO WO-2018056453 A1 3/2018
WO WO-2018075650 A1 4/2018
WO WO-2018109607 A1 6/2018
WO WO-2019144835 A1 8/2019
WO WO-2019239319 A1 12/2019
WO WO-2019239371 A1 12/2019
WO WO-2019240938 A1 * 12/2019 ............. A61K 31/53
WO WO-2020041741 A1 2/2020
WO WO-2020049556 A1 3/2020
WO WO-2020061086 A2 3/2020
WO WO-2020073974 A1 4/2020
WO WO-2020077123 A1 4/2020
WO WO-2020103815 A1 5/2020
WO WO-2020123827 A1 * 6/2020 ............. A61K 31/53
WO WO-2020169069 A1 8/2020
WO WO-2020207474 A1 10/2020
WO WO-2020227549 A1 11/2020
WO WO-2020239076 A1 12/2020
WO WO-2020263695 A1 12/2020
WO WO-2021018023 A1 2/2021
WO WO-2021041237 A1 3/2021
WO WO-2021050945 A1 3/2021
WO WO-2021081207 A1 4/2021
WO WO-2021096284 A1 5/2021
WO WO-2021096304 A1 5/2021
WO WO-2021112538 A1 6/2021
WO WO-2021116874 A1 6/2021
WO WO-2021121210 A1 6/2021
WO WO-2021154796 A1 8/2021
WO WO-2021155841 A1 8/2021
WO WO-2021160127 A1 8/2021
WO WO-2021187886 A1 9/2021
WO WO-2021191812 A1 9/2021
WO WO-2021197464 A1 10/2021
WO WO-2021219019 A1 11/2021
WO WO-2021231646 A1 11/2021
WO WO-2021242817 A1 12/2021
WO WO-2021244391 A1 12/2021
WO WO-2021244645 A1 12/2021
WO WO-2021249492 A1 12/2021
WO WO-2021254470 A1 12/2021
WO WO-2021259309 A1 12/2021
WO WO-2022007979 A1 1/2022
WO WO-2022017338 A1 1/2022
WO WO-2022028572 A1 2/2022
WO WO-2022031994 A1 2/2022
WO WO-2022040600 A1 2/2022
WO WO-2022042691 A1 3/2022
WO WO-2022048665 A1 3/2022
WO WO-2022052958 A1 3/2022
WO WO-2022068772 A1 4/2022
WO WO-2022078152 A1 4/2022
WO WO-2022078352 A1 4/2022
WO WO-2022078380 A1 4/2022

(56) References Cited

FOREIGN PATENT DOCUMENTS

| | | | |
|---|---|---|---|
| WO | WO-2022078407 | A1 | 4/2022 |
| WO | WO-2022109182 | A1 | 5/2022 |
| WO | WO-2022111624 | A1 | 6/2022 |
| WO | WO-2022116693 | A1 | 6/2022 |
| WO | WO-2022135572 | A1 | 6/2022 |
| WO | WO-2022152770 | A1 | 7/2022 |
| WO | WO-2022165076 | A1 | 8/2022 |
| WO | WO-2022187403 | A1 | 9/2022 |
| WO | WO-2022192428 | A1 | 9/2022 |
| WO | WO-2022192430 | A1 | 9/2022 |
| WO | WO-2022199458 | A1 | 9/2022 |
| WO | WO-2022199661 | A1 | 9/2022 |
| WO | WO-2022202864 | A1 | 9/2022 |
| WO | WO-2022207950 | A1 | 10/2022 |
| WO | WO-2022216094 | A1 | 10/2022 |
| WO | WO-2022219495 | A1 | 10/2022 |
| WO | WO-2022225941 | A1 | 10/2022 |
| WO | WO-2022228490 | A1 | 11/2022 |
| WO | WO-2022235717 | A1 | 11/2022 |
| WO | WO-2022236136 | A1 | 11/2022 |
| WO | WO-2022246019 | A1 | 11/2022 |
| WO | WO-2022258805 | A1 | 12/2022 |
| WO | WO-2022268152 | A1 | 12/2022 |
| WO | WO-2023000834 | A1 | 1/2023 |
| WO | WO-2023001237 | A1 | 1/2023 |
| WO | WO-2023011539 | A1 | 2/2023 |
| WO | WO-2023016546 | A1 | 2/2023 |
| WO | WO-2023028606 | A1 | 3/2023 |
| WO | WO-2023029380 | A1 | 3/2023 |
| WO | WO-2023031741 | A1 | 3/2023 |
| WO | WO-2023038039 | A1 | 3/2023 |
| WO | WO-2023049518 | A1 | 3/2023 |
| WO | WO-2023049887 | A1 | 3/2023 |
| WO | WO-2023057414 | A1 | 4/2023 |
| WO | WO-2023057427 | A1 | 4/2023 |
| WO | WO-2023057429 | A1 | 4/2023 |
| WO | WO-2023066356 | A1 | 4/2023 |
| WO | WO-2023076237 | A1 | 5/2023 |
| WO | WO-2023083288 | A1 | 5/2023 |
| WO | WO-2023086561 | A1 | 5/2023 |
| WO | WO-2023103310 | A1 | 6/2023 |
| WO | WO-2023106310 | A1 | 6/2023 |
| WO | WO-2023111144 | A1 | 6/2023 |
| WO | WO-2023111145 | A1 | 6/2023 |
| WO | WO-2023124824 | A1 | 7/2023 |
| WO | WO-2023138684 | A1 | 7/2023 |
| WO | WO-2023151574 | A1 | 8/2023 |
| WO | WO-2023151575 | A1 | 8/2023 |
| WO | WO-2023152698 | A1 | 8/2023 |
| WO | WO-2023164050 | A1 | 8/2023 |
| WO | WO-2023164358 | A1 | 8/2023 |
| WO | WO-2023169456 | A1 | 9/2023 |
| WO | WO-2023179542 | A1 | 9/2023 |
| WO | WO-2023198140 | A1 | 10/2023 |
| WO | WO-2023220404 | A1 | 11/2023 |
| WO | WO-2023222084 | A1 | 11/2023 |
| WO | WO-2023222124 | A1 | 11/2023 |
| WO | WO-2024041609 | A1 | 2/2024 |
| WO | WO-2024046342 | A1 | 3/2024 |
| WO | WO-2024051700 | A1 | 3/2024 |
| WO | WO-2024063140 | A1 | 3/2024 |
| WO | WO-2024063143 | A1 | 3/2024 |
| WO | WO-2024102625 | A1 | 5/2024 |
| WO | WO-2024107781 | A1 | 5/2024 |
| WO | WO-2024131869 | A1 | 6/2024 |
| WO | WO-2024149080 | A1 | 7/2024 |
| WO | WO-2024206647 | A1 | 10/2024 |
| WO | WO-2024206878 | A1 | 10/2024 |
| WO | WO-2024211898 | A1 | 10/2024 |

OTHER PUBLICATIONS

Alkhouri, N., et al., "Sex Hormone Binding Globulin as an Effective Predictor of Treatment Response to TERN-501, a Potent, Highly Selective Thyroid Hormone Receptor-B Agonist: Post-HOC Analyses From a 12-Week Phase 2a Trial," Poster No. SAT-208, Poster Presentation at the European Association for the Study of the Liver (EASL) Congress, Jun. 5-8, 2024, Milan, Italy, 1 page.

Alkhouri, N., et al., "Sex hormone binding globulin as an effective predictor of treatment response to TERN-501, a potent, highly selective thyroid hormone receptor β agonist: post-hoc analyses from a 12-week phase 2a trial," SAT-208, Abstract, Journal of Hepatology 2024, vol. 80(S1), S78-S836, p. S609.

Armstrong, M. J., et al., "Glucagon-like Peptide-1 Analogues in Nonalcoholic Steatohepatitis: From Bench to Bedside," Clinical Liver Disease, vol. 10, No. 2, Aug. 2017, pp. 32-35.

Arshad, M. F., et al., "Thiazole: A Versatile Standalone Moiety Contributing to the Development of Various Drugs and Biologically Active Agents," Molecules 2022, 27, 3994, https://doi.org/10.3390/molecules27133994, 54 pages.

Ashburner, et al., "Gene ontology: Tool for the unification of biology," Nature Genetics, 25(1): 25-9 (2000).

Balaban, A. T., et al., Aromaticity as a Cornerstone of Heterocyclic Chemistry, Chem. Rev. 2004, 104, 2777-2812.

Ballatore, C., et al., "Carboxylic Acid (Bio) Isosteres in Drug Design," ChemMedChem 2013, 8, 385-395, DOI: 10.1002/cmdc.201200585.

Bashir, M., et al., "Liver Volume Reduction in Resmetirom Treated Non-Cirrhotic and Cirrhotic NASH Patients," Hepatology, Oct. 2021, vol. 74, No. 1(Suppl), pp. 1142A-1143A.

Basnak, I. et al. (1975). "Synthesis of 5-cyclopropyl-6-azauracil," Collection of Czechoslovak Chemical Communications, 40(4):1038-1042.

Baxter, J. D. et al., "Thyroid hormone mimetics: potential applications in atherosclerosis, obesity and type 2 diabetes," Nature Reviews Drug Discovery, vol. 8, No. 4, pp. 308-320 (Apr. 2009).

Beker, W, et al., "Reactivity Patterns of Imidazole, Oxazole, and Thiazole as Reflected by the Polarization Justified Fukui Functions," J. Phys. Chem. A 2013, 117, 1596-1600.

Belaidi, S., et al., "Electronic Structure and Physico-Chemical Property Relationship for Thiazole Derivatives," Asian Journal of Chemistry, 2013, vol. 25, No. 16, 9241-9245.

Belikov, V. G., "Relationship between the chemical structure, the properties of substances and their effects on the body," Medpress Inform, Moscow, 2007, pp. 27-29, with English translation, 14 pages.

Berrington De Gonzalez, A., et al., "Body-mass index and mortality among 1.46 million white adults," The New England Journal of Medicine, 2010, 363; 23: 2211-2219.

Berry, M. J, et al., "Thyroid hormone regulates type I deiodinase messenger RNA in rat liver," Molecular Endocrinology, 1990, 4:743-748.

Beulah, K., et al., "Design, Synthesis and Biological Evaluation of Benzimidazole-pyridine-Piperidine Hybrids as a New Class of Potent Antimicrobial Agents," Letters in Drug Design & Discovery, 2015, vol. 12, No. 1, pp. 38-45.

Bjerregaard, L. G., et al., "Change in Overweight from Childhood to Early Adulthood and Risk of Type 2 Diabetes," The New England Journal of Medicine, Apr. 5, 2018, 378(14):1302-1312, DOI: 10.1056/NEJMoa1713231 doi:10.1056/NEJMoa1713231.

Blanco, F. J., et al., "Effect of Antiinflammatory Drugs on COX-1 and COX-2 Activity in Human Articular Chondrocytes," The Journal of Rheumatology, 1999, 26:6, pp. 1366-1373.

Blanpied, T. A., et al., "Trapping Channel Block of NMDA-Activated Responses by Amantadine and Memantine," The American Physiological Society, 1997, pp. 309-323.

Bray, G. A., et al., World Obesity Federation, "Obesity: a chronic relapsing progressive disease process. A position statement of the World Obesity Federation," Obesity Reviews 18: 715-723, Jul. 2017, doi: 10.1111/obr.12551.

Brown, N., Bioisosteres in Medicinal Chemistry, 2012, Contents, Part one: Principles, Chapter 1, Bioisosterism in Medicinal Chemistry, Nathan Brown and Part Two: Data, Chapter 4, Bioster: A Database of Bioisosteres and Bioanalogues, Istvan Ujvary and Julian Hayward, 51 total pages.

(56) References Cited

OTHER PUBLICATIONS

Buckeridge, C. et al., "Once-daily oral small molecule GLP-1R agonist PF-07081532 robustly reduces glucose and body weight within 4-6 weeks in adults with type 2 diabetes and non-diabetic adults with obesity," EASD Presentation 2022, No. 114, Diabetologia 2022, 65 (Suppl 1):S1-S469, p. S60.
Burki, T., et al., "European Commission classifies obesity as a chronic disease," Lancet Diabetes Endocrinol, Jul. 2021, vol. 9, p. 418, Published online: Jun. 1, 2021, https://doi.org/10.1016/S2213-8587(21)00145-5.
Chen, L., et al., "Discovery of Novel 5,6-Dihydro-1,2,4-triazine Derivatives as Efficacious Glucagon-Like Peptide-1 Receptor Agonists," Journal of Medicinal Chemistry 2023, 66, pp. 7988-8010.
Coll, B., et al., "A Phase 1b/2a Study of the Safety and Tolerability of GSBR-1290, a Novel Oral Small Molecule Glucagon-Like Peptide 1 Receptor Agonist (GLP-1RA), in Healthy Overweight/Obese Volunteers (HOV) and Participants with Type 2 Diabetes Mellitus (T2DM)," ADA Poster Presentation, Jun. 23, 2024, Abstract 767-P, 1 page.
Collins, L., Costello, R. A., "Glucagon-like Peptide-1 Receptor Agonists," StatPearls. Treasure Island (FL): StatPearls Publishing; Jan. 2025, Last Update: Feb. 29, 2024, 15 pages.
Davies, D. T., Aromatic Heterocyclic Chemistry, Chapters 3 and 4, Oxford University Press 1992, 21 pages.
Davies, M. J., et al., "Efficacy of Liraglutide for Weight Loss Among Patients With Type 2 Diabetes: The SCALE Diabetes Randomized Clinical Trial," JAMA 2015, 314(7): 687-699, doi: 10.1001/jama.2015.9676.
Davies, M. J., et al., "Semaglutide 2.4 mg once a week in adults with overweight or obesity, and type 2 diabetes (STEP 2): a randomised, double-blind, double-dummy, placebo-controlled, phase 3 trial," Lancet 2021, 397: 971-984, Published online Mar. 2, 2021, https://doi.org/10.1016/S0140-6736(21)00213-0.
Dennis, A., et al., "Correlations Between MRI Biomarkers PDFF and cT1 with Histopathological Features on Non-Alcoholic Steatohepatitis," Frontiers in Endocrinology, Jan. 2021, vol. 11, Article 575843, 10 pages.
Dermer, G.B.., "Another Anniversary for the War on Cancer," Bio/Technology, 12:320, 1 page (Mar. 1994).
Dibonaventura, M. D., et al., "Multinational Internet-based survey of patient preference for newer oral or injectable Type 2 diabetes medication," Patient Prefer Adherence, Nov. 2, 2010, 4: 397-406, DOI: 10.2147/PPA.S14477.
Dolomanov, O. V., et al., "OLEX2: a complete structure solution, refinement and analysis program," J. Appl. Cryst. 2009, 42, 339-341, doi:10.1107/S0021889808042726.
Dorwald, Side Reactions in Organic Synthesis. Wiley-VCH, pp. 1-16 (2005).
Dutta, D., et al., "Orforglipron, a novel non-peptide oral daily glucagon-like peptide-1 receptor agonist as an anti-obesity medicine: A systematic review and meta-analysis," Obseity Science and Pratice 2024, e743, 9 pages, https://doi.org/10.1002/osp4.743.
Erion, M.D., "Targeting thyroid hormone receptor-β agonists to the liver reduces cholesterol and triglycerides and improves the therapeutic index," PNAS USA 2007, 104(39), 15490-15495.
Escobar-Morreale, H. F., "Polycystic ovary syndrome: definition, aetiology, diagnosis and treatment," Nature Reviews Endocrinology, May 2018, vol. 14, pp. 270-284, doi:10.1038/nrendo.2018.24.
Extended European Search Report and Search Opinion, dated Dec. 23, 2024, for European Patent Application No. 22764006.7, 10 pages.
Extended European Search Report and Search Opinion, dated May 18, 2022, for European Patent Application No. 19870196.3 (5 total pages).
Extended European Search Report and Search Opinion, dated May 22, 2025, for European Patent Application No. 25157448.9, 11 pages.
Extended European Search Report and Search Opinion, dated May 27, 2025, for European Patent Application No. 24211557.4, 11 pages.
Extended European Search Report and Search Opinion for European Application No. 25157450.5 dated May 22, 2025, 11 pages.
Extended European Search Report and Search Opinion, mailed Aug. 17, 2023, for European Patent Application No. 20863146.5, 7 pages.
Extended European Search Report and Search Opinion, mailed Jul. 6, 2022, for European Application No. 19896475.1 (8 total pages).
Extended European Search Report and Search Opinion, mailed Mar. 30, 2023, for European Application No. 20856291.8 (8 total pages).
Extended European Search Report for European Application No. 21859247.5 mailed Nov. 27, 2024, 15 pages.
Extended Search Report and Search Opinion, mailed Mar. 22, 2022, for European Patent Application No. 19852050.4 (7 total pages).
Farrugia, L. J., "WinGX and ORTEP for Windows: an update," Applied Crystallography 2012, 45, 849-854, doi:10.1107/S0021889812029111.
Flack , H. D., "On Enantiomorph-Polarity Estimation," Acta Cryst. 1983, A39, 876-881.
Flack, H. D., et al., "The Use of X-ray Crystallography to Determine Absolute Configuration," CHIRALITY 20:681-690, 2008, DOI: 10.1002/chir.20473.
Fontaine, K. R., et al., "Years of life lost due to obesity," JAMA, Jan. 8, 2003, vol. 289, No. 2, pp. 187-193.
Freshney, R. I., et al., "Culture of Animal Cells," A Manual of Basic Technique, 1983, Alan R. Liss, Inc., New York, p. 4 and pp. 129-133 (9 total pages).
Frias, J. P., et al., "Efficacy and safety of oral orforglipron in patients with type 2 diabetes: a muticentre randomised, dose-response, phase 2 study," Lancet, Aug. 5, 2023; 402: 472-483, Published Online Jun. 24, 2023, https://doi.org/10.1016/S0140-6736(23)01302-8.
Gene Ontology Consortium, Creating the Gene Ontology Resource: Design and Implementation. Genome Research 11: 1425-1433 (2001).
Glass, L. M., et al., "Comorbidities and Nonalcoholic Fatty Liver Disease: The Chicken, the Egg, or Both?" Federal Practitioner, Feb. 2019, 36(2), pp. 64-71.
Granhall, C., et al., "Pharmacokinetics, Safety and Tolerability of Oral Semaglutide in Subjects with Renal Impairment," Clin Pharmacokinet 2018, 57:1571-1580, https://doi.org/10.1007/s40262-018-0649-2.
Griffith, D. A., et al., "A Small-Molecule Oral Agonist of the Human Glucagon-like Peptide-1 Receptor," Journal of Medicinal Chemistry, 2022, 65, pp. 8208-8226.
Guerrero-Pepinosa, N. Y., et al., "Antiproliferative activity of thiazole and oxazole derivatives: A systematic review of in vitro and in vivo studies," Biomedicine & Pharmacotherapy 138 (2021) 111495, https://doi.org/10.1016/j.biopha.2021.111495, 15 pages.
Guidance for Industry: Estimating the Maximum Safe Starting Dose in Initial Clinical Trials for Therapeutics in Adult Healthy Volunteers. US Department of Health and Human Services, Food and Drug Administration (FDA), Center for Drug Evaluation and Research, Jul. 2005, 30 pages, https://www.fda.gov/media/72309/download.
Guidance for Industry: Toxicity Grading Scale for Healthy Adult and Adolescent Volunteers Enrolled in Preventive Vaccine Clinical Trials. U.S. Department of Health and Human Services, Food and Drug Administration, Center for Biologics Evaluation and Research, Sep. 2007, 10 pages.
Haake, P., et al., "A Comparison of Thiazoles and Oxazoles," Communications to the Editor, vol. 85, Dec. 20, 1963, pp. 4044-4045.
Haberhauer, G., et al., "Structural Investigation of Westiellamide Analogues," Tetrahedron 2008, 64, 1853-1859.
Hamdan, F., et al., "Synthesis of novel cyclopeptides containing heterocyclic skeletons," RSC Advances 2018, 8, 33893-33926, DOI: 10.1039/c8ra03899f.
Hampp, C. et al., "Use of Antidiabetic Drugs in the U.S., 2003-2012," Diabetes Care, May 2014, vol. 37, pp. 1367-1374, DOI: 10.2337/dc13-2289.
Hansen, H. H., et al., "Human translatability of the GAN diet-induced obese mouse model of non-alcoholic steatohepatitis," BMC Gastroenterology 2020, 20:210, pp. 1-12.
Harrison, S. A., et al., "A 52-Week Phase 3 Clinical Trial of Resmetirom in 180 Patients with Well-Compensated NASH Cirrhosis," AASLD, Nov. 4-8, 2022, 6 pages.

(56) References Cited

OTHER PUBLICATIONS

Harrison, S. A., et al., "A Phase 3, Randomized, Controlled Trial of Resmetirom in NASH with Liver Fibrosis," The New England Journal of Medicine, Feb. 8, 2024, vol. 390, No. 6, pp. 497-509.
Harrison, S. A., et al., "Resmetirom for nonalcoholic fatty liver disease: a randomized, double-blind, placebo-controlled phase 3 trial," Nature Medicine, Nov. 2023, vol. 29, 2919-2928, including additional material, 19 pages, DOI: 10.1038/s41591-023-02603-1.
Hennessey, J. V., et al., "The emergence of levothyroxine as a treatment for hypothyroidism," Endocrine, 2017, 55: 6-18, DOI: 10.1007/s12020-016-1199-8.
Hill, S. R. Jr., et al., "The Metabolic Effects of the Acetic and Propionic Acid Analogs of Thyroxine and Triiodothyronine," J Clin. Invest. 1960, (39):523-533.
Holst, J. J., et al., The Physiology of Glucagon-like Peptide 1, Physiological Reviews, 2007, vol. 87, pp. 1409-1439, doi:10.1152/physrev.00034.2006.
Hooft, R. W. W., et al., "Determination of absolute structure using Bayesian statistics on Bijvoet differences," J. Appl. Cryst. 2008, 41, 96-103, doi:10.1107/S0021889807059870.
Horner, K. E., et al., "Shielding in and around Oxazole, Imidazole, and Thiazole: How Does the Second Heteroatom Affect Aromaticity and Bonding?," J. Org. Chem. 2015, 80, 7150-7157.
Huang, K.-P., et al., "Dissociable hindbrain GLP1R circuits for satiety and aversion," Nature, Aug. 15, 2024, vol. 632, pp. 585-593, including Methods, Extended Data & Reporting Summary, 25 pages, https://doi.org/10.1038/s41586-024-07685-6.
Husain, M., et al., "Oral Semaglutide and Cardiovascular Outcomes in Patients with Type 2 Diabetes," The New England Journal of Medicine, 2019, 381: 841-851, DOI: 10.1056/NEJMoa1901118.
Ichiki, T., et al., "Thyroid Hormone and Vascular Remodeling," Journal of Atherosclerosis and Thrombosis, 2016, vol. 23, No. 3, pp. 266-275.
International Preliminary Report on Patentability for International Application No. PCT/US2022/047687, mailed May 10, 2024, 8 pages.
International Preliminary Report on Patentability for International Application No. PCT/US2023/013700 mailed Sep. 6, 2024 8 pages.
International Preliminary Report on Patentability, mailed Apr. 11, 2024, for International Application No. PCT/US2022/044915, 8 pages.
International Preliminary Report on Patentability, mailed Apr. 22, 2021, for International Application No. PCT/US2019/055689, 9 pages.
International Preliminary Report on Patentability, mailed Jun. 24, 2021, for International Application No. PCT/US2019/066013, 6 pages.
International Preliminary Report on Patentability, mailed Mar. 11, 2021, for International Application No. PCT/US2019/047968 (7 total pages).
International Preliminary Report on Patentability, mailed Mar. 2, 2023, for International Application No. PCT/US2021/047015, 8 pages.
International Preliminary Report on Patentability, mailed Mar. 24, 2022, for International Application No. PCT/US2020/050497 (7 total pages).
International Preliminary Report on Patentability, mailed Mar. 3, 2022, for International Application No. PCT/US2020/047467 (9 total pages).
International Preliminary Report on Patentability, mailed May 23, 2024, for International Application No. PCT/CN2022/131297, 7 pages.
International Preliminary Report on Patentability, mailed Nov. 28, 2024, for International Application No. PCT/US2023/022093, 6 pages.
International Preliminary Report on Patentability, mailed Sep. 14, 2023, for International Application No. PCT/US2022/018575, 18 pages.
International Search Report and Written Opinion for International Application No. PCT/US2021/047015, mailed Jan. 13, 2022, 11 Pages.
International Search Report and Written Opinion for International Application No. PCT/US2022/047687, mailed Feb. 16, 2023, 13 pages.
International Search Report and Written Opinion for International Application No. PCT/US2024/021994 mailed Jul. 30, 2024, 16 pages.
International Search Report and Written Opinion for International Application No. PCT/US2024/022311 mailed Aug. 14, 2024, 19 pages.
International Search Report and Written Opinion, mailed Apr. 28, 2023, for International Application No. PCT/US2023/013700, 11 pages.
International Search Report and Written Opinion, mailed Aug. 2, 2023, for International Application No. PCT/US2023/022093, 8 pages.
International Search Report and Written Opinion, mailed Aug. 26, 2024, for International Application No. PCT/US2024/023598, 24 pages.
International Search Report and Written Opinion, mailed Dec. 5, 2022, for International Application No. PCT/US2022/044915 (13 total pages).
International Search Report and Written Opinion, mailed Dec. 8, 2020, for International Application No. PCT/US2020/050497 (9 total pages).
International Search Report and Written Opinion, mailed Feb. 10, 2023, for International Application No. PCT/CN2022/131297, 10 Pages.
International Search Report and Written Opinion, mailed Feb. 28, 2020, for International Application No. PCT/US2019/066013, 8 pages.
International Search Report and Written Opinion, mailed Jan. 15, 2021, for International Application No. PCT/US2020/047467, 12 pages.
International Search Report and Written Opinion, mailed Jan. 23, 2020, for International Application No. PCT/US2019/055689, 12 Pages.
International Search Report and Written Opinion, mailed May 23, 2022, for International Application No. PCT/US2022/018575 (21 total pages).
International Search Report and Written Opinion, mailed Nov. 21, 2019, for International Application No. PCT/US19/47968, 9 pages.
Invitation to Pay Additional Fees and, Where Applicable, Protest Fee, dated Jul. 5, 2024, for International Application No. PCT/US2024/023598, 18 pages.
Invitation to Pay Additional Fees and, Where Applicable, Protest Fee for International Application No. PCT/US2024/022311, mailed Jun. 24, 2024, 14 pages.
Invitation to Pay Additional Fees and, Where Applicable, Protest Fee, mailed Oct. 25, 2021, for International Application No. PCT/US2021/047015 (2 total pages).
Invitation to Pay Additional Fees, dated Nov. 21, 2019, for International Application No. PCT/US2019/055689, 2 pages.
Invitation to Pay Additional Fees, mailed Oct. 4, 2020, for International Application No. PCT/US2020/047467, 2 pages.
Jones, C. T., et al., "TERN-501 Enhances Weight Loss Efficacy of a GLP-1R Agonist in Obese Mice via Increased Fat Mass Loss without Additional Loss of Lean Mass," Poster Presentation at American Diabetes Association (ADA) 84th Scientific Sessions, Jun. 21-24, 2024, retrieved at https://www.ternspharma.com/scientific-publications, retrieved on Jul. 26, 2024, 1 page.
Kalra, S., et al., "Consensus Recommendations on GLP-1 RA Use in the Management of Type 2 Diabetes Mellitus: South Asian Task Force," Diabetes Ther 2019, 10: 1645-1717, https://doi.org/10.1007/s13300-019-0669-4.
Kannt, A., et al., "Activation of thyroid hormone receptor-β improved disease activity and metabolism independent of body weight in a mouse model of non-alcoholic steatohepatitis and fibrosis," British Journal of Pharmacology, 2021, 178:2412-2423, doi: 10.1111/bph.15427.

(56) References Cited

OTHER PUBLICATIONS

Kaspady, M., et al., "Synthesis, Antibacterial Activity of 2,4-Disubstituted Oxazoles and Thiazoles as Bioisosteres," Letters in Drug Design & Discovery, 2009, 6, pp. 21-28.
Kelly M. J., et al., "Discovery of 2-[3,5-Dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL3196), a Highly Selective Thyroid Hormone Receptor beta Agonist in Clinical Trials for the Treatment of Dyslipidemia," Journal of Medicinal Chemistry 2014, vol. 57, No. 10, pp. 3912-3923, DOI: 10.1021/jm4019299.
Kim D., et al., "Critical Roles of the Histone Methyltransferase MLL4/KMT2D in Murine Hepatic Steatosis Directed by ABL1 and PPARgamma2," Cell Reports 2016, vol. 17(6), pp. 1671-1682, DOI: 10.1016/j.celrep.2016.10.023.
Kirschberg, T., et al., EASL, Aug. 29, 2020, "TERN-501, a potent and selective agonist of thyroid hormone receptor beta, strongly reduces histological features and biomarkers of non-alcoholic steatohepatitis associated pathology in rodent models," poster, 1 page.
Loomba, R., et al., "Nonalcoholic fatty liver disease progression rates to cirrhosis and progression of cirrhosis to decompensation and mortality: a real world analysis of Medicare data," Alimentary Pharmacology and Therapeutics, 2020, 51:1149-59.
Loomba, R., et al., Relationship of Non-Invasive Measures with Histological Response in Patients with NonAlcoholic Steatohepatitis and Fibrosis: 52-Week Data from the Phase 3 Maestro-NASH Trial, Hepatology, 2023, 78 (Suppl 1):S155-S159, Abstract 149.
Macrae, C. F., et al., "Mercury: visualization and analysis of crystal structures," J. Appl. Cryst. 2006, 39, 453-457, doi: 10.1107/S002188980600731X.
Mao, T., et al., "760-P: Discovery of GSBR-1290, a Highly Potent, Orally Available, Novel Small Molecule GLP-1 Receptor Agonist,". Diabetes.2023; 72 (Supplement_1):760-P, 1 page,.https://doi.org/10.2337/db23-760-P.
Meier, J. J., et al., "Glucagon-Like Peptide 1 and Gastric Inhibitory Polypeptide," Biodrugs 2003, 17(2), pp. 93-102.
Meier, J. J., "GLP-1 receptor agonists for individualized treatment of type 2 diabetes mellitus," Nature Reviews Endocrinology, Dec. 2012, vol. 8, p. 728-742, Published online Sep. 4, 2012, doi:10.1038/nrendo.2012.140.
Milaneschi, Y., et al., "Depression and obesity: evidence of shared biological mechanisms," Molecular Psychiatry, 2019, 24: 18-33, https://doi.org/10.1038/s41380-018-0017-5.
Muller, T. D., et al., "Anti-obesity drug discovery: advances and challenges," Nature Reviews Drug Discovery, vol. 21, Mar. 2022, pp. 201-223.
Muller, T.D., et al., "Anti-Obesity Therapy: from Rainbow Pills to Polyagonists," Pharmacological Reviews, Oct. 2018, 70: 712-746, doi:10.1124/pr.117.014803.
Nauck, M. A., et al., "Another milestone in the evolution of GLP-1-based diabetes therapies," Nature Medicine, vol. 27, Jun. 2021, pp. 949-953.
NCBI Reference Sequence: NM_002062.5. *Homo sapiens* glucagon like peptide 1 receptor (GLP1 R), transcript variant 1, mRNA: 7 pages, Record created Nov. 22, 2018. Retrieved Jul. 9, 2025. Retrieved from: https://www.ncbi.nlm.nih.gov/nuccore/NM_002062.5/.
NCT01237119: "Liraglutide Efficacy and Action in Non-Alcoholic Steatohepatitis (LEAN)," Aug. 2010, Phase 2, 7 pages, Retrieved on Feb. 13, 2025, Retrieved from https://clinicaltrials.gov/study/NCT01237119.
NCT03590626. "Effect of Dulaglutide on Liver Fat in Patients With Type 2 Diabetes and Nonalcoholic Fatty Liver Disease (D-LIFT)," Jan. 1, 2019, 11 pages, Retrieved on Feb. 13, 2025, Retrieved from https://clinicaltrials.gov/study/NCT03590626.
NCT04074161. "Research Study to Investigate How Well Semaglutide Works Compared to Liraglutide in People Living With Overweight or Obesity (STEP 8)," Sep. 11, 2019, 18 pages, Retrieved on Jul. 8, 2025, Retrieved from https://clinicaltrials.gov/study/NCT04074161.
Nelson, C., et al., 307-OR: Effect of Oral Small Molecule GLP-1 Receptor Agonist TERN-601 in Healthy Participants with Obesity or Overweight—A First-In-Human Study, Jun. 20, 2025, Diabetes 2025, 74 (Supplement_1):307-OR, https://doi.org/10.2337/db25-307-OR, 4 pages.
Nelson, C., et al., 767-P: No Effect of Food or Proton Pump Inhibitors on the Pharmacokinetics of TERN-601, and Oral Small Molecule GLP-1 Receptor Agonist, Jun. 20, 2025, Diabetes 2025;74(Supplement_1):767-P, https://doi.org/10.2337/db25-767-P, 4 pages.
Nelson, R. H., "Hyperlipidemia as a risk factor for cardiovascular disease," Primary Care, Mar. 2013, 40(1):195-211.
Noureddin, M., et al., "Head-to-Head Comparison of Fast, Mast, MEFIB and cT1 in Identifying At-Risk NASH Patients in a Low-Prevalence Population," Hepatology, 2023, 78(Supplement 1):S1-S2154, pp. S806-S810, Abstract 2050-A.
Noureddin, M., et al., "5000 | Topline Results from a 12-Week Phase 2a Trial (Duet) Evaluating Tern-501, A Highly Selective Thyroid Hormone Receptor (THR) Beta Agonist, Either as Monotherapy or in Combination with TERN-101, A Nonsteroidal Farnesoid X Receptor (FXR) Agonist, Demonstrated Significant Reductions in MR-Based Liver Fat Content and Fibroinflammation in Patients with Presumed MASH," Hepatology 2024, 79:E33-E85, p. E33.
Ognyaov, V. I., et al., "Design of Potent, Orally Available Antagonists of the Transient Receptor Potential Vanilloid 1. Structure-Activity Relationships of 2-Piperazin-1-yl-1H-benzimidazoles," J. Med Chem, 2006, vol. 49, No. 12, pp. 3719-3742, including Supplemental Information S1-S31.
Overgaard, R. V., et al., "Clinical Pharmacokinetics of Oral Semaglutide: Analyses of Data from Clinical Pharmacology Trials," Clinical Pharmacokinetics, 2021, 60: 1335-1348, published online May 10, 2021, https://doi.org/10.1007/s40262-021-01025-x.
Pagadala, M. R, et al., "Prevalence of hypothyroidism in nonalcoholic fatty liver disease," Digestive Diseases and Sciences, 2012, 57:528-34.
Partial Supplementary European Search Report for European Application No. 21859247.5 dated Sep. 6, 2024, 16 pages.
Pathway: HSA04911, Insulin secretion—*Homo sapiens* (human), KEGG, Jun. 6, 2017, 6 pages.
Pfizer. Pfizer Provides Update on Oral GLP-1 Receptor Agonist Danuglipron. Apr. 14, 2025, 3 pages, https://www.pfizer.com/news/press-release/press-release-detail/pfizer-provides-update-oral-glp-1-receptor-agonist.
Pfizer Press release—Pfizer Announces Topline Phase 2b Results of Oral GLP-1R Agonist, Danuglipron, in Adults with Obesity, Dec. 1, 2023, 4 pages, businesswire.com: https://www.businesswire.com/news/home/20231130108413/en/.
Pirner, M. et al., "94-LB: A Phase 1, Double-Blind, Placebo-Controlled Multiple Escalating Dose Study of RGT-075 Novel Small-Molecule Oral GLP-1 Receptor Agonist in Adults with Type 2 Diabetes," Diabetes 2022;71 (Supplement_1):94-LB, 1 page, https://doi.org/10.2337/db22-94-LB.
Plamboeck, A., et al., "The effect of exogenous GLP-1 on food intake is lost in male truncally vagotomized subjects with pyloroplasty," Am J Physiol Gastrointest Liver Physiol 304: G1117-G1127, 2013, https://doi.org/10.1152/ajpgi.00035.2013.
Polyzos, S. A., et al., "Obesity and nonalcoholic fatty liver disease: From pathophysiology to therapeutics," Metabolism Clinical and Experimental 2019, 92:82-97, doi:10.1016/j.metabol.2018.11.014.
Pratt, E., et al., "Orforglipron (LY3502970), a novel, oral non-peptide glucagon-like peptide-1 receptor agonist: A Phase 1a, blinded, placebo-controlled, randomized, single- and multiple-ascending-dose study in healthy participants," Diabetes Obes. Metab. 2023, 25:2634-2641, DOI: 10.1111/dom.15184.
Pratt, E., et al., "Orforglipron (LY3502970), a novel, oral non-peptide glucagon-like peptide-1 receptor agonist: A Phase 1b, multicentre, blinded, placebo-controlled, randomized, multiple-ascending-dose study in people with type 2 diabetes," Diabetes Obes Metab. 2023; 25:2642-2649, DOI: 10.1111/dom.15150.
Prospective Studies Collaboration, Whitlock, G., et al., "Body-mass index and cause-specific mortality in 900,000 adults: collaborative

(56) References Cited

OTHER PUBLICATIONS analyses of 57 prospective studies," Lancet 2009, 373:1083-1096, published online Mar. 18, 2009, DOI:10.1016/S0140-6736(09)60318-4.
Pubchem "Danuglipron," CID: 134611040, Created Jun. 23, 2018; Modified Feb. 8, 2025, 32 pages, Retrieved on Feb. 13, 2025, Retrieved from https://pubchem.ncbi.nlm.nih.gov/compound/134611040#section=Information-Sources.
Pubchem (Jan. 12, 2016). "4-(1,2,4-Benzotriazin-3-Yloxy)-N-Methylaniline," CID: 103204817, 7 pages.
Rich, N. E., et al., "Racial and Ethnic Disparities in Nonalcoholic Fatty Liver Disease Prevalence, Severity, and Outcomes in the United States: A Systematic Review and Meta-analysis," Clinical Gastroenterology and Hepatology 2018, 16, 198-210, 210.e1-210.e2.
Rinella, M. E., et al., "AASLD Practice Guidance on the clinical assessment and management of nonalcoholic fatty liver disease," Hepatology 2023, 77, 1797-1835.
Roche, Ad hoc announcement pursuant to Art. 53 LR, "Roche announces positive Phase I results of its oral GLP-1 receptor agonist CT-996 for the treatment of people with obesity," Jul. 17, 2024, 5 pages, https://www.roche.com/media/releases/med-cor-2024-07-17.
Rubino, D., et al., Effect of Continued Weekly Subcutaneous Semaglutide vs Placebo on Weight Loss Maintenance in Adults With Overweight or Obesity: The STEP 4 Randomized Clinical Trial, JAMA 2021, 325(14): 1414-1425, published online Mar. 23, 2021, doi: 10.1001/jama.2021.3224.
Russak, E. M., et al., "Impact of Deuterium Substitution on the Pharmacokinetics of Pharmaceuticals," Annals of Pharmacotherapy 2019; 53(2):211-216, DOI: 10.1177/1060028018797110.
Sarma, S., et al., "Weight loss between glucagon-like peptide-1 receptor agonists and bariatric surgery in adults with obesity: A systematic review and meta-analysis," Obesity (Silver Spring) 2022, 30(11): 2111-2121, doi:10.1002/oby.23563.
Saxena, A., et al., "Tolerability, safety and pharmacodynamics of oral, small-molecule glucagon-like peptide-1 receptor agonist danuglipron for type 2 diabetes: A 12-week, randomized, placebo-controlled, Phase 2 study comparing different dose- escalation schemes," Diabetes Obes Metab. 2023;25:2805-2814, DOI: 10.1111/dom.15168.
Saxena, A. R., et al., "Danuglipron (PF-06882961) in type 2 diabetes: a randomized, placebo-controlled, multiple ascending-dose phase 1 trial," Nature Medicine, vol. 27, Jun. 2021, pp. 1079-1087, doi: 10.1038/s41591-021-01391-w.
Saxena, A. R., et al., "Efficacy and Safety of Oral Small Molecule Glucagon-Like Peptide 1 Receptor Agonist Danuglipron for Glycemic Control Among Patients With Type 2 Diabetes: A Randomized Clinical Trial," JAMA Network Open, May 22, 2023, vol. 6(5), e2314493, 12 pages, doi:10.1001/jamanetworkopen.2023.14493.
SAXENDA® (liraglutide) injection, for subcutaneous use. United States Prescribing Information (USPI). 2022. Accessed: Feb. 2, 2023. 13 pages. https://www.novo-pi.com/saxenda.pdf.
Schwimmer, et al., "Prevalence of Fatty Liver in Children and Adolescents," Pediatrics, 2006, 118:1388-1393.
Selva, D. M., et al., "Monosaccharide-induced lipogenesis regulates the human hepatic sex hormone-binding globulin gene," J. Clin. Inv., Dec. 2007; 117(12); 3979-3987, doi: 10.1172/JCI32249.
Shaffer, A. A, et al., "Comparison of Computational Methods Applied to Oxazole, Thiazole, and Other Heterocyclic Compounds," Journal of Computational Chemistry, vol. 14, No. 1, pp. 75-88 (1993).
Sharma, M. C., "QSAR studies of novel 1-(4-methoxyphenethyl)-1H-benzimidazole-5-carboxylic acid derivatives and their precursors as antileukaemic agents," Journal of Taibah University for Science, 2016, vol. 10, pp. 122-130.
Sheldrick, G. M., "Crystal structure refinement with SHELXL," ActaCryst. 2015, C71, 3-8, doi:10.1107/S2053229614024218.
Sheldrick, G. M., "SHELXL—Integrated space-group and crystal-structure determination" ActaCryst. 2015, A71, 3-8, doi: 10.1107/S2053273314026370.
Simone "Part XIV: Oncology" in Cecil Textbook of Medicine 20th Ed., Eds. Bennet & Plum, W.B. Saunders Company (1996); 1:1004-1010.
Sinha, R. A et al., "Direct Effects of Thyroid Hormones on Hepatic Lipid Metabolism," Nat. Rev. Endocrinology, May 2018, 14(5):259-269 (26 total pages).
Sinha, R. A., et al., "Nonalcoholic Fatty Liver Disease and Hypercholesterolemia: Roles of Thyroid Hormones, Metabolites, and Agonists," Thyroid 2019, vol. 29, No. 9, pp. 1173-1191, DOI: 10.1089/thy.2018.0664.
Sloop, K. W., et al., "Novel Small Molecules Glucagon-Like Peptide-1 Receptor Agonist Stimulates Isulin Secretion in Rodents and From Human Islets," Diabetes, vol. 59, Dec. 2010, p. 3099-3107.
Stas, M., et al., "Thiazole-amino acids: influence of thiazole ring on conformational properties of amino acid residues," Amino Acids 2021, 53: 673-686, https://doi.org/10.1007/s00726-021-02974-0.
Stemmer, K., et al., "CNS-targeting pharmacological interventions for the metabolic syndrome," The Journal of Clinical Investigation, Oct. 2019, 129(10), pp. 4058-4071, https://www.jci.org/articles/view/129195/pdf.
Stevens, E., Medicinal Chemistry: The Modern Drug Discovery Process, 2013, Chapter 10, Lead Discovery, pp. 247-272.
Stine, J. G., et al., "Change in MRI-PDFF and Histologic Response in Patients with Nonalcohlic Steatohepatitis: A Systematic Review and Meta-Analysis," Clinical Gastroenterology and Hepatology 2021, vol. 19, No. 11, 2274-2283, 2283.e1-2283.e5.
Structure Therapeutics Corporate Presentation, GSBR-1290 Phase 1b MAD Results. Sep. 29, 2023, 24 pages.
Taub, R., et al., 'Lipid lowering in healthy volunteers treated with multiple doses of MGL-3196, a liver-targeted thyroid hormone receptor-β agonist,' Atherosclerosis, 2013, 230:373-80.
Teague, S. J., et al., "The Design of Leadlike Combinatorial Libraries," Communications, Angew. Chem. Int. Ed., 1999, 38, No. 24, pp. 3743-3748.
Terns Pharmaceuticals Announces Positive Phase 1 Clinical Trial Results with TERN-601 Once-Daily Oral GLP-1R Agonist for the Treatment of Obesity, Sep. 9, 2024, 3 pages, retrieved on Feb. 12, 2025, retrieved from URL: https://ir.ternspharma.com/news-releases/news-release-details/terns-pharmaceuticals-announces-positive-phase-1-clinical-trial.
Terns Pharmaceuticals Highlights New Preclinical Data Supporting TERN-501 in Combination with a GLP-1R Agonist for Obesity at the ADA's 84th Annual Scientific Sessions and Upcoming Conference Participation, Jun. 21, 2024, 2 pages, retrieved on Jul. 26, 2024, retrieved from URL: https://ir.ternspharma.com/news-releases/news-release-details/terns-pharmaceuticals-highlights-new-preclinical-data-supporting.
Terns. Terns Pharmaceuticals. Our Programs, retrieved Jul. 8, 2025, available at: https://www.ternspharma.com/our-programs. 6 pages.
Twig, G., et al., "Body-Mass Index in 2.3 Million Adolescents and Cardiovascular Death in Adulthood," The New England Journal of Medicine, Jun. 23, 2016, 374;25: 2430-2440, DOI: 10.1056/NEJMoa1503840.
U.S. Appl. No. 17/305,302, filed Jul. 2, 2021, by Shanghai Yu et al.
U.S. Appl. No. 18/818,705, filed Aug. 29, 2024, by Kirschberg et al.
U.S. Appl. No. 19/242,909, filed Jun. 18, 2025, by Reeves et al.
Van Can, J., et al., "Effects of the once-daily GLP-1 analog liraglutide on gastric emptying, glycemic parameters, appetite and energy metabolism in obese, non-diabetic adults," International Journal of Obesity, 2014, 38: 784-793, advance online publication Oct. 1, 2013.
Viking Therapeutics Announces Results from Phase 1 Clinical Trial of Oral Tablet Formulation of Dual GLP-1/GIP Receptor Agonist VK2735, provided by Viking Therapeutics, Inc., Mar. 26, 2024, 6 pages, https://www.prnewswire.com/news-releases/viking-therapeutics-announces-results-from-phase-1-clinical-trial-of-oral-tablet-formulation-of-dual-glp-1gip-receptor-agonist-vk2735-302098869.html.

(56) References Cited

OTHER PUBLICATIONS

Vilsboll, T., et al., Reduced Postprandial Concentrations of Intact Biologically Active Glucagon-Like Peptide 1 in Type 2 Diabetic Patients, Diabetes, vol. 50, Mar. 2001, pp. 609-613.
Voldum-Clausen, K., et al., "Synergistic hepatoprotective effects of semaglutide and resmetirom combination therapy in the GAN diet-induced obese and biopsy- confirmed mouse model of MASH," Abstract THU-244, Journal of Hepatology 2024, vol. 80(S1), p. S580.
Voldum-Clausen, K., et al., "Additive hepatoprotective effects of semaglutide and resmetirom combination therapy in the GAN diet-induced obese and biopsy-confirmed mouse model of MASH," presented in European Association for the Study of the Liver Congress (EASL), Milan, Italy, Jun. 5-8, 2024, Poster, 1 page.
Wadden, T. A., et al., "Treatment of obesity by very low calorie diet, behavior therapy, and their combination: a five-year perspective," International Journal of Obesity, 1989, 13, suppl. 2, pp. 39-46.
Waise, T. M. Z., et al., The metabolic role of vagal afferent innervation, Nature Reviews Gastroenterology & Hepatology, vol. 15, Oct. 2018, pp. 625-636, https://doi.org/10.1038/s41575-018-0062-1.
Walenbergh S. A., et al., "Cholesterol is a significant risk factor for nonalcoholic steatohepatitis," Expert Review of Gastroenterology & Hepatology, 2015, 9(11):1343-1346.
WEGOVY® (semaglutide) injection, for subcutaneous use. United States Prescribing Information (USPI). 2023. Accessed: Feb. 2, 2023. 15 pages. https://www.novo-pi.com/wegovy.pdf.
Wharton, S, et al., "Daily Oral GLP-1 Receptor Agonist Orforglipron for Adults with Obesity," The New England Journal of Medicine, Sep. 7, 2023, vol. 389, No. 10, pp. 877-888.
Wharton, S., et al., "Obesity in adults: a clinical practice guideline," CMAJ, Aug. 4, 2020, vol. 192, Issue 31, E875-E891, doi: 10.1503/cmaj.191707.
Wilding, J. P. H., et al., Once-Weekly Semaglutide in Adults with Overweight or Obesity, The New England Journal of Medicine, Mar. 18, 2021, vol. 384, No. 11, 989-1002.
Wong, C., et al., "Glucagon-Like Peptide-1 Receptor Agonists for Non-Alcoholic Fatty Liver Disease in Type 2 Diabetes: A Meta-Analysis," Frontiers in Endocrinology, Apr. 2021, vol. 12, Article 609110, pp. 1-11, doi: 10.3389/fendo.2021.609110.
Zhang, X. et al., "Differential GLP-1R Binding and Activation by Peptide and Non-peptide Agonists," Molecular Cell 80, Nov. 5, 2020; pp. 485-500 & 485-500.e1-e7, doi: 10.1016/j.molcel.2020.09.020.
Zinman, B., et al., "Semaglutide once weekly as add-on to SGLT-2 inhibitor therapy in type 2 diabetes (SUSTAIN 9): a randomised, placebo-controlled trial," Lancet Diabetes Endocrinol 2019, 7: 356-367, Published online Mar. 1, 2019, http://dx.doi.org/10.1016/S2213-8587(19)30066-X.
Kirschberg, T., et al., "TERN-501, a potent and selective agonist of thyroid hormone receptor beta, strongly redcues histological features and biomarkers of non-alcoholic steatohepatitis associated pathology in rodent models," Journal of Hepatology 2020, vol. 73, S653-S915, p. S684, SAT066.
Klein, I. et al. (Oct. 9, 2007). "Cardiovascular Involvement in General Medical Conditions, Thyroid Disease and the Heart," Circulation 116(15):1725-1735.
Kleiner, D. E., et al., "Design and validation of a histological scoring system for nonalcoholic fatty liver disease," Hepatology, Jun. 2005, 41(6):1313-1321.
Kogler, M. (Mar. 2012). "Synthesis and Evaluation of 6-aza-2'-deoxyuridine Monophosphate Analogs as Inhibitors of Thymidylate Synthases, and as Substrates or Inhibitors of Thymidine Monophosphate Kinase in Mycobacterium Tuberculosis," Chemistry and Biodiversity, 9(3):536-556.
Kowalik et al., "Thyroid Hormones, Thyromimetics and Their Metabolites in the Treatment of Liver Disease," Frontiers in Endocrinology, vol. 9, Article 382, pp. 1-11 (Jul. 2018).
Krchnak, V. et al., "Novel Pyrimidine Derivatives, Reactions and Ultraviolet Spectra," Collect. Czech. Chem. Commun. 1975, 40(5):1038-1042.
Krieger, J.-P., "Intestinal glucagon-like peptide-1 effects on food intake: Physiological relevance and emerging mechanisms," Peptides 2020, 131:170342, 8 pages, https://doi.org/10.1016/j.peptides.2020.170342.
Le, T. N., et al., "Sex hormone-binding globulin and type 2 diabetes mellitus," Trends in Endocrinology Metabolism, Jan. 2012, vol. 23, No. 1, pp. 32-40;, doi: 10.1016/j.tem.2011.09.005.
Lega, I. C., et al., "Review: Diabetes, Obesity, and Cancer-Pathophysiology and Clinical Implications," Endocrine Reviews, Feb. 2020, 41(1):35-52, doi:10.1210/endrev/bnz014.
International Search Report and Written Opinion for the International Application No. PCT/US2025/030358 mailed Jul. 30, 2025, 15 pages.
U.S. Appl. No. 18/956,385, filed Nov. 22, 2024, by Reeves et al.
U.S. Appl. No. 62/731,364, filed Sep. 14, 2018, by Jin et al., 149 pages.
U.S. Appl. No. 62/767,402, filed Nov. 14, 2016, by Jin et al., 150 pages.
U.S. Appl. No. 62/684,113, filed Jun. 12, 2018, by Jin et al., 137 pages.
WEGOVY® (semaglutide) injection 2.4mg, for subcutaneous use, 2024, 15 pages.
Adult Obesity Prevalence Maps 2023; updated Sep. 12, 2024 | Obesity | CDC, 6 pages. Retrieved Sep. 15, 2025. Retrieved from https://www.cdc.gov/obesity/data-and-statistics/adult-obesity-prevalence-maps.html.
Amorim, B. S. et al., "A TRß-selective agonist confers resistance to diet-induced obesity," Journal of Endocrinology 2009, 203, 291-299, DOI: 10.1677/JOE-08-0539.
Aronne, L. J. et al., "Tirzepatide as Compared with Semaglutide for the Treatment of Obesity," The New England Journal of Medicine 393, 1, Jul. 3, 2025, pp. 26-36.
Bhaskaran, K. et al., "Body-mass index and risk of 22 specific cancers: a population-based cohort study of 5.24 million UK adults," The Lancet, vol. 384, Aug. 30, 2014, pp. 755-765.
Borner, T., et al., "Hypophagia and body weight loss by tirzepatide are accompanied by fewer GI adverse events compared to semaglutide in preclinical models," Science Advances 11, eadu1589 (2025), Jun. 18, 2025, pp. 1-14.
Buckeridge, C., et al., "Efficacy and safety of danuglipron (PF-06882961) in adults with obesity: A randomized, placebo-controlled, dose-ranging phase 2b study," Diabetes Obes Metab. 2025, pp. 1-12, DOI: 10.1111/dom.16534.
Cable, E. E., et al., "Reduction of Hepatic Steatosis in Rats and Mice After Treatment with a Liver-Targeted Thyroid Hormone Receptor Agonist," Hepatology, Feb. 2009, vol. 49, No. 2, pp. 407-417, DOI: 10.1002/hep.22572.
Chao, A. M., et al., "Clinical Insight on Semaglutide for Chronic Weight Management in Adults: Patient Selection and Special Considerations," Drug, Design, Development and Therapy 2022, 16: 4449-4461, published Dec. 29, 2022.
Chouchani, E. T., et al., "New Advances in Adaptive Thermogenesis: UCP1 and Beyond," Cell Metabolism 29, Jan. 8, 2019, pp. 27-37, https://doi.org/10.1016/j.cmet.2018.11.002.
Christoffersen, B. Ø., et al., "Beyond appetite regulation: Targeting energy expenditure, fat oxidation, and lean mass preservation for sustainable weight loss," Obesity (Silver Spring) 2022, 30: 841-857, doi: 10.1002/oby.23374.
Cioffi, F., et al., "Bioenergetic Aspects of Mitochondrial Actions of Thyroid Hormones," Cells 2022, 11, 997, pp. 1-22, published Mar. 15, 2022, https://doi.org/10.3390/cells11060997.
Corbin, K. D., et al., "GLP-1/Glucagon Receptor Agonism Associates with Reduced Metabolic Adaptation and Higher Fat Oxidation: A Randomized Trial," Obesity, Feb. 2023, 31(2), 350-362, 25 total pages, doi: 10.1002/oby.23633.
Drucker, D. J., "Efficacy and Safety of GLP-1 Medicines for Type 2 Diabetes and Obesity," Diabetes Care, Nov. 2024, 47(11): 1873-1888, https://doi.org/10.2337/dci24-0003.
Drucker, "Mechanisms of Action and Therapeutic Application of Glucagon-like Peptide-1," Cell Metab, Apr. 2018, 27(4):740-756.

(56) References Cited

OTHER PUBLICATIONS

Frias et al., "Tirzepatide versus Semaglutide Once Weekly in Patients with Type 2 Diabetes," The New England Journal of Medicine, 385;6, Aug. 5, 2021, pp. 503-515.
Ganeshan, K. and Chawla, A., "Warming the mouse to model human diseases," Nat Rev Endocrinol., Aug. 2017, 13(8): 458-465, 18 total pages, doi: 10.1038/nrendo.2017.48.
Garvey, W. T. et al., "Two-year effects of semaglutide in adults with overweight or obesity: the STEP 5 trial," Nature Medicine, vol. 28, Oct. 2022, pp. 2083-2091, 23 total pages.
Golozoubova, V., et al., "Depressed Thermogenesis but Competent Brown Adipose Tissue Recruitment in Mice Devoid of All Hormone-Binding Thyroid Hormone Receptors," Molecular Endocrinology , Feb. 2004, 18(2): 384-401, doi: 10.1210/me.2003-0267.
Greenway, F. L., "Physiological adaptations to weight loss and factors favouring weight regain," International Journal of Obesity 2015, 39, 1188-1196, doi: 10.1038/ijo.2015.59.
Grover, G. J., et al., "Selective thyroid hormone receptor-ß activation: A strategy for reduction of weight, cholesterol, and lipoprotein (a) with reduced cardiovascular liability," PNAS, Aug. 19, 2003, vol. 100, No. 17, p. 10067-10072, www.pnas.org/cgi/doi/10.1073/pnas.1633737100.
Guo, J. & Hall, K. D., "Estimating the Continuous-Time Dynamics of Energy and Fat Metabolism in Mice," PLOS Computational Biology, Sep. 2009, vol. 5, Issue 9, e1000511, 7 pages.
Hall, K. D. & Kahan, S., et al., "Maintenance of lost weight and long-term management of obesity," Medical Clinics of North America, Jan. 2018, 102(1): 183-197, 19 total pages, doi: 10.1016/jmcna.2017.08.012.
Hall, K. D., "Modeling Metabolic Adaptations and Energy Regulation in Humans," The Annual Review of Nutrition 2012, 32: 35-54, first published online Apr. 23, 2012, doi: 10.1146/annurev-nutr-071811-150705.
Harms et al., "Brown and beige fat: development, function and therapeutic potential," Nature Medicine, 19(10):1252-1263 (2013).
Horn, P., et al., "Metabolic reprogramming in liver fibrosis," Cell Metabolism 36, Jul. 2, 2024, pp. 1439-1455, https://doi.org/10.1016/j.cmet.2024.05.003.
Huang, D. Q., et al., "Metabolic dysfunction-associated steatotic liver disease in adults," Nature Reviews Disease Primers 2025, 11:14, pp. 1-25.
Ireton-Jones, C., Adjusted Body Weight, Con: Why Adjust Body Weight in Energy-Expenditure Calculations? Nutrition in Clinical Practice 20: 474-479, Aug. 2005.
Iwen, K. A., et al., "Effects of thyroid hormones on thermogenesis and energy partitioning," Journal of Molecular Endocrinology 2018, 60:3, R157-R170, https://doi.org/10.1530/ME-17-0319.
Jacobsen, J. M., et al., "Housing mice near vs. below thermoneutrality affects drug-induced weight loss but does not improve prediction of efficacy in humans," Cell Reports 43, 114501, Aug. 27, 2024, pp. 1-17, including Supplemental Information, 17 pages.
Jakobsson, T., et al., "Potential Role of Thyroid Receptor ß Agonists in the Treatment of Hyperlipidemia," Drugs 2017, 77: 1613-1621, DOI: 10.1007/s40265-017-0791-4.
Jastreboff, A. M., et al., "Tirzepatide Once Weekly for the Treatment of Obesity," The New England Journal of Medicine, Jul. 21, 2022, vol. 387, No. 3, pp. 205-216, DOI: 10.1056/NEJMoa2206038.
Jastreboff, A. M., et al., "Triple-Hormone-Receptor Agonist Retatrutide for Obesity—A Phase 2 Trial," The New England Journal of Medicine, Aug. 10, 2023, 389(6), pp. 514-526, DOI: 10.1056/NEJMoa2301972.
Jiang, Y., et al., "Why does GLP-1 agonist combined with GIP and/or CGC agonist have great weight loss effect than GLP-1 agonist alone in obese adults without type 2 diabetes?," Diabetes Obes Metab. 2025: 27:1079-1095.
Johann, K., et al., "Thyroid-Hormone-Induced Browning of White Adipose Tissue Does Not Contribute to Thermogenesis and Glucose Consumption," Cell Reports, Jun. 11, 2019, 27, pp. 3385-3400 & 3385-3400.e1-e3, https://doi.org/10.1016/j.celrep.2019.05.054.
Jones, C., et al., 767-P: TERN-601, a Novel Oral GLP-1R Agonist, Suppresses Food Intake and Improves Glucose Tolerance in Transgenic Mice Expressing Human GLP-1 Receptor, Diabetes. 2023;72(Supplement_1), including slide, 2 pages, doi:10.2337/db23-767-P.
Karakasis, P., et al., "Effect of glucagon-like peptide-1 receptor agonists and co-agonists on body composition: Systematic review and network meta-analysis," Metabolism 2025, 164, 156113, 13 pages, https://doi.org/10.1016/j.metabol.2024.156113.
Kawai, T. et al., "Structural basis for GLP-1 receptor activation by LY3502970, an orally active nonpeptide agonist," Proc Natl Acad Sci, Nov. 24, 2020, vol. 117, No. 47, first published Nov. 11, 2020, pp. 29959-29967, www.pnas.org/cgi/doi/10.1073/pnas.2014879117.
Knuth, N. D. et al., "Metabolic Adaptation Following Massive Weight Loss is Related to the Degree of Energy Imbalance and Changes in Circulating Leptin," Obesity, vol. 22, No. 12, Dec. 2014, pp. 2563-2569.
Koskinas, K. C. et al., "Obesity and cardiovascular disease: an ESC clinical consensus statement," European Heart Journal 2024, 45, 4063-4098, https://doi.org/10.1093/eurheart/ehae508.
Krause, K., "Novel Aspects of White Adipose Tissue Browning by Thyroid Hormones," Experimental and Clinical Endocrinology and Diabetes 2020, 128: 446-449, published online Nov. 7, 2019, https://doi.org/10.1055/a-1020-5354.
Kusminski, C. M. et al., "Transforming obesity: The advancement of multi-receptor drugs," Cell 187, Jul. 25, 2024, pp. 3829-3853.
Leibel, R. L., et al., "Changes in Energy Expenditure Resulting from Altered Body Weight," New England Journal of Medicine, Mar. 9, 1995, vol. 332, No. 10, pp. 621-628.
Lilly's oral GLP-1, orforglipron, delivers weight loss of up to an average of 27.3 lbs in first of two pivotal Phase 3 trials in adults with obesity | Eli Lilly and Company, Aug. 7, 2025, 3 pages, https://investor.lilly.com/news-releases/news-release-details/lillys-oral-glp-1-orforglipron-delivers-weight-loss-average-273.
Lilly'S oral GLP-1, orforglipron, demonstrated statistically significant efficacy results and a safety profile consistent with injectable GLP-1 medicines in successful Phase 3 trial | Eli Lilly and Company, Apr. 17, 2025, 3 pages, https://investor.lilly.com/news- releases/news-release-details/lillys-oral-glp-1-orforglipron-demonstrated-statistically.
Lin, J. Z. et al., "Pharmacological Activation of Thyroid Hormone Receptors Elicits a Functional Conversion of White to Brown Fat," Cell Reports 13, 1528-1537, Nov. 24, 2015, http://dx.doi.org/10.1016/j.celrep.2015.10,022.
Lopez, M., et al., "Hypothalamic AMPK and fatty acid metabolism mediate thyroid regulation of energy balance," Nat Med., Sep. 2010, 16(9): 1001-1008, 23 pages, doi: 10.1038/nm.2207.
McCrimmon, R. J., et al., "Effects of once-weekly semaglutide vs once-daily canagliflozin on body composition in type 2 diabetes: a substudy of the Sustain 8 randomised controlled clinical trial," Diabetologia 2020, 63: 473-485, https://doi.org/10.1007/s00125-019-05065-8.
Mechanick, J. I., et al., "Strategies for minimizing muscle loss during use of incretin-mimetic drugs for treatment of obesity," Obesity Reviews 2025, 26:e13841, pp. 1-11, https://doi.org/10.1111/obr.13841.
Moiz, A., et al., "Long-Term Efficacy and Safety of Once-Weekly Semaglutide for Weight Loss in Patients Without Diabetes: A Systematic Review and Meta-Analysis of Randomized Controlled Trials," The American Journal of Cardiology 2024, 222:121-130, https://doi.org/10.1016/j.amjcard.2024.04.041.
Moiz, A., et al., "Mechanisms of GLP-1 Receptor Agonist-Induced Weight Loss: A Review of Central and Peripheral Pathways in Appetite and Energy Regulation," The American Journal of Medicine 2025, 138: 934-940.
Moruppa, S. M., "Energy expenditure and locomotor activity in mice selected for food intake adjusted for body weight," Theoretical and Applied Genetics 1990, 79, 131-136.
Most, J. & Redman, L. M., "Impact of calorie restriction on energy metabolism in humans," Experimental Gerontology 2020, 133, 110875, 10 pages, available online Feb. 11, 2020, https://doi.org/10.1016/j.exger.2020.110875.

(56) References Cited

OTHER PUBLICATIONS

Muller, M. J., et al., "Changes in Energy Expenditures with Weight Gain and Weight Loss in Humans," Curr Obes Rep 2016, 5:413-423, DOI: 10.1007/s13679-016-0237-4.

Muller, T. D., et al., "Adaptive Thermogenesis with Weight Loss in Humans," Feb. 2013, vol. 21, No. 2, pp. 218-228, published online Sep. 13, 2012, doi: 10.1002/oby.20027.

Muller, T.D., et al., "Revisiting energy expenditure: how to correct mouse metabolic rate for body mass," Nat Metab.; 3(9):1134-1136, Sep. 2021.

Mullur, R., et al., "Thyroid Hormone Regulation of Metabolism," Physiol Rev 94: 355-382, Apr. 2014, doi: 10.1152/physrev.00030.2013.

Ng, M., et al., "Global, regional, and national prevalence of adult overweight and obesity, 1990-2021, with forecasts to 2050: a forecasting study for the Global Burden of Disease Study 2021," The Lancet , vol. 405, Mar. 8, 2025, pp. 813-838.

Nie, Y., et al., "Measurement of Resting Energy Metabolism in Mice Using Oxymax Open Circuit Indirect Calorimeter," Bio-Protocol, Sep. 20, 2015, 5(18):e1602, 7 pages, DOI: 10.21769/BioProtoc.1602.

Noureddin, M. et al., "TERN-501 monotherapy and combination therapy with TERN-101 in metabolic dysfunction-associated steatohepatitis: the randomized phase 2a DUET trial," Nature Medicine, published online Jun. 11, 2025, 25 pages, doi:10.1038/S41591-025-03722-7.

Novikoff, A., et al., "Tirzepatide differentially affects body weight in mice and humans," Nature Reviews Endocrinology, published online Jun. 9, 2025, 2 pages, https://doi.org/10.1038/s41574-025-01139-3.

PCT International Patent Application No. PCT/US2025/041465, filed Aug. 11, 2025, by Terns Pharmaceuticals, Inc.; 149 pages.

PCT International Patent Application No. PCT/US2025/044812, filed Sep. 4, 2025, by Terns Pharmaceuticals, Inc.; 162 pages.

Ratziu, V., et al., "Thyroid hormone receptor-B analogues for the treatment of metabolic dysfunction-associated steatohepatitis (MASH), "Journal of Hepatology, Feb. 2025, vol. 82, pp. 375-387, https://doi.org/10.1016/j.jhep.2024.10.018.

Ravussin, E., et al., "Physiology of Energy Expenditure in the Weight-Reduced State," Obesity, vol. 29, Supp. 1, Apr. 1, 2021, pp. S31-S38, published online Mar. 24, 2021, doi: 10.1002/oby.23095.

Ravussin, E., et al., "Tirzepatide did not impact metabolic adaptation in people with obesity, but increased fat oxidation," Cell Metabolism 37, 1060-1074 & 1060-1074.e1-e4, May 6, 2025, https://doi.org/10.1016/j.cmet.2025.03.011.

Ribeiro, M. O., et al., "Expression of Uncoupling Protein 1 in Mouse Brown Adipose Tissue is Thyroid Hormone Receptor—Isoform Specific and Required for Adaptive Thermogenesis," Endocrinology , Jan. 2010, 151(1), pp. 432-440, first published online Nov. 11, 2019.

Ribeiro, M. O., et al., "Thyroid hormone-sympathetic interaction and adaptive thermogenesis are thyroid hormone receptor isoform-specific," The Journal of Clinical Investigation, Jul. 2001, vol. 108, No. 1, pp. 97-105.

Rodriguez, P. J. et al., "Semaglutide vs Tirzepatide for Weight Loss in Adults With Overweight or Obesity," JAMA Intern Med 2024, 184(9): 1056-1064; published online Jul. 8, 2024, doi: 10.1001/jamainternmed.2024.2525.

Rosenstock, J. et al., "Orforglipron, an Oral Small-Molecule GLP-1 Receptor Agonist, in Early Type 2 Diabetes," The New England Journal of Medicine, published Jun. 21, 2025, 12 pages, DOI: 10.1056/NEJMoa2505669.

Roth, L., et al., "Thyroid hormones are required for thermogenesis of beige adipocytes induced by Zfp423 inactivation," Cell Reports 43, 114987, Dec. 24, 2024, pp. 1-18, including Supplemental information, 7 pages.

Sanyal, A. J. et al., 'A Phase 2 Randomized Trial of Survodutide in MASH and Fibrosis,' The New England Journal of Medicine 391(4), Jul. 25, 2024, pp. 311-319, DOI: 10.1056/NEJMoa2401755.

Sanyal, A. J., et al., "Triple hormone receptor agonist retatrutide for metabolic dysfunction-associated steatotic liver disease: a randomized phase 2a trial," Nature Medicine, vol. 30, Jul. 2024, pp. 2037-2048, 31 total pages, https://doi.org/10.1038/s41591-024-03018-2.

Saponaro, F., et al., "Selective Thyroid Hormone Receptor-Beta (TRB) Agonists: New Perspectives for the Treatment of Metabolic and Neurodegenerative Disorders," Frontiers in Medicine, Jul. 2020, vol. 7, Article 331, pp. 1-14, doi: 10.3389/fmed.2020.00331.

Sidossis, L. & Kajimura, S., "Brown and beige fat in humans: thermogenic adipocytes that control energy and glucose homeostasis," Journal of Clinical Investigation, Feb. 2015, 125(2): 478-486, https://doi.org.10.1172/JCI78362.

Terns Pharmaceuticals Company Overview Jan. 2023, 56 pages, retrieved Aug. 26, 2025, from https://web.archive.org/web/20230125104334/https://ir.ternspharma.com/static-files/9497d66a-13a2-476a-b5f4-99597e0aac21.

The U.S. Food and Drug Administration. FDA Approves Treatment for Serious Liver Disease Known as 'MASH' | FDA. Content current as of Aug. 15, 2025. Retrieved Sep. 15, 2025. Retrieved from https://www.fda.gov/drugs/news-events-human-drugs/fda-approves-treatment-serious-liver-disease-known-mash.

Tran, K. B. et al., "The global burden of cancer attributable to risk factors, 2010-19: a systematic analysis for the Global Burden of Disease Study 2019," The Lancet, vol. 400, Aug. 20, 2022, pp. 563-591.

Tseng, Y.-H., et al., "Cellular bioenergetics as a target for obesity therapy," Nature Reviews Drug Discovery, Jun. 2010, vol. 9, pp. 465-481, doi:10.1038/nrd3138.

U.S. Appl. No. 19/306,676, filed Aug. 21, 2025 by Kirschberg et al.

Vaitkus, J. A., et al., "Thyroid Hormone Mediated Modulation of Energy Expenditure," Int. J. Mol. Sci. 2015, 16, 16158-16175, doi: 10.3390/ijms160716158.

Vettor, R., et al., "Regulation of energy intake and mechanisms of metabolic adaptation or maladaptation after caloric restriction," Reviews in Endocrine and Metabolic Disorders 2020, 21: 399-409, published online May 26, 2020, https://doi.org/10.1007/s11154-020-09565-6.

Villicev, C. M. et al., "Thyroid hormone receptor ß-specific agonist GC-1 increases energy expenditure and prevents fat-mass accumulation in rats," Journal of Endocrinology 2007, 193, 21-29, DOI: 10.1677/joe.1.07066.

Wharton, S. et al., "Gastrointestinal tolerability of once-weekly semaglutide 2.4 mg in adults with overweight or obesity, and the relationship between gastrointestinal adverse events and weight loss," Diabetes Obes Metab 2022, 24: 94-105, DOI: 10.1111/dom.14551.

Wharton, S. et al., "Survodutide for treatment of obesity: rationale and design of two randomized phase 3 clinical trials (SYNCHRONIZETM-1 and -2)," Obesity (Silver Spring) 2025, 33(1): 67-77, DOI: 10.1002/oby.24184.

Wilding, J. P. H., et al., Weight regain and cardiometabolic effects after withdrawal of semaglutide: The STEP 1 trial extension, Diabetes Obes Metab. 2022, 24:1553-1564, DOI: 10.1111/dom.14725.

Wu et al., "Beige adipocytes are a distinct type of thermogenic fat cell in mouse and human", Cell, (2012); 150(2):366-376.

Wu, R. et al., "Genetically prolonged beige fat in male mice confers long-lasting metabolic health," Nature Communications 2023, 14:2731, 17 pages, https://doi.org/10.1038/s41467-023-38471-z.

Yau, K., et al., "Obesity and the kidney: mechanistic links and therapeutic advances," Nature Reviews Endocrinology, Jun. 2024, vol. 20, pp. 321-335, https://doi.org/10.1038/s41574-024-00951-7.

Yau, W. W., et al., "Thermogenesis in Adipose Tissue Activated by Thyroid Hormone," International Journal of Molecular Sciences, 2020, 21, 3020, 16 pages, doi:10.3390/ijms21083020.

Yehuda-Shnaidman, E., et al., "Thyroid Hormone, Thyromimetics, and Metabolic Efficiency," Endocrine Reviews, Feb. 2014, 35(1):35-58, doi: 10.1210/er.2013-1006.

Yu, X., et al., "The GIP receptor activates futile calcium cycling in white adipose tissue to increase energy expenditure and drive weight loss in mice," Cell Metabolism 37, Jan. 7, 2025, pp. 187-204 & 187-204.e1-e7.

(56) References Cited

OTHER PUBLICATIONS

Zekri, Y., et al., "Central vs. Peripheral Action of Thyroid Hormone in Adaptive Thermogenesis: A Burning Topic," Cells 2021, 10, 1327, pp. 1-19, https://doi.org/10.3390/cells10061327.
Zhou, M., et al., "Beneficial effects of MGL-3196 and BAM15 combination in a mouse model of fatty liver disease," Acta Physiologica, 2024, 240:e14217, pp. 1-14, doi: 10.1111/apha.14217.

* cited by examiner

COMBINATIONS OF GLP-1R AND THRβ AGONISTS AND METHODS OF USE THEREOF

CROSS-REFERENCE TO RELATED APPLICATIONS

This application is a continuation of U.S. application Ser. No. 18/629,151, filed on Apr. 8, 2024, which claims priority to and the benefit of U.S. Provisional Application No. 63/495,049, filed on Apr. 7, 2023, 63/526,362, filed on Jul. 12, 2023, and 63/615,985, filed on Dec. 29, 2023, each of which are incorporated by reference herein in their entirety for all purposes.

BACKGROUND

GLP-1 is a 30 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of beta-cells. Marketed GLP-1R agonists are peptides that are typically administered by subcutaneous injection. Liraglutide and semaglutide were the first GLP-1 peptides to be approved for both the treatment of type II diabetes mellitus (T2DM) and obesity. Semaglutide has also been approved for the treatment of T2DM as a bioavailable oral formulation.

In a healthy subject, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption.

Thyroid hormone (TH) is synthesized in the thyroid gland in response to the thyroid stimulating hormone (TSH) secreted by the pituitary. Thyroid hormones function by binding to the thyroid hormone receptors (THR). The thyroid hormone receptor belongs to a family of nuclear receptors and regulates the target gene expressions. Thyroid hormone receptors include two different subtypes, i.e., THRα and THRβ. THRα is mainly distributed in cardiac tissues and plays an important role in regulating heart function. The THRβ subtype is mainly expressed in the liver and the pituitary, and regulates cholesterol metabolism and thyrotropin secretion.

At normal levels, thyroid hormones THs maintain body weight, metabolic rate, body temperature, and mood, and are responsible for regulating serum cholesterol. Attempts have been made to use thyroid hormones to regulate serum cholesterol. However, given the possible side effects on the heart from taking natural thyroid hormone (e.g., tachycardia and arrhythmia, heart failure, and thyroid axis function, muscle metabolism, and osteoporosis,) they are unsuitable for treating high cholesterol and obesity. Research results regarding the study of animals with selective knock-out of the THR gene, and research results of some selective THR ligands show that the side effects on the heart caused by these thyroid hormones can be attributed to THRα but not THRα. Therefore, THRβ-selective ligands may provide the benefits of THR agonism (e.g., cholesterol lowering) without the undesirable effects associated with THRα.

Combination therapies of known agonists can yield unexpected synergies and improved effects to a significantly greater extent than administration of either agent alone but effects of combination therapies are highly unpredictable. Developing new combination therapies for the treatment of various liver disorders and cardiometabolic diseases, including obesity, remains a critical unmet clinical need.

GLP-1R regulates post prandial blood glucose and satiety, which can induce weight loss but efficacy is limited by metabolic adaptation, a compensatory process that lowers energy expenditure (EE). Moreover, the higher dose levels of GLP-1R needed to achieve clinical meaningful weight loss, are associated with more severe and frequent GI-related side effects including nausea and emesis, which can negatively impact patient compliance. In a meta-analysis evaluating the efficacy and safety of orforglipron as an anti-obesity medication it has been shown that the total adverse events were significantly higher with all the doses of orforglipron compared to placebo, with the hazard ratios being higher with higher doses. Gastrointestinal side-effects were predominant side effects, being dose-dependent, with nausea, vomiting, constipation, and gastroesophageal reflux being the predominant ones (Dutta et al., *Obes Sci Pracl.* 2024 April; 10(2):e743 PMID: 38414573). Compared to placebo, the occurrence of total adverse events was significantly higher with orforglipron 12 mg, 24 mg, 36 mg and 45 mg daily doses. (Frias et al., *Lancet.* 2023; 402(10400):472-483, Wharton et al., *N Eng J Med.* 2023; 389(10):877-888, Pratt et al, *Diabetes Obes Metabol.* 2023; 25:2642-2649). Therefore, dose dependent gastrointestinal side effects are a persistent challenge in the field of GLP-1 therapeutics.

Mechanisms to improve the effectiveness of GLP-1 based therapies at lower doses, could mitigate GI-related side effects and improve patient compliance and outcomes.

SUMMARY

In one aspect, the present disclosure is directed to a combination of a THRβ agonist, or a pharmaceutically acceptable salt thereof, and a GLP-1R agonist, or a pharmaceutically acceptable salt thereof, for the treatment of a liver disorder or a cardiometabolic disease in a patient in need thereof.

In one aspect, the present disclosure is directed to a method of administering a THRβ agonist, or a pharmaceutically acceptable salt thereof, and administering a GLP-1R agonist, or a pharmaceutically acceptable salt thereof, for the treatment of a liver disorder or a cardiometabolic disease in a patient in need thereof.

In one aspect, the present disclosure is directed to a method of administering a pharmaceutical composition comprising a THRβ agonist, or a pharmaceutically acceptable salt thereof, and administering a pharmaceutical composition comprising a GLP-1R agonist, or a pharmaceutically acceptable salt thereof, for the treatment of a liver disorder or a cardiometabolic disease in a patient in need thereof.

In one aspect, the present disclosure is directed to a method of administering a pharmaceutical composition comprising a THRβ agonist, or a pharmaceutically acceptable salt thereof, and a GLP-1R agonist, or a pharmaceutically acceptable salt thereof, for the treatment of a liver disorder or a cardiometabolic disease in a patient in need thereof.

In some embodiments, the THR agonist of the combination of the present disclosure is a compound of Formula (II-1)

(II-1)

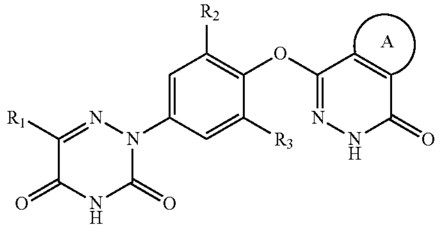

wherein:

$R^1$ is selected from the group consisting of hydrogen, cyano, substituted or unsubstituted $C_{1-6}$ alkyl, and substituted or unsubstituted $C_{3-6}$ cycloalkyl, the substituent being selected from the group consisting of halogen atoms, hydroxy, and $C_{1-6}$ alkoxy;

$R^2$ and $R^3$ are each independently selected from the group consisting of halogen atoms and substituted or unsubstituted $C_{1-6}$ alkyl, the substituent being selected from the group consisting of halogen atoms, hydroxy, and $C_{1-6}$ alkoxy;

ring A is a substituted or unsubstituted saturated or unsaturated $C_{5-10}$ aliphatic ring, or a substituted or unsubstituted $C_{5-10}$ aromatic ring, the substituent being one or more substances selected from the group consisting of hydrogen, halogen atoms, hydroxy, $—OCF_3$, $—NH_2$, $—NHC_{1-4}$ alkyl, $—N(C_{1-4}$ alkyl$)_2$, $—CONH_2$, $—CONHC_{1-4}$ alkyl, $—CON(C_{1-4}$ alkyl$)_2$, $—NHCOC_{1-4}$ alkyl, $C_{1-6}$ alkyl, $C_{1-6}$ alkoxy or $C_{3-6}$ cycloalkyl, and when two substituents are contained, the two substituents can form a ring structure together with the carbon connected thereto; and the halogen atoms are selected from the group consisting of F, Cl and Br, or a pharmaceutically acceptable salt thereof.

In some embodiments, the THRβ agonist of the combination of the present disclosure is a compound of Formula (II-1a)

(II-1a)

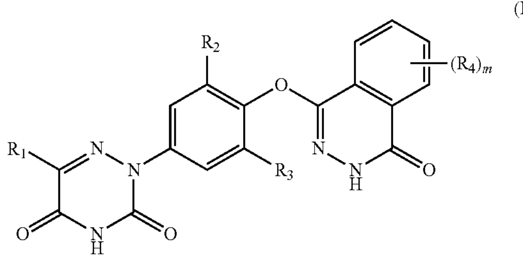

wherein:

$R^1$ to $R^3$ are defined as detailed herein for Formula (II-1);

$R^4$ is selected from the group consisting of hydrogen, halogen atoms, hydroxy, $—OCF_3$, $—NH_2$, $—NHC_{1-4}$ alkyl, $—N(C_{1-4}$ alkyl$)_2$, $—CONH_2$, $—CONHC_{1-4}$ alkyl, $—CON(C_{1-4}$ alkyl$)_2$, $—NHCOC_{1-4}$ alkyl, $C_{1-6}$ alkyl, $C_{1-6}$ alkoxy and $C_{3-6}$ cycloalkyl;

m is an integer from the range 1 to 4; and the halogen atoms are selected from the group consisting of F, Cl and Br. or a pharmaceutically acceptable salt thereof.

In some embodiments, the THRβ agonist of the combination of the present disclosure is Compound 9.

(9)

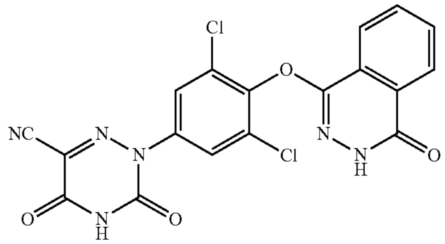

or a pharmaceutically acceptable salt thereof.

In some embodiments, the THRβ agonist of the combination of the present disclosure is a potassium salt of Compound 9.

In some embodiments, the GLP-1R agonist of the combination of the present disclosure is a compound of Formula (I-1):

(I-1)

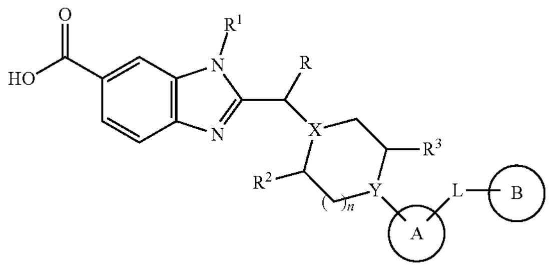

or a pharmaceutically acceptable salt thereof, wherein:

X is N or CH;

Y is N or $CR^4$:

n is 0 or 1;

R is hydrogen;

$R^1$ is $—C_1$-$C_6$ alkylene-$R^5$;

$R^2$ is hydrogen, oxo, or $C_1$-$C_6$ alkyl;

$R^3$ is hydrogen, oxo, or $C_1$-$C_6$ alkyl and $R^4$ is hydrogen, OH, or $C_1$-$C_6$ alkyl; or $R^1$ and $R^4$ are taken together with the carbon atoms to which they are attached to form $C_3$-$C_6$ cycloalkyl optionally substituted by halo or $C_1$-$C_3$ alkyl; $R^5$ is 5-membered heterocyclyl or 5-membered heteroaryl, each of which comprises 1, 2, or 3 heteroatoms independently selected from O, N, and S, wherein at least one heteroatom of $R^5$ is S, and further wherein R is optionally substituted by halo, $—O—C_{1-6}$ alkyl, $C_{1-6}$ alkyl, $C_{1-6}$, alkenyl, or $C_1$-$C_6$ haloalkyl;

Ring A is 5- to 12-membered heterocyclene or 5- to 12-membered heteroarylene, each of which is independently optionally substituted by halo, CN, $C_3$-$C_5$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-, wherein represents the point of attachment to ring A and  represents the point of attachment to ring B;

when L is *—O—$C_1$-$C_6$ alkylene-**, the $C_1$-$C_6$ alkylene of L is optionally substituted by $R^L$, wherein each $R^L$ is independently $C_1$-$C_6$ alkyl or halo, or two $R^L$ are taken together with the carbon atom or atoms to which they are attached to form $C_3$-$C_6$ cycloalkyl or 3- to 6-membered heterocyclyl; and when L is $C_1$-$C_6$ alkylene, the $C_1$-$C_6$ alkylene is optionally substituted by $R^{L1}$, wherein each R is independently halo, OH, oxo, or $C_1$-$C_6$ alkyl, or two $R^L$ are taken together with the carbon atom or atoms to which they are attached to form $C_3$-$C_6$ cycloalkyl or 3- to 6-membered heterocyclyl;

$R^6$ is hydrogen or $C_1$-$C_6$ alkyl; and

Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

In some embodiments, the GLP-1R agonist of the combination of the present disclosure is a compound of Formula (I-1a):

(I-1a)

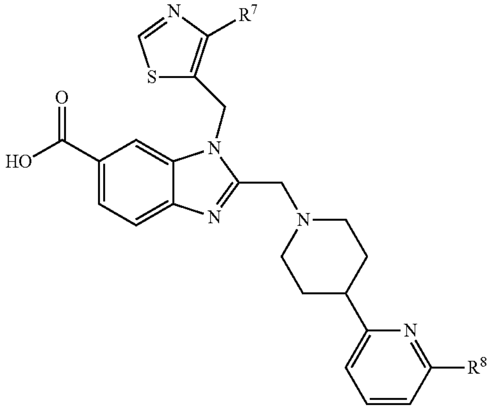

wherein $R^7$ is hydrogen, chloro, bromo, fluoro, methyl, or vinyl; and $R^8$ is

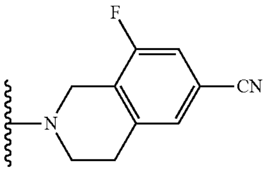
,
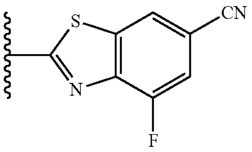
,
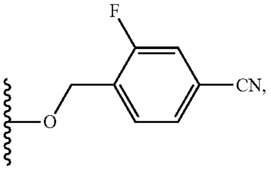
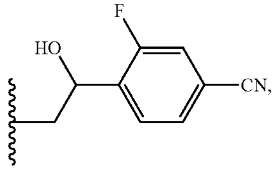
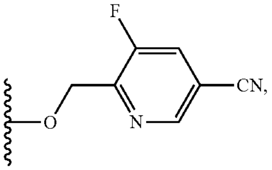
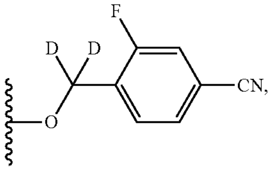
or

-continued

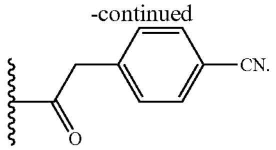

In some embodiments, the GLP-1R agonist is a compound of Formula (I**):

(I**)

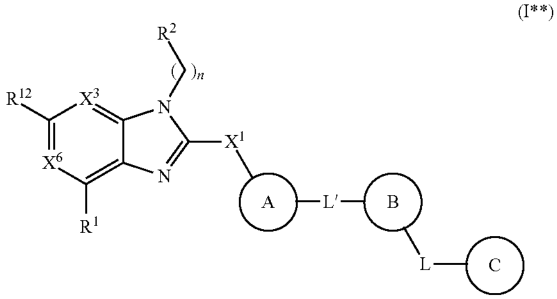

or a pharmaceutically acceptable salt thereof; wherein:

$X^3$ is $CR^6$ or N;

$X^6$ is $CR^4$ or N;

$R^1$ is —$C_{1-6}$ haloalkyl, halogen, —O—$X^4$, or —$NR^8R^9$, or $R^1$ and $R^4$, together with the atoms to which they are attached, combine to form a 5- or 6-membered heterocyclyl;

$X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}$—$CH_3$—($CH_2$—CH(—$OCH_3$)—$CH_2$—O$)_{1-5}$—$CH_3$ $C_{3-10}$ cycloalkyl, or $C_{6-10}$ aryl, wherein the alkyl, alkylene, heteroalkyl, or haloalkyl group is optionally substituted with one or more deuterium, $C_{1-6}$ alkoxy, hydroxyl, —CN, or oxo, and the cycloalkyl, heterocyclyl, or aryl group is optionally substituted with one or more halogen, $C_{1-6}$ alkoxy, or —CN;

$R^6$ is hydrogen, halogen, or —O—$R^7$;

wherein $R^1$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocycyl; wherein the $C_{1-6}$ alkyl is optionally substituted by one or more oxo;

n is 0, 1, 2, 3, 4, 5, or 6;

$R^2$ is:

hydrogen;

$C_{1-6}$ alkyl optionally substituted with deuterium;

$C_{1-6}$ haloalkyl;

—(O)—$C_{1-6}$ alkyl;

—CN;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

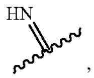, or $C_{1-6}$ alkyl;

a 5-membered heteroaryl, comprising 1 or 2 heteroatoms independently selected from N, and S, wherein at least one heteroatom of $R^5$ is S; or $R^2$ and $R^7$, together with the atoms to which they are attached, combine to form a 5- or 6-membered heterocyclyl;

$R^4$ is halogen, hydrogen, —C(O)OH, or —O—$R^8$, wherein $R^8$ and $R^1$, together with the atoms to which they are attached, combine to form a 6-membered heterocyclyl;

$R^{12}$ is hydrogen, —C(O)OH, —C(O)$NR^{N12}R^{N12'}$, —C(O)$NR^{12}S(O)_2R^{2'}$, —($C_{2-6}$ alkynylene)-C(O)OH, —($C_{1-6}$ alkylene)-C(O)OH, —$NR^{N12}$—($C_{1-6}$ alkylene)-C(O)OH, 5-10 membered heteroaryl or 5- to 10-membered heterocyclyl optionally substituted with one or more oxo, $C_{1-6}$ alkyl or $C_{1-6}$ haloalkyl;

$R^{N12}$ and $R^{N12'}$ independently are H or $C_{1-6}$ alkyl; $X^1$ is

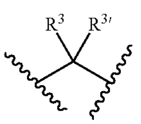 or 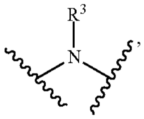, wherein $R^3$ and $R^{3'}$ independently are H, D or $C_{1-6}$ alkyl, wherein the $C_{1-6}$ alkyl is optionally substituted with deuterium;

Ring A is

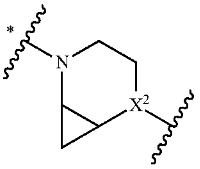

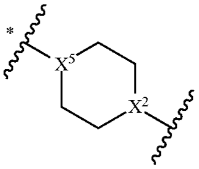,

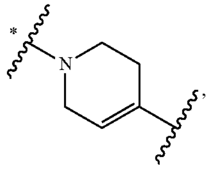, or more halo or $C_{1-6}$ alkyl, or 6-membered heteroarylene optionally substituted with one or more halo or $C_{1-6}$ alkyl;

wherein * indicates attachment to $X^1$, $X^5$ is $CR^3$ or N, and $X^2$ is $CR^3$ or N;

L' is a bond or —O—;

Ring B is a $C_{6-10}$ arylene, a 5-10 membered heteroarylene, or a 3-10 membered heterocyclene, wherein the $C_{6-10}$ arylene, 5-10 membered heteroarylene, or 3-10 membered heterocyclene is optionally substituted with one or more oxo, $C_{1-6}$ alkyl, $C_{1-6}$ alkoxy, or halogen;

L is a bond, *—($C_{1-6}$ alkylene)-, *—$NR^L$—($C_{1-6}$ alkylene)-, *—O—($C_{1-6}$ alkylene)-, or *—($C_{1-6}$ alkylene)-O—, wherein * indicates attachment to Ring B and the $C_{1-6}$ alkylene is optionally substituted with deuterium;

wherein $R^1$ is H or $C_{1-6}$ alkyl; and

Ring C is:

a 6-membered aryl optionally substituted with one or more $C_{3-10}$ cycloalkyl, $C_{1-6}$ alkyl, $C_{1-6}$ haloalkyl, 3-10 membered heterocyclyl, halogen, $C_{1-6}$ alkoxy, $C_{1-6}$ haloalkoxy, —CN, $C_{3-10}$ cycloalkyl, or —C(O)$NR^{2t}$; wherein $R^1$ is H or $C_{1-6}$ alkyl a 6-membered heteroaryl comprising a nitrogen atom optionally substituted with one or more halogen, —CN, $C_{1-6}$ haloalkyl, —O—$C_{1-6}$ alkyl, $C_{3-10}$ cycloalkyl, —C(═O)—($C_{3-10}$ cycloalkyl),

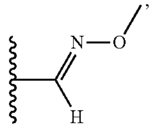, 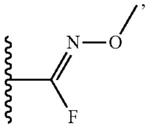, or 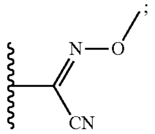;

a bicylic 9- or 10-membered heteroaryl or heterocyclyl optionally substituted with one or more $C_{1-6}$ alkyl, halogen, —CN, or oxo.

In some embodiments, the GLP-1R agonist of the combination of the present disclosure is a compound of Formula (I-5)

(I-5)

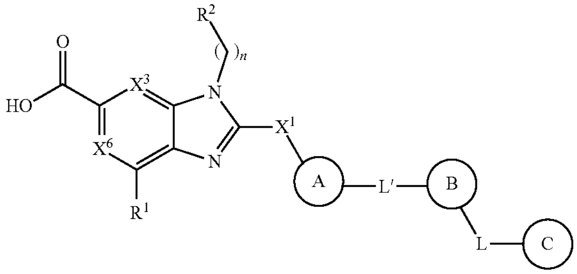

or a pharmaceutically acceptable salt thereof; wherein:

$X^3$ is $CR^6$ or N;

$X^6$ is $CR^4$ or N;

$R^1$ is —$C_{1-6}$ haloalkyl, —O—$X^4$, or —$NR^8R^9$, or $R^1$ and $R^4$, together with the atoms to which they are attached, combine to form a 6-membered heterocyclyl;

$X^4$ is hydrogen, $C_{1-6}$ alkyl, $C_{1-6}$ heteroalkyl, $C_{1-6}$ haloalkyl, —($C_{1-6}$ alkylene)-($C_3$i-o cycloalkyl), or —($C_{1-6}$ alkylene)-(3- to 8-membered heterocyclyl), 3- to 8-membered heterocyclyl, —$(CH_2CH_2—O)_{1-5}$-$CH_3$, or —$(CH_2—CH(—OCH_3)—CH_2—O)_{1-5}$—$CH_3$, wherein the alkyl, heteroalkyl, alkylene, or haloalkyl group is optionally substituted with one or more deuterium, hydroxyl, —CN, or oxo, and the cycloalkyl or heterocyclyl group is optionally substituted with one or more halogen or —CN;

$R^6$ is hydrogen, halogen, or —O—$R^7$;

wherein $R^1$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocyclyl; wherein the $C_{1-6}$ alkyl is optionally substituted by one or more oxo;

n is 0, 1, 2, 3, 4, 5, or 6;

$R^2$ is:

hydrogen;

branched $C_{1-6}$ alkyl;

$C_{1-6}$ haloalkyl;

—(O)—$C_{1-6}$ alkyl;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

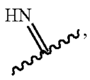, or $C_{1-6}$ alkyl;

a 5-membered heteroaryl, comprising 1 or 2 heteroatoms independently selected from N, and S, wherein at least one heteroatom of $R^5$ is S; or $R^2$ and $R^7$, together with the atoms to which they are attached, combine to form a 5- or 6-membered heterocyclyl;

$R^4$ is hydrogen or —O—$R^8$, wherein $R^8$ and $R^1$, together with the atoms to which they are attached, combine to form a 6-membered heterocyclyl;

$X^1$ is

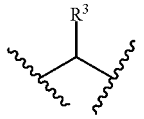 or 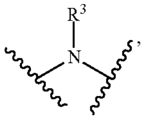, wherein $R^3$ is H or $C_{1-6}$ alkyl;

Ring A is

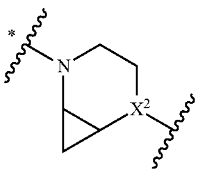 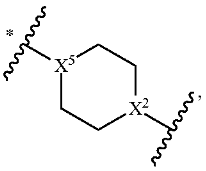, 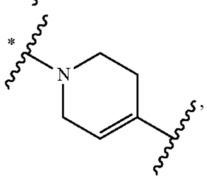, phenylene optionally substituted with one or more halo or $C_{1-6}$ alkyl, or 6-membered heteroarylene optionally substituted with one or more halo or $C_{1-6}$ alkyl;

wherein * indicates attachment to $X^1$, $X^5$ is $CR^3$ or N, and $X^2$ is $CR^3$ or N;

L' is a bond or —O—;

Ring B is a $C_{6-10}$ arylene, a 6-10 membered heteroarylene, or a 3-10 membered heterocyclene, wherein the $C_{6-10}$ arylene, 6-10 heteroarylene, or 3-10 membered heterocyclene is optionally substituted with one or more $C_{1-6}$ alkyl, $C_{1-6}$ alkoxy, or halogen;

L is a bond, *—$CH_2$—, *—O—($C_{1-6}$ alkylene)-, or *—($C_{1-6}$ alkylene)-O—, wherein * indicates attachment to Ring B and the $C_{1-6}$ alkylene is optionally substituted with deuterium; and Ring C is:

a 6-membered aryl optionally substituted with one or more $C_{1-6}$ alkyl, 3-10 membered heterocyclyl, halogen, —$OCH_3$, —CN, or $C_{3-10}$ cycloalkyl;

a 6-membered heteroaryl comprising a nitrogen atom optionally substituted with one or more halogen, —CN, —O—$C_{1-6}$ alkyl, $C_{3-10}$ cycloalkyl,

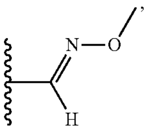, 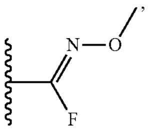, or 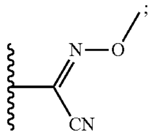;

a bicylic 9- or 10-membered heteroaryl comprising two nitrogen atoms optionally substituted with one or more $C_{1-6}$ alkyl, or oxo.

In some embodiments, the GLP-1R agonist of the combination of the present disclosure is Compound 1-2:

(1-2)

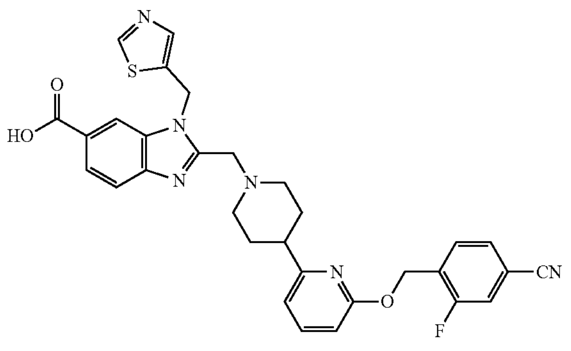

or a pharmaceutically acceptable salt thereof.

In some embodiments, the GLP-1R agonist of the combination of the present disclosure is a meglumine salt of Compound 1-2.

In some embodiments, the THRβ agonist of the combination of the present disclosure is selected from those listed in Tables 6-11.

In some embodiments, the GLP-1R agonist of the combination of the present disclosure is selected from those listed in Tables 1-5.

In some embodiments, the GLP-1R agonist of the combination of the present disclosure is selected from those listed in Table 5A.

In some embodiments, the THRβ agonist of the combination of the present disclosure is compound 9

(9)

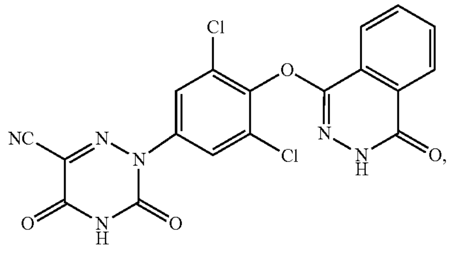

and the GLP-1R agonist is orforglipron, danuglipron, liraglutide, exenatide, dulaglutide, albiglutide, lixisenatide, tirzepatide, or semaglutide, or a pharmaceutically acceptable salt thereof.

In some embodiments, the THRβ agonist of the combination of the present disclosure is compound 9

(9)

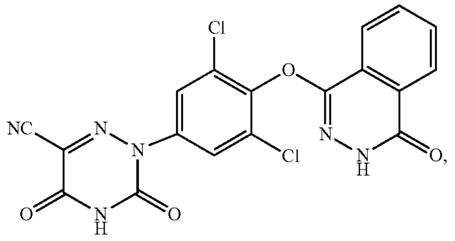

and the GLP-1R agonist is orforglipron, or a pharmaceutically acceptable salt thereof.

In some embodiments, the THRβ agonist of the combination of the present disclosure is resmetirom, VK2809, sobetirome, eprotirome, ALG-055009, CNPT-101101, CNPT-101207, ASC41 or a pharmaceutically acceptable salt thereof and the GLP-1R agonist is compound 1-2

(1-2)

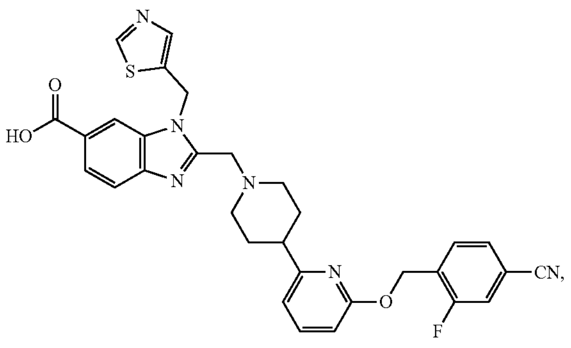

or a pharmaceutically acceptable salt thereof.

In some embodiments, the THRβ agonist of the combination of the present disclosure is compound 9

(9)

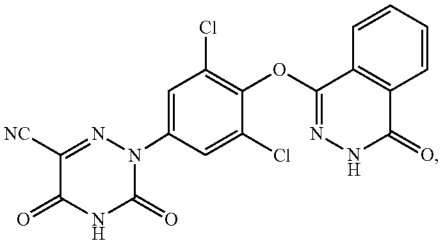

or a pharmaceutically acceptable salt thereof, and the GLP-1R agonist is compound 1-2

(1-2)

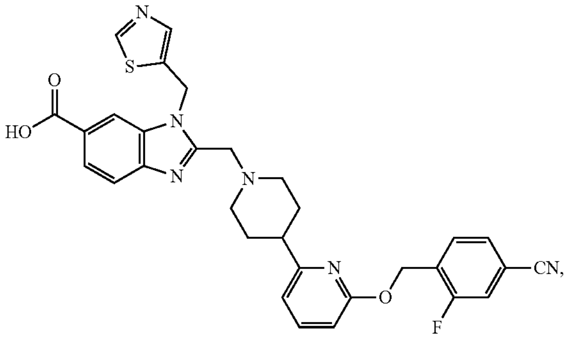

or a pharmaceutically acceptable salt thereof.

In one aspect, the present disclosure is directed to a method of treating a liver disorder or a cardiometabolic disease in a patient in need thereof, comprising administering to the patient a combination disclosed herein.

In one aspect, the present disclosure is directed to a method of treating a liver disorder or a cardiometabolic disease in a patient in need thereof, comprising administering to the patient a therapeutically effective amount of a combination disclosed herein.

In one aspect, the present disclosure is directed to a method of increasing the proportion of lean body mass relative to total body mass in a patient in need thereof, comprising administering to the patient a combination disclosed herein.

In one aspect, the present disclosure is directed to a method of decreasing the proportion of fat mass relative to total body mass in a patient in need thereof, comprising administering to the patient a combination disclosed herein.

In one aspect, the present disclosure is directed to a method of effectuating weight loss in a patient in need thereof, comprising administering to the patient a combination disclosed herein.

In some embodiments, the patient has a Body Mass Index (BMI) of 20 $kg/m^2$ to 25 $kg/m^2$.

In some embodiments, the patient has a BMI of 25 $kg/m^2$ to 30 $kg/m^2$.

In some embodiments, the patient has a BMI of 20 $kg/m^2$ or greater.

In some embodiments, the patient has a BMI of 25 $kg/m^2$ or greater.

In some embodiments, the patient has a BMI of 27 $kg/m^2$ or greater.

In some embodiments, the patient has a BMI or 30 $kg/m^2$ or greater.

In some embodiments, the cardiometabolic disease is obesity.

In some embodiments, the liver disorder is NASH.

In some embodiments, the liver disorder is liver fibrosis.

In some embodiments, the THRβ agonist is administered at substantially the same time as the GLP-1R agonist.

In some embodiments, the THRβ agonist is administered after the GLP-1R agonist.

In some embodiments, the THRβ agonist is administered prior to the GLP-1R agonist.

In some embodiments, the THRβ agonist is selective to THRβ.

DETAILED DESCRIPTION

Definitions

Figure 1:
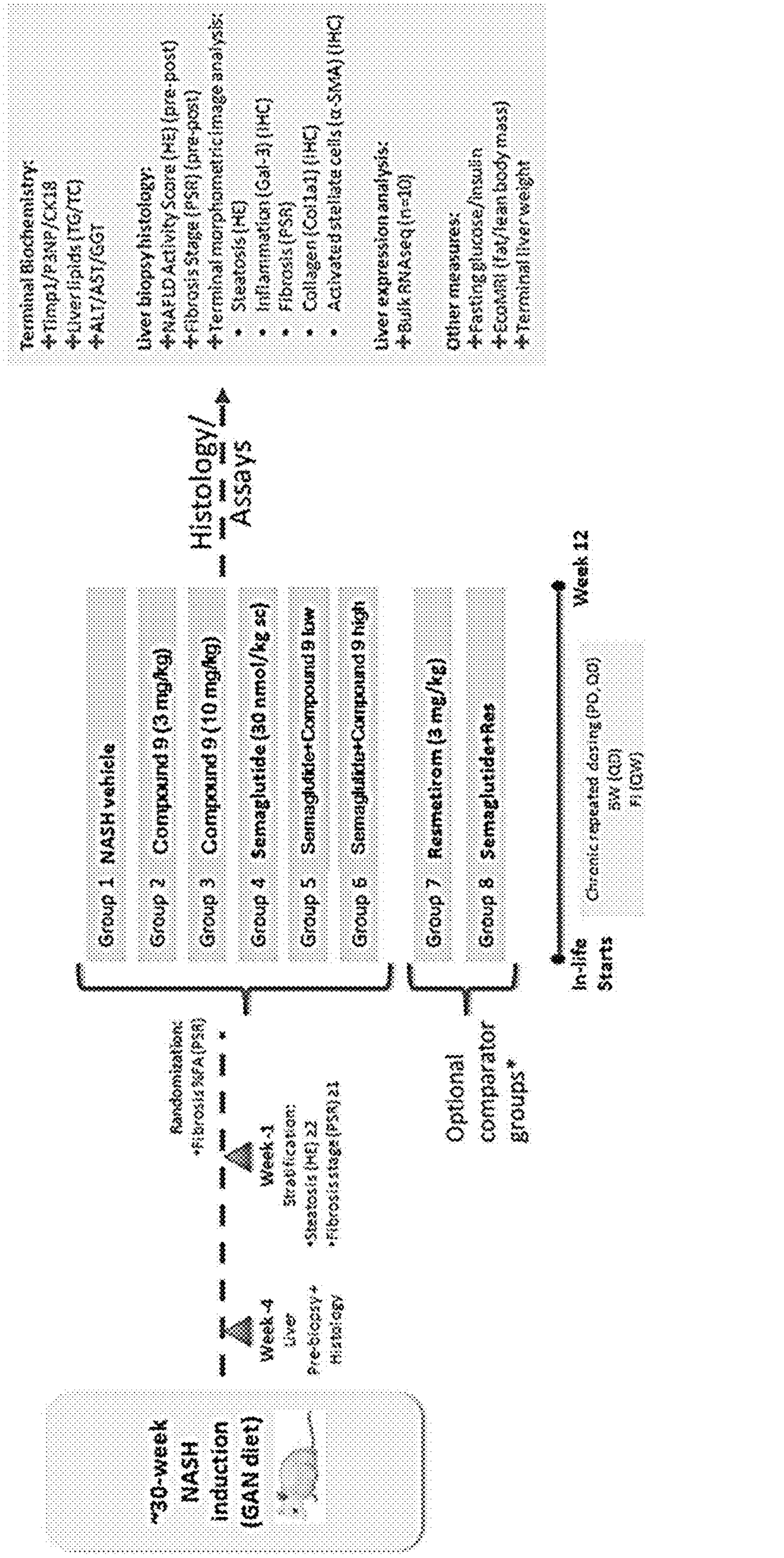
FIG. 1 depicts the study design for usage of a THRβ agonist (Compound 9) and a GLP-1R agonist (semaglutide) in combination to treat NASH.
Figure 2:
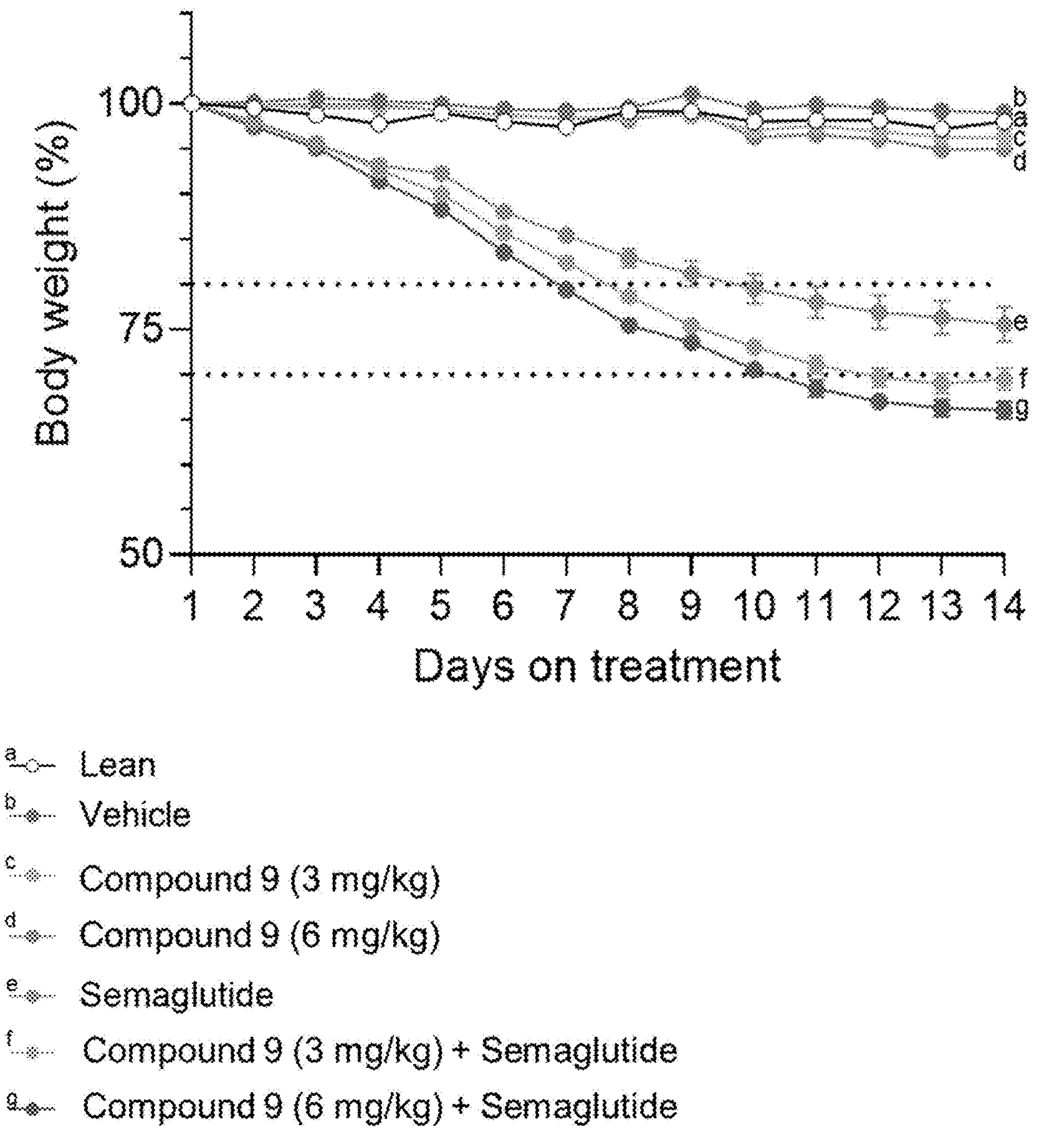
FIG. 2 depicts a graph showing the change from baseline in the body weight (%) of DIO-NASH mice over days of treatment with Compound 9 alone and in combination with semaglutide.

As used herein, the following definitions shall apply unless otherwise indicated. Further, if any term or symbol used herein is not defined as set forth below, it shall have its ordinary meaning in the art.

"Comprising" is intended to mean that the compositions and methods include the recited elements, but not exclude others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of, e.g., other ingredients and substantial method steps recited. Embodiments defined by each of these transition terms are within the scope of this invention.

"Combination therapy" or "combination treatment" (also referred to herein as a combinational therapy) refers to the use of two or more drugs or agents in treatment, e.g., the use of a compound of formula (I-1), (I-1a), (I-2), (I-3), (I-4), (I-5), (I-5a), (I-5b), (I-5c), (I-5d), (I-5e), (I-5f), (I-5 g), (I-5h), (I-5i), (I-5j), (I-5k), (I-51), (I-5m), (I-5n), (I-5o), (I-5p), (IQ), (IR), (IS), (IT), (IU), (IX), (IY), (IZ), (IAA), (IAB), (IAC), (IAD), (IAE), (IAG), (IAH), (IAI), (IAJ), (I**), (I''), (I'''*), (I'''), (I*), (I'), (I), (I-P01), (II**), (II*), (II-1), (II-1a), (II-2), (II-3), (II-4), (II-5), or (II-6) as utilized herein together with another agent (e.g., one useful to treat liver disorders, such as NAFLD, NASH, and symptoms and manifestations of each thereof) is a combination therapy.

Administration in "combination" refers to the administration of two agents (e.g., a compound of formula (I-1), (I-1a), (I-2), (I-3), (I-4), (I-5), (I-5a), (I-5b), (I-5c), (I-5d), (I-5e), (I-5f), (I-5 g), (I-5h), (I-5i), (I-5j), (I-5k), (I-51), (I-5m), (I-5n), (I-5o), (I-5p), (IQ), (IR), (IS), (IT), (IU), (IX), (IY), (IZ), (IAA), (IAB), (IAC), (IAD), (IAE), (IAG), (IAH), (IAI), (IAJ), (I**), (I''), (I'''*), (I'''), (I*), (I'), (I), (I-P01), (II**), (II*), (II-1), (II-a), (II-2), (II-3), (II-4), (II-5), or (II-6) as utilized herein, and another agent) in any manner in which the pharmacological effects of both manifest in the patient at the same time. Thus, administration in combination does not require that a single pharmaceutical composition, the same dosage form, or even the same route of administration be used for administration of both agents or that the two agents be administered at precisely the same time. The agents can be formulated in two separate pharmaceutically acceptable compositions. Both agents can also be formulated in a single pharmaceutically acceptable composition. A non-limiting example of such a single composition is an oral composition or an oral dosage form. For example, and without limitation, it is contemplated that a compound of formula (I-1), (I-1a), (I-2), (I-3), (I-4), (I-5), (I-5a), (I-5b), (I-5c), (I-5d), (I-5e), (I-5f), (I-5 g), (I-5h), (I-5i), (I-5j), (I-5k), (I-51), (I-5m), (I-5n), (I-5o), (I-5p), (IQ), (IR), (IS), (IT), (IU), (IX), (IY), (IZ), (IAA), (IAB), (IAC), (IAD), (IAE), (IAG), (IAH), (IAI), (IAJ), (I**), (I''), (I'''*), (I'''), (I*), (I'), (I), (I-P01), (II**), (II*), (1I-1), (II-Ia), (II-2), (II-3), (II-4), (II-5), or (II-6) can be administered in combination therapy with another agent in accordance with the present invention.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Patient" refers to mammals and includes humans and non-human mammals. Examples of patients include, but are not limited to mice, rats, hamsters, guinea pigs, pigs, rabbits, cats, dogs, goats, sheep, cows, and humans. In some embodiments, patient refers to a human.

"Patient's response" as used herein refers to magnitude of treatment efficacy (e.g., amount of weight loss, percentage of fat loss, etc.). Improving a "patient's response" to a treatment can include, but are not limited to, increasing the magnitude of efficacy of the treatment (e.g. increasing weight loss, increasing fat loss, etc.). In some embodiments, improving a patient's response to a treatment (e.g. the combinations and methods of the present disclosure) comprises maintaining the efficacy while decreasing side effects.

"Pharmaceutically acceptable" refers to safe and non-toxic, preferably for in vivo, more preferably, for human administration.

"Pharmaceutically acceptable salt" refers to a salt that is pharmaceutically acceptable. A compound described herein may be administered as a pharmaceutically acceptable salt.

"Salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary and non-limiting cations useful in pharmaceutically acceptable salts include Na, K, Rb, Cs, $NH_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, fumarate, maleate, acetate, propionate, succinate, tartrate, chloride, sulfate, bisulfate, mono-, di-, and tribasic phosphate, mesylate, tosylate, and the likes.

"Therapeutically effective amount" or dose of a compound or a composition refers to that amount of the compound or the composition that results in reduction or inhibition of symptoms or a prolongation of survival in a patient. The results may require multiple doses of the compound or the composition.

"Treatment" or "treating" refers to an approach for obtaining beneficial or desired results including clinical results. For purposes of this invention, beneficial or desired results include, but are not limited to, one or more of the following: decreasing one or more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delaying or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient. Also encompassed by "treatment" is a reduction of pathological consequence of the disease or disorder. The methods of the invention contemplate any one or more of these aspects of treatment.

As used herein, "delaying" development of a disease means to defer, hinder, slow, retard, stabilize and/or postpone development of the disease and/or slowing the progression or altering the underlying disease process and/or course once it has developed. This delay can be of varying lengths of time, depending on the history of the disease and/or subject being treated. As is evident to one skilled in the art, a sufficient or significant delay can, in effect, encompass prevention, in that the subject does not develop clinical symptoms associated with the disease. A method that "delays" development of a disease is a method that reduces probability of disease development in a given time frame and/or reduces extent of the disease in a given time frame, when compared to not using the method, including stabilizing one or more symptoms resulting from the disease.

A subject who is "at risk" of developing a disease may or may not have detectable disease, and may or may not have displayed detectable disease prior to the treatment methods described herein. "At risk" denotes that a subject has one or more so-called risk factors, which are measurable parameters that correlate with development of a disease. A subject having one or more of these risk factors has a higher probability of developing the disease than a subject without these risk factor(s). These risk factors include, but are not limited to, age, sex, race, diet, history of previous disease, presence of precursor disease and genetic (i.e., hereditary) considerations. Compounds may, in some embodiments, be administered to a subject (including a human) who is at risk or has a family history of the disease or condition.

"Stereoisomer" or "stereoisomers" refer to compounds that differ in the stereogenicity of the constituent atoms such as, without limitation, in the chirality of one or more stereocenters or related to the cis or trans configuration of a carbon-carbon or carbon-nitrogen double bond. Stereoisomers include enantiomers and diastereomers.

"Alkyl" refers to monovalent saturated aliphatic hydrocarbyl groups having from 1 to 12 carbon atoms, from 1 to 10 carbon atoms, or from 1 to 6 carbon atoms. This term includes, by way of example, linear and branched hydrocarbyl groups such as methyl ($CH_3$—), ethyl ($CHCH_2$—), n-propyl ($CH_3CH_2CH_2$—), isopropyl ($(CH_3)_2CH$—), n-butyl ($CH_3CH_2CH_2CH_2$—), isobutyl ($(CH_3)_2CHCH_2$—), sec-butyl ($(CH_3)(CH_3CH_2)CH$—), t-butyl ($(CH_3)_3C$—), n-pentyl ($CH_3CH_2CH_2CH_2CH_2$—), and neopentyl ($(CH_3)_3CCH_2$—). $C_x$ alkyl refers to an alkyl group having x number of carbon atoms.

"Alkylene" refers to a divalent saturated aliphatic hydrocarbyl group having from 1 to 12 carbon atoms, for example from 1 to 10 carbon atoms, and from 1 to 6 carbon atoms. This term includes, by way of example, linear and branched hydrocarbyl groups such as methylene (—$CH_2$—), ethylene (—$CH_2CH_2$— or —CH(Me)-), propylene (—$CH_2CH_2CH_2$— or —CH(Me)$CH_2$—, or —CH(Et)-) and the like.

"Alkenyl" refers to straight or branched monovalent hydrocarbyl groups having from 2 to 6 carbon atoms, for example 2 to 4 carbon atoms and having at least 1, or from 1 to 2 sites of vinyl (>C═C<) unsaturation. Such groups are exemplified, for example, by vinyl, allyl, and but-3-en-1-yl. Included within this term are the cis and trans isomers or mixtures of these isomers. $C_x$ alkenyl refers to an alkenyl group having x number of carbon atoms.

"Alkynyl" refers to straight or branched monovalent hydrocarbyl groups having from 2 to 6 carbon atoms, for example 2 to 3 carbon atoms and having at least 1 or from 1 to 2 sites of acetylenic (—C≡C—) unsaturation. Examples of such alkynyl groups include acetylenyl (—C≡CH), and propargyl (—$CH_2$C≡CH). $C_x$ alkynyl refers to an alkynyl group having x number of carbon atoms.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Aryl" refers to a monovalent aromatic carbocyclic group of from 6 to 14 carbon atoms having a single ring (e.g., phenyl (Ph)) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Examplary aryl groups include phenyl and naphthyl. A divalent aryl group is referred to herein as "arylene." A divalent phenyl group is referred to herein as "phenylene".

"Cyano" refers to the group —C≡N.

"Cycloalkyl" refers to saturated or unsaturated but non-aromatic cyclic alkyl groups of, for example, from 3 to 10 carbon atoms, from 3 to 8 carbon atoms, or from 3 to 6 carbon atoms, having single or multiple cyclic rings including fused, bridged, and spiro ring systems. $C_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Halo" or "halogen" refers to fluoro, chloro, bromo and iodo and in some embodiments is fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Exemplary heteroaryls include 5 or 6 membered heteroaryls such as pyridinyl, pyrrolyl, thiophenyl, and furanyl. Other exemplary heteroaryls include 9 or 10 membered heteroaryls, such as indolyl, quinolinyl, quinolonyl, isoquinolinyl, and isoquinolonyl. A divalent heteroaryl group is referred to herein as "heteroarylene."

"Heterocycle" or "heterocyclic" or "heterocycloalkyl" or "heterocyclyl" refers to a saturated or partially saturated, but not aromatic, group having from 1 to 10 ring carbon atoms, from 1 to 8 carbon atoms, and from 1 to 6 carbon atoms, from 1 to 4 ring heteroatoms, from 1 to 3 heteroatoms, and from 1 to 2 heteroatoms selected from the group consisting of nitrogen, sulfur, or oxygen. $C_x$ heterocycloalkyl refers to a heterocycloalkyl group having x number of ring atoms including the ring heteroatoms. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties. A divalent heterocyclyl group is referred to herein as "heterocyclene."

Examples of heterocyclyl and heteroaryl include, but are not limited to, azetidinyl, pyrrolyl, imidazolyl, pyrazolyl, pyridyl, pyrazyl, pyrimidyl, pyridazyl, indolizyl, isoindolyl, indolyl, dihydroindolyl, indazolyl, purinyl, quinolizinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, isoxazolyl, phenoxazinyl, phenothiazinyl, imidazolidinyl, imidazolinyl, piperidinyl, piperazinyl, indolinyl, phthalimidyl, 1,2,3,4-tetrahydroisoquinolinyl, 4,5,6,7-tetrahydrobenzo[b]thiophenyl, thiazolyl, thiazolidinyl, thiophenyl, benzo[b]thiophenyl, morpholinyl, thiomorpholinyl (also referred to as thiamorpholinyl), 1,1-dioxothiomorpholinyl, piperidinyl, pyrrolidinyl, and tetrahydrofuranyl.

"Oxo" refers to the atom (═O) or (O).

The terms "optional" or "optionally" as used throughout the specification means that the subsequently described event or circumstance may but need not occur, and that the description includes instances where the event or circumstance occurs and instances in which it does not. For example, "the nitrogen atom is optionally oxidized to provide for the N-oxide (N→O) moiety" means that the nitrogen atom may but need not be oxidized, and the description includes situations where the nitrogen atom is not oxidized and situations where the nitrogen atom is oxidized.

The dosage amount of a compound as described herein is determined based on the free acid or free base of a compound, as appropriate.

Provided herein are compositions and methods for treating obesity and/or related comorbidities. The methods comprise administering to the patient a glucagon-like peptide-1 receptors (GLP-1R) agonist and a thyroid hormone receptor beta (THRβ) agonist, as described herein. In some embodiments, provided herein is a method of treating a cardiometabolic disease in a subject (e.g., a human patient) in need thereof, comprising administering to the subject a therapeutically effective amount of a compound described herein, or a pharmaceutically acceptable salt thereof.

GLP-JR Agonists

Suitable GLP-1R agonists that can be used in accordance with the combinations and/or methods described herein include, but are not limited to orforglipron, danuglipron, liraglutide, exenatide, dulaglutide, albiglutide, lixisenatide, tirzepatide, orforglipron, or semaglutide, or a pharmaceutically acceptable salt of the GLP-1R agonist, or a pharmaceutically acceptable solvates of either the GLP-1R agonist or the salt of the GLP-1R agonist. Suitable GLP-1R agonists that can be used in accordance with the combinations and/or methods described herein also include danuglipron tromethamine, SAL-0112, exenatide biobetter, E-2HSA, ECC-5004, dapiglutide, HDM-1002, AZD-9550, BGM-0504, VK2735, AMG-133, HL-08, HZ-010, exenatide SR, DD-01, CT-388, CT-868, CT-996, GL-0034, GMA-105, GMA-106, GLP-06, SCO-094, CagriSema, amycretin (e.g., oral amycretin), ZT-002, DR-10624, DR-10627, retatrutide, NN-6177, NN-9490, NN-9847, NN-9904, efocipegtrutide, GSBR-1290, HB-1085, 4P-004, HM15211, survodutide, froniglutide, efinopegdutide, PF-06954522, YH-25724, YN-012, YN-015, mazdutide, MDR-001, KN-056, MWN-101, emvidutide ALT-801, AP-026, PEG-loxenatide, PEGylated exenatide, ITCA 650, XW-004, XW-014, or efpeglenatide, or a pharmaceutically acceptable salt of the GLP-1R agonist, or a pharmaceutically acceptable solvates of either the GLP-1R agonist or the salt of the GLP-1R agonist.

Suitable GLP-1R agonists that can be used in accordance with the combinations and/or methods described herein are also described in, e.g., PCT Pub. Nos. WO/2023/049518, WO/2022/040600, WO/2023/076237, WO/2023/164050, PCT Application Nos. PCT/US2022/047687, PCT/US2023/013700, PCT/US2024/022311, or U.S. Provisional Application No. 63/492,895, incorporated herein by reference.

In some embodiments, the GLP-1R agonist is a compound of Formula (I-1)

(I-1)

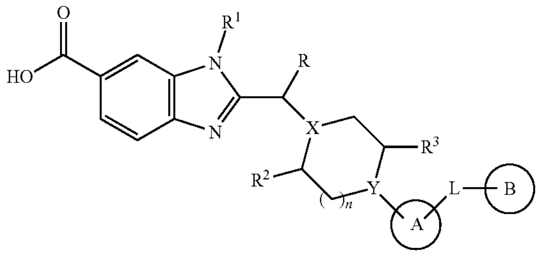

or a pharmaceutically acceptable salt thereof, wherein:

X is N or CH;

Y is N or $CR^4$;

n is 0 or 1;

R is hydrogen;

$R^1$ is —$C_1$-$C_6$ alkylene-$R^5$;

$R^2$ is hydrogen, oxo, or $C_1$-$C_6$ alkyl;

$R^3$ is hydrogen, oxo, or $C_1$-$C_6$ alkyl and $R^4$ is hydrogen, OH, or $C_1$-$C_6$ alkyl;

or $R^3$ and $R^4$ are taken together with the carbon atoms to which they are attached to form $C_3$-$C_6$ cycloalkyl optionally substituted by halo or $C_1$-$C_3$ alkyl;

$R^5$ is 5-membered heterocyclyl or 5-membered heteroaryl, each of which comprises 1, 2, or 3 heteroatoms independently selected from O, N, and S, wherein at least one heteroatom of $R^5$ is S, and further wherein $R^5$ is optionally substituted by halo, —O—$C_{1-6}$ alkyl, $C_{1-6}$ alkyl, $C_{1-6}$ alkenyl, or $C_1$-$C_6$ haloalkyl;

Ring A is 5- to 12-membered heterocyclene or 5- to 12-membered heteroarylene, each of which is independently optionally substituted by halo, CN, $C_3$-$C_6$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-, wherein represents the point of attachment to ring A and  represents the point of attachment to ring B;

when L is *—O—$C_1$-$C_6$ alkylene-**, the $C_1$-$C_6$ alkylene of L is optionally substituted by $R^L$, wherein each $R^L$ is independently $C_1$-$C_6$ alkyl or halo, or two $R^L$ are taken together with the carbon atom or atoms to which they are attached to form $C_3$-$C_6$ cycloalkyl or 3- to 6-membered heterocyclyl; and when L is $C_1$-$C_6$ alkylene, the $C_1$-$C_6$ alkylene is optionally substituted by $R^{L1}$, wherein each $R^{L1}$ is independently halo, OH, oxo, or $C_1$-$C_6$ alkyl, or two $R^L$ are taken together with the carbon atom or atoms to which they are attached to form $C_3$-$C_6$ cycloalkyl or 3- to 6-membered heterocyclyl;

$R^6$ is hydrogen or $C_1$-$C_6$ alkyl; and

Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

In some embodiments, the GLP-1R agonist is a compound of Formula (I-1a)

(I-1a)

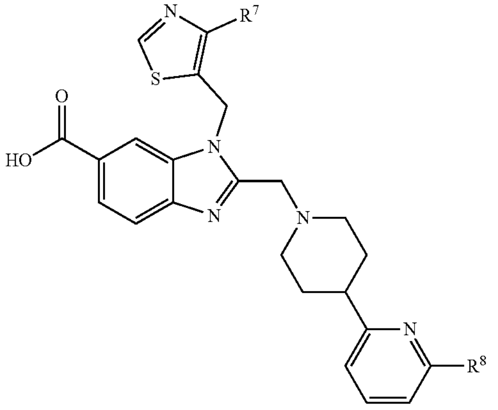

wherein $R^7$ is hydrogen, chloro, bromo, fluoro, methyl, or vinyl; and $R^8$ is

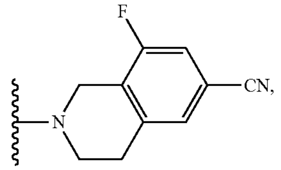

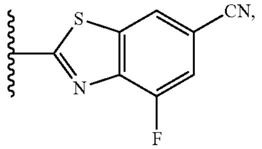

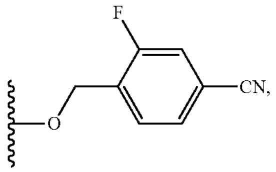

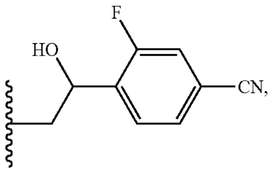

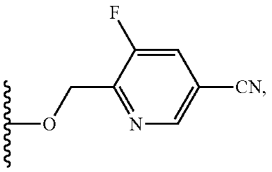

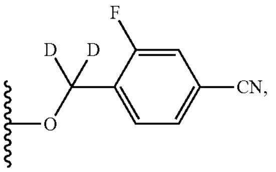

or

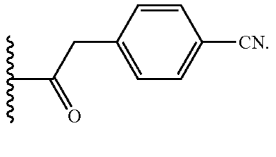

In some embodiments, the GLP-1R agonist is a compound of Formula (I-2)

(I-2)

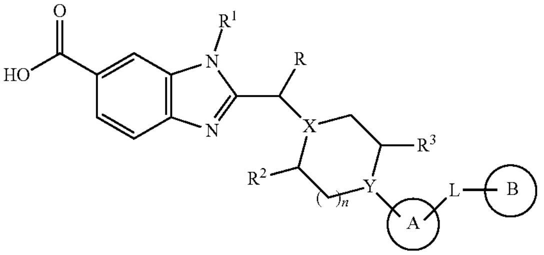

or a stereoisomer, tautomer, or a pharmaceutically acceptable salt of any of the foregoing, wherein:

X is N or CH;

Y is N or $CR^4$, wherein $R^4$ is hydrogen, OH or $C_1$-$C_6$ alkyl;

n is 0 or 1;

R is hydrogen;

$R^1$ is —$C_1$-$C_6$ alkylene-R, wherein R is 3- to 6-membered heterocyclyl or 5- to 6-membered heteroaryl, each of which is independently optionally substituted by $C_1$-$C_6$ alkyl, or $R^1$ is taken together with R and the intervening atoms to form a Ring C, wherein Ring C is a 5- to 7-membered heterocyclyl optionally substituted by $C_1$-$C_6$ alkyl;

$R^2$ and $R^3$ are independently hydrogen, oxo, or $C_1$-$C_6$ alkyl, wherein when Y is $CR^4$, $R^3$ and $R^4$ are optionally taken together with the carbon atoms to which they are attached to form $C_3$-$C_6$ cycloalkyl;

Ring A is 5- to 12-membered heterocyclene or 5- to 12-membered heteroarylene, each of which is independently optionally substituted by halo, CN, $C_3$-$C_6$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein

* represents the point of attachment to ring A and ** represents the point of attachment to ring B, when L is *—O—$C_1$-$C_6$ alkylene-**, the $C_1$-$C_6$ alkylene is optionally substituted by $R^L$, wherein;

each $R^1$ is independently $C_1$-$C_6$ alkyl or halo, or two $R^L$ are taken together with the carbon atom or atoms to which they are attached to form $C_3$-$C_6$ cycloalkyl or 3- to 6-membered heterocyclyl, when L is $C_1$-$C_6$ alkylene, the C, —$C_6$ alkylene is optionally substituted by $R^{L1}$, wherein:

each $R^{L1}$ is independently halo, OH, or $C_1$-$C_6$ alkyl; or two $R^{L1}$ are taken together with the carbon atom or atoms to which they are attached to form $C_3$-$C_6$ cycloalkyl or 3- to 6-membered heterocyclyl; and $R^6$ is hydrogen or $C_1$-$C_6$ alkyl; and Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl, with the proviso that when $R^1$ is —$C_1$-$C_6$ alkylene-$R^5$, wherein $R^5$ is 3- to 6-membered heterocyclyl or 3- to 6-membered heteroaryl, each of which is optionally substituted by $C_1$-$C_6$ alkyl, Y is N or CH, n is 1, $R^2$ and $R^3$ are independently hydrogen or $C_1$-$C_6$ alkyl, ring A is 6-membered heteroaryl optionally substituted one or two substituents each independently selected from the group consisting of F, Cl and CN, and L is *—$OCH_2$—**, then ring B is not phenyl optionally substituted by one or two substituents each independently selected from the group consisting of halo, CN, and $C_1$-$C_6$ alkyl;

when $R^1$ is —$C_1$-$C_6$ alkylene-$R^5$, wherein $R^5$ is 3- to 6-membered heterocyclyl or 3- to 6-membered heteroaryl, each of which is optionally substituted by $C_1$-$C_6$ alkyl, Y is N or CH, n is 1, $R^2$ and $R^3$ are independently hydrogen or $C_1$-$C_6$ alkyl, ring A is

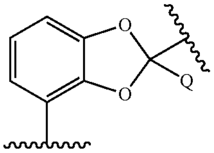
, wherein Q is H or $CH_3$, and L is a bond, then ring B is neither phenyl or pyridinyl, each of which is optionally substituted by one or two substituents each independently selected from the group consisting of halo, CN, and $C_1$-$C_6$ alkyl; and when $R^1$ is —$C_1$-$C_6$ alkylene-$R^5$, wherein R is 4-membered heterocyclyl or 5-membered heteroaryl, each of which is optionally substituted by $C_1$-$C_6$ alkyl, X is N, Y is N or CH, n is 1, and $R^2$ and $R^3$ are independently hydrogen or oxo, then ring B is not

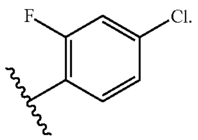 [SMILES: *c1ccc(Cl)cc1F]

In some such embodiments of Formula (I-2), Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl, —$COCH_3$, —$CONH_2$, —$S(O)_2CH_3$, and phenyl. In some such embodiments of Formula (I-2), when L is *—O—$C_1$-$C_6$ alkylene-**, the $C_1$-$C_6$ alkylene is optionally substituted by $R^L$, wherein each $R^L$ is independently $C_1$-$C_6$ alkyl, or two $R^L$ are taken together with the carbon atom or atoms to which they are attached to form $C_3$-$C_6$ cycloalkyl or 3- to 6-membered heterocyclyl. In some such embodiments of Formula (I-2), when L is $C_1$-$C_6$ alkylene, the $C_1$-$C_6$ alkylene is unsubstituted.

In some embodiments, the GLP-1R agonist is a compound of Formula (I-3)

(I-3)

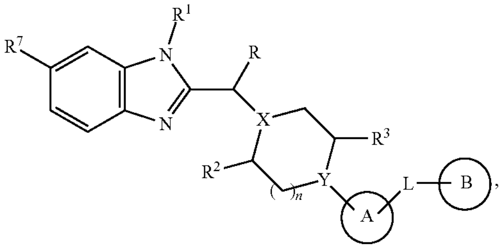

or a pharmaceutically acceptable salt thereof, wherein:

X is N or CH;

Y is N or $CR^4$;

n is 0 or 1;

R is hydrogen;

$R^1$ is —$C_1$-$C_6$ alkylene-$R^3$;

$R^2$ is hydrogen, oxo, or $C_1$-$C_6$ alkyl;

$R^3$ is hydrogen, oxo, or $C_1$-$C_6$ alkyl and $R^4$ is hydrogen, OH or $C_1$-$C_6$ alkyl, or $R^3$ and $R^4$ are taken together with the carbon atoms to which they are attached to form $C_3$-$C_6$ cycloalkyl optionally substituted by halo or $C_1$-$C_3$ alkyl;

R is 3- to 6-membered heterocyclyl or 5- to 6-membered heteroaryl, wherein the 3- to 6-membered heterocyclyl or 5- to 6-membered heteroaryl of $R^5$ is independently optionally substituted by halo, $C_1$-$C_6$ alkyl, $C_1$-$C_6$ alkoxy, $C_1$-$C_6$ alkenyl, or $C_1$-$C_6$ haloalkyl;

$R^7$ is selected from the group consisting of

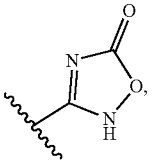
,
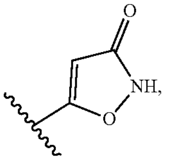
,
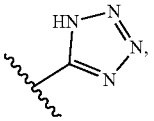
,
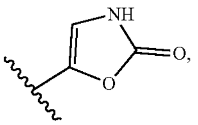
,
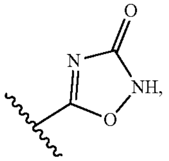
,
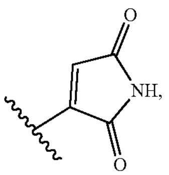
and
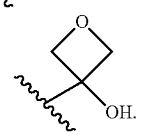
.

or $R^7$ is —C(O)NH—$R^8$, wherein $R^8$ is hydrogen, —OH, —$S(O)_2$—$C_1$-$C_6$ alkyl, or —$C_1$-$C_6$ alkyl optionally substituted by halo;

Ring A is 5- to 12-membered heterocyclene, 5- to 12-membered heteroarylene, or $C_6$-$C_{14}$ arylene, each of which is independently optionally substituted by halo, oxo, —CN, $C_3$-$C_6$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein:

* represents the point of attachment to ring A and ** represents the point of attachment to ring B; when L is

*—O—$C_1$-$C_6$ alkylene-**, the $C_1$-$C_6$ alkylene is optionally substituted by $R^L$, wherein each $R^L$ is independently C, —$C_6$ alkyl or halo, or two $R^L$ are taken together with the carbon atom or atoms to which they are attached to form $C_3$-$C_6$ cycloalkyl or 3- to 6-membered heterocyclyl; and when L is $C_1$-$C_6$ alkylene, the $C_1$-$C_6$ alkylene is optionally substituted by $R^{L1}$, wherein each $R^{L1}$ is independently halo, OH, oxo, or $C_1$-$C_6$ alkyl, or two $R^{L1}$ are taken together with the carbon atom or atoms to which they are attached to form $C_3$-$C_6$ cycloalkyl or 3- to 6-membered heterocyclyl;

$R^6$ is hydrogen or $C_1$-$C_6$ alkyl; and

Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl, $C_1$-$C_6$ haloalkyl, —C(O)$CH_3$, —C(O)$NH_2$, —S(O)$_2$$CH_3$, cyclopropyl, and phenyl, with the proviso that: when $R^7$ is —C(O)NH—$R^8$, $R^1$ is

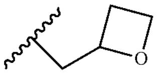

,

X is N, Y is CH, n is 1, $R^2$ and $R^3$ are each hydrogen, ring A is 6-membered heteroaryl, and L is *—$OCH_2$—**, then ring B is not

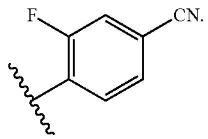 [SMILES: *c1ccc(C#N)cc1F]

.

In some embodiments, the GLP-1R agonist is a compound of Formula (I-4)

(I-4)

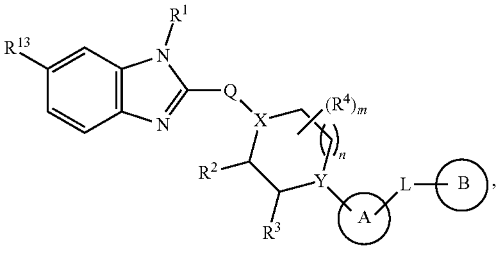

, or a pharmaceutically acceptable salt, wherein:

$R^{13}$ is —C(O)OH or H

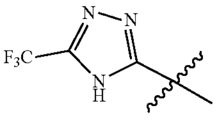

;

X is N or $CR^x$, wherein $R^x$ is hydrogen, OH or $C_1$-$C_6$ alkyl;

Y is N or $CR^y$, wherein $R^y$ is hydrogen, OH or $C_1$-$C_6$ alkyl;

n is 0 or 1;

Q is selected from the group consisting of —C($R^7$)($R^8$)—, —O—, —N($R^9$)—, and —S—, wherein $R^7$ and $R^8$ are independently hydrogen, halogen, or $C_1$-$C_6$ alkyl; and $R^9$ is hydrogen or $C_1$-$C_6$ alkyl;

$R^1$ is optionally substituted —$C_1$-$C_6$ alkyl or —$C_1$-$C_6$ alkylene-R, wherein $R^1$ is $C_3$-$C_6$ cycloalkyl, 3-to 6-membered heterocyclyl, or 5- to 6-membered heteroaryl, each of which is independently optionally substituted by one to three substituents independently selected from the group consisting of halo, oxo, CN, $C_1$-$C_6$ alkyl, $C_3$-$C_6$ cycloalkyl, and —O$C_1$-$C_6$ alkyl, wherein each $C_1$-$C_6$ alkyl, $C_3$-$C_6$ cycloalkyl, and —O$C_1$-$C_6$ alkyl substituent is independently optionally substituted by halo or CN;

$R^2$ and $R^3$ are taken together with the carbon atoms to which they are attached to form an optionally substituted $C_3$-$C_4$ cycloalkyl ring; or $R^2$ and $R^x$, when present, are taken together with the carbon atoms to which they are attached to form an optionally substituted $C_3$-$C_5$ cycloalkyl ring, and $R^3$ is hydrogen, oxo, or $C_1$-$C_6$ alkyl;

m is 0, 1, 2, or 3;

$R^4$ is oxo or $C_1$-$C_6$ alkyl;

Ring A is $C_6$-$C_1$4 arylene, 5- to 12-membered heterocyclene or 5- to 12-membered heteroarylene, each of which is independently optionally substituted by halo, OH, CN, $C_3$-$C_6$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein * represents the point of attachment to ring A and ** represents the point of attachment to ring B, and wherein:

when L is $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, L is optionally substituted by one to three $R^L$ substituents, wherein each $R^L$ is independently halo, OH, or $C_1$-$C_6$ alkyl; or two $R^L$ are taken together with the carbon atom or atoms to which they are attached to form $C_3$-$C_6$ cycloalkyl or 3- to 6-membered heterocyclyl;

$R^6$, when present, is hydrogen or $C_1$-$C_6$ alkyl; and

Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl optionally substituted by halo or CN, —O$C_1$-$C_6$ alkyl optionally substituted by halo or CN, —$COCH_3$, —$CONH_2$, —S(O)$_2$$CH_3$, and phenyl optionally substituted by halo or CN.

In some embodiments, the GLP-1R agonist is a compound of Formula (I**):

(I**)

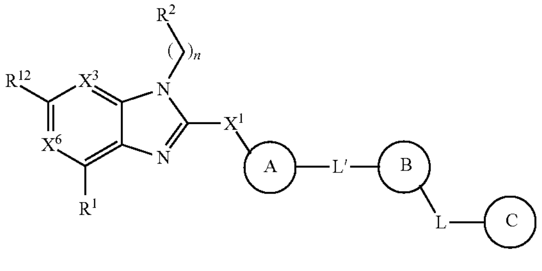

or a pharmaceutically acceptable salt thereof, wherein:

$X^3$ is $CR^6$ or N;

$X^6$ is $CR^4$ or N;

$R^1$ is —$C_{1-6}$ haloalkyl, halogen, —O—$X^4$, or —$NR^8R^9$, or $R^1$ and $R^4$, together with the atoms to which they are attached, combine to form a 5- or 6-membered heterocyclyl;

$X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —($CH_2CH_2$—O)$_{1-5}$-$CH_3$, —($CH_2$—CH(—$OCH_3$)—$CH_2$—O)$_{1-5}$—$CH_3$, $C_{3-10}$ cycloalkyl, or $C_{6-10}$ aryl, wherein the alkyl, heteroalkyl, alkylene, or haloalkyl group is optionally substituted with one or more deuterium, $C_{1-6}$ alkoxy, hydroxyl, —CN, or oxo, and the cycloalkyl, heterocyclyl, or aryl group is optionally substituted with one or more halogen, $C_{1-6}$ alkoxy, or —CN;

$R^6$ is hydrogen, halogen, or —O-$R^7$;

wherein $R^1$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocycyl; wherein the $C_{1-6}$ alkyl is optionally substituted by one or more oxo; n is 0, 1, 2, 3, 4, 5, or 6;

$R^2$ is:

hydrogen;

$C_{1-6}$ alkyl optionally substituted with deuterium;

$C_{1-6}$ haloalkyl, (O)—$C_{1-6}$ alkyl;

—CN;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

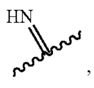, or $C_{1-6}$ alkyl;

a 5-membered heteroaryl, comprising 1 or 2 heteroatoms independently selected from N, and S, wherein at least one heteroatom of $R^3$ is S; or $R^2$ and $R^7$, together with the atoms to which they are attached, combine to form a 5- or 6-membered heterocyclyl;

$R^4$ is halogen, hydrogen, —C(O)OH, or —O—$R^8$, wherein $R^8$ and $R^1$, together with the atoms to which they are attached, combine to form a 6-membered heterocyclyl;

$R^{12}$ is hydrogen, —C(O)OH, —C(O)$NR^{N12}R^{N12}$—C(O)$NR^{12}S(O)_2R^2$, —($C_{2-6}$ alkynylene)-C(O)OH, —($C_{1-6}$ alkylene)-C(O)OH, —$NR^{N12}$—($C_{1-6}$ alkylene)-C(O)OH, 5-10 membered heteroaryl or 5- to 10-membered heterocyclyl optionally substituted with one or more oxo, $C_{1-6}$ alkyl or $C_{1-6}$ haloalkyl;

$R^{N12}$ and $R^{N12}$ independently are H or $C_{1-6}$ alkyl;

$X^1$ is

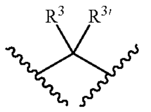 or 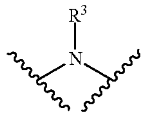, wherein $R^3$ and $R^{3'}$ independently are H, D or $C_{1-6}$ alkyl, wherein the $C_{1-6}$ alkyl is optionally substituted with detuerium;

Ring A is

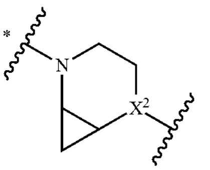 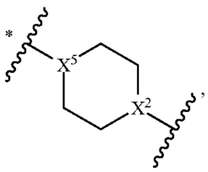, 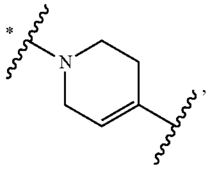, phenylene optionally substituted with one or more halo or $C_{1-6}$ alkyl, or 6-membered heteroarylene optionally substituted with one or more halo or $C_{1-6}$ alkyl;

wherein * indicates attachment to $X^1$, $X^1$ is $CR^3$ or N, and $X^2$ is $CR^3$ or N;

L' is a bond or —O—;

Ring B is a $C_{6-10}$ arylene, a 5-10 membered heteroarylene, or a 3-10 membered heterocycylene, wherein the $C_{6-10}$ arylene, 5-10 membered heteroarylene, or 3-10 membered heterocyclene is optionally substituted with one or more oxo, $C_{1-6}$ alkyl, $C_{1-6}$ alkoxy, or halogen;

L is a bond, *—($C_{1-6}$ alkylene)-, *—$NR^L$—($C_{1-6}$ alkylene)-, *—O—($C_{1-6}$ alkylene)-, or *—($C_{1-6}$ alkylene)-O—, wherein * indicates attachment to Ring B and the $C_{1-6}$ alkylene is optionally substituted with deuterium;

wherein $R^L$ is H or $C_{1-6}$ alkyl; and

Ring C is:

a 6-membered aryl optionally substituted with one or more $C_{3-10}$ cycloalkyl, $C_{1-6}$ alkyl, $C_{1-6}$ haloalkyl, 3-10 membered heterocyclyl, halogen, $C_{1-6}$ alkoxy, $C_{1-6}$ haloalkoxy, —CN, $C_{3-10}$ cycloalkyl, or —C(O)$NR^{2'}$; wherein $R^1$ is H or $C_{1-6}$ alkyl a 6-membered heteroaryl comprising a nitrogen atom optionally substituted with one or more halogen, —CN, $C_{1-6}$ haloalkyl, —O—$C_{1-6}$ alkyl, $C_{3-10}$ cycloalkyl, —C(═O)—($C_{3-10}$ cycloalkyl),

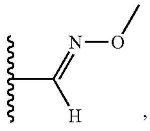
,
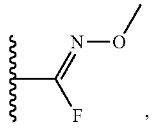
, or
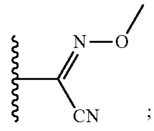
;

a bicylic 9- or 10-membered heteroaryl or heterocyclyl optionally substituted with one or more $C_{1-6}$ alkyl, halogen, —CN, or oxo.

In some embodiments, the GLP-1R agonist is a compound of Formula (I**):

(I**)

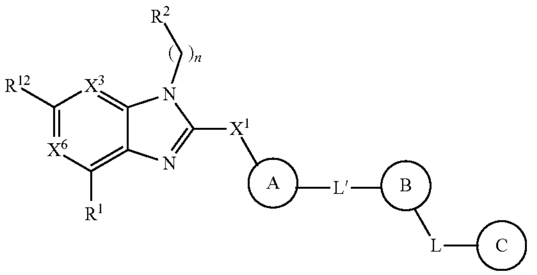

or a pharmaceutically acceptable salt thereof; wherein:

$X^3$ is $CR^6$ or N;

$X^6$ is $CR^4$ or N;

$R^1$ is —$C_{1-6}$ haloalkyl, halogen, —O—$X^4$, or —$NR^8R^9$, or $R^1$ and $R^4$, together with the atoms to which they are attached, combine to form a 6-membered heterocyclyl;

$X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}$-$CH_3$, or —$(CH_2—CH(—OCH_3)—CH_2—O)_{1-5}—CH_3$, wherein the alkyl, heteroalkyl, alkylene, or haloalkyl group is optionally substituted with one or more deuterium, $C_{1-6}$ alkoxy, hydroxyl, —CN, or oxo, and the cycloalkyl or heterocyclyl group is optionally substituted with one or more halogen or —CN;

$R^6$ is hydrogen, halogen, or —O—$R^7$;

wherein $R^7$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^1$ and $R^9$, together with the atoms to which they are attached, combine to form a 6-membered heterocyclyl; wherein the $C_{1-6}$ alkyl is optionally substituted by one or more oxo;

n is 0, 1, 2, 3, 4, 5, or 6;

$R^2$ is:

hydrogen;

$C_{1-6}$ alkyl optionally substituted with deuterium;

$C_{1-6}$ haloalkyl;

—(O)—$C_{1-6}$ alkyl;

—CN;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

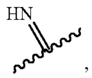
, or $C_{1-6}$ alkyl;

a 5-membered heteroaryl, comprising 1 or 2 heteroatoms independently selected from N, and S, wherein at least one heteroatom of $R^5$ is S; or $R^2$ and $R^7$, together with the atoms to which they are attached, combine to form a 5- or 6-membered heterocyclyl;

$R^4$ is hydrogen, —C(O)OH, or —O—$R^8$, wherein $R^8$ and $R^1$, together with the atoms to which they are attached, combine to form a 6-membered heterocyclyl;

$R^{12}$ is hydrogen, —C(O)OH or 5-10 membered heteroaryl optionally substituted with one or more oxo, $C_{1-6}$ alkyl or $C_{1-6}$ haloalkyl;

$X^1$ is

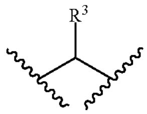
or
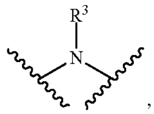
, wherein $R^3$ is H or $C_{1-6}$ alkyl;

Ring A is

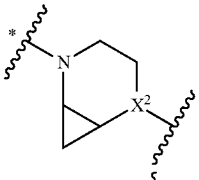
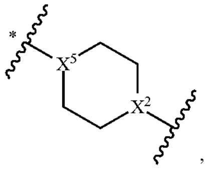
,
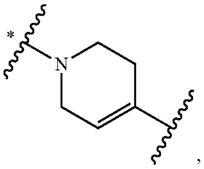
, phenylene optionally substituted with one or more halo or $C_{1-6}$ alkyl, or 6-membered heteroaryl optionally substituted with one or more halo or $C_{1-6}$ alkyl;

wherein * indicates attachment to $X^1$, $X^5$ is $CR^3$ or N, and $X^2$ is $CR^3$ or N;

L' is a bond or —O—;

Ring B is a $C_{6-10}$ arylene, a 5-10 membered heteroarylene, or a 3-10 membered heterocyclene, wherein the $C_{6-10}$ arylene, 5-10 membered heteroarylene, or 3-10 membered heterocyclene is optionally substituted with one or more oxo, $C_{1-6}$ alkyl, $C_{1-6}$ alkoxy, or halogen;

L is a bond, *—($C_{1-6}$ alkylene)-, *—$NR^L$—($C_{1-6}$ alkylene)-, *—O—($C_{1-6}$ alkylene)-, or *—($C_{1-6}$ alkylene)-O—, wherein * indicates attachment to Ring B and the $C_{1-6}$ alkylene is optionally substituted with deuterium;

wherein $R^L$ is H or $C_{1-6}$ alkyl; and

Ring C is:

a 6-membered aryl optionally substituted with one or more $C_{1-6}$ alkyl, $C_{1-6}$ haloalkyl, 3-10 membered heterocyclyl, halogen, $C_{1-6}$ alkoxy, $C_{1-6}$ haloalkoxy, —CN, $C_{3-10}$ cycloalkyl, or —C(O)$NR^{2'}$;

wherein $R^1$ is H or $C_{1-6}$ alkyl a 6-membered heteroaryl comprising a nitrogen atom optionally substituted with one or more halogen, —CN, $C_{1-6}$ haloalkyl, —O—$C_{1-6}$ alkyl, $C_3$—,o cycloalkyl, —C(=O)—($C_{3-10}$ cycloalkyl),

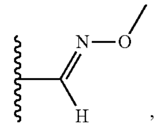
,
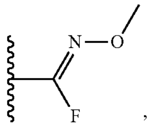
, or
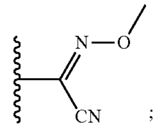
;

a bicylic 9- or 10-membered heteroaryl optionally substituted with one or more $C_{1-6}$ alkyl, halogen, or oxo.

In some embodiments, the GLP-1R agonist is a compound of Formula I*:

(I*)

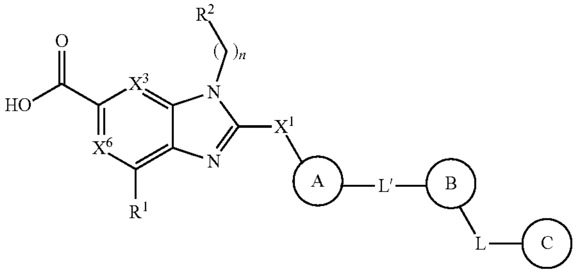

or a pharmaceutically acceptable salt thereof; wherein:

$X^3$ is $CR^6$ or N;

$X^6$ is $CR^4$ or N;

$R^1$ is —$C_{1-6}$ haloalkyl, —O—$X^4$, or —$NR^8R^9$, or $R^1$ and $R^4$, together with the atoms to which they are attached, combine to form a 6-membered heterocyclyl;

$X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}$—$CH_3$, or —$(CH_2—CH(—OCH_3)—CH_2—O)_{1-5}$—$CH_3$, wherein the alkyl, heteroalkyl, alkylene, or haloalkyl group is optionally substituted with one or more deuterium, hydroxyl, —CN, or oxo, and the cycloalkyl or heterocyclyl group is optionally substituted with one or more halogen or —CN;

$R^6$ is hydrogen, halogen, or —O—$R^7$;

wherein $R^7$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocycyl; wherein the $C_{1-6}$ alkyl is optionally substituted by one or more oxo;

n is 0, 1, 2, 3, 4, 5, or 6;

$R^1$ is:

hydrogen;

$C_{1-6}$ alkyl;

$C_{1-6}$ haloalkyl;

—(O)—$C_{1-6}$ alkyl;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

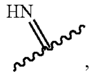
, or $C_{1-6}$ alkyl;

a 5-membered heteroaryl, comprising 1 or 2 heteroatoms independently selected from N, and S, wherein at least one heteroatom of $R^5$ is S; or $R^2$ and $R^7$, together with the atoms to which they are attached, combine to form a 5- or 6-membered heterocyclyl;

$R^4$ is hydrogen or —O—$R^8$, wherein $R^8$ and $R^1$, together with the atoms to which they are attached, combine to form a 6-membered heterocyclyl;

$X^1$ is

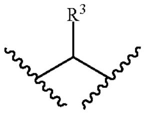
or
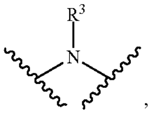
, wherein $R^3$ is H or $C_{1-6}$ alkyl;

Ring A is

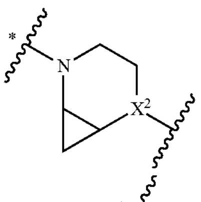
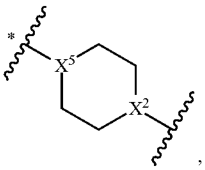
,
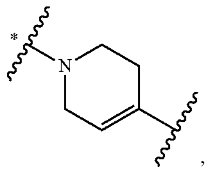
, phenylene optionally substituted with one or more halo or $C_{1-6}$ alkyl, or 6-membered heteroarylene optionally substituted with one or more halo or $C_{1-6}$ alkyl;

wherein * indicates attachment to $X^1$, $X^5$ is $CR^3$ or N, and $X^2$ is $CR^3$ or N;

L' is a bond or —O—;

Ring B is a $C_{6}$—,o arylene, a 6-10 membered heteroarylene, or a 3-10 membered heterocycylene, wherein the $C_{6-10}$ arylene, 6-10 heteroarylene, or 3-10 membered heterocyclene is optionally substituted with one or more $C_{1-6}$ alkyl, $C_{1-6}$ alkoxy, or halogen;

L is a bond, *—$CH_2$—, *—O—($C_{1-6}$ alkylene)-, or *—($C_{1-6}$ alkylene)-O—, wherein * indicates attachment to Ring B and the $C_{1-6}$ alkylene is optionally substituted with deuterium; and Ring C is:

a 6-membered aryl optionally substituted with one or more $C_{1-6}$ alkyl, 3-10 membered heterocyclyl, halogen, —$OCH_3$, —CN, or $C_{3-10}$ cycloalkyl;

a 6-membered heteroaryl comprising a nitrogen atom optionally substituted with one or more halogen, —CN, —O—$C_{1-6}$ alkyl, $C_{3-10}$ cycloalkyl, —C(═O)—($C_{3-10}$ cycloalkyl),

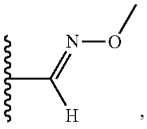 , 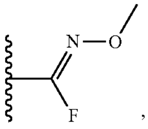 , or 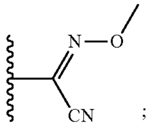 ;

a bicylic 9- or 10-membered heteroaryl comprising two nitrogen atoms optionally substituted with one or more $C_{1-6}$ alkyl, or oxo.

In some embodiments, the compound of Formula (I*) is of Formula (I'):

(I')

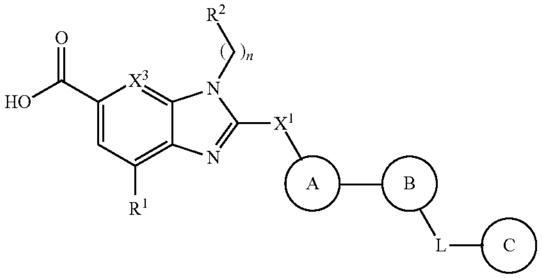

or a pharmaceutically acceptable salt thereof; wherein:

$X^3$ is CH or N;

$R^1$ is —$C_{1-6}$ haloalkyl or —O—$X^4$;

wherein $X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), —($C_{1-6}$ alkylene)-(3- to 8-membered heterocyclyl), 3- to 8-membered heterocyclyl, —($CH_2CH_2$—O)$_{1-5}$—$CH_3$, or —($CH_2$—CH(—OCR)—$CH_2$—O)$_{1-5}$—$CH_3$, wherein the alkyl, heteroalkyl, alkylene, or haloalkyl group is optionally substituted with one or more —CN, and the cycloalkyl or heterocyclyl group is optionally substituted with one or more halogen or —CN;

n is 0, 1, 2, 3, 4, 5, or 6;

$R^2$ is hydrogen;

—(O)—$C_{1-6}$ alkyl;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

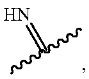 , or $C_{1-6}$ alkyl; or a 5-membered heteroaryl, comprising 1 or 2 heteroatoms independently selected from N, and S, wherein at least one heteroatom of $R^5$ is S;

$X^1$ is

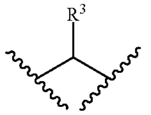 or 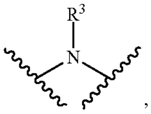 , wherein $R^3$ is H or $C_{1-6}$ alkyl;

Ring A is

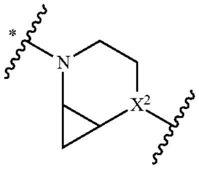 or 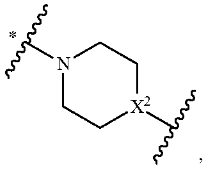 , wherein * indicates attachment to $X^1$, and wherein $X^2$ is CH or N;

Ring B is a 6-10 membered heteroarylene, or a 3-10 membered heterocycylene optionally substituted with one or more $C_{1-6}$ alkyl;

L is a bond or *—O—($C_{1-6}$ alkylene)-, wherein * indicates attachment to Ring B;

Ring C is:

a 6-membered aryl optionally substituted with one or more halogen, —$OCH_3$, —CN, or $C_{3-10}$ cycloalkyl;

a 6-membered heteroaryl comprising a nitrogen atom optionally substituted with one or more halogen, —CN, —O—$C_{1-6}$ alkyl, $C_{3-10}$ cycloalkyl, —C(═O)—($C_{3-10}$ cycloalkyl),

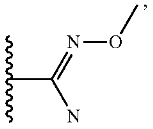 , 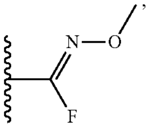 , or 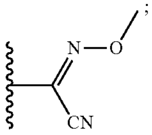 ;

a bicylic 9- or 10-membered heteroaryl comprising two nitrogen atoms optionally substituted with one or more $C_{1-6}$ alkyl, or oxo.

In some embodiments, the GLP-1R agonist is a compound of Formula I":

(I'')

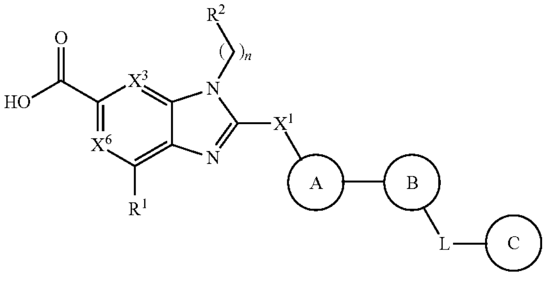

or a pharmaceutically acceptable salt thereof; wherein:

$X^3$ is $CR^6$ or N;

$X^6$ is $CR^4$ or N;

$R^1$ is —$C_{1-6}$ haloalkyl, —O—$X^4$, or —$NR^8R^9$, or $R^1$ and $R^4$, together with the atoms to which they are attached, combine to form a 6-membered heterocyclyl;

wherein $X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}$—$CH_3$, or —$(CH_2—CH(—OCH_3)—CH_2—O)_{1-5}$—$CH_3$, wherein the alkyl, heteroalkyl, alkylene, or haloalkyl group is optionally substituted with one or more deuterium, hydroxyl, —CN, or oxo, and the cycloalkyl or heterocyclyl group is optionally substituted with one or more halogen or —CN;

$R^6$ is hydrogen, halogen, or —O—$R^7$;

wherein $R^7$ and $R^2$, together with the atoms to which they are attached, combine to form a 5- or 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocycyl; wherein the $C_{1-6}$ alkyl is optionally substituted by one or more oxo;

n is 0, 1, 2, 3, 4, 5, or 6;

$R^1$ is:

hydrogen;

$C_{1-6}$ alkyl;

—(O)—$C_{1-6}$ alkyl;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

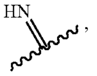

or $C_{1-6}$ alkyl;

a 5-membered heteroaryl, comprising 1 or 2 heteroatoms independently selected from N, and S, wherein at least one heteroatom of $R^5$ is S; or $R^2$ and $R^7$, together with the atoms to which they are attached, combine to form a $C_{2-9}$ heterocyclyl;

$R^4$ is hydrogen or —O—$R^8$, wherein $R^8$ and $R^1$, together with the atoms to which they are attached, combine to form a 6-membered heterocyclyl;

$X^1$ is

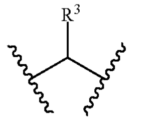

or

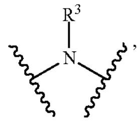

wherein $R^3$ is H or $C_{1-6}$ alkyl;

Ring A is

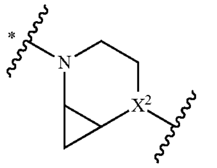

or

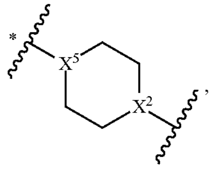

wherein * indicates attachment to $X^1$, $X^5$ is CH or N, and $X^2$ is CH or N, Ring B is a 6-10 membered heteroarylene, or a 3-10 membered heterocycylene optionally substituted with one or more $C_{1-6}$ alkyl;

L is a bond or *—O—($C_{1-6}$ alkylene)-, wherein * indicates attachment to Ring B; and Ring C is:

a 6-membered aryl optionally substituted with one or more halogen, —$OCH_3$, —CN, or $C_{3-10}$ cycloalkyl;

a 6-membered heteroaryl comprising a nitrogen atom optionally substituted with one or more halogen, —CN, —O—$C_{1-6}$ alkyl, $C_{3-10}$ cycloalkyl, —C(=O)—($C_{3-10}$ cycloalkyl),

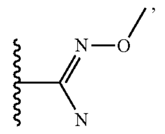

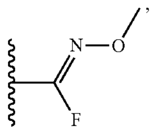

or

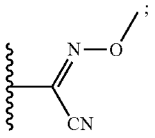

or a bicylic 9- or 10-membered heteroaryl comprising two nitrogen atoms optionally substituted with one or more $C_{1-6}$ alkyl, or oxo.

In some embodiments, the GLP-1R agonist is a compound of Formula (I'''*):

(I'''*)

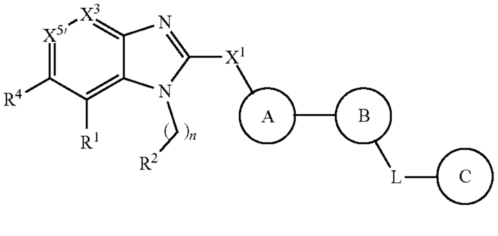

or a pharmaceutically acceptable salt thereof; wherein:

$X^3$ is CR or N;

wherein $R^{X3}$ is H, halogen, $C_{1-6}$ alkyl, $C_{1-6}$ haloalkoxy, —O—$(CH_2CH_2—O)_{1-5}—CH_3$, or $C_{1-6}$ alkoxy;

$X^{5'}$ is $CR^{5'}$ $R^1$ is —$C_{1-6}$ haloalkyl or —O—$X^4$, or $R^1$ and $R^4$, together with the atoms to which they are attached, combine to form a 6-membered heterocyclyl;

wherein $X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}$—$CH_3$, or —$(CH_2—CH(—OCH_3)—CH_2—O)_{1-5}$-$CH_3$, wherein the alkyl, heteroalkyl, alkylene, or haloalkyl group is optionally substituted with one or more deuterium, halogen, or —CN, and the cycloalkyl or heterocyclyl group is optionally substituted with one or more halogen or —CN;

n is 0, 1, 2, 3, 4, 5, or 6;

$R^2$ is:

hydrogen;

halogen;

branched $C_{3-6}$ alkyl;

—(O)—$C_{1-6}$ alkyl;

$C_{3-10}$ cycloalkyl optionally substituted with one or more —CN, $C_{1-6}$ haloalkyl, or $C_{1-6}$ alkyl optionally substituted with one or more —CN;

4 or 5-membered heterocyclyl comprising at least one oxygen or at least one sulfur atom, wherein the 4- or 5-membered heterocyclyl is optionally substituted with one or more oxo,

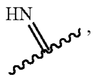, or $C_{1-6}$ alkyl;

5-membered heteroaryl, comprising 1 or 2 heteroatoms independently selected from N, and S, wherein at least one heteroatom of $R^5$ is S; or $R^2$ and $R^1$, together with the atoms to which they are attached, combine to form a 6-membered heterocyclyl;

$R^{5'}$ is hydrogen or —C(O)—OH;

$R^4$ is hydrogen, halogen, —C(O)—OH, or —O—$R^8$, wherein $R^8$ and $R^1$, together with the atoms to which they are attached, combine to form a 6-membered heterocyclyl;

$X^1$ is

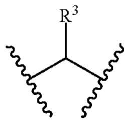

or

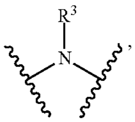, wherein $R^3$ is H or $C_{1-6}$ alkyl;

Ring A is

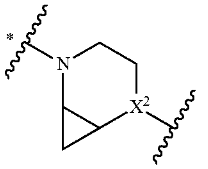

or

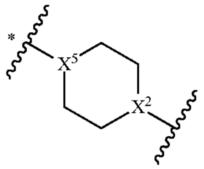, wherein * indicates attachment to $X^1$, wherein $X^5$ is CH or N, and $X^2$ is CH or N;

Ring B is a 6-10 membered heteroarylene, or a 3-10 membered heterocycylene optionally substituted with one or more $C_{1-6}$ alkyl;

L is a bond or *—O—($C_{1-6}$ alkylene)-, wherein * indicates attachment to Ring B;

Ring C is:

a 6-membered aryl optionally substituted with one or more halogen, —$OCH_3$, —CN, or $C_{3-10}$ cycloalkyl;

a 6-membered heteroaryl comprising a nitrogen atom optionally substituted with one or more halogen, —CN, —O—$C_{1-6}$ alkyl, $C_{3-10}$ cycloalkyl, —C(=O)—($C_{3-10}$ cycloalkyl),

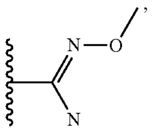,

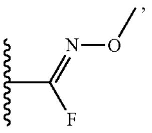, or

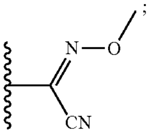;

a bicylic 9- or 10-membered heteroaryl comprising two nitrogen atoms optionally substituted with one or more $C_{1-6}$ alkyl, or oxo.

In some embodiments, the GLP-1R agonist is a compound of Formula (I''')

(I''')

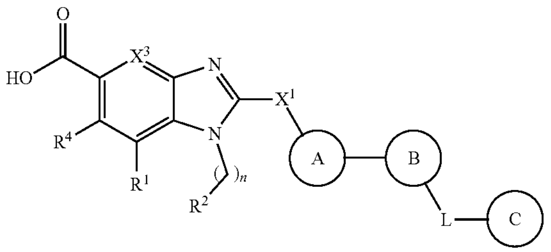

or a pharmaceutically acceptable salt thereof; wherein:

$X^3$ is $CR^{X3}$ or N;

wherein $R^{X3}$ is H, halogen, $C_{1-6}$ alkyl, $C_{1-6}$ haloalkoxy, or $C_{1-6}$ alkoxy;

$R^1$ is —$C_{1-6}$ haloalkyl or —O—$X^4$, or $R^1$ and $R^4$, together with the atoms to which they are attached, combine to form a 6-membered heterocyclyl;

wherein $X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or -($C_{1-6}$ alkylene)-(3- to 8-membered heterocyclyl), 3- to 8-membered heterocyclyl, —$(CH_2CH_2—O)_{1-5}$-—$CH_3$, or —$(CH_2—CH(—OCH_3)—CH_2—O)_{1-5}$—$CH_3$, wherein the alkyl, heteroalkyl, alkylene, or haloalkyl group is optionally substituted with one or more deuterium, —CN, and the cycloalkyl or heterocyclyl group is optionally substituted with one or more halogen or —CN;

n is 0, 1, 2, 3, 4, 5, or 6;

$R^2$ is:

hydrogen;

halogen;

$C_{3-6}$ alkyl;

—(O)—$C_{1-6}$ alkyl;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

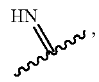, or $C_{1-6}$ alkyl;

a 5-membered heteroaryl, comprising 1 or 2 heteroatoms independently selected from N, and S, wherein at least one heteroatom of $R^5$ is S; or $R^2$ and $R^1$, together with the atoms to which they are attached, combine to form a 6-membered heterocyclyl;

$R^4$ is hydrogen or —O—$R^8$, wherein $R^8$ and $R^1$, together with the atoms to which they are attached, combine to form a 6-membered heterocyclyl;

$X^1$ is

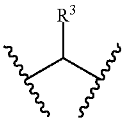

or

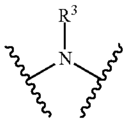, wherein $R^3$ is H or $C_{1-6}$ alkyl;

Ring A is

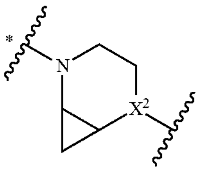

or

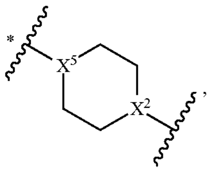, wherein * indicates attachment to $X^1$, wherein $X^5$ is CH or N, and $X^2$ is CH or N;

Ring B is a 6-10 membered heteroarylene, or a 3-10 membered heterocycylene optionally substituted with one or more $C_{1-6}$ alkyl;

L is a bond or *—O—($C_{1-6}$ alkylene)-, wherein * indicates attachment to Ring B;

Ring C is:

a 6-membered aryl optionally substituted with one or more halogen, —OCH, —CN, or $C_{3-10}$ cycloalkyl;

a 6-membered heteroaryl comprising a nitrogen atom optionally substituted with one or more halogen, —CN, —O—$C_{1-6}$ alkyl, $C_{3-10}$ cycloalkyl, —C(═O)—($C_{3-10}$ cycloalkyl),

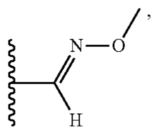,

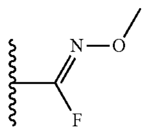, or

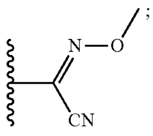;

a bicylic 9- or 10-membered heteroaryl comprising two nitrogen atoms optionally substituted with one or more $C_{1-6}$ alkyl, or oxo.

In some embodiments of Formula (I'''), or a pharmaceutically acceptable salt thereof, $X^3$ is CH or N;

$R^1$ is —$C_{1-6}$ haloalkyl or —O—$X^4$, or $R^1$ and $R^4$, together with the atoms to which they are attached, combine to form a 6-membered heterocyclyl;

wherein $X^1$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}$—$CH_3$, or —$(CH_2—CH(—OCH_3)—CH_2—O)_{1-5}$—$CH_3$, wherein the alkyl, heteroalkyl, alkylene, or haloalkyl group is optionally substituted with one or more deuterium, —CN, and the cycloalkyl or heterocyclyl group is optionally substituted with one or more halogen or —CN;

n is 0, 1, 2, 3, 4, 5, or 6;

$R^2$ is:

hydrogen;

$C_{3-6}$ alkyl;

—(O)—$C_{1-6}$ alkyl;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

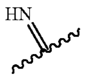, or $C_{1-6}$ alkyl;

a 5-membered heteroaryl, comprising 1 or 2 heteroatoms independently selected from N, and S, wherein at least one heteroatom of $R^5$ is S; or $R^2$ and $R^1$, together with the atoms to which they are attached, combine to form a 6-membered heterocyclyl;

$R^4$ is hydrogen or —O—$R^8$, wherein $R^8$ and $R^1$, together with the atoms to which they are attached, combine to form a 6-membered heterocyclyl;

$X^1$ is

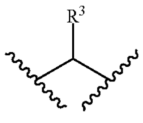

or

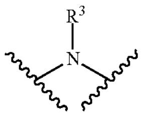, wherein $R^3$ is H or $C_{1-6}$ alkyl;

Ring A is

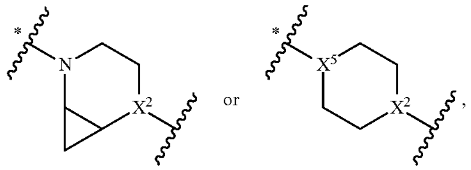

wherein * indicates attachment to $X^1$, wherein $X^1$ is CH or N, and $X^2$ is CH or N;

Ring B is a 6-10 membered heteroarylene, or a 3-10 membered heterocyclylene optionally substituted with one or more $C_{1-6}$ alkyl;

L is a bond or *—O—($C_{1-6}$ alkylene)-, wherein * indicates attachment to Ring B;

Ring C is:

a 6-membered aryl optionally substituted with one or more halogen, —OC-1, —CN, or $C_{3-10}$ cycloalkyl;

a 6-membered heteroaryl comprising a nitrogen atom optionally substituted with one or more halogen, —CN, —O—$C_{1-6}$ alkyl, $C_{3-10}$ cycloalkyl, —C(═O)—($C_{3-10}$ cycloalkyl),

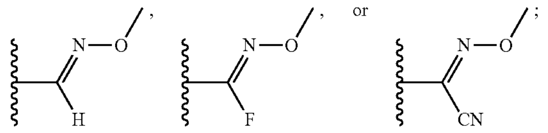

a bicyclic 9- or 10-membered heteroaryl comprising two nitrogen atoms optionally substituted with one or more $C_{1-6}$ alkyl, or oxo.

In some embodiments, the compound of Formula (I''') is of Formula (I):

(I)

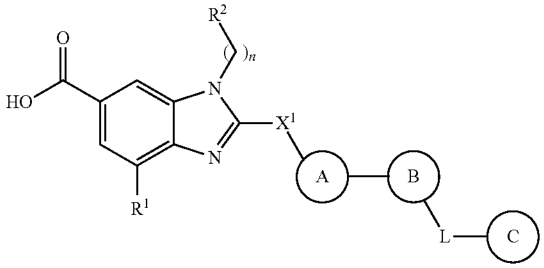

or a pharmaceutically acceptable salt thereof; wherein $R^1$ is —$C_{1-6}$ haloalkyl or —O—$X^4$;

wherein $X^4$ is $C_{1-6}$ alkyl, $C_{1-6}$ heteroalkyl, $C_{1-6}$ haloalkyl, —($C_{1-6}$ alkylene)-($C_{3-10}$ cycloalkyl), or -($C_{1-6}$ alkylene)-(3- to 8-membered heterocyclyl), —(—$CH_2CH_2$—O)$_{1-5}$—$CH_3$, or —($CH_2$—CH(—$OCH_3$)—$CH_2$—O)$_{1-5}$—$CH_3$, wherein the alkyl, heteroalkyl, alkylene, or haloalkyl group is optionally substituted with one or more —CN, and the cycloalkyl or heterocyclyl group is optionally substituted with one or more halogen or —CN;

n is 0, 1, 2, 3, 4, 5, or 6;

$R^2$ is:

hydrogen;

—(O)—$C_{1-6}$ alkyl;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

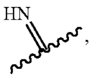

or $C_{1-6}$ alkyl; or a 5-membered heteroaryl, comprising 1 or 2 heteroatoms independently selected from N, and S, wherein at least one heteroatom of $R^5$ is S;

$X^1$ is

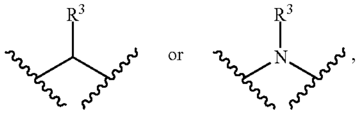

wherein $R^3$ is H or $C_{1-6}$ alkyl;

Ring A is

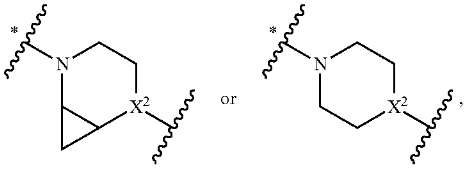

wherein * indicates attachment to $X^1$, and wherein $X^2$ is CH or N;

Ring B is:

a 6-membered heteroarylene comprising nitrogen;

a 9-membered heterocyclene comprising two oxygen atoms optionally substituted with one or more $C_{1-6}$ alkyl; or a 10-membered heterocyclene comprising two oxygen atoms;

L is a bond or *—O—($C_{1-6}$ alkylene)-, wherein * indicates attachment to Ring B;

Ring C is:

a 6-membered aryl optionally substituted with one or more halogen, —$OCH_3$, —CN, or $C_{3-10}$ cycloalkyl;

a 6-membered heteroaryl comprising a nitrogen atom optionally substituted with one or more halogen, —CN, —O—$C_{1-6}$ alkyl, $C_{3-10}$ cycloalkyl, —C(═O)—($C_{3-10}$ cycloalkyl),

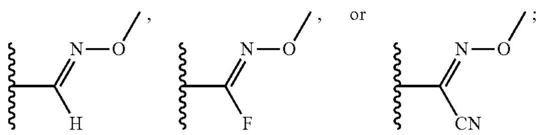

a bicylic 9- or 10-membered heteroaryl comprising two nitrogen atoms optionally substituted with one or more $C_{1-6}$ alkyl, or oxo.

In some embodiments, the GLP-1R agonist is a compound of Formula (I-5)

(I-5)

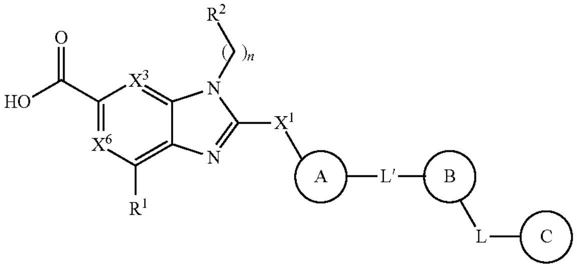

or a pharmaceutically acceptable salt thereof; wherein:

$X^3$ is $CR^6$ or N;

$X^6$ is $CR^4$ or N, $R^1$ is —$C_{1-6}$ haloalkyl, —O—$X^4$, or —$NR^8R^9$, or $R^1$ and $R^4$, together with the atoms to which they are attached, combine to form a 6-membered heterocyclyl;

$X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}$—$CH_3$, or —($CH_2$—ClH(—$OCH_3$)—$CH_2$—$O)_{1-5}$—$CH_3$, wherein the alkyl, heteroalkyl, alkylene, or haloalkyl group is optionally substituted with one or more deuterium, hydroxyl, —CN, or oxo, and the cycloalkyl or heterocyclyl group is optionally substituted with one or more halogen or —CN;

$R^6$ is hydrogen, halogen, or —O—$R^7$;

wherein $R^7$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocyclyl; wherein the $C_{1-6}$ alkyl is optionally substituted by one or more oxo;

n is 0, 1, 2, 3, 4, 5, or 6;

$R^2$ is:

hydrogen;

branched $C_{1-6}$ alkyl;

$C_{1-6}$ haloalkyl;

—(O)—$C_{1-6}$ alkyl;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

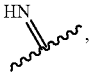, or $C_{1-6}$ alkyl;

a 5-membered heteroaryl, comprising 1 or 2 heteroatoms independently selected from N, and S, wherein at least one heteroatom of $R^5$ is S; or $R^2$ and $R^1$, together with the atoms to which they are attached, combine to form a 5- or 6-membered heterocyclyl;

$R^4$ is hydrogen or —O—$R^8$, wherein $R^8$ and $R^1$, together with the atoms to which they are attached, combine to form a 6-membered heterocyclyl;

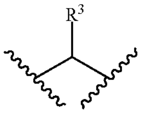 or 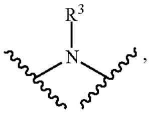, $X^1$ is or N wherein $R^3$ is H or $C_{1-6}$ alkyl;

Ring A is

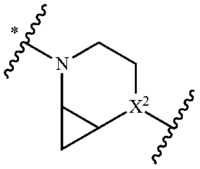 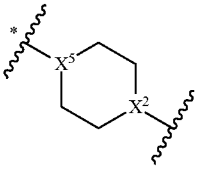, 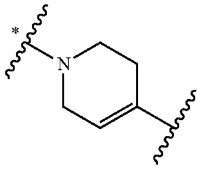, phenylene optionally substituted with one or more halo or $C_{1-6}$ alkyl, or 6-membered heteroarylene optionally substituted with one or more halo or $C_{1-6}$ alkyl;

wherein * indicates attachment to $X^1$, $X^5$ is $CR^3$ or N, and $X^2$ is $CR^3$ or N;

L' is a bond or —O—;

Ring B is a $C_{6-10}$ arylene, a 6-10 membered heteroarylene, or a 3-10 membered heterocyclene, wherein the $C_6$0.4o arylene, 6-10 heteroarylene, or 3-10 membered heterocyclene is optionally substituted with one or more $C_{1-6}$ alkyl, $C_{1-6}$ alkoxy, or halogen;

L is a bond, *—$CH_2$—, *—O—($C_{1-6}$ alkylene)-, or *-($C_{1-6}$ alkylene)-O—, wherein * indicates attachment to Ring B and the $C_{1-6}$ alkylene is optionally substituted with deuterium; and Ring C is:

a 6-membered aryl optionally substituted with one or more $C_{1-6}$ alkyl, 3-10 membered heterocyclyl, halogen, —$OCH_3$, —CN, or $C_3$-o cycloalkyl;

a 6-membered heteroaryl comprising a nitrogen atom optionally substituted with one or more halogen, —CN, —O—$C_{1-6}$ alkyl, $C_{3-10}$ cycloalkyl, —C(═O)—($C_{3-10}$ cycloalkyl),

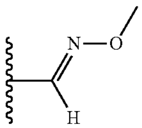, 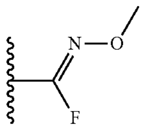, or 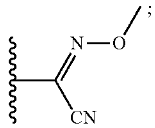;

or a bicylic 9- or 10-membered heteroaryl comprising two nitrogen atoms optionally substituted with one or more $C_{1-6}$ alkyl, or oxo.

In some embodiments, the GLP-1R agonist is a compound of Formula (I-P01):

(I-P01)

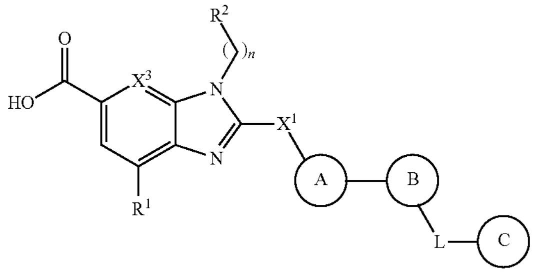

or a pharmaceutically acceptable salt thereof; wherein:

$X^3$ is CH or N;

$R^1$ is —$C_{1-6}$ haloalkyl or —O—$X^4$;

wherein $X^4$ is $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}$—$CH_3$, or —$(CH_2—CH(—OCH_3)—CH_2—O)_{1-5}$—$CH_3$, wherein the alkyl, heteroalkyl, alkylene, or haloalkyl group is optionally substituted with one or more —CN, and the cycloalkyl or heterocyclyl group is optionally substituted with one or more halogen or —CN;

n is 0, 1, 2, 3, 4, 5, or 6;

$R^2$ is:

hydrogen;

—(O)—$C_{1-6}$ alkyl;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

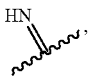, or $C_{1-6}$ alkyl; or a 5-membered heteroaryl, comprising 1 or 2 heteroatoms independently selected from N, and S, wherein at least one heteroatom of $R^5$ is S;

$X^1$ is

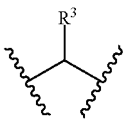 or 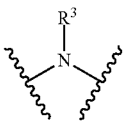, wherein $R^3$ is H or $C_{1-6}$ alkyl,

Ring A is

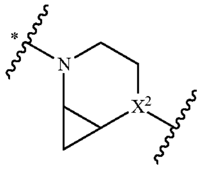 or 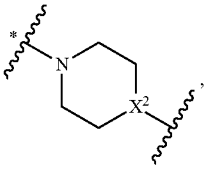, wherein * indicates attachment to $X^1$, and wherein $X^2$ is CH or N;

Ring B is a 6-10 membered heteroarylene, or a 3-10 membered heterocycylene optionally substituted with one or more $C_{1-6}$ alkyl;

L is a bond or *—O—($C_{1-6}$ alkylene)-, wherein * indicates attachment to Ring B;

Ring C is:

a 6-membered aryl optionally substituted with one or more halogen, —$OCH_3$, —CN, or $C_{3-10}$ cycloalkyl;

a 6-membered heteroaryl comprising a nitrogen atom optionally substituted with one or more halogen, —CN, —O—$C_{1-6}$ alkyl, $C_{3-10}$ cycloalkyl, —C(═O)—($C_{3-10}$ cycloalkyl),

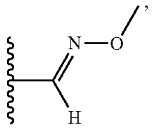, 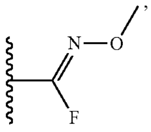, or 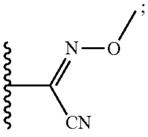;

a bicylic 9- or 10-membered heteroaryl comprising two nitrogen atoms optionally substituted with one or more $C_{1-6}$ alkyl, or oxo.

In some embodiments the compound of Formula (I-5) is of Formula (I-5a):

(I-5a)

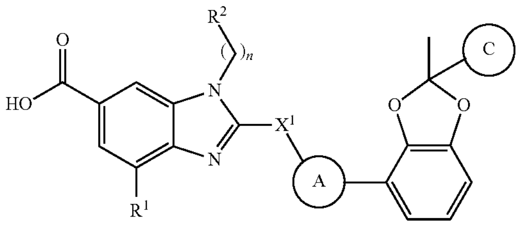

or a pharmaceutically acceptable salt thereof;

wherein $R^1$, n, $R^2$, $X^1$, Ring A, and Ring C are as defined for Formula (I-5).

In some embodiments, the compound of Formula (I-5) is of Formula (I-5b):

(I-5b)

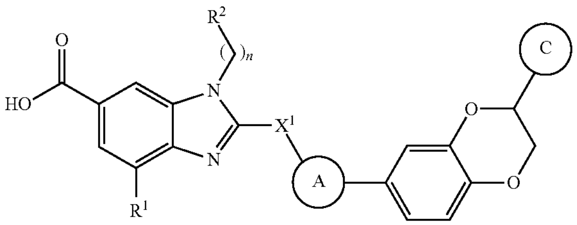

or a pharmaceutically acceptable salt thereof;

wherein $R^1$, n, $R^2$, $X^1$, Ring A, and Ring C are as defined for Formula (I-5).

In some embodiments, the compound of Formula (I-5) is of Formula (I-5c):

(I-5c)

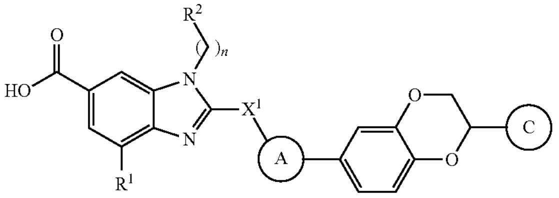

or a pharmaceutically acceptable salt thereof;

wherein $R^1$, n, $R^2$, $X^1$, Ring A, and Ring C are as defined for Formula (I-5).

In some embodiments, the compound of Formula (I-5) is of Formula (I-5d):

(I-5d)

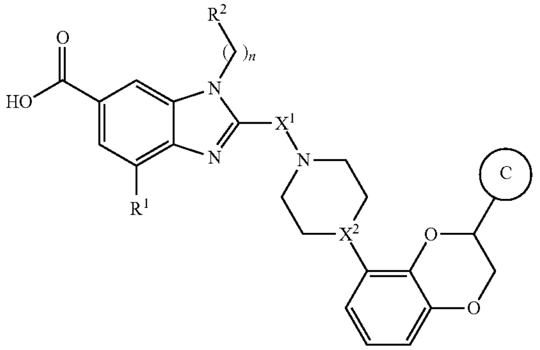

or a pharmaceutically acceptable salt thereof;

wherein $R^1$, n, $R^2$, $X^1$, $X^2$, and Ring C are as defined for Formula (I-5).

In some embodiments, the compound of Formula (I-5) is of Formula (I-5e):

(I-5e)

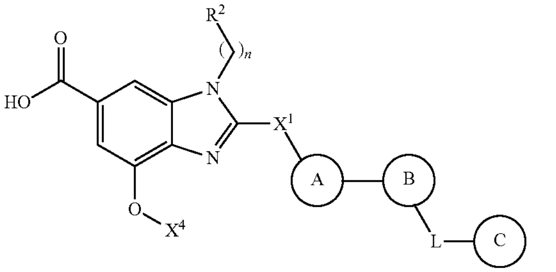

or a pharmaceutically acceptable salt thereof;

wherein $X^4$, n, $R^2$, $X^1$, Ring A, Ring B, and Ring C are as defined for Formula (I-5).

In some embodiments, the compound of Formula (I-5) is of Formula (I-5f):

(I-5f)

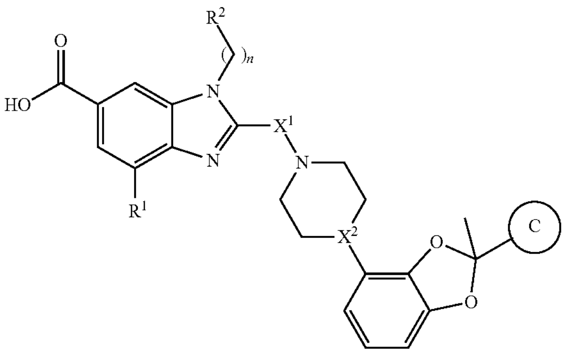

or a pharmaceutically acceptable salt thereof;

wherein $R^1$, n, $R^2$, $X^1$, and Ring C are as defined for Formula (I-5).

In some embodiments, the compound of Formula (I-5) is of Formula (I-5 g);

(I-5g)

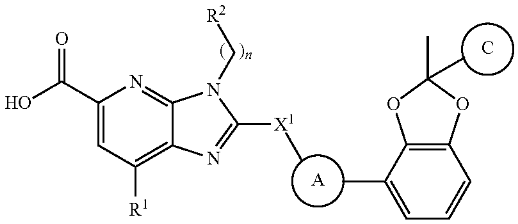

or a pharmaceutically acceptable salt thereof;

wherein $R^1$, n, $R^2$, $X^1$, Ring A, and Ring C are as defined for Formula (I-5).

In some embodiments, the compound of Formula (I-5) is of Formula (I-5h):

(I-5h)

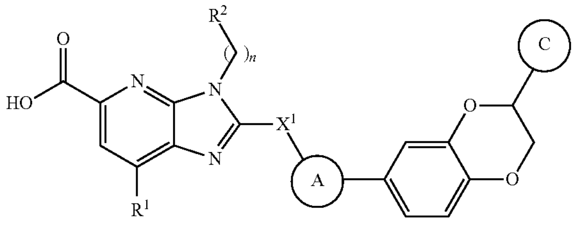

or a pharmaceutically acceptable salt thereof;

wherein $R^1$, n, $R^2$, $X^1$, Ring A, and Ring C are as defined for Formula (I-5).

In some embodiments, the compound of Formula (I-5) is of Formula (I-5i):

(I-5i)

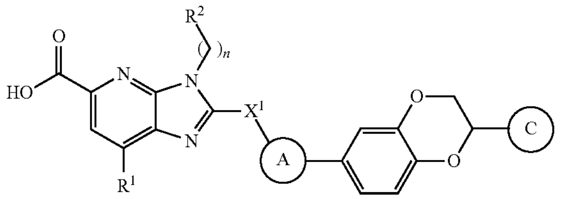

or a pharmaceutically acceptable salt thereof;

wherein $R^1$, n, $R^2$, $X^1$, and Ring A, Ring C are as defined for Formula (I-5).

In some embodiments, the compound of Formula (I-5) is of Formula (I-5j)

(I-5j)

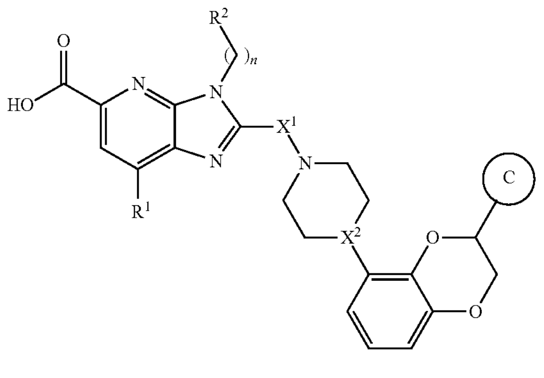

or a pharmaceutically acceptable salt thereof;

wherein $R^1$, n, $R^2$, $X^1$, and Ring C are as defined for Formula (I-5).

In some embodiments, the compound of Formula (I-5) is of Formula (I-5k)

(I-5k)

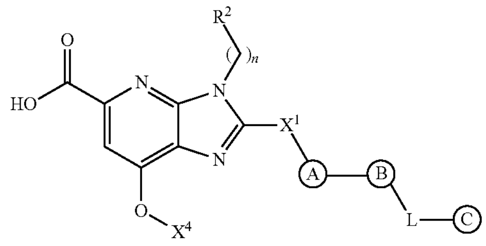

or a pharmaceutically acceptable salt thereof;

wherein $X^4$, $R^2$, $X^1$, n Ring A, Ring B, L, and Ring C are as defined for Formula (I-5).

In some embodiments, the compound of Formula (I-5) is of Formula (I-51)

(I-51)

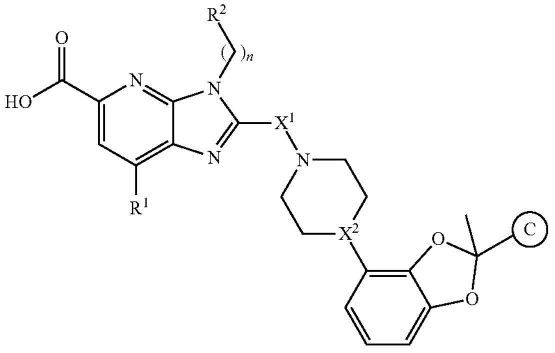

or a pharmaceutically acceptable salt thereof;

wherein $R^1$, $R^2$, $X^1$, n, and Ring C are as defined for Formula (I-5).

In some embodiments, the compound of Formula (I-5) is of Formula (I-5m)

(I-5m)

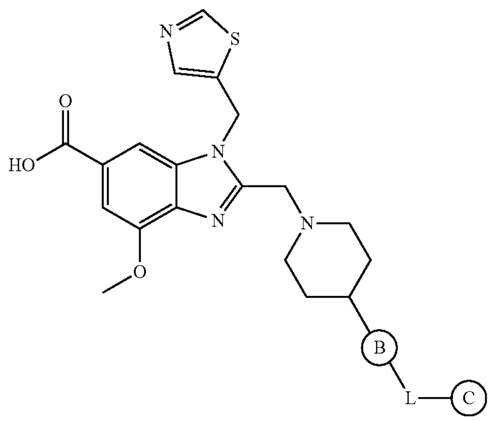

or a pharmaceutically acceptable salt thereof;

wherein Ring B, L, and Ring C are as defined for Formula (I-5).

In some embodiments, the compound of Formula (I-5) is of Formula (I-5n)

(I-5n)

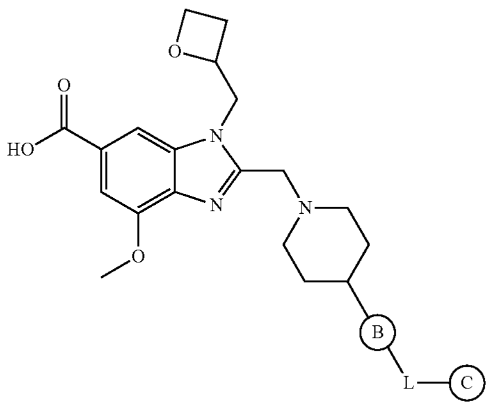

or a pharmaceutically acceptable salt thereof;

wherein Ring B, L, and Ring C are as defined for Formula (I-5).

In some embodiments, the compound of Formula (I-5) is of Formula (I-5O)

(I-5o)

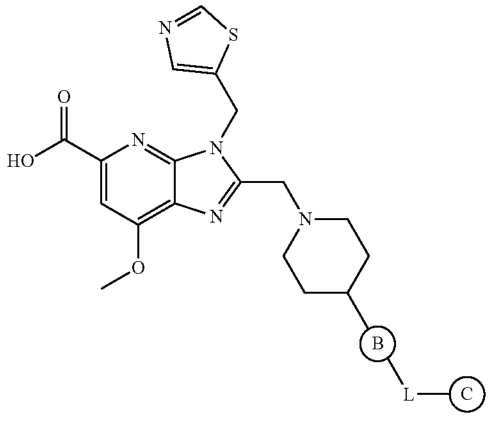

or a pharmaceutically acceptable salt thereof;

wherein Ring B, L, and Ring C are as defined for Formula (I-5).

In some embodiments, the compound of Formula (I-5) is of Formula (I-5p)

(I-5p)

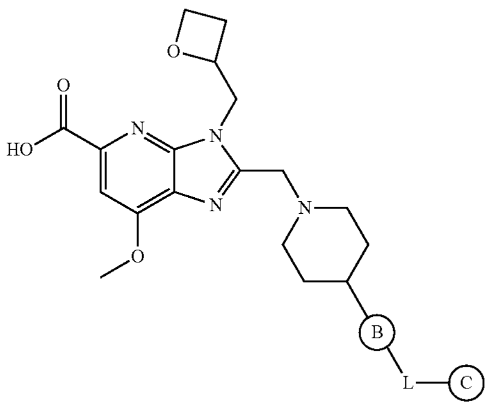

or a pharmaceutically acceptable salt thereof;

wherein Ring B, L, and Ring C are as defined for Formula (I-5).

In some embodiments, the compound of Formula (I-5) is of Formula (IQ)

(IQ)

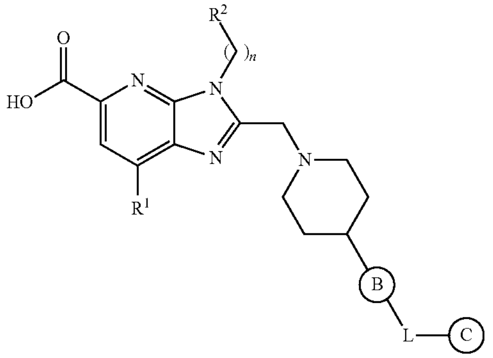

or a pharmaceutically acceptable salt thereof;

wherein $R^1$, $R^2$, n, Ring B, L, and Ring C are as defined for Formula (I-5).

In some embodiments, the compound of Formula (I-5) is of Formula (IR)

(IR)

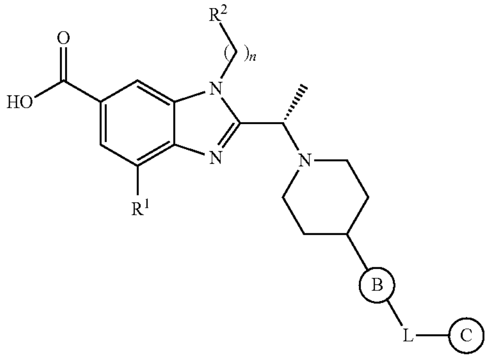

or a pharmaceutically acceptable salt thereof;

wherein $R^1$, $R^2$, n, Ring B, L, and Ring C are as defined for Formula (I-5).

In some embodiments, the compound of Formula (I-5) is of Formula (IS)

(IS)

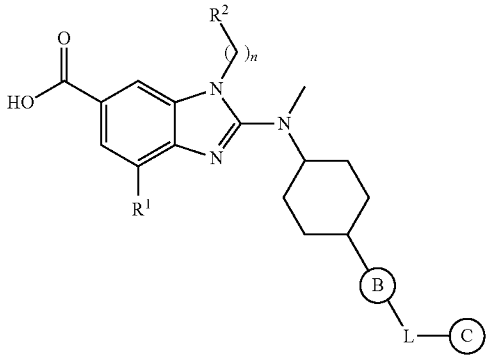

Wherein $R^1$, $R^2$, n, Ring B, L, and Ring C are as defined for Formula (I-5).

In some embodiments, the compound of Formula (I-5) is of Formula (IT)

(IT)

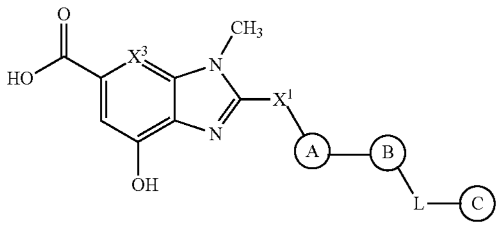

or a pharmaceutically acceptable salt thereof;

wherein X, $X^3$, Ring A, Ring B, L, and Ring C are as defined for Formula (I-5).

In some embodiments, the compound of Formula (I-5) is of Formula (IU)

(IU)

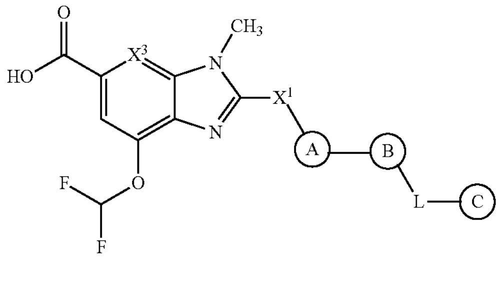

or a pharmaceutically acceptable salt thereof;

wherein $X^3$, $X^1$, Ring A, Ring B, L, and Ring C are as defined for Formula (I-5). or a pharmaceutically acceptable salt thereof;

wherein $X^3$, $R^4$, $R^1$, n, and $R^2$ are as defined for Formula (I-5).

In some embodiments, the compound of Formula (I-5) is of Formula (IX)

(IX)

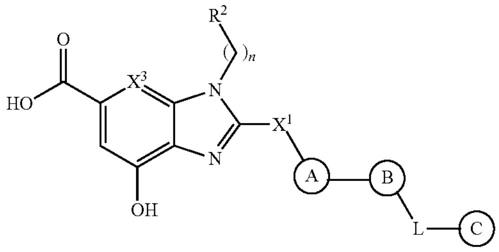

or a pharmaceutically acceptable salt thereof;

wherein $X^3$, n, $R^2$, $X^1$, Ring A, Ring B, L, and Ring C are as defined for Formula (I-5).

In some embodiments, the compound of Formula (I-5) is of Formula (IY)

(IY)

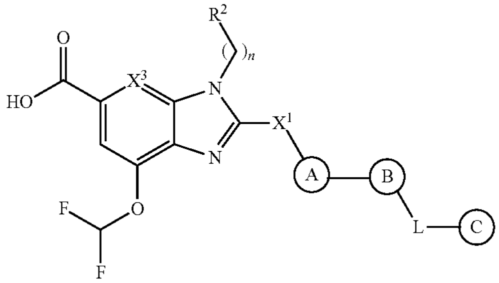

or a pharmaceutically acceptable salt thereof;

wherein $X^3$, n, $R^2$, $X^1$, Ring A, Ring B, L, and Ring C are as defined for Formula (I-5).

In some embodiments, the compound of Formula (I-5) is of Formula (IZ)

(IZ)

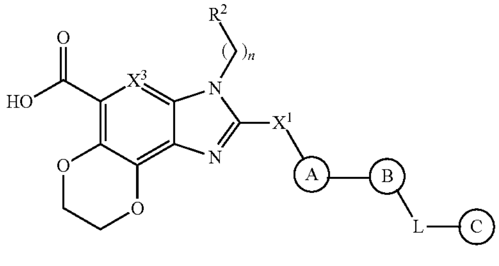

or a pharmaceutically acceptable salt thereof;

wherein $X^3$, n, $R^2$, $X^1$, Ring A, Ring B, L, and Ring C are as defined for Formula (I-5).

In some embodiments, the compound of Formula (I''') is of Formula (IAA)

(IAA)

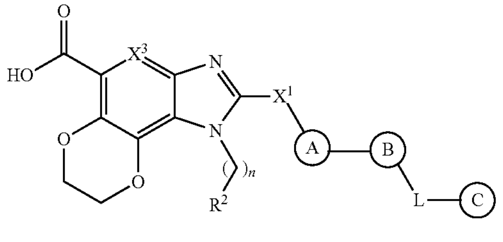

or a pharmaceutically acceptable salt thereof;

wherein X, n, $R^2$, $X^1$, Ring A, Ring B, L, and Ring C are as defined for Formula (I-5).

In some embodiments, the compound of Formula (I-5) is of Formula (IAB)

(IAB)

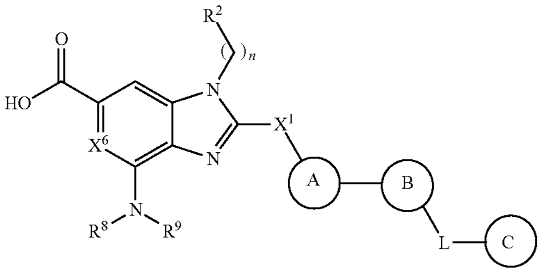

or a pharmaceutically acceptable salt thereof;

wherein $X^6$, $R^8$, $R^9$, n, $R^2$, $X^1$, Ring A, Ring B, L, and Ring C are as defined for Formula (I-5).

In some embodiments, the compound of Formula (I-5) is of Formula (IAC)

(IAC)

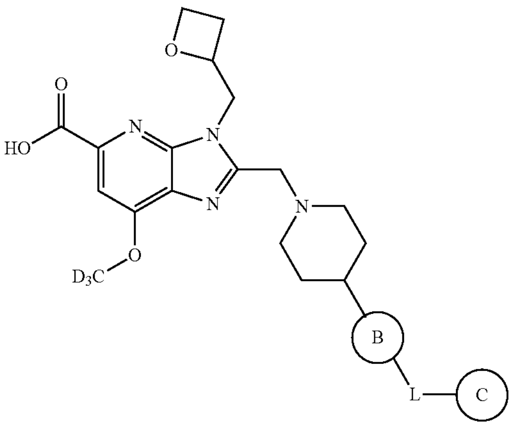

or a pharmaceutically acceptable salt thereof;

wherein Ring B, L, and Ring C are as defined for Formula (I-5).

In some embodiments, the compound of Formula (I-5) is of Formula (IAD)

(IAD)

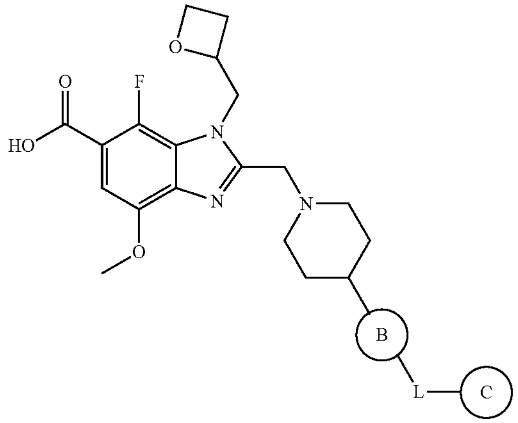

or a pharmaceutically acceptable salt thereof;

wherein Ring B, L, and Ring C are as defined for Formula (I-5).

In some embodiments, the compound of Formula (I-5) is of Formula (IAE)

(IAE)

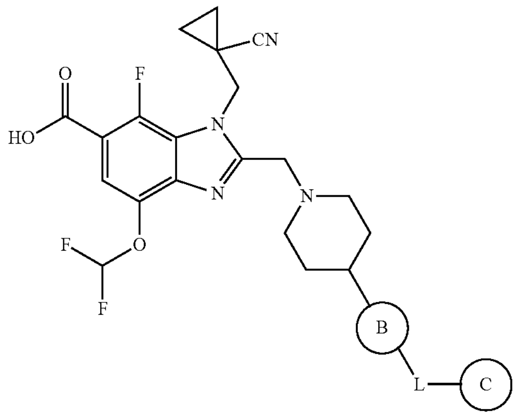

or a pharmaceutically acceptable salt thereof;

wherein Ring B, L, and Ring C are as defined for Formula (I-5).

In some embodiments, the compound of Formula (I-5) is of Formula (IAG)

(IAG)

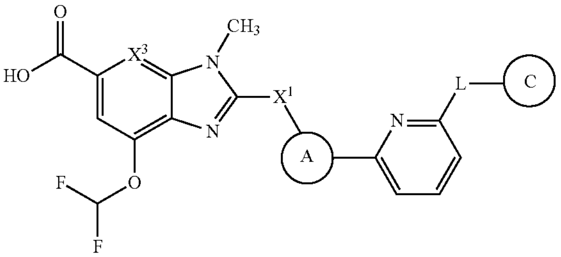

or a pharmaceutically acceptable salt thereof;

wherein $X^3$, $X^1$, Ring A, L, and Ring C are as defined for Formula (I-5).

In some embodiments, the compound of Formula (I-5) is of Formula (IAH):

(IAH)

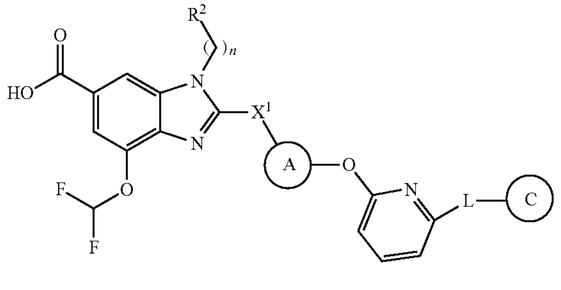

or a pharmaceutically acceptable salt thereof;

wherein n, $R^2$, $X^1$, Ring A, L, and Ring C are as defined for Formula (I-5).

In some embodiments, the compound of Formula (I-5) is of Formula (IAI):

(IAI)

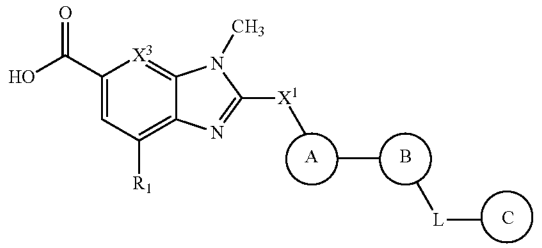

wherein $R^1$ is —O—($C_1$. haloalkyl);

X3, X1, Ring A, Ring B, L, and Ring C are as defined for Formula (I-5);

or a pharmaceutically acceptable salt thereof.

In some embodiments, the compound of Formula (I-5) is of Formula (IAJ):

(IAJ)

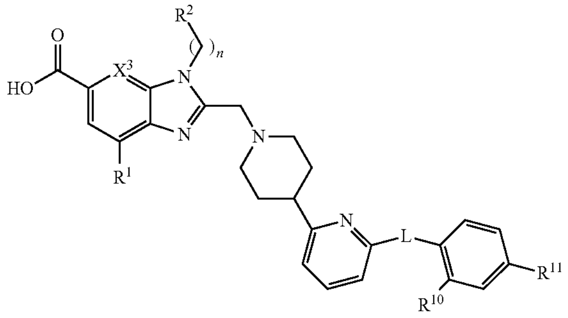

wherein $R^2$ is hydrogen, thiazolyl, oxetanyl, cyclopropyl optionally substituted with cyano, or methoxy;

n is 1 or 2;

$R^1$ is —O—$C_{1-6}$ alkyl, —OH, or —$NH_2$, wherein the $C_{1-6}$ alkyl is optionally substituted with one or more halo or deuterium;

$X^3$ is $CR^6$, wherein $R^6$ is halo or hydrogen;

L is *—O—$C_{1-6}$ alkylene)-, wherein * indicates attachment to Ring B and the $C_{1-6}$ alkylene is optionally substituted with deuterium;

$R^{10}$ is halo; and $R^{11}$ is halo or cyano;

or a pharmaceutically acceptable salt thereof.

In some embodiments, the compound of Formula (I) is of Formula (II):

(II**)

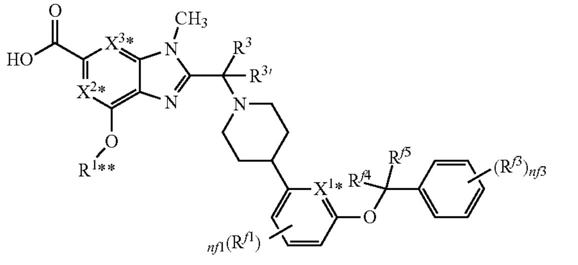

or a pharmaceutically acceptable salt thereof; wherein $R^{f4}$ and $R^{f5}$ are each independently selected from $C_{1-6}$ alkyl, H and D nf1 is 0, 1, 2, 3, or 4;

nf3 is 0, 1, 2, 3, 4, or 5;

each $R^{f1}$ is halogen;

$R^3$ and $R^{3'}$ independently are H or D;

$X^{1}$* is N or $CR^{f1}$;

$X^{2'}$ and $X^{3'}$ independently are CH or CF;

each $R^{f3}$ is independently selected from halogen, —CN, $C_{1-6}$ alkyl, $C_{1-6}$ haloalkyl, $C_1$—. alkoxy, or —C(O)N$(R^{f1})_2$, each $R^{L1}$ is indepdendently selected from H or $C_{1-6}$ alkyl; and $R^{1**}$ is H or $C_{1-2}$ alkyl optionally substituted with one or more deuterium or halogen.

In some embodiments, the compound of Formula (I**) is of Formula (II*):

(II*)

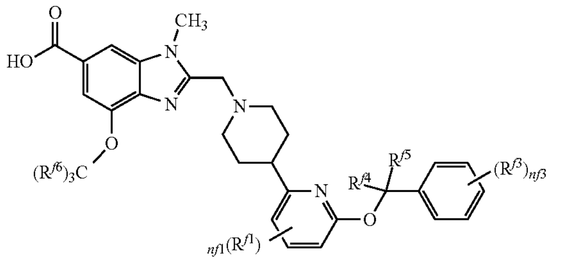

or a pharmaceutically acceptable salt thereof;

each $R^{f1}$ is independently selected from halogen $R^{f4}$ and $R^{f5}$ are each independently selected from $C_{1-6}$ alkyl, H and D nf1 is 0, 1, 2, or 3;

nf3 is 0, 1, 2, 3, 4, or 5;

each $R^{f1}$ is halogen;

each $R^{f3}$ is independently selected from halogen, —CN, $C_{1-6}$ alkyl, $C_{1-6}$ haloalkyl, $C_{1-6}$ alkoxy, or —C(O)N$(R^{f3})_2$, each $R^1$ is independently selected from H or $C_{1-6}$ alkyl; each $R^{f6}$ is independently selected from H, D or F.

In some embodiments, $R^{f}a$ and RP are each independently selected from $CH_3$, H, and D.

In some embodiments, each $R^{f1}$ is fluorine.

In some embodiments, $X^3$ is N. In some embodiments, $X^3$ is CH.

In some embodiments, $X^6$ is N. In some embodiments, $X^6$ is $CR^4$.

In some embodiments, $R^1$ is $R^1$ is —O—$C_{1-6}$ alkyl. In some embodiments, the alkyl group is linear. In some embodiments, the alkyl group is branched. In some embodiments, the alkyl group is linear and is optionally substituted with one or more deuterium, —CN or —O—$C_{1-6}$ alkyl. In some embodiments, the alkyl group is unsubstituted. In some embodiments, the alkyl group is substituted with one or more —CN or —O—$C_{1-6}$ alkyl. In some embodiments, $R^1$ is —O—$CH_2$—$CH_3$, —O—CH, —O—$CH_2$—CN, —O—$CH_2$—$CH_2$—O—$CH_3$, or —O—$CH_2CH$(—O—$CH_3$)—CH. In some embodiments, $R^1$ is branched and optionally substituted with one or more —CN. In some embodiments, $R^1$ is

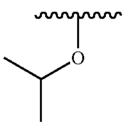 or 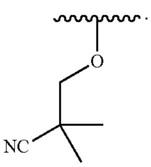.

In some embodiments, $R^1$ is —O—$C_{1-6}$ haloalkyl, wherein the haloalkyl group is linear. In some embodiments, the haloalkyl group is substituted with one or more fluorine. In some embodiments, $R^1$ is —O—$CHF_2$, —O—$CF_3$, —O—$CH_2$—$CH_2F$, —O—$CH_2$—$CF_3$, —O—$CH_2$—CHF—$CH_3$, —O—CHF-$CH_3$i, —O—CHF—$CH_2F$, or —O—$CH_2$—$CH_2F$.

In some embodiments, $R^1$ is —O—$C_{3-10}$ cycloalkyl optionally substituted with $C_{1-6}$ alkoxy or halogen. In some embodiments, $R^1$ is —O-cyclopropyl or —O-cyclobutyl, wherein the cyclopropyl or cyclobutyl is optionally substituted with fluorine or methoxy. In some embodiments, $R^1$ is —O—$C_{3-10}$ cycloalkyl optionally substituted with one or more halogen, e.g., fluorine, —$OCH_3$, or —CN.

In some embodiments, $R^1$ is —O-(3- to 8-membered heterocyclyl). In some embodiments, the 3- to 8-membered heterocyclyl comprises one oxygen atom. In some embodiments, the 3- to 8-membered heterocyclyl comprises two oxygen atoms. In some embodiments, the $R^1$ is —O—$CH_2$-(1,4-dioxan-2-yl) or —O—$CH_2$-tetrahydrofuran-2-yl.

In some embodiments, $R^1$ is —O—($C_{1-6}$ alkylene)-($C_{3-10}$ cycloalkyl). In some embodiments, $R^1$ is —O—($C_{1-6}$ alkylene)-($C_{3-10}$ cycloalkyl) optionally substituted with one or more halogen, cyano, or —$OCH_3$. In some embodiments, $R^1$ is

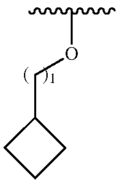, 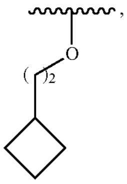, 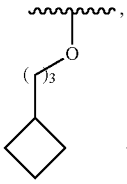, 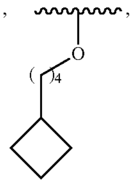,

-continued

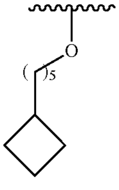, 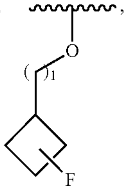, 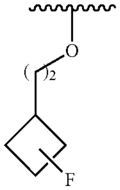, 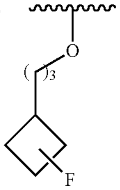,

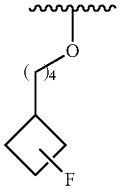, 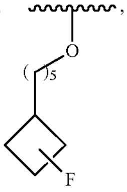, 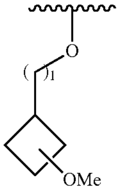, 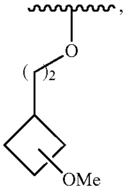,

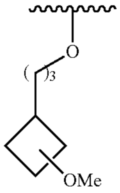, 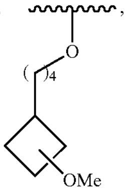, 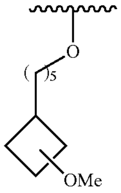, 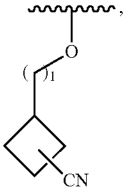,

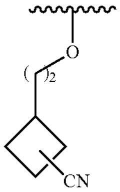, 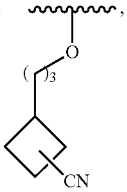, 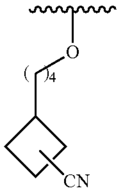, 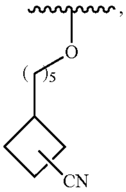,

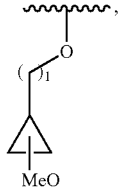, 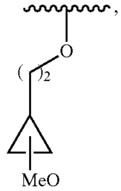, 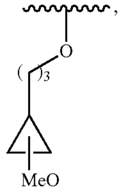, 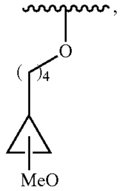,

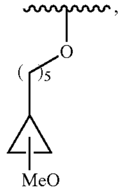, 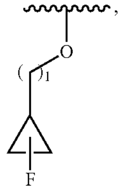, 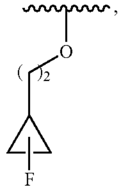, 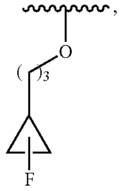,

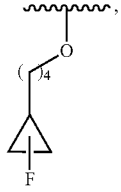, 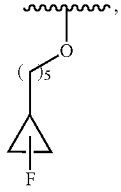, 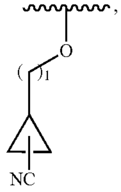, 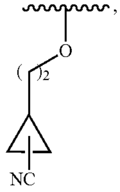,

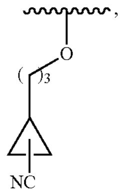, 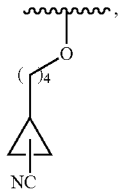, 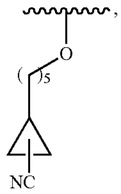, 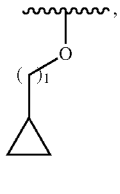,

-continued

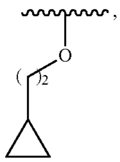, 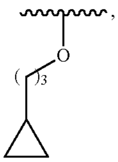, 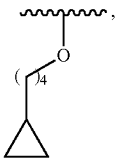, or 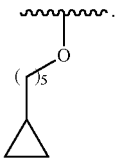.

In some embodiments, $R^1$ is

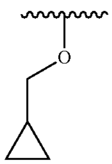 or 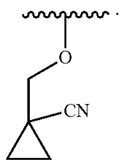.

In some embodiments, $R^1$ is —O—($C_{1-6}$ alkylene)-(3- to 8-membered heterocyclyl). In some embodiments, —O—($C_{1-6}$ alkylene)-(3- to 8-membered heterocyclyl) optionally substituted with one or more halogen, cyano, or —$OCH_3$. In some embodiments, $R^1$ is

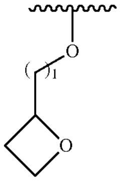, 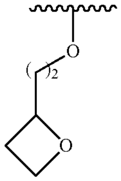, 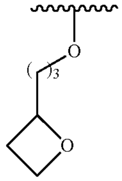, 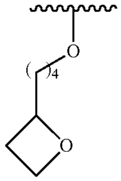,

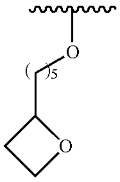, 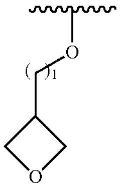, 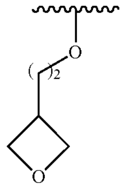, 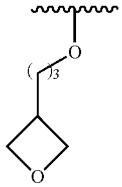,

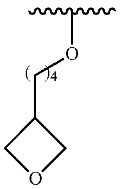, 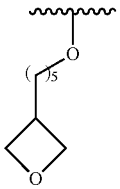, 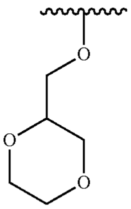, or

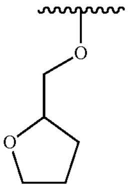.

In some embodiments, $R^1$ is

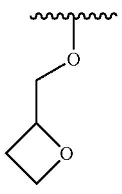 or 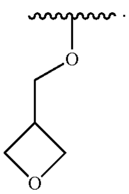.

In some embodiments, $R^1$ is

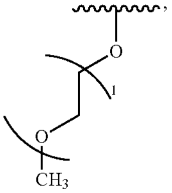, 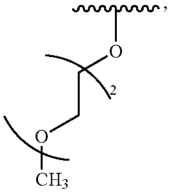, 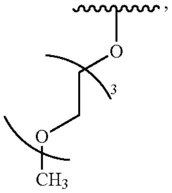,

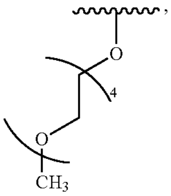, or 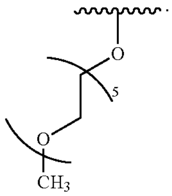.

In some embodiments, $R^1$ is $C_{1-6}$ haloalkyl. In some embodiments, $R^1$ is —$CF_2$—$CH_3$.

In some embodiments, $R^1$ is —O-(3- to 8-membered heterocyclyl). In some embodiments, $R^1$ is oxetanyl. In some embodiments, $R^1$ is oxetan-3-yl.

In some embodiments, $R^1$ is —O—($CH_2$—CH(—$OCH_3$)—$CH_2$—O)$_{1-5}$—$CH_3$. In some embodiments, $R^1$ is

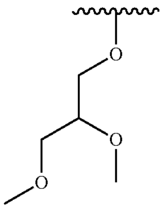 or 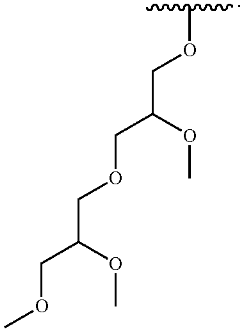.

In some embodiments, $R^1$ is —$NR^8R^9$. In some embodiments, $R^8$ and $R^9$ combine with the atom to which they are attached to form a 6-membered heterocyclyl. In some embodiments, $R^8$ and $R^9$ combine with the atom to which they are attached to form morpholine. In some embodiments, $R^8$ and $R^9$ are hydrogen. In some embodiments, $R^1$ is $NH_2$. In some embodiments, $R^1$ is $NR^8R^9$, wherein $R^8$ is H and $R^9$ is $C_{1-6}$ alkyl optionally substituted with oxo.

In some embodiments, $R^2$ is $C_{3-10}$ cycloalkyl optionally substituted with one or more —CN, $C_{1-6}$ haloalkyl, or $C_{1-6}$ alkyl optionally substituted with one or more —CN. In some embodiments, $R^2$ is cyclopropyl optionally substituted with one or more —CN, $C_{1-6}$ haloalkyl, or $C_{1-6}$ alkyl optionally substituted with one or more —CN. In some embodiments, $R^2$ is

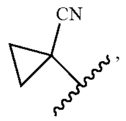, 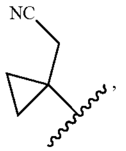, or 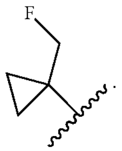.

In some embodiments, $R^2$ is 4 or 5-membered heterocyclyl comprising at least one oxygen or at least one sulfur atom, wherein the 4- or 5-membered heterocyclyl is optionally substituted with one or more oxo,

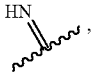, or $C_6$ alkyl. In some embodiments, $R^2$ is (i) thietane optionally substituted with one or more oxo or

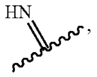, (ii) oxetane, or (iii) tetrahydrofuran optionally substituted with one or more $C_{1-6}$ alkyl. In some embodiments, $R^2$ is

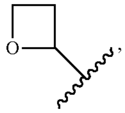, 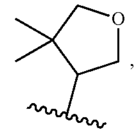,

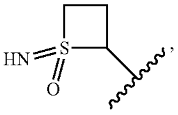, or 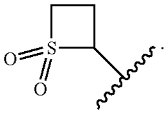.

In some embodiments, $R^2$ is 5-membered heteroaryl, comprising 1 or 2 heteroatoms independently selected from N, and S, wherein at least one heteroatom of $R^5$ is S. In some embodiments, $R^2$ is thiazole. In some embodiments, $R^2$ is

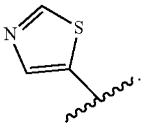 [SMILES: *c1cncs1].

In some embodiments, $R^2$ is H. In some embodiments, $R^2$ is —$OCH_3$.

In some embodiments, n is 1.

In some embodiments, X is

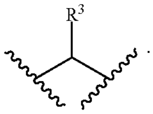.

In some embodiments, $X^1$ is

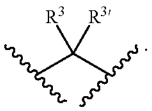.

In some embodiments, $X^1$ is

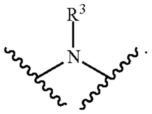.

In some embodiments, $R^3$ is methyl. In some embodiments, $R^3$ is hydrogen. In some embodiments, $R^3$ and $R^{3'}$ independently are $CH_3$, $CD_3$, deuterium, or hydrogen.

In some embodiments, $X^1$ is

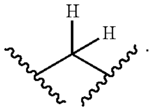.

In some embodiments, $X^1$ is

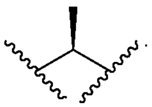.

In some embodiments, $X^1$ is

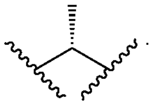.

In some embodiments, X is

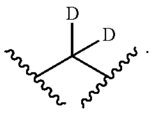 [SMILES: *C(*)([2H])[2H]].

In some embodiments, Ring A is

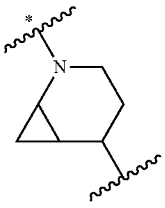 or 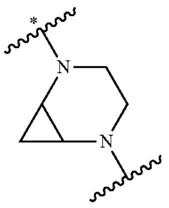, herein * indicates attachment to $X^1$. In some embodiments, Ring A is

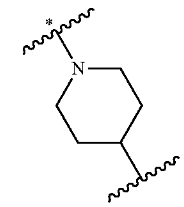 or 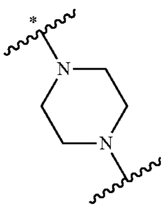 , wherein * indicates attachment to $X^1$. In some embodiments, Ring A is a phenylene ring optionally substituted with one or more halogen or $C_{1-6}$ alkyl. In some embodiments, Ring A is

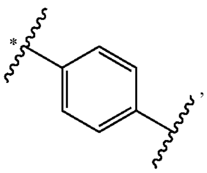 , 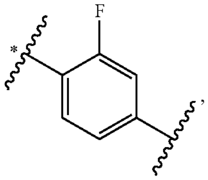 ,

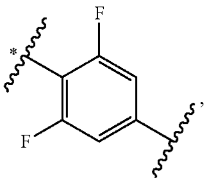 , 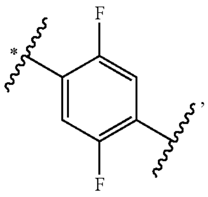 ,

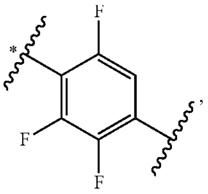 , 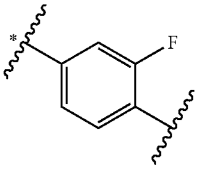 , or

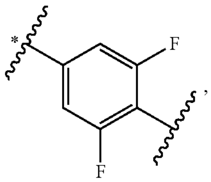 , wherein *ʃ indicates attachment to $X^1$. In some embodiments, Ring A is a 6-membered heteroarylene ring optionally substituted with one or more halogen. In some embodiments, Ring A is

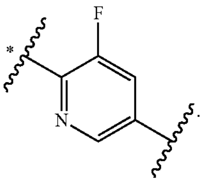 [SMILES: *c1cnc(*)c(F)c1] .

In some embodiments, Ring A is

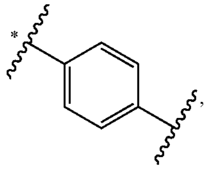 , 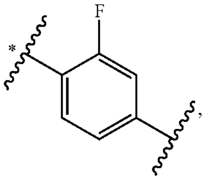 ,

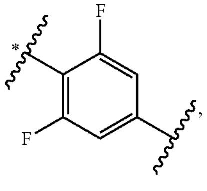 , 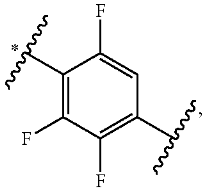 ,

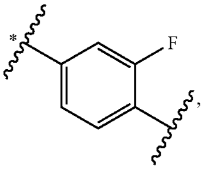 , 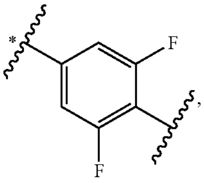 , or

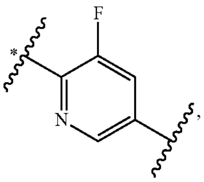 , wherein *ʃ indicates attachment to $X^1$.

In some embodiments, Ring B is a 6-membered heteroarylene comprising nitrogen. In some embodiments, Ring B is pyridinylene or pyrimidinylene optionally substituted with one or more halogen. In some embodiments, Ring B is pyridinylene. In some embodiments, Ring B is

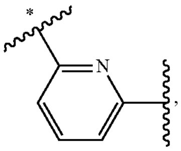 [SMILES: *c1cccc(*)n1] , wherein * indicates attachment to Ring A or L'. In some embodiments, Ring B is

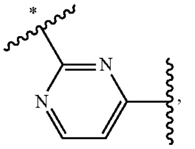 , 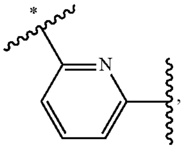 ,

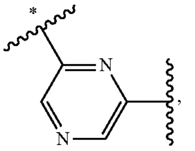 , 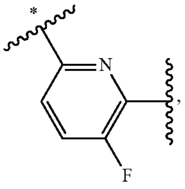 ,

-continued

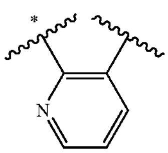

,

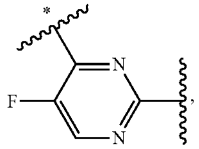

, or

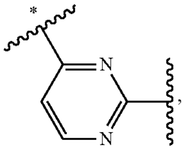

, wherein * indicates attachment to Ring A or L'.

In some embodiments, Ring B is a 9-membered heterocycylene comprising two oxygen atoms optionally substituted with one or more $C_{1-6}$ alkyl. In some embodiments, Ring B is benzoidoxolylene optionally substituted with one or more $C_{1-6}$ alkyl. In some embodiments, Ring B is

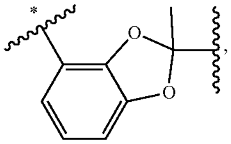 [SMILES: *c1cccc2c1OC(*)(C)O2]

, wherein * indicates attachment to Ring A or L'. In some embodiments, Ring B is B is a 10-membered heterocycylene comprising two oxygen atoms. In some embodiments, Ring B is benzodioxanylene. In some embodiments, Ring B is

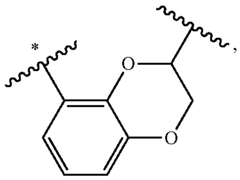 [SMILES: *c1cccc2c1OC(*)CO2]

, wherein * indicates attachment to Ring A or L'. In some embodiments, Ring B is

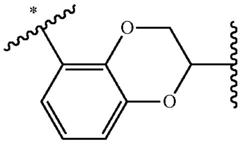

, wherein * indicates attachment to Ring A or L'.

In some embodiments, Ring B is a 10-membered heterocyclene comprising one oxygen atom and one nitrogen atom. In some embodiments, Ring B

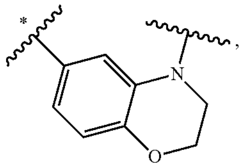 [SMILES: *c1ccc2c(c1)N(*)CCO2]

, wherein * indicates attachment to Ring A or L'.

In some embodiments, L is a bond. In some embodiments, L is *—O—$CH_2$—, wherein * indicates attachment to Ring B.

In some embodiments, Ring C is phenyl optionally substituted with one or more halogen, —CN, —$OCH_3$,

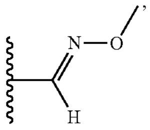

, or cyclopropyl. In some embodiments, Ring C is,

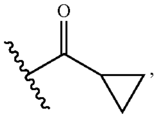

,

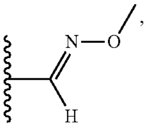

,

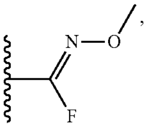

, or

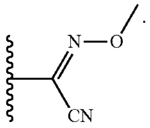

.

In some embodiments, Ring C is a 6-membered heteroaryl comprising a nitrogen atom optionally substituted with one or more halogen, —CN, —O—$C_{1-6}$ alkyl, —C(═O)—($C_{3-10}$ cycloalkyl), or $C_{3-10}$ cycloalkyl. In some embodiments, Ring C is pyridinyl optionally substituted with one or more —$C_1$, —F, —CN, —$OCH_3$, cyclopropyl,

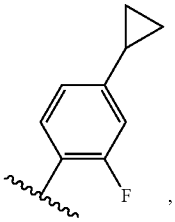

,

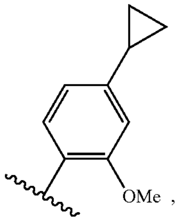

,

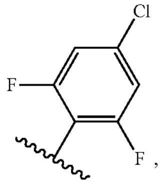

,

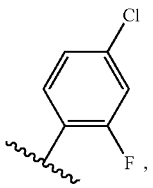

,

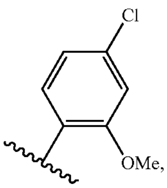

,

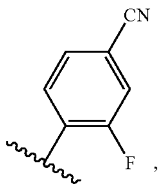

,

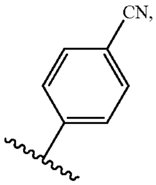

,

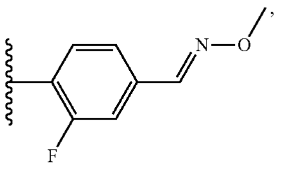

,

-continued

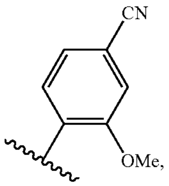 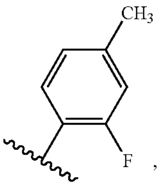 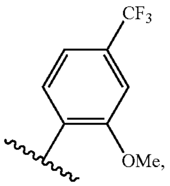

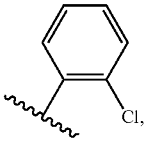 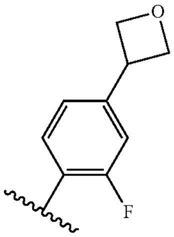 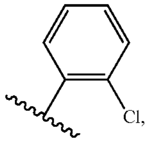

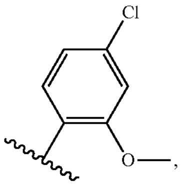 or 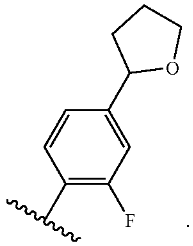

In some embodiments, Ring C is

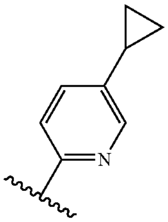 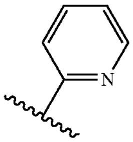 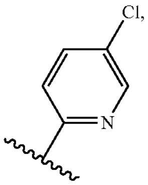

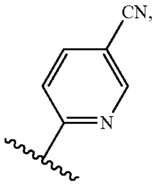 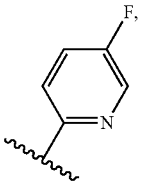 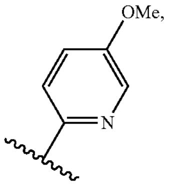

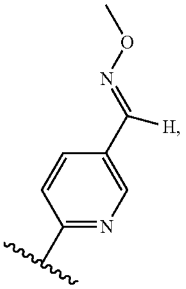 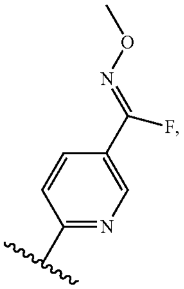

-continued

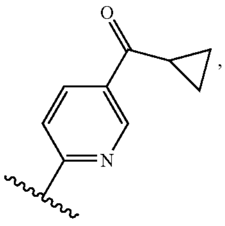 or 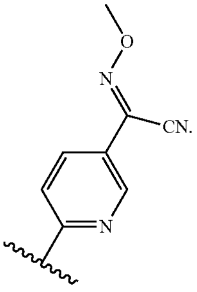

In some embodiments, Ring C is a bicylic 9- or 10-membered heteroaryl comprising two nitrogen atoms optionally substituted with one or more $C_{1-6}$ alkyl, or oxo. In some embodiments, Ring C is pyrazolopyridine, triazolopyridine, 2,3-dihydro-1H-pyrrolopyridine, 1,2-dihydrooxazolopyridine, 1,2,3,4-tetrahydronaphthyridine, 2,3-dihydro-pyridooxazine, 2,3-dihydro-1H-pyrrolopyridine, or 2,3-dihydrooxazolopyridine, wherein the pyrazolopyridine, triazolopyridine, 2,3-dihydro-1H-pyrrolopyridine, 1,2-dihydrooxazolopyridine, 1,2,3,4-tetrahydronaphthyridine, 2,3-dihydro-pyridooxazine, 2,3-dihydro-1H-pyrrolopyridine, or 2,3-dihydrooxazolopyridine is optionally substituted with one or more $C_{1-6}$ alkyl or oxo. In some embodiments, Ring C is

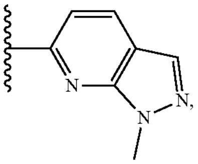 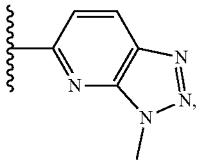

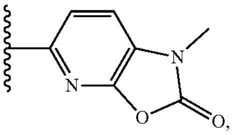 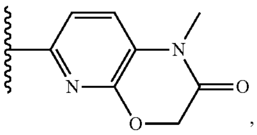

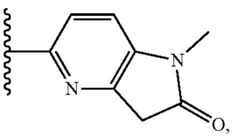 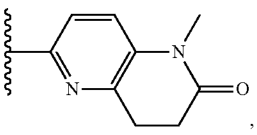

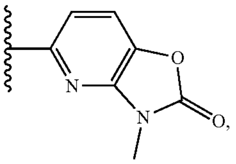 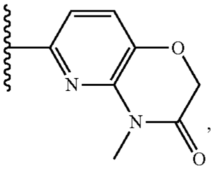

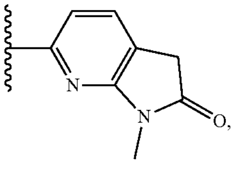 or 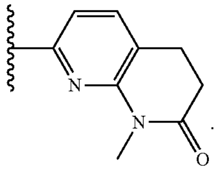

In some embodiments,
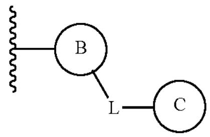
is
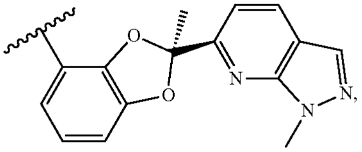
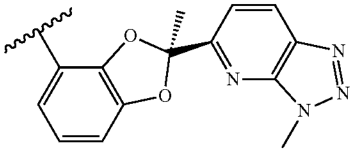
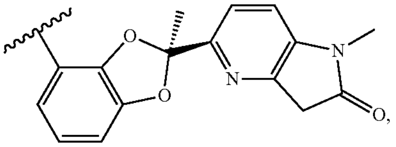
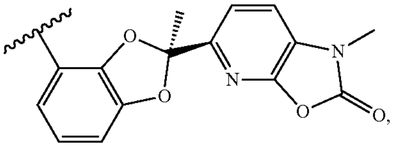
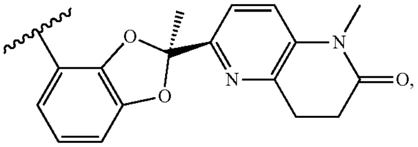
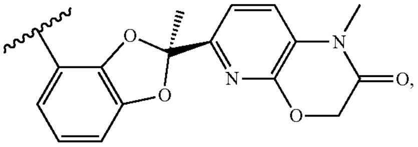
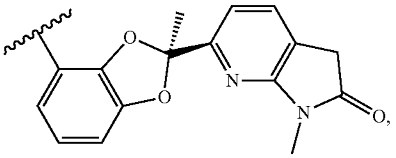
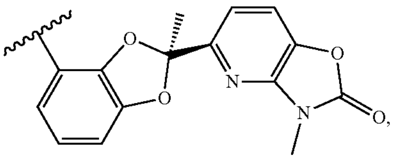
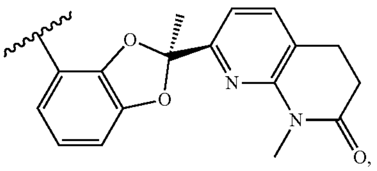
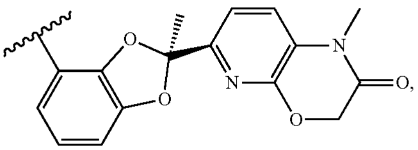
-continued
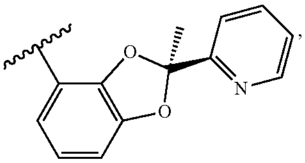
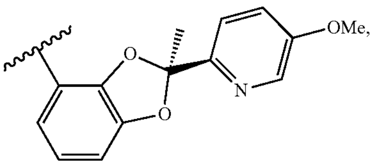
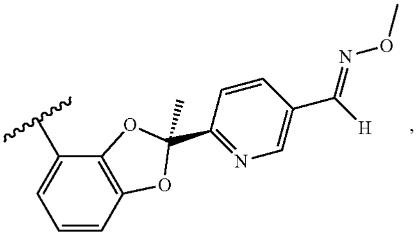
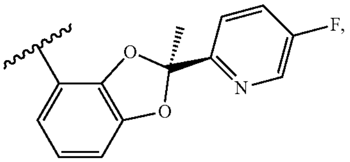
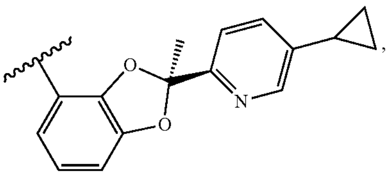
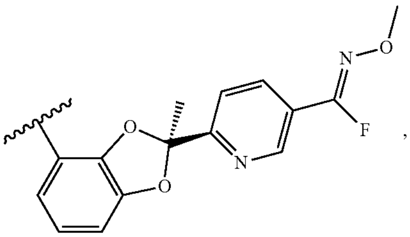
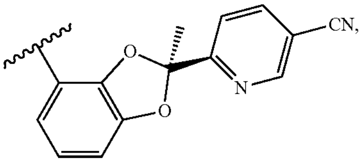
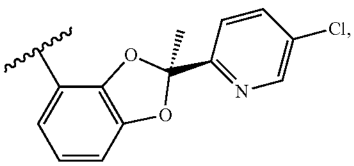
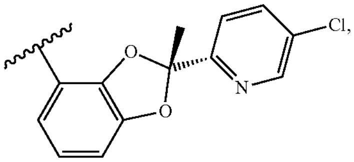

-continued
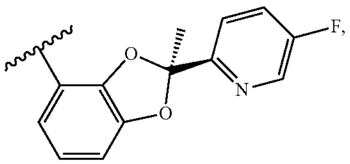
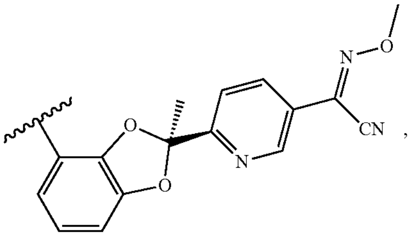
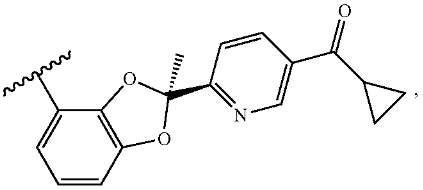
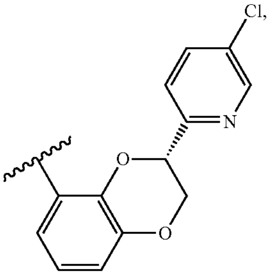
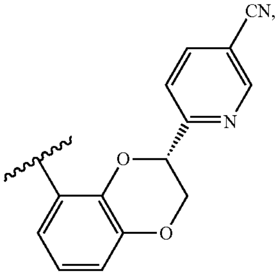
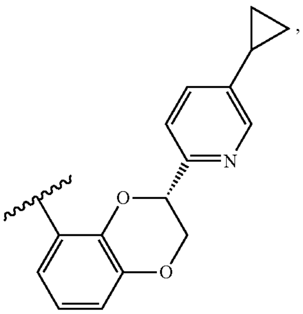
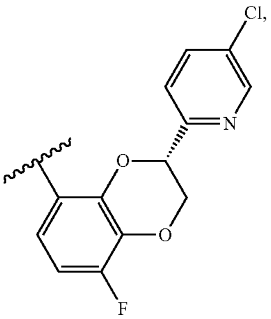
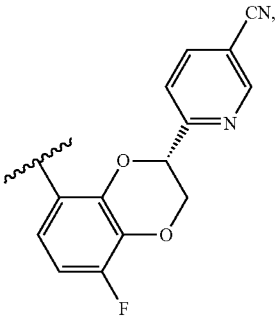
-continued
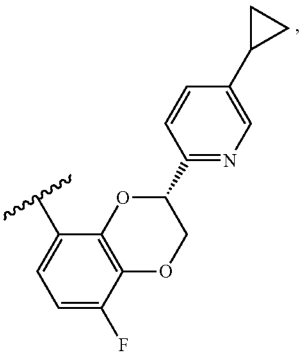
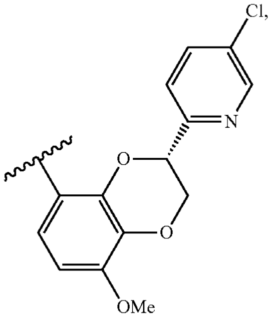
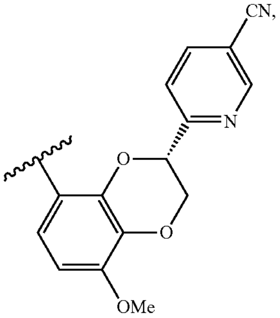
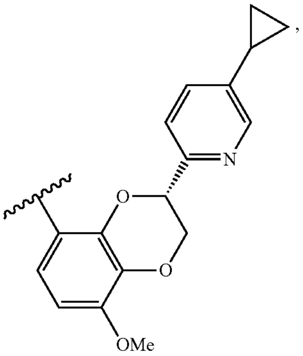
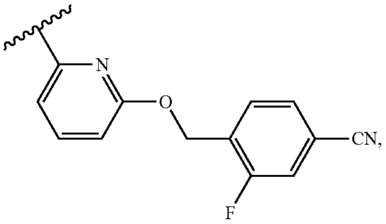
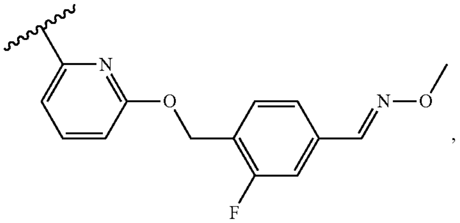
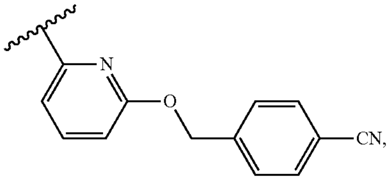

-continued
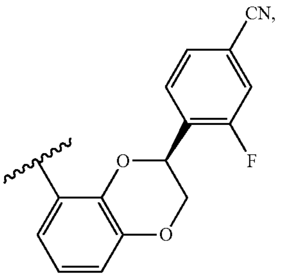 or
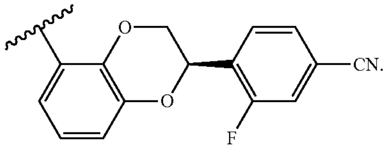
In some embodiments, $R^{12}$ is —COOH. In some embodiments, $R^{12}$ is
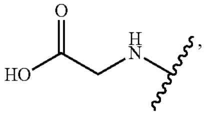, 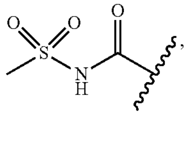, 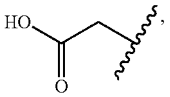,
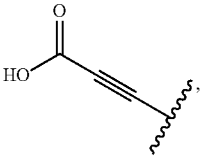, 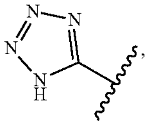, 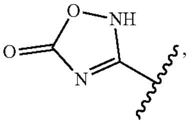,
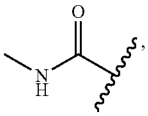, 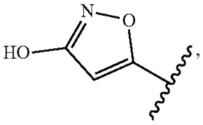, 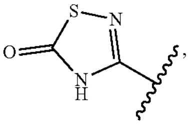,
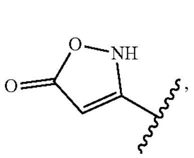, or 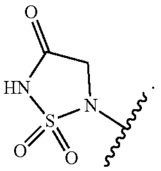.
The present disclosure contemplates the combination of any one of Formula (I-5e), (I-5k), (1-51), (I-5m), (I-5n), (I-5o), (I-5p), (I-5q), (I-5r), (I-5s), (I-5t), (I-5u), (I-5v), (I-5w), (I-5x), (I-5y), (I-5z), (I-5aa), (I-5ab), (I-5ac), or (I-5af) with any one of the following
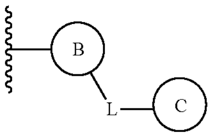
moieties:
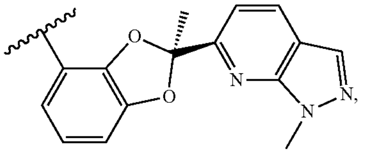
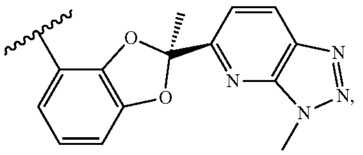
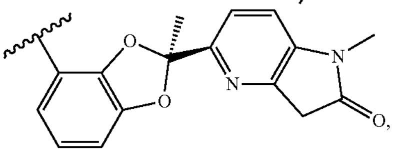
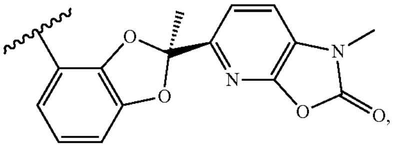
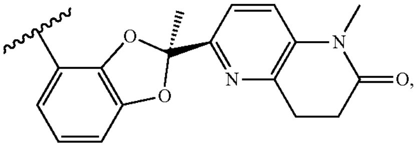
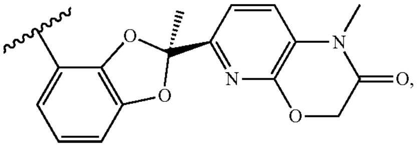
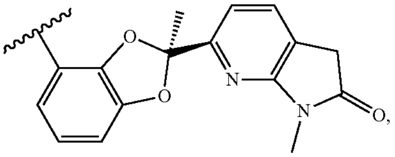
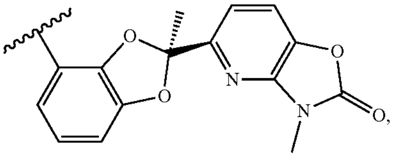
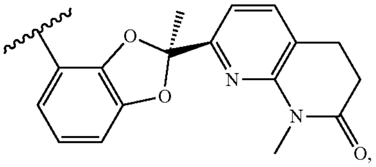
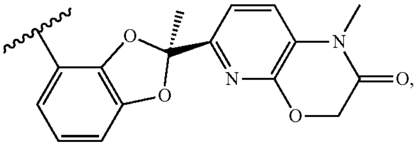
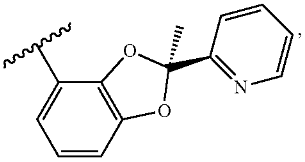

-continued
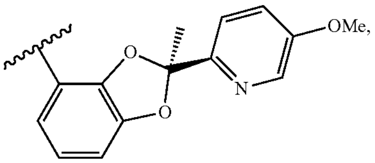
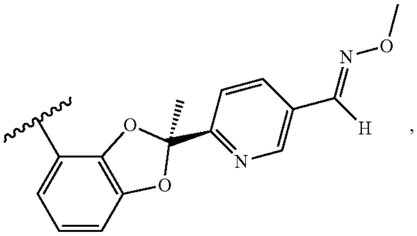
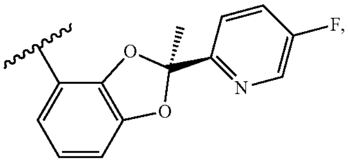
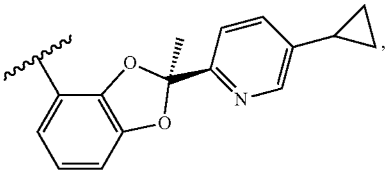
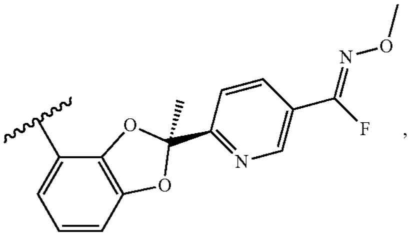
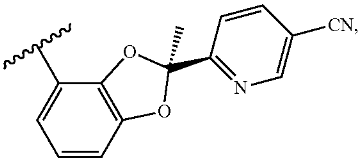
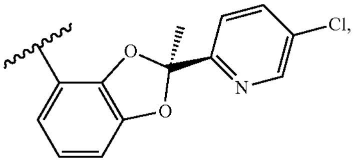
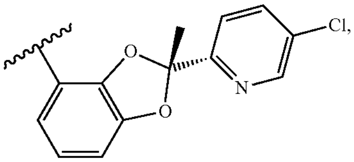
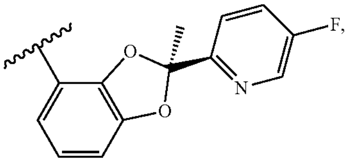
-continued
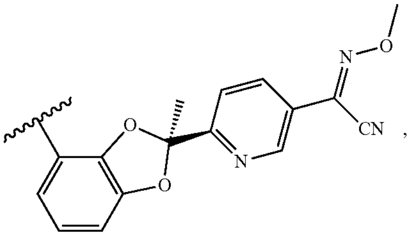
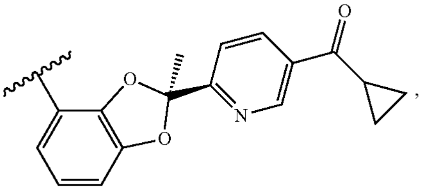
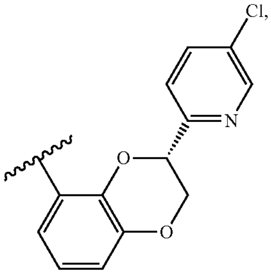
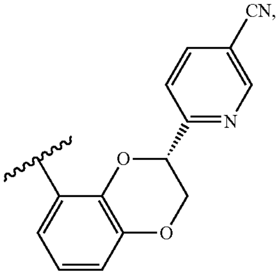
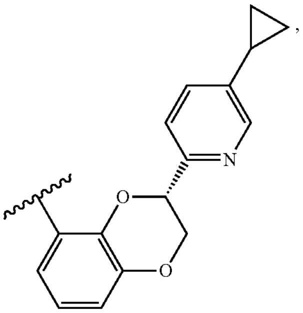
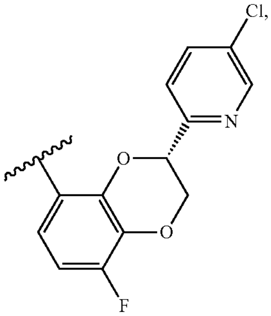
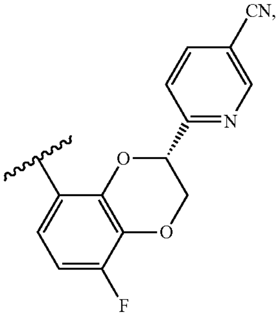
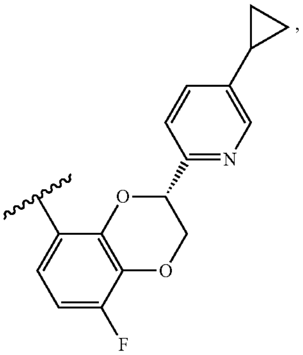

-continued
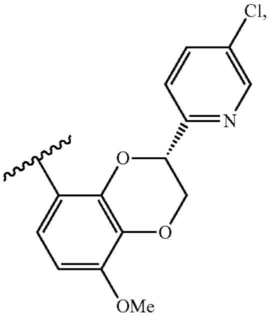
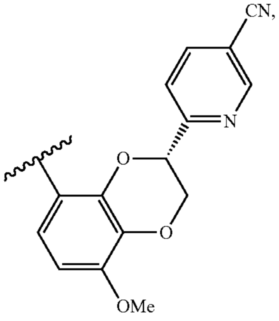
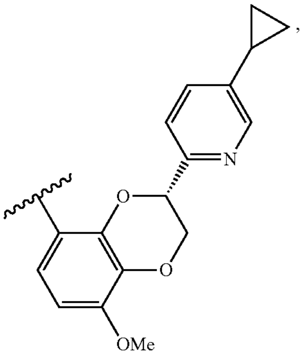
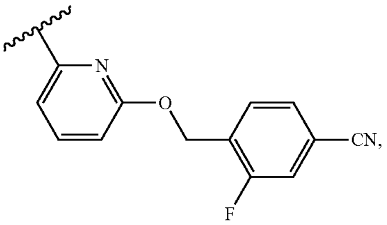
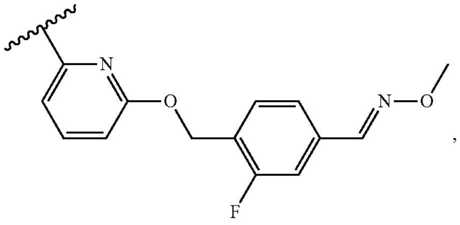
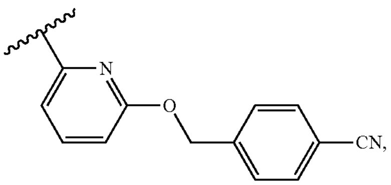
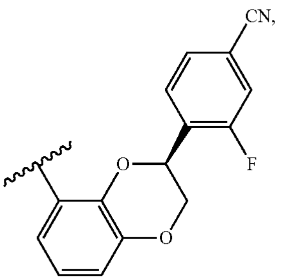
or
-continued
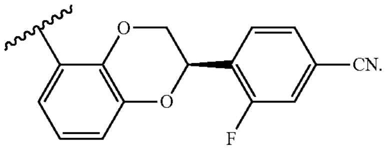
The present disclosure contemplates the combination of any one of Formula (I-5e), (I-5k), (I-51), (I-5m), (I-5n), (I-5o), (I-5p), (I-5q), (I-5r), (I-5s), (I-5t), (I-5u), (I-5v), (I-5w), (I-5x), (I-5y), (I-5z), (I-5aa), (I-5ab), (I-5ac), or (I-5af) with any one of the following
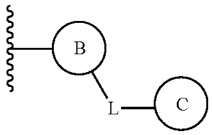
moieties:
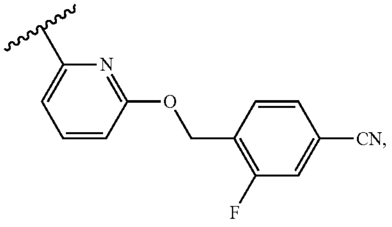
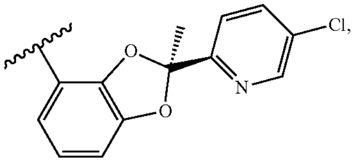
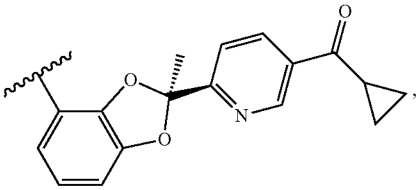
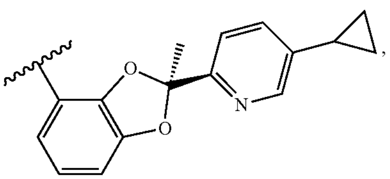
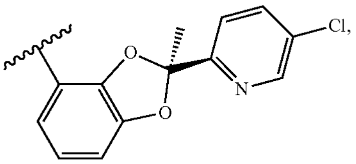

-continued
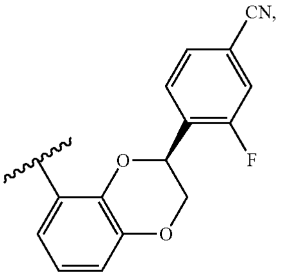
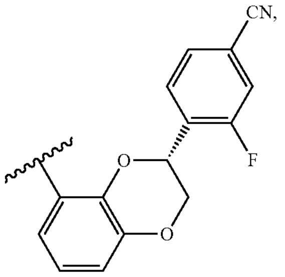
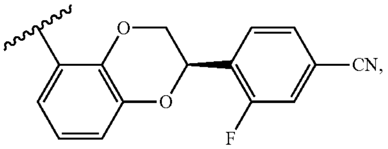
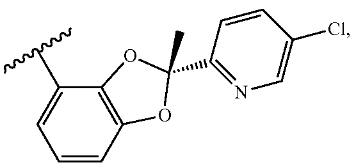
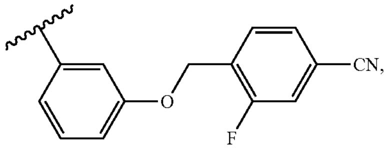
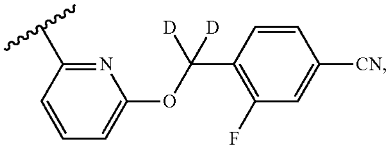
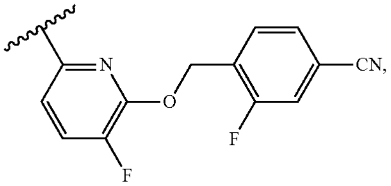
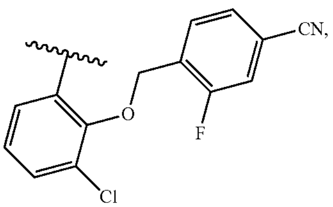
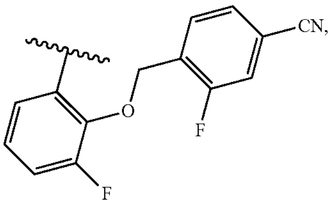
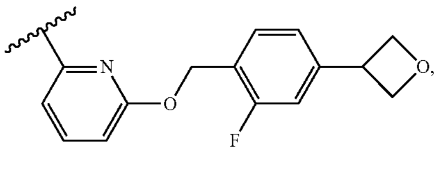
-continued
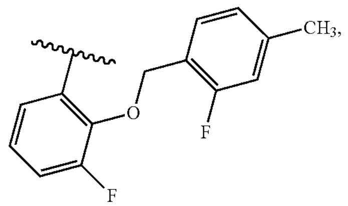
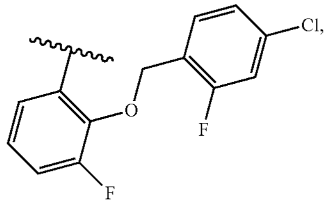
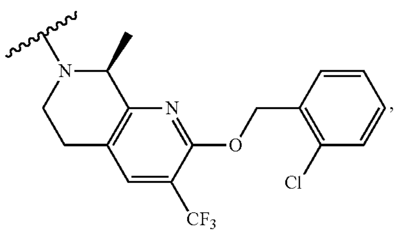
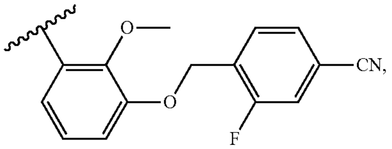
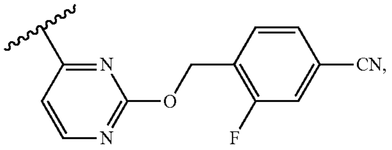
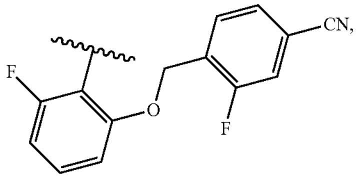
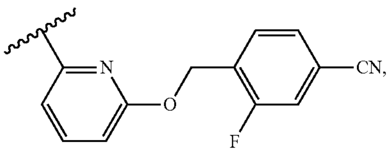
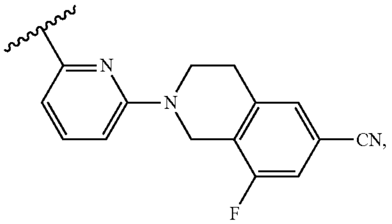
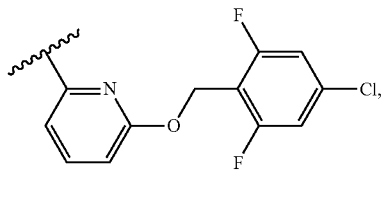

-continued

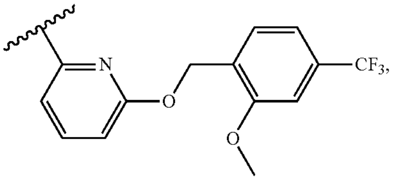

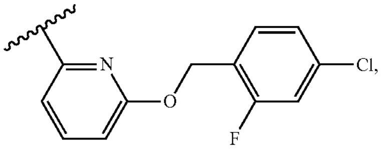

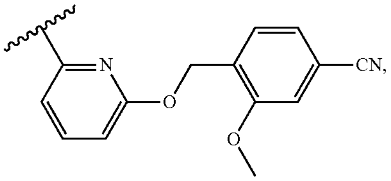

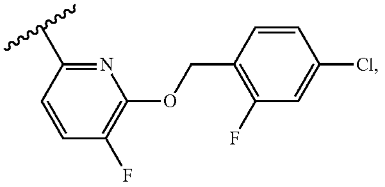

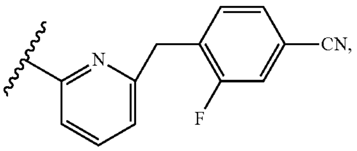

-continued

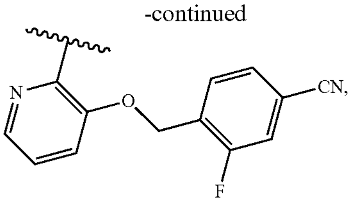

or

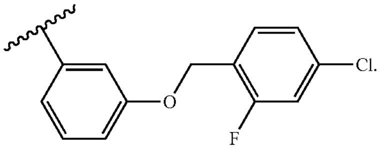

In some embodiments, the GLP-1R agonist is

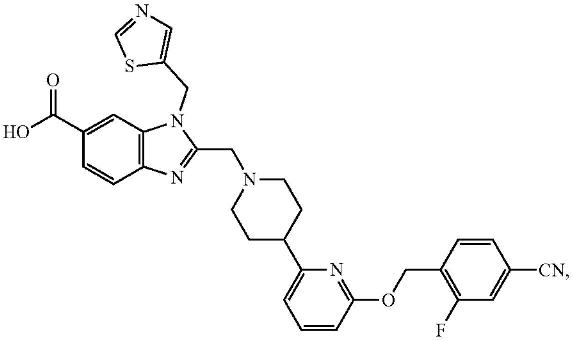 [SMILES: N#Cc1ccc(COc2cccc(C3CCN(Cc4nc5ccc(C(=O)O)cc5n4Cc4cncs4)CC3)n2)c(F)c1]

which is 2-((4-(6-((4-cyano-2-fluorobenzyl)oxy)pyridin-2-yl)piperidin-1-yl)methyl)-1-(thiazol-5-ylmethyl)-1H-benzo[d]imidazole-6-carboxylic acid, or a pharmaceutically acceptable salt thereof. In some embodiments, the GLP-1R agonist is 2-((4-(6-((4-cyano-2-fluorobenzyl)oxy)pyridin-2-yl)piperidin-1-yl)methyl)-1-(thiazol-5-ylmethyl)-1H-benzo[d]imidazole-6-carboxylic acid meglumine salt.

In some embodiments, the GLP-1R agonist is selected from those listed in Table 1 below, or a pharmaceutically acceptable salt thereof:

TABLE 1

| Compound No. | Structure |
|---|---|
| 1-1 | 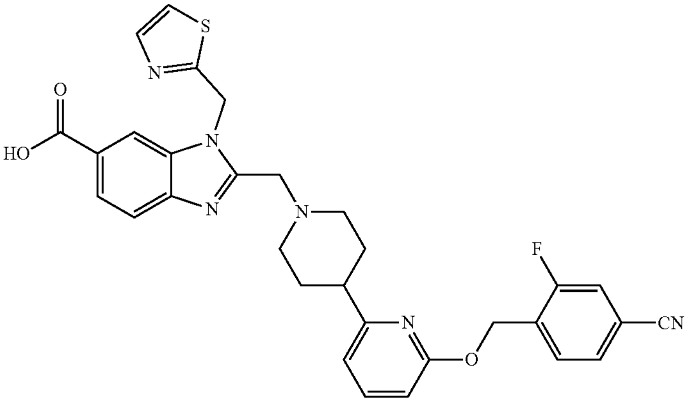 [SMILES: N#Cc1ccc(COc2cccc(C3CCN(Cc4nc5ccc(C(=O)O)cc5n4Cc4nccs4)CC3)n2)c(F)c1] |

TABLE 1-continued
| Compound No. | Structure |
| --- | --- |
| 1-2 | 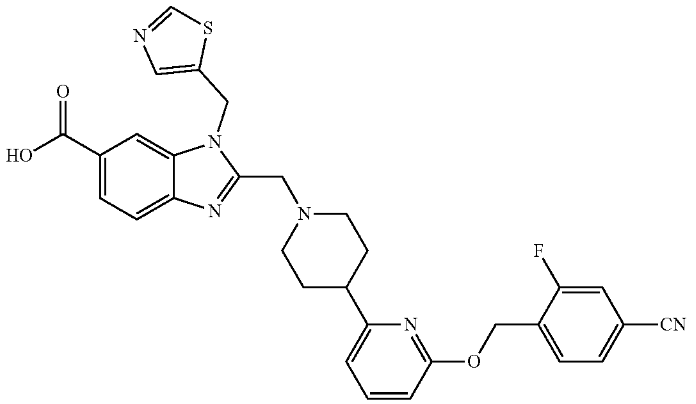 [SMILES: N#Cc1ccc(COc2cccc(C3CCN(Cc4nc5ccc(C(=O)O)cc5n4Cc4cncs4)CC3)n2)c(F)c1] |
| 1-3 | 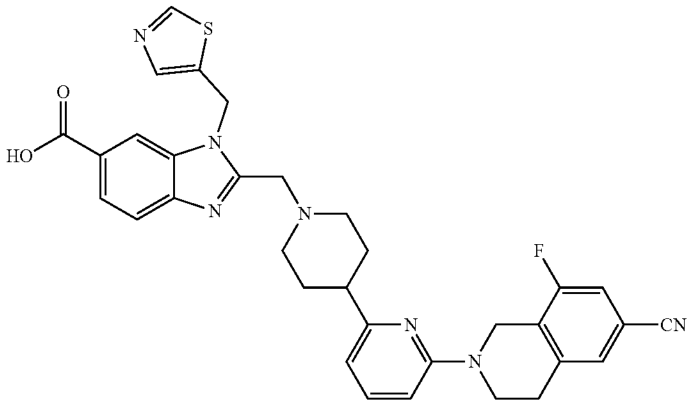 [SMILES: N#Cc1cc(F)c2c(c1)CCN(c1cccc(C3CCN(Cc4nc5ccc(C(=O)O)cc5n4Cc4cncs4)CC3)n1)C2] |
| 1-4 | 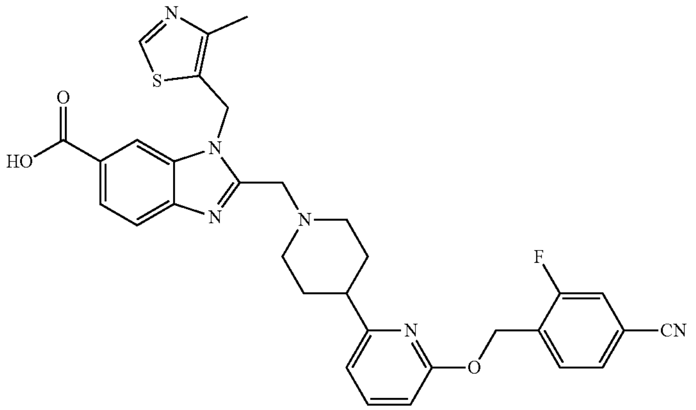 [SMILES: Cc1ncsc1Cn1c(CN2CCC(c3cccc(OCc4ccc(C#N)cc4F)n3)CC2)nc2ccc(C(=O)O)cc21] |

TABLE 1-continued
| Compound No. | Structure |
|---|---|
| 1-5 | 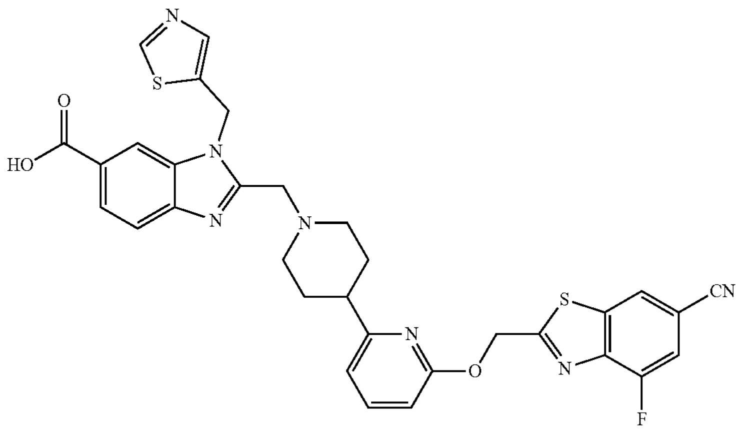 [SMILES: N#Cc1cc(F)c2nc(COc3cccc(C4CCN(Cc5nc6ccc(C(=O)O)cc6n5Cc5cncs5)CC4)n3)sc2c1] |
| 1-6 | 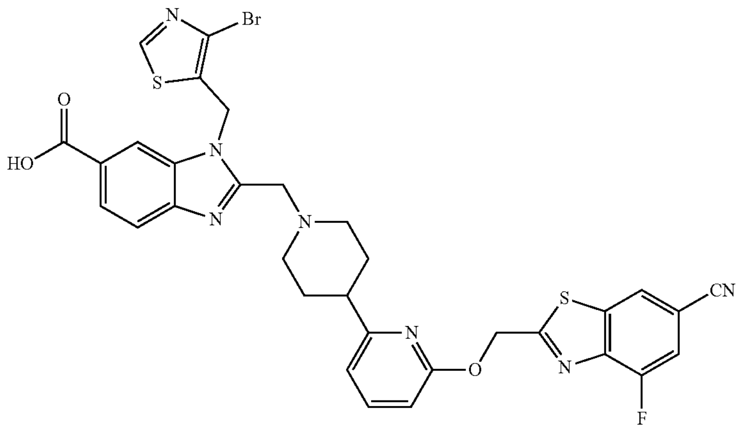 [SMILES: N#Cc1cc(F)c2nc(COc3cccc(C4CCN(Cc5nc6ccc(C(=O)O)cc6n5Cc5scnc5Br)CC4)n3)sc2c1] |
| 1-7 | 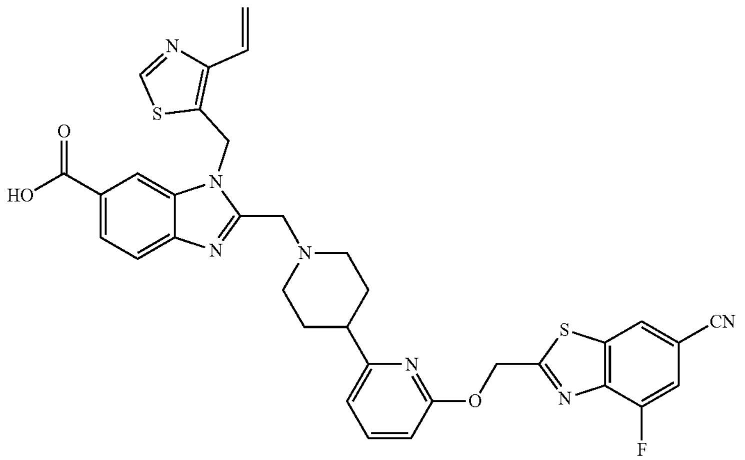 [SMILES: C=Cc1ncsc1Cn1c(CN2CCC(c3cccc(OCc4nc5c(F)cc(C#N)cc5s4)n3)CC2)nc2ccc(C(=O)O)cc21] |

TABLE 1-continued
| Compound No. | Structure |
| --- | --- |
| 1-8 | 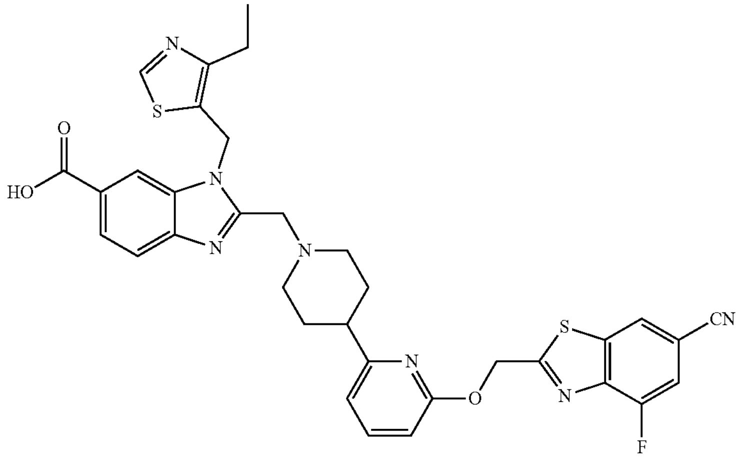 [SMILES: CCc1ncsc1Cn1c(CN2CCC(c3cccc(OCc4nc5c(F)cc(C#N)cc5s4)n3)CC2)nc2ccc(C(=O)O)cc21] |
| 1-9 | 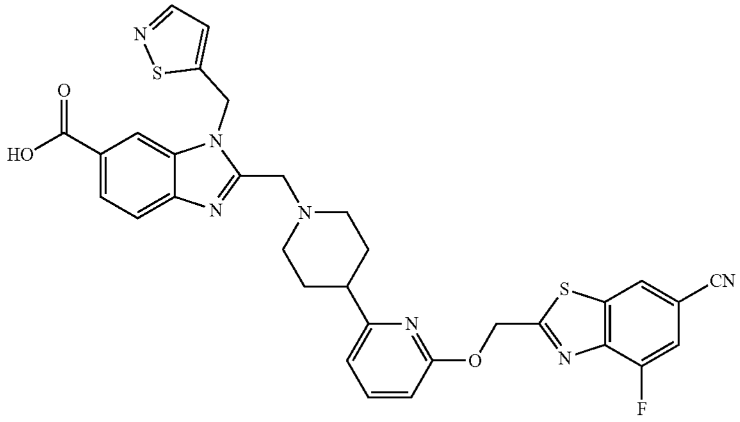 [SMILES: N#Cc1cc(F)c2nc(COc3cccc(C4CCN(Cc5nc6ccc(C(=O)O)cc6n5Cc5ccns5)CC4)n3)sc2c1] |
| 1-10 | 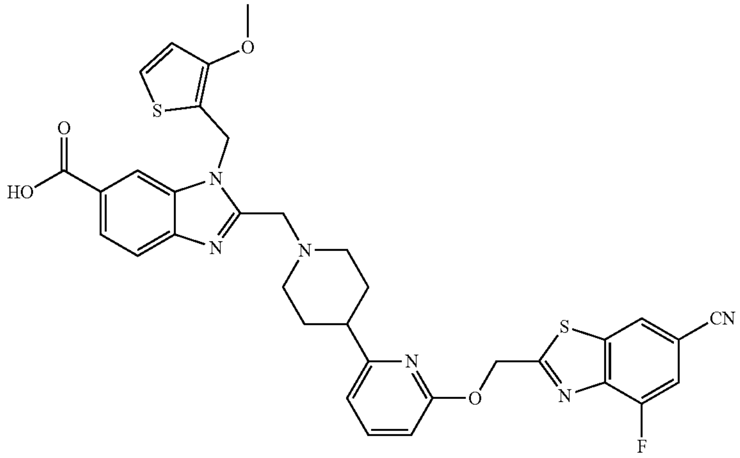 [SMILES: COc1ccsc1Cn1c(CN2CCC(c3cccc(OCc4nc5c(F)cc(C#N)cc5s4)n3)CC2)nc2ccc(C(=O)O)cc21] |

TABLE 1-continued
| Compound No. | Structure |
|---|---|
| 1-11 | 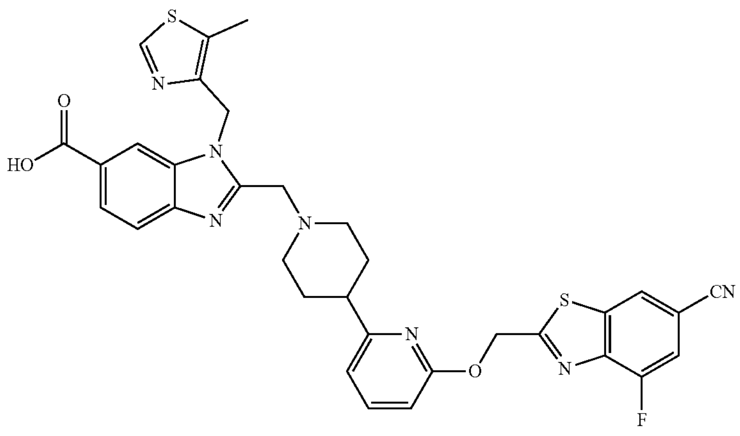 [SMILES: Cc1scnc1Cn1c(CN2CCC(c3cccc(OCc4nc5c(F)cc(C#N)cc5s4)n3)CC2)nc2ccc(C(=O)O)cc21] |
| 1-12 | 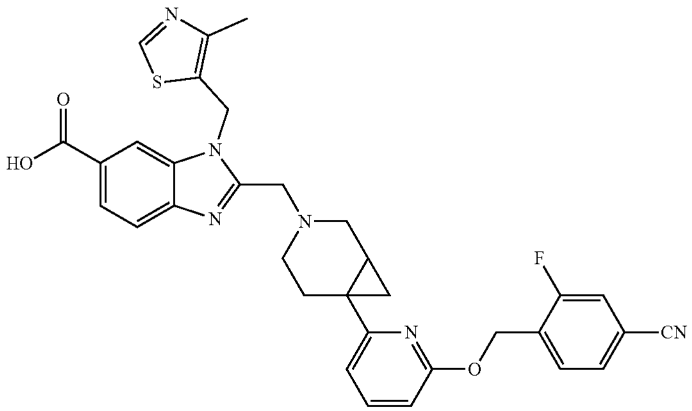 [SMILES: Cc1ncsc1Cn1c(CN2CCC3(c4cccc(OCc5ccc(C#N)cc5F)n4)CC3C2)nc2ccc(C(=O)O)cc21] |
| 1-13 | 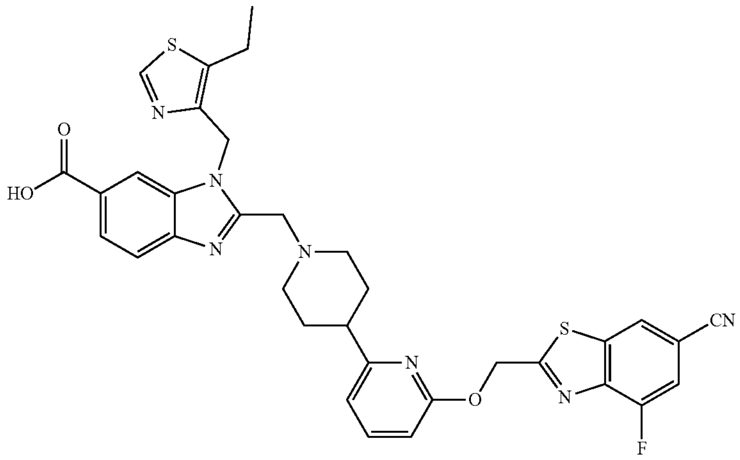 [SMILES: CCc1scnc1Cn1c(CN2CCC(c3cccc(OCc4nc5c(F)cc(C#N)cc5s4)n3)CC2)nc2ccc(C(=O)O)cc21] |

TABLE 1-continued
| Compound No. | Structure |
| --- | --- |
| 1-14 | 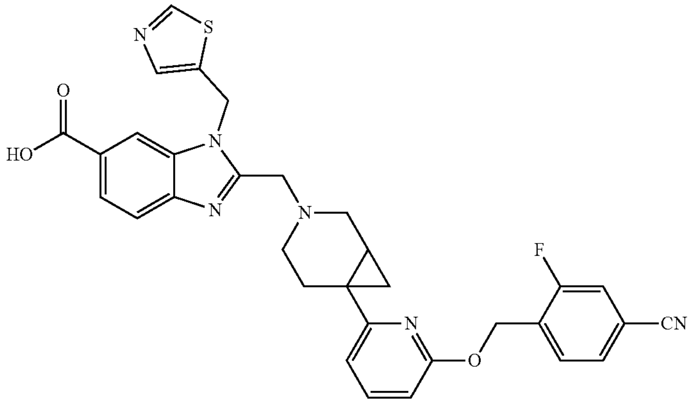 [SMILES: N#Cc1ccc(COc2cccc(C34CCN(Cc5nc6ccc(C(=O)O)cc6n5Cc5cncs5)CC3C4)n2)c(F)c1] |
| 1-15 | 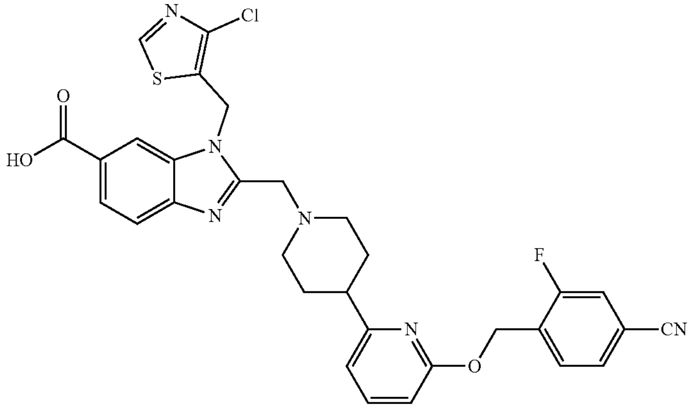 [SMILES: N#Cc1ccc(COc2cccc(C3CCN(Cc4nc5ccc(C(=O)O)cc5n4Cc4scnc4Cl)CC3)n2)c(F)c1] |
| 1-16 | 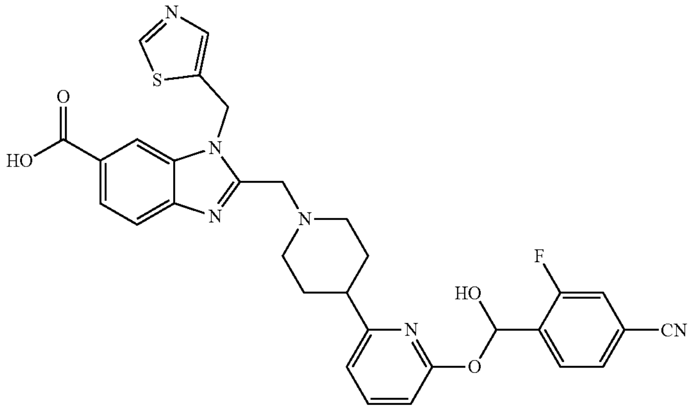 [SMILES: N#Cc1ccc(C(O)Oc2cccc(C3CCN(Cc4nc5ccc(C(=O)O)cc5n4Cc4cncs4)CC3)n2)c(F)c1] |

TABLE 1-continued
| Compound No. | Structure |
|---|---|
| 1-17 | 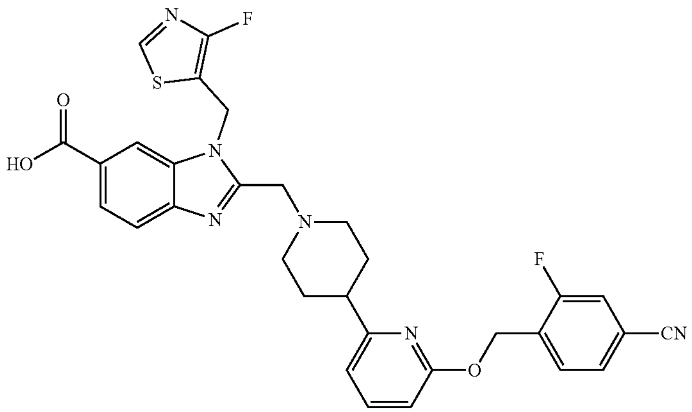 [SMILES: N#Cc1ccc(COc2cccc(C3CCN(Cc4nc5ccc(C(=O)O)cc5n4Cc4scnc4F)CC3)n2)c(F)c1] |
| 1-18 | 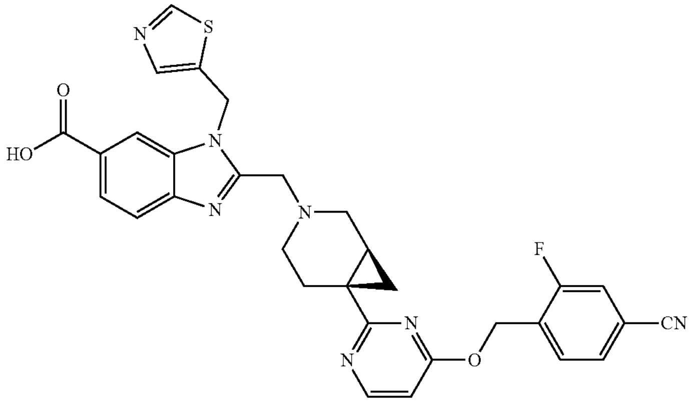 [SMILES: N#Cc1ccc(COc2ccnc([C@]34CCN(Cc5nc6ccc(C(=O)O)cc6n5Cc5cncs5)C[C@H]3C4)n2)c(F)c1] |
| 1-19 | 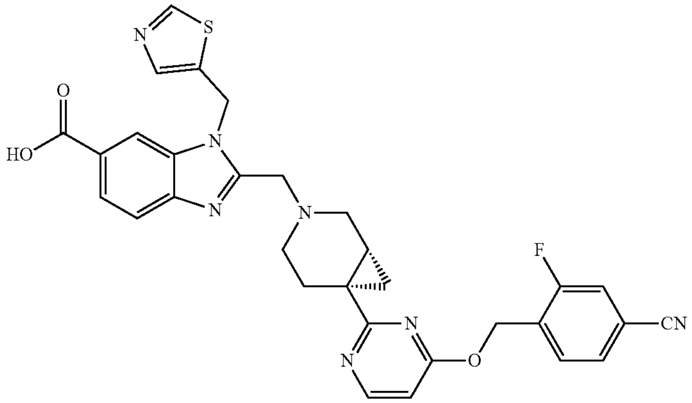 [SMILES: N#Cc1ccc(COc2ccnc([C@@]34CCN(Cc5nc6ccc(C(=O)O)cc6n5Cc5cncs5)C[C@@H]3C4)n2)c(F)c1] |

TABLE 1-continued
| Compound No. | Structure |
| --- | --- |
| 1-20 | 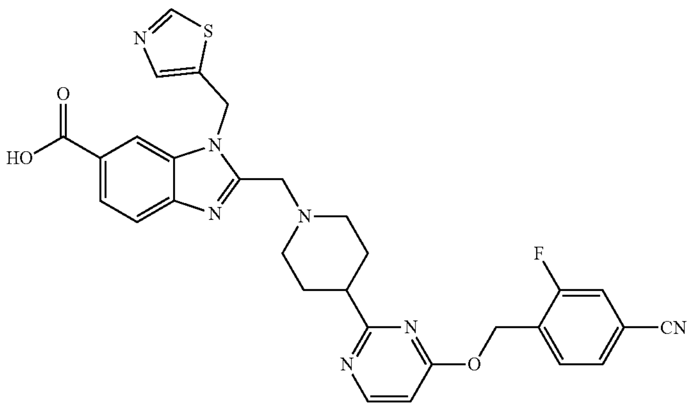 [SMILES: N#Cc1ccc(COc2ccnc(C3CCN(Cc4nc5ccc(C(=O)O)cc5n4Cc4cncs4)CC3)n2)c(F)c1] |
| 1-21 | 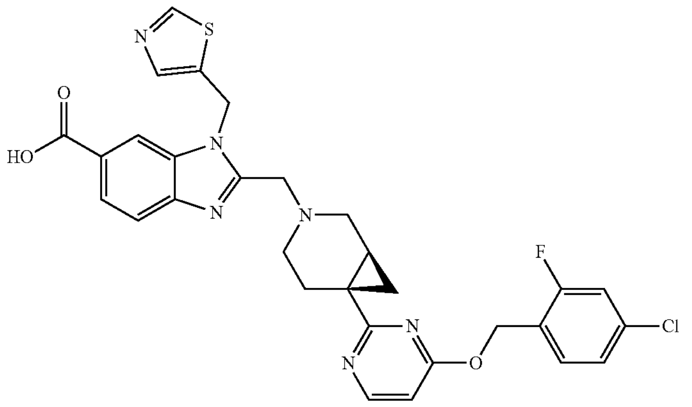 [SMILES: O=C(O)c1ccc2nc(CN3CC[C@]4(c5nccc(OCc6ccc(Cl)cc6F)n5)C[C@@H]4C3)n(Cc3cncs3)c2c1] |
| 1-22 | 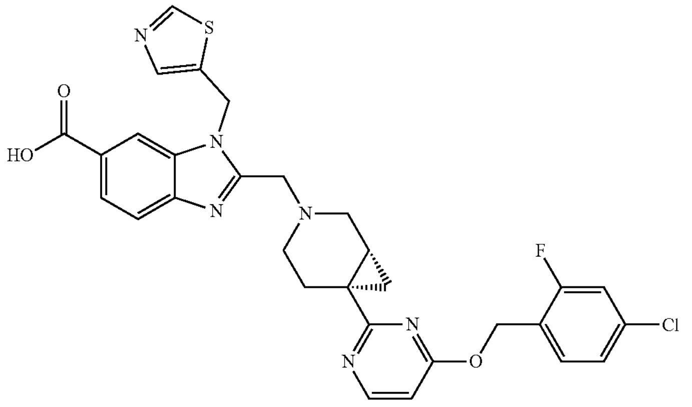 [SMILES: O=C(O)c1ccc2nc(CN3CC[C@@]4(c5nccc(OCc6ccc(Cl)cc6F)n5)C[C@H]4C3)n(Cc3cncs3)c2c1] |

TABLE 1-continued
| Compound No. | Structure |
| --- | --- |
| 1-23 | 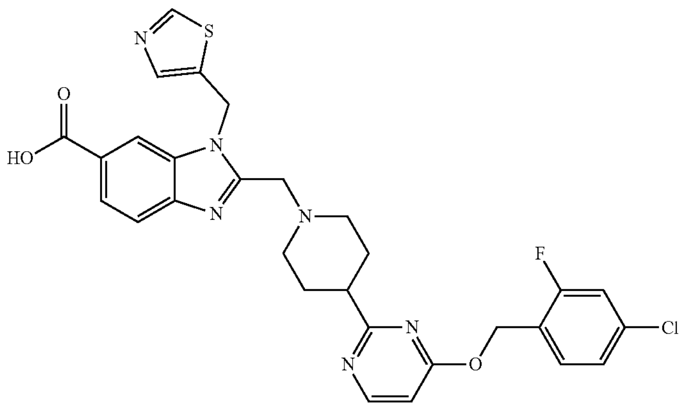 [SMILES: O=C(O)c1ccc2nc(CN3CCC(c4nccc(OCc5ccc(Cl)cc5F)n4)CC3)n(Cc3cncs3)c2c1] |
| 1-24 | 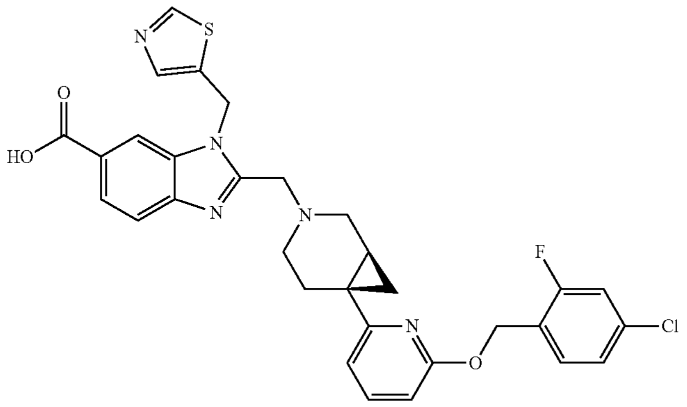 [SMILES: O=C(O)c1ccc2nc(CN3CC[C@]4(c5cccc(OCc6ccc(Cl)cc6F)n5)C[C@@H]4C3)n(Cc3cncs3)c2c1] |
| 1-25 | 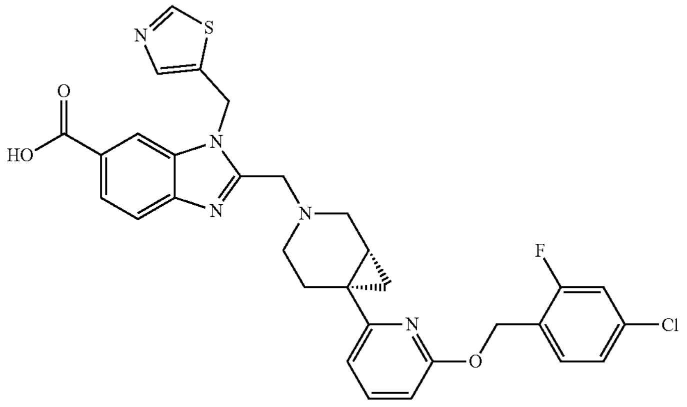 [SMILES: O=C(O)c1ccc2nc(CN3CC[C@@]4(c5cccc(OCc6ccc(Cl)cc6F)n5)C[C@H]4C3)n(Cc3cncs3)c2c1] |

TABLE 1-continued
| Compound No. | Structure |
| --- | --- |
| 1-26 | 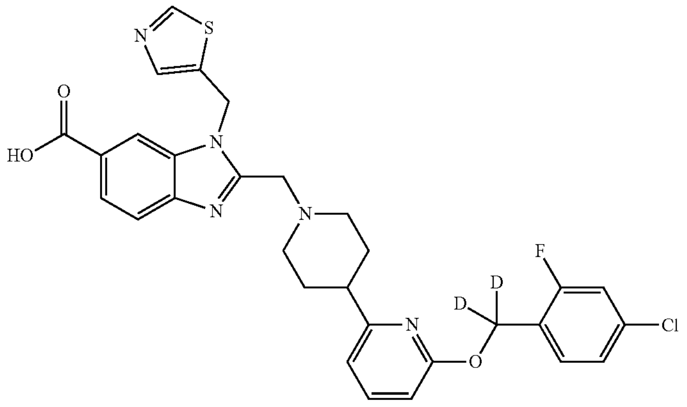 [SMILES: [2H]C([2H])(Oc1cccc(C2CCN(Cc3nc4ccc(C(=O)O)cc4n3Cc3cncs3)CC2)n1)c1ccc(Cl)cc1F] |
| 1-27 | 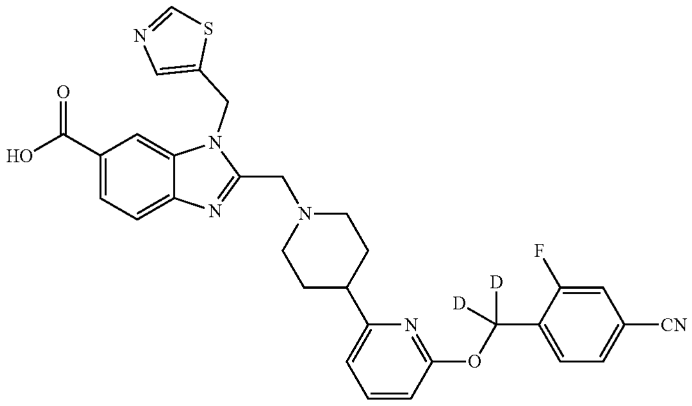 [SMILES: [2H]C([2H])(Oc1cccc(C2CCN(Cc3nc4ccc(C(=O)O)cc4n3Cc3cncs3)CC2)n1)c1ccc(C#N)cc1F] |
| 1-28 | 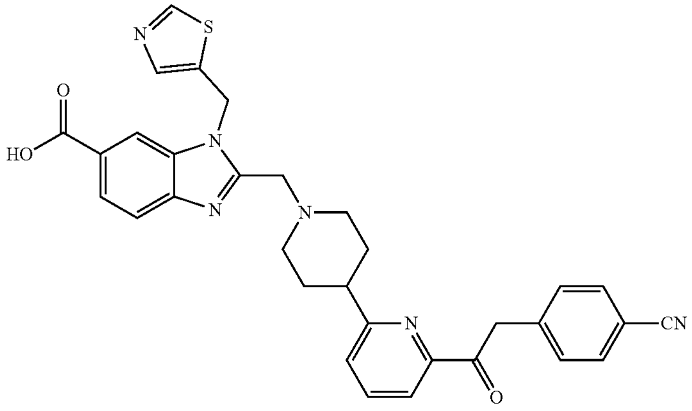 [SMILES: N#Cc1ccc(CC(=O)c2cccc(C3CCN(Cc4nc5ccc(C(=O)O)cc5n4Cc4cncs4)CC3)n2)cc1] |

TABLE 1-continued
| Compound No. | Structure |
| --- | --- |
| 1-29 | 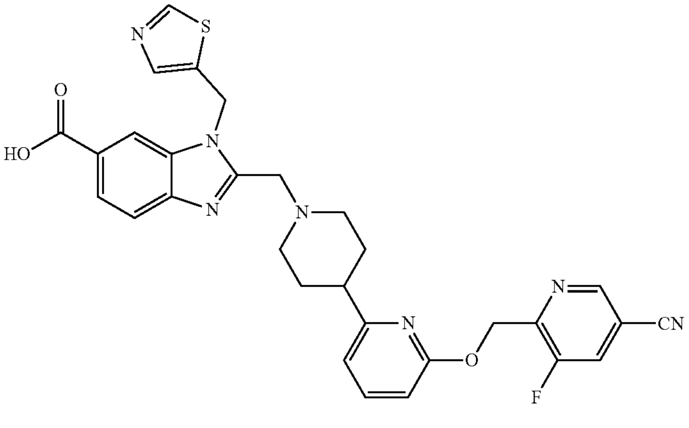 [SMILES: N#Cc1cnc(COc2cccc(C3CCN(Cc4nc5ccc(C(=O)O)cc5n4Cc4cncs4)CC3)n2)c(F)c1] |
| 1-30 | 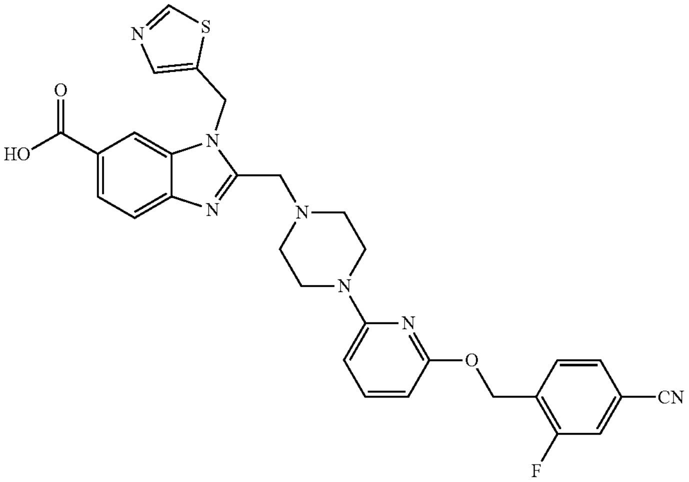 [SMILES: N#Cc1ccc(COc2cccc(N3CCN(Cc4nc5ccc(C(=O)O)cc5n4Cc4cncs4)CC3)n2)c(F)c1] |
| 1-31 | 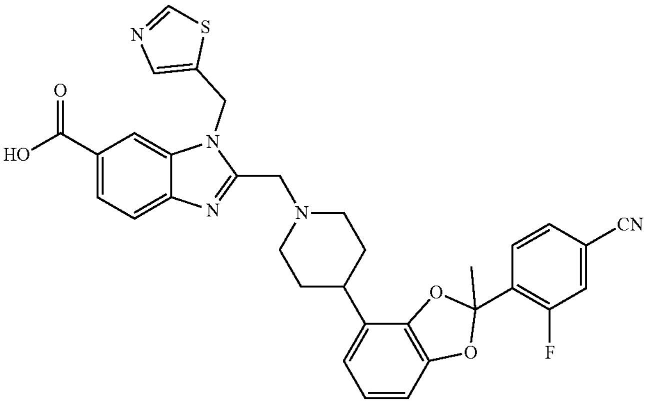 [SMILES: CC1(c2ccc(C#N)cc2F)Oc2cccc(C3CCN(Cc4nc5ccc(C(=O)O)cc5n4Cc4cncs4)CC3)c2O1] |
In some embodiments, the GLP-1R agonist is selected from those listed in Table 2 below, or a pharmaceutically acceptable salt thereof.

TABLE 3
| Compound No. | Structure |
|---|---|
| 2-1 | 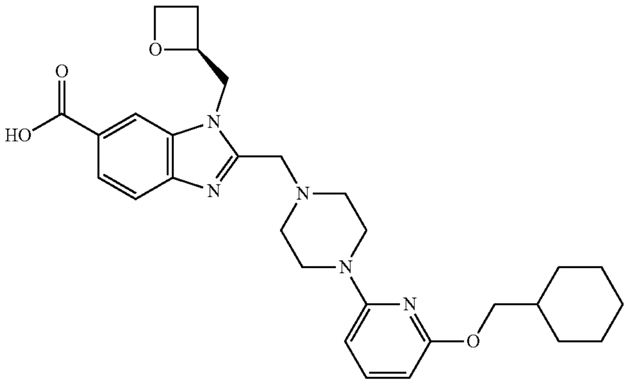 [SMILES: O=C(O)c1ccc2nc(CN3CCN(c4cccc(OCC5CCCCC5)n4)CC3)n(C[C@@H]3CCO3)c2c1] |
| 2-2 | 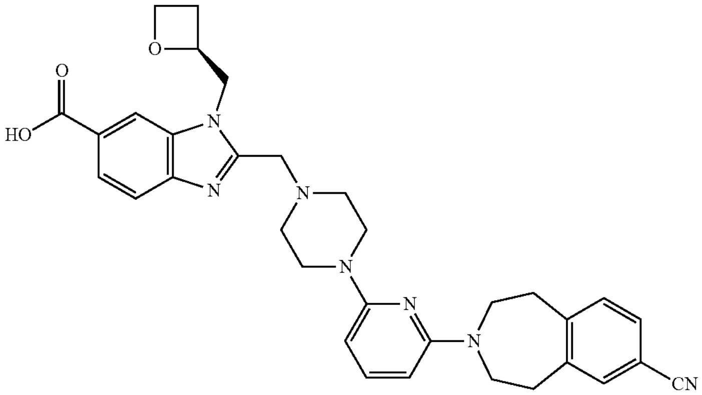 [SMILES: N#Cc1ccc2c(c1)CCN(c1cccc(N3CCN(Cc4nc5ccc(C(=O)O)cc5n4C[C@@H]4CCO4)CC3)n1)CC2] |
| 2-3 | 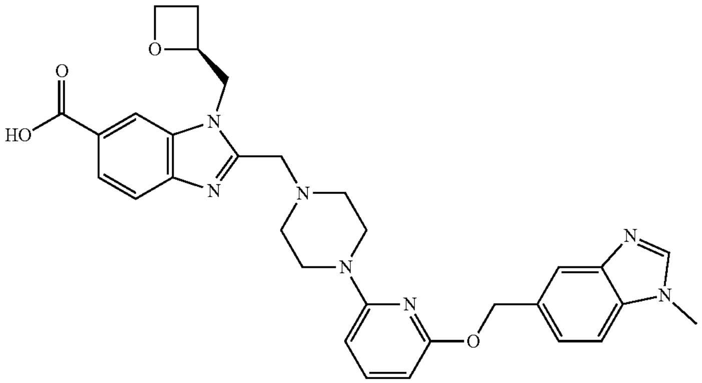 [SMILES: Cn1cnc2cc(COc3cccc(N4CCN(Cc5nc6ccc(C(=O)O)cc6n5C[C@@H]5CCO5)CC4)n3)ccc21] |
| 2-4 | 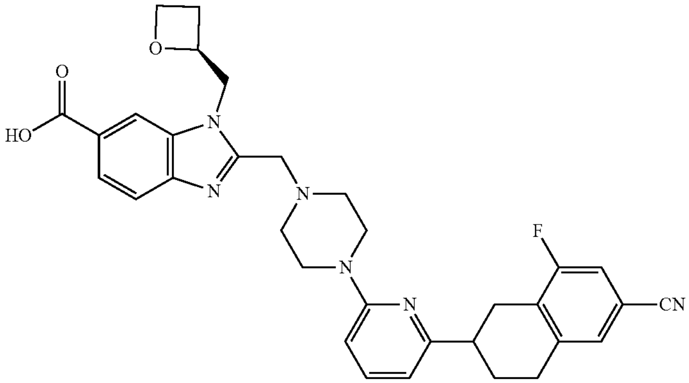 [SMILES: N#Cc1cc(F)c2c(c1)CCC(c1cccc(N3CCN(Cc4nc5ccc(C(=O)O)cc5n4C[C@@H]4CCO4)CC3)n1)C2] |

TABLE 3-continued
| Compound No. | Structure |
| --- | --- |
| 2-5 | 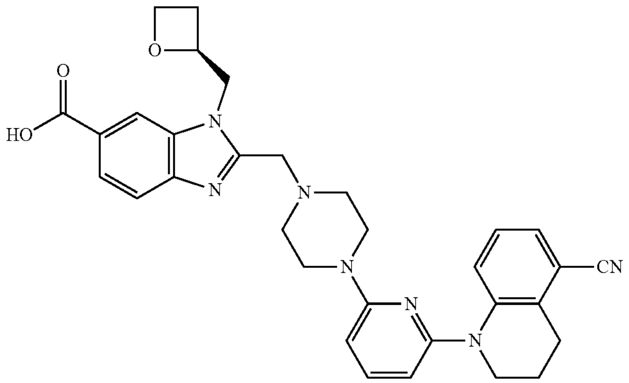 [SMILES: N#Cc1cccc2c1CCCN2c1cccc(N2CCN(Cc3nc4ccc(C(=O)O)cc4n3C[C@@H]3CCO3)CC2)n1] |
| 2-6-P1 | 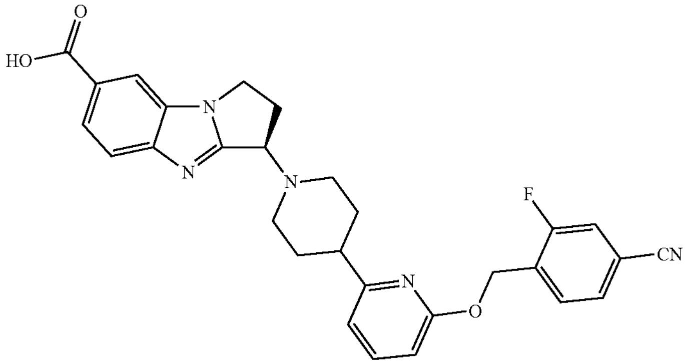 [SMILES: N#Cc1ccc(COc2cccc(C3CCN([C@@H]4CCn5c4nc4ccc(C(=O)O)cc45)CC3)n2)c(F)c1] |
| 2-6-P2 | 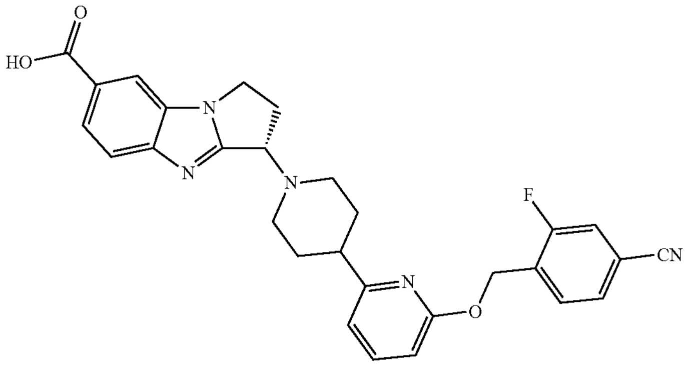 [SMILES: N#Cc1ccc(COc2cccc(C3CCN([C@H]4CCn5c4nc4ccc(C(=O)O)cc45)CC3)n2)c(F)c1] |
| 2-7-P1 | 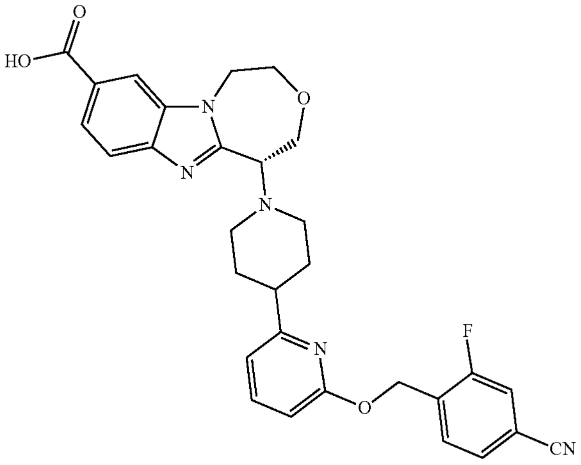 [SMILES: N#Cc1ccc(COc2cccc(C3CCN([C@H]4COCCn5c4nc4ccc(C(=O)O)cc45)CC3)n2)c(F)c1] |

TABLE 3-continued
| Compound No. | Structure |
|---|---|
| 2-7-P2 | 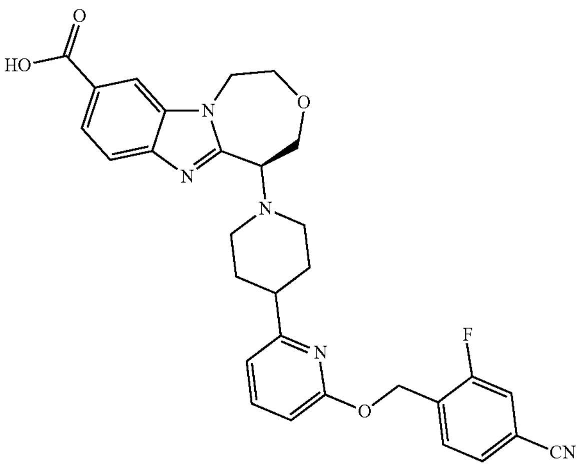 [SMILES: N#Cc1ccc(COc2cccc(C3CCN([C@@H]4COCCn5c4nc4ccc(C(=O)O)cc45)CC3)n2)c(F)c1] |
| 2-8-P1 | 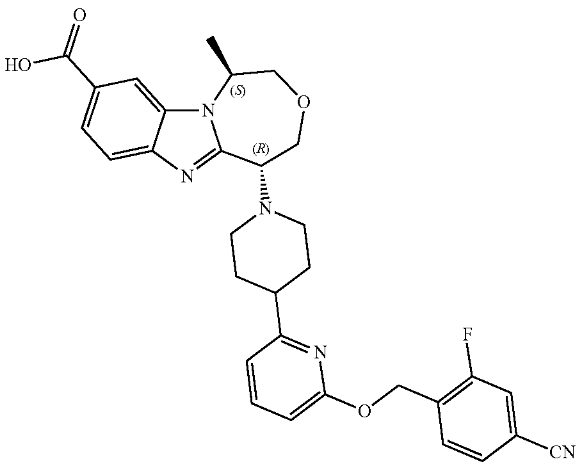 |
| 2-8-P2 | 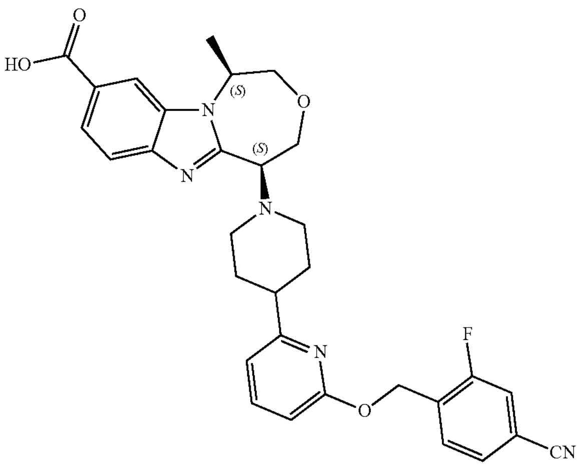 |

TABLE 3-continued
| Compound No. | Structure |
| --- | --- |
| 2-9 | 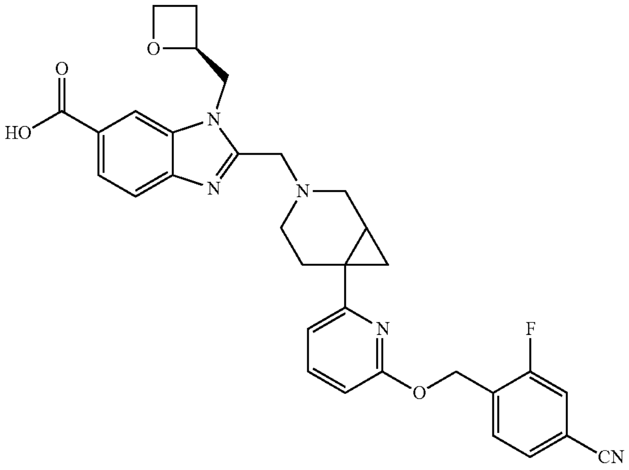 [SMILES: N#Cc1ccc(COc2cccc(C34CCN(Cc5nc6ccc(C(=O)O)cc6n5C[C@@H]5CCO5)CC3C4)n2)c(F)c1] |
| 2-9-P1 | 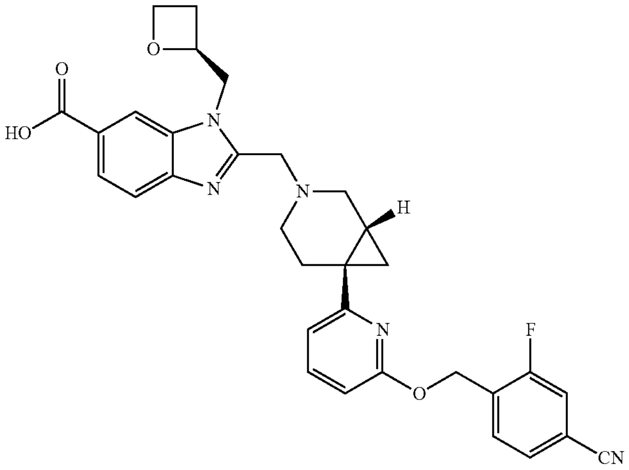 [SMILES: N#Cc1ccc(COc2cccc([C@@]34CCN(Cc5nc6ccc(C(=O)O)cc6n5C[C@@H]5CCO5)C[C@@H]3C4)n2)c(F)c1] |
| 2-9-P2 | 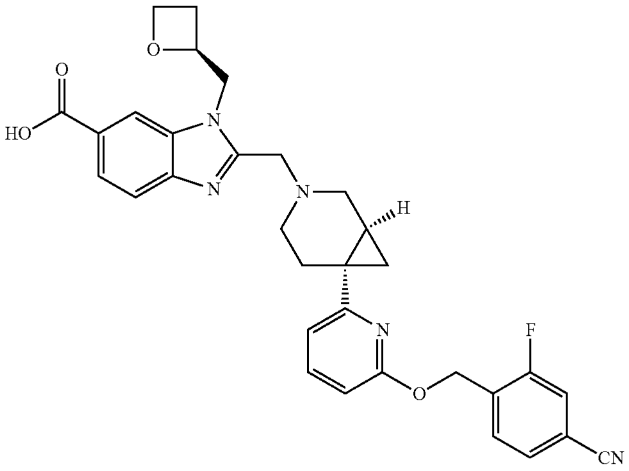 [SMILES: N#Cc1ccc(COc2cccc([C@]34CCN(Cc5nc6ccc(C(=O)O)cc6n5C[C@@H]5CCO5)C[C@H]3C4)n2)c(F)c1] |

TABLE 3-continued
| Compound No. | Structure |
| --- | --- |
| 2-10-P1 | 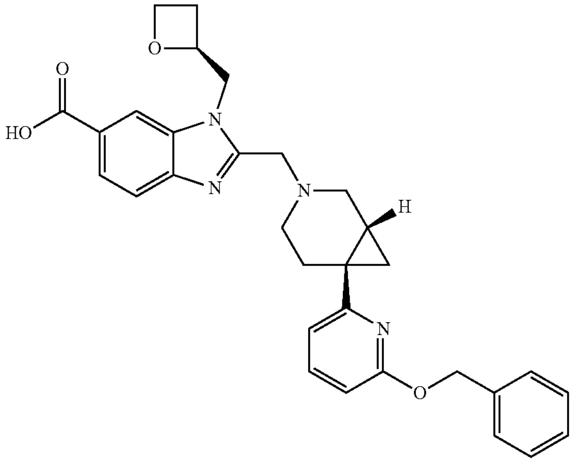 [SMILES: O=C(O)c1ccc2nc(CN3CC[C@@]4(c5cccc(OCc6ccccc6)n5)C[C@H]4C3)n(C[C@@H]3CCO3)c2c1] |
| 2-10-P2 | 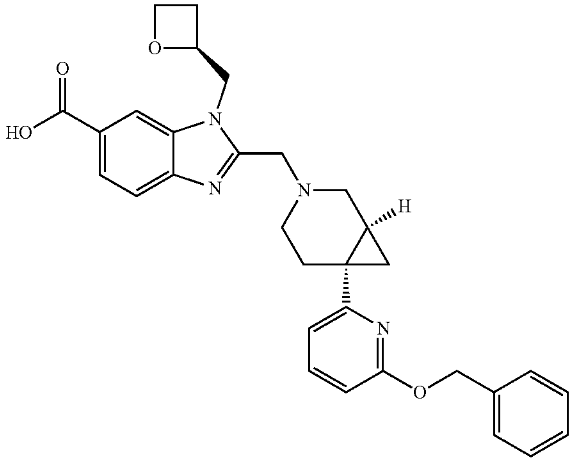 [SMILES: O=C(O)c1ccc2nc(CN3CC[C@]4(c5cccc(OCc6ccccc6)n5)C[C@@H]4C3)n(C[C@@H]3CCO3)c2c1] |
| 2-11-P1 | 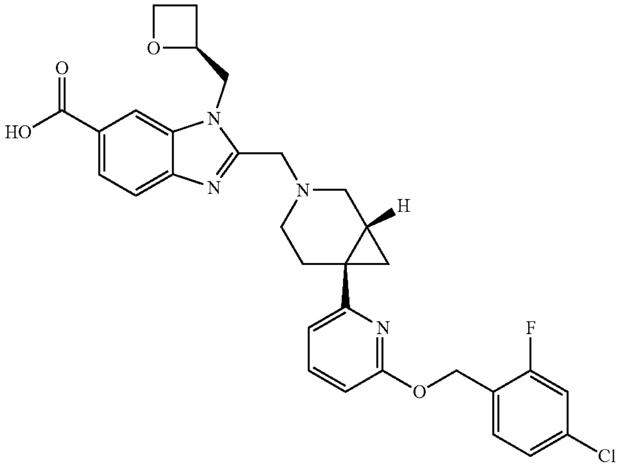 [SMILES: O=C(O)c1ccc2nc(CN3CC[C@@]4(c5cccc(OCc6ccc(Cl)cc6F)n5)C[C@H]4C3)n(C[C@@H]3CCO3)c2c1] |

TABLE 3-continued
| Compound No. | Structure |
| --- | --- |
| 2-11-P2 | 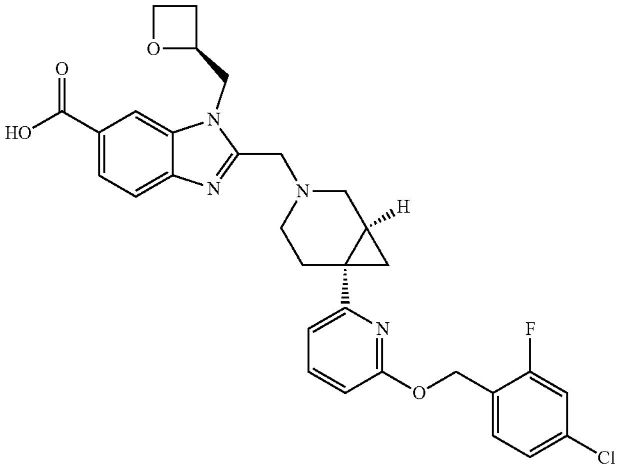 [SMILES: O=C(O)c1ccc2nc(CN3CC[C@]4(c5cccc(OCc6ccc(Cl)cc6F)n5)C[C@@H]4C3)n(C[C@@H]3CCO3)c2c1] |
| 2-12 | 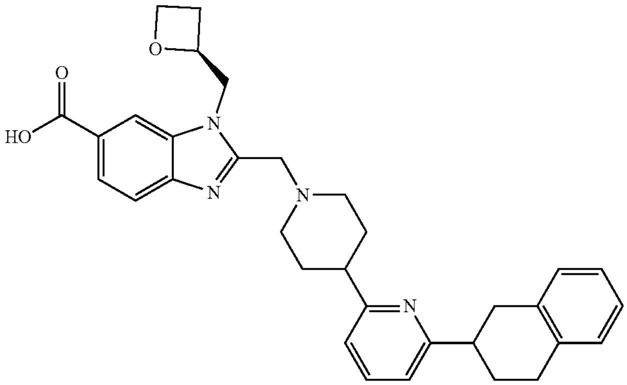 [SMILES: O=C(O)c1ccc2nc(CN3CCC(c4cccc(C5CCc6ccccc6C5)n4)CC3)n(C[C@@H]3CCO3)c2c1] |
| 2-13 | 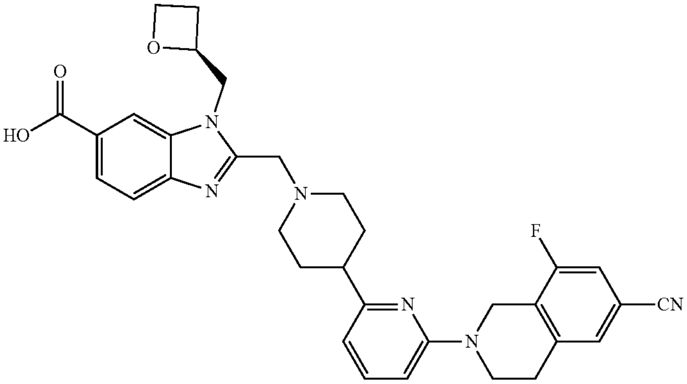 [SMILES: N#Cc1cc(F)c2c(c1)CCN(c1cccc(C3CCN(Cc4nc5ccc(C(=O)O)cc5n4C[C@@H]4CCO4)CC3)n1)C2] |

TABLE 3-continued
| Compound No. | Structure |
| --- | --- |
| 2-14 | 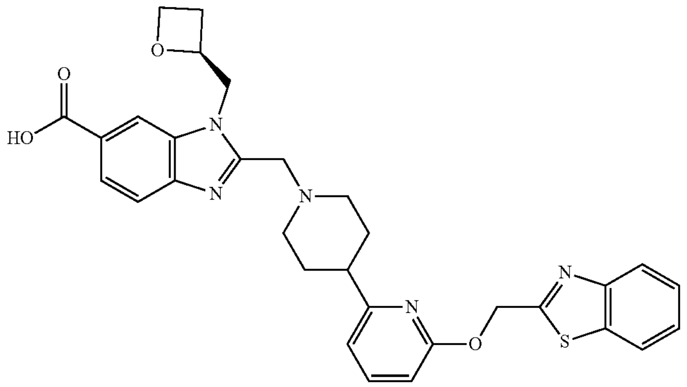 [SMILES: O=C(O)c1ccc2nc(CN3CCC(c4cccc(OCc5nc6ccccc6s5)n4)CC3)n(C[C@@H]3CCO3)c2c1] |
| 2-15 | 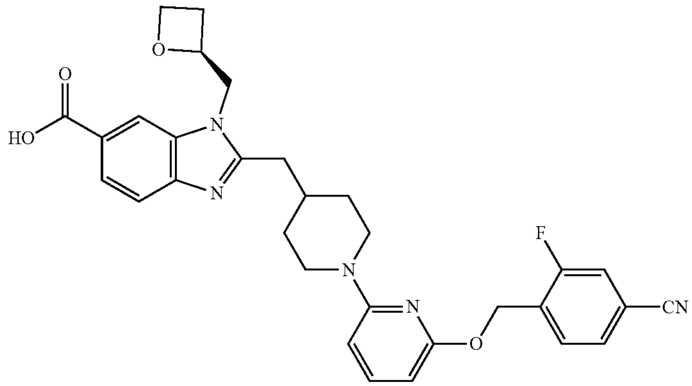 [SMILES: N#Cc1ccc(COc2cccc(N3CCC(Cc4nc5ccc(C(=O)O)cc5n4C[C@@H]4CCO4)CC3)n2)c(F)c1] |
| 2-16 | 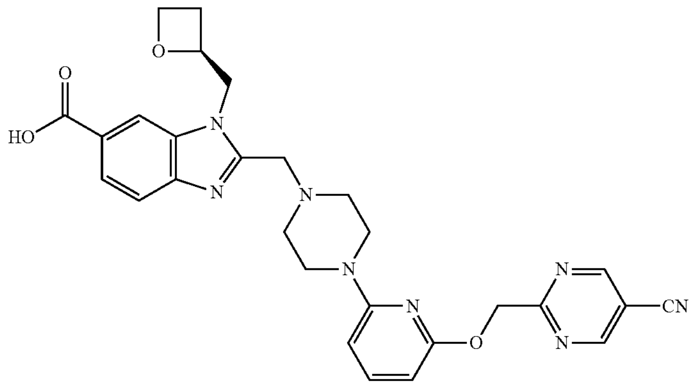 |
| 2-17 | 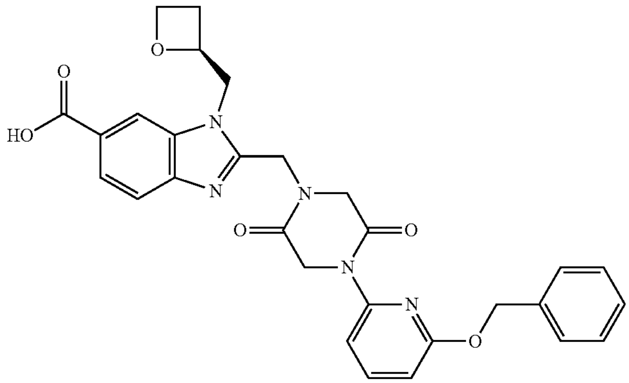 [SMILES: O=C(O)c1ccc2nc(CN3CC(=O)N(c4cccc(OCc5ccccc5)n4)CC3=O)n(C[C@@H]3CCO3)c2c1] |

TABLE 3-continued
| Compound No. | Structure |
| --- | --- |
| 2-18 | 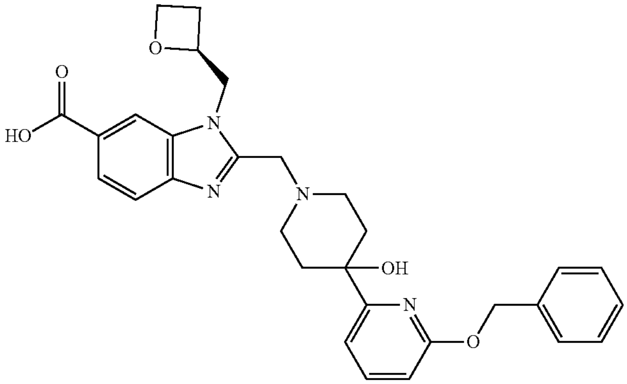 [SMILES: O=C(O)c1ccc2nc(CN3CCC(O)(c4cccc(OCc5ccccc5)n4)CC3)n(C[C@@H]3CCO3)c2c1] |
| 2-19 | 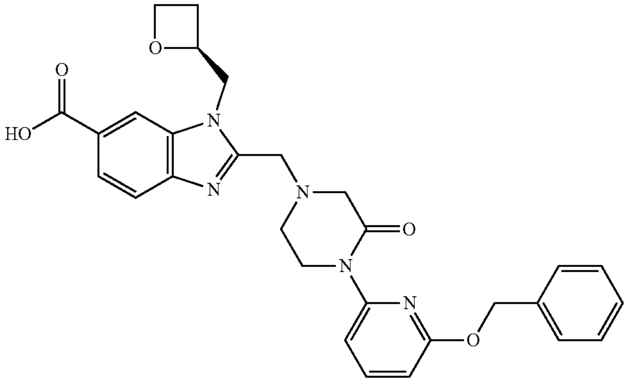 [SMILES: O=C(O)c1ccc2nc(CN3CCN(c4cccc(OCc5ccccc5)n4)C(=O)C3)n(C[C@@H]3CCO3)c2c1] |
| 2-20-P1 | 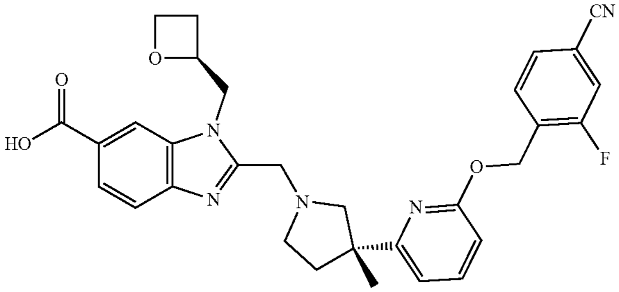 [SMILES: C[C@@]1(c2cccc(OCc3ccc(C#N)cc3F)n2)CCN(Cc2nc3ccc(C(=O)O)cc3n2C[C@@H]2CCO2)C1] |
| 2-20-P2 | 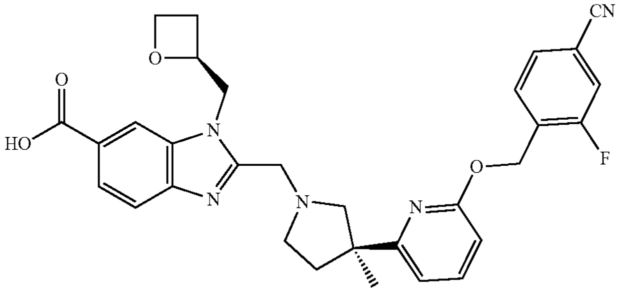 [SMILES: C[C@]1(c2cccc(OCc3ccc(C#N)cc3F)n2)CCN(Cc2nc3ccc(C(=O)O)cc3n2C[C@@H]2CCO2)C1] |

TABLE 3-continued
| Compound No. | Structure |
| --- | --- |
| 2-21 | 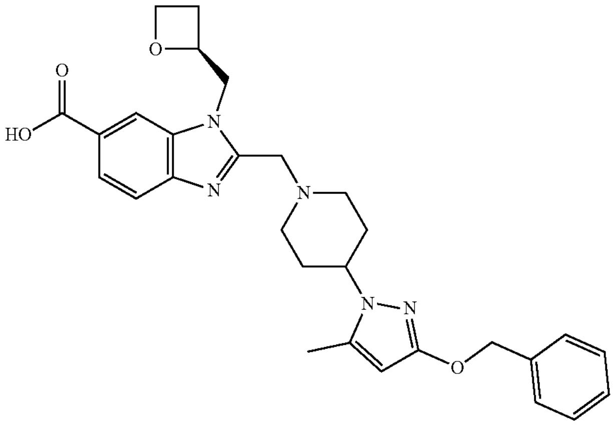 [SMILES: Cc1cc(OCc2ccccc2)nn1C1CCN(Cc2nc3ccc(C(=O)O)cc3n2C[C@@H]2CCO2)CC1] |
| 2-22 | 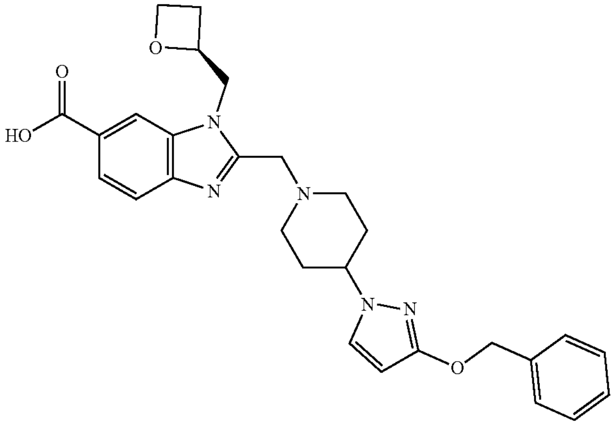 [SMILES: O=C(O)c1ccc2nc(CN3CCC(n4ccc(OCc5ccccc5)n4)CC3)n(C[C@@H]3CCO3)c2c1] |
| 2-23 | 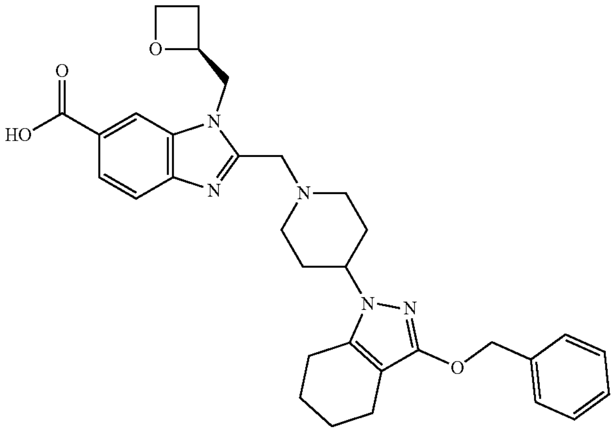 [SMILES: O=C(O)c1ccc2nc(CN3CCC(n4nc(OCc5ccccc5)c5c4CCCC5)CC3)n(C[C@@H]3CCO3)c2c1] |

TABLE 3-continued
| Compound No. | Structure |
|---|---|
| 2-24 | 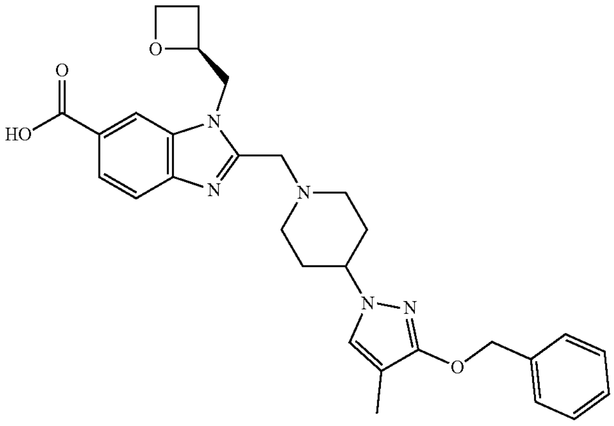 [SMILES: Cc1cn(C2CCN(Cc3nc4ccc(C(=O)O)cc4n3C[C@@H]3CCO3)CC2)nc1OCc1ccccc1] |
| 2-25 | 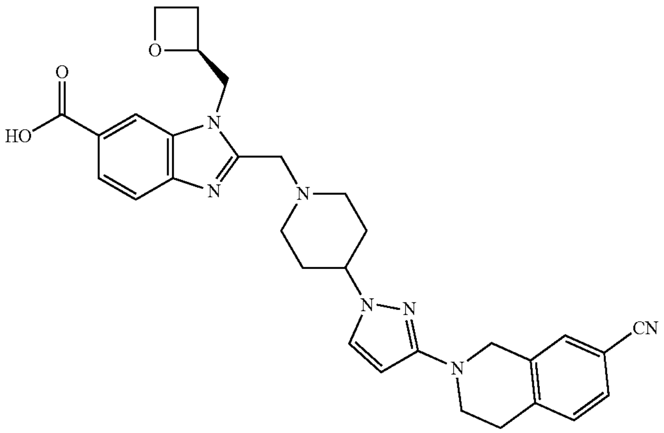 [SMILES: N#Cc1ccc2c(c1)CN(c1ccn(C3CCN(Cc4nc5ccc(C(=O)O)cc5n4C[C@@H]4CCO4)CC3)n1)CC2] |
| 2-26-P1 | 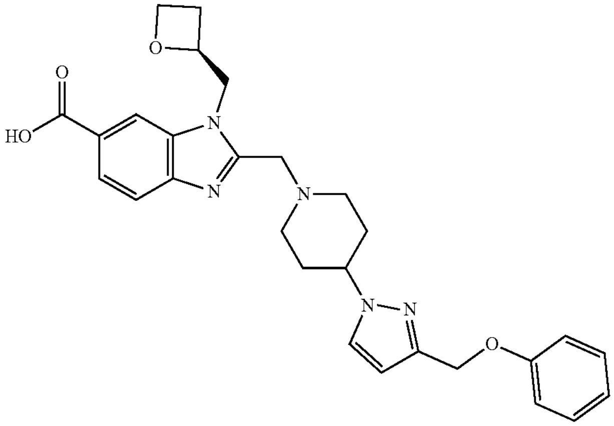 [SMILES: O=C(O)c1ccc2nc(CN3CCC(n4ccc(COc5ccccc5)n4)CC3)n(C[C@@H]3CCO3)c2c1] |

TABLE 3-continued
| Compound No. | Structure |
|---|---|
| 2-26-P2 | 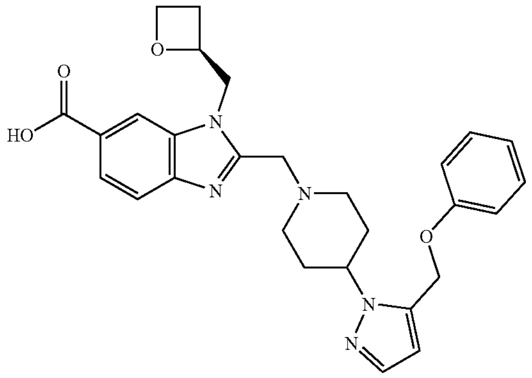 [SMILES: O=C(O)c1ccc2nc(CN3CCC(n4nccc4COc4ccccc4)CC3)n(C[C@@H]3CCO3)c2c1] |
| 2-27 | 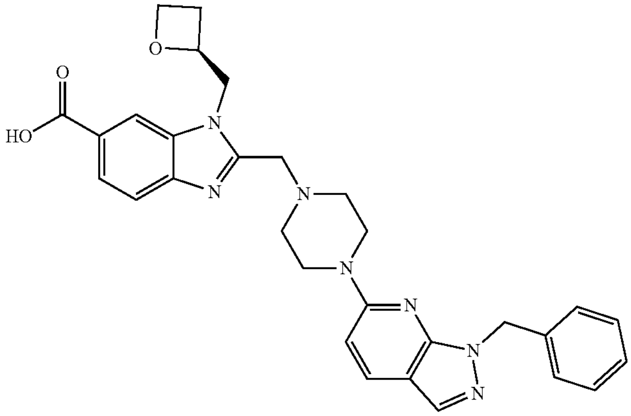 [SMILES: O=C(O)c1ccc2nc(CN3CCN(c4ccc5cnn(Cc6ccccc6)c5n4)CC3)n(C[C@@H]3CCO3)c2c1] |
| 2-28 | 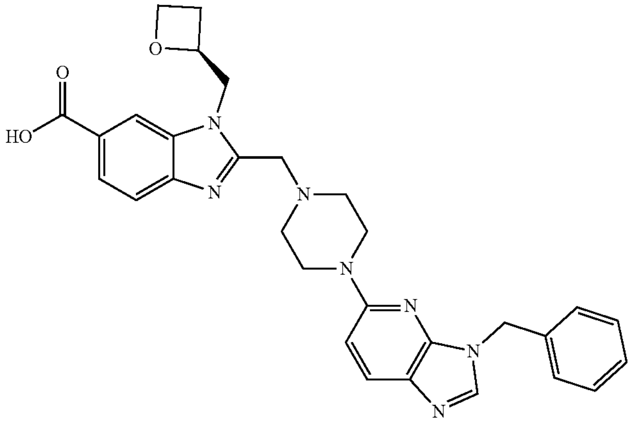 [SMILES: O=C(O)c1ccc2nc(CN3CCN(c4ccc5ncn(Cc6ccccc6)c5n4)CC3)n(C[C@@H]3CCO3)c2c1] |

TABLE 3-continued
| Compound No. | Structure |
|---|---|
| 2-29 | 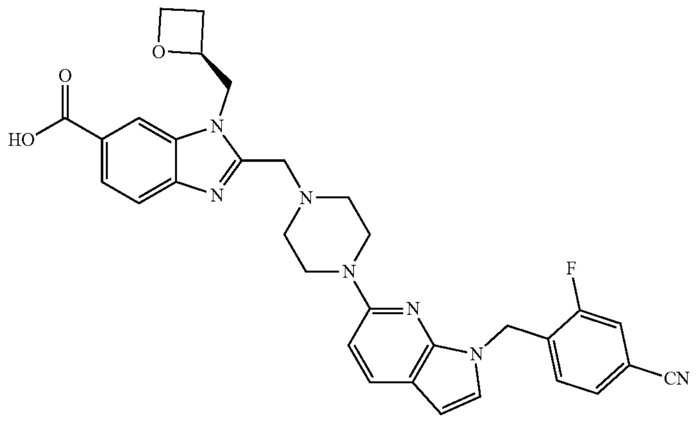 [SMILES: N#Cc1ccc(Cn2ccc3ccc(N4CCN(Cc5nc6ccc(C(=O)O)cc6n5C[C@@H]5CCO5)CC4)nc32)c(F)c1] |
| 2-30 | 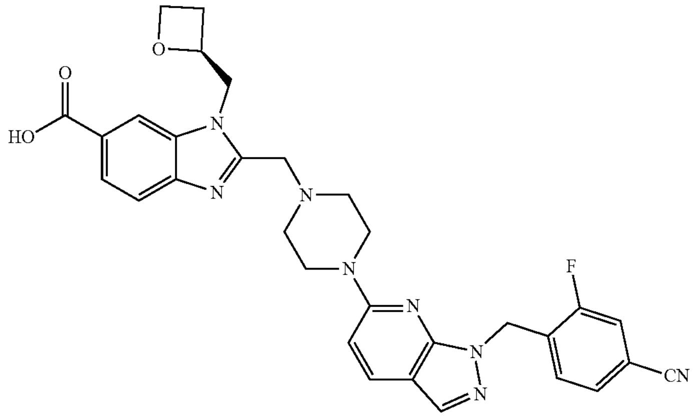 [SMILES: N#Cc1ccc(Cn2ncc3ccc(N4CCN(Cc5nc6ccc(C(=O)O)cc6n5C[C@@H]5CCO5)CC4)nc32)c(F)c1] |
| 2-31 | 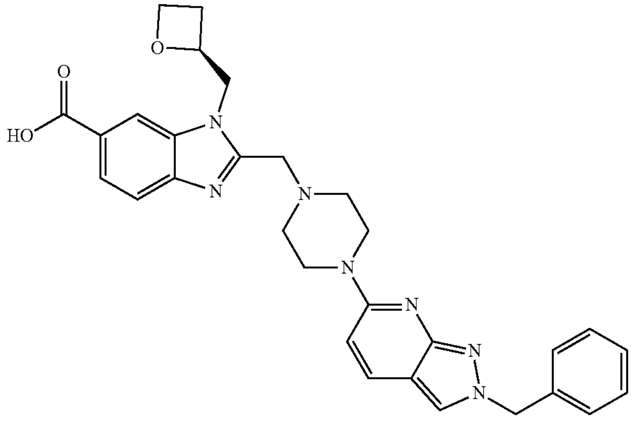 [SMILES: O=C(O)c1ccc2nc(CN3CCN(c4ccc5cn(Cc6ccccc6)nc5n4)CC3)n(C[C@@H]3CCO3)c2c1] |

TABLE 3-continued
| Compound No. | Structure |
|---|---|
| 2-32 | 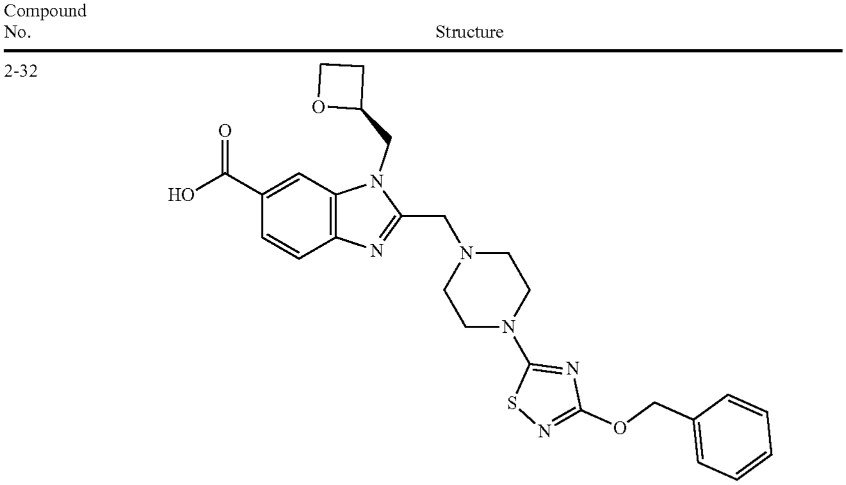 |
| 2-33 | 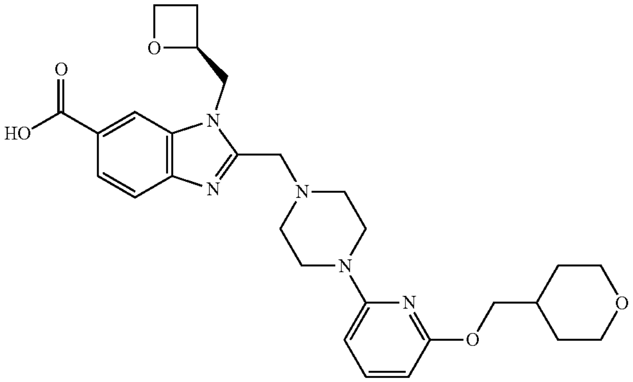 [SMILES: O=C(O)c1ccc2nc(CN3CCN(c4cccc(OCC5CCOCC5)n4)CC3)n(C[C@@H]3CCO3)c2c1] |
| 2-34 | 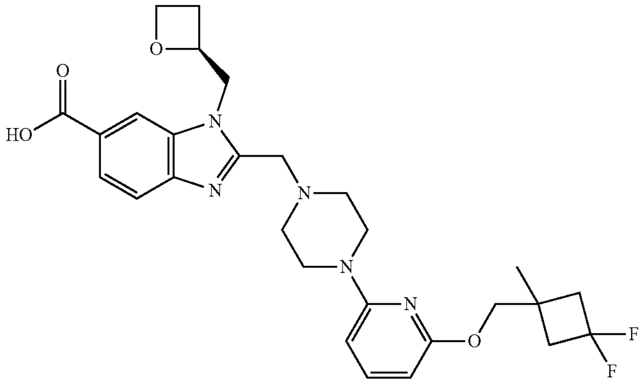 [SMILES: CC1(COc2cccc(N3CCN(Cc4nc5ccc(C(=O)O)cc5n4C[C@@H]4CCO4)CC3)n2)CC(F)(F)C1] |
| 2-35 | 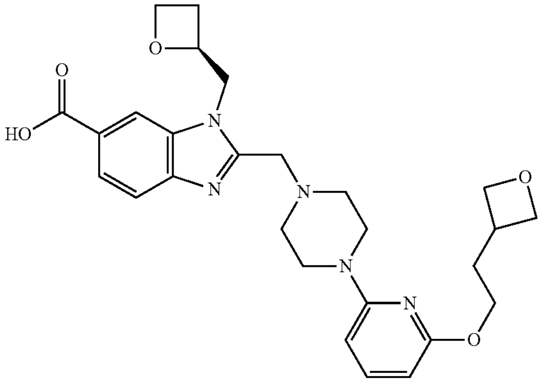 [SMILES: O=C(O)c1ccc2nc(CN3CCN(c4cccc(OCCC5COC5)n4)CC3)n(C[C@@H]3CCO3)c2c1] |

TABLE 3-continued
| Compound No. | Structure |
|---|---|
| 2-36 | 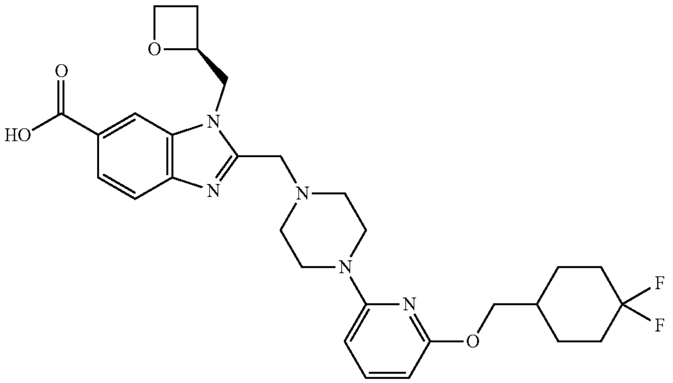 [SMILES: O=C(O)c1ccc2nc(CN3CCN(c4cccc(OCC5CCC(F)(F)CC5)n4)CC3)n(C[C@@H]3CCO3)c2c1] |
| 2-37 | 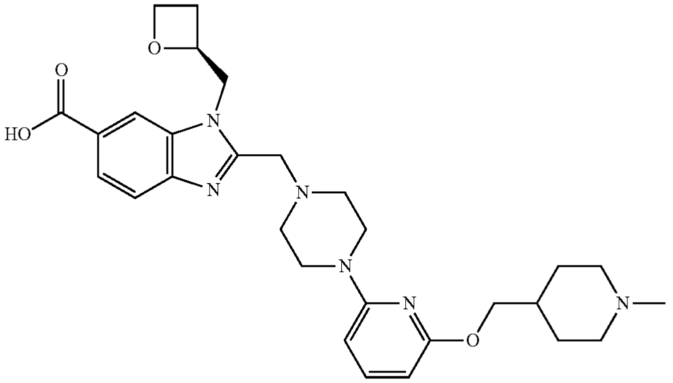 [SMILES: CN1CCC(COc2cccc(N3CCN(Cc4nc5ccc(C(=O)O)cc5n4C[C@@H]4CCO4)CC3)n2)CC1] |
| 2-38 | 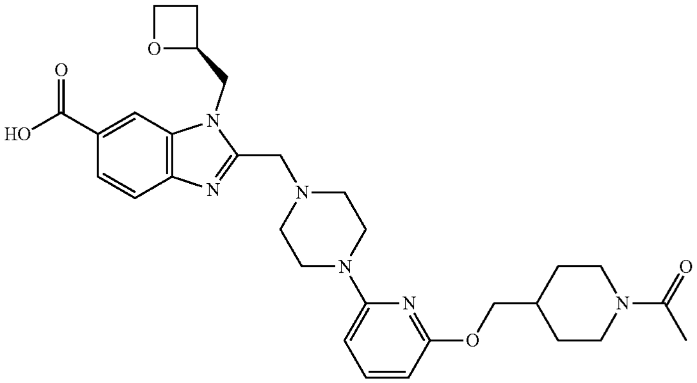 [SMILES: CC(=O)N1CCC(COc2cccc(N3CCN(Cc4nc5ccc(C(=O)O)cc5n4C[C@@H]4CCO4)CC3)n2)CC1] |
| 2-39 | 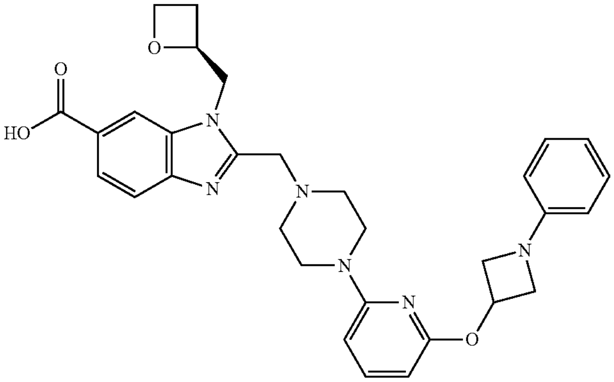 [SMILES: O=C(O)c1ccc2nc(CN3CCN(c4cccc(OC5CN(c6ccccc6)C5)n4)CC3)n(C[C@@H]3CCO3)c2c1] |

TABLE 3-continued
| Compound No. | Structure |
|---|---|
| 2-40 | 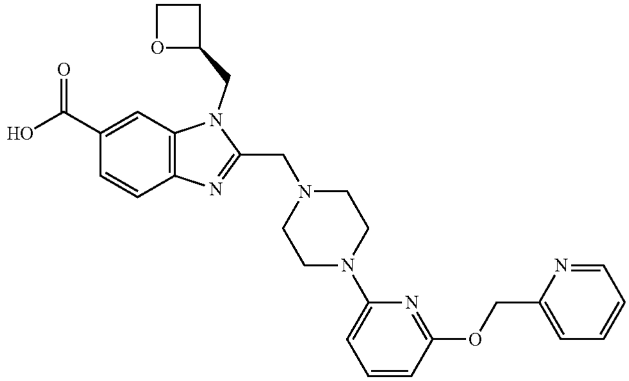 [SMILES: O=C(O)c1ccc2nc(CN3CCN(c4cccc(OCc5ccccn5)n4)CC3)n(C[C@@H]3CCO3)c2c1] |
| 2-41 | 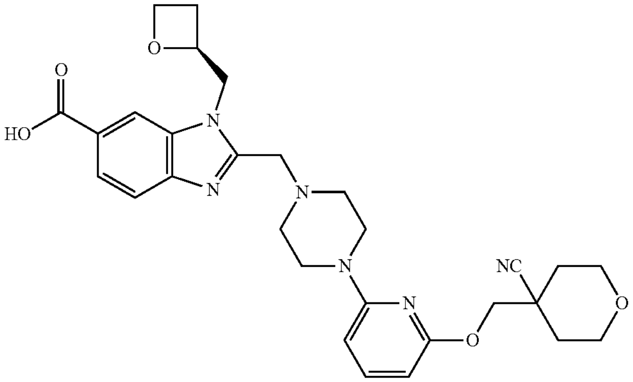 [SMILES: N#CC1(COc2cccc(N3CCN(Cc4nc5ccc(C(=O)O)cc5n4C[C@@H]4CCO4)CC3)n2)CCOCC1] |
| 2-42 | 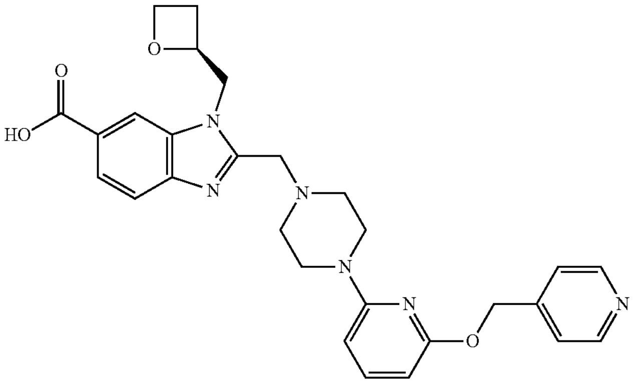 [SMILES: O=C(O)c1ccc2nc(CN3CCN(c4cccc(OCc5ccncc5)n4)CC3)n(C[C@@H]3CCO3)c2c1] |
| 2-43 | 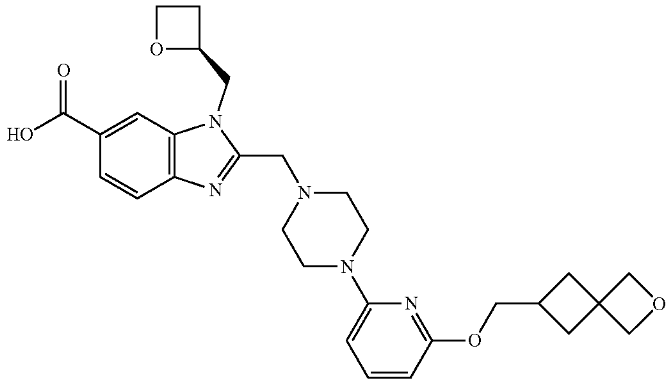 [SMILES: O=C(O)c1ccc2nc(CN3CCN(c4cccc(OCC5CC6(COC6)C5)n4)CC3)n(C[C@@H]3CCO3)c2c1] |

TABLE 3-continued
| Compound No. | Structure |
| --- | --- |
| 2-44 | 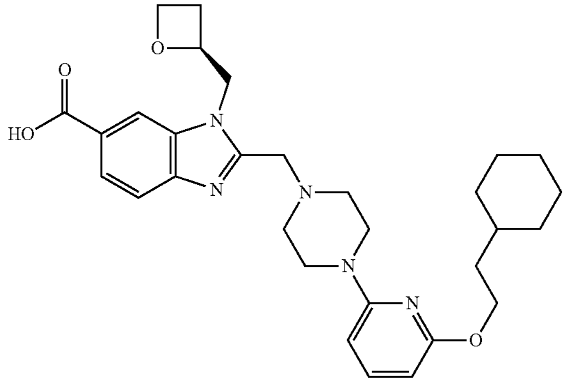 [SMILES: O=C(O)c1ccc2nc(CN3CCN(c4cccc(OCCC5CCCCC5)n4)CC3)n(C[C@@H]3CCO3)c2c1] |
| 2-45 | 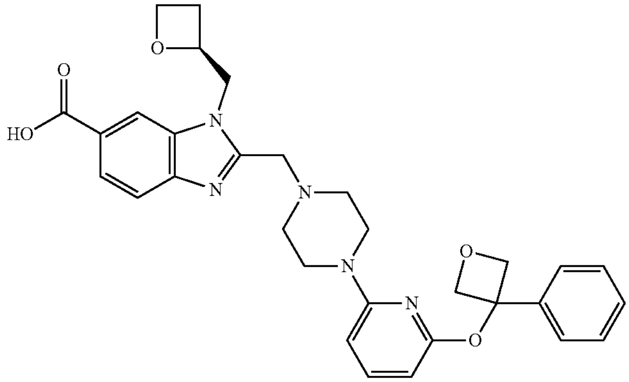 [SMILES: O=C(O)c1ccc2nc(CN3CCN(c4cccc(OC5(c6ccccc6)COC5)n4)CC3)n(C[C@@H]3CCO3)c2c1] |
| 2-46 | 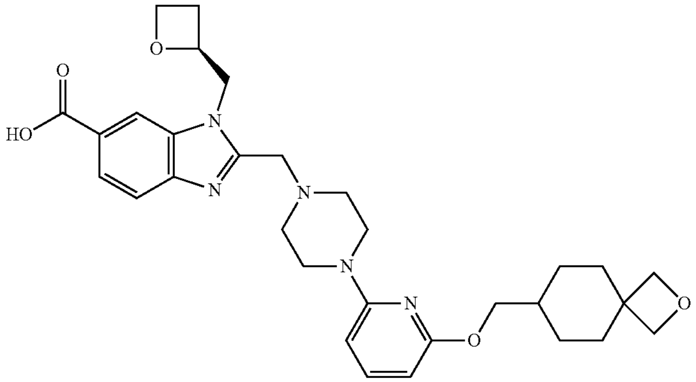 [SMILES: O=C(O)c1ccc2nc(CN3CCN(c4cccc(OCC5CCC6(CC5)COC6)n4)CC3)n(C[C@@H]3CCO3)c2c1] |
| 2-47 | 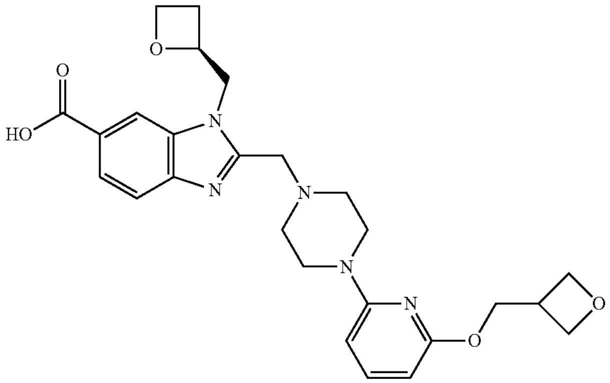 [SMILES: O=C(O)c1ccc2nc(CN3CCN(c4cccc(OCC5COC5)n4)CC3)n(C[C@@H]3CCO3)c2c1] |

TABLE 3-continued
| Compound No. | Structure |
| --- | --- |
| 2-48 | 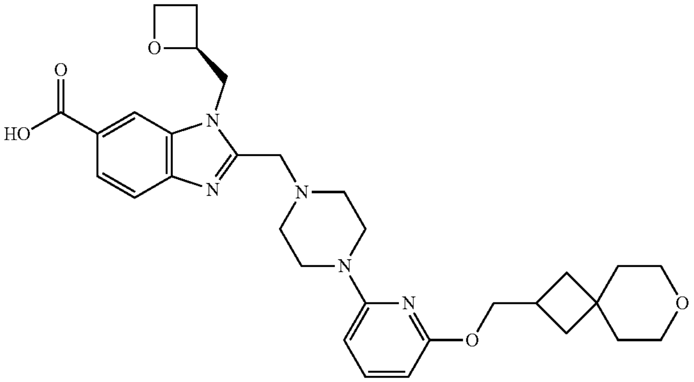 [SMILES: O=C(O)c1ccc2nc(CN3CCN(c4cccc(OCC5CC6(CCOCC6)C5)n4)CC3)n(C[C@@H]3CCO3)c2c1] |
| 2-49 | 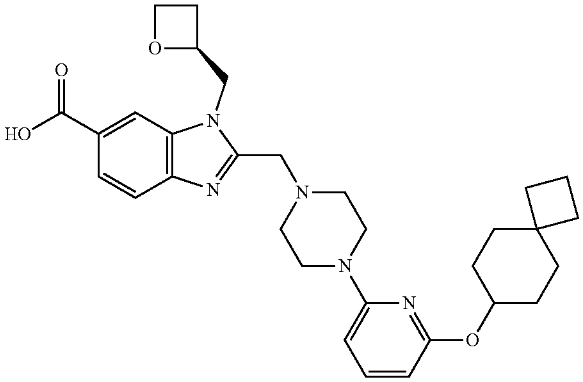 [SMILES: O=C(O)c1ccc2nc(CN3CCN(c4cccc(OC5CCC6(CCC6)CC5)n4)CC3)n(C[C@@H]3CCO3)c2c1] |
| 2-50 | 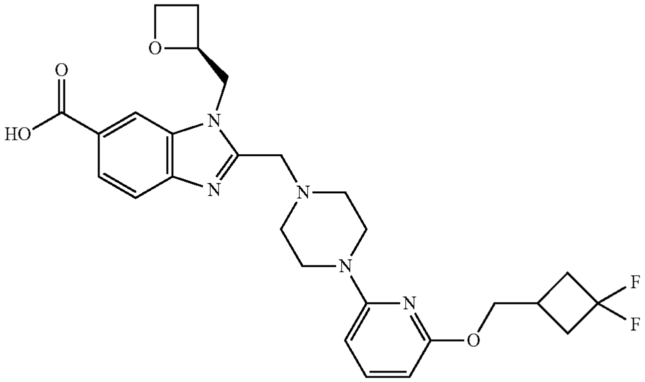 [SMILES: O=C(O)c1ccc2nc(CN3CCN(c4cccc(OCC5CC(F)(F)C5)n4)CC3)n(C[C@@H]3CCO3)c2c1] |
| 2-51 | 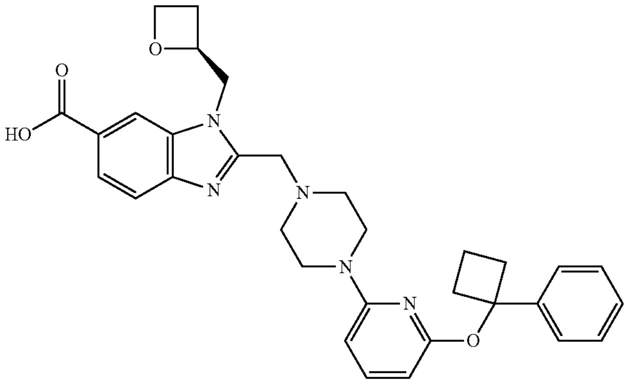 [SMILES: O=C(O)c1ccc2nc(CN3CCN(c4cccc(OC5(c6ccccc6)CCC5)n4)CC3)n(C[C@@H]3CCO3)c2c1] |

TABLE 3-continued
| Compound No. | Structure |
| --- | --- |
| 2-52 | 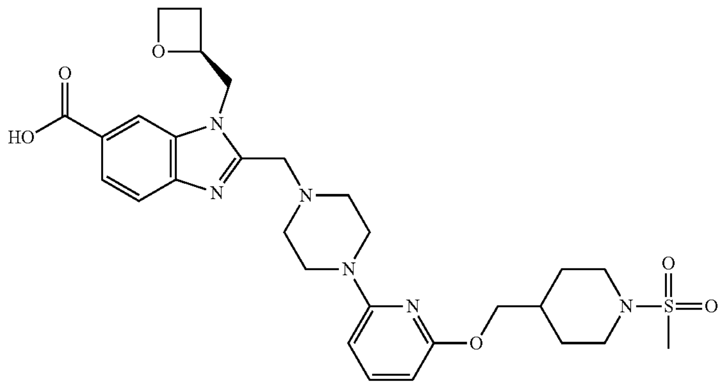 [SMILES: CS(=O)(=O)N1CCC(COc2cccc(N3CCN(Cc4nc5ccc(C(=O)O)cc5n4C[C@@H]4CCO4)CC3)n2)CC1] |
| 2-53 | 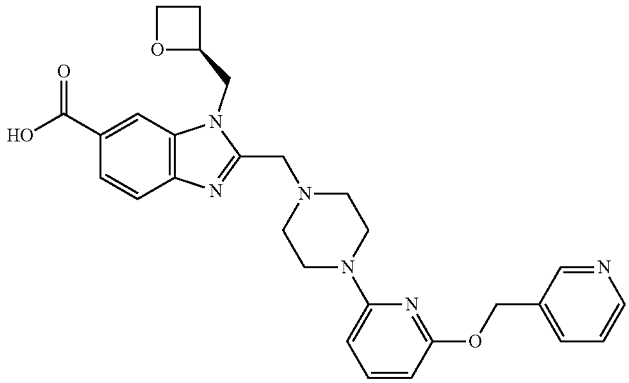 |
| 2-54 | 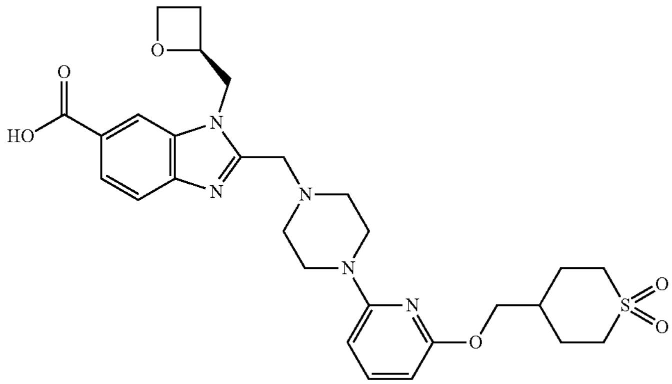 [SMILES: O=C(O)c1ccc2nc(CN3CCN(c4cccc(OCC5CCS(=O)(=O)CC5)n4)CC3)n(C[C@@H]3CCO3)c2c1] |
| 2-55 | 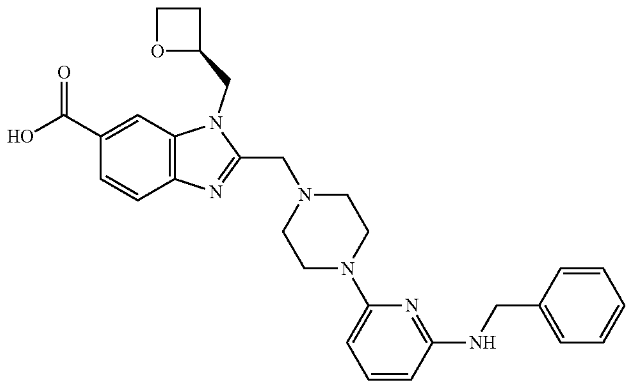 [SMILES: O=C(O)c1ccc2nc(CN3CCN(c4cccc(NCc5ccccc5)n4)CC3)n(C[C@@H]3CCO3)c2c1] |

TABLE 3-continued
| Compound No. | Structure |
|---|---|
| 2-56 | 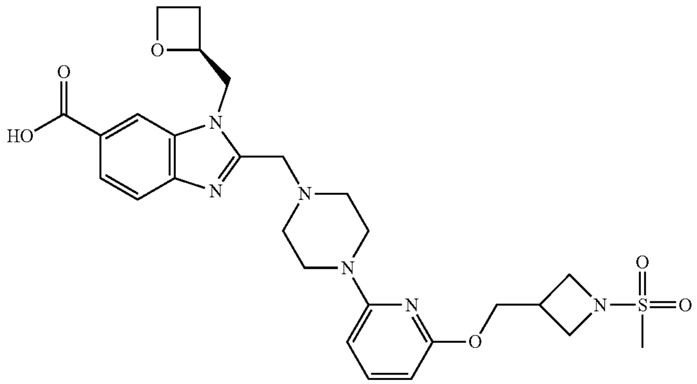 [SMILES: CS(=O)(=O)N1CC(COc2cccc(N3CCN(Cc4nc5ccc(C(=O)O)cc5n4C[C@@H]4CCO4)CC3)n2)C1] |
| 2-57 | 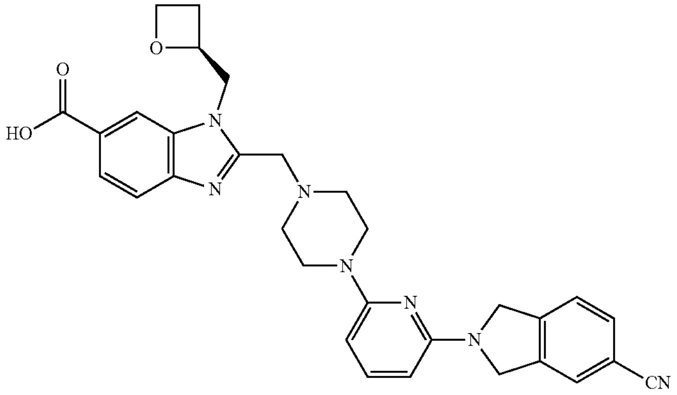 [SMILES: N#Cc1ccc2c(c1)CN(c1cccc(N3CCN(Cc4nc5ccc(C(=O)O)cc5n4C[C@@H]4CCO4)CC3)n1)C2] |
| 2-58 | 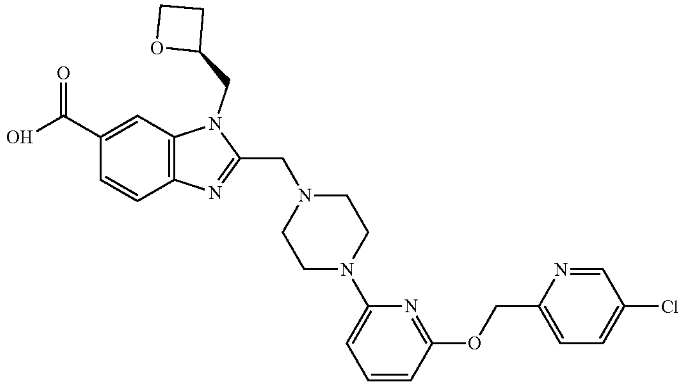 [SMILES: O=C(O)c1ccc2nc(CN3CCN(c4cccc(OCc5ccc(Cl)cn5)n4)CC3)n(C[C@@H]3CCO3)c2c1] |
| 2-59 | 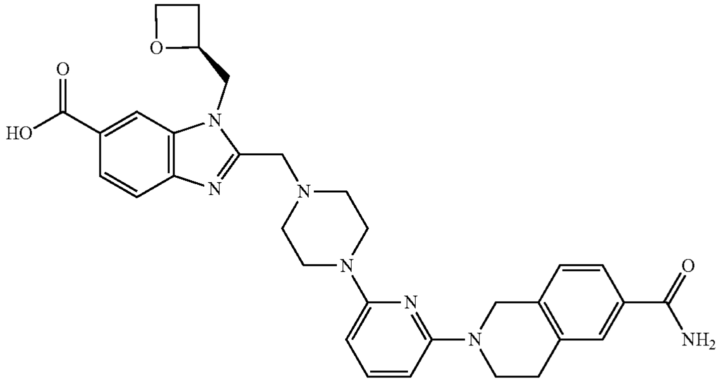 [SMILES: NC(=O)c1ccc2c(c1)CCN(c1cccc(N3CCN(Cc4nc5ccc(C(=O)O)cc5n4C[C@@H]4CCO4)CC3)n1)C2] |

TABLE 3-continued
| Compound No. | Structure |
|---|---|
| 2-60 | 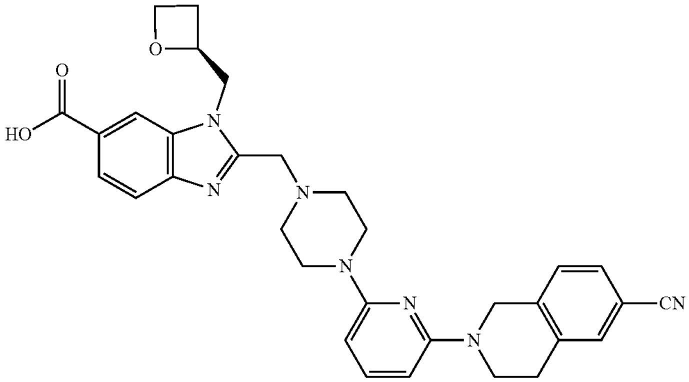 [SMILES: N#Cc1ccc2c(c1)CCN(c1cccc(N3CCN(Cc4nc5ccc(C(=O)O)cc5n4C[C@@H]4CCO4)CC3)n1)C2] |
| 2-61 | 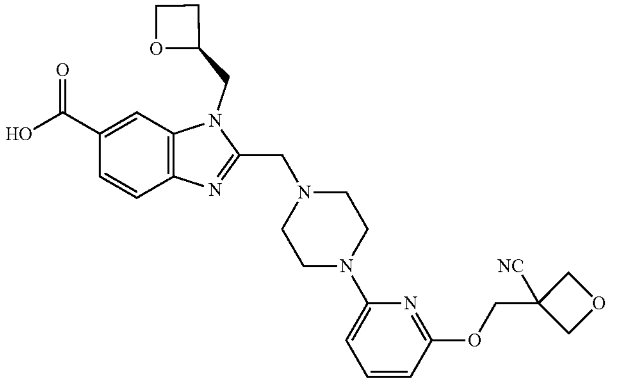 [SMILES: N#CC1(COc2cccc(N3CCN(Cc4nc5ccc(C(=O)O)cc5n4C[C@@H]4CCO4)CC3)n2)COC1] |
| 2-62 | 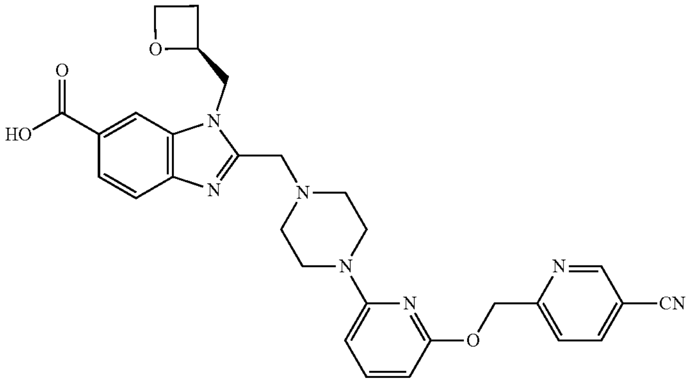 [SMILES: N#Cc1ccc(COc2cccc(N3CCN(Cc4nc5ccc(C(=O)O)cc5n4C[C@@H]4CCO4)CC3)n2)nc1] |
| 2-63 | 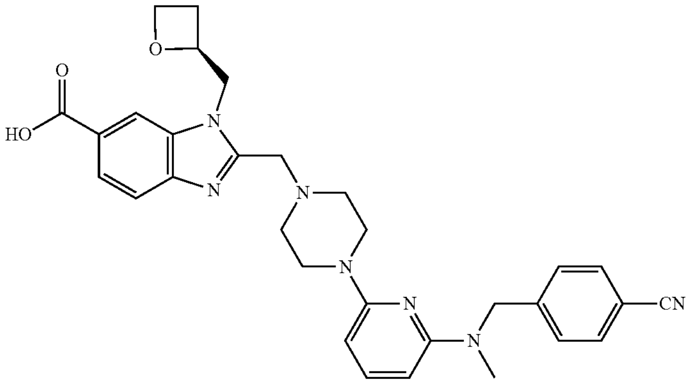 [SMILES: CN(Cc1ccc(C#N)cc1)c1cccc(N2CCN(Cc3nc4ccc(C(=O)O)cc4n3C[C@@H]3CCO3)CC2)n1] |

TABLE 3-continued
| Compound No. | Structure |
|---|---|
| 2-64 | 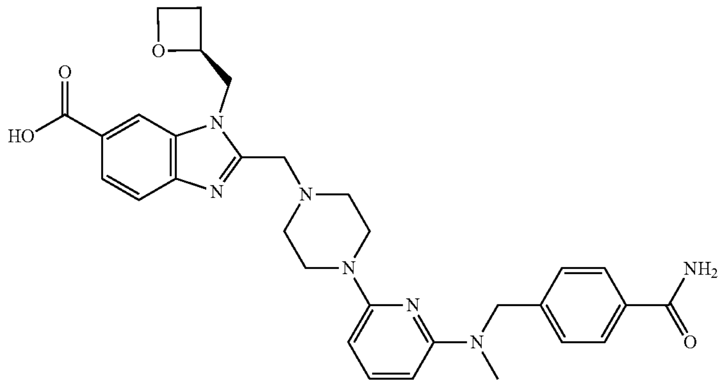 [SMILES: CN(Cc1ccc(C(N)=O)cc1)c1cccc(N2CCN(Cc3nc4ccc(C(=O)O)cc4n3C[C@@H]3CCO3)CC2)n1] |
| 2-65 | 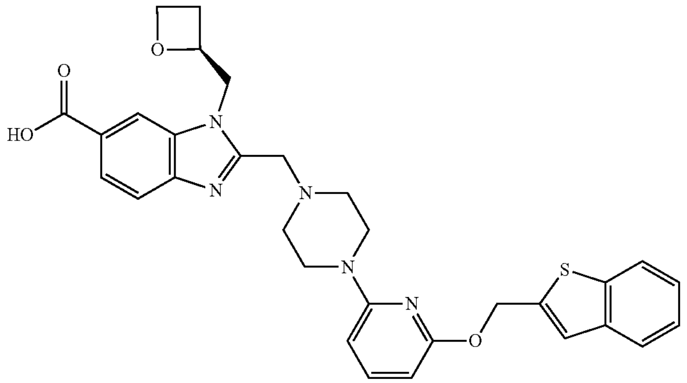 [SMILES: O=C(O)c1ccc2nc(CN3CCN(c4cccc(OCc5cc6ccccc6s5)n4)CC3)n(C[C@@H]3CCO3)c2c1] |
| 2-66 | 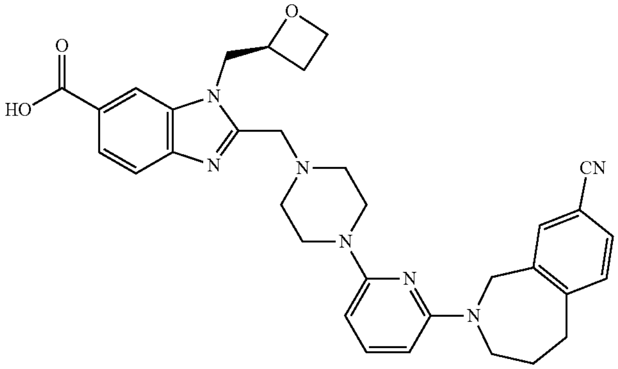 [SMILES: N#Cc1ccc2c(c1)CN(c1cccc(N3CCN(Cc4nc5ccc(C(=O)O)cc5n4C[C@@H]4CCO4)CC3)n1)CCC2] |
| 2-67 | 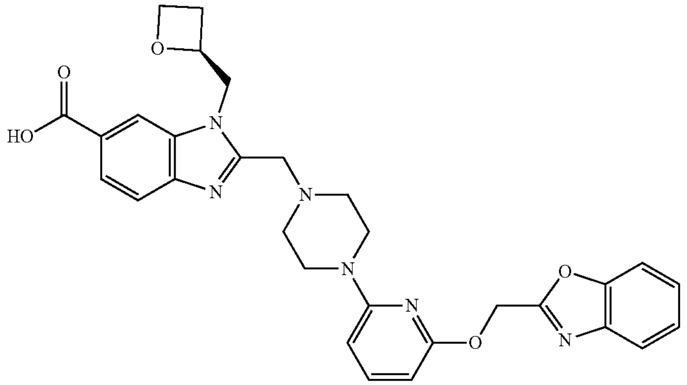 [SMILES: O=C(O)c1ccc2nc(CN3CCN(c4cccc(OCc5nc6ccccc6o5)n4)CC3)n(C[C@@H]3CCO3)c2c1] |

TABLE 3-continued
| Compound No. | Structure |
|---|---|
| 2-68 | 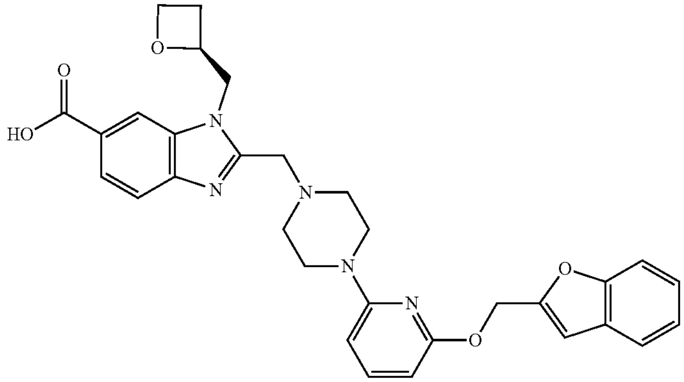 [SMILES: O=C(O)c1ccc2nc(CN3CCN(c4cccc(OCc5cc6ccccc6o5)n4)CC3)n(C[C@@H]3CCO3)c2c1] |
| 2-69 | 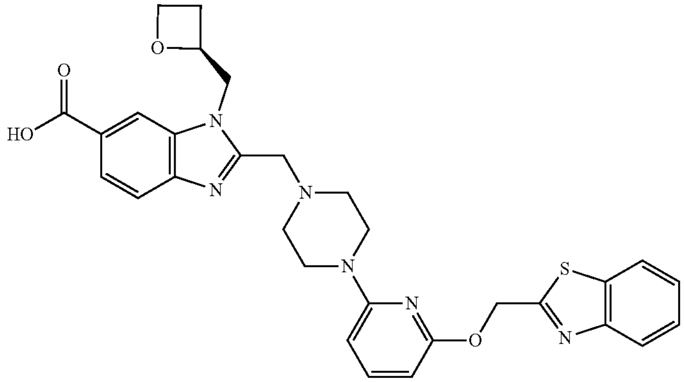 |
| 2-70 | 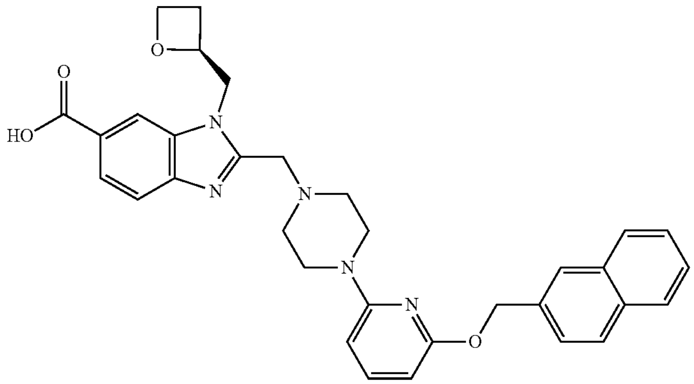 [SMILES: O=C(O)c1ccc2nc(CN3CCN(c4cccc(OCc5ccc6ccccc6c5)n4)CC3)n(C[C@@H]3CCO3)c2c1] |
| 2-71 | 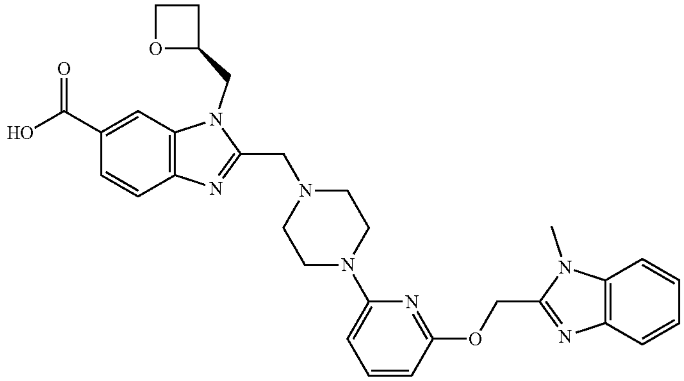 [SMILES: Cn1c(COc2cccc(N3CCN(Cc4nc5ccc(C(=O)O)cc5n4C[C@@H]4CCO4)CC3)n2)nc2ccccc21] |

TABLE 3-continued
| Compound No. | Structure |
|---|---|
| 2-72 | 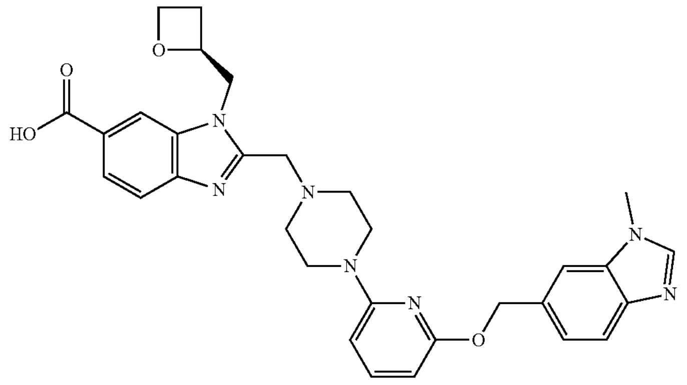 [SMILES: Cn1cnc2ccc(COc3cccc(N4CCN(Cc5nc6ccc(C(=O)O)cc6n5C[C@@H]5CCO5)CC4)n3)cc21] |
| 2-73 | 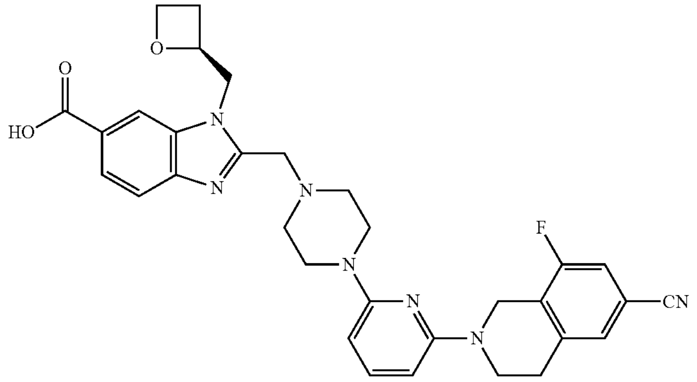 [SMILES: N#Cc1cc(F)c2c(c1)CCN(c1cccc(N3CCN(Cc4nc5ccc(C(=O)O)cc5n4C[C@@H]4CCO4)CC3)n1)C2] |
| 2-74 | 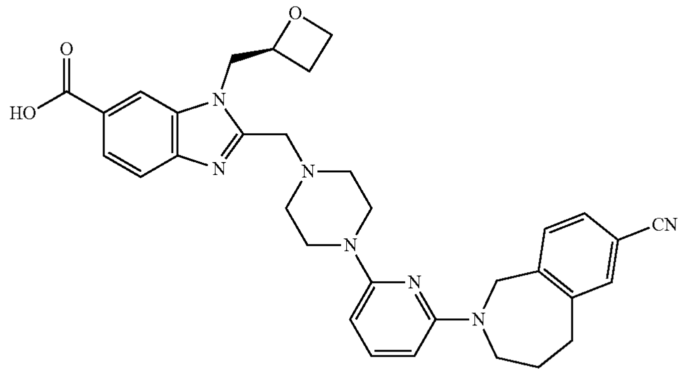 [SMILES: N#Cc1ccc2c(c1)CCCN(c1cccc(N3CCN(Cc4nc5ccc(C(=O)O)cc5n4C[C@@H]4CCO4)CC3)n1)C2] |
| 2-75 | 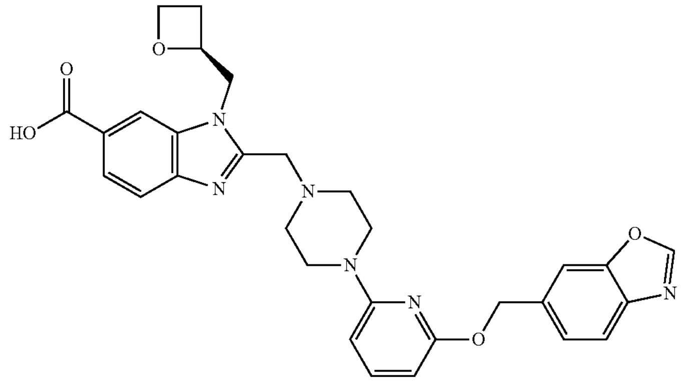 [SMILES: O=C(O)c1ccc2nc(CN3CCN(c4cccc(OCc5ccc6ncoc6c5)n4)CC3)n(C[C@@H]3CCO3)c2c1] |

TABLE 3-continued
| Compound No. | Structure |
| --- | --- |
| 2-76 | 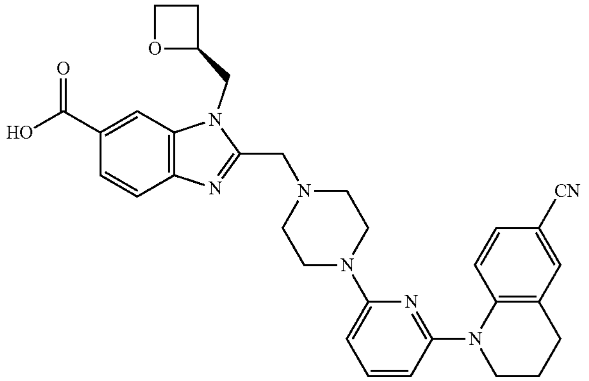 [SMILES: N#Cc1ccc2c(c1)CCCN2c1cccc(N2CCN(Cc3nc4ccc(C(=O)O)cc4n3C[C@@H]3CCO3)CC2)n1] |
| 2-77 | 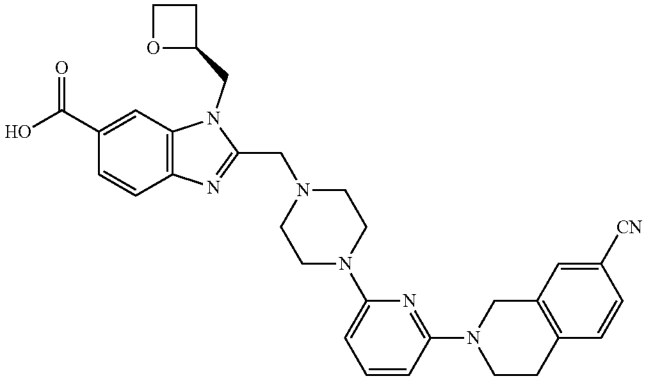 [SMILES: N#Cc1ccc2c(c1)CN(c1cccc(N3CCN(Cc4nc5ccc(C(=O)O)cc5n4C[C@@H]4CCO4)CC3)n1)CC2] |
| 2-78 | 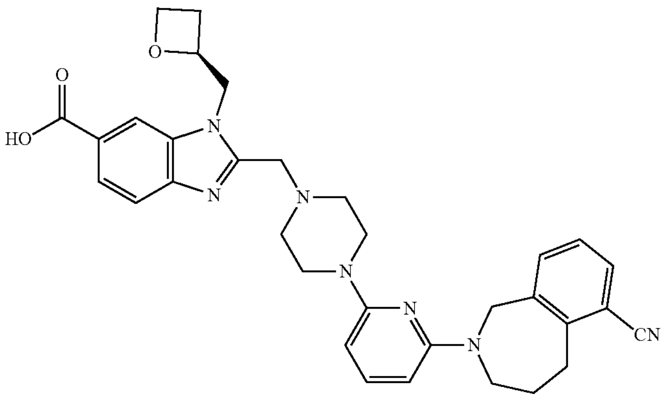 [SMILES: N#Cc1cccc2c1CCCN(c1cccc(N3CCN(Cc4nc5ccc(C(=O)O)cc5n4C[C@@H]4CCO4)CC3)n1)C2] |

TABLE 3-continued
| Compound No. | Structure |
|---|---|
| 2-79 | 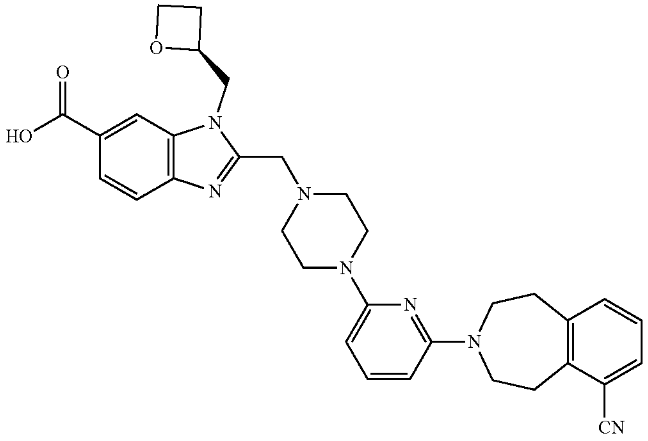 [SMILES: N#Cc1cccc2c1CCN(c1cccc(N3CCN(Cc4nc5ccc(C(=O)O)cc5n4C[C@@H]4CCO4)CC3)n1)CC2] |
| 2-80 | 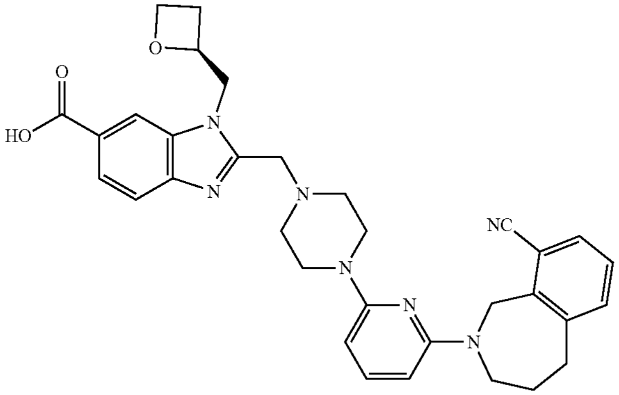 [SMILES: N#Cc1cccc2c1CN(c1cccc(N3CCN(Cc4nc5ccc(C(=O)O)cc5n4C[C@@H]4CCO4)CC3)n1)CCC2] |
| 2-81 | 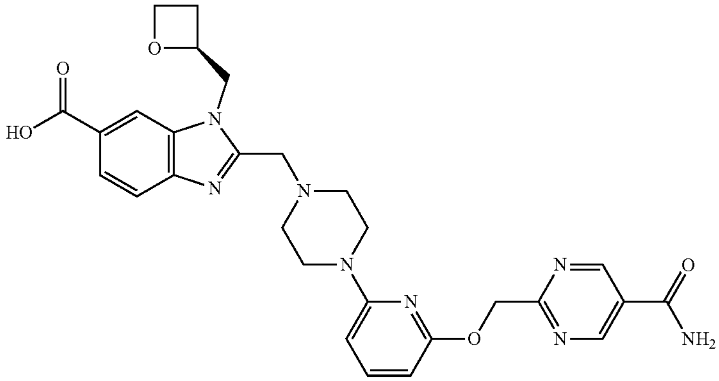 [SMILES: NC(=O)c1cnc(COc2cccc(N3CCN(Cc4nc5ccc(C(=O)O)cc5n4C[C@@H]4CCO4)CC3)n2)nc1] |

TABLE 3-continued
| Compound No. | Structure |
|---|---|
| 2-82 | 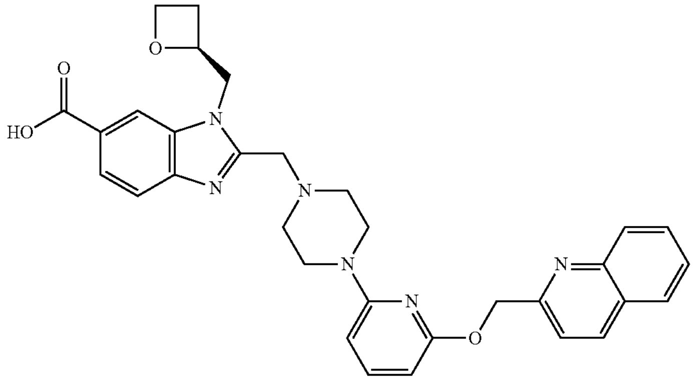 [SMILES: O=C(O)c1ccc2nc(CN3CCN(c4cccc(OCc5ccc6ccccc6n5)n4)CC3)n(C[C@@H]3CCO3)c2c1] |
| 2-83 | 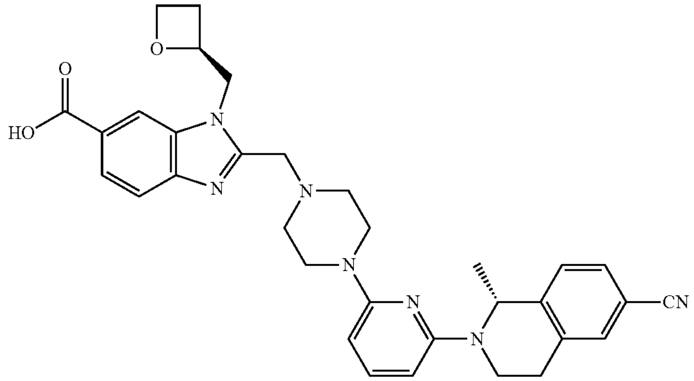 [SMILES: C[C@@H]1c2ccc(C#N)cc2CCN1c1cccc(N2CCN(Cc3nc4ccc(C(=O)O)cc4n3C[C@@H]3CCO3)CC2)n1] |
| 2-84 | 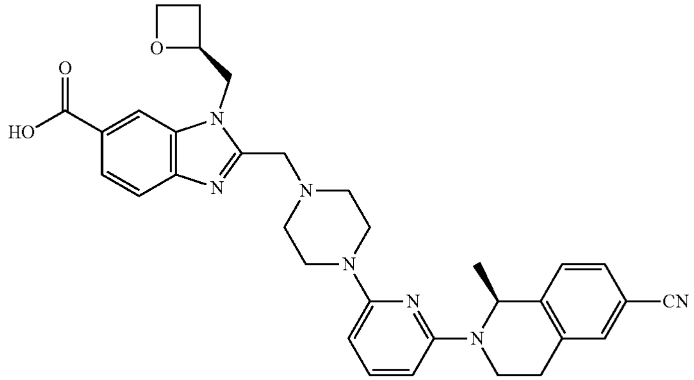 [SMILES: C[C@H]1c2ccc(C#N)cc2CCN1c1cccc(N2CCN(Cc3nc4ccc(C(=O)O)cc4n3C[C@@H]3CCO3)CC2)n1] |
| 2-85 | 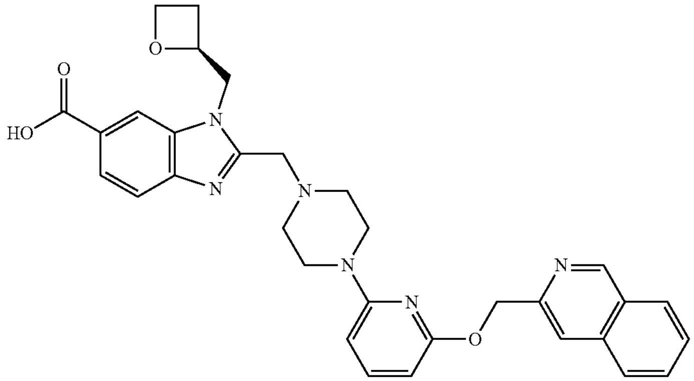 [SMILES: O=C(O)c1ccc2nc(CN3CCN(c4cccc(OCc5cc6ccccc6cn5)n4)CC3)n(C[C@@H]3CCO3)c2c1] |

TABLE 3-continued
| Compound No. | Structure |
|---|---|
| 2-86 | 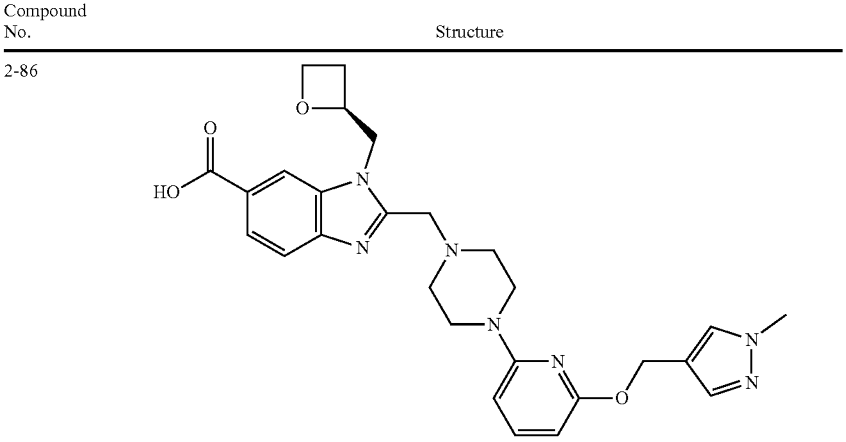 |
| 2-87 | 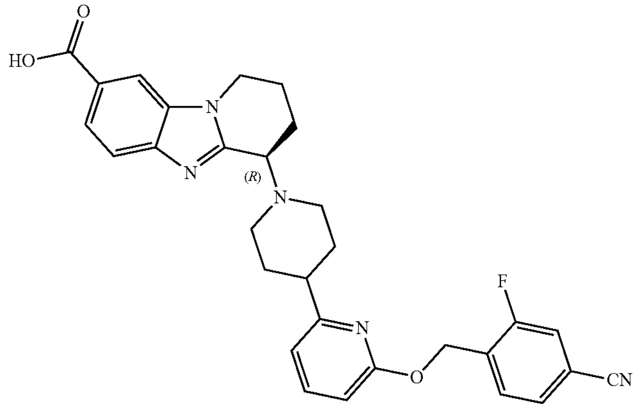 |
| 2-88 | 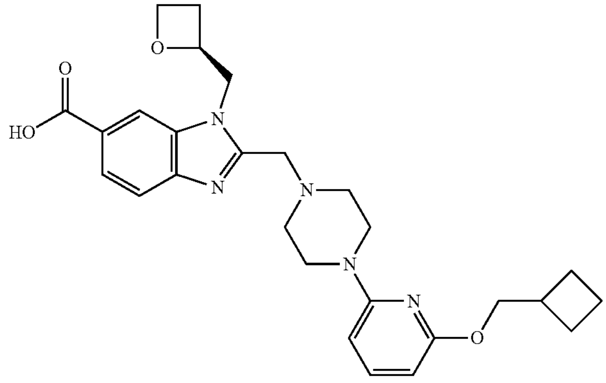 [SMILES: O=C(O)c1ccc2nc(CN3CCN(c4cccc(OCC5CCC5)n4)CC3)n(C[C@@H]3CCO3)c2c1] |
| 2-89 | 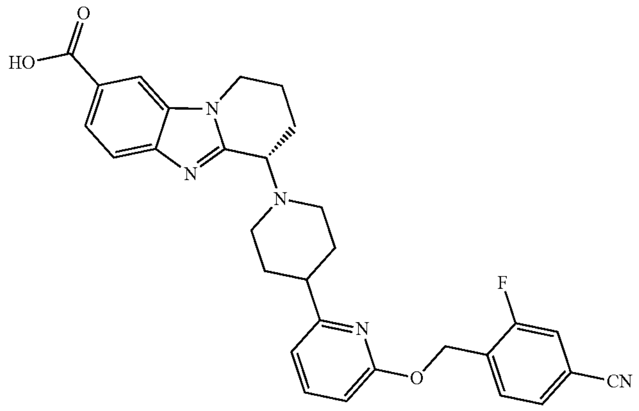 [SMILES: N#Cc1ccc(COc2cccc(C3CCN([C@H]4CCCn5c4nc4ccc(C(=O)O)cc45)CC3)n2)c(F)c1] |

TABLE 3-continued
| Compound No. | Structure |
|---|---|
| 2-90 | 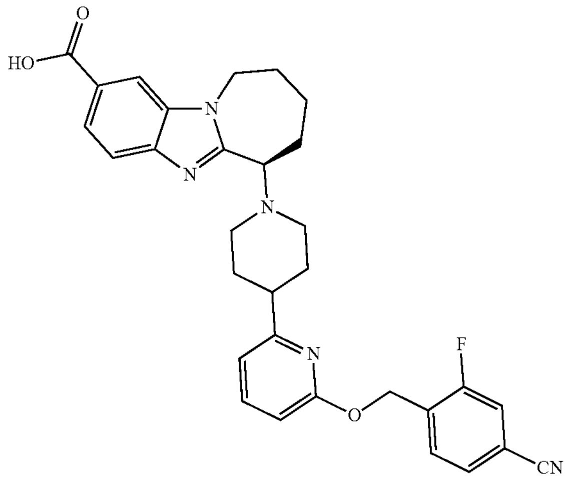 [SMILES: N#Cc1ccc(COc2cccc(C3CCN([C@@H]4CCCCn5c4nc4ccc(C(=O)O)cc45)CC3)n2)c(F)c1] |
| 2-91 | 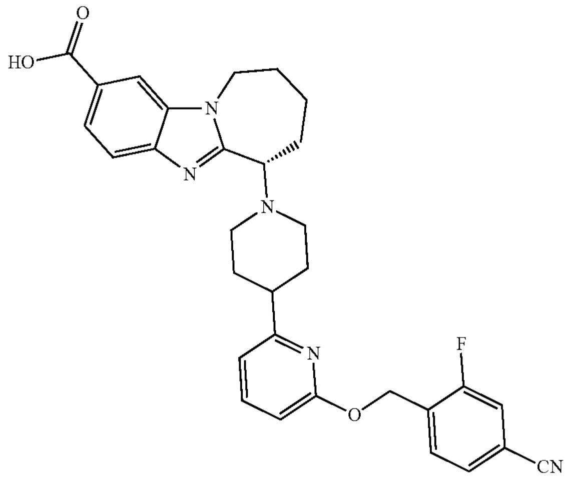 [SMILES: N#Cc1ccc(COc2cccc(C3CCN([C@H]4CCCCn5c4nc4ccc(C(=O)O)cc45)CC3)n2)c(F)c1] |
| 2-92 | 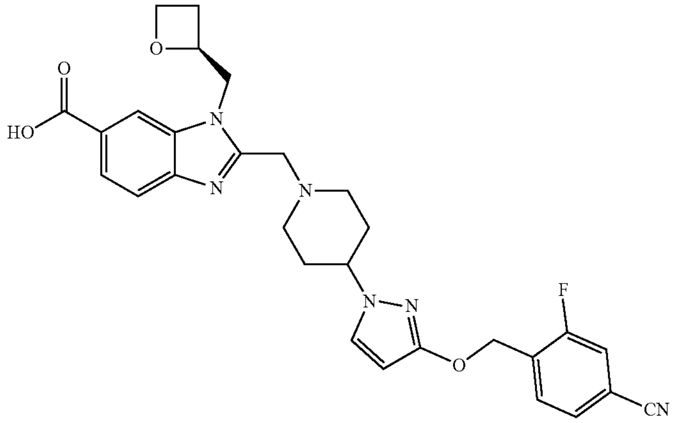 [SMILES: N#Cc1ccc(COc2ccn(C3CCN(Cc4nc5ccc(C(=O)O)cc5n4C[C@@H]4CCO4)CC3)n2)c(F)c1] |

TABLE 3-continued
| Compound No. | Structure |
| --- | --- |
| 2-93 | 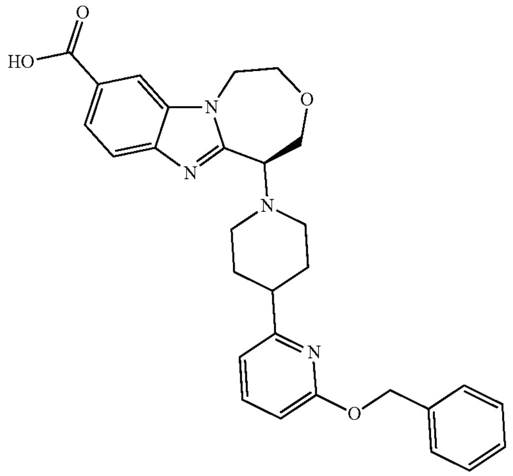 [SMILES: O=C(O)c1ccc2nc3n(c2c1)CCOC[C@H]3N1CCC(c2cccc(OCc3ccccc3)n2)CC1] |
| 2-94 | 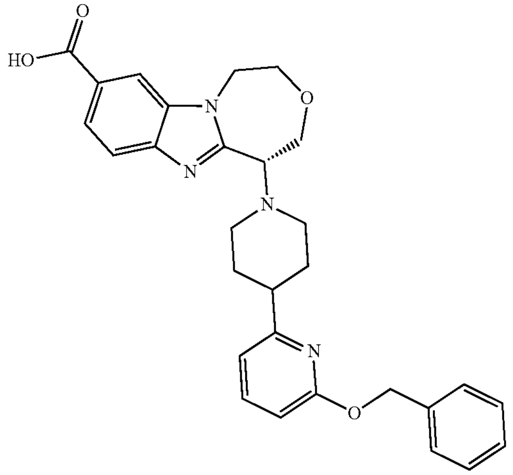 [SMILES: O=C(O)c1ccc2nc3n(c2c1)CCOC[C@@H]3N1CCC(c2cccc(OCc3ccccc3)n2)CC1] |
| 2-95 | 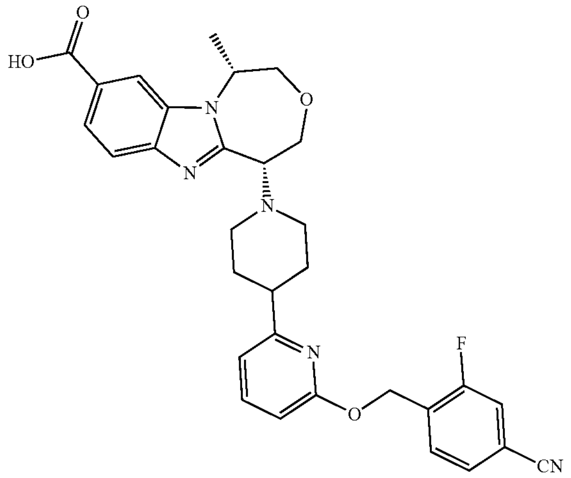 [SMILES: C[C@@H]1COC[C@H](N2CCC(c3cccc(OCc4ccc(C#N)cc4F)n3)CC2)c2nc3ccc(C(=O)O)cc3n21] |

TABLE 3-continued
| Compound No. | Structure |
| --- | --- |
| 2-96 | 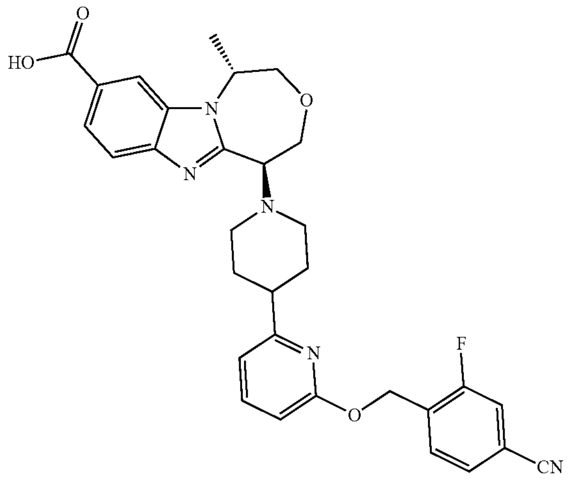 [SMILES: C[C@@H]1COC[C@@H](N2CCC(c3cccc(OCc4ccc(C#N)cc4F)n3)CC2)c2nc3ccc(C(=O)O)cc3n21] |
| 2-97 | 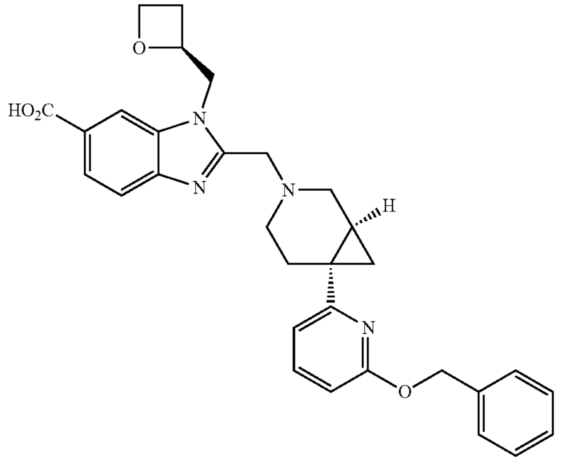 [SMILES: O=C(O)c1ccc2nc(CN3CC[C@]4(c5cccc(OCc6ccccc6)n5)C[C@@H]4C3)n(C[C@@H]3CCO3)c2c1] |
| 2-98 | 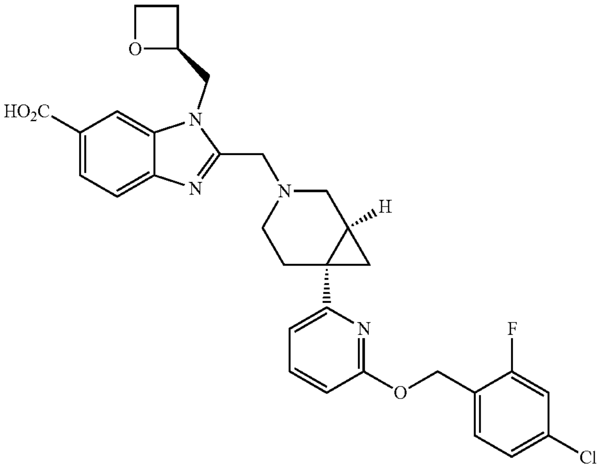 [SMILES: O=C(O)c1ccc2nc(CN3CC[C@]4(c5cccc(OCc6ccc(Cl)cc6F)n5)C[C@@H]4C3)n(C[C@@H]3CCO3)c2c1] |

TABLE 3-continued
| Compound No. | Structure |
|---|---|
| 2-99 | 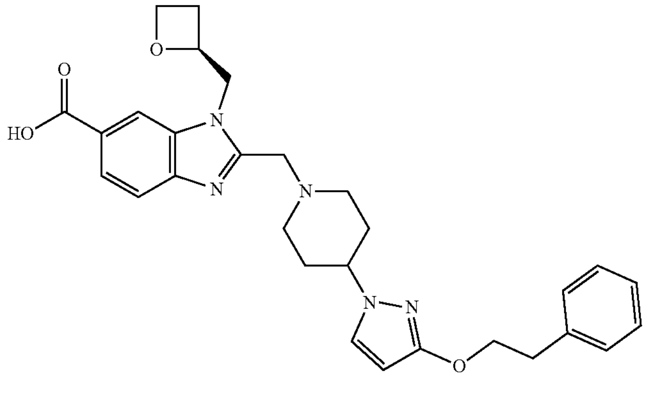 [SMILES: O=C(O)c1ccc2nc(CN3CCC(n4ccc(OCCc5ccccc5)n4)CC3)n(C[C@@H]3CCO3)c2c1] |
| 2-100 | 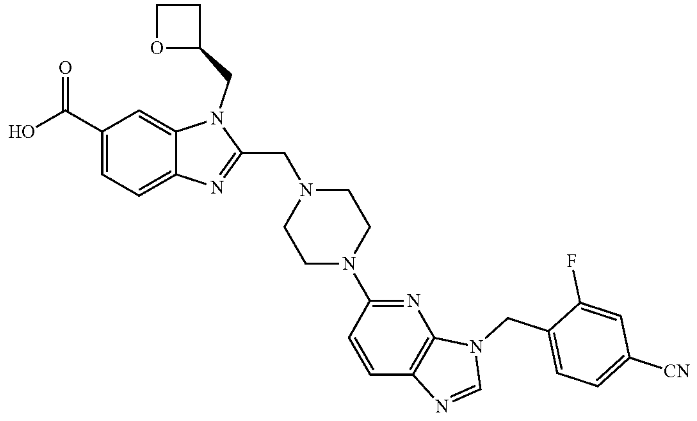 [SMILES: N#Cc1ccc(Cn2cnc3ccc(N4CCN(Cc5nc6ccc(C(=O)O)cc6n5C[C@@H]5CCO5)CC4)nc32)c(F)c1] |
| 2-101 | 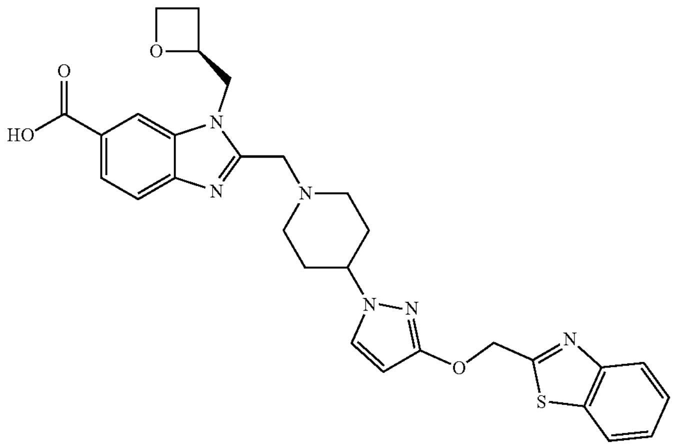 [SMILES: O=C(O)c1ccc2nc(CN3CCC(n4ccc(OCc5nc6ccccc6s5)n4)CC3)n(C[C@@H]3CCO3)c2c1] |

TABLE 3-continued
| Compound No. | Structure |
| --- | --- |
| 2-102 | 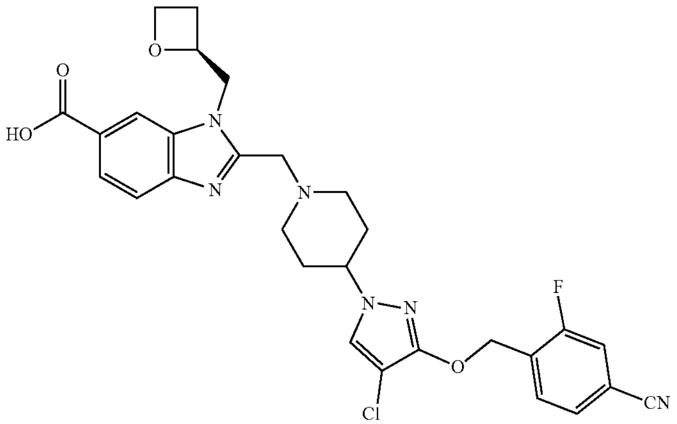 [SMILES: N#Cc1ccc(COc2nn(C3CCN(Cc4nc5ccc(C(=O)O)cc5n4C[C@@H]4CCO4)CC3)cc2Cl)c(F)c1] |
| 2-103 | 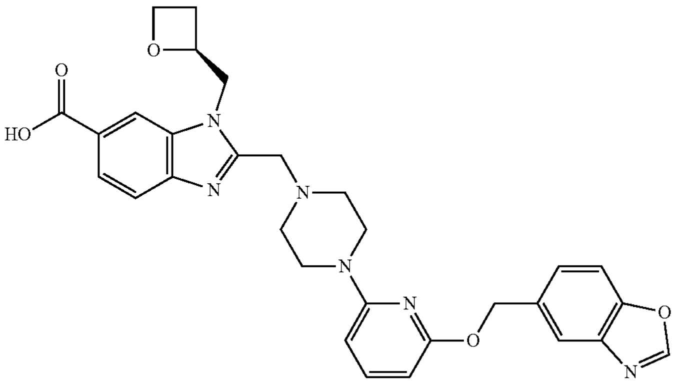 [SMILES: O=C(O)c1ccc2nc(CN3CCN(c4cccc(OCc5ccc6ocnc6c5)n4)CC3)n(C[C@@H]3CCO3)c2c1] |
| 2-104-P1 | 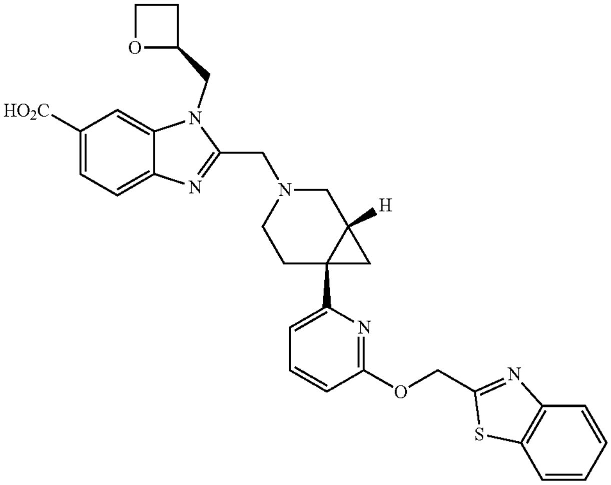 [SMILES: O=C(O)c1ccc2nc(CN3CC[C@@]4(c5cccc(OCc6nc7ccccc7s6)n5)C[C@H]4C3)n(C[C@@H]3CCO3)c2c1] |

TABLE 3-continued
| Compound No. | Structure |
|---|---|
| 2-104-P2 | 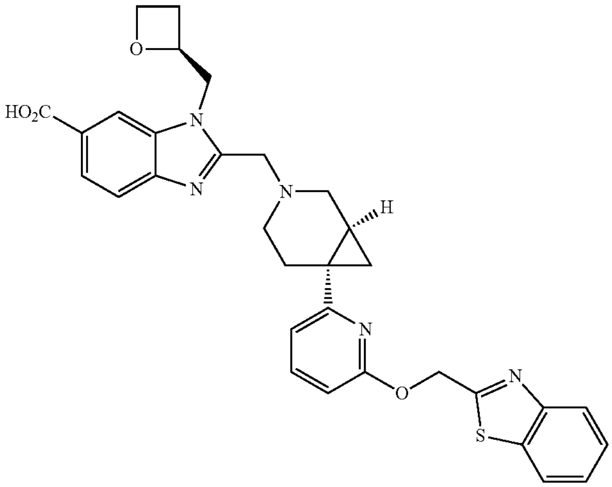 [SMILES: O=C(O)c1ccc2nc(CN3CC[C@]4(c5cccc(OCc6nc7ccccc7s6)n5)C[C@@H]4C3)n(C[C@@H]3CCO3)c2c1] |
| 2-105 | 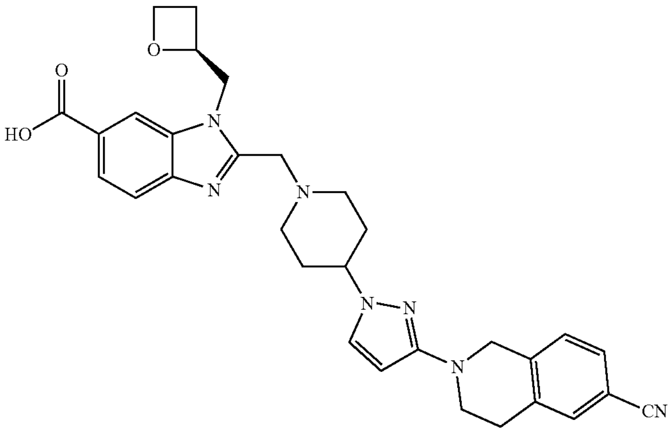 [SMILES: N#Cc1ccc2c(c1)CCN(c1ccn(C3CCN(Cc4nc5ccc(C(=O)O)cc5n4C[C@@H]4CCO4)CC3)n1)C2] |
| 2-106 | 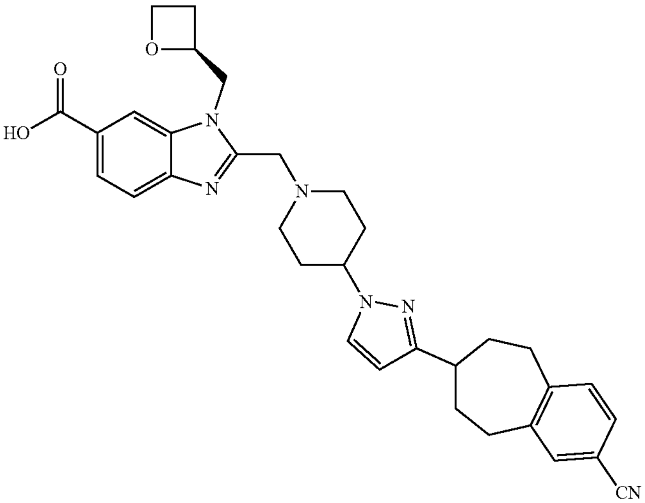 [SMILES: N#Cc1ccc2c(c1)CCC(c1ccn(C3CCN(Cc4nc5ccc(C(=O)O)cc5n4C[C@@H]4CCO4)CC3)n1)CC2] |

TABLE 3-continued
| Compound No. | Structure |
|---|---|
| 2-107 | 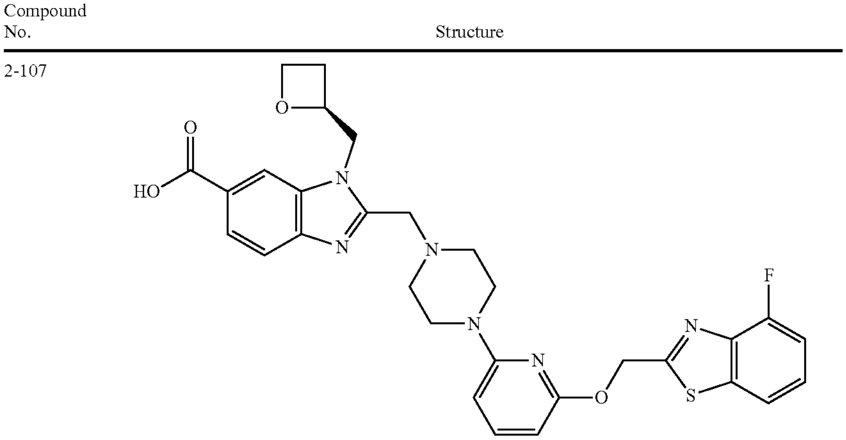 |
| 2-108 | 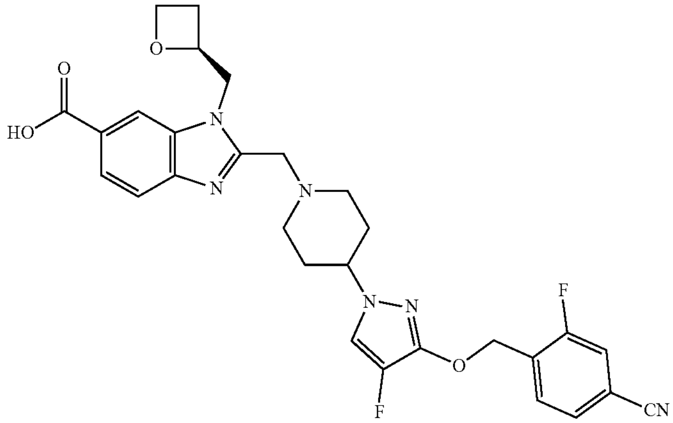 [SMILES: N#Cc1ccc(COc2nn(C3CCN(Cc4nc5ccc(C(=O)O)cc5n4C[C@@H]4CCO4)CC3)cc2F)c(F)c1] |
| 2-109 | 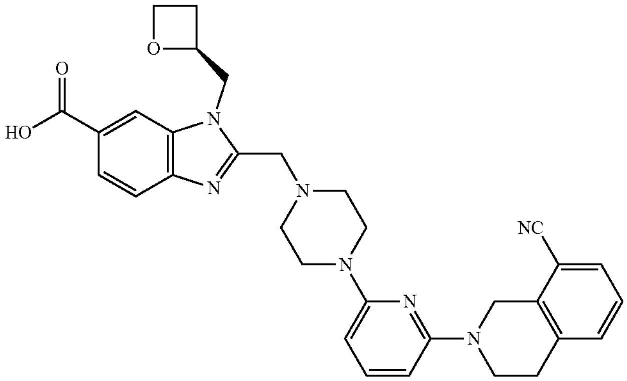 [SMILES: N#Cc1cccc2c1CN(c1cccc(N3CCN(Cc4nc5ccc(C(=O)O)cc5n4C[C@@H]4CCO4)CC3)n1)CC2] |
| 2-110 | 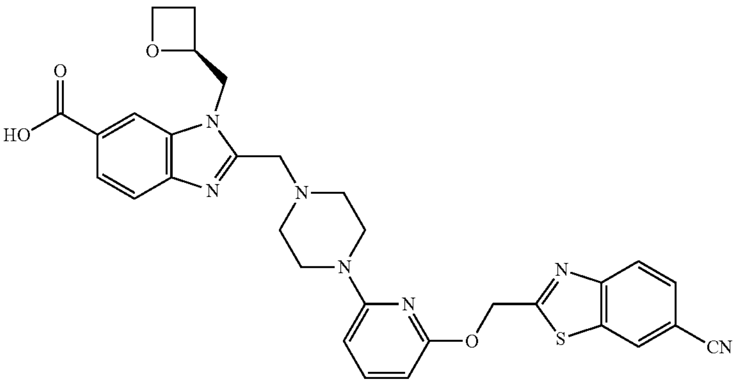 [SMILES: N#Cc1ccc2nc(COc3cccc(N4CCN(Cc5nc6ccc(C(=O)O)cc6n5C[C@@H]5CCO5)CC4)n3)sc2c1] |

TABLE 3-continued
| Compound No. | Structure |
|---|---|
| 2-111 | 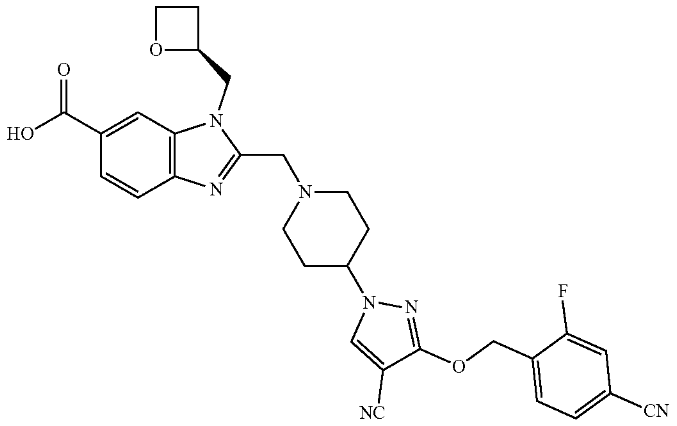 [SMILES: N#Cc1ccc(COc2nn(C3CCN(Cc4nc5ccc(C(=O)O)cc5n4C[C@@H]4CCO4)CC3)cc2C#N)c(F)c1] |
| 2-112 | 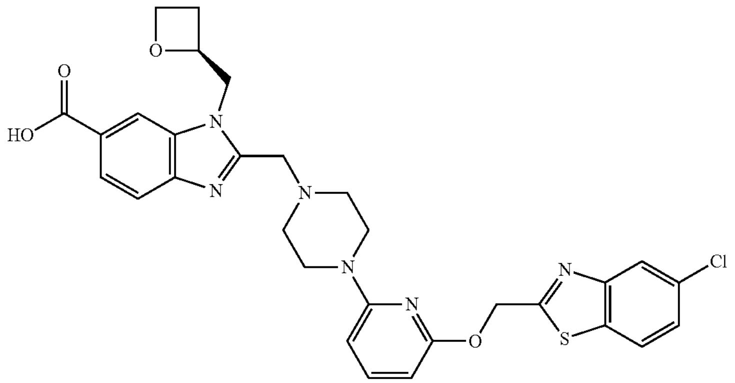 [SMILES: O=C(O)c1ccc2nc(CN3CCN(c4cccc(OCc5nc6cc(Cl)ccc6s5)n4)CC3)n(C[C@@H]3CCO3)c2c1] |
| 2-113 | 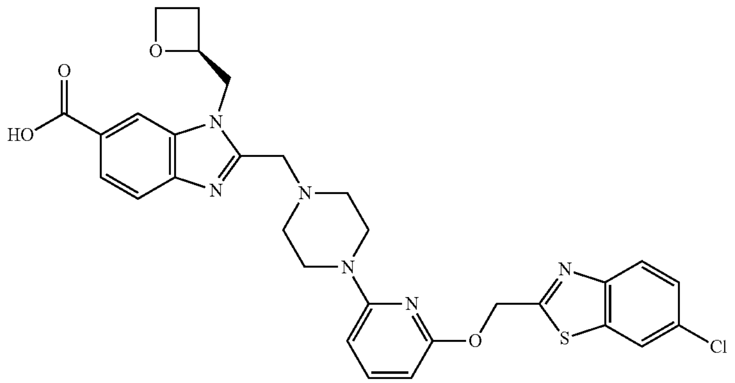 [SMILES: O=C(O)c1ccc2nc(CN3CCN(c4cccc(OCc5nc6ccc(Cl)cc6s5)n4)CC3)n(C[C@@H]3CCO3)c2c1] |

TABLE 3-continued
| Compound No. | Structure |
| --- | --- |
| 2-114 | 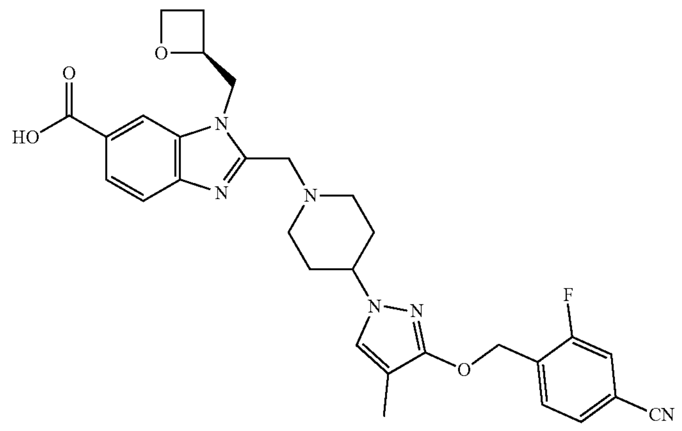 [SMILES: Cc1cn(C2CCN(Cc3nc4ccc(C(=O)O)cc4n3C[C@@H]3CCO3)CC2)nc1OCc1ccc(C#N)cc1F] |
| 2-115 | 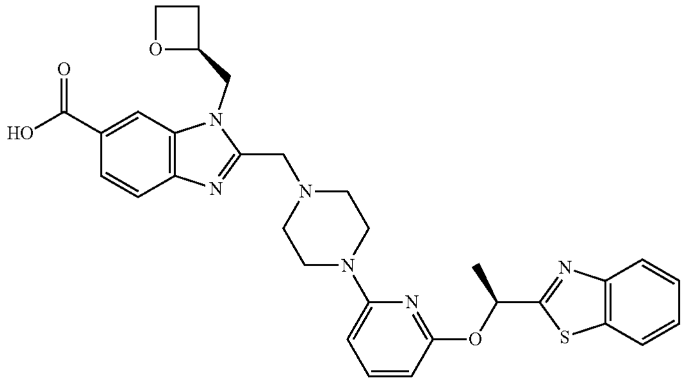 [SMILES: C[C@H](Oc1cccc(N2CCN(Cc3nc4ccc(C(=O)O)cc4n3C[C@@H]3CCO3)CC2)n1)c1nc2ccccc2s1] |
| 2-116 | 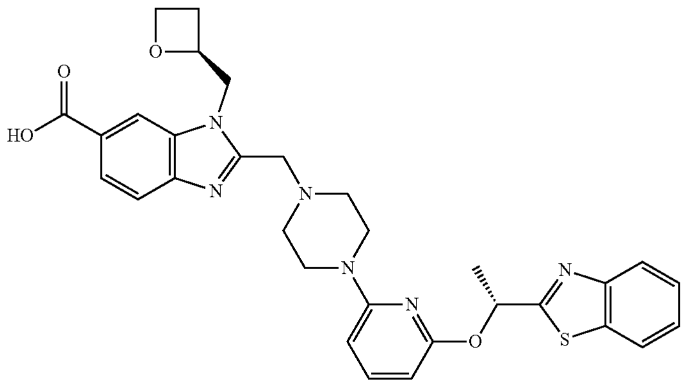 [SMILES: C[C@@H](Oc1cccc(N2CCN(Cc3nc4ccc(C(=O)O)cc4n3C[C@@H]3CCO3)CC2)n1)c1nc2ccccc2s1] |

TABLE 3-continued
| Compound No. | Structure |
|---|---|
| 2-117 | 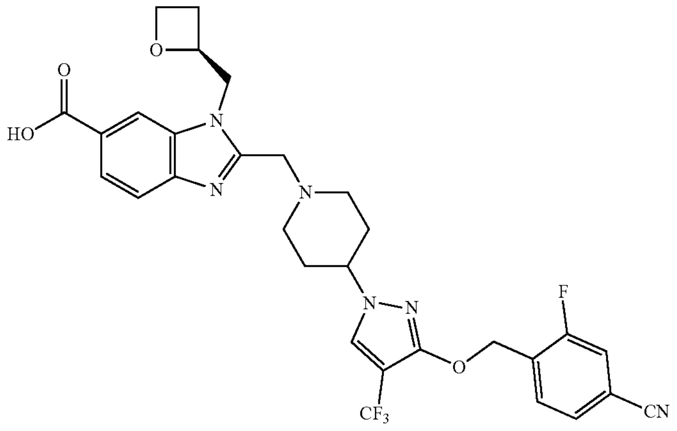 [SMILES: N#Cc1ccc(COc2nn(C3CCN(Cc4nc5ccc(C(=O)O)cc5n4C[C@@H]4CCO4)CC3)cc2C(F)(F)F)c(F)c1] |
| 2-118 | 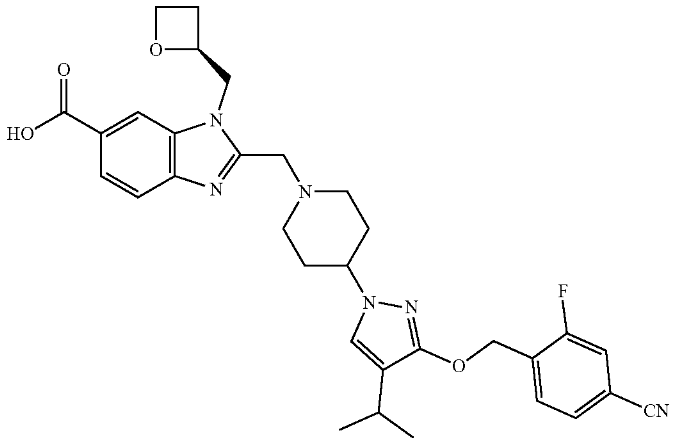 [SMILES: CC(C)c1cn(C2CCN(Cc3nc4ccc(C(=O)O)cc4n3C[C@@H]3CCO3)CC2)nc1OCc1ccc(C#N)cc1F] |
| 2-119 | 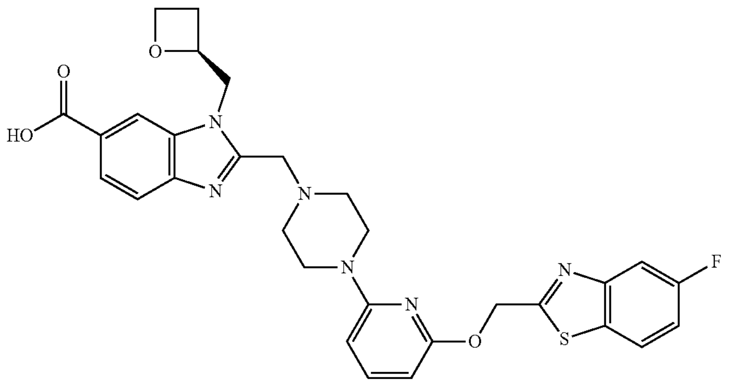 [SMILES: O=C(O)c1ccc2nc(CN3CCN(c4cccc(OCc5nc6cc(F)ccc6s5)n4)CC3)n(C[C@@H]3CCO3)c2c1] |

TABLE 3-continued
| Compound No. | Structure |
|---|---|
| 2-120 | 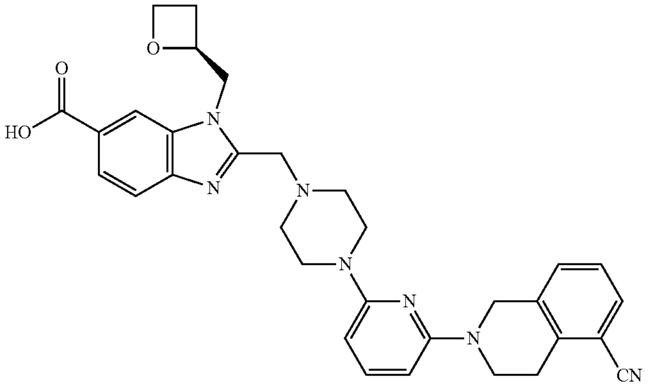 [SMILES: N#Cc1cccc2c1CCN(c1cccc(N3CCN(Cc4nc5ccc(C(=O)O)cc5n4C[C@@H]4CCO4)CC3)n1)C2] |
| 2-121-P1 | 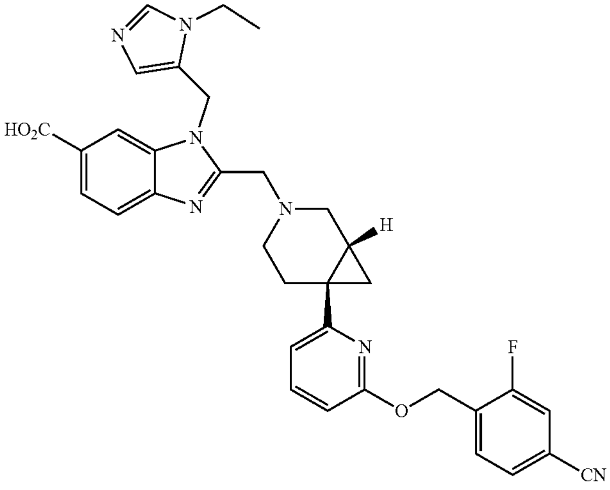 [SMILES: CCn1cncc1Cn1c(CN2CC[C@@]3(c4cccc(OCc5ccc(C#N)cc5F)n4)C[C@H]3C2)nc2ccc(C(=O)O)cc21] |
| 2-121-P2 | 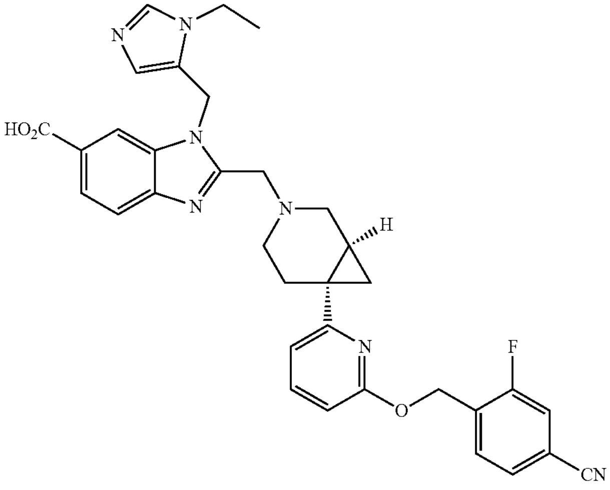 [SMILES: CCn1cncc1Cn1c(CN2CC[C@]3(c4cccc(OCc5ccc(C#N)cc5F)n4)C[C@@H]3C2)nc2ccc(C(=O)O)cc21] |

TABLE 3-continued
| Compound No. | Structure |
|---|---|
| 2-122 | 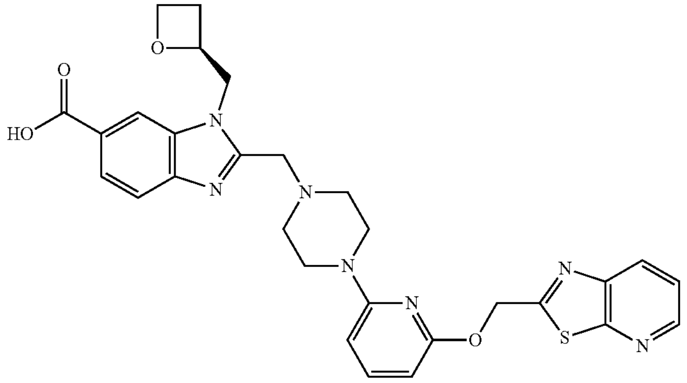 [SMILES: O=C(O)c1ccc2nc(CN3CCN(c4cccc(OCc5nc6cccnc6s5)n4)CC3)n(C[C@@H]3CCO3)c2c1] |
| 2-123 | 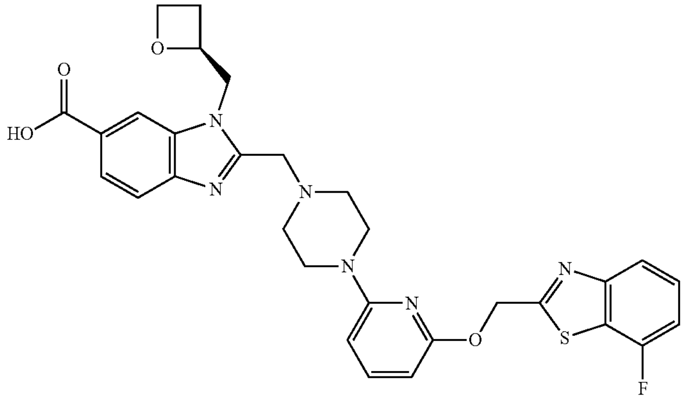 [SMILES: O=C(O)c1ccc2nc(CN3CCN(c4cccc(OCc5nc6cccc(F)c6s5)n4)CC3)n(C[C@@H]3CCO3)c2c1] |
| 2-124 | 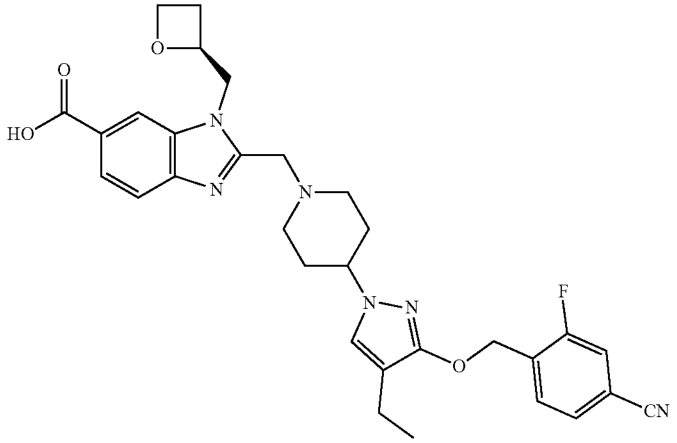 [SMILES: CCc1cn(C2CCN(Cc3nc4ccc(C(=O)O)cc4n3C[C@@H]3CCO3)CC2)nc1OCc1ccc(C#N)cc1F] |

TABLE 3-continued
| Compound No. | Structure |
| --- | --- |
| 2-125 | 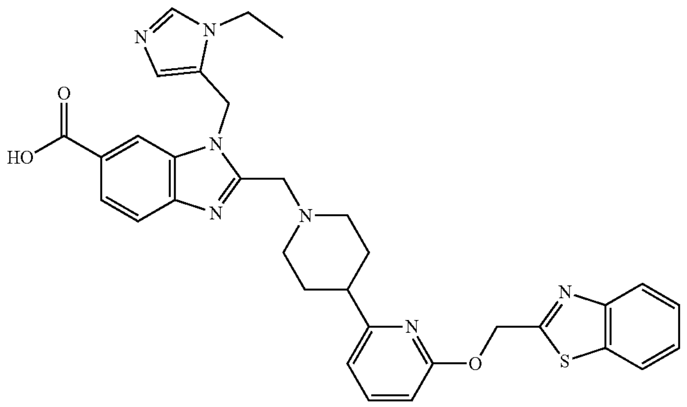 [SMILES: CCn1cncc1Cn1c(CN2CCC(c3cccc(OCc4nc5ccccc5s4)n3)CC2)nc2ccc(C(=O)O)cc21] |
| 2-126-P1 | 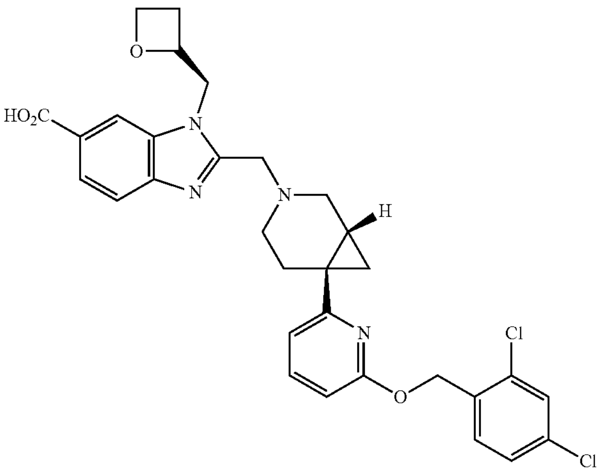 |
| 2-126-P2 | 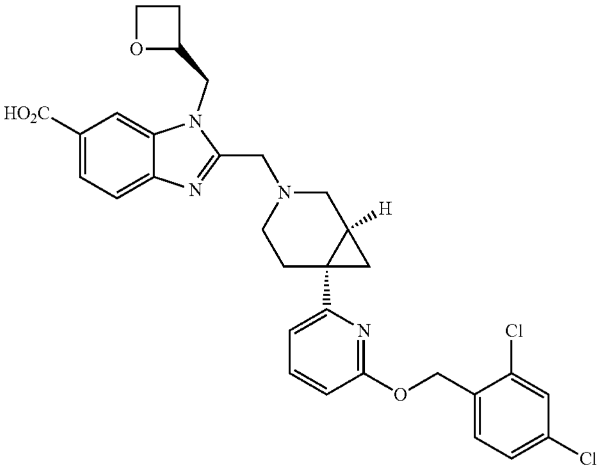 |

TABLE 3-continued
| Compound No. | Structure |
|---|---|
| 2-127 | 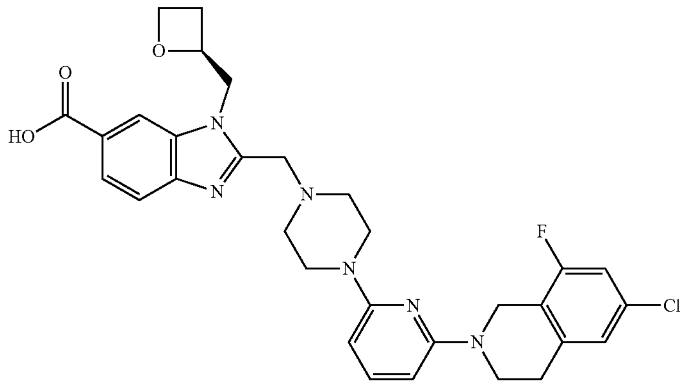 [SMILES: O=C(O)c1ccc2nc(CN3CCN(c4cccc(N5CCc6cc(Cl)cc(F)c6C5)n4)CC3)n(C[C@@H]3CCO3)c2c1] |
| 2-128 | 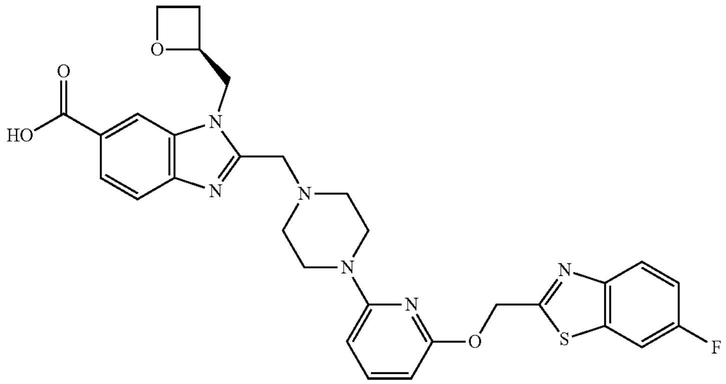 [SMILES: O=C(O)c1ccc2nc(CN3CCN(c4cccc(OCc5nc6ccc(F)cc6s5)n4)CC3)n(C[C@@H]3CCO3)c2c1] |
| 2-129 | 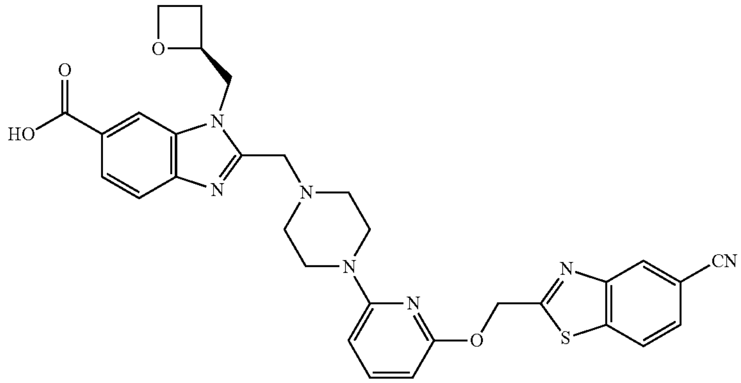 [SMILES: N#Cc1ccc2sc(COc3cccc(N4CCN(Cc5nc6ccc(C(=O)O)cc6n5C[C@@H]5CCO5)CC4)n3)nc2c1] |
| 2-130 | 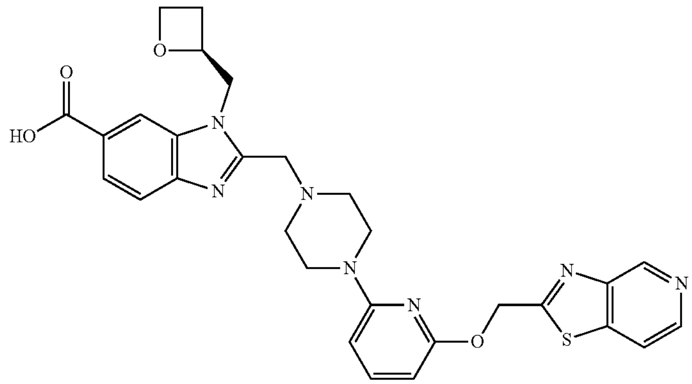 [SMILES: O=C(O)c1ccc2nc(CN3CCN(c4cccc(OCc5nc6cnccc6s5)n4)CC3)n(C[C@@H]3CCO3)c2c1] |

TABLE 3-continued
| Compound No. | Structure |
|---|---|
| 2-131 | 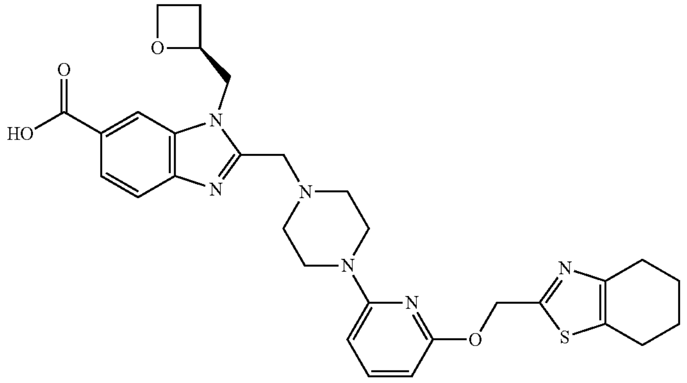 [SMILES: O=C(O)c1ccc2nc(CN3CCN(c4cccc(OCc5nc6c(s5)CCCC6)n4)CC3)n(C[C@@H]3CCO3)c2c1] |
| 2-132 | 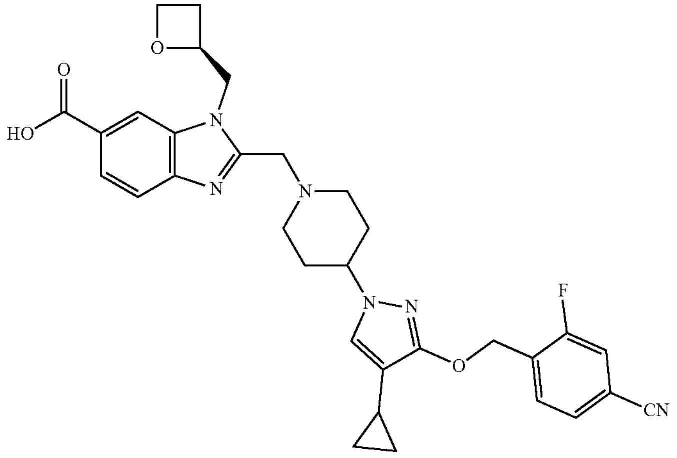 [SMILES: N#Cc1ccc(COc2nn(C3CCN(Cc4nc5ccc(C(=O)O)cc5n4C[C@@H]4CCO4)CC3)cc2C2CC2)c(F)c1] |
| 2-133 | 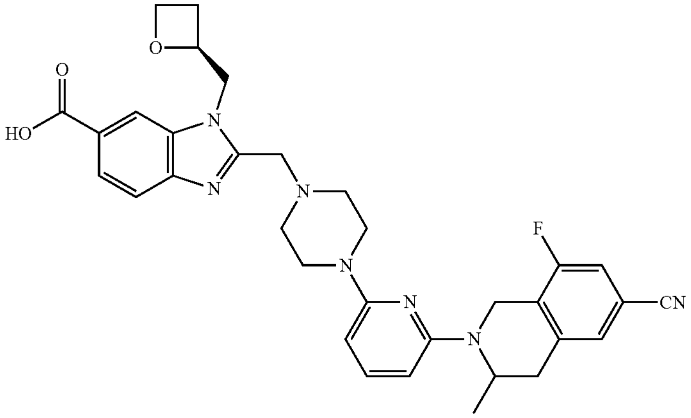 [SMILES: CC1Cc2cc(C#N)cc(F)c2CN1c1cccc(N2CCN(Cc3nc4ccc(C(=O)O)cc4n3C[C@@H]3CCO3)CC2)n1] |

TABLE 3-continued
| Compound No. | Structure |
|---|---|
| 2-134 | 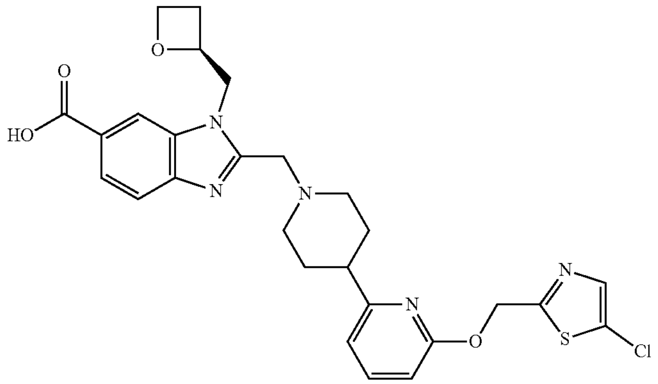 [SMILES: O=C(O)c1ccc2nc(CN3CCC(c4cccc(OCc5ncc(Cl)s5)n4)CC3)n(C[C@@H]3CCO3)c2c1] |
| 2-135 | 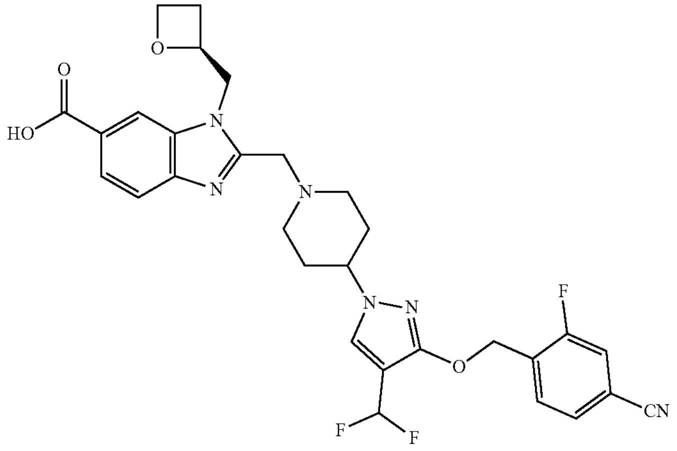 [SMILES: N#Cc1ccc(COc2nn(C3CCN(Cc4nc5ccc(C(=O)O)cc5n4C[C@@H]4CCO4)CC3)cc2C(F)F)c(F)c1] |
| 2-136 | 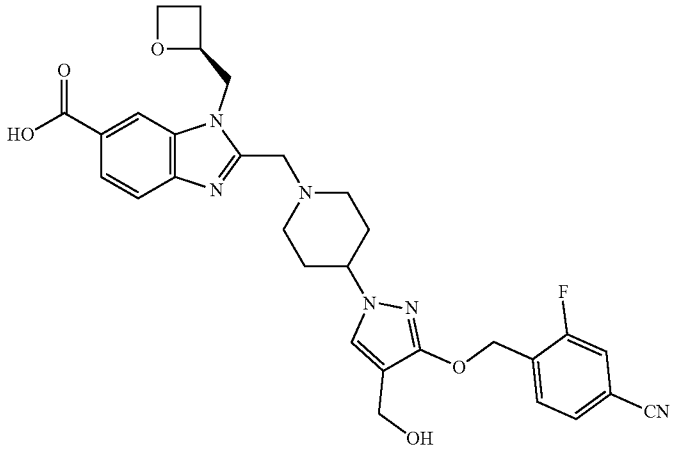 [SMILES: N#Cc1ccc(COc2nn(C3CCN(Cc4nc5ccc(C(=O)O)cc5n4C[C@@H]4CCO4)CC3)cc2CO)c(F)c1] |

TABLE 3-continued
| Compound No. | Structure |
|---|---|
| 2-137 | 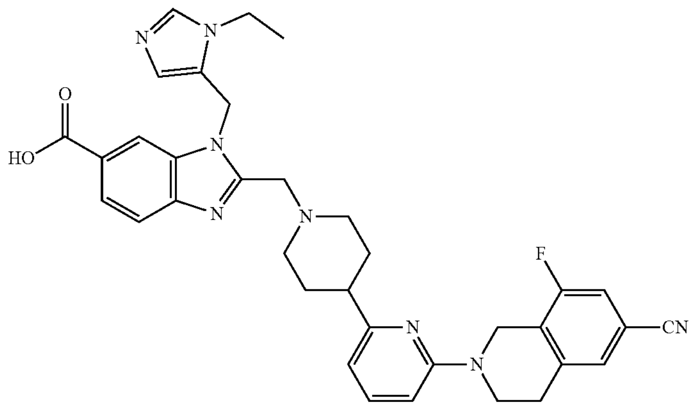 [SMILES: CCn1cncc1Cn1c(CN2CCC(c3cccc(N4CCc5cc(C#N)cc(F)c5C4)n3)CC2)nc2ccc(C(=O)O)cc21] |
| 2-138 | 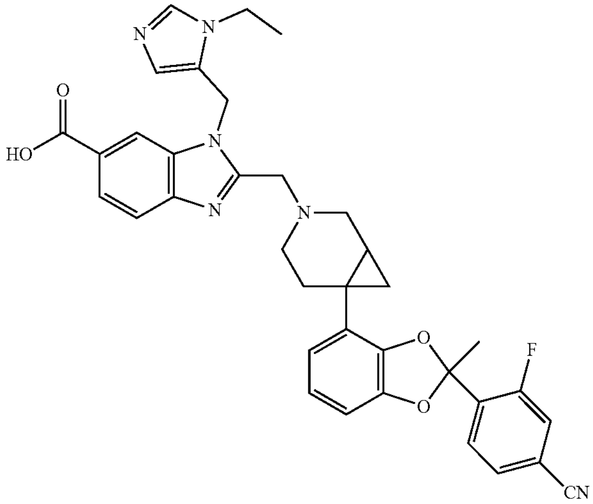 [SMILES: CCn1cncc1Cn1c(CN2CCC3(c4cccc5c4OC(C)(c4ccc(C#N)cc4F)O5)CC3C2)nc2ccc(C(=O)O)cc21] |
| 2-139 | 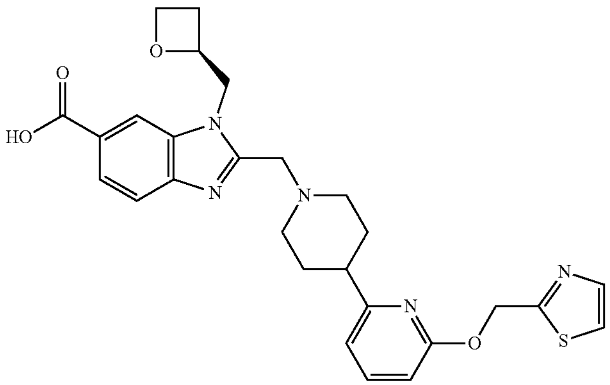 [SMILES: O=C(O)c1ccc2nc(CN3CCC(c4cccc(OCc5nccs5)n4)CC3)n(C[C@@H]3CCO3)c2c1] |

TABLE 3-continued
| Compound No. | Structure |
| --- | --- |
| 2-140-P1 | 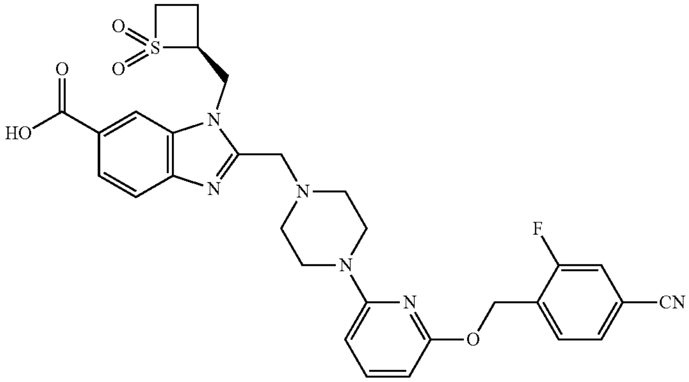 [SMILES: N#Cc1ccc(COc2cccc(N3CCN(Cc4nc5ccc(C(=O)O)cc5n4C[C@@H]4CCS4(=O)=O)CC3)n2)c(F)c1] |
| 2-140-P2 | 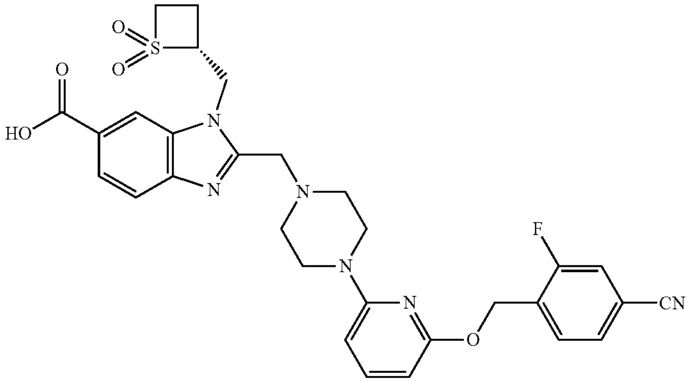 [SMILES: N#Cc1ccc(COc2cccc(N3CCN(Cc4nc5ccc(C(=O)O)cc5n4C[C@H]4CCS4(=O)=O)CC3)n2)c(F)c1] |
| 2-141-P1 | 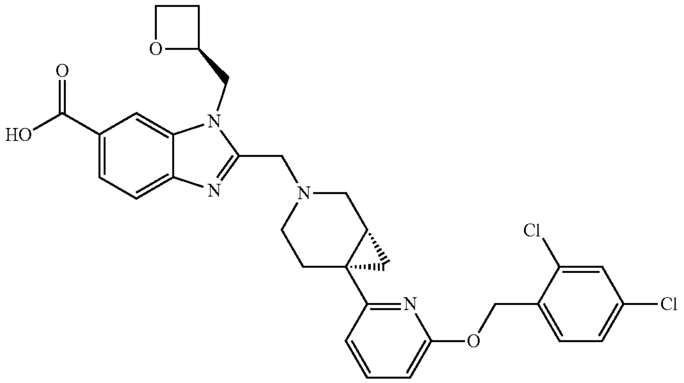 [SMILES: O=C(O)c1ccc2nc(CN3CC[C@@]4(c5cccc(OCc6ccc(Cl)cc6Cl)n5)C[C@H]4C3)n(C[C@@H]3CCO3)c2c1] |
| 2-141-P2 | 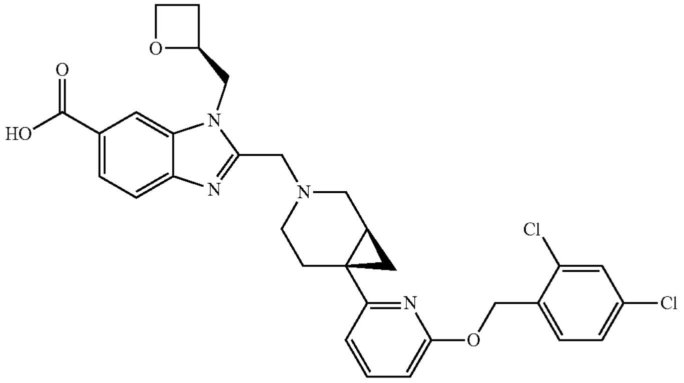 [SMILES: O=C(O)c1ccc2nc(CN3CC[C@]4(c5cccc(OCc6ccc(Cl)cc6Cl)n5)C[C@@H]4C3)n(C[C@@H]3CCO3)c2c1] |

TABLE 3-continued
| Compound No. | Structure |
|---|---|
| 2-142 | 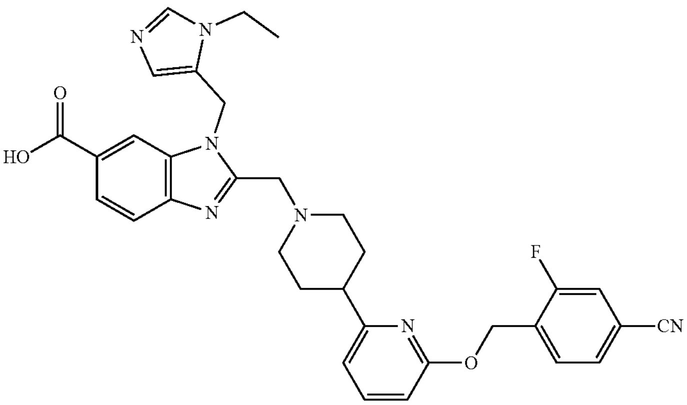 [SMILES: CCn1cncc1Cn1c(CN2CCC(c3cccc(OCc4ccc(C#N)cc4F)n3)CC2)nc2ccc(C(=O)O)cc21] |
| 2-143 | 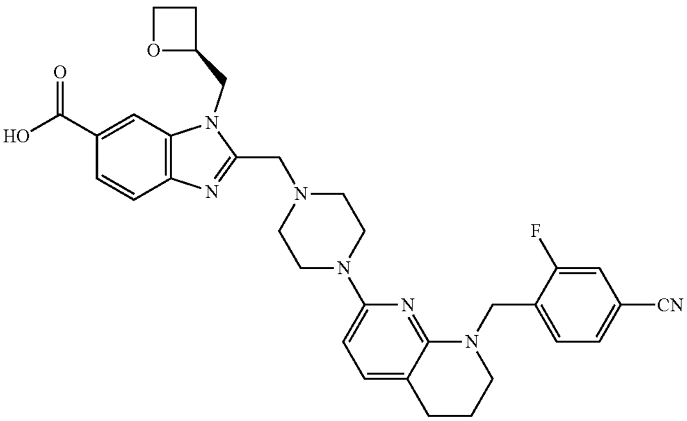 [SMILES: N#Cc1ccc(CN2CCCc3ccc(N4CCN(Cc5nc6ccc(C(=O)O)cc6n5C[C@@H]5CCO5)CC4)nc32)c(F)c1] |
| 2-144 | 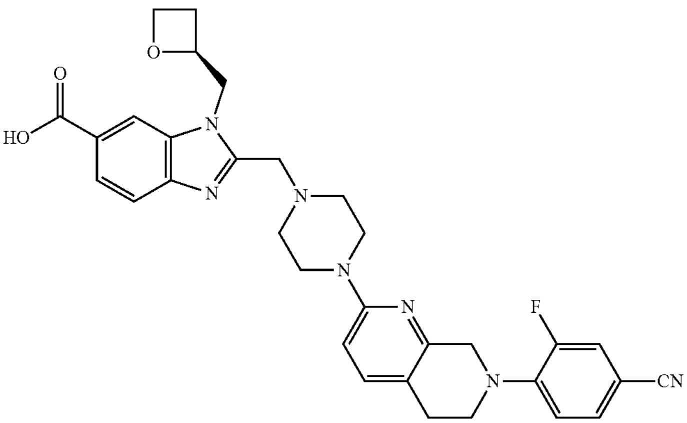 [SMILES: N#Cc1ccc(N2CCc3ccc(N4CCN(Cc5nc6ccc(C(=O)O)cc6n5C[C@@H]5CCO5)CC4)nc3C2)c(F)c1] |

TABLE 3-continued
| Compound No. | Structure |
|---|---|
| 2-145 | 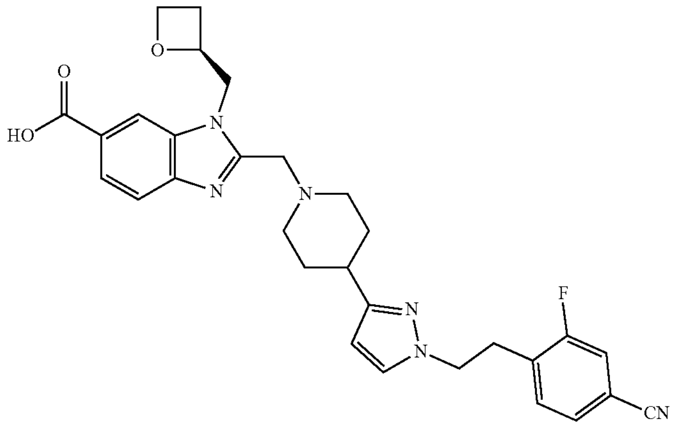 [SMILES: N#Cc1ccc(CCn2ccc(C3CCN(Cc4nc5ccc(C(=O)O)cc5n4C[C@@H]4CCO4)CC3)n2)c(F)c1] |
| 2-146-P1 | 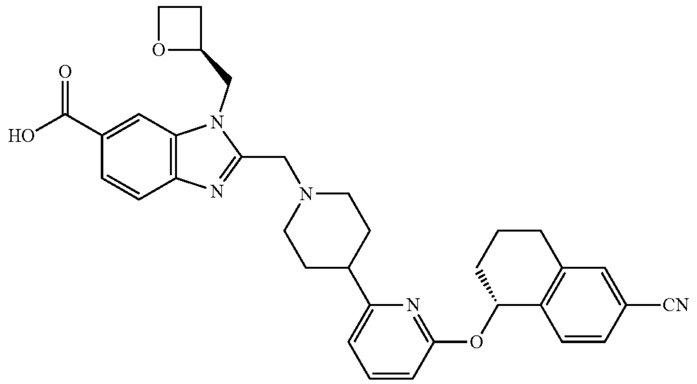 [SMILES: N#Cc1ccc2c(c1)CCC[C@H]2Oc1cccc(C2CCN(Cc3nc4ccc(C(=O)O)cc4n3C[C@@H]3CCO3)CC2)n1] |
| 2-146-P2 | 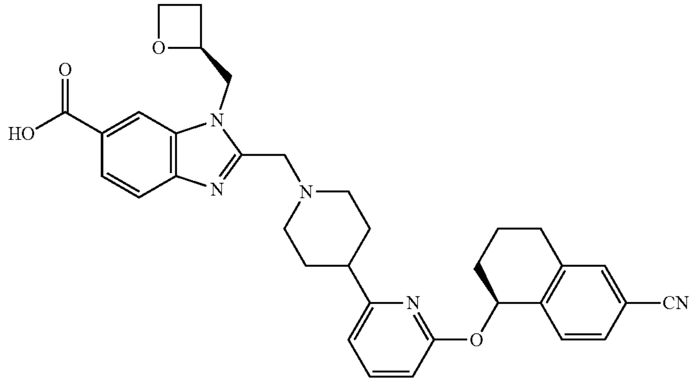 [SMILES: N#Cc1ccc2c(c1)CCC[C@@H]2Oc1cccc(C2CCN(Cc3nc4ccc(C(=O)O)cc4n3C[C@@H]3CCO3)CC2)n1] |
| 2-147 | 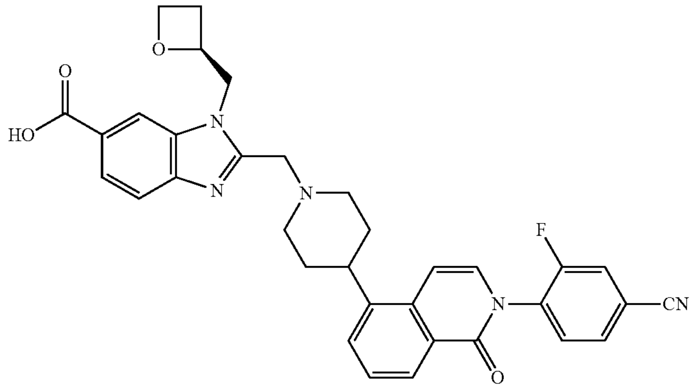 [SMILES: N#Cc1ccc(-n2ccc3c(C4CCN(Cc5nc6ccc(C(=O)O)cc6n5C[C@@H]5CCO5)CC4)cccc3c2=O)c(F)c1] |

TABLE 3-continued
| Compound No. | Structure |
|---|---|
| 2-148 | 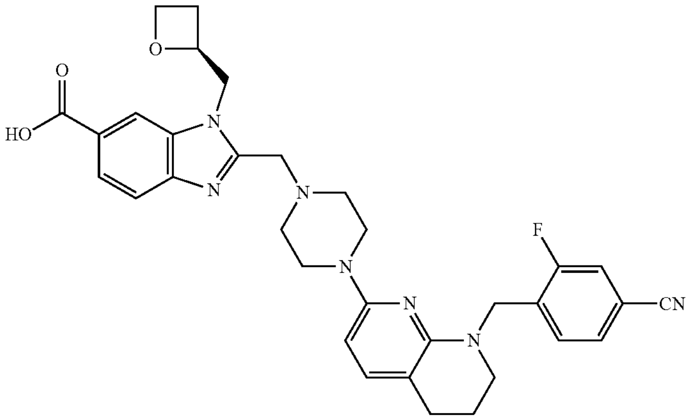 [SMILES: N#Cc1ccc(CN2CCCc3ccc(N4CCN(Cc5nc6ccc(C(=O)O)cc6n5C[C@@H]5CCO5)CC4)nc32)c(F)c1] |
| 2-149 | 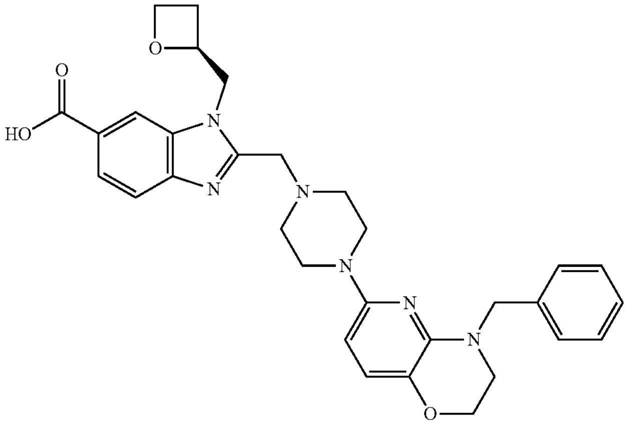 [SMILES: O=C(O)c1ccc2nc(CN3CCN(c4ccc5c(n4)N(Cc4ccccc4)CCO5)CC3)n(C[C@@H]3CCO3)c2c1] |
| 2-150 | 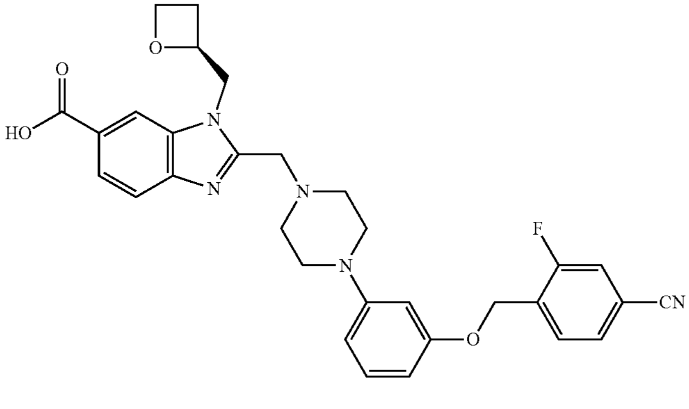 [SMILES: N#Cc1ccc(COc2cccc(N3CCN(Cc4nc5ccc(C(=O)O)cc5n4C[C@@H]4CCO4)CC3)c2)c(F)c1] |

TABLE 3-continued
| Compound No. | Structure |
|---|---|
| 2-151-P1 | 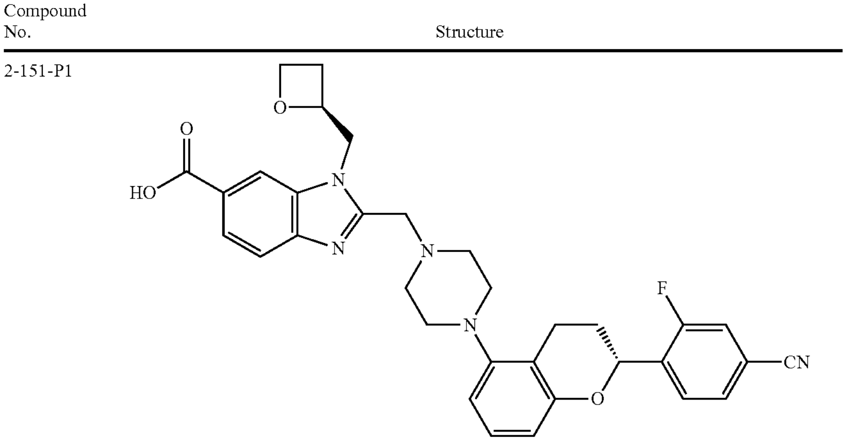 |
| 2-151-P2 | 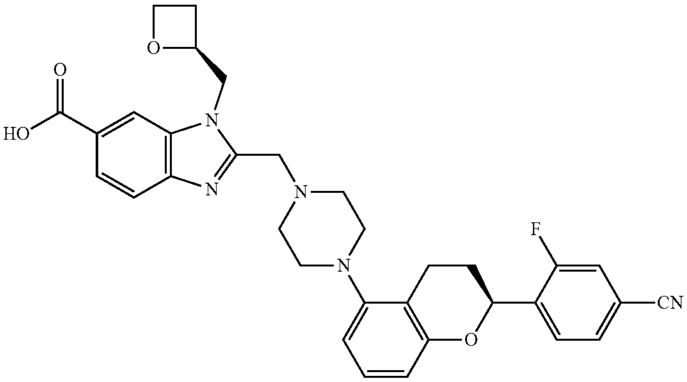 [SMILES: N#Cc1ccc([C@@H]2CCc3c(cccc3N3CCN(Cc4nc5ccc(C(=O)O)cc5n4C[C@@H]4CCO4)CC3)O2)c(F)c1] |
| 2-152 | 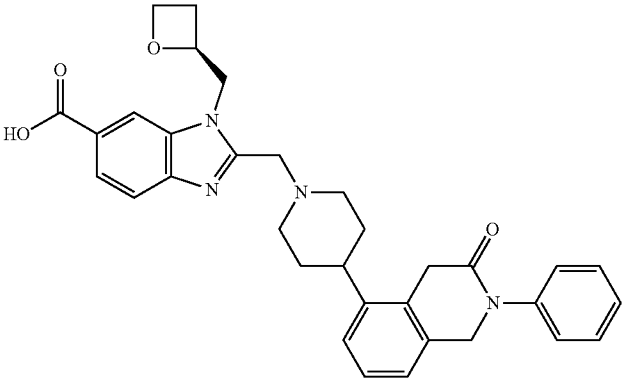 [SMILES: O=C(O)c1ccc2nc(CN3CCC(c4cccc5c4CC(=O)N(c4ccccc4)C5)CC3)n(C[C@@H]3CCO3)c2c1] |
| 2-153 | 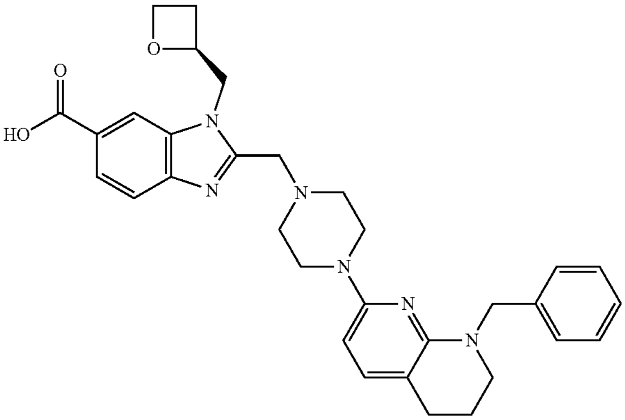 [SMILES: O=C(O)c1ccc2nc(CN3CCN(c4ccc5c(n4)N(Cc4ccccc4)CCC5)CC3)n(C[C@@H]3CCO3)c2c1] |

TABLE 3-continued
| Compound No. | Structure |
|---|---|
| 2-154 | 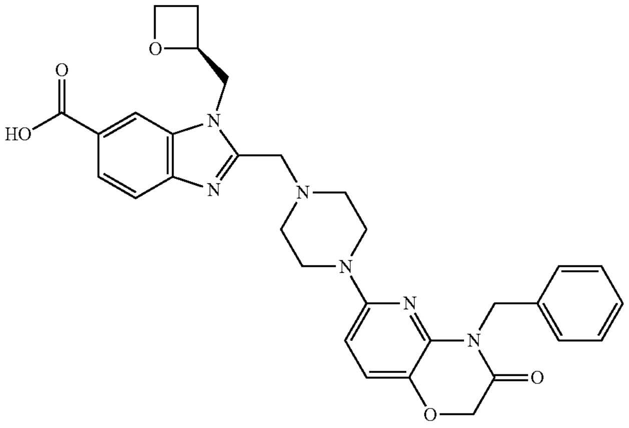 [SMILES: O=C(O)c1ccc2nc(CN3CCN(c4ccc5c(n4)N(Cc4ccccc4)C(=O)CO5)CC3)n(C[C@@H]3CCO3)c2c1] |
| 2-155 | 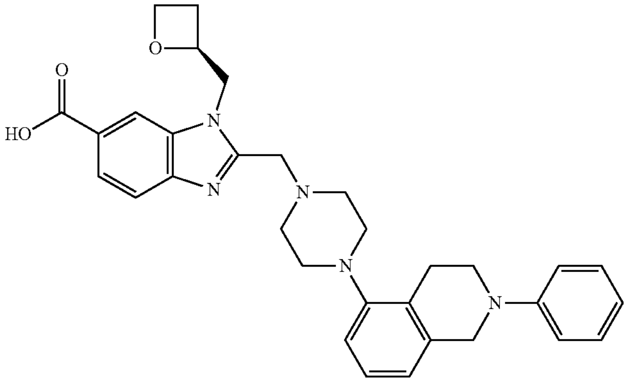 [SMILES: O=C(O)c1ccc2nc(CN3CCN(c4cccc5c4CCN(c4ccccc4)C5)CC3)n(C[C@@H]3CCO3)c2c1] |
| 2-156 | 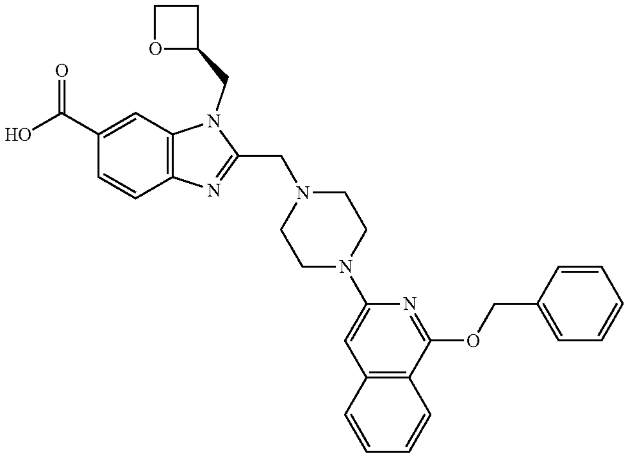 [SMILES: O=C(O)c1ccc2nc(CN3CCN(c4cc5ccccc5c(OCc5ccccc5)n4)CC3)n(C[C@@H]3CCO3)c2c1] |

TABLE 3-continued
| Compound No. | Structure |
|---|---|
| 2-157 | 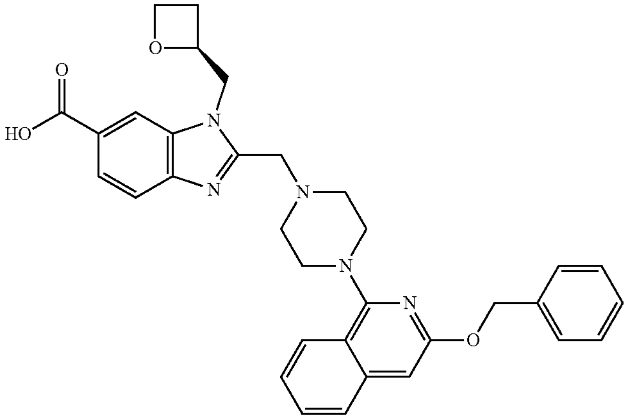 [SMILES: O=C(O)c1ccc2nc(CN3CCN(c4nc(OCc5ccccc5)cc5ccccc45)CC3)n(C[C@@H]3CCO3)c2c1] |
| 2-158 | 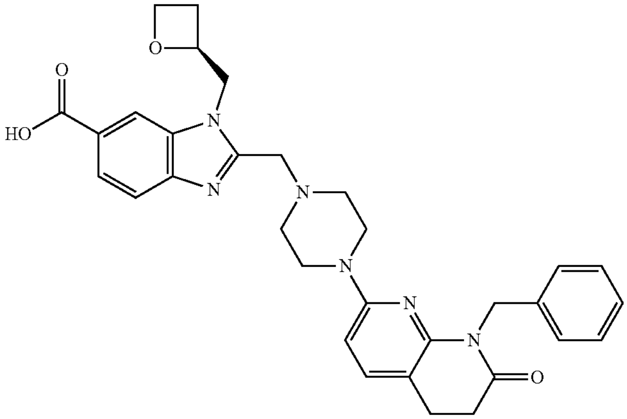 [SMILES: O=C(O)c1ccc2nc(CN3CCN(c4ccc5c(n4)N(Cc4ccccc4)C(=O)CC5)CC3)n(C[C@@H]3CCO3)c2c1] |
| 2-159 | 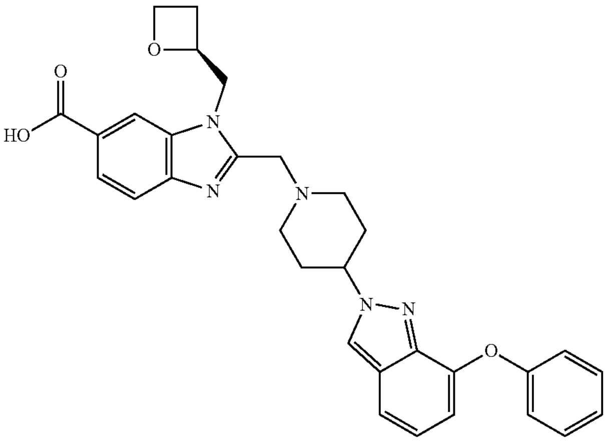 [SMILES: O=C(O)c1ccc2nc(CN3CCC(n4cc5cccc(Oc6ccccc6)c5n4)CC3)n(C[C@@H]3CCO3)c2c1] |

TABLE 3-continued
| Compound No. | Structure |
|---|---|
| 2-160 | 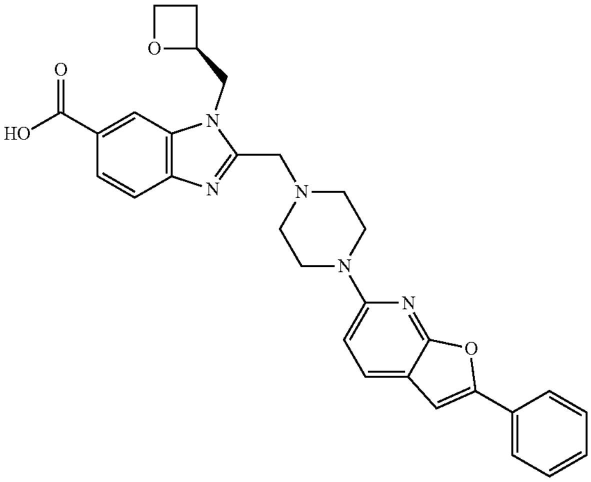 [SMILES: O=C(O)c1ccc2nc(CN3CCN(c4ccc5cc(-c6ccccc6)oc5n4)CC3)n(C[C@@H]3CCO3)c2c1] |
| 2-161 | 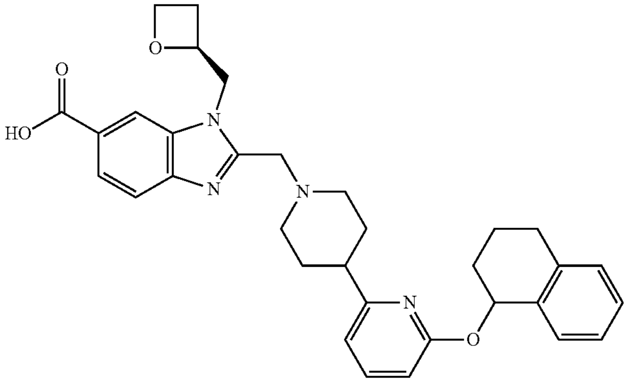 [SMILES: O=C(O)c1ccc2nc(CN3CCC(c4cccc(OC5CCCc6ccccc65)n4)CC3)n(C[C@@H]3CCO3)c2c1] |
| 2-162 | 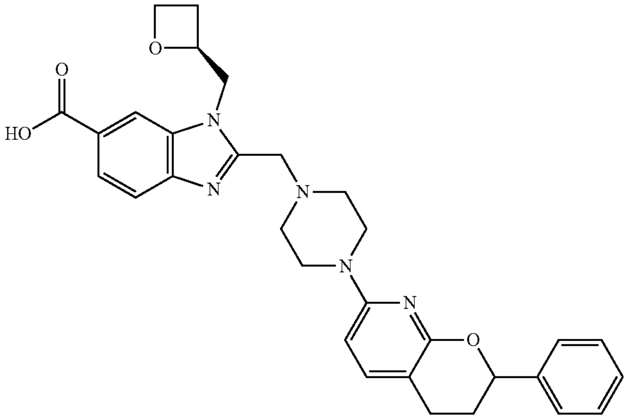 [SMILES: O=C(O)c1ccc2nc(CN3CCN(c4ccc5c(n4)OC(c4ccccc4)CC5)CC3)n(C[C@@H]3CCO3)c2c1] |

TABLE 3-continued
| Compound No. | Structure |
|---|---|
| 2-163-P1 | 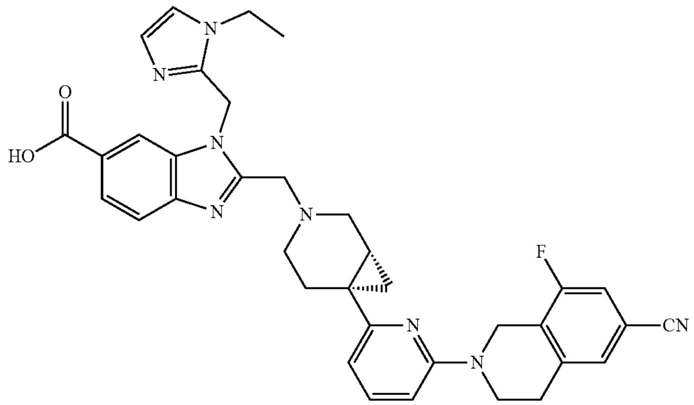 [SMILES: CCn1ccnc1Cn1c(CN2CC[C@@]3(c4cccc(N5CCc6cc(C#N)cc(F)c6C5)n4)C[C@H]3C2)nc2ccc(C(=O)O)cc21] |
| 2-163-P2 | 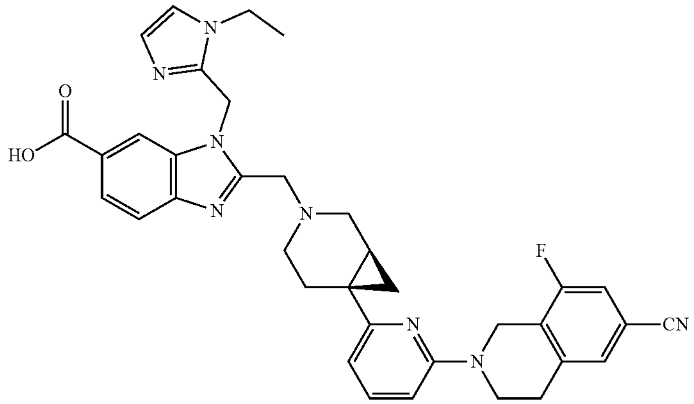 [SMILES: CCn1ccnc1Cn1c(CN2CC[C@]3(c4cccc(N5CCc6cc(C#N)cc(F)c6C5)n4)C[C@@H]3C2)nc2ccc(C(=O)O)cc21] |
| 2-164 | 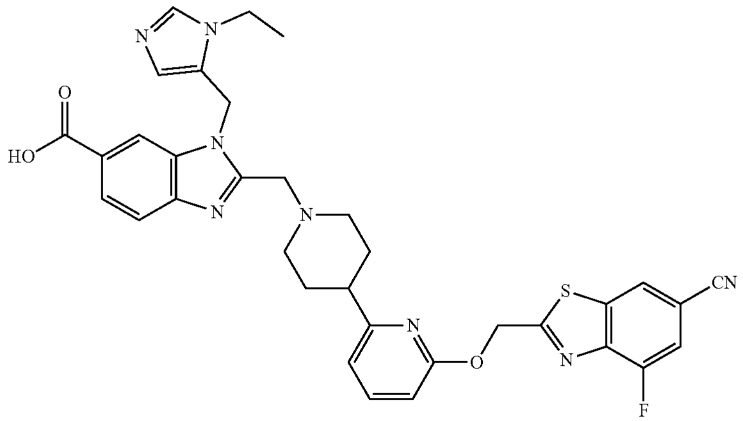 [SMILES: CCn1cncc1Cn1c(CN2CCC(c3cccc(OCc4nc5c(F)cc(C#N)cc5s4)n3)CC2)nc2ccc(C(=O)O)cc21] |

TABLE 3-continued
| Compound No. | Structure |
| --- | --- |
| 2-165 | 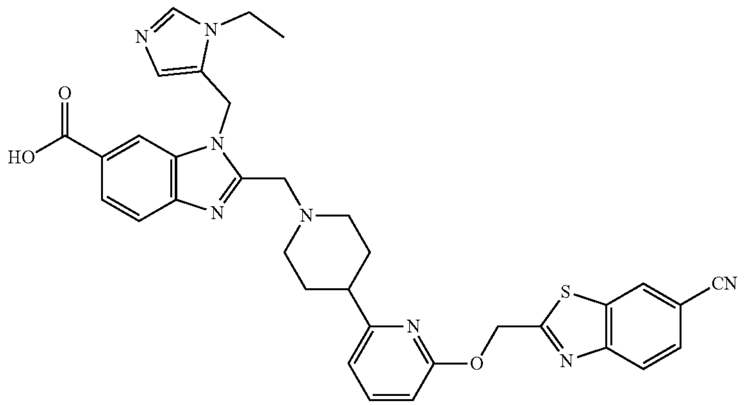 [SMILES: CCn1cncc1Cn1c(CN2CCC(c3cccc(OCc4nc5ccc(C#N)cc5s4)n3)CC2)nc2ccc(C(=O)O)cc21] |
| 2-166 | 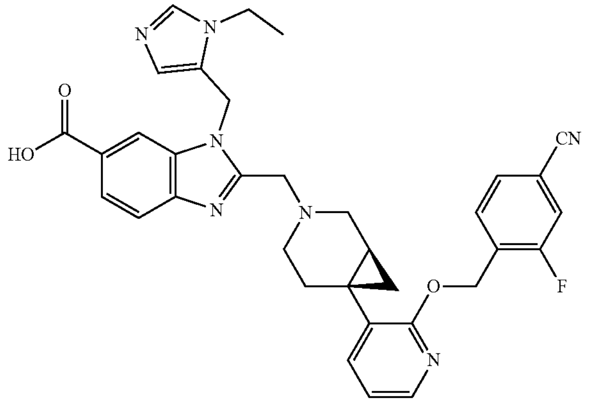 [SMILES: CCn1cncc1Cn1c(CN2CC[C@]3(c4cccnc4OCc4ccc(C#N)cc4F)C[C@@H]3C2)nc2ccc(C(=O)O)cc21] |
| 2-167 | 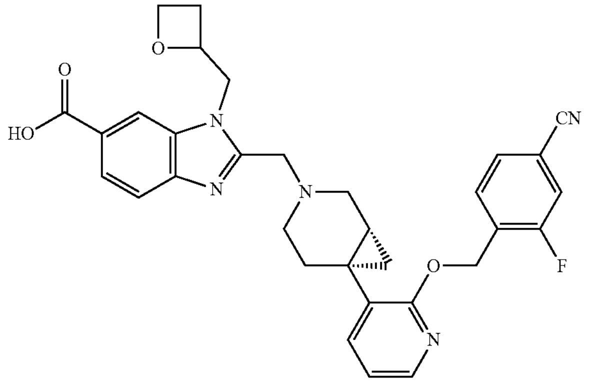 [SMILES: N#Cc1ccc(COc2ncccc2[C@@]23CCN(Cc4nc5ccc(C(=O)O)cc5n4CC4CCO4)C[C@@H]2C3)c(F)c1] |
| 2-168 | 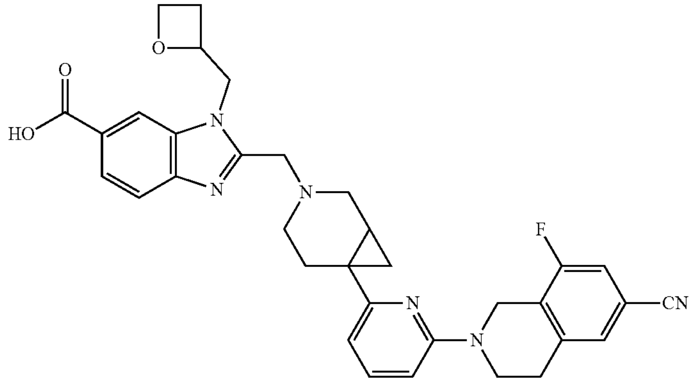 [SMILES: N#Cc1cc(F)c2c(c1)CCN(c1cccc(C34CCN(Cc5nc6ccc(C(=O)O)cc6n5CC5CCO5)CC3C4)n1)C2] |

TABLE 3-continued
| Compound No. | Structure |
|---|---|
| 2-169 | 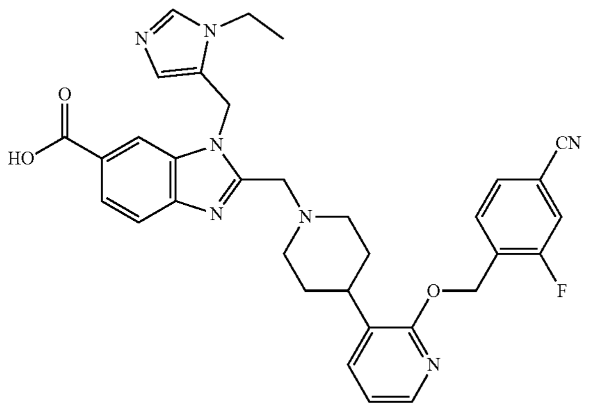 [SMILES: CCn1cncc1Cn1c(CN2CCC(c3cccnc3OCc3ccc(C#N)cc3F)CC2)nc2ccc(C(=O)O)cc21] |
| 2-170 | 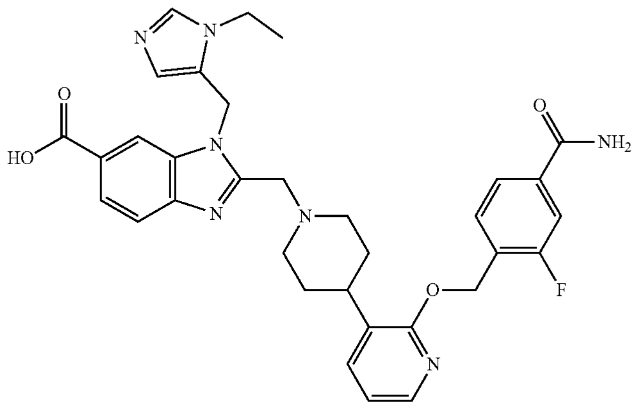 [SMILES: CCn1cncc1Cn1c(CN2CCC(c3cccnc3OCc3ccc(C(N)=O)cc3F)CC2)nc2ccc(C(=O)O)cc21] |
| 2-171 | 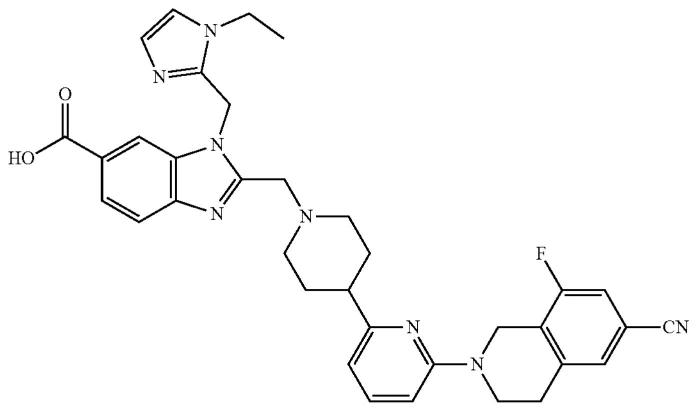 [SMILES: CCn1ccnc1Cn1c(CN2CCC(c3cccc(N4CCc5cc(C#N)cc(F)c5C4)n3)CC2)nc2ccc(C(=O)O)cc21] |

TABLE 3-continued
| Compound No. | Structure |
| --- | --- |
| 2-172 | 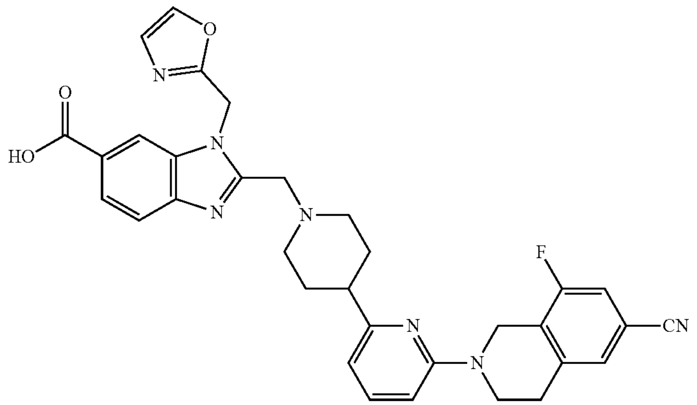 [SMILES: N#Cc1cc(F)c2c(c1)CCN(c1cccc(C3CCN(Cc4nc5ccc(C(=O)O)cc5n4Cc4ncco4)CC3)n1)C2] |
| 2-173 | 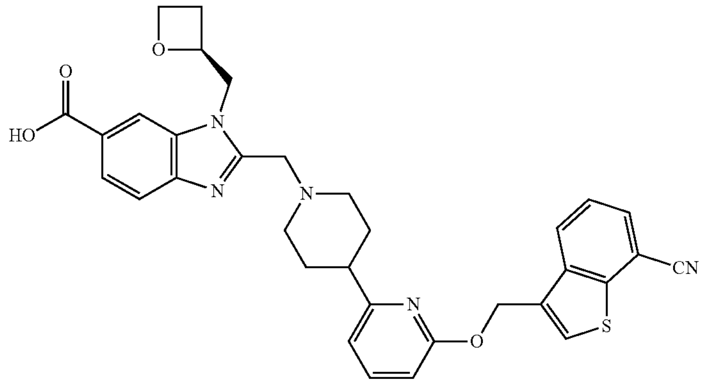 [SMILES: N#Cc1cccc2c(COc3cccc(C4CCN(Cc5nc6ccc(C(=O)O)cc6n5C[C@@H]5CCO5)CC4)n3)csc12] |
| 2-174 | 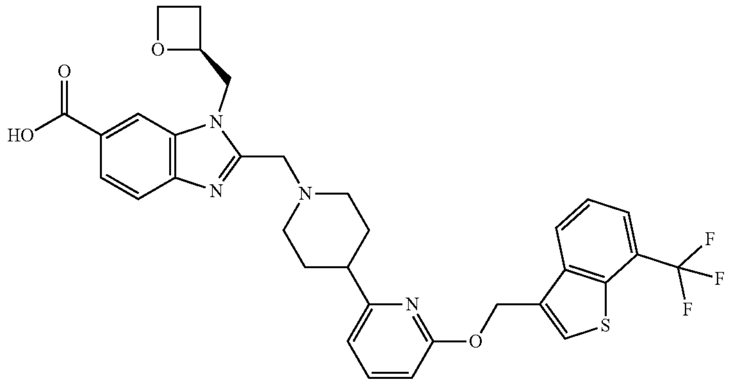 |
| 2-175 | 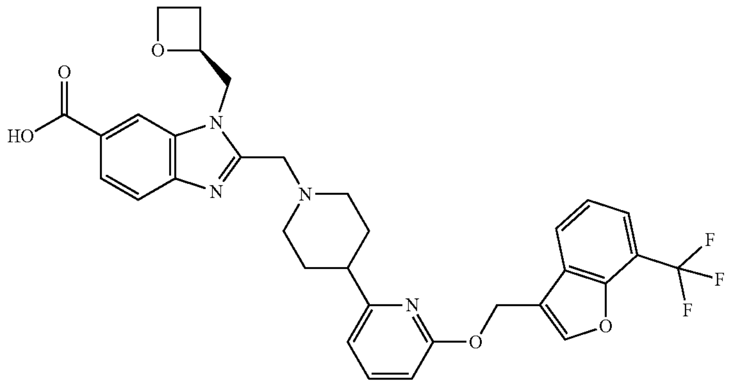 [SMILES: O=C(O)c1ccc2nc(CN3CCC(c4cccc(OCc5coc6c(C(F)(F)F)cccc56)n4)CC3)n(C[C@@H]3CCO3)c2c1] |

TABLE 3-continued
| Compound No. | Structure |
|---|---|
| 2-176 | 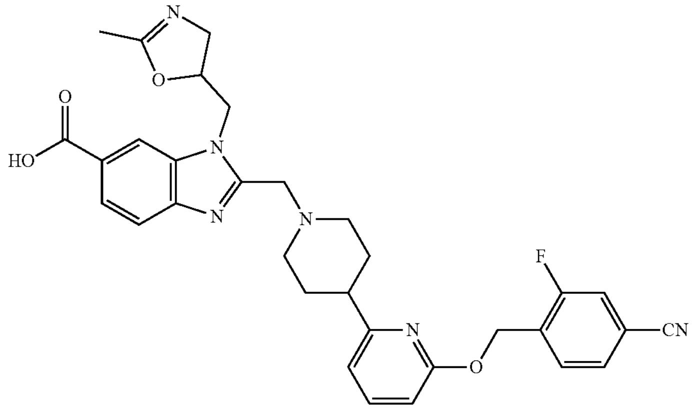 [SMILES: CC1=NCC(Cn2c(CN3CCC(c4cccc(OCc5ccc(C#N)cc5F)n4)CC3)nc3ccc(C(=O)O)cc32)O1] |
| 2-177 | 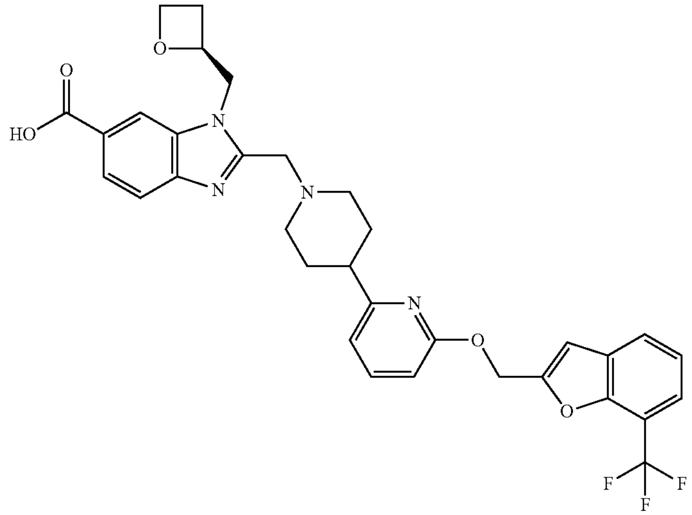 [SMILES: O=C(O)c1ccc2nc(CN3CCC(c4cccc(OCc5cc6cccc(C(F)(F)F)c6o5)n4)CC3)n(C[C@@H]3CCO3)c2c1] |
| 2-178 | 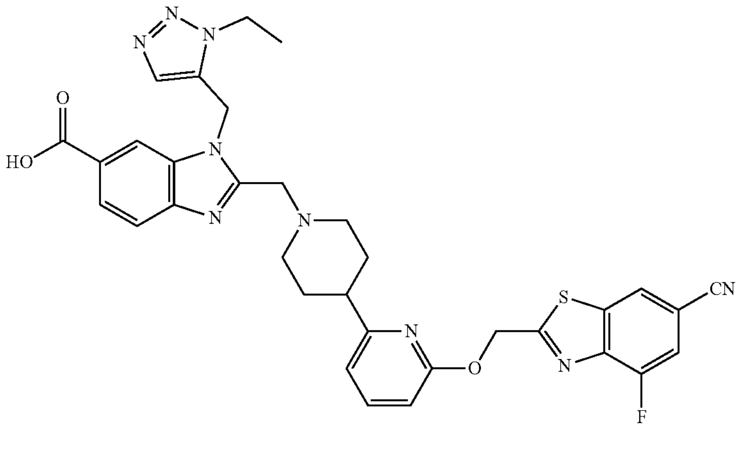 [SMILES: CCn1nncc1Cn1c(CN2CCC(c3cccc(OCc4nc5c(F)cc(C#N)cc5s4)n3)CC2)nc2ccc(C(=O)O)cc21] |

TABLE 3-continued
| Compound No. | Structure |
| --- | --- |
| 2-179 | 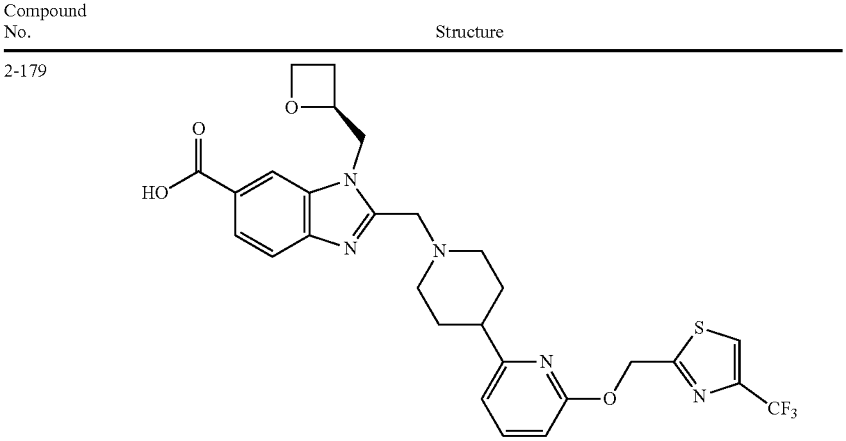 |
| 2-180 | 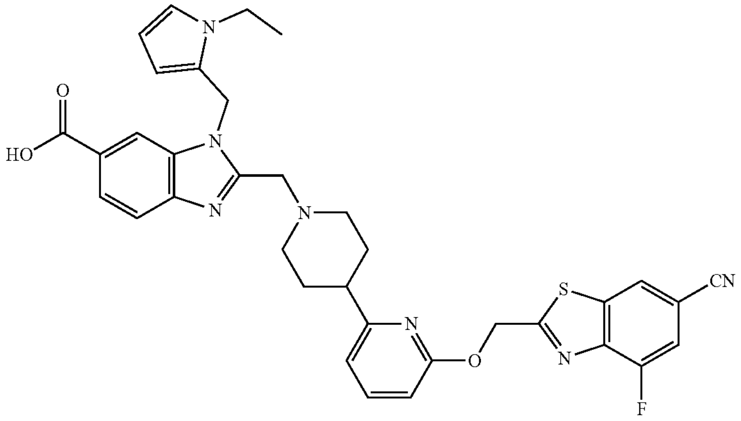 |
| 2-181 | 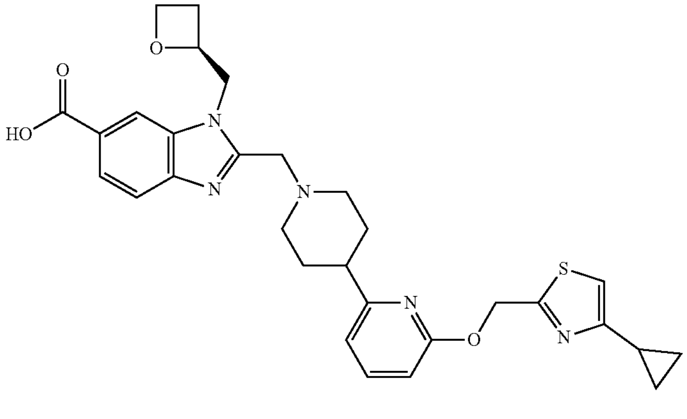 [SMILES: O=C(O)c1ccc2nc(CN3CCC(c4cccc(OCc5nc(C6CC6)cs5)n4)CC3)n(C[C@@H]3CCO3)c2c1] |
| 2-182 | 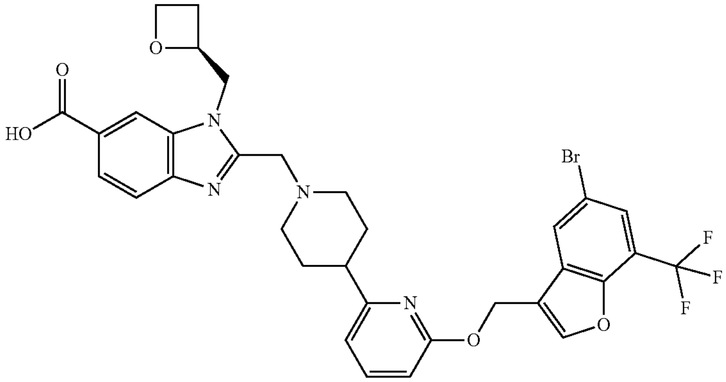 [SMILES: O=C(O)c1ccc2nc(CN3CCC(c4cccc(OCc5coc6c(C(F)(F)F)cc(Br)cc56)n4)CC3)n(C[C@@H]3CCO3)c2c1] |

TABLE 3-continued
| Compound No. | Structure |
|---|---|
| 2-183 | 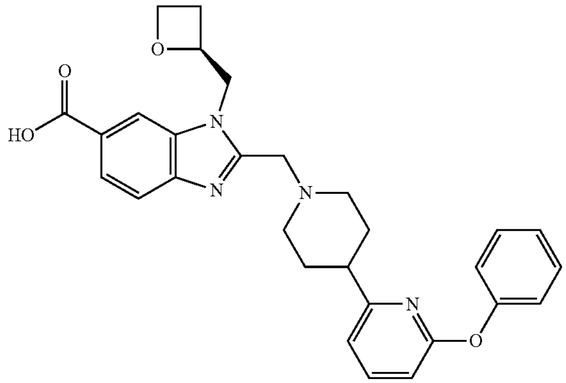 [SMILES: O=C(O)c1ccc2nc(CN3CCC(c4cccc(Oc5ccccc5)n4)CC3)n(C[C@@H]3CCO3)c2c1] |
| 2-184-P1 | 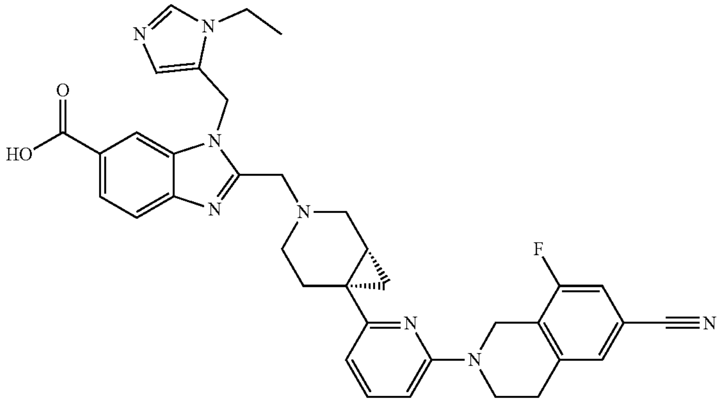 [SMILES: CCn1cncc1Cn1c(CN2CC[C@@]3(c4cccc(N5CCc6cc(C#N)cc(F)c6C5)n4)C[C@H]3C2)nc2ccc(C(=O)O)cc21] |
| 2-184-P2 | 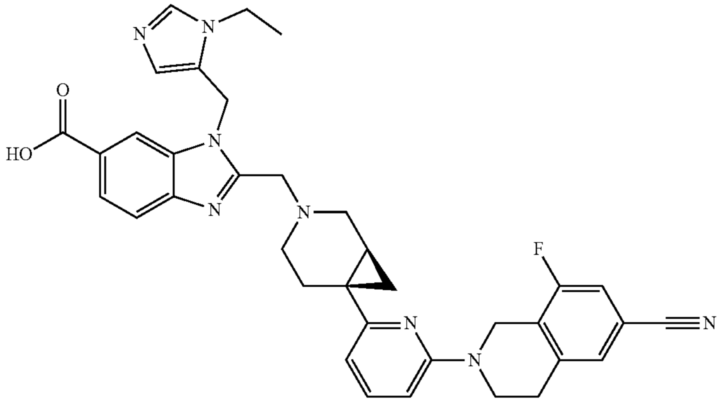 [SMILES: CCn1cncc1Cn1c(CN2CC[C@]3(c4cccc(N5CCc6cc(C#N)cc(F)c6C5)n4)C[C@@H]3C2)nc2ccc(C(=O)O)cc21] |

TABLE 3-continued
| Compound No. | Structure |
| --- | --- |
| 2-185-P1 | 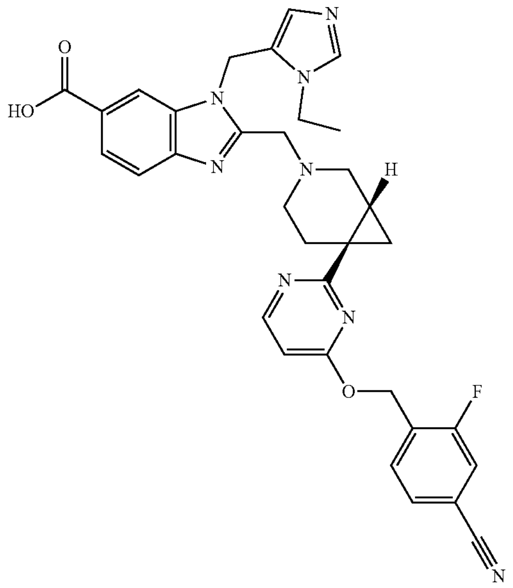 [SMILES: CCn1cncc1Cn1c(CN2CC[C@@]3(c4nccc(OCc5ccc(C#N)cc5F)n4)C[C@H]3C2)nc2ccc(C(=O)O)cc21] |
| 2-185-P2 | 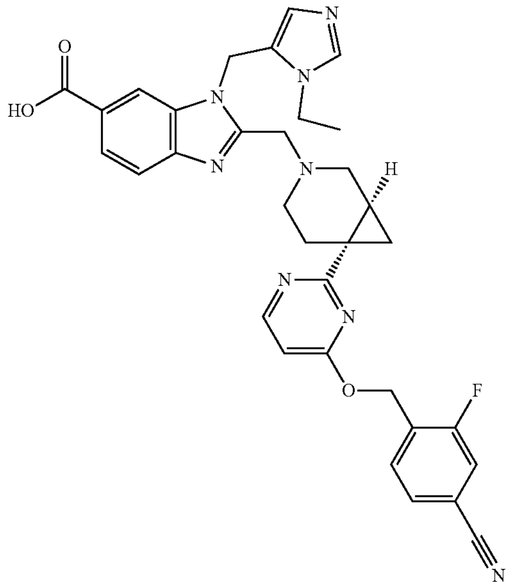 [SMILES: CCn1cncc1Cn1c(CN2CC[C@]3(c4nccc(OCc5ccc(C#N)cc5F)n4)C[C@@H]3C2)nc2ccc(C(=O)O)cc21] |

TABLE 3-continued
| Compound No. | Structure |
| --- | --- |
| 2-186-P1 | 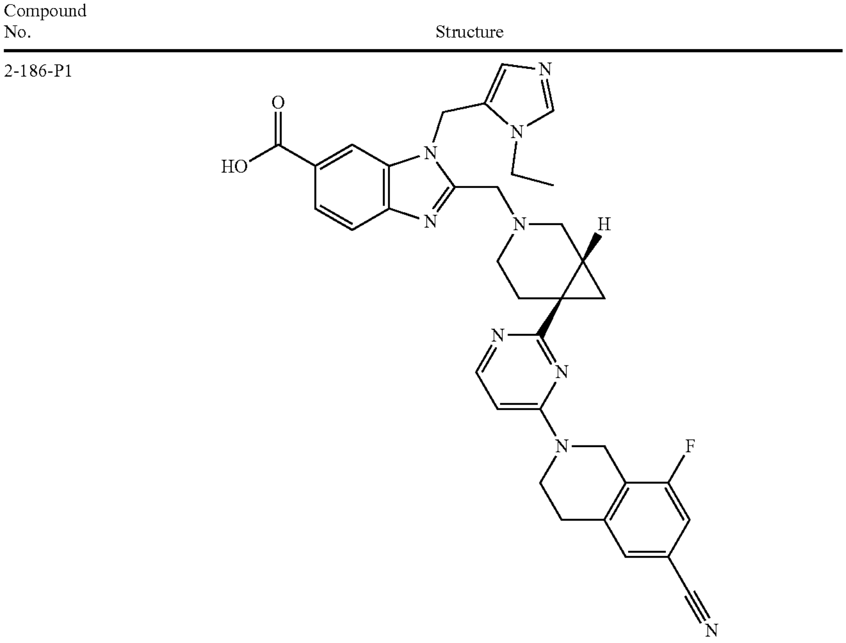 |
| 2-186-P2 | 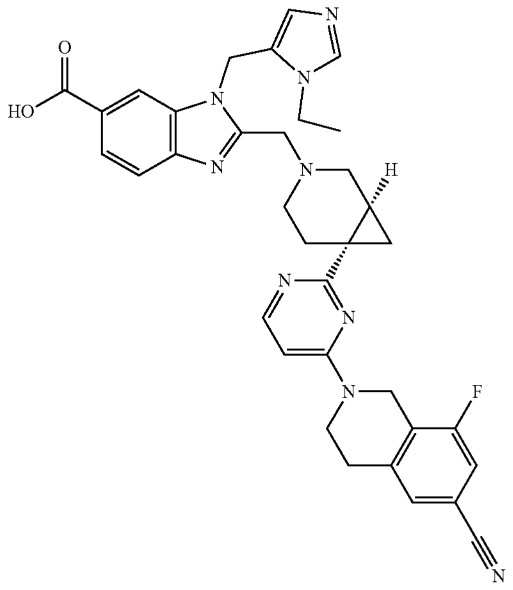 [SMILES: CCn1cncc1Cn1c(CN2CC[C@]3(c4nccc(N5CCc6cc(C#N)cc(F)c6C5)n4)C[C@@H]3C2)nc2ccc(C(=O)O)cc21] |

TABLE 3-continued
| Compound No. | Structure |
| --- | --- |
| 2-187 | 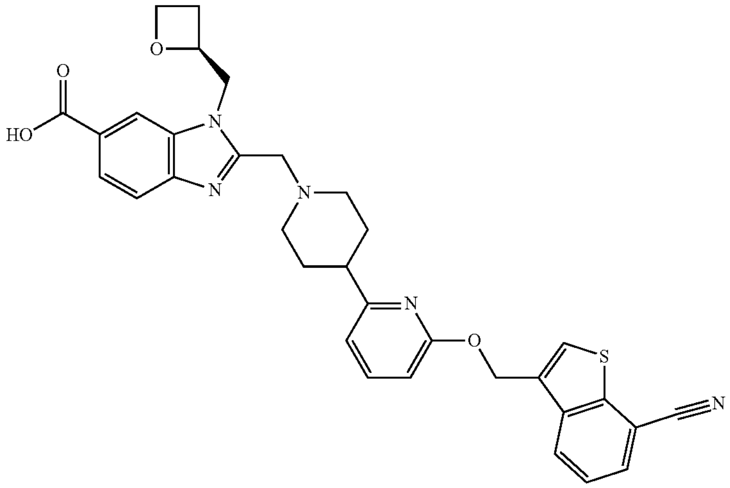 [SMILES: N#Cc1cccc2c(COc3cccc(C4CCN(Cc5nc6ccc(C(=O)O)cc6n5C[C@@H]5CCO5)CC4)n3)csc12] |
TABLE 3
| Compound No. | Structure | Name |
| --- | --- | --- |
| 3-1 | 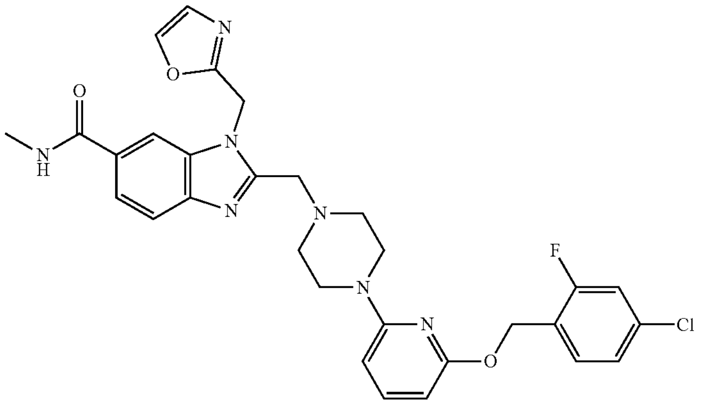 [SMILES: CNC(=O)c1ccc2nc(CN3CCN(c4cccc(OCc5ccc(Cl)cc5F)n4)CC3)n(Cc3ncco3)c2c1] | 2-((4-(6-((4-cyano-2-fluorobenzyl)oxy)pyridin-2-yl)piperazin-1-yl)methyl)-N-methyl-1-(oxazol-2-ylmethyl)-1H-benzo[d]imidazole-6-carboxamide |
| 3-2 | 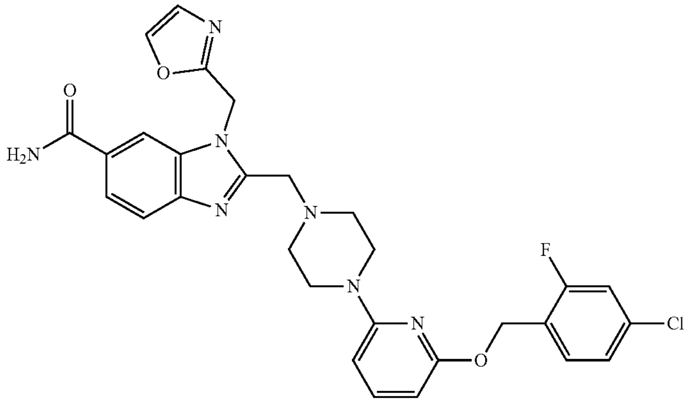 [SMILES: NC(=O)c1ccc2nc(CN3CCN(c4cccc(OCc5ccc(Cl)cc5F)n4)CC3)n(Cc3ncco3)c2c1] | 2-((4-(6-((4-cyano-2-fluorobenzyl)oxy)pyridin-2-yl)piperazin-1-yl)methyl)-1-(oxazol-2-ylmethyl)-1H-benzo[d]imidazole-6-carboxamide |

TABLE 3-continued

| Compound No. | Structure | Name |
| --- | --- | --- |
| 3-3 | 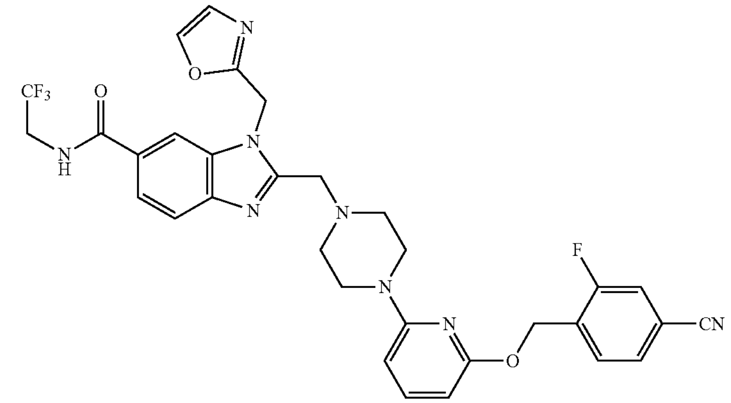 [SMILES: N#Cc1ccc(COc2cccc(N3CCN(Cc4nc5ccc(C(=O)NCC(F)(F)F)cc5n4Cc4ncco4)CC3)n2)c(F)c1] | 2-((4-(6-((4-cyano-2-fluorobenzyl)oxy)pyridin-2-yl)piperazin-1-yl)methyl)-1-(oxazol-2-ylmethyl)-N-(2,2,2-trifluoroethyl)-1H-benzo[d]imidazole-6-carboxamide |
| 3-4 | 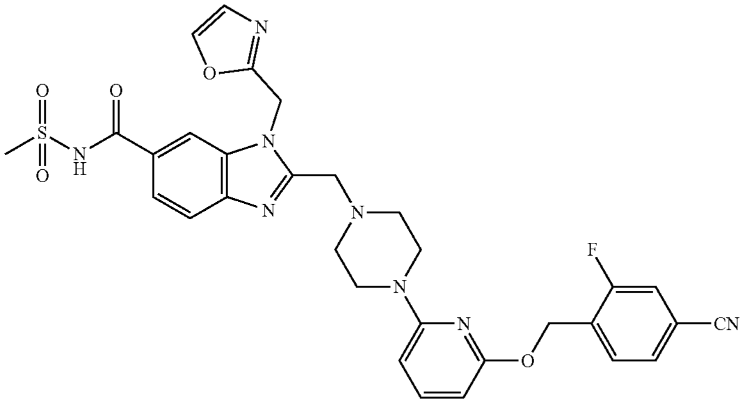 [SMILES: CS(=O)(=O)NC(=O)c1ccc2nc(CN3CCN(c4cccc(OCc5ccc(C#N)cc5F)n4)CC3)n(Cc3ncco3)c2c1] | 2-((4-(6-((4-cyano-2-fluorobenzyl)oxy)pyridin-2-yl)piperazin-1-yl)methyl)-N-(dioxo-15-sulfaneyl)-1-(oxazol-2-ylmethyl)-1H-benzo[d]imidazole-6-carboxamide |
| 3-5 | 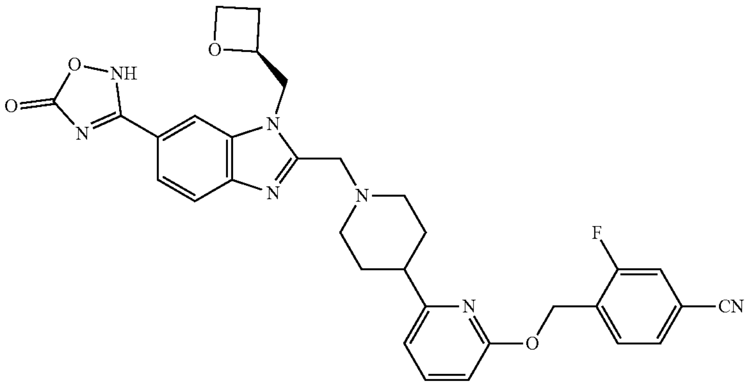 [SMILES: N#Cc1ccc(COc2cccc(C3CCN(Cc4nc5ccc(-c6nc(=O)o[nH]6)cc5n4C[C@@H]4CCO4)CC3)n2)c(F)c1] | (S)-3-fluoro-4-(((6-(1-((1-(oxetan-2-ylmethyl)-6-(5-oxo-2,5-dihydro-1,2,4-oxadiazol-3-yl)-1H-benzo[d]imidazol-2-yl)methyl)piperidin-4-yl)pyridin-2-yl)oxy)methyl)benzonitrile |
| 3-6 | 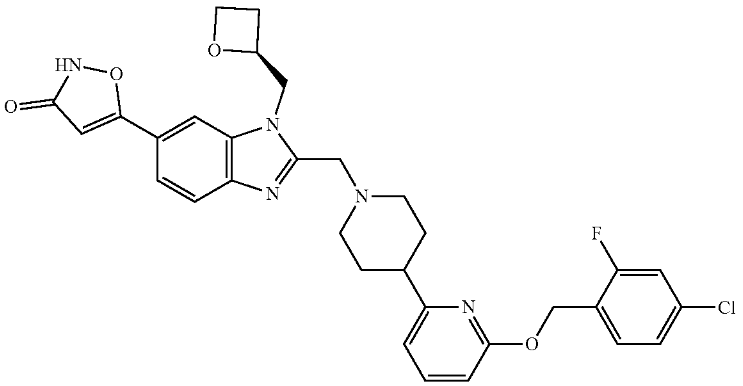 [SMILES: O=c1cc(-c2ccc3nc(CN4CCC(c5cccc(OCc6ccc(Cl)cc6F)n5)CC4)n(C[C@@H]4CCO4)c3c2)o[nH]1] | (S)-5-(2-((4-(6-((4-chloro-2-fluorobenzyl)oxy)pyridin-2-yl)piperidin-1-yl)methyl)-1-(oxetan-2-ylmethyl)-1H-benzo[d]imidazol-6-yl)isoxazol-3(2H)-one |

TABLE 3-continued

| Compound No. | Structure | Name |
|---|---|---|
| 3-7 | 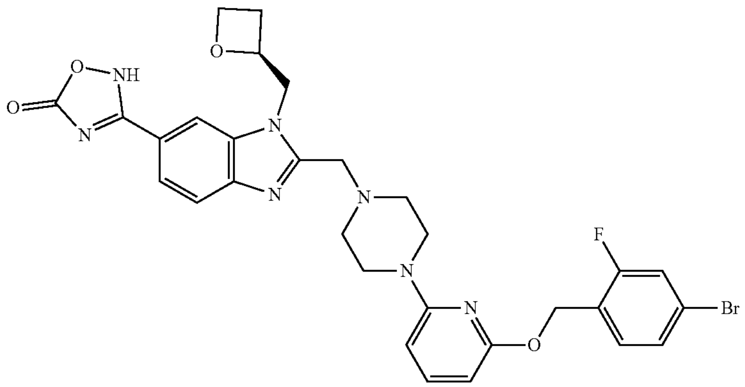 [SMILES: O=c1nc(-c2ccc3nc(CN4CCN(c5cccc(OCc6ccc(Br)cc6F)n5)CC4)n(C[C@@H]4CCO4)c3c2)[nH]o1] | (S)-3-(2-((4-(6-((4-bromo-2-fluorobenzyl)oxy)pyridin-2-yl)piperazin-1-yl)methyl)-1-(oxetan-2-ylmethyl)-1H-benzo[d]imidazol-6-yl)-1,2,4-oxadiazol-5(2H)-one |
| 3-8 | 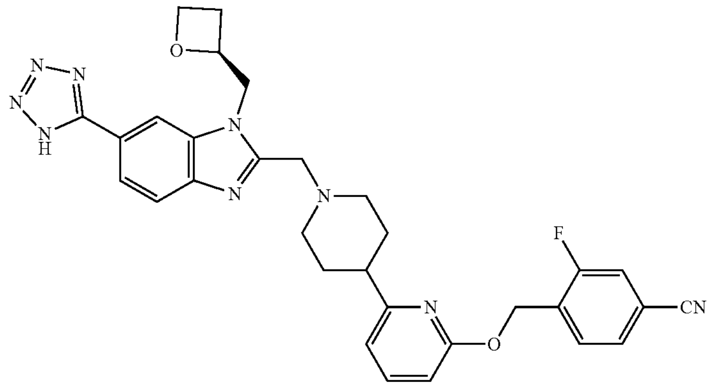 [SMILES: N#Cc1ccc(COc2cccc(C3CCN(Cc4nc5ccc(-c6nnn[nH]6)cc5n4C[C@@H]4CCO4)CC3)n2)c(F)c1] | (S)-3-fluoro-4-(((6-(1-((1-(oxetan-2-ylmethyl)-6-(1H-tetrazol-5-yl)-1H-benzo[d]imidazol-2-yl)methyl)piperidin-4-yl)pyridin-2-yl)oxy)methyl)benzonitrile |
| 3-9 | 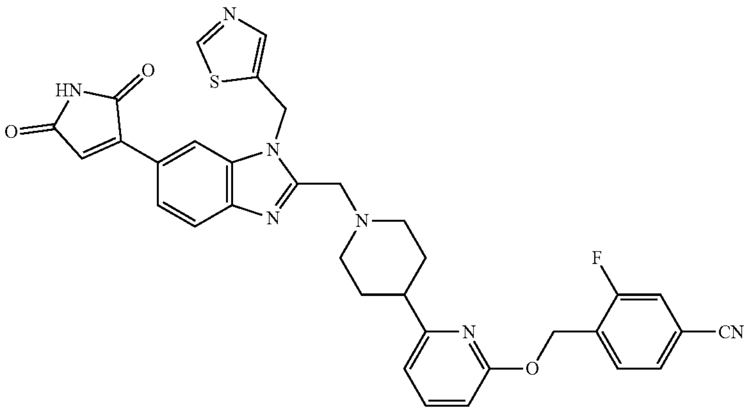 [SMILES: N#Cc1ccc(COc2cccc(C3CCN(Cc4nc5ccc(C6=CC(=O)NC6=O)cc5n4Cc4cncs4)CC3)n2)c(F)c1] | 4-(((6-(1-((6-(2,5-dioxo-2,5-dihydro-1H-pyrrol-3-yl)-1-(thiazol-5-ylmethyl)-1H-benzo[d]imidazol-2-yl)methyl)piperidin-4-yl)pyridin-2-yl)oxy)methyl)-3-fluorobenzonitrile |

TABLE 3-continued

| Compound No. | Structure | Name |
|---|---|---|
| 3-10 | 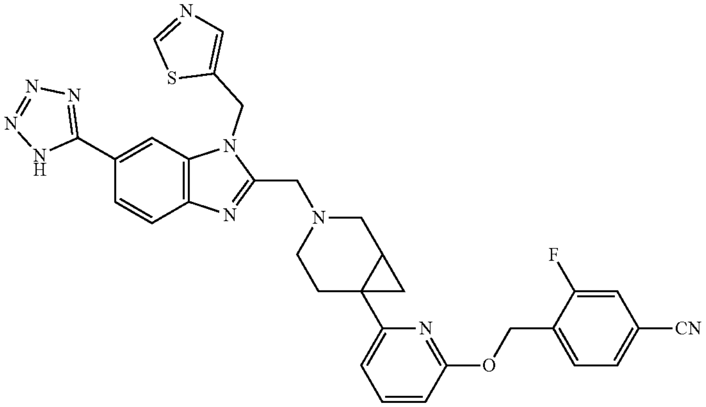 [SMILES: N#Cc1ccc(COc2cccc(C34CCN(Cc5nc6ccc(-c7nnn[nH]7)cc6n5Cc5cncs5)CC3C4)n2)c(F)c1] | 4-(((6-(3-((6-(1H-tetrazol-5-yl)-1-(thiazol-5-ylmethyl)-1H-benzo[d]imidazol-2-yl)methyl)-3-azabicyclo[4.1.0]heptan-6-yl)pyridin-2-yl)oxy)methyl)-3-fluorobenzonitrile |
| 3-11 | 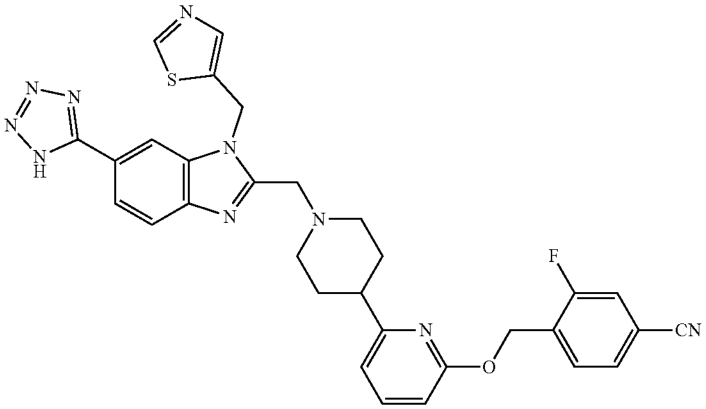 [SMILES: N#Cc1ccc(COc2cccc(C3CCN(Cc4nc5ccc(-c6nnn[nH]6)cc5n4Cc4cncs4)CC3)n2)c(F)c1] | 4-(((6-(1-((6-(1H-tetrazol-5-yl)-1-(thiazol-5-ylmethyl)-1H-benzo[d]imidazol-2-yl)methyl)piperidin-4-yl)pyridin-2-yl)oxy)methyl)-3-fluorobenzonitrile |
| 3-12 | 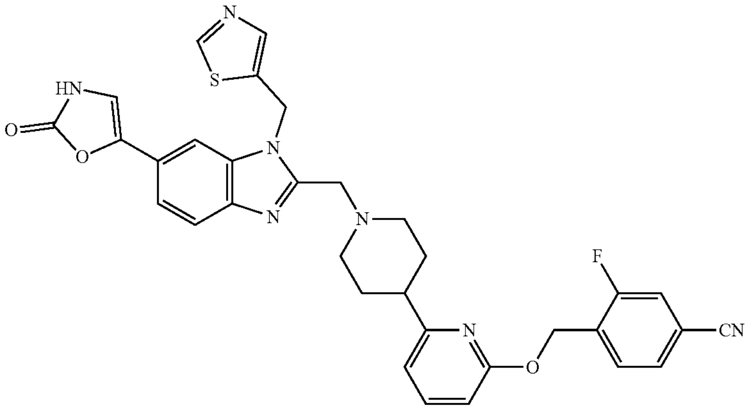 [SMILES: N#Cc1ccc(COc2cccc(C3CCN(Cc4nc5ccc(-c6c[nH]c(=O)o6)cc5n4Cc4cncs4)CC3)n2)c(F)c1] | 3-fluoro-4-(((6-(1-((6-(2-oxo-2,3-dihydrooxazol-5-yl)-1-(thiazol-5-ylmethyl)-1H-benzo[d]imidazol-2-yl)methyl)piperidin-4-yl)pyridin-2-yl)oxy)methyl)benzonitrile |

TABLE 3-continued

| Compound No. | Structure | Name |
|---|---|---|
| 3-13 | 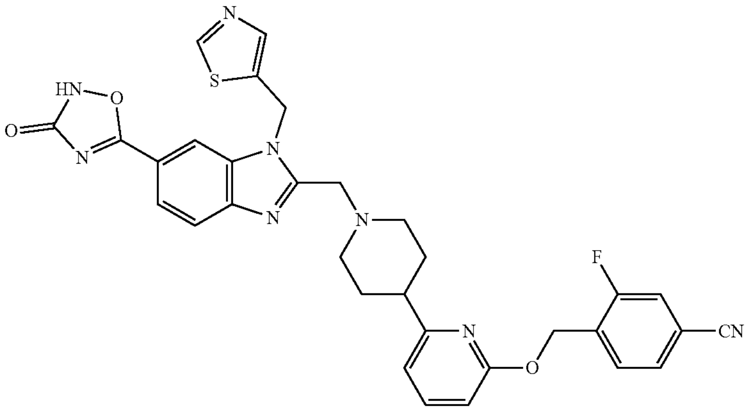 [SMILES: N#Cc1ccc(COc2cccc(C3CCN(Cc4nc5ccc(-c6nc(=O)[nH]o6)cc5n4Cc4cncs4)CC3)n2)c(F)c1] | 3-fluoro-4-(((6-(1-((6-(3-oxo-2,3-dihydro-1,2,4-oxadiazol-5-yl)-1-(thiazol-5-ylmethyl)-1H-benzo[d]imidazol-2-yl)methyl)piperidin-4-yl)pyridin-2-yl)oxy)methyl)benzonitrile |
| 3-14 | 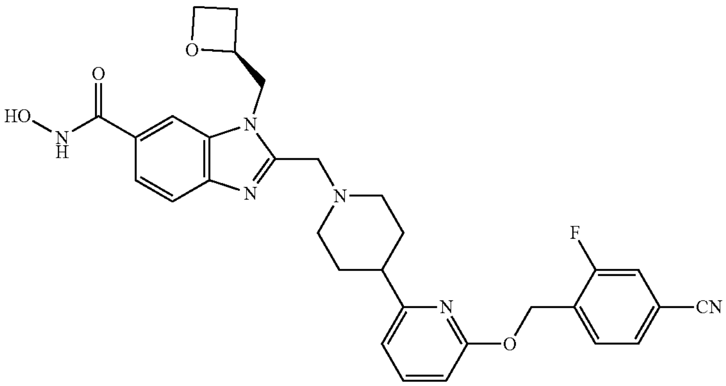 [SMILES: N#Cc1ccc(COc2cccc(C3CCN(Cc4nc5ccc(C(=O)NO)cc5n4C[C@@H]4CCO4)CC3)n2)c(F)c1] | (S)-2-((4-(6-((4-cyano-2-fluorobenzyl)oxy)pyridin-2-yl)piperidin-1-yl)methyl)-N-hydroxy-1-(oxetan-2-ylmethyl)-1H-benzo[d]imidazole-6-carboxamide |
| 3-15 | 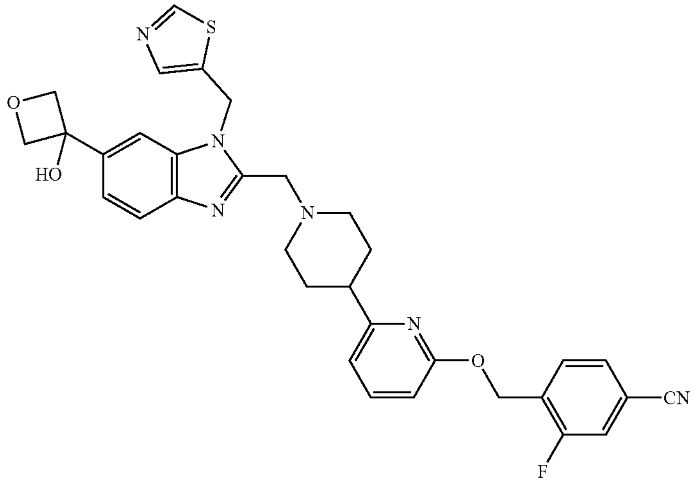 [SMILES: N#Cc1ccc(COc2cccc(C3CCN(Cc4nc5ccc(C6(O)COC6)cc5n4Cc4cncs4)CC3)n2)c(F)c1] | 3-fluoro-4-(((6-(1-((6-(3-hydroxyoxetan-3-yl)-1-(thiazol-5-ylmethyl)-1H-benzo[d]imidazol-2-yl)methyl)piperidin-4-yl)pyridin-2-yl)oxy)methyl)benzonitrile |

TABLE 3-continued
| Compound No. | Structure | Name |
|---|---|---|
| 3-16 | 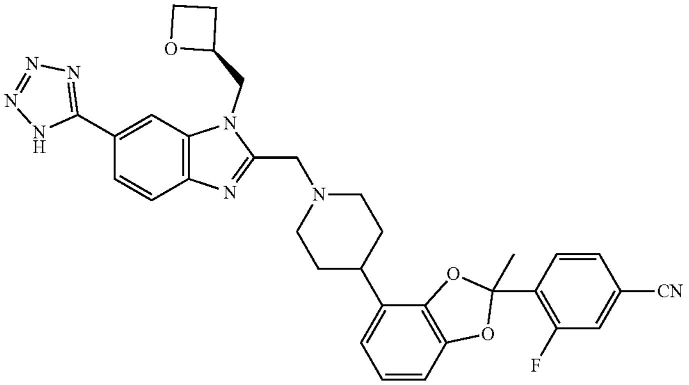 [SMILES: CC1(c2ccc(C#N)cc2F)Oc2cccc(C3CCN(Cc4nc5ccc(-c6nnn[nH]6)cc5n4C[C@@H]4CCO4)CC3)c2O1] | 3-fluoro-4-(2-methyl-4-(1-((1-(((S)-oxetan-2-yl)methyl)-6-(1H-tetrazol-5-yl)-1H-benzo[d]imidazol-2-yl)methyl)piperidin-4-yl)benzo[d][1,3]dioxol-2-yl)benzonitrile |
In some embodiments, the GLP-1R agonist is selected from those listed in Table 4 below, or a pharmaceutically acceptable salt thereof.
TABLE 4
| Compound No. | Structure |
|---|---|
| 4-1 | 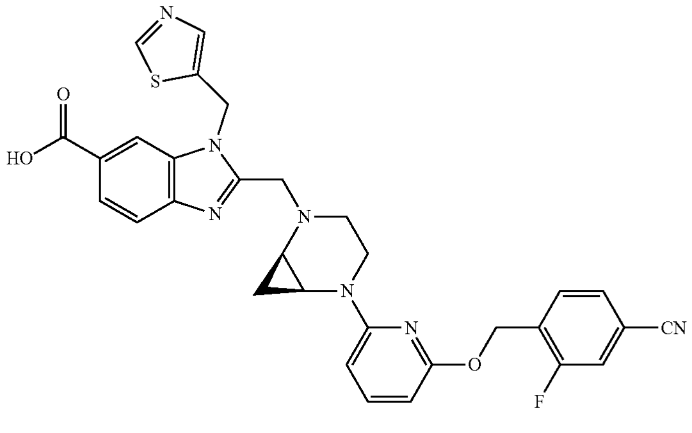 [SMILES: N#Cc1ccc(COc2cccc(N3CCN(Cc4nc5ccc(C(=O)O)cc5n4Cc4cncs4)[C@@H]4C[C@@H]43)n2)c(F)c1] |
| 4-2 | 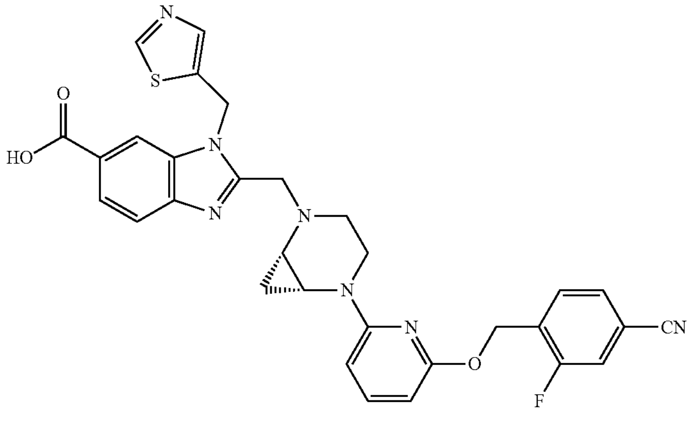 [SMILES: N#Cc1ccc(COc2cccc(N3CCN(Cc4nc5ccc(C(=O)O)cc5n4Cc4cncs4)[C@H]4C[C@H]43)n2)c(F)c1] |

TABLE 4-continued
| Compound No. | Structure |
|---|---|
| 4-3 | 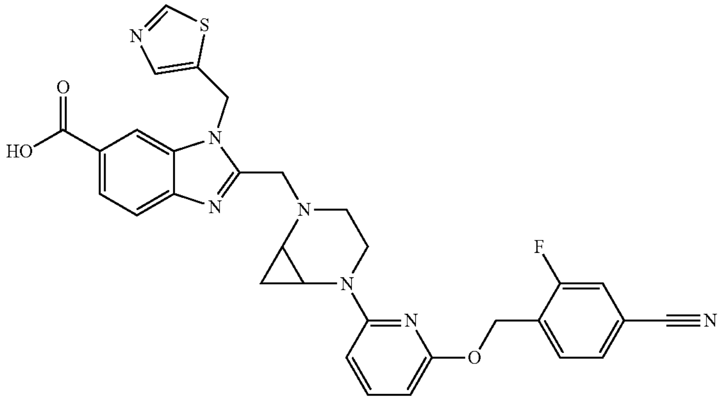 [SMILES: N#Cc1ccc(COc2cccc(N3CCN(Cc4nc5ccc(C(=O)O)cc5n4Cc4cncs4)C4CC43)n2)c(F)c1] |
| 4-4 | 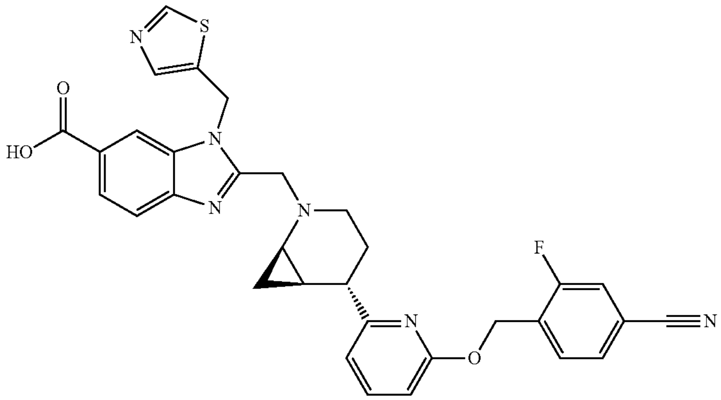 [SMILES: N#Cc1ccc(COc2cccc([C@H]3CCN(Cc4nc5ccc(C(=O)O)cc5n4Cc4cncs4)[C@@H]4C[C@H]34)n2)c(F)c1] |
| 4-5 | 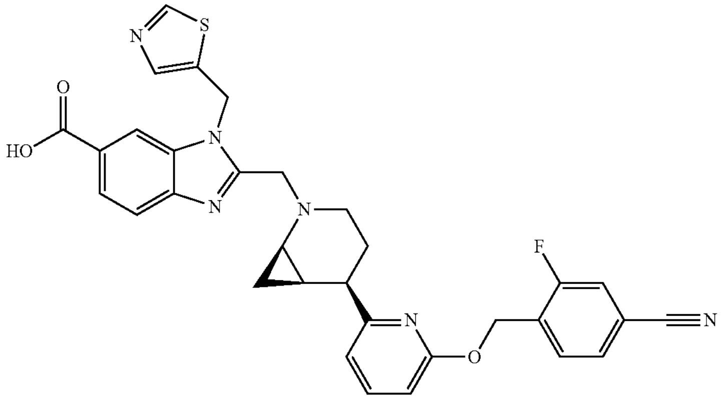 [SMILES: N#Cc1ccc(COc2cccc([C@@H]3CCN(Cc4nc5ccc(C(=O)O)cc5n4Cc4cncs4)[C@@H]4C[C@@H]43)n2)c(F)c1] |
| 4-6 | 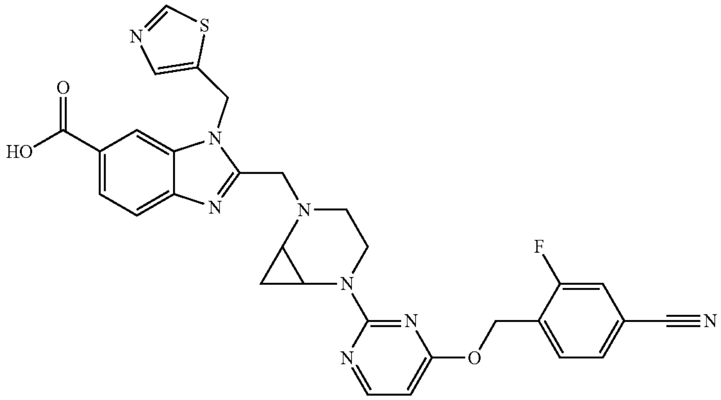 [SMILES: N#Cc1ccc(COc2ccnc(N3CCN(Cc4nc5ccc(C(=O)O)cc5n4Cc4cncs4)C4CC43)n2)c(F)c1] |

TABLE 4-continued
| Compound No. | Structure |
| --- | --- |
| 4-7 | 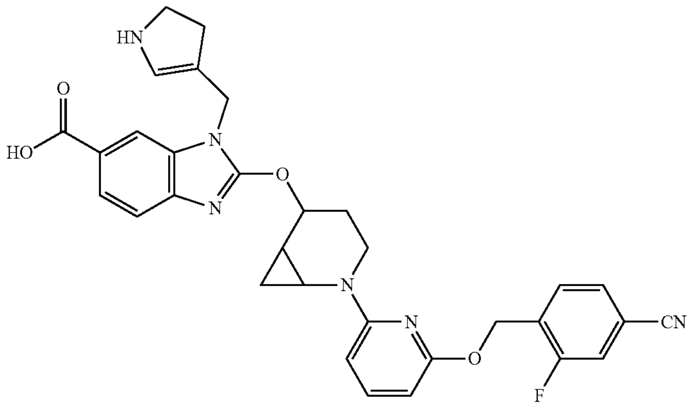 [SMILES: N#Cc1ccc(COc2cccc(N3CCC(Oc4nc5ccc(C(=O)O)cc5n4CC4=CNCC4)C4CC43)n2)c(F)c1] |
| 4-8 | 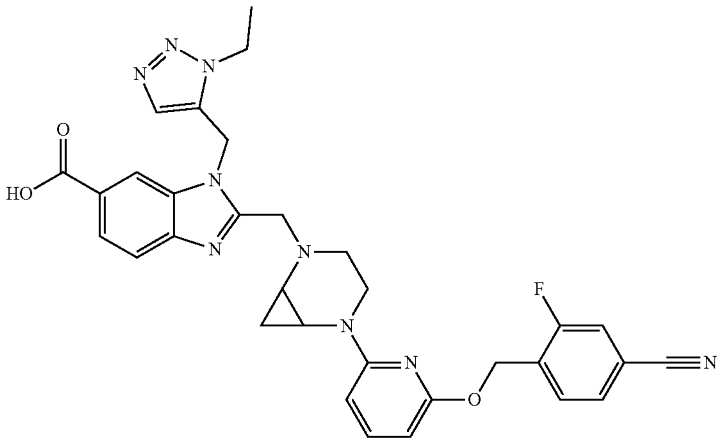 [SMILES: CCn1nncc1Cn1c(CN2CCN(c3cccc(OCc4ccc(C#N)cc4F)n3)C3CC32)nc2ccc(C(=O)O)cc21] |
| 4-9 | 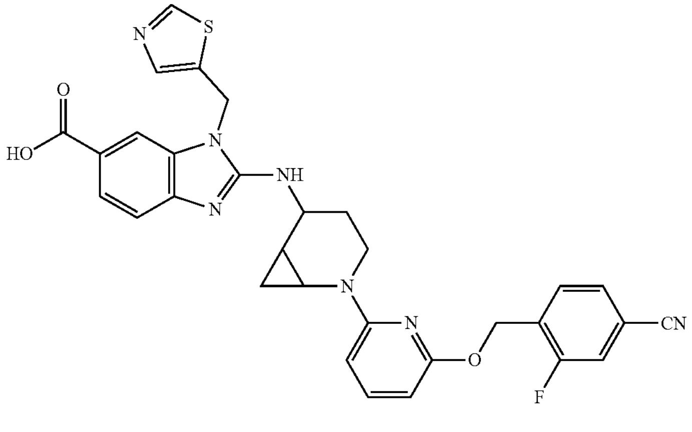 [SMILES: N#Cc1ccc(COc2cccc(N3CCC(Nc4nc5ccc(C(=O)O)cc5n4Cc4cncs4)C4CC43)n2)c(F)c1] |

TABLE 4-continued
| Compound No. | Structure |
|---|---|
| 4-10 | 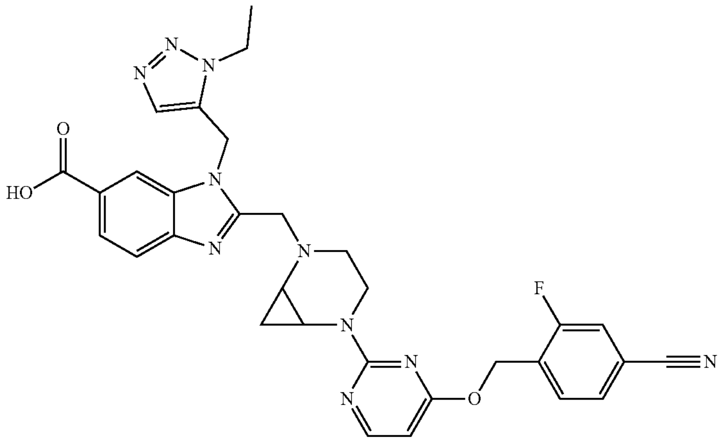 [SMILES: CCn1nncc1Cn1c(CN2CCN(c3nccc(OCc4ccc(C#N)cc4F)n3)C3CC32)nc2ccc(C(=O)O)cc21] |
| 4-11 | 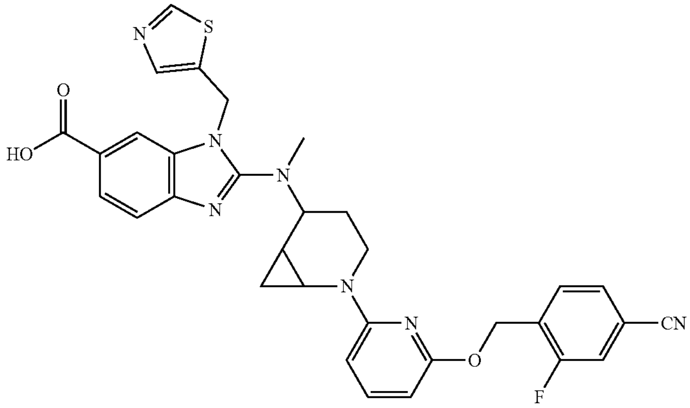 [SMILES: CN(c1nc2ccc(C(=O)O)cc2n1Cc1cncs1)C1CCN(c2cccc(OCc3ccc(C#N)cc3F)n2)C2CC12] |
| 4-12 | 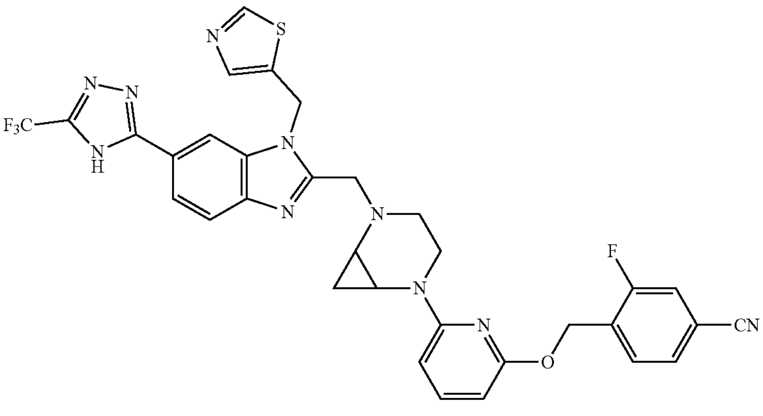 [SMILES: N#Cc1ccc(COc2cccc(N3CCN(Cc4nc5ccc(-c6nnc(C(F)(F)F)[nH]6)cc5n4Cc4cncs4)C4CC43)n2)c(F)c1] |

TABLE 4-continued
| Compound No. | Structure |
| --- | --- |
| 4-13 | 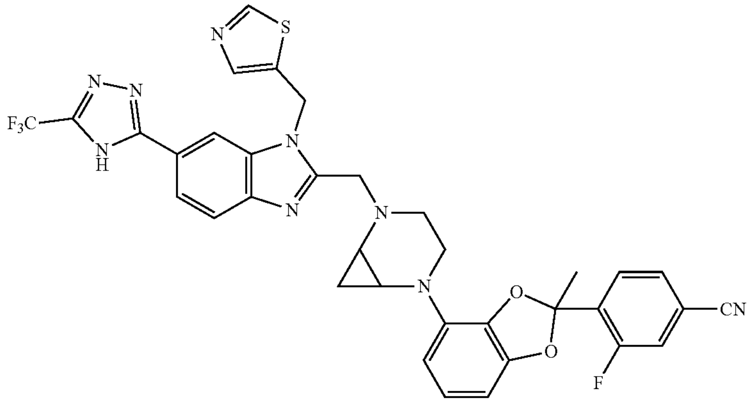 [SMILES: CC1(c2ccc(C#N)cc2F)Oc2cccc(N3CCN(Cc4nc5ccc(-c6nnc(C(F)(F)F)[nH]6)cc5n4Cc4cncs4)C4CC43)c2O1] |
| 4-14 | 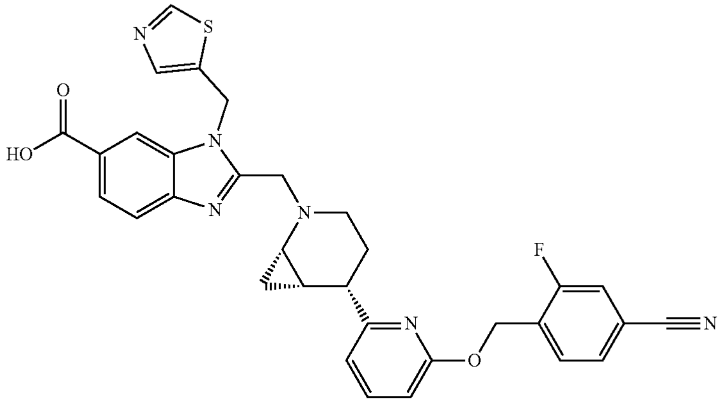 [SMILES: N#Cc1ccc(COc2cccc([C@H]3CCN(Cc4nc5ccc(C(=O)O)cc5n4Cc4cncs4)[C@H]4C[C@@H]34)n2)c(F)c1] |
| 4-15 | 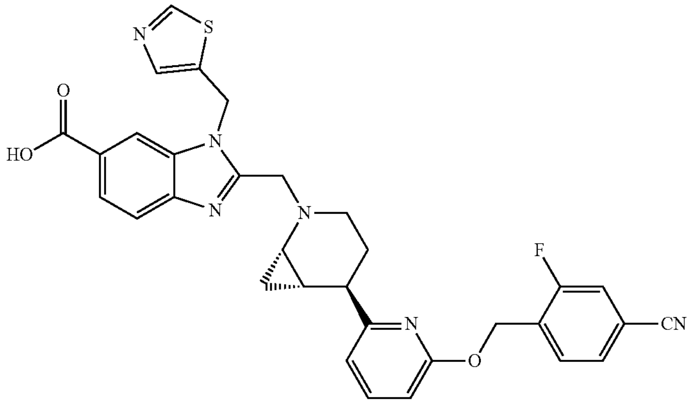 [SMILES: N#Cc1ccc(COc2cccc([C@@H]3CCN(Cc4nc5ccc(C(=O)O)cc5n4Cc4cncs4)[C@H]4C[C@@H]34)n2)c(F)c1] |

TABLE 4-continued
| Compound No. | Structure |
| --- | --- |
| 4-16 | 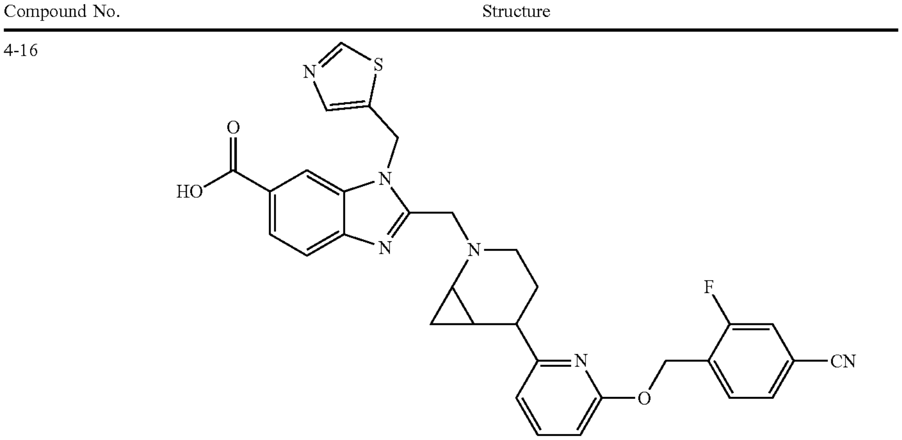 |
| 4-17 | 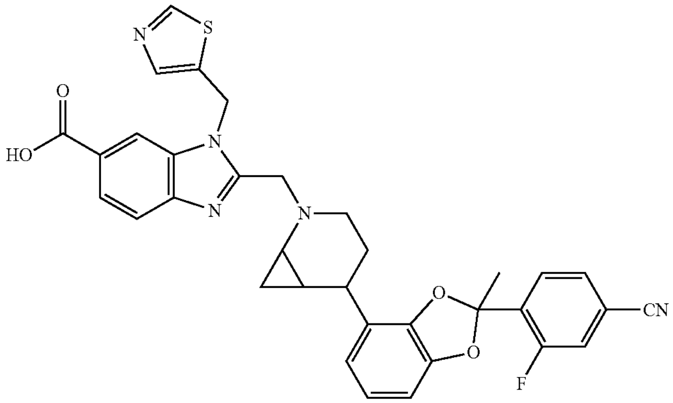 |
| 4-18 | 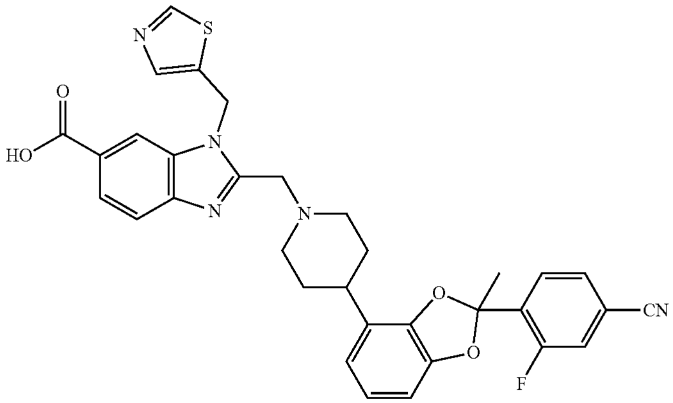 [SMILES: CC1(c2ccc(C#N)cc2F)Oc2cccc(C3CCN(Cc4nc5ccc(C(=O)O)cc5n4Cc4cncs4)CC3)c2O1] |
| 4-19 | 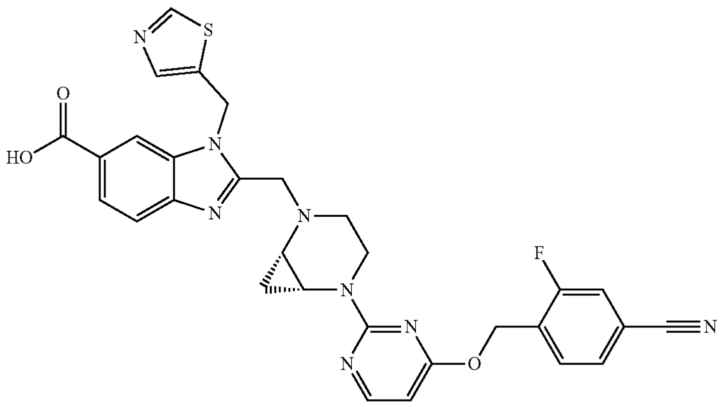 [SMILES: N#Cc1ccc(COc2ccnc(N3CCN(Cc4nc5ccc(C(=O)O)cc5n4Cc4cncs4)[C@H]4C[C@H]43)n2)c(F)c1] |

TABLE 4-continued
| Compound No. | Structure |
|---|---|
| 4-20 | 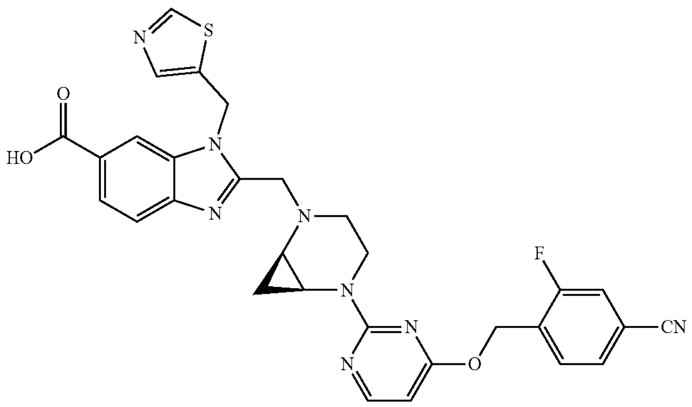 [SMILES: N#Cc1ccc(COc2ccnc(N3CCN(Cc4nc5ccc(C(=O)O)cc5n4Cc4cncs4)[C@@H]4C[C@@H]43)n2)c(F)c1] |
| 4-21 | 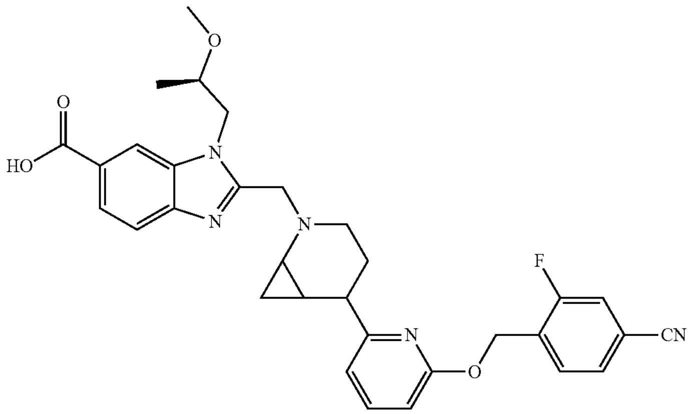 [SMILES: CO[C@H](C)Cn1c(CN2CCC(c3cccc(OCc4ccc(C#N)cc4F)n3)C3CC32)nc2ccc(C(=O)O)cc21] |
| 4-22 | 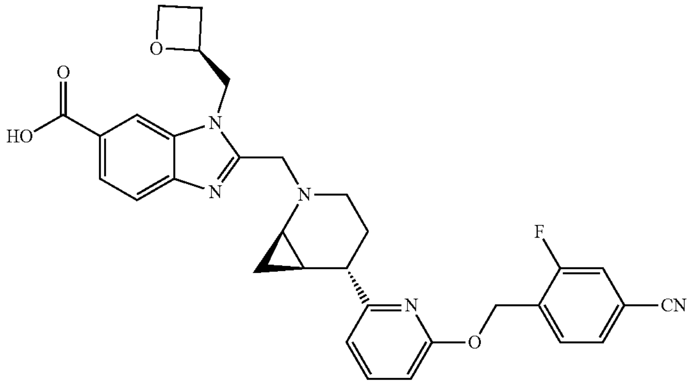 [SMILES: N#Cc1ccc(COc2cccc([C@H]3CCN(Cc4nc5ccc(C(=O)O)cc5n4C[C@@H]4CCO4)[C@@H]4C[C@H]34)n2)c(F)c1] |
| 4-23 | 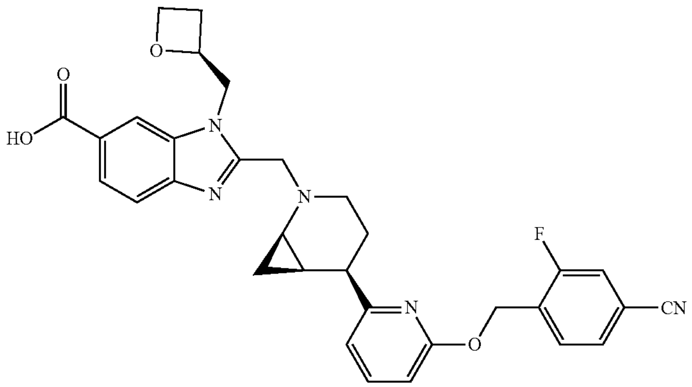 [SMILES: N#Cc1ccc(COc2cccc([C@@H]3CCN(Cc4nc5ccc(C(=O)O)cc5n4C[C@@H]4CCO4)[C@@H]4C[C@@H]43)n2)c(F)c1] |

TABLE 4-continued
| Compound No. | Structure |
| --- | --- |
| 4-24 | 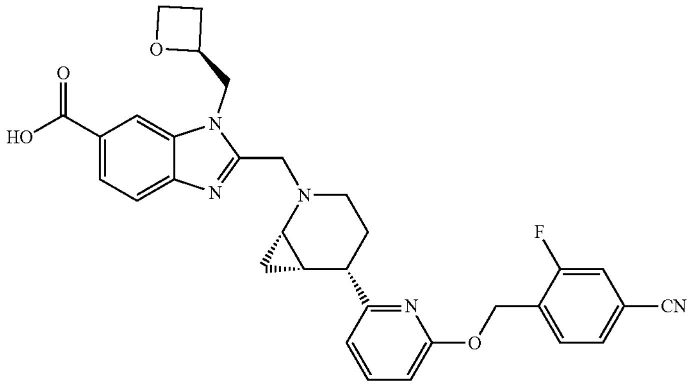 [SMILES: N#Cc1ccc(COc2cccc([C@H]3CCN(Cc4nc5ccc(C(=O)O)cc5n4C[C@@H]4CCO4)[C@H]4C[C@@H]34)n2)c(F)c1] |
| 4-25 | 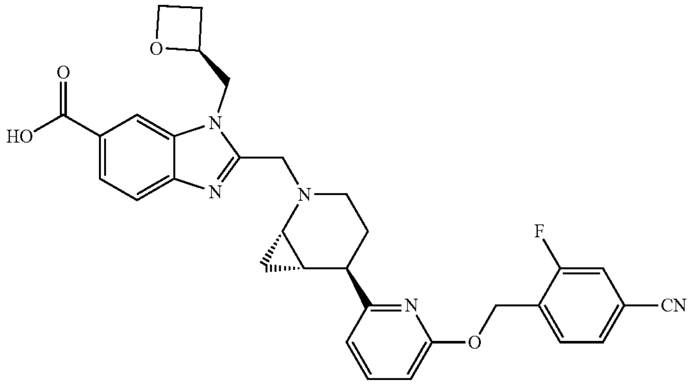 [SMILES: N#Cc1ccc(COc2cccc([C@@H]3CCN(Cc4nc5ccc(C(=O)O)cc5n4C[C@@H]4CCO4)[C@H]4C[C@@H]34)n2)c(F)c1] |
| 4-26 | 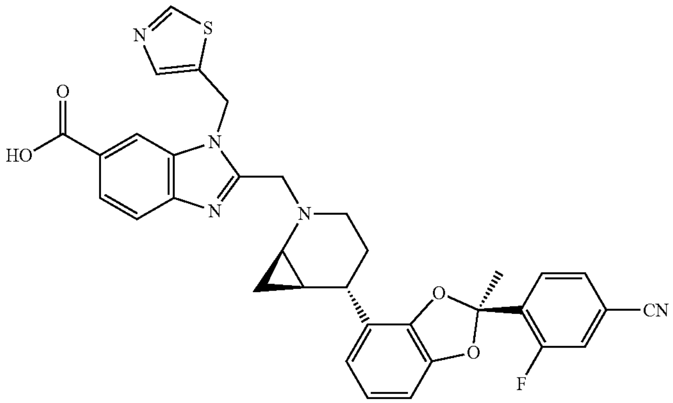 |
| 4-27 | 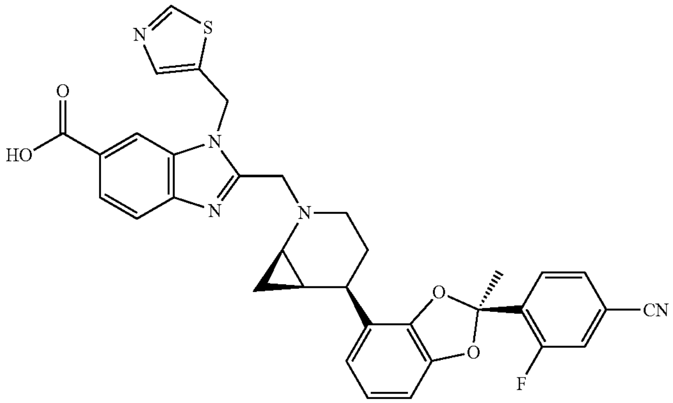 [SMILES: C[C@]1(c2ccc(C#N)cc2F)Oc2cccc([C@@H]3CCN(Cc4nc5ccc(C(=O)O)cc5n4Cc4cncs4)[C@@H]4C[C@@H]43)c2O1] |

TABLE 4-continued
| Compound No. | Structure |
| --- | --- |
| 4-28 | 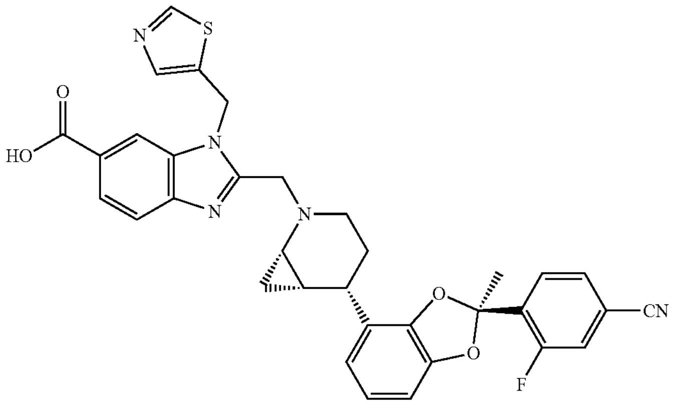 [SMILES: C[C@]1(c2ccc(C#N)cc2F)Oc2cccc([C@H]3CCN(Cc4nc5ccc(C(=O)O)cc5n4Cc4cncs4)[C@H]4C[C@@H]34)c2O1] |
| 4-29 | 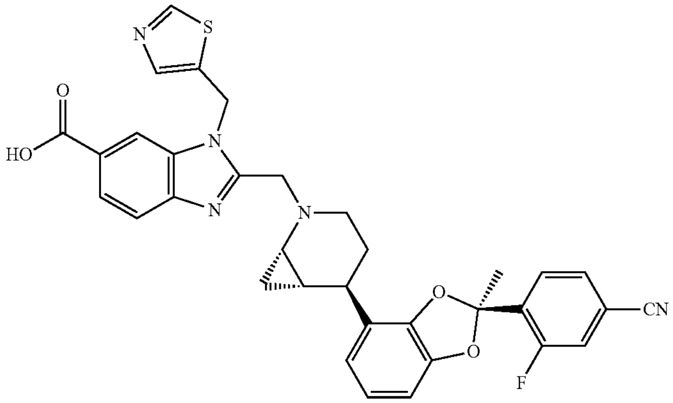 [SMILES: C[C@]1(c2ccc(C#N)cc2F)Oc2cccc([C@@H]3CCN(Cc4nc5ccc(C(=O)O)cc5n4Cc4cncs4)[C@H]4C[C@@H]34)c2O1] |
| 4-30 | 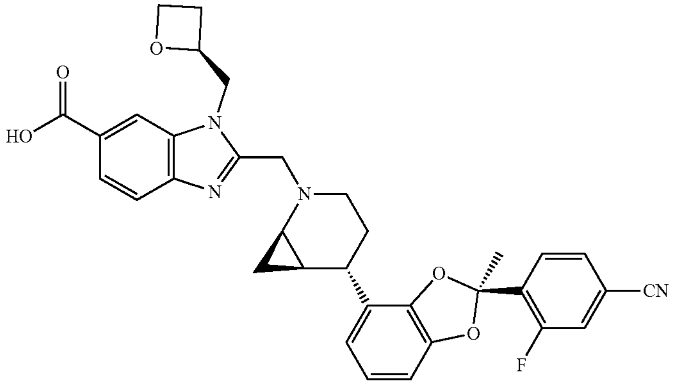 [SMILES: C[C@]1(c2ccc(C#N)cc2F)Oc2cccc([C@H]3CCN(Cc4nc5ccc(C(=O)O)cc5n4C[C@@H]4CCO4)[C@@H]4C[C@H]34)c2O1] |
| 4-31 | 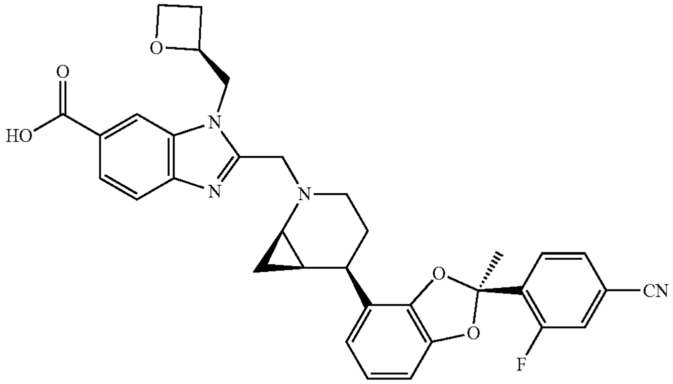 [SMILES: C[C@]1(c2ccc(C#N)cc2F)Oc2cccc([C@@H]3CCN(Cc4nc5ccc(C(=O)O)cc5n4C[C@@H]4CCO4)[C@@H]4C[C@@H]43)c2O1] |

TABLE 4-continued
| Compound No. | Structure |
| --- | --- |
| 4-32 | 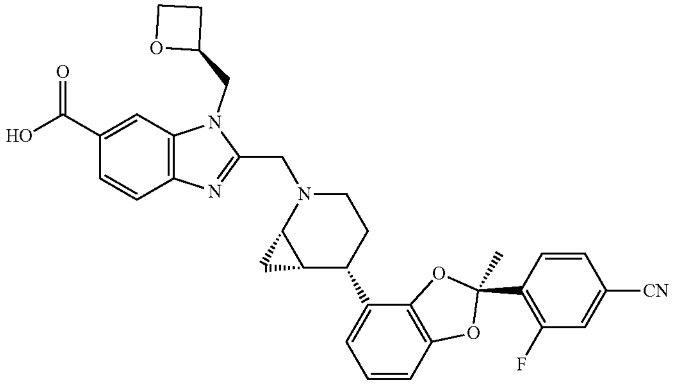 [SMILES: C[C@]1(c2ccc(C#N)cc2F)Oc2cccc([C@H]3CCN(Cc4nc5ccc(C(=O)O)cc5n4C[C@@H]4CCO4)[C@H]4C[C@@H]34)c2O1] |
| 4-33 | 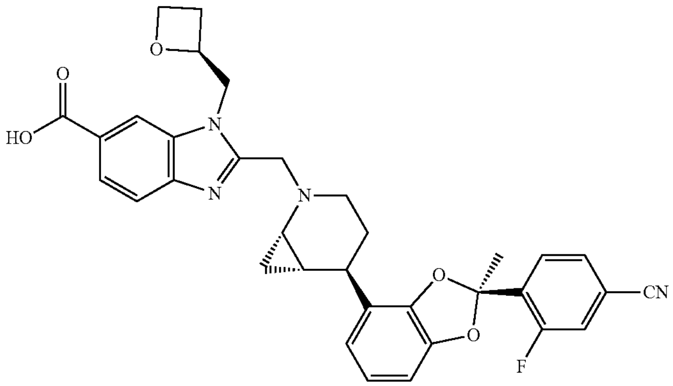 [SMILES: C[C@]1(c2ccc(C#N)cc2F)Oc2cccc([C@@H]3CCN(Cc4nc5ccc(C(=O)O)cc5n4C[C@@H]4CCO4)[C@H]4C[C@@H]34)c2O1] |
| 4-34 | 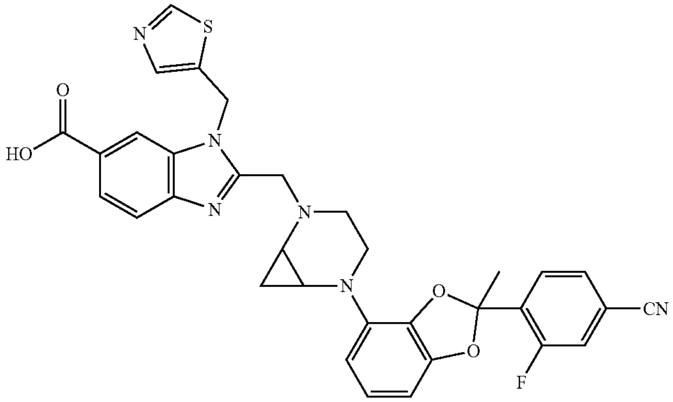 [SMILES: CC1(c2ccc(C#N)cc2F)Oc2cccc(N3CCN(Cc4nc5ccc(C(=O)O)cc5n4Cc4cncs4)C4CC43)c2O1] |
| 4-35 | 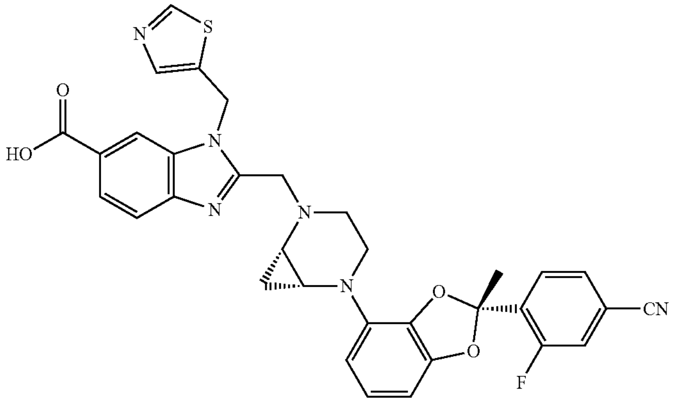 [SMILES: C[C@@]1(c2ccc(C#N)cc2F)Oc2cccc(N3CCN(Cc4nc5ccc(C(=O)O)cc5n4Cc4cncs4)[C@H]4C[C@H]43)c2O1] |

TABLE 4-continued
| Compound No. | Structure |
| --- | --- |
| 4-36 | 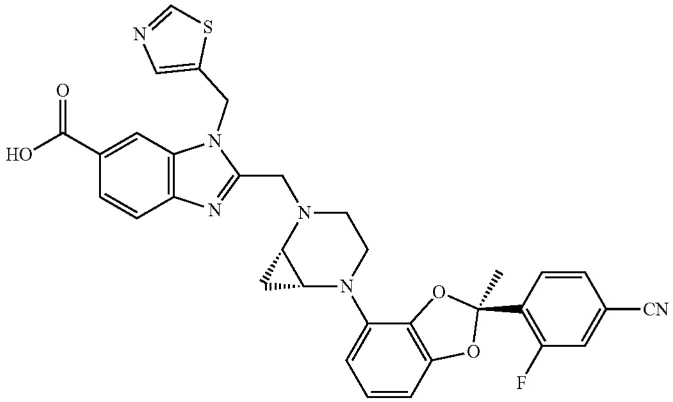 [SMILES: C[C@]1(c2ccc(C#N)cc2F)Oc2cccc(N3CCN(Cc4nc5ccc(C(=O)O)cc5n4Cc4cncs4)[C@H]4C[C@H]43)c2O1] |
| 4-37 | 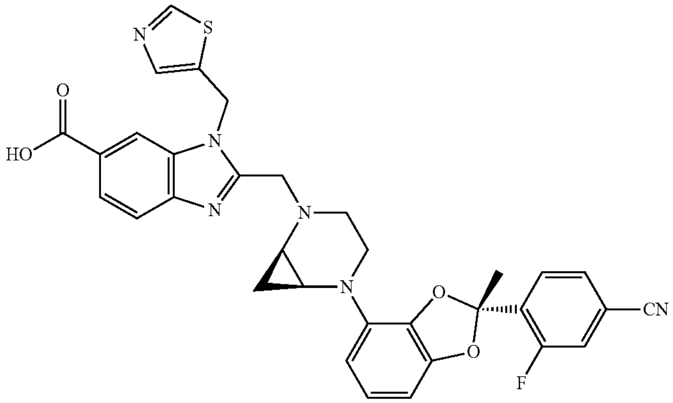 [SMILES: C[C@@]1(c2ccc(C#N)cc2F)Oc2cccc(N3CCN(Cc4nc5ccc(C(=O)O)cc5n4Cc4cncs4)[C@@H]4C[C@@H]43)c2O1] |
| 4-38 | 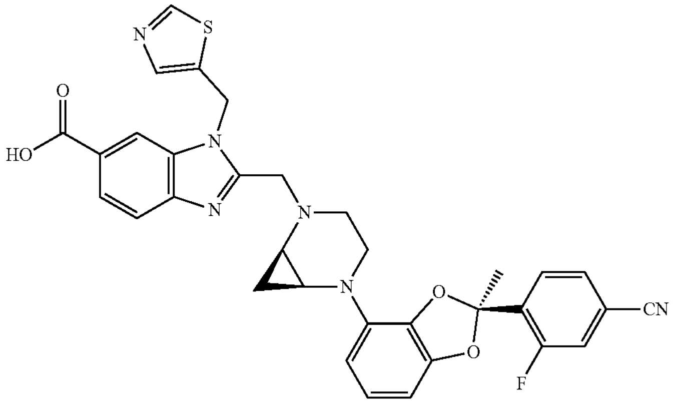 [SMILES: C[C@]1(c2ccc(C#N)cc2F)Oc2cccc(N3CCN(Cc4nc5ccc(C(=O)O)cc5n4Cc4cncs4)[C@@H]4C[C@@H]43)c2O1] |

TABLE 4-continued
| Compound No. | Structure |
|---|---|
| 4-39 | 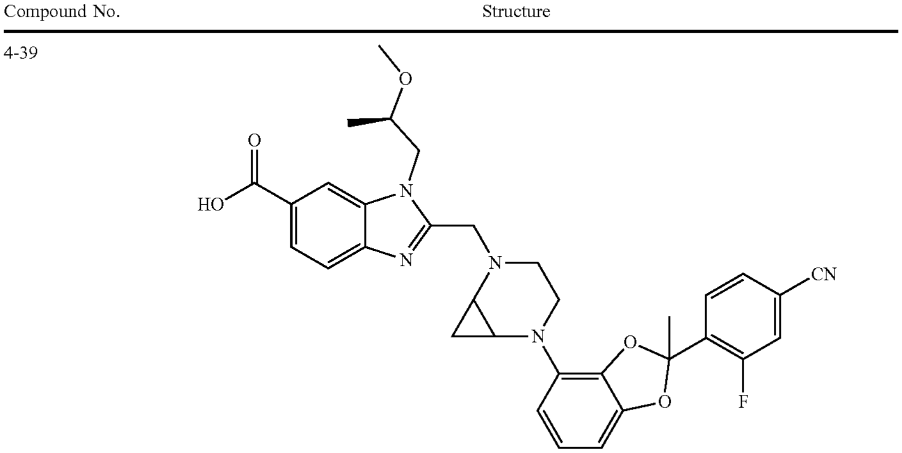 |
| 4-40 | 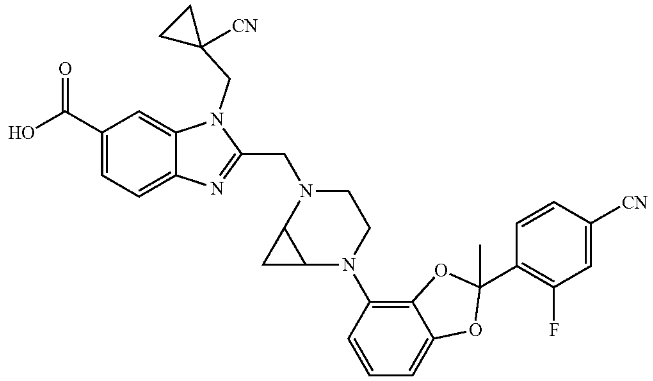 [SMILES: CC1(c2ccc(C#N)cc2F)Oc2cccc(N3CCN(Cc4nc5ccc(C(=O)O)cc5n4CC4(C#N)CC4)C4CC43)c2O1] |
| 4-41 | 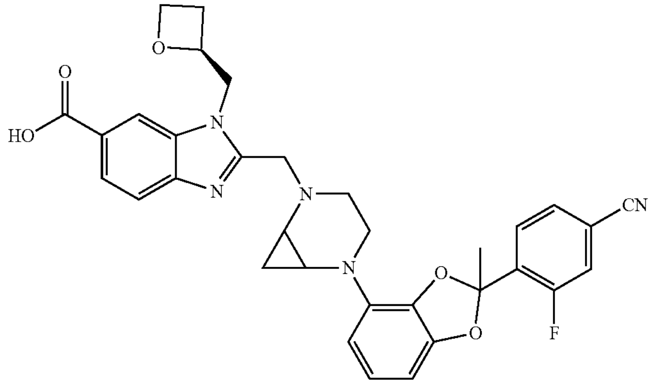 [SMILES: CC1(c2ccc(C#N)cc2F)Oc2cccc(N3CCN(Cc4nc5ccc(C(=O)O)cc5n4C[C@@H]4CCO4)C4CC43)c2O1] |
| 4-42 | 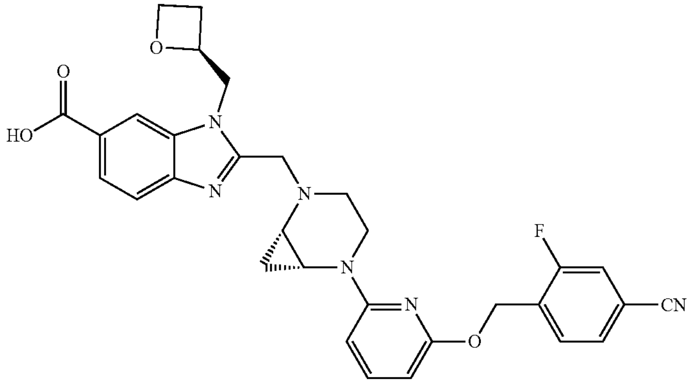 [SMILES: N#Cc1ccc(COc2cccc(N3CCN(Cc4nc5ccc(C(=O)O)cc5n4C[C@@H]4CCO4)[C@H]4C[C@H]43)n2)c(F)c1] |

TABLE 4-continued
| Compound No. | Structure |
| --- | --- |
| 4-43 | 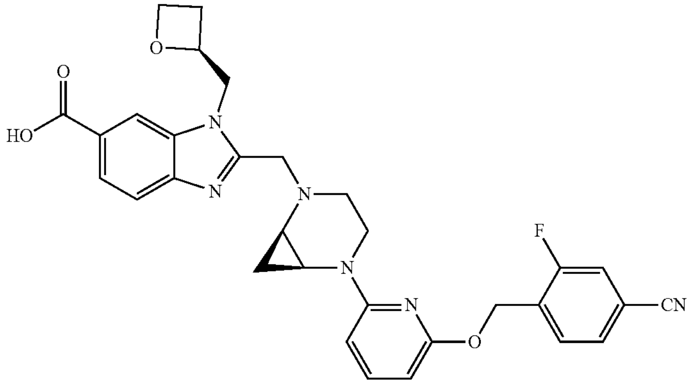 [SMILES: N#Cc1ccc(COc2cccc(N3CCN(Cc4nc5ccc(C(=O)O)cc5n4C[C@@H]4CCO4)[C@@H]4C[C@@H]43)n2)c(F)c1] |
| 4-44 | 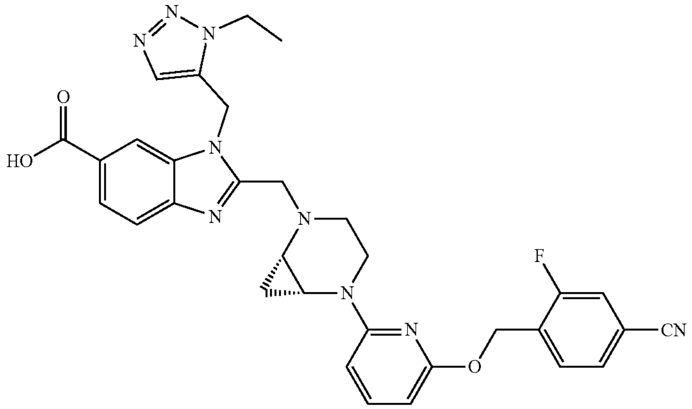 [SMILES: CCn1nncc1Cn1c(CN2CCN(c3cccc(OCc4ccc(C#N)cc4F)n3)[C@@H]3C[C@@H]32)nc2ccc(C(=O)O)cc21] |
| 4-45 | 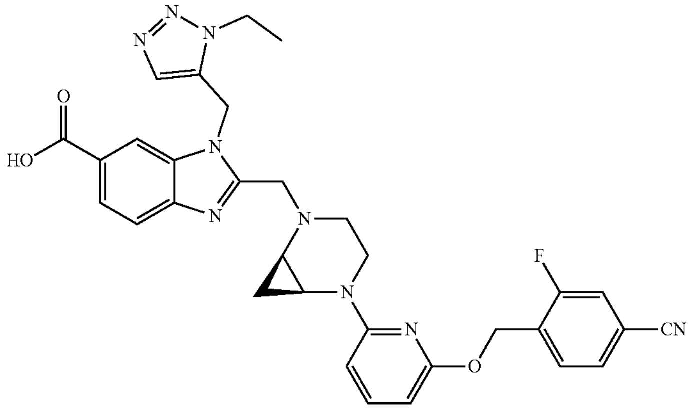 [SMILES: CCn1nncc1Cn1c(CN2CCN(c3cccc(OCc4ccc(C#N)cc4F)n3)[C@H]3C[C@H]32)nc2ccc(C(=O)O)cc21] |

TABLE 4-continued
| Compound No. | Structure |
| --- | --- |
| 4-46 | 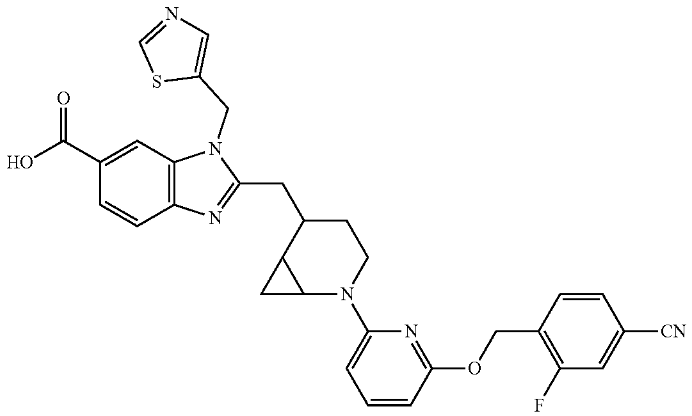 [SMILES: N#Cc1ccc(COc2cccc(N3CCC(Cc4nc5ccc(C(=O)O)cc5n4Cc4cncs4)C4CC43)n2)c(F)c1] |
In some embodiments, the GLP-1R agonist is selected from those listed in Table 5 below, or a pharmaceutically acceptable salt thereof:
TABLE 5
| Compound No. | Structure |
| --- | --- |
| 5-1 | 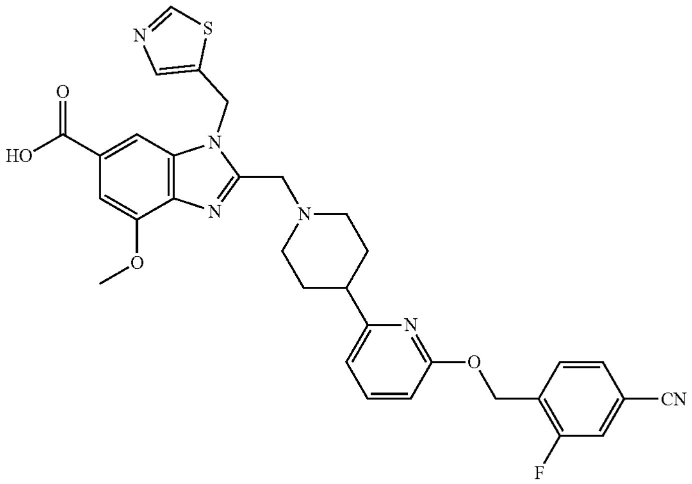 [SMILES: COc1cc(C(=O)O)cc2c1nc(CN1CCC(c3cccc(OCc4ccc(C#N)cc4F)n3)CC1)n2Cc1cncs1] |
| 5-2 | 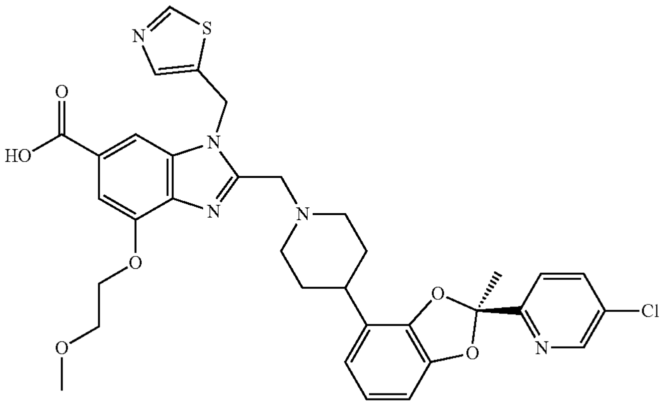 [SMILES: COCCOc1cc(C(=O)O)cc2c1nc(CN1CCC(c3cccc4c3O[C@@](C)(c3ccc(Cl)cn3)O4)CC1)n2Cc1cncs1] |

TABLE 5-continued
| Compound No. | Structure |
|---|---|
| 5-3 | 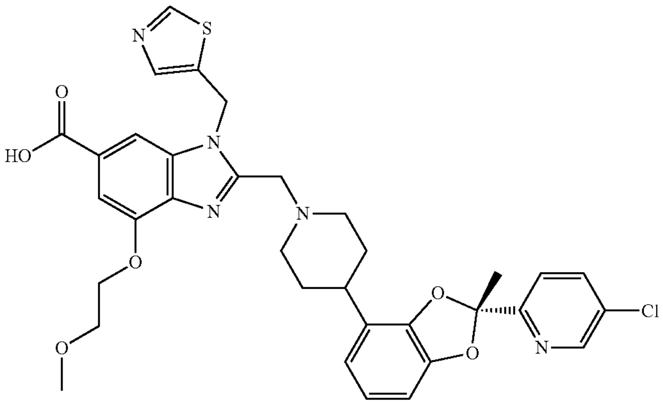 [SMILES: COCCOc1cc(C(=O)O)cc2c1nc(CN1CCC(c3cccc4c3O[C@](C)(c3ccc(Cl)cn3)O4)CC1)n2Cc1cncs1] |
| 5-4 | 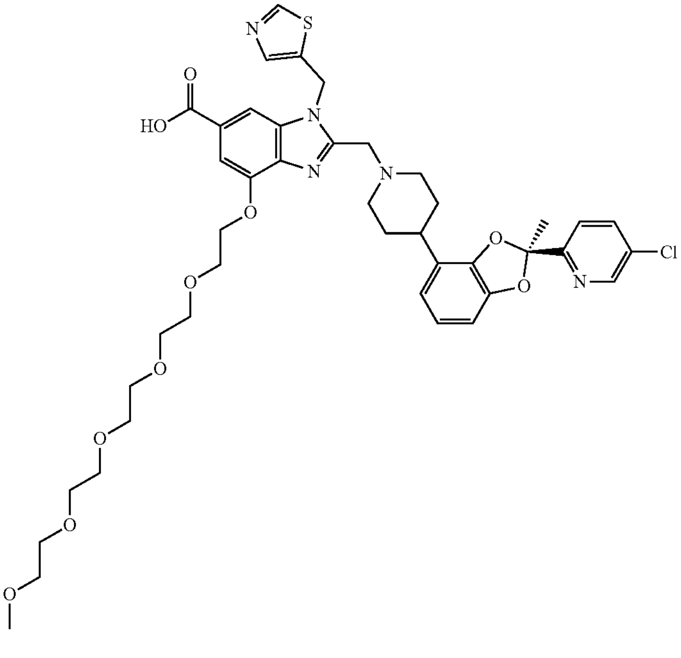 [SMILES: COCCOCCOCCOCCOCCOc1cc(C(=O)O)cc2c1nc(CN1CCC(c3cccc4c3O[C@@](C)(c3ccc(Cl)cn3)O4)CC1)n2Cc1cncs1] |

TABLE 5-continued
| Compound No. | Structure |
|---|---|
| 5-5 | 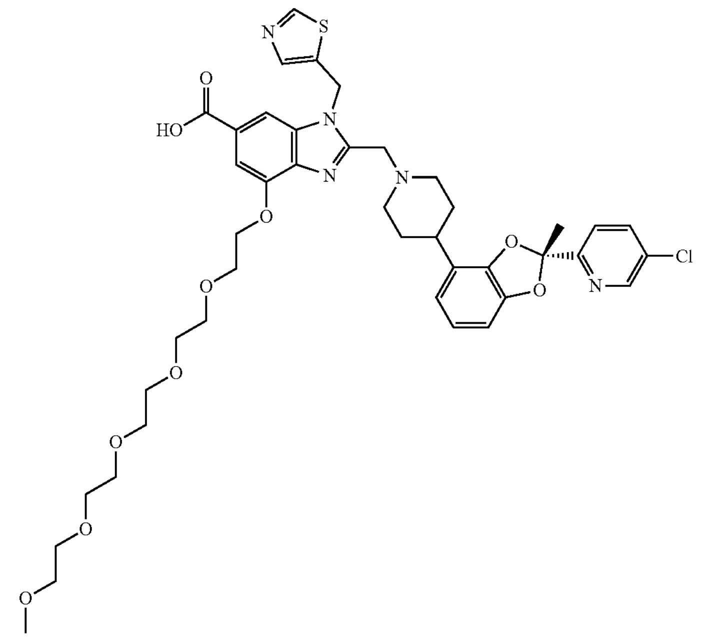 [SMILES: COCCOCCOCCOCCOCCOc1cc(C(=O)O)cc2c1nc(CN1CCC(c3cccc4c3O[C@](C)(c3ccc(Cl)cn3)O4)CC1)n2Cc1cncs1] |
| 5-6 | 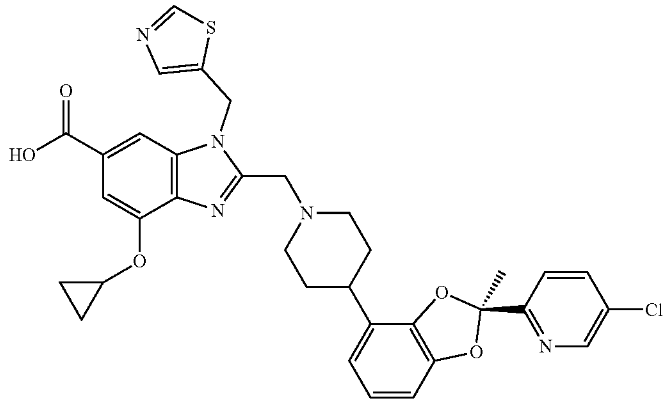 [SMILES: C[C@]1(c2ccc(Cl)cn2)Oc2cccc(C3CCN(Cc4nc5c(OC6CC6)cc(C(=O)O)cc5n4Cc4cncs4)CC3)c2O1] |
| 5-7 | 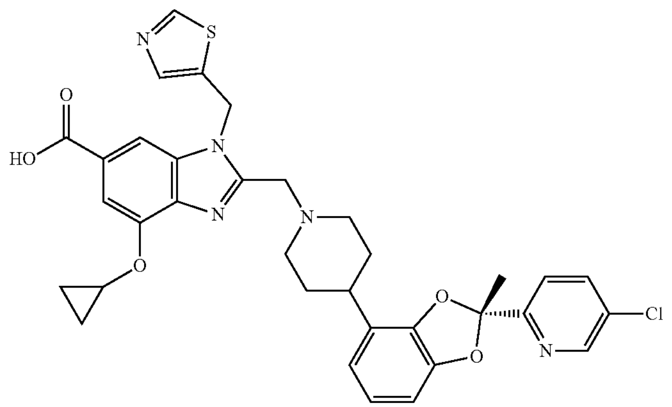 [SMILES: C[C@@]1(c2ccc(Cl)cn2)Oc2cccc(C3CCN(Cc4nc5c(OC6CC6)cc(C(=O)O)cc5n4Cc4cncs4)CC3)c2O1] |

TABLE 5-continued
| Compound No. | Structure |
| --- | --- |
| 5-8 | 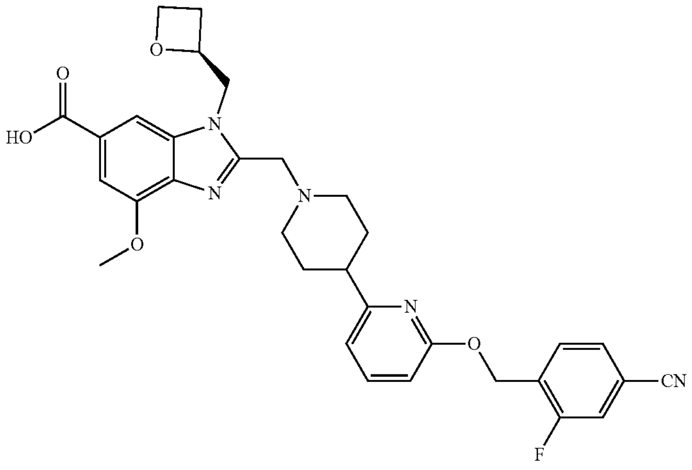 [SMILES: COc1cc(C(=O)O)cc2c1nc(CN1CCC(c3cccc(OCc4ccc(C#N)cc4F)n3)CC1)n2C[C@@H]1CCO1] |
| 5-9 | 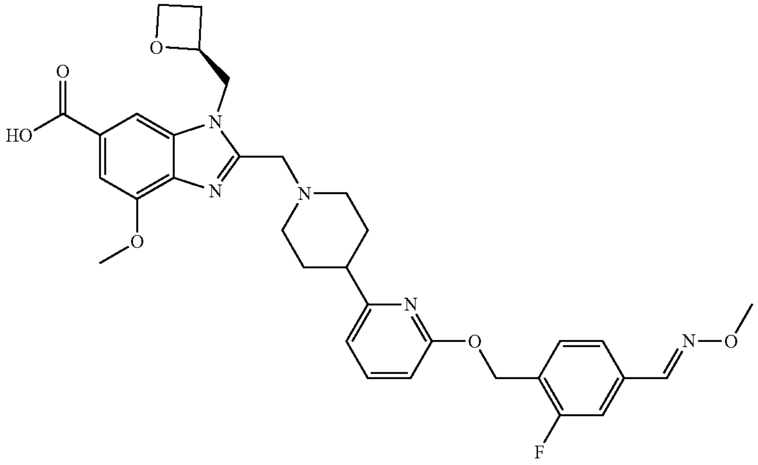 [SMILES: CO/N=C/c1ccc(COc2cccc(C3CCN(Cc4nc5c(OC)cc(C(=O)O)cc5n4C[C@@H]4CCO4)CC3)n2)c(F)c1] |
| 5-10 | 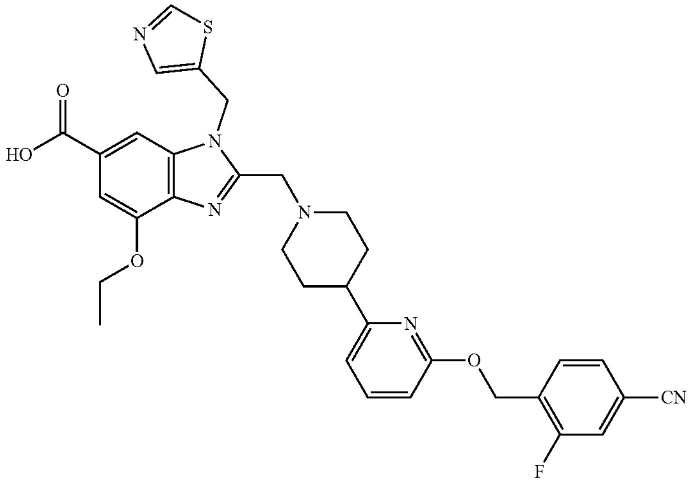 [SMILES: CCOc1cc(C(=O)O)cc2c1nc(CN1CCC(c3cccc(OCc4ccc(C#N)cc4F)n3)CC1)n2Cc1cncs1] |

TABLE 5-continued
| Compound No. | Structure |
| --- | --- |
| 5-11 | 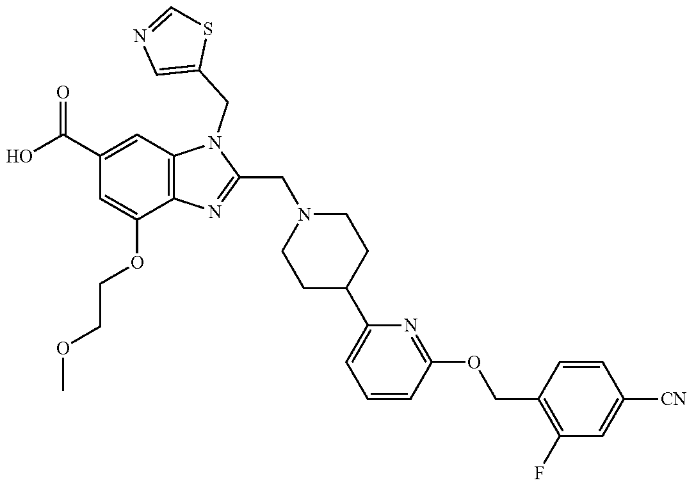 [SMILES: COCCOc1cc(C(=O)O)cc2c1nc(CN1CCC(c3cccc(OCc4ccc(C#N)cc4F)n3)CC1)n2Cc1cncs1] |
| 5-12 | 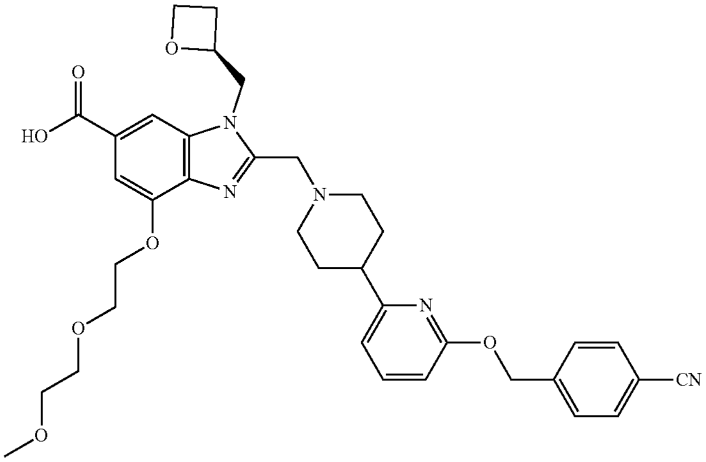 [SMILES: COCCOCCOc1cc(C(=O)O)cc2c1nc(CN1CCC(c3cccc(OCc4ccc(C#N)cc4)n3)CC1)n2C[C@@H]1CCO1] |
| 5-13 | 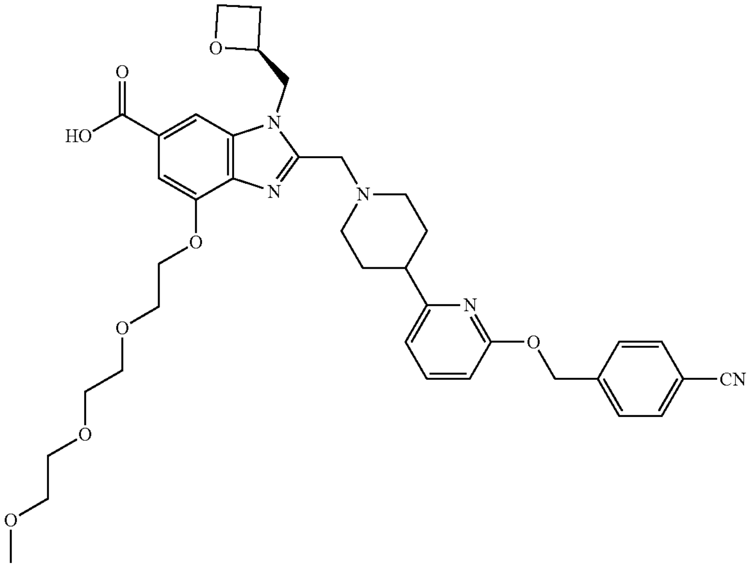 [SMILES: COCCOCCOCCOc1cc(C(=O)O)cc2c1nc(CN1CCC(c3cccc(OCc4ccc(C#N)cc4)n3)CC1)n2C[C@@H]1CCO1] |

TABLE 5-continued
| Compound No. | Structure |
| --- | --- |
| 5-14 | 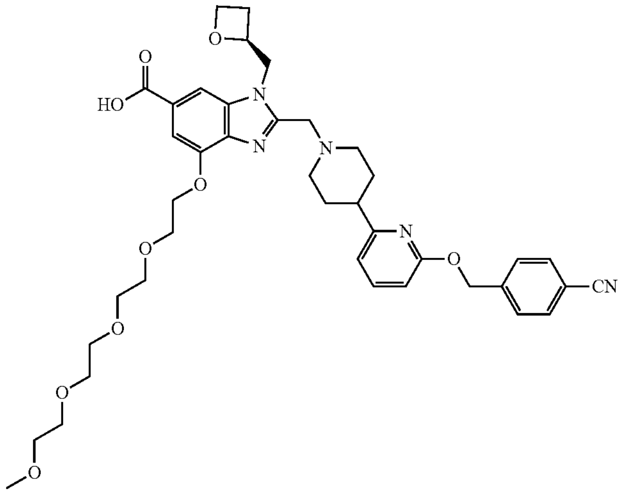 [SMILES: COCCOCCOCCOCCOc1cc(C(=O)O)cc2c1nc(CN1CCC(c3cccc(OCc4ccc(C#N)cc4)n3)CC1)n2C[C@@H]1CCO1] |
| 5-15 | 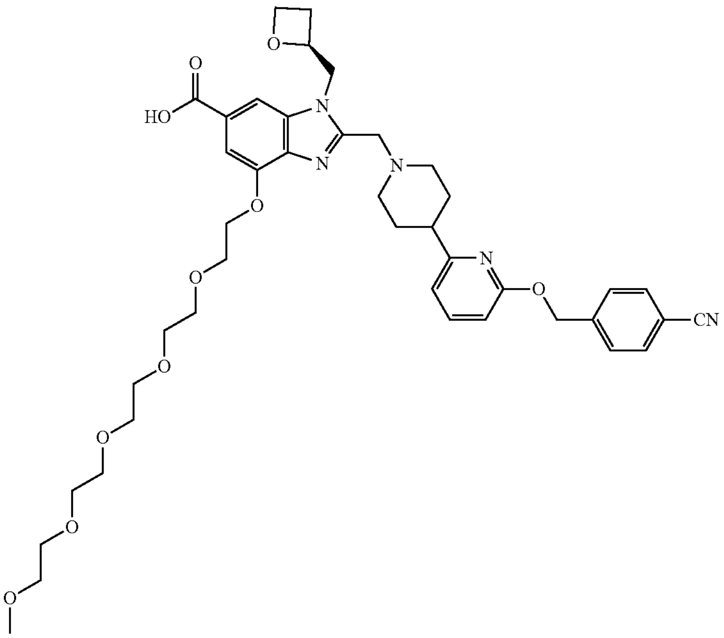 [SMILES: COCCOCCOCCOCCOCCOc1cc(C(=O)O)cc2c1nc(CN1CCC(c3cccc(OCc4ccc(C#N)cc4)n3)CC1)n2C[C@@H]1CCO1] |

TABLE 5-continued
| Compound No. | Structure |
| --- | --- |
| 5-16 | 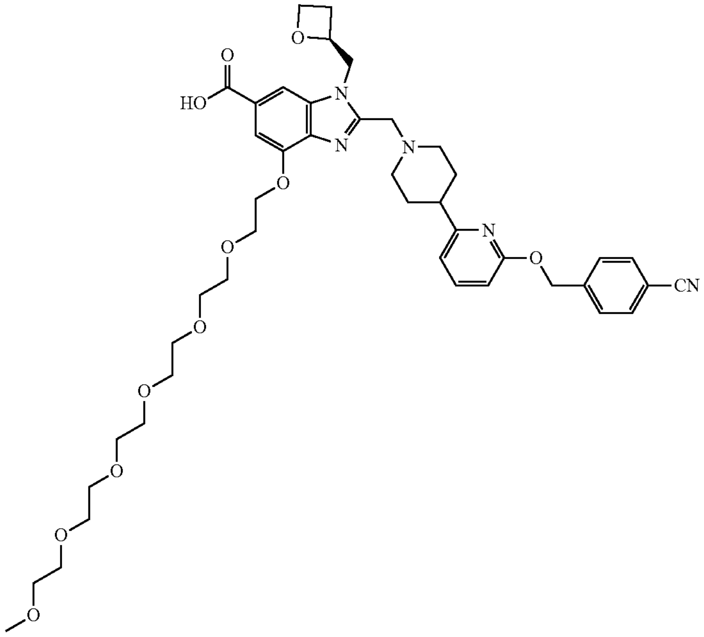 [SMILES: COCCOCCOCCOCCOCCOCCOc1cc(C(=O)O)cc2c1nc(CN1CCC(c3cccc(OCc4ccc(C#N)cc4)n3)CC1)n2C[C@@H]1CCO1] |
| 5-17 | 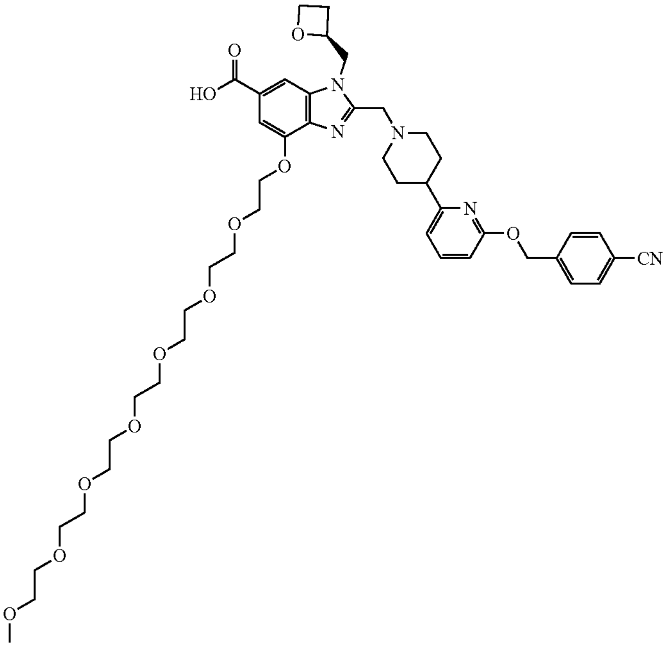 [SMILES: COCCOCCOCCOCCOCCOCCOCCOc1cc(C(=O)O)cc2c1nc(CN1CCC(c3cccc(OCc4ccc(C#N)cc4)n3)CC1)n2C[C@@H]1CCO1] |

TABLE 5-continued
| Compound No. | Structure |
| --- | --- |
| 5-18 | 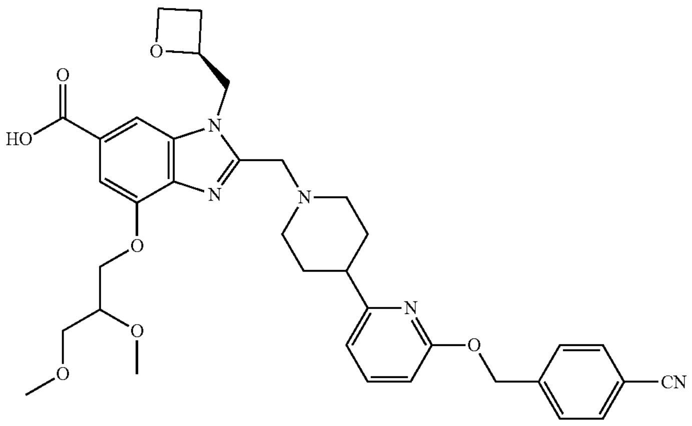 [SMILES: COCC(COc1cc(C(=O)O)cc2c1nc(CN1CCC(c3cccc(OCc4ccc(C#N)cc4)n3)CC1)n2C[C@@H]1CCO1)OC] |
| 5-19 | 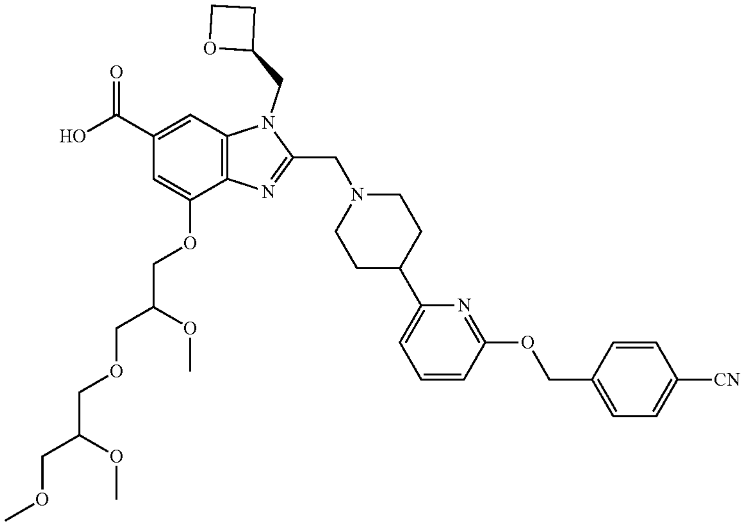 [SMILES: COCC(COCC(COc1cc(C(=O)O)cc2c1nc(CN1CCC(c3cccc(OCc4ccc(C#N)cc4)n3)CC1)n2C[C@@H]1CCO1)OC)OC] |
| 5-20 | 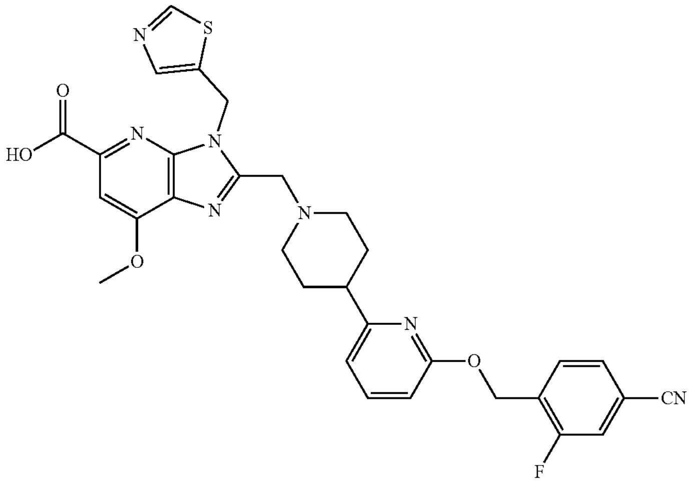 [SMILES: COc1cc(C(=O)O)nc2c1nc(CN1CCC(c3cccc(OCc4ccc(C#N)cc4F)n3)CC1)n2Cc1cncs1] |

TABLE 5-continued
| Compound No. | Structure |
| --- | --- |
| 5-21 | 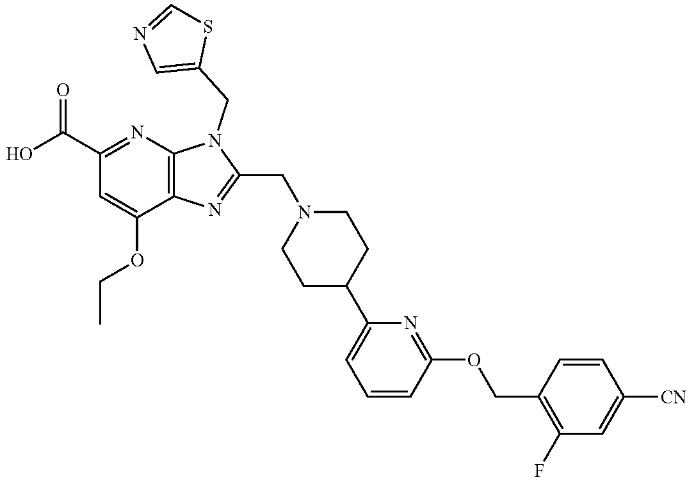 [SMILES: CCOc1cc(C(=O)O)nc2c1nc(CN1CCC(c3cccc(OCc4ccc(C#N)cc4F)n3)CC1)n2Cc1cncs1] |
| 5-22 | 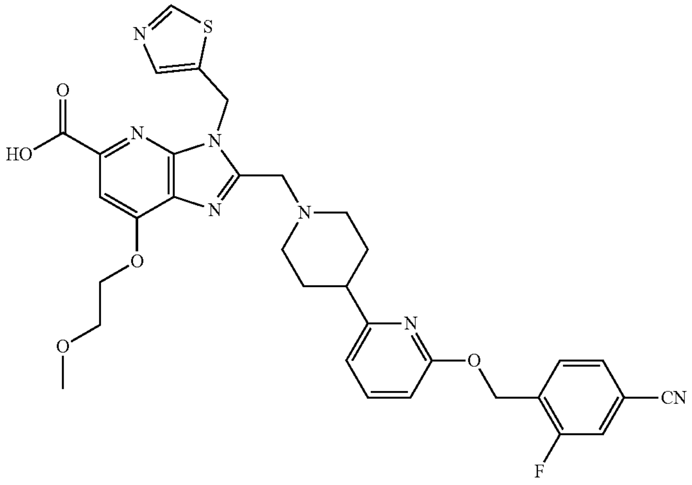 [SMILES: COCCOc1cc(C(=O)O)nc2c1nc(CN1CCC(c3cccc(OCc4ccc(C#N)cc4F)n3)CC1)n2Cc1cncs1] |
| 5-23 | 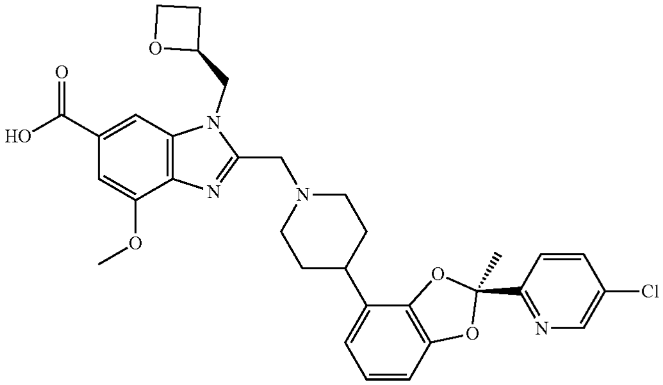 [SMILES: COc1cc(C(=O)O)cc2c1nc(CN1CCC(c3cccc4c3O[C@@](C)(c3ccc(Cl)cn3)O4)CC1)n2C[C@@H]1CCO1] |

TABLE 5-continued
| Compound No. | Structure |
| --- | --- |
| 5-24 | 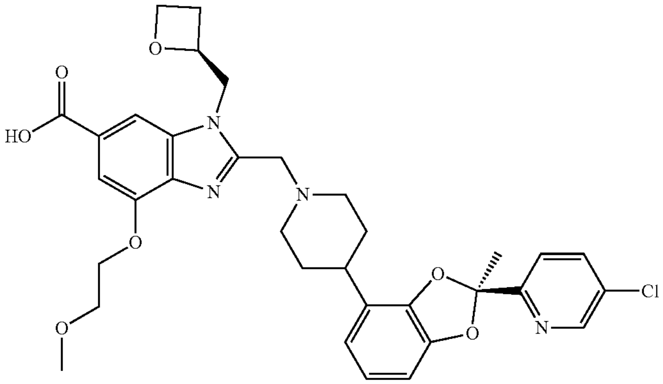 [SMILES: COCCOc1cc(C(=O)O)cc2c1nc(CN1CCC(c3cccc4c3O[C@@](C)(c3ccc(Cl)cn3)O4)CC1)n2C[C@@H]1CCO1] |
| 5-25 | 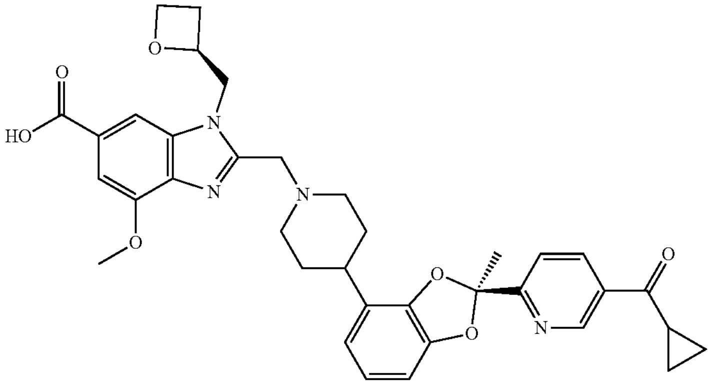 [SMILES: COc1cc(C(=O)O)cc2c1nc(CN1CCC(c3cccc4c3O[C@@](C)(c3ccc(C(=O)C5CC5)cn3)O4)CC1)n2C[C@@H]1CCO1] |
| 5-26 | 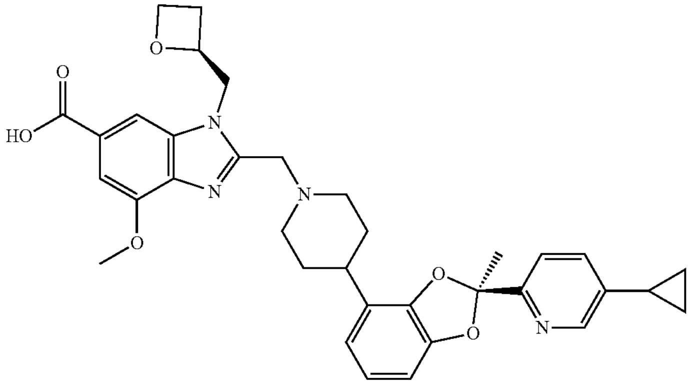 [SMILES: COc1cc(C(=O)O)cc2c1nc(CN1CCC(c3cccc4c3O[C@@](C)(c3ccc(C5CC5)cn3)O4)CC1)n2C[C@@H]1CCO1] |
| 5-27 | 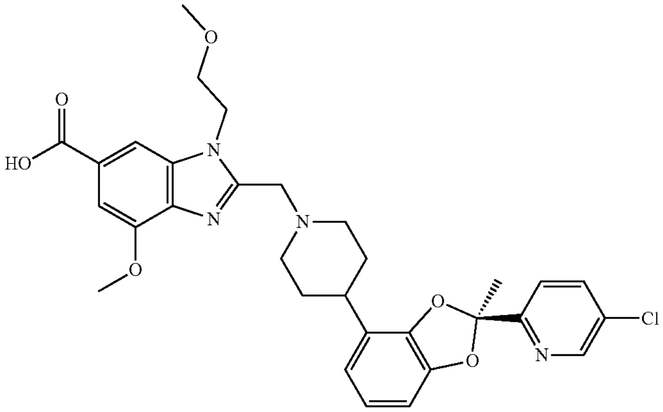 [SMILES: COCCn1c(CN2CCC(c3cccc4c3O[C@@](C)(c3ccc(Cl)cn3)O4)CC2)nc2c(OC)cc(C(=O)O)cc21] |

TABLE 5-continued
| Compound No. | Structure |
|---|---|
| 5-28 | 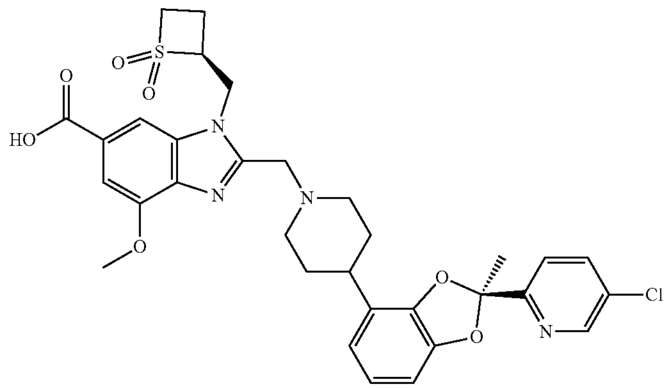 [SMILES: COc1cc(C(=O)O)cc2c1nc(CN1CCC(c3cccc4c3O[C@@](C)(c3ccc(Cl)cn3)O4)CC1)n2C[C@@H]1CCS1(=O)=O] |
| 5-29 | 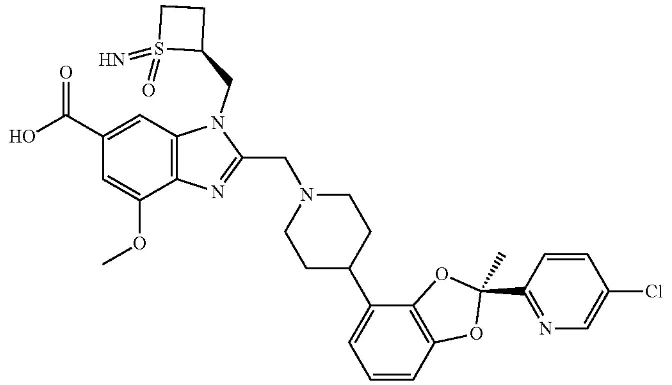 [SMILES: COc1cc(C(=O)O)cc2c1nc(CN1CCC(c3cccc4c3O[C@@](C)(c3ccc(Cl)cn3)O4)CC1)n2C[C@@H]1CCS1(=N)=O] |
| 5-30 | 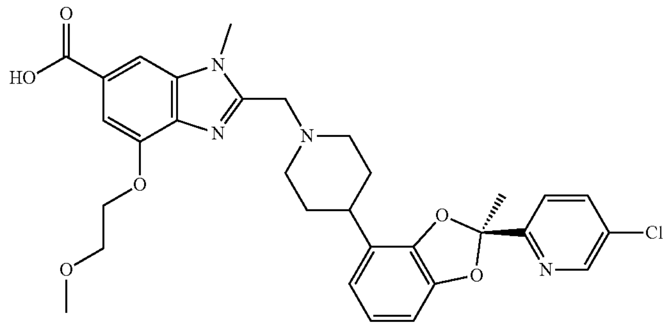 [SMILES: COCCOc1cc(C(=O)O)cc2c1nc(CN1CCC(c3cccc4c3O[C@@](C)(c3ccc(Cl)cn3)O4)CC1)n2C] |
| 5-31 | 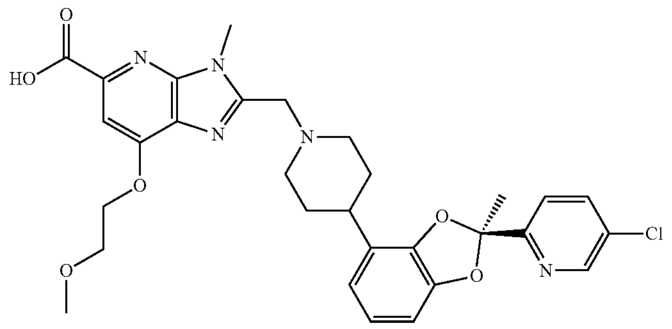 [SMILES: COCCOc1cc(C(=O)O)nc2c1nc(CN1CCC(c3cccc4c3O[C@@](C)(c3ccc(Cl)cn3)O4)CC1)n2C] |

TABLE 5-continued
| Compound No. | Structure |
|---|---|
| 5-32 | 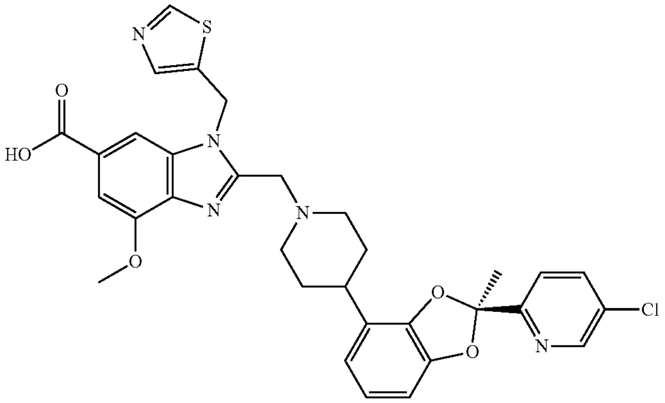 [SMILES: COc1cc(C(=O)O)cc2c1nc(CN1CCC(c3cccc4c3O[C@@](C)(c3ccc(Cl)cn3)O4)CC1)n2Cc1cncs1] |
| 5-33 | 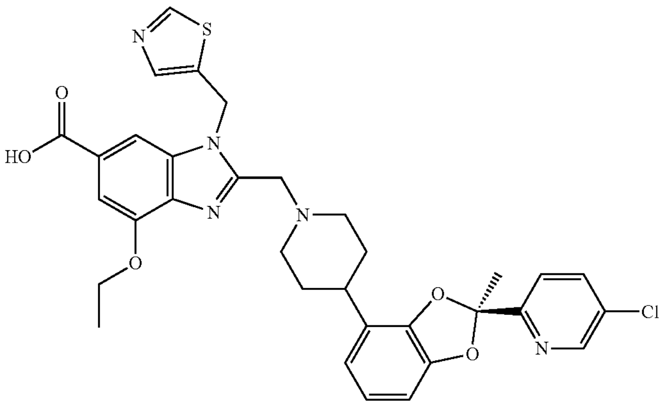 [SMILES: CCOc1cc(C(=O)O)cc2c1nc(CN1CCC(c3cccc4c3O[C@@](C)(c3ccc(Cl)cn3)O4)CC1)n2Cc1cncs1] |
| 5-34 | 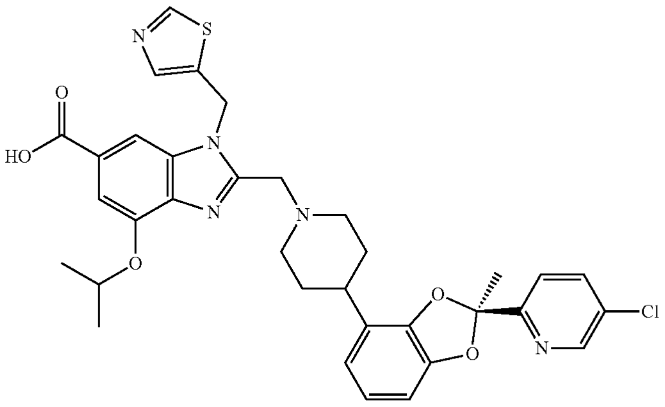 |

TABLE 5-continued
| Compound No. | Structure |
| --- | --- |
| 5-35 | 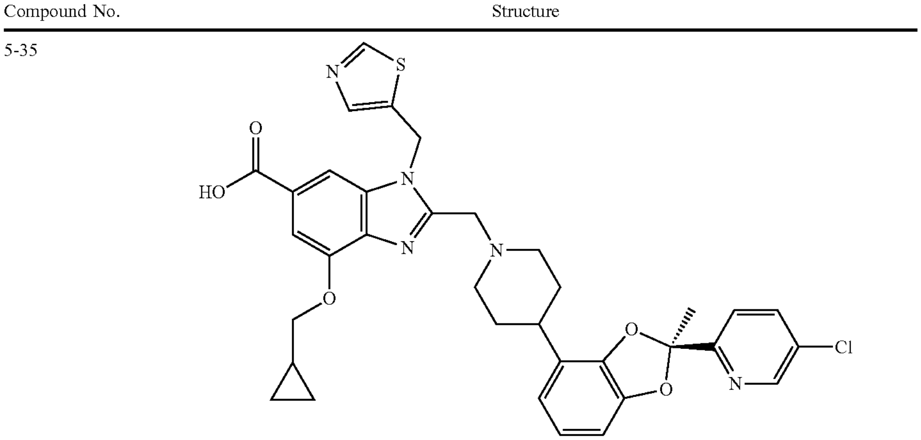 |
| 5-36 | 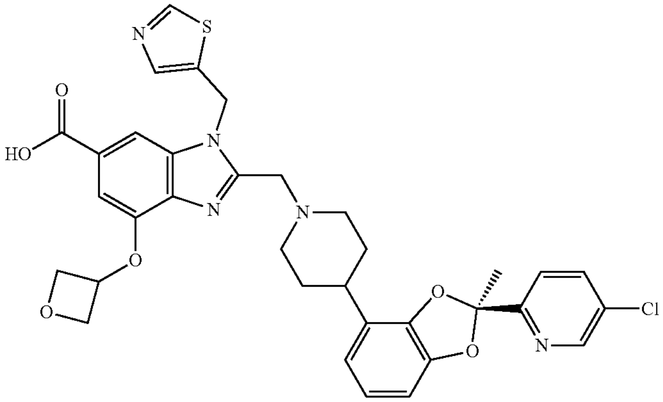 [SMILES: C[C@]1(c2ccc(Cl)cn2)Oc2cccc(C3CCN(Cc4nc5c(OC6COC6)cc(C(=O)O)cc5n4Cc4cncs4)CC3)c2O1] |
| 5-37 | 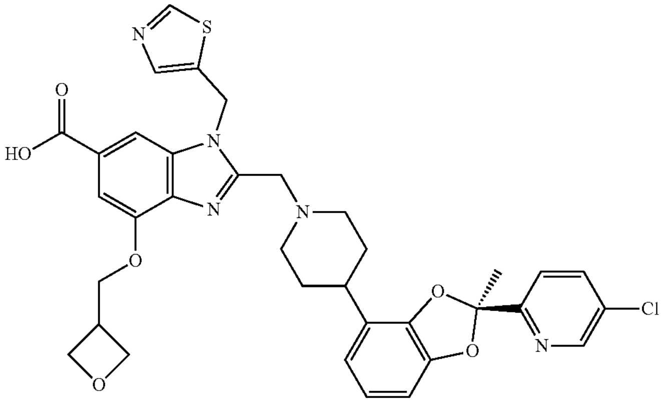 [SMILES: C[C@]1(c2ccc(Cl)cn2)Oc2cccc(C3CCN(Cc4nc5c(OCC6COC6)cc(C(=O)O)cc5n4Cc4cncs4)CC3)c2O1] |
| 5-38 | 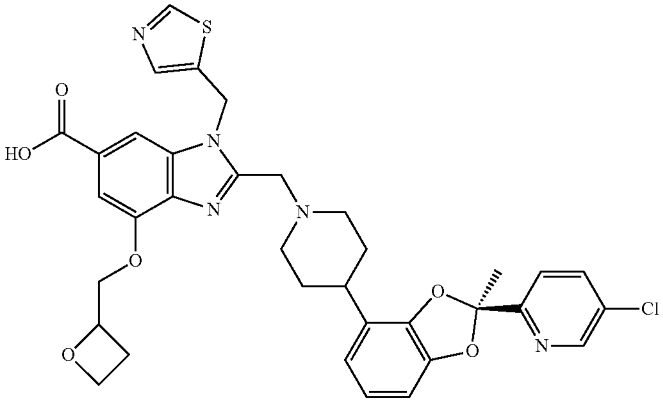 [SMILES: C[C@]1(c2ccc(Cl)cn2)Oc2cccc(C3CCN(Cc4nc5c(OCC6CCO6)cc(C(=O)O)cc5n4Cc4cncs4)CC3)c2O1] |

TABLE 5-continued
| Compound No. | Structure |
| --- | --- |
| 5-39 | 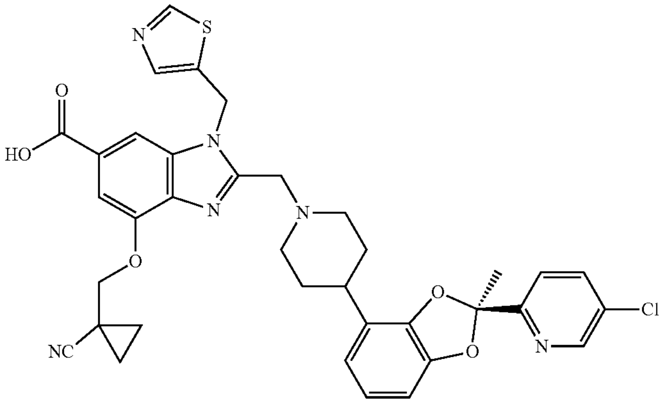 [SMILES: C[C@]1(c2ccc(Cl)cn2)Oc2cccc(C3CCN(Cc4nc5c(OCC6(C#N)CC6)cc(C(=O)O)cc5n4Cc4cncs4)CC3)c2O1] |
| 5-40 | 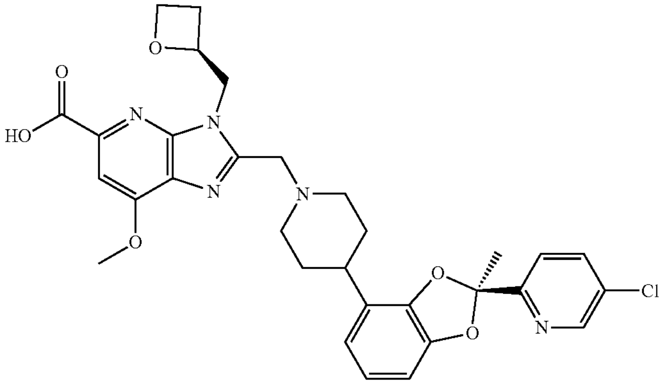 [SMILES: COc1cc(C(=O)O)nc2c1nc(CN1CCC(c3cccc4c3O[C@@](C)(c3ccc(Cl)cn3)O4)CC1)n2C[C@@H]1CCO1] |
| 5-41 | 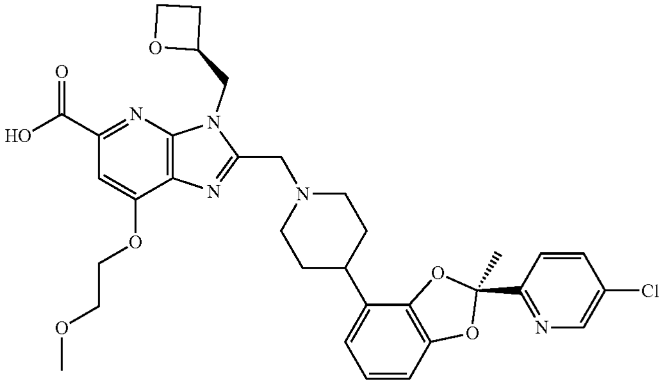 |
| 5-42 | 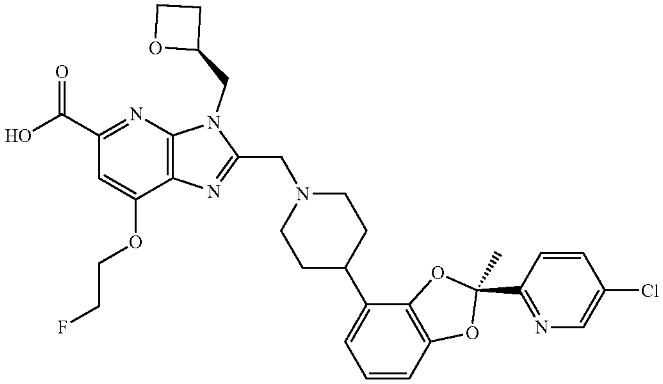 [SMILES: C[C@]1(c2ccc(Cl)cn2)Oc2cccc(C3CCN(Cc4nc5c(OCCF)cc(C(=O)O)nc5n4C[C@@H]4CCO4)CC3)c2O1] |

TABLE 5-continued
| Compound No. | Structure |
| --- | --- |
| 5-43 | 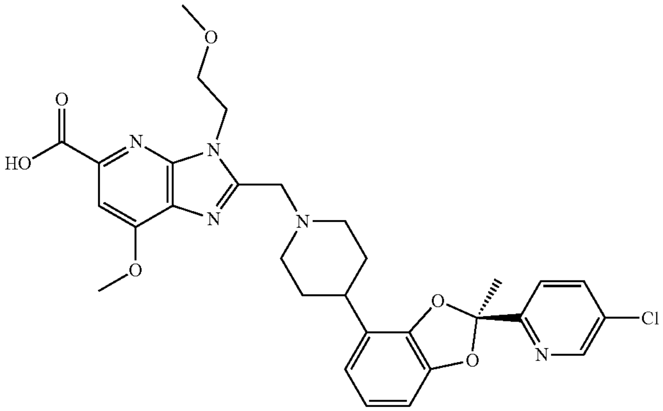 [SMILES: COCCn1c(CN2CCC(c3cccc4c3O[C@@](C)(c3ccc(Cl)cn3)O4)CC2)nc2c(OC)cc(C(=O)O)nc21] |
| 5-44 | 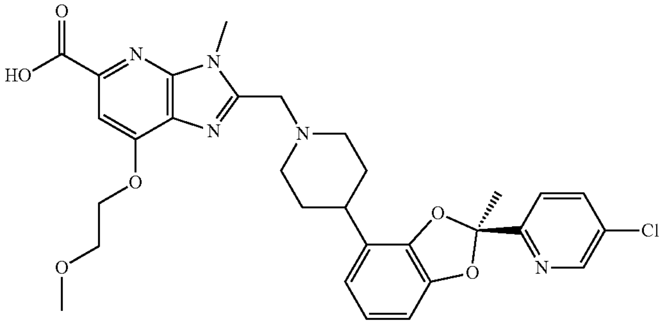 [SMILES: COCCOc1cc(C(=O)O)nc2c1nc(CN1CCC(c3cccc4c3O[C@@](C)(c3ccc(Cl)cn3)O4)CC1)n2C] |
| 5-45 | 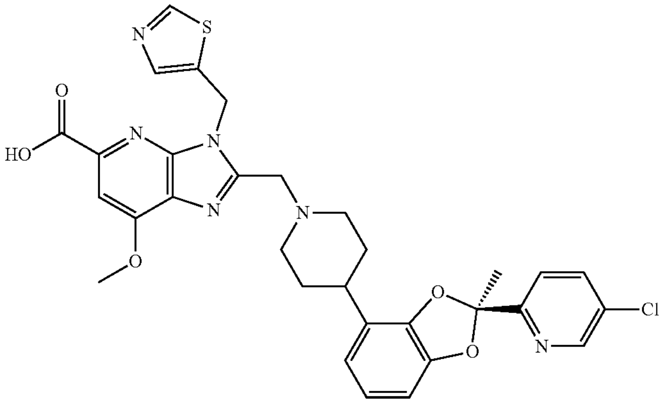 [SMILES: COc1cc(C(=O)O)nc2c1nc(CN1CCC(c3cccc4c3O[C@@](C)(c3ccc(Cl)cn3)O4)CC1)n2Cc1cncs1] |
| 5-46 | 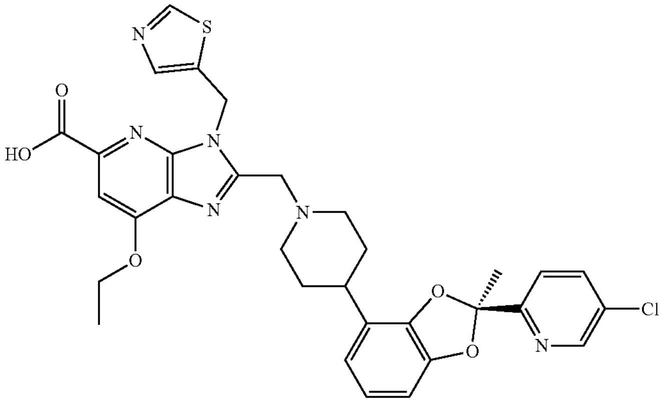 [SMILES: CCOc1cc(C(=O)O)nc2c1nc(CN1CCC(c3cccc4c3O[C@@](C)(c3ccc(Cl)cn3)O4)CC1)n2Cc1cncs1] |

TABLE 5-continued
| Compound No. | Structure |
|---|---|
| 5-47 | 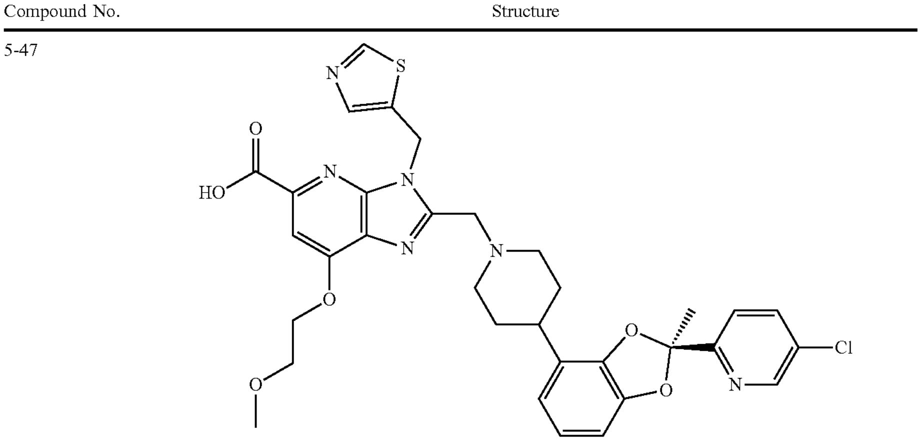 |
| 5-48 | 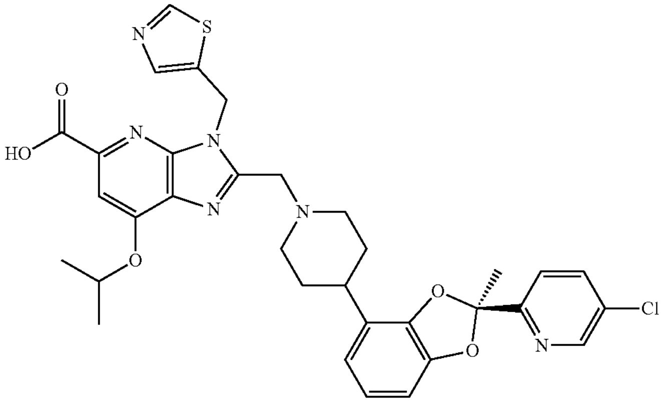 [SMILES: CC(C)Oc1cc(C(=O)O)nc2c1nc(CN1CCC(c3cccc4c3O[C@@](C)(c3ccc(Cl)cn3)O4)CC1)n2Cc1cncs1] |
| 5-49 | 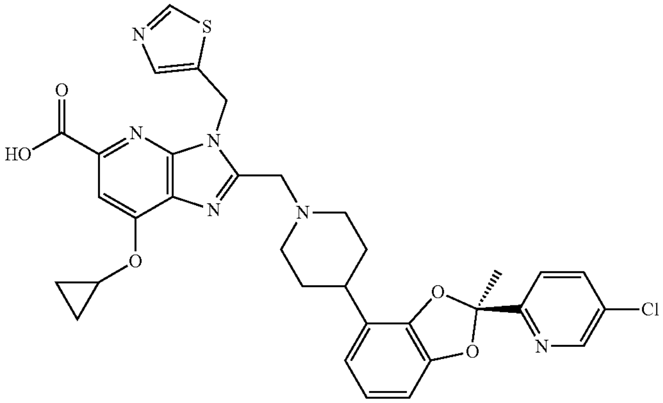 [SMILES: C[C@]1(c2ccc(Cl)cn2)Oc2cccc(C3CCN(Cc4nc5c(OC6CC6)cc(C(=O)O)nc5n4Cc4cncs4)CC3)c2O1] |
| 5-50 | 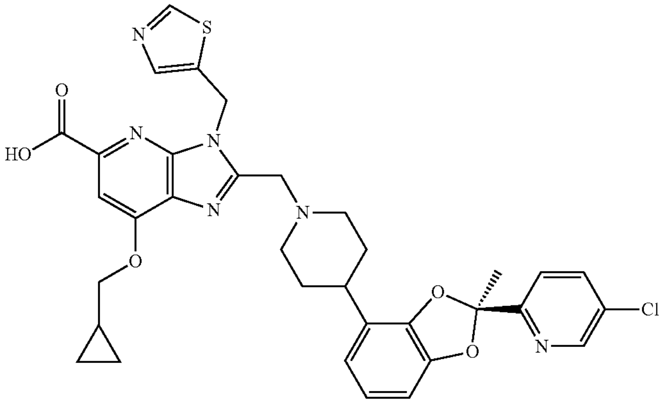 |

TABLE 5-continued
| Compound No. | Structure |
| --- | --- |
| 5-51 | 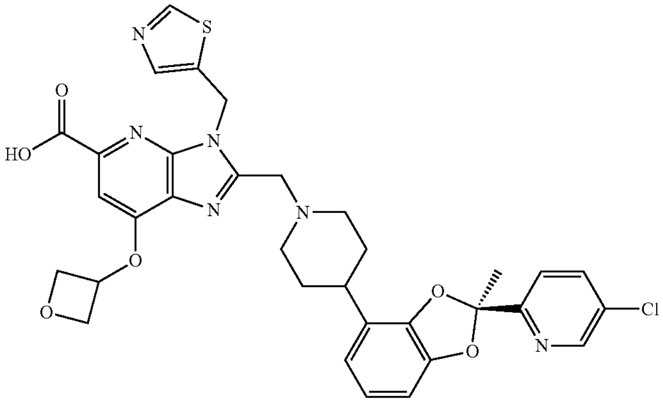 [SMILES: C[C@]1(c2ccc(Cl)cn2)Oc2cccc(C3CCN(Cc4nc5c(OC6COC6)cc(C(=O)O)nc5n4Cc4cncs4)CC3)c2O1] |
| 5-52 | 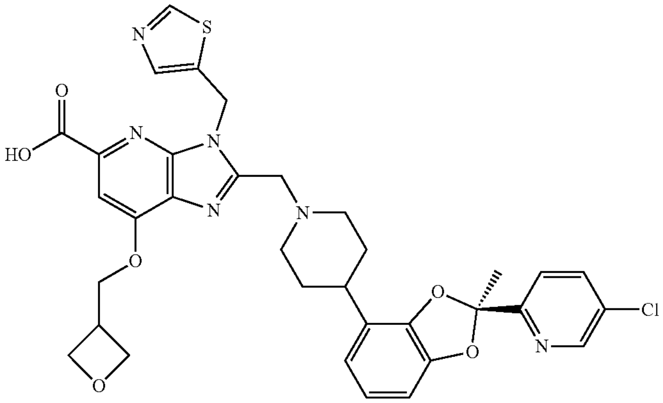 [SMILES: C[C@]1(c2ccc(Cl)cn2)Oc2cccc(C3CCN(Cc4nc5c(OCC6COC6)cc(C(=O)O)nc5n4Cc4cncs4)CC3)c2O1] |
| 5-53 | 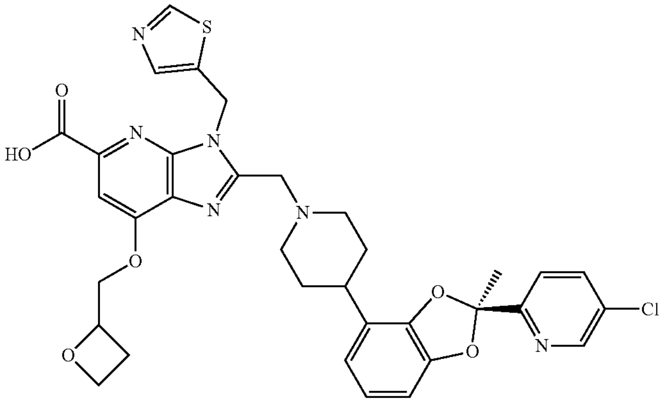 [SMILES: C[C@]1(c2ccc(Cl)cn2)Oc2cccc(C3CCN(Cc4nc5c(OCC6CCO6)cc(C(=O)O)nc5n4Cc4cncs4)CC3)c2O1] |

TABLE 5-continued
| Compound No. | Structure |
| --- | --- |
| 5-54 | 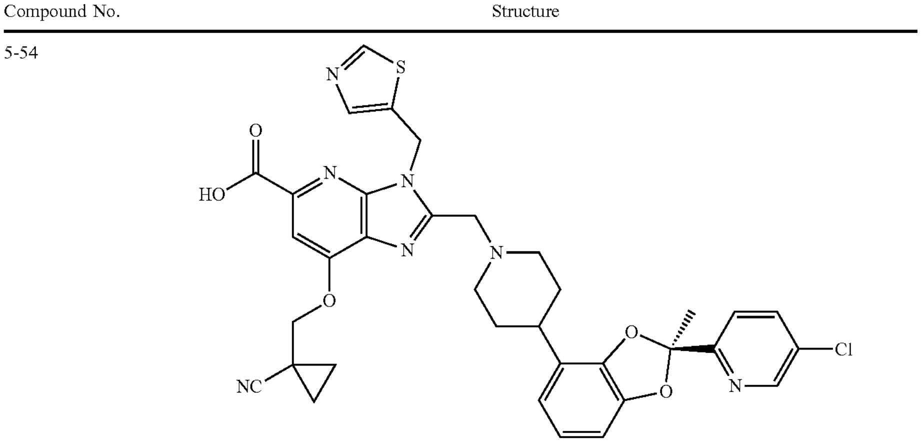 |
| 5-55 | 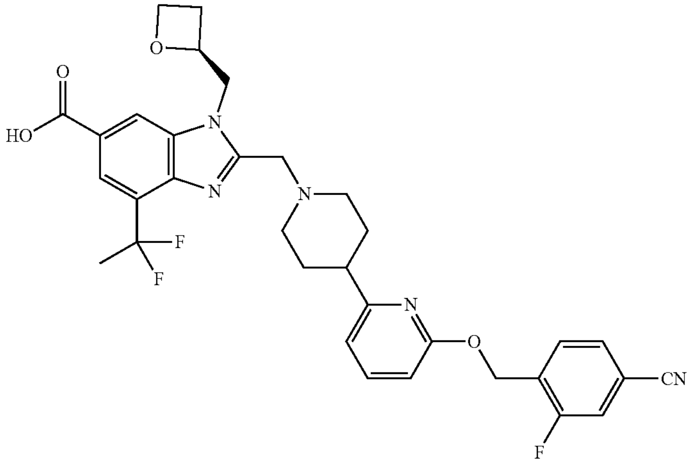 [SMILES: CC(F)(F)c1cc(C(=O)O)cc2c1nc(CN1CCC(c3cccc(OCc4ccc(C#N)cc4F)n3)CC1)n2C[C@@H]1CCO1] |
| 5-56 | 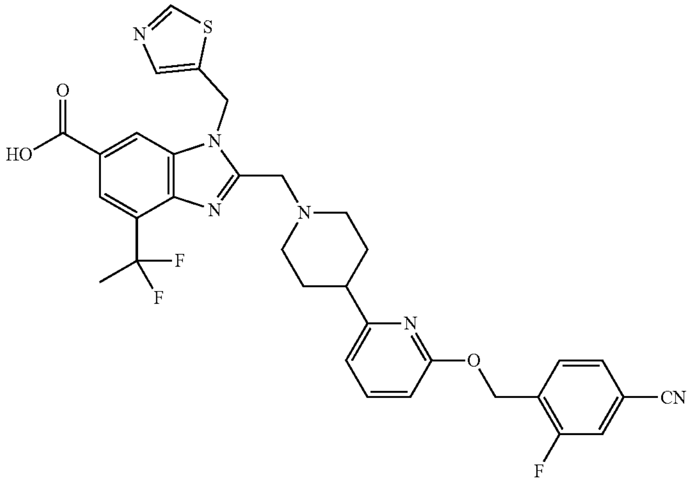 [SMILES: CC(F)(F)c1cc(C(=O)O)cc2c1nc(CN1CCC(c3cccc(OCc4ccc(C#N)cc4F)n3)CC1)n2Cc1cncs1] |

TABLE 5-continued
| Compound No. | Structure |
|---|---|
| 5-57 | 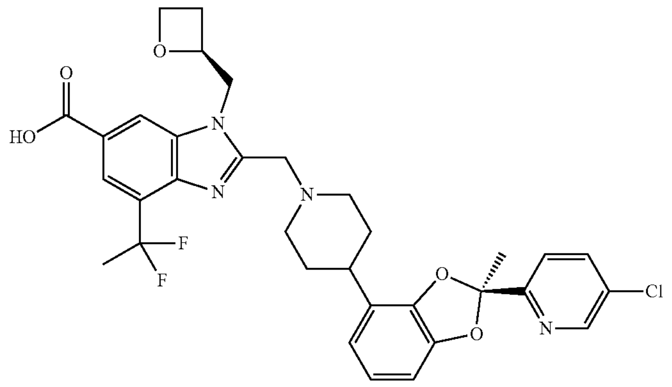 [SMILES: CC(F)(F)c1cc(C(=O)O)cc2c1nc(CN1CCC(c3cccc4c3O[C@@](C)(c3ccc(Cl)cn3)O4)CC1)n2C[C@@H]1CCO1] |
| 5-58 | 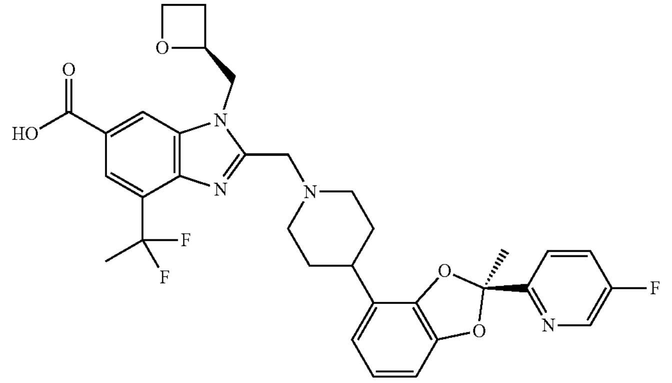 [SMILES: CC(F)(F)c1cc(C(=O)O)cc2c1nc(CN1CCC(c3cccc4c3O[C@@](C)(c3ccc(F)cn3)O4)CC1)n2C[C@@H]1CCO1] |
| 5-59 | 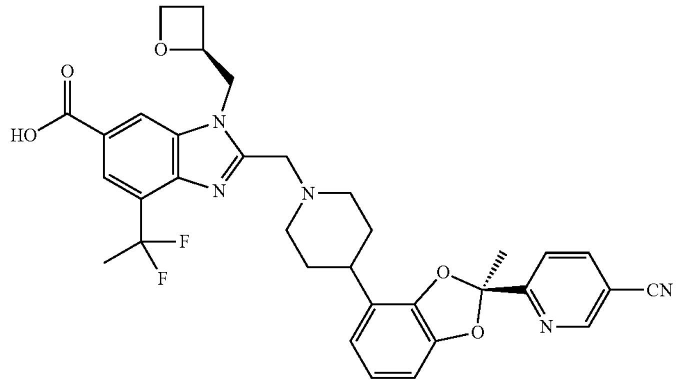 [SMILES: CC(F)(F)c1cc(C(=O)O)cc2c1nc(CN1CCC(c3cccc4c3O[C@@](C)(c3ccc(C#N)cn3)O4)CC1)n2C[C@@H]1CCO1] |
| 5-60 | 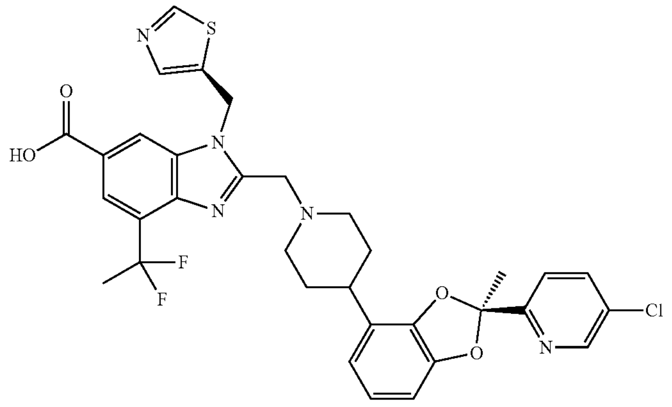 |

TABLE 5-continued
| Compound No. | Structure |
| --- | --- |
| 5-61 | 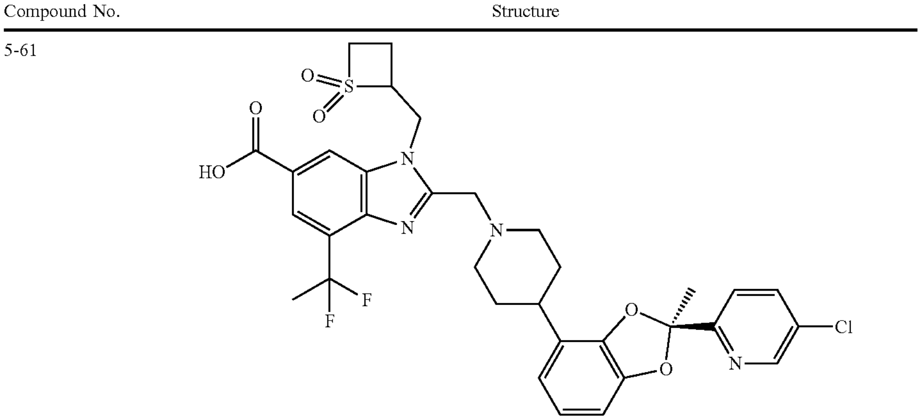 |
| 5-62 | 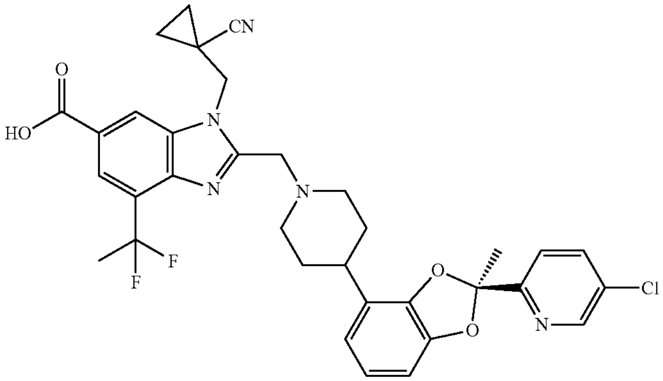 [SMILES: CC(F)(F)c1cc(C(=O)O)cc2c1nc(CN1CCC(c3cccc4c3O[C@@](C)(c3ccc(Cl)cn3)O4)CC1)n2CC1(C#N)CC1] |
| 5-63 | 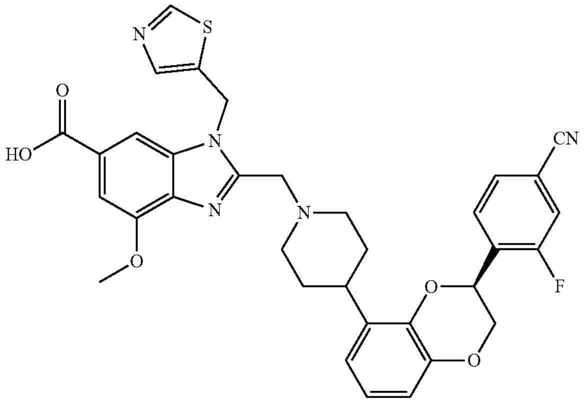 [SMILES: COc1cc(C(=O)O)cc2c1nc(CN1CCC(c3cccc4c3O[C@@H](c3ccc(C#N)cc3F)CO4)CC1)n2Cc1cncs1] |
| 5-64 | 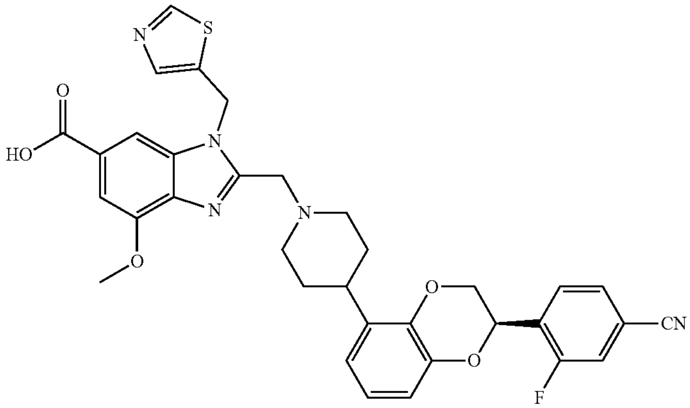 [SMILES: COc1cc(C(=O)O)cc2c1nc(CN1CCC(c3cccc4c3OC[C@@H](c3ccc(C#N)cc3F)O4)CC1)n2Cc1cncs1] |

TABLE 5-continued
| Compound No. | Structure |
| --- | --- |
| 5-65 | 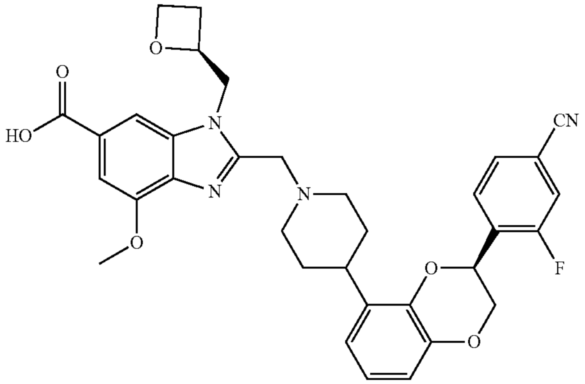 [SMILES: COc1cc(C(=O)O)cc2c1nc(CN1CCC(c3cccc4c3O[C@@H](c3ccc(C#N)cc3F)CO4)CC1)n2C[C@@H]1CCO1] |
| 5-66 | 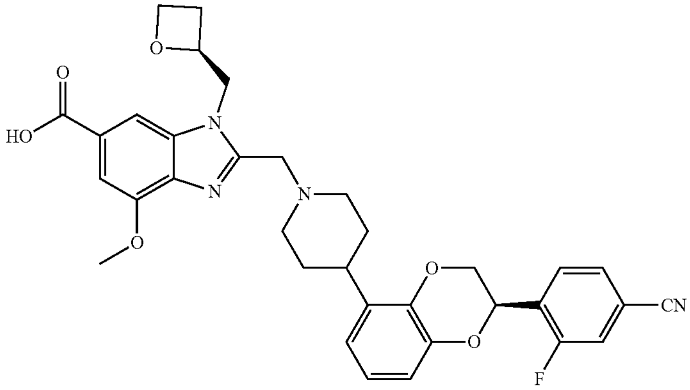 [SMILES: COc1cc(C(=O)O)cc2c1nc(CN1CCC(c3cccc4c3OC[C@@H](c3ccc(C#N)cc3F)O4)CC1)n2C[C@@H]1CCO1] |
| 5-67 | 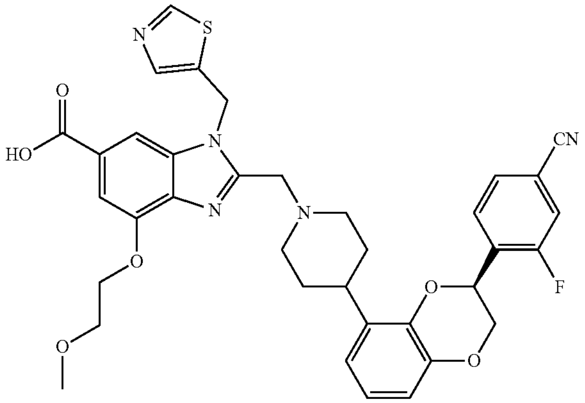 [SMILES: COCCOc1cc(C(=O)O)cc2c1nc(CN1CCC(c3cccc4c3O[C@@H](c3ccc(C#N)cc3F)CO4)CC1)n2Cc1cncs1] |
| 5-68 | 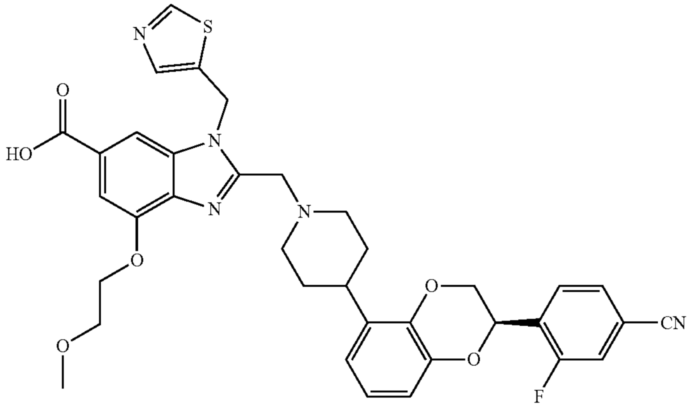 [SMILES: COCCOc1cc(C(=O)O)cc2c1nc(CN1CCC(c3cccc4c3OC[C@@H](c3ccc(C#N)cc3F)O4)CC1)n2Cc1cncs1] |

TABLE 5-continued
| Compound No. | Structure |
| --- | --- |
| 5-69 | 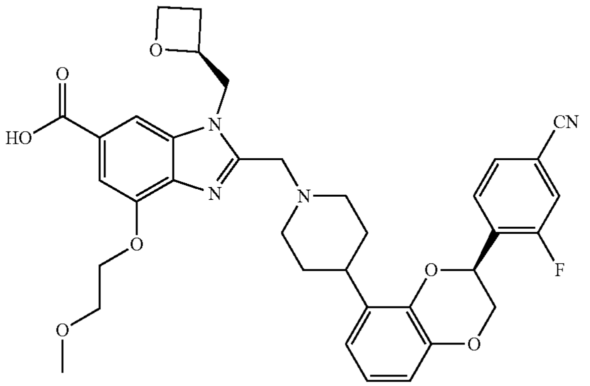 [SMILES: COCCOc1cc(C(=O)O)cc2c1nc(CN1CCC(c3cccc4c3O[C@@H](c3ccc(C#N)cc3F)CO4)CC1)n2C[C@@H]1CCO1] |
| 5-70 | 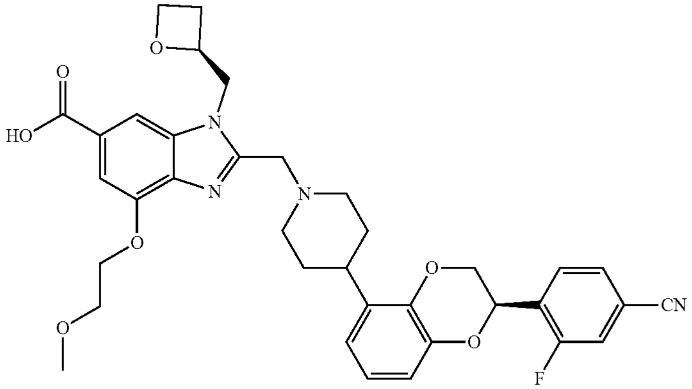 [SMILES: COCCOc1cc(C(=O)O)cc2c1nc(CN1CCC(c3cccc4c3OC[C@@H](c3ccc(C#N)cc3F)O4)CC1)n2C[C@@H]1CCO1] |
| 5-71 | 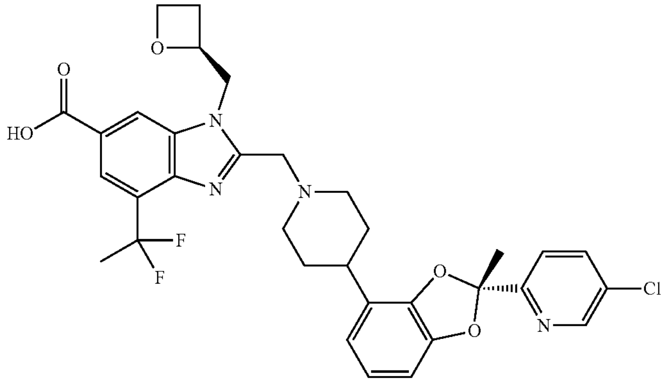 [SMILES: CC(F)(F)c1cc(C(=O)O)cc2c1nc(CN1CCC(c3cccc4c3O[C@](C)(c3ccc(Cl)cn3)O4)CC1)n2C[C@@H]1CCO1] |
| 5-72 | 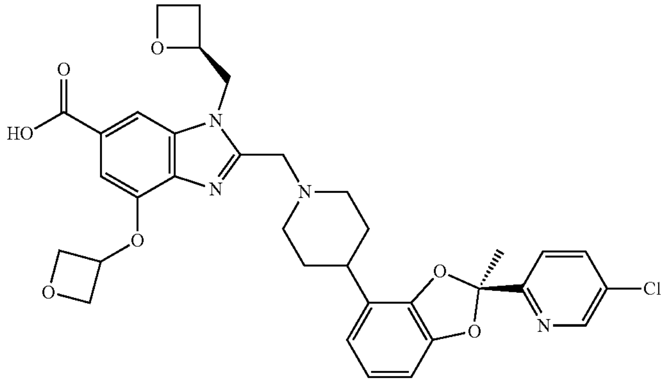 [SMILES: C[C@]1(c2ccc(Cl)cn2)Oc2cccc(C3CCN(Cc4nc5c(OC6COC6)cc(C(=O)O)cc5n4C[C@@H]4CCO4)CC3)c2O1] |

TABLE 5-continued
| Compound No. | Structure |
|---|---|
| 5-73 | 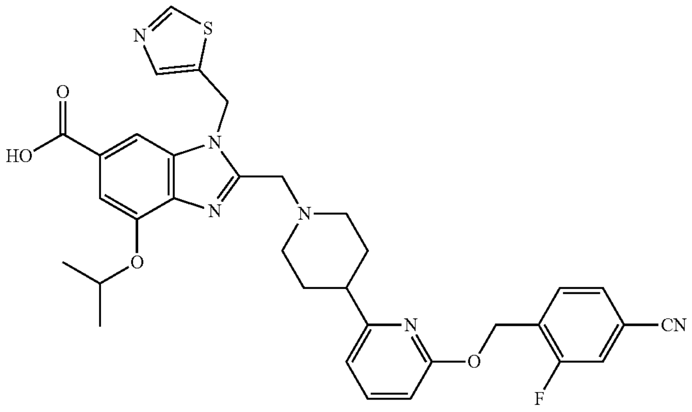 [SMILES: CC(C)Oc1cc(C(=O)O)cc2c1nc(CN1CCC(c3cccc(OCc4ccc(C#N)cc4F)n3)CC1)n2Cc1cncs1] |
| 5-74 | 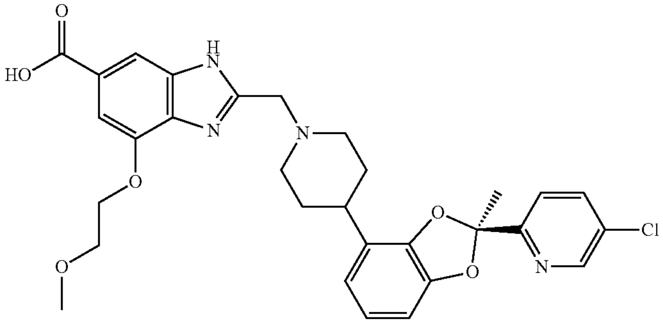 [SMILES: COCCOc1cc(C(=O)O)cc2[nH]c(CN3CCC(c4cccc5c4O[C@@](C)(c4ccc(Cl)cn4)O5)CC3)nc12] |
| 5-75 | 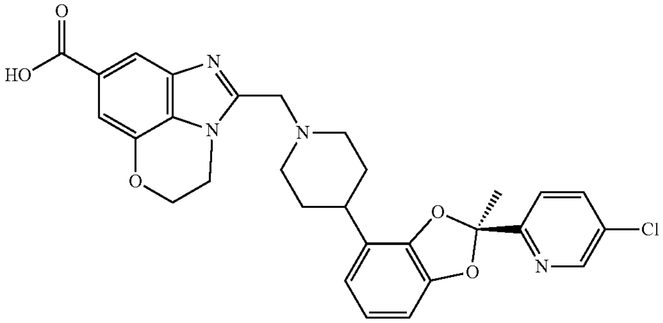 [SMILES: C[C@]1(c2ccc(Cl)cn2)Oc2cccc(C3CCN(Cc4nc5cc(C(=O)O)cc6c5n4CCO6)CC3)c2O1] |
| 5-76 | 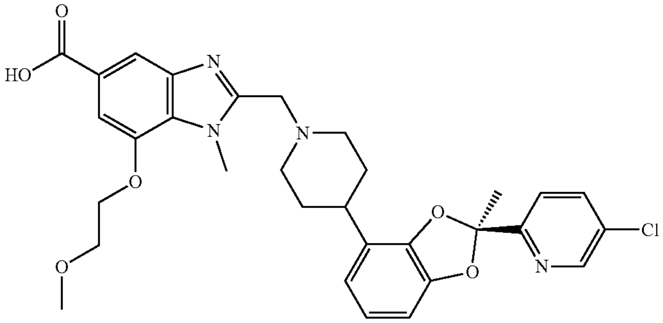 [SMILES: COCCOc1cc(C(=O)O)cc2nc(CN3CCC(c4cccc5c4O[C@@](C)(c4ccc(Cl)cn4)O5)CC3)n(C)c12] |

TABLE 5-continued
| Compound No. | Structure |
| --- | --- |
| 5-77 | 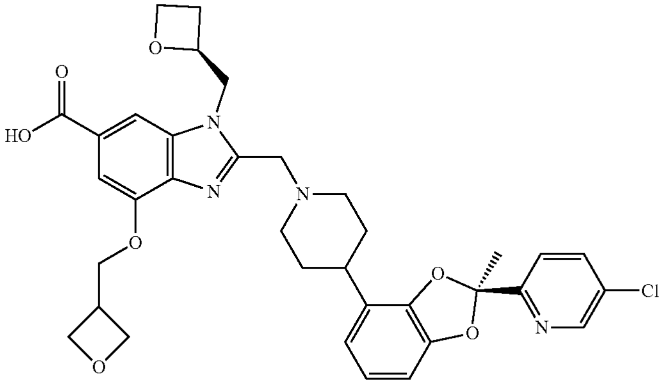 [SMILES: C[C@]1(c2ccc(Cl)cn2)Oc2cccc(C3CCN(Cc4nc5c(OCC6COC6)cc(C(=O)O)cc5n4C[C@@H]4CCO4)CC3)c2O1] |
| 5-78 | 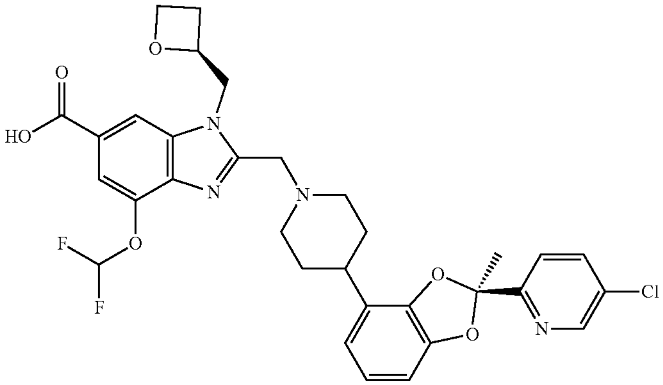 [SMILES: C[C@]1(c2ccc(Cl)cn2)Oc2cccc(C3CCN(Cc4nc5c(OC(F)F)cc(C(=O)O)cc5n4C[C@@H]4CCO4)CC3)c2O1] |
| 5-79 | 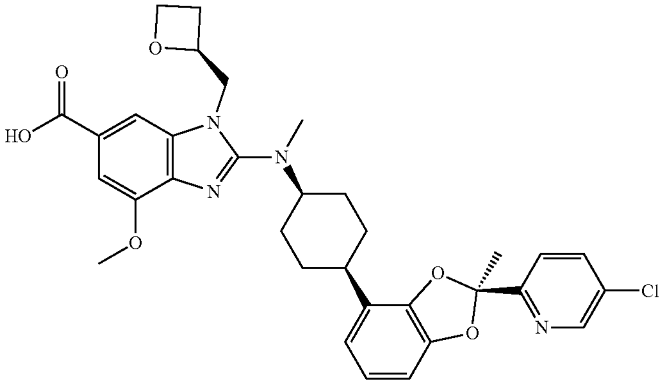 [SMILES: COc1cc(C(=O)O)cc2c1nc(N(C)[C@H]1CC[C@@H](c3cccc4c3O[C@@](C)(c3ccc(Cl)cn3)O4)CC1)n2C[C@@H]1CCO1] |
| 5-80 | 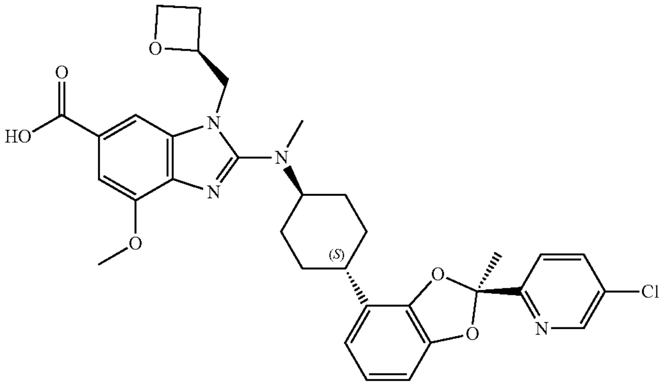 |

TABLE 5-continued
| Compound No. | Structure |
| --- | --- |
| 5-81 | 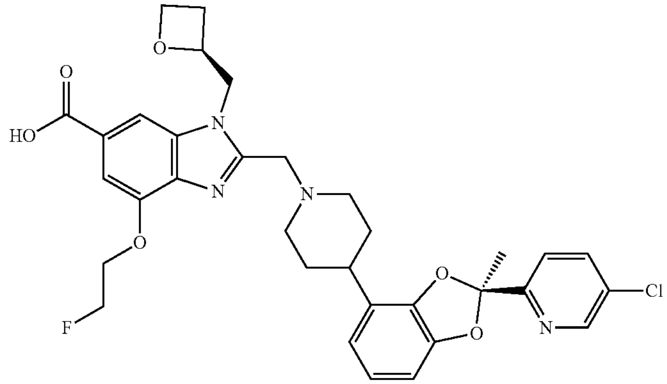 [SMILES: C[C@]1(c2ccc(Cl)cn2)Oc2cccc(C3CCN(Cc4nc5c(OCCF)cc(C(=O)O)cc5n4C[C@@H]4CCO4)CC3)c2O1] |
| 5-82 | 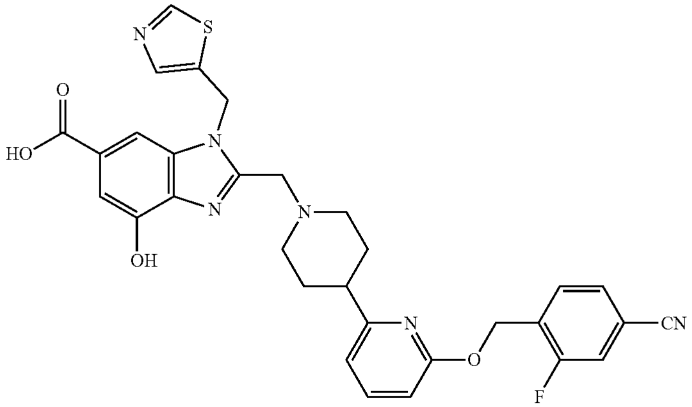 [SMILES: N#Cc1ccc(COc2cccc(C3CCN(Cc4nc5c(O)cc(C(=O)O)cc5n4Cc4cncs4)CC3)n2)c(F)c1] |
| 5-83 | 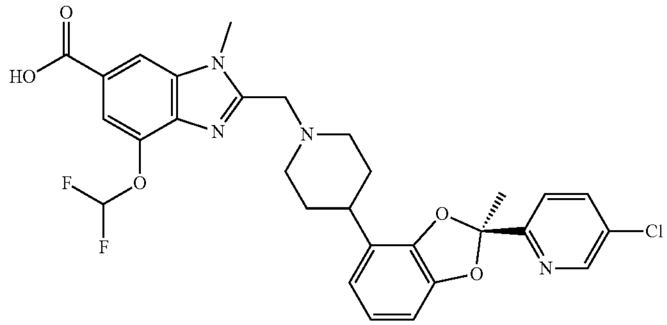 [SMILES: Cn1c(CN2CCC(c3cccc4c3O[C@@](C)(c3ccc(Cl)cn3)O4)CC2)nc2c(OC(F)F)cc(C(=O)O)cc21] |
| 5-84 | 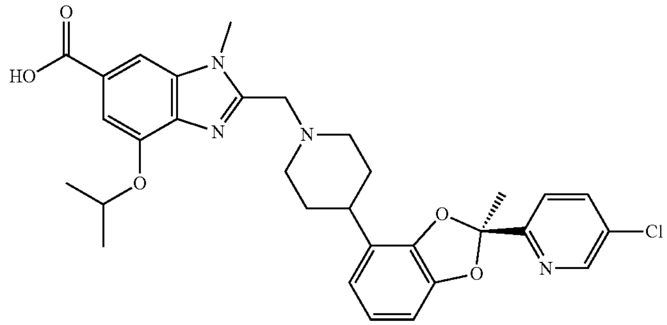 [SMILES: CC(C)Oc1cc(C(=O)O)cc2c1nc(CN1CCC(c3cccc4c3O[C@@](C)(c3ccc(Cl)cn3)O4)CC1)n2C] |

TABLE 5-continued
| Compound No. | Structure |
|---|---|
| 5-85 | 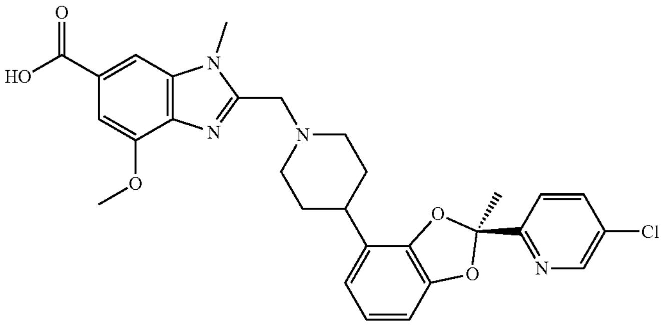 [SMILES: COc1cc(C(=O)O)cc2c1nc(CN1CCC(c3cccc4c3O[C@@](C)(c3ccc(Cl)cn3)O4)CC1)n2C] |
| 5-86 | 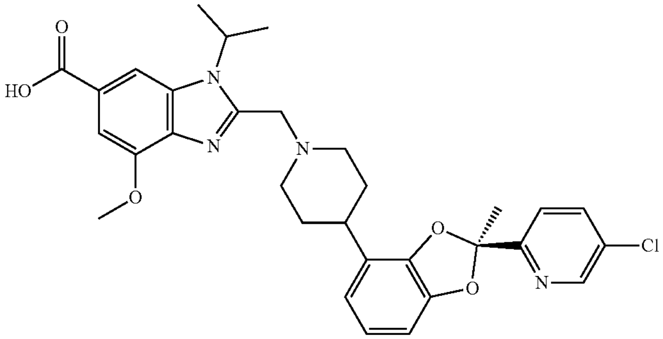 [SMILES: COc1cc(C(=O)O)cc2c1nc(CN1CCC(c3cccc4c3O[C@@](C)(c3ccc(Cl)cn3)O4)CC1)n2C(C)C] |
| 5-87 | 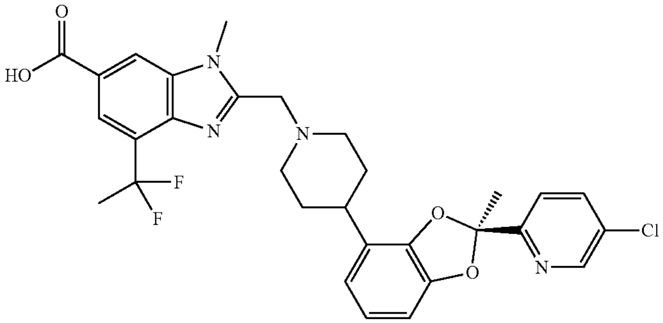 [SMILES: Cn1c(CN2CCC(c3cccc4c3O[C@@](C)(c3ccc(Cl)cn3)O4)CC2)nc2c(C(C)(F)F)cc(C(=O)O)cc21] |
| 5-88 | 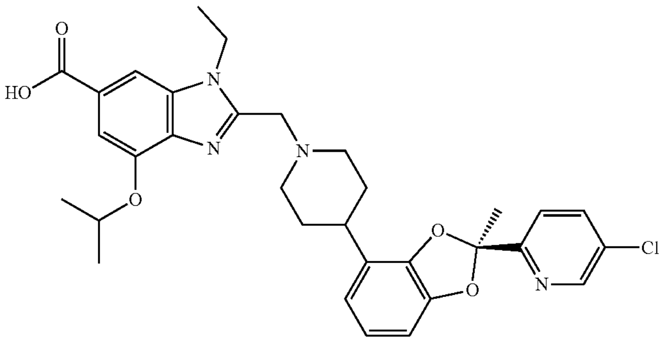 [SMILES: CCn1c(CN2CCC(c3cccc4c3O[C@@](C)(c3ccc(Cl)cn3)O4)CC2)nc2c(OC(C)C)cc(C(=O)O)cc21] |

TABLE 5-continued
| Compound No. | Structure |
| --- | --- |
| 5-89 | 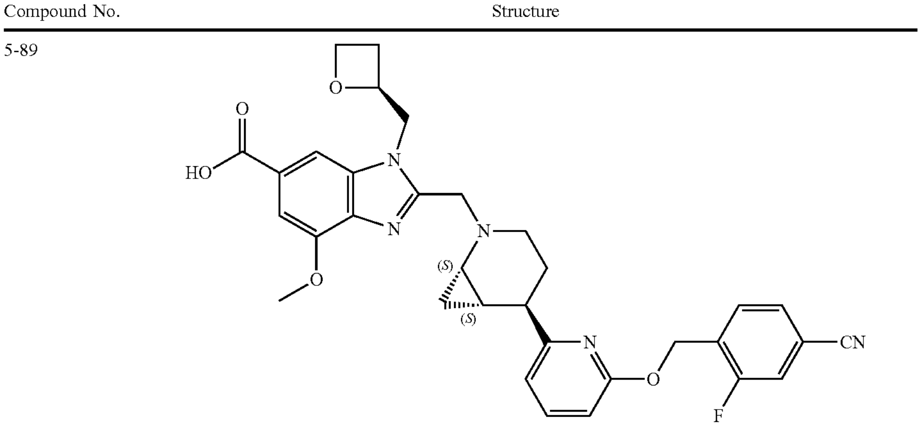 |
| 5-90 | 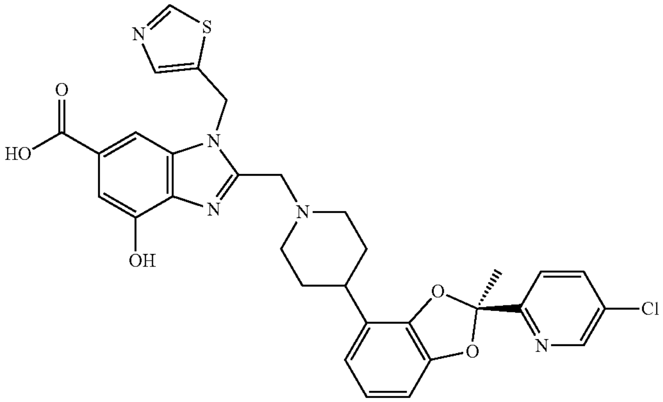 [SMILES: C[C@]1(c2ccc(Cl)cn2)Oc2cccc(C3CCN(Cc4nc5c(O)cc(C(=O)O)cc5n4Cc4cncs4)CC3)c2O1] |
| 5-91 | 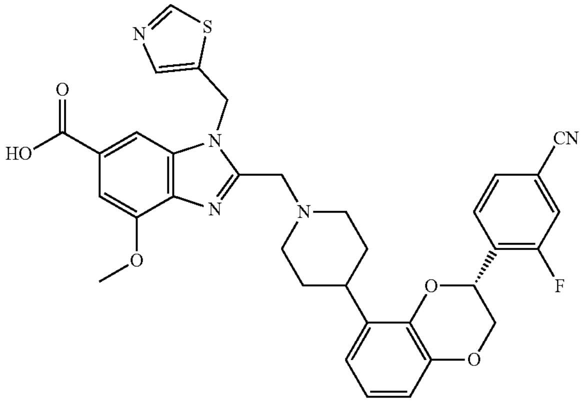 [SMILES: COc1cc(C(=O)O)cc2c1nc(CN1CCC(c3cccc4c3O[C@H](c3ccc(C#N)cc3F)CO4)CC1)n2Cc1cncs1] |
| 5-92 | 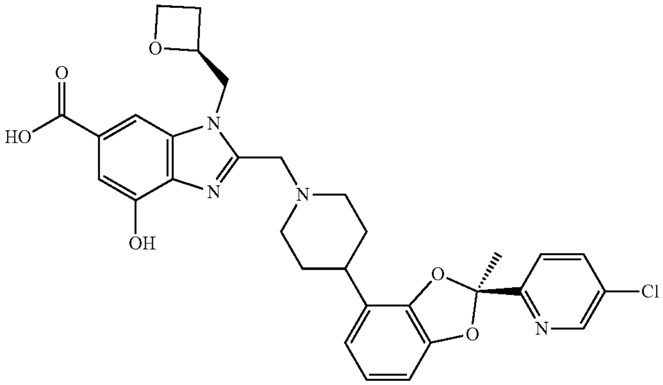 [SMILES: C[C@]1(c2ccc(Cl)cn2)Oc2cccc(C3CCN(Cc4nc5c(O)cc(C(=O)O)cc5n4C[C@@H]4CCO4)CC3)c2O1] |

TABLE 5-continued
| Compound No. | Structure |
|---|---|
| 5-93 | 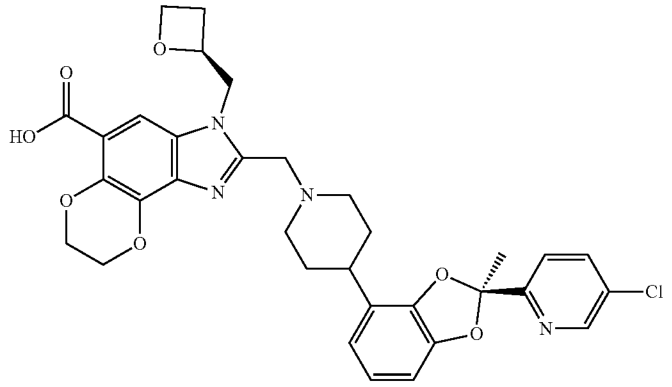 [SMILES: C[C@]1(c2ccc(Cl)cn2)Oc2cccc(C3CCN(Cc4nc5c6c(c(C(=O)O)cc5n4C[C@@H]4CCO4)OCCO6)CC3)c2O1] |
| 5-94 | 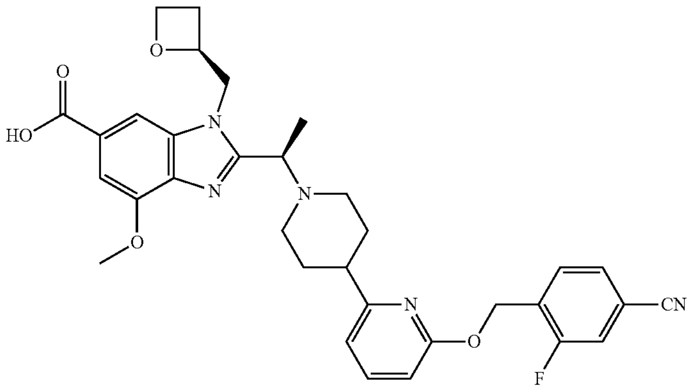 [SMILES: COc1cc(C(=O)O)cc2c1nc([C@@H](C)N1CCC(c3cccc(OCc4ccc(C#N)cc4F)n3)CC1)n2C[C@@H]1CCO1] |
| 5-95 | 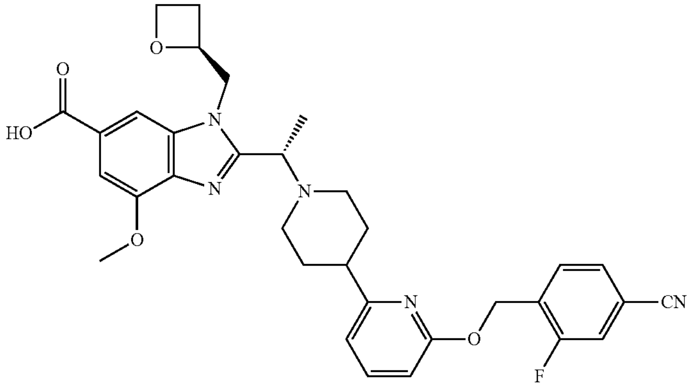 [SMILES: COc1cc(C(=O)O)cc2c1nc([C@H](C)N1CCC(c3cccc(OCc4ccc(C#N)cc4F)n3)CC1)n2C[C@@H]1CCO1] |
| 5-96 | 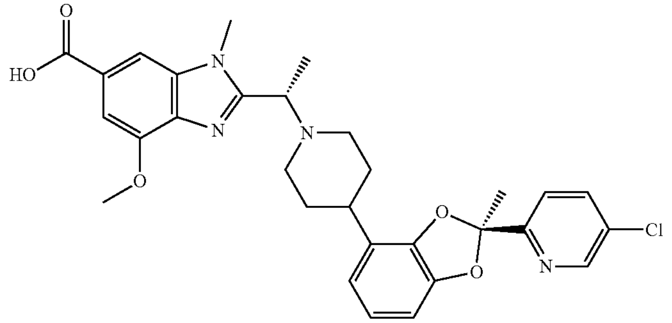 [SMILES: COc1cc(C(=O)O)cc2c1nc([C@H](C)N1CCC(c3cccc4c3O[C@@](C)(c3ccc(Cl)cn3)O4)CC1)n2C] |

TABLE 5-continued
| Compound No. | Structure |
|---|---|
| 5-97 | 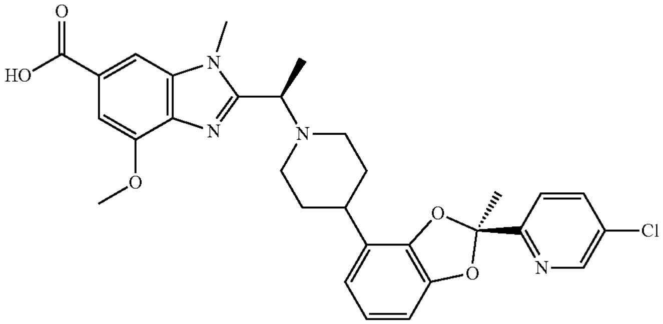 [SMILES: COc1cc(C(=O)O)cc2c1nc([C@@H](C)N1CCC(c3cccc4c3O[C@@](C)(c3ccc(Cl)cn3)O4)CC1)n2C] |
| 5-98 | 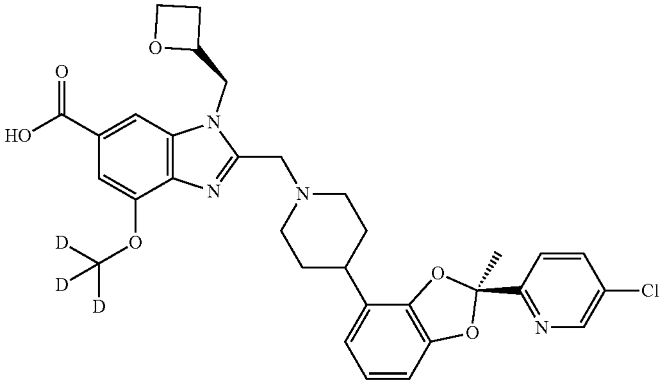 |
| 5-99 | 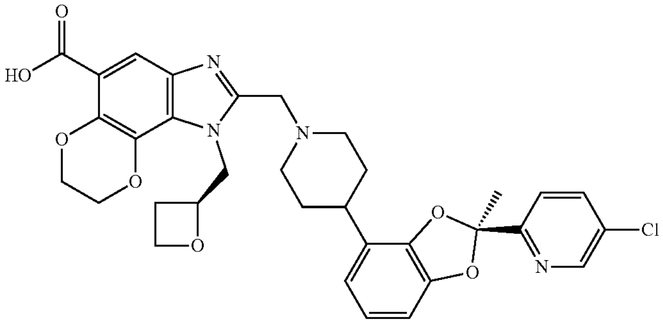 [SMILES: C[C@]1(c2ccc(Cl)cn2)Oc2cccc(C3CCN(Cc4nc5cc(C(=O)O)c6c(c5n4C[C@@H]4CCO4)OCCO6)CC3)c2O1] |
| 5-100 | 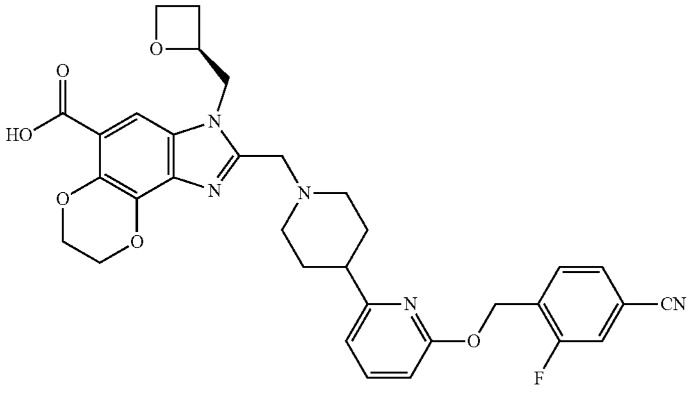 [SMILES: N#Cc1ccc(COc2cccc(C3CCN(Cc4nc5c6c(c(C(=O)O)cc5n4C[C@@H]4CCO4)OCCO6)CC3)n2)c(F)c1] |

TABLE 5-continued
| Compound No. | Structure |
| --- | --- |
| 5-101 | 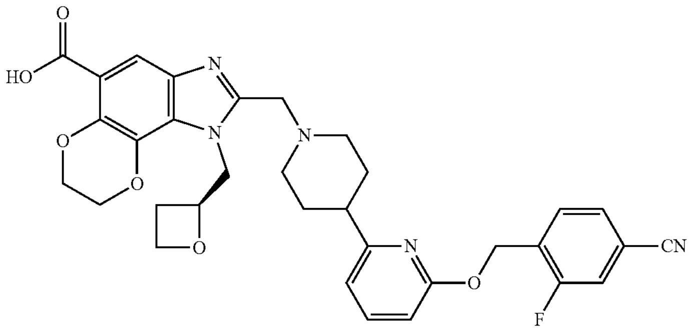 [SMILES: N#Cc1ccc(COc2cccc(C3CCN(Cc4nc5cc(C(=O)O)c6c(c5n4C[C@@H]4CCO4)OCCO6)CC3)n2)c(F)c1] |
| 5-102 | 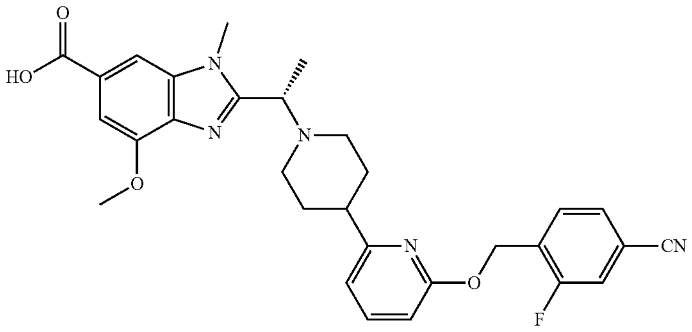 |
| 5-103 | 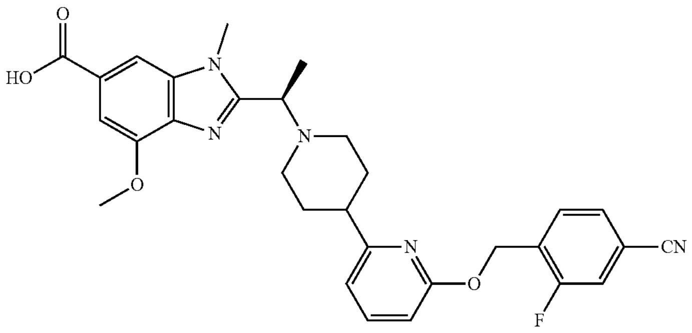 [SMILES: COc1cc(C(=O)O)cc2c1nc([C@@H](C)N1CCC(c3cccc(OCc4ccc(C#N)cc4F)n3)CC1)n2C] |
| 5-104 | 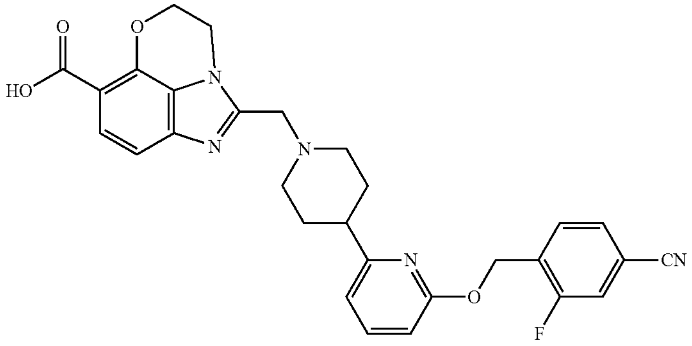 [SMILES: N#Cc1ccc(COc2cccc(C3CCN(Cc4nc5ccc(C(=O)O)c6c5n4CCO6)CC3)n2)c(F)c1] |

TABLE 5-continued
| Compound No. | Structure |
| --- | --- |
| 5-105 | 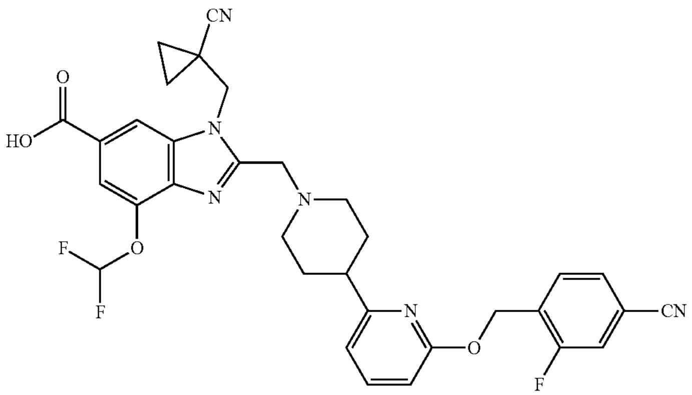 [SMILES: N#Cc1ccc(COc2cccc(C3CCN(Cc4nc5c(OC(F)F)cc(C(=O)O)cc5n4CC4(C#N)CC4)CC3)n2)c(F)c1] |
| 5-106 | 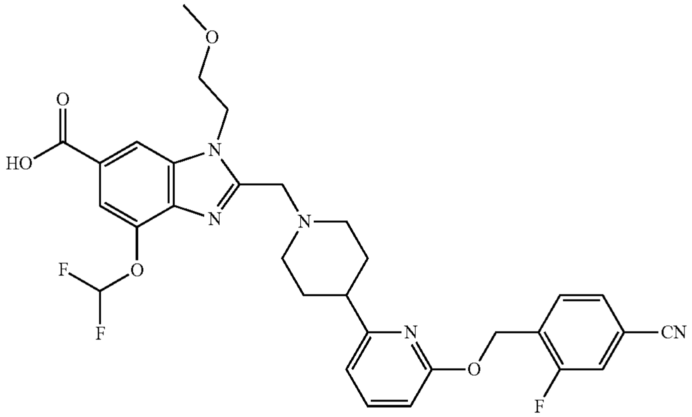 [SMILES: COCCn1c(CN2CCC(c3cccc(OCc4ccc(C#N)cc4F)n3)CC2)nc2c(OC(F)F)cc(C(=O)O)cc21] |
| 5-107 | 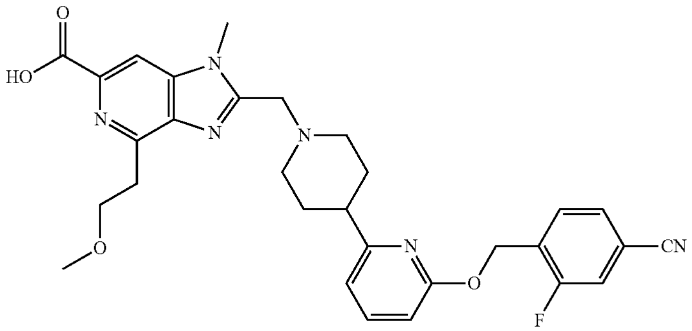 |
| 5-108 | 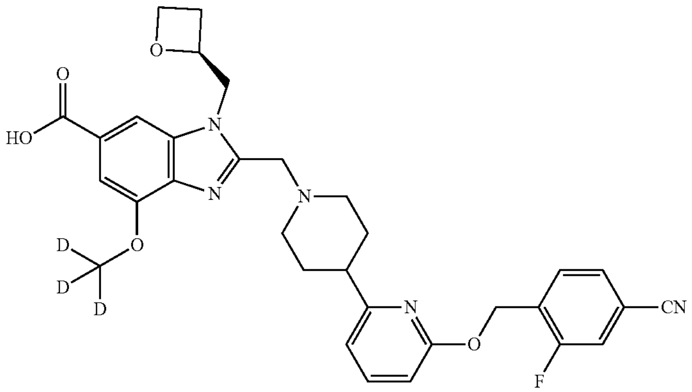 [SMILES: [2H]C([2H])([2H])Oc1cc(C(=O)O)cc2c1nc(CN1CCC(c3cccc(OCc4ccc(C#N)cc4F)n3)CC1)n2C[C@@H]1CCO1] |

TABLE 5-continued
| Compound No. | Structure |
| --- | --- |
| 5-109 | 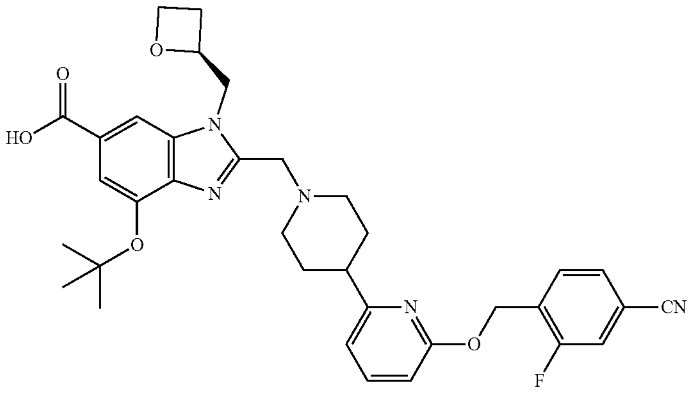 [SMILES: CC(C)(C)Oc1cc(C(=O)O)cc2c1nc(CN1CCC(c3cccc(OCc4ccc(C#N)cc4F)n3)CC1)n2C[C@@H]1CCO1] |
| 5-110 | 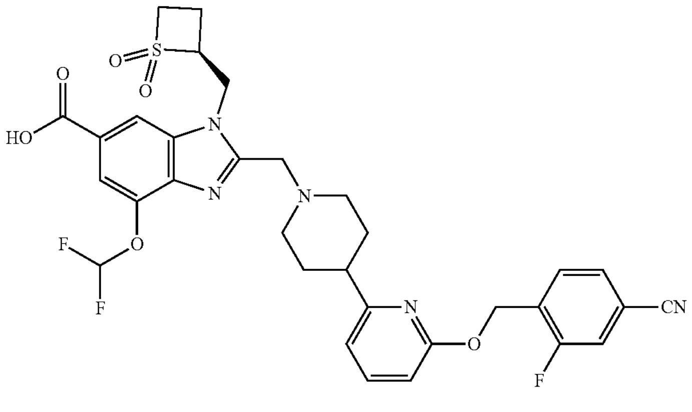 [SMILES: N#Cc1ccc(COc2cccc(C3CCN(Cc4nc5c(OC(F)F)cc(C(=O)O)cc5n4C[C@@H]4CCS4(=O)=O)CC3)n2)c(F)c1] |
| 5-111 | 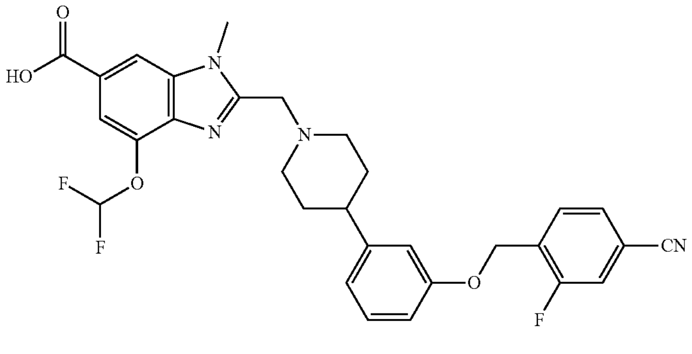 [SMILES: Cn1c(CN2CCC(c3cccc(OCc4ccc(C#N)cc4F)c3)CC2)nc2c(OC(F)F)cc(C(=O)O)cc21] |
| 5-112 | 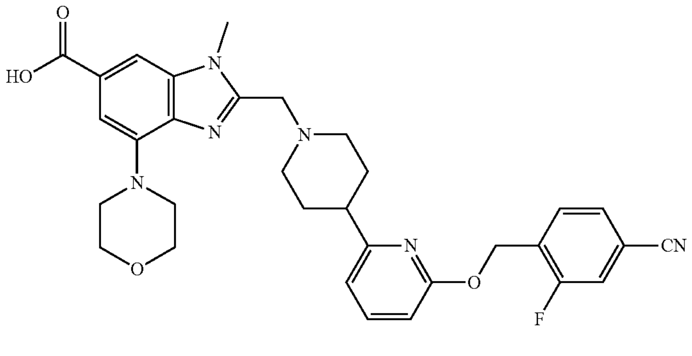 [SMILES: Cn1c(CN2CCC(c3cccc(OCc4ccc(C#N)cc4F)n3)CC2)nc2c(N3CCOCC3)cc(C(=O)O)cc21] |

TABLE 5-continued
| Compound No. | Structure |
| --- | --- |
| 5-113 | 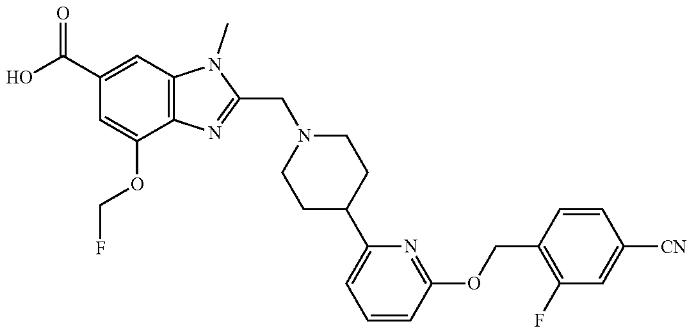 [SMILES: Cn1c(CN2CCC(c3cccc(OCc4ccc(C#N)cc4F)n3)CC2)nc2c(OCF)cc(C(=O)O)cc21] |
| 5-114 | 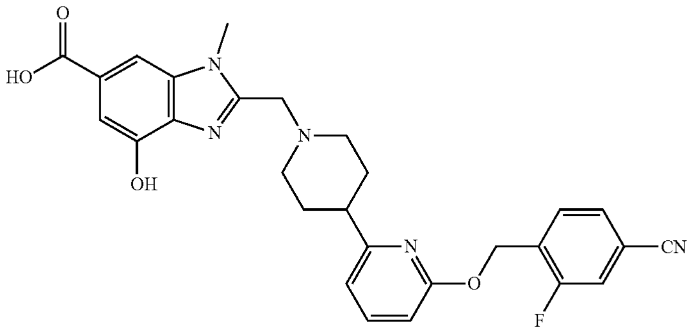 [SMILES: Cn1c(CN2CCC(c3cccc(OCc4ccc(C#N)cc4F)n3)CC2)nc2c(O)cc(C(=O)O)cc21] |
| 5-115 | 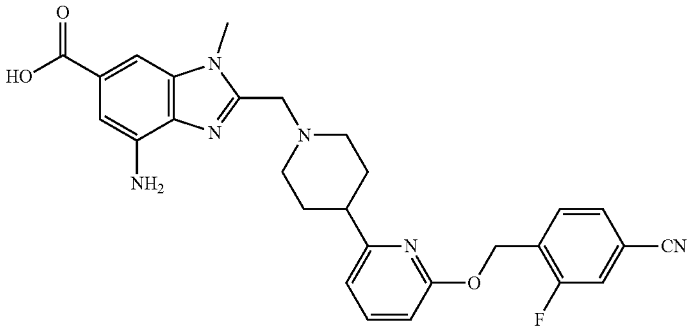 |
| 5-116 | 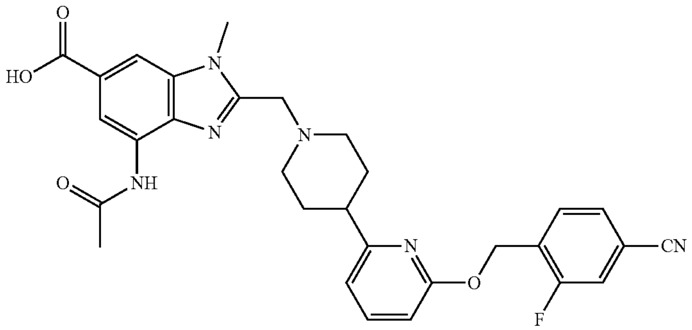 [SMILES: CC(=O)Nc1cc(C(=O)O)cc2c1nc(CN1CCC(c3cccc(OCc4ccc(C#N)cc4F)n3)CC1)n2C] |

TABLE 5-continued
| Compound No. | Structure |
| --- | --- |
| 5-117 | 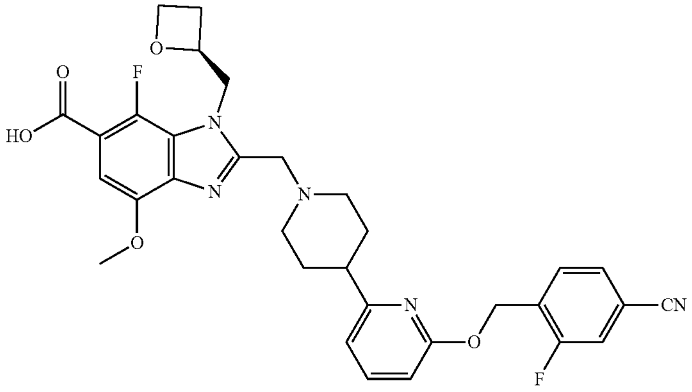 [SMILES: COc1cc(C(=O)O)c(F)c2c1nc(CN1CCC(c3cccc(OCc4ccc(C#N)cc4F)n3)CC1)n2C[C@@H]1CCO1] |
| 5-118 | 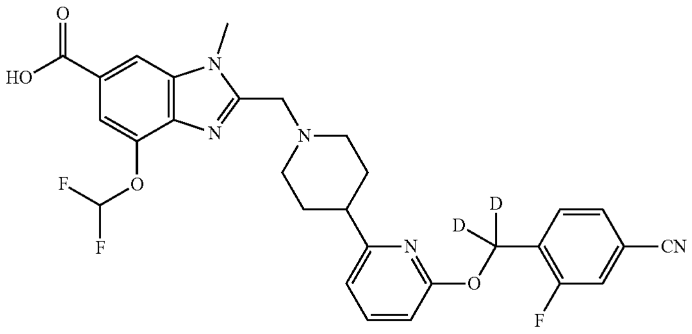 [SMILES: [2H]C([2H])(Oc1cccc(C2CCN(Cc3nc4c(OC(F)F)cc(C(=O)O)cc4n3C)CC2)n1)c1ccc(C#N)cc1F] |
| 5-119 | 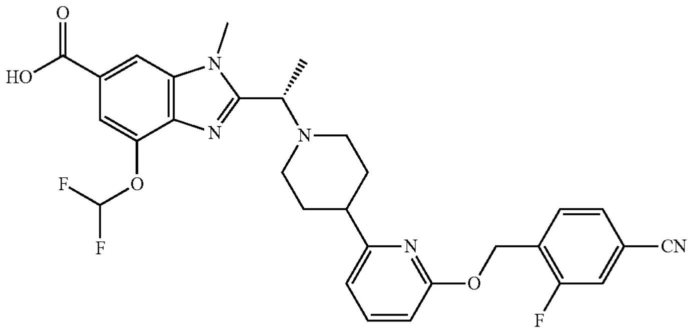 [SMILES: C[C@@H](c1nc2c(OC(F)F)cc(C(=O)O)cc2n1C)N1CCC(c2cccc(OCc3ccc(C#N)cc3F)n2)CC1] |
| 5-120 | 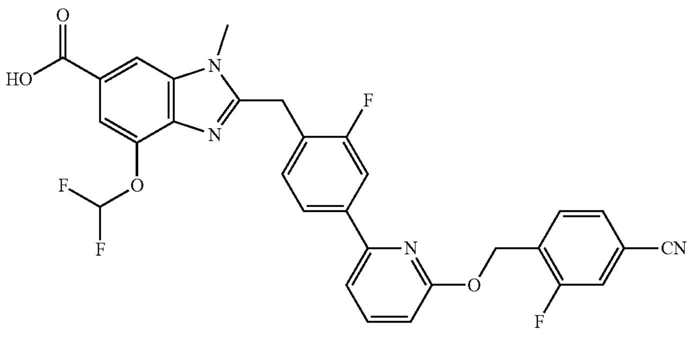 [SMILES: Cn1c(Cc2ccc(-c3cccc(OCc4ccc(C#N)cc4F)n3)cc2F)nc2c(OC(F)F)cc(C(=O)O)cc21] |

TABLE 5-continued
| Compound No. | Structure |
|---|---|
| 5-121 | 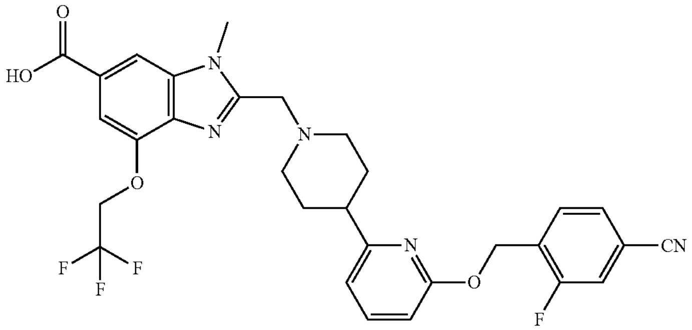 [SMILES: Cn1c(CN2CCC(c3cccc(OCc4ccc(C#N)cc4F)n3)CC2)nc2c(OCC(F)(F)F)cc(C(=O)O)cc21] |
| 5-122 | 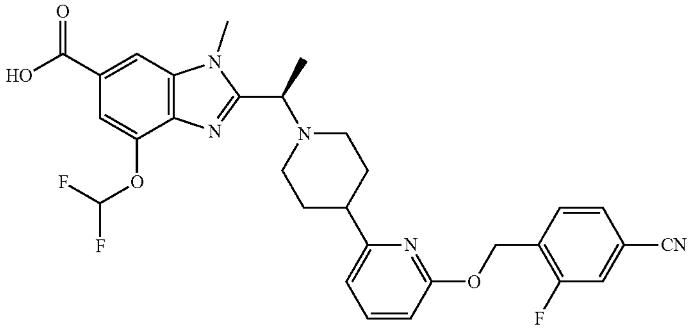 [SMILES: C[C@H](c1nc2c(OC(F)F)cc(C(=O)O)cc2n1C)N1CCC(c2cccc(OCc3ccc(C#N)cc3F)n2)CC1] |
| 5-123 | 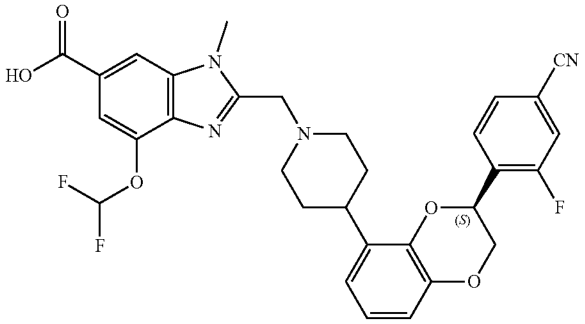 |
| 5-124 | 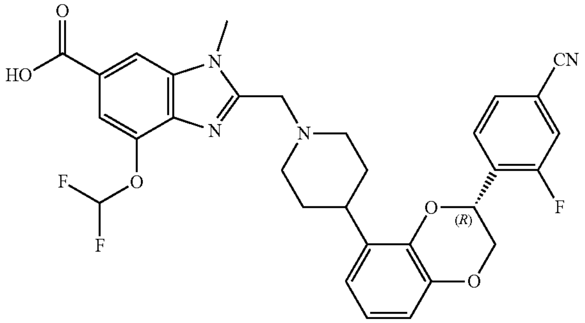 |

TABLE 5-continued
| Compound No. | Structure |
| --- | --- |
| 5-125 | 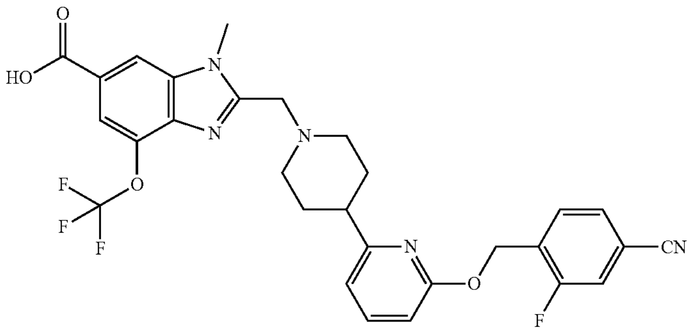 [SMILES: Cn1c(CN2CCC(c3cccc(OCc4ccc(C#N)cc4F)n3)CC2)nc2c(OC(F)(F)F)cc(C(=O)O)cc21] |
| 5-126 | 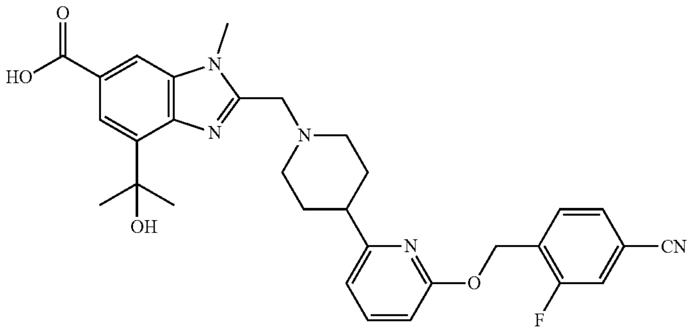 [SMILES: Cn1c(CN2CCC(c3cccc(OCc4ccc(C#N)cc4F)n3)CC2)nc2c(C(C)(C)O)cc(C(=O)O)cc21] |
| 5-127 | 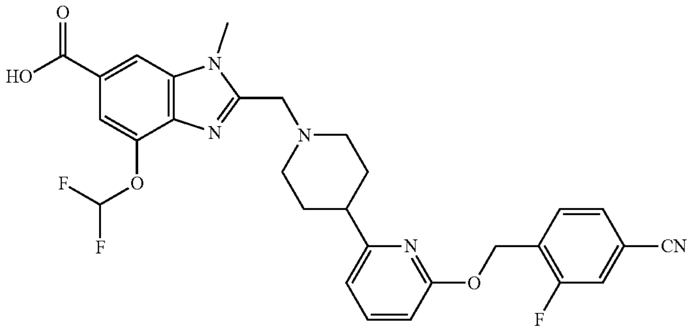 [SMILES: Cn1c(CN2CCC(c3cccc(OCc4ccc(C#N)cc4F)n3)CC2)nc2c(OC(F)F)cc(C(=O)O)cc21] |
| 5-128 | 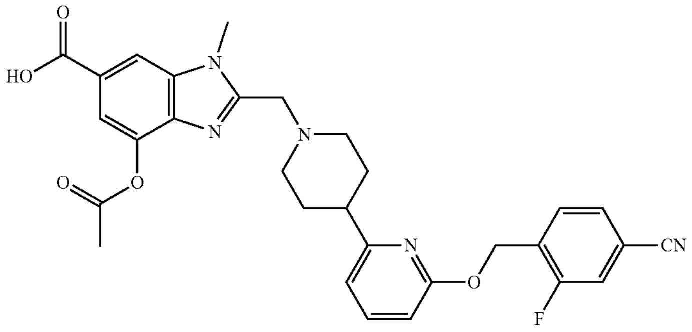 [SMILES: CC(=O)Oc1cc(C(=O)O)cc2c1nc(CN1CCC(c3cccc(OCc4ccc(C#N)cc4F)n3)CC1)n2C] |

TABLE 5-continued
| Compound No. | Structure |
|---|---|
| 5-129 | 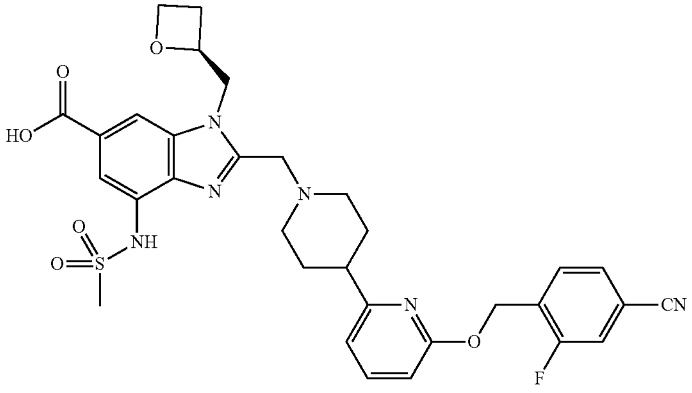 [SMILES: CS(=O)(=O)Nc1cc(C(=O)O)cc2c1nc(CN1CCC(c3cccc(OCc4ccc(C#N)cc4F)n3)CC1)n2C[C@@H]1CCO1] |
| 5-130 | 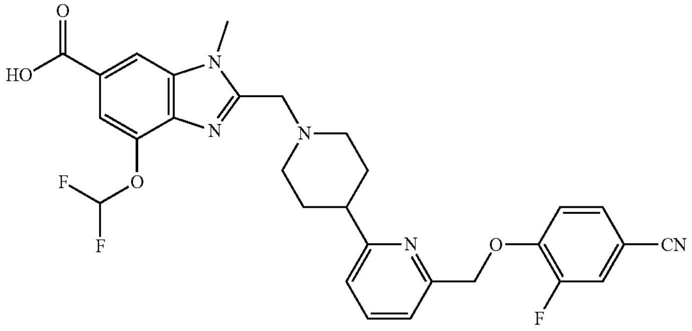 |
| 5-131 | 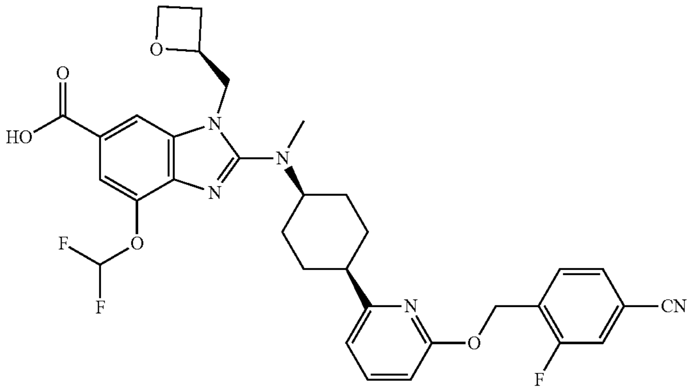 [SMILES: CN(c1nc2c(OC(F)F)cc(C(=O)O)cc2n1C[C@@H]1CCO1)[C@H]1CC[C@@H](c2cccc(OCc3ccc(C#N)cc3F)n2)CC1] |
| 5-132 | 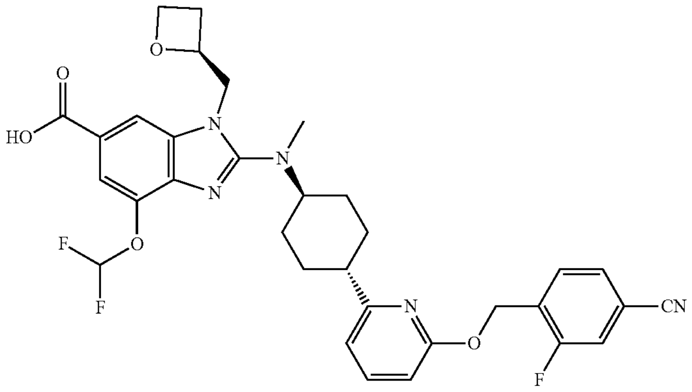 [SMILES: CN(c1nc2c(OC(F)F)cc(C(=O)O)cc2n1C[C@@H]1CCO1)[C@H]1CC[C@H](c2cccc(OCc3ccc(C#N)cc3F)n2)CC1] |

TABLE 5-continued
| Compound No. | Structure |
| --- | --- |
| 5-133 | 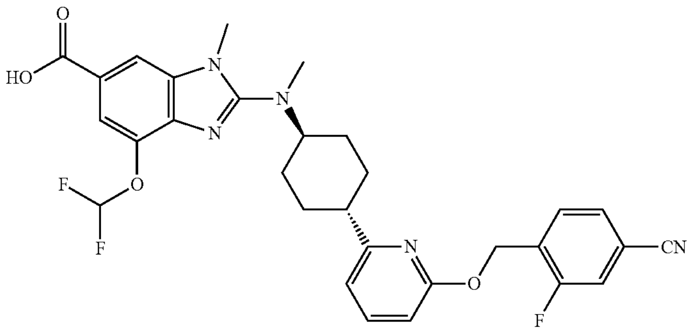 [SMILES: Cn1c(N(C)[C@H]2CC[C@H](c3cccc(OCc4ccc(C#N)cc4F)n3)CC2)nc2c(OC(F)F)cc(C(=O)O)cc21] |
| 5-134 | 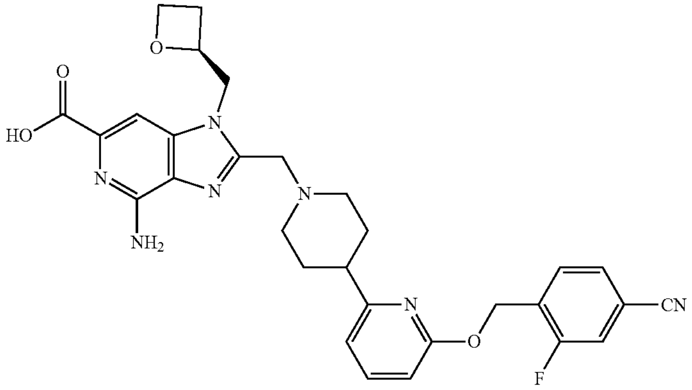 [SMILES: N#Cc1ccc(COc2cccc(C3CCN(Cc4nc5c(N)nc(C(=O)O)cc5n4C[C@@H]4CCO4)CC3)n2)c(F)c1] |
| 5-135 | 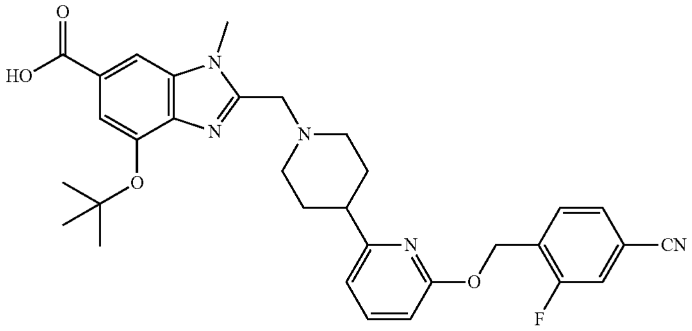 [SMILES: Cn1c(CN2CCC(c3cccc(OCc4ccc(C#N)cc4F)n3)CC2)nc2c(OC(C)(C)C)cc(C(=O)O)cc21] |
| 5-136 | 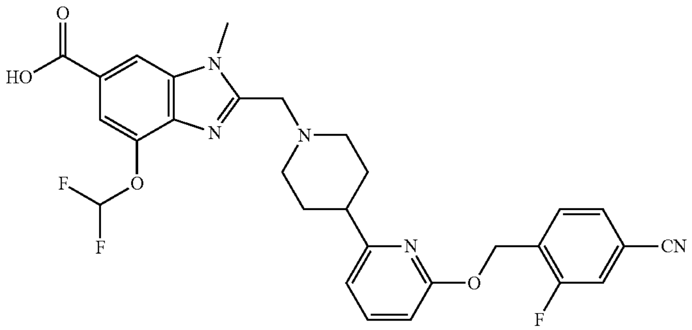 [SMILES: Cn1c(CN2CCC(c3cccc(OCc4ccc(C#N)cc4F)n3)CC2)nc2c(OC(F)F)cc(C(=O)O)cc21] |

TABLE 5-continued
| Compound No. | Structure |
|---|---|
| 5-137 | 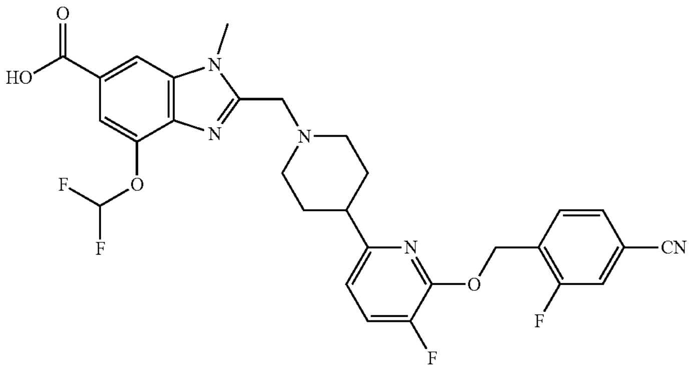 [SMILES: Cn1c(CN2CCC(c3ccc(F)c(OCc4ccc(C#N)cc4F)n3)CC2)nc2c(OC(F)F)cc(C(=O)O)cc21] |
| 5-138 | 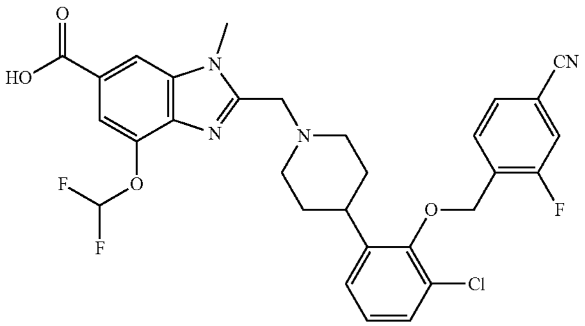 [SMILES: Cn1c(CN2CCC(c3cccc(Cl)c3OCc3ccc(C#N)cc3F)CC2)nc2c(OC(F)F)cc(C(=O)O)cc21] |
| 5-139 | 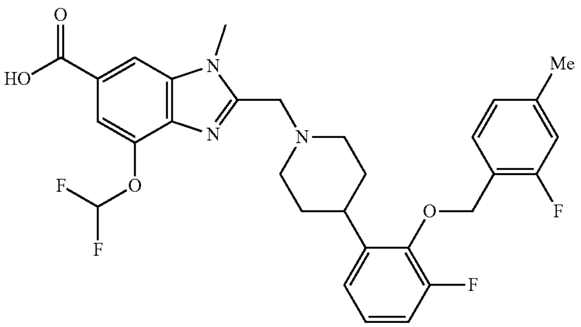 [SMILES: Cc1ccc(COc2c(F)cccc2C2CCN(Cc3nc4c(OC(F)F)cc(C(=O)O)cc4n3C)CC2)c(F)c1] |
| 5-140 | 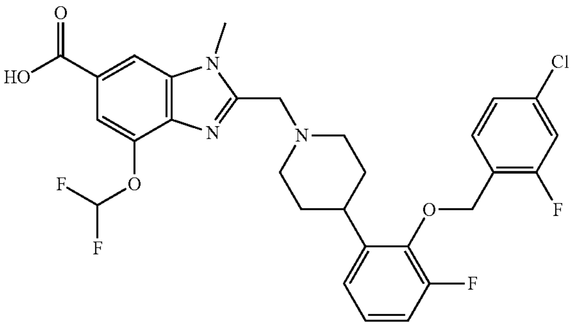 [SMILES: Cn1c(CN2CCC(c3cccc(F)c3OCc3ccc(Cl)cc3F)CC2)nc2c(OC(F)F)cc(C(=O)O)cc21] |

TABLE 5-continued
| Compound No. | Structure |
|---|---|
| 5-141 | 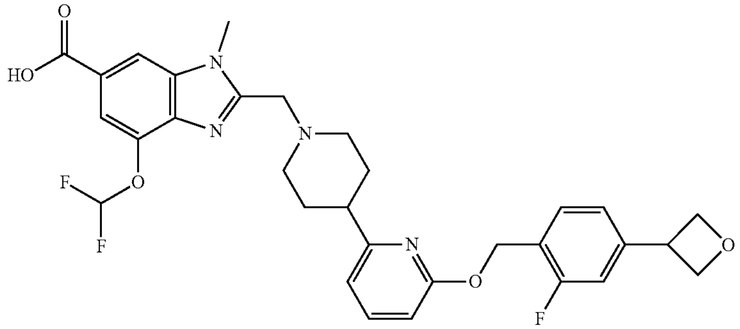 [SMILES: Cn1c(CN2CCC(c3cccc(OCc4ccc(C5COC5)cc4F)n3)CC2)nc2c(OC(F)F)cc(C(=O)O)cc21] |
| 5-142 | 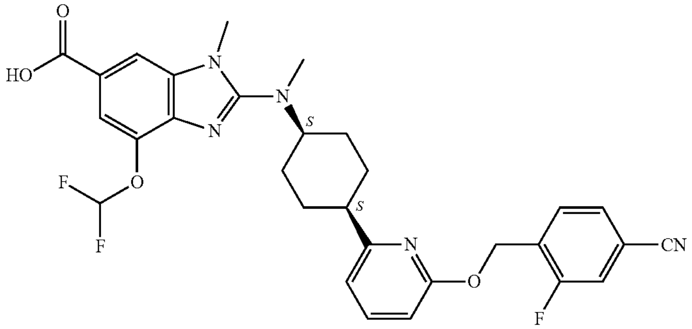 |
| 5-143 | 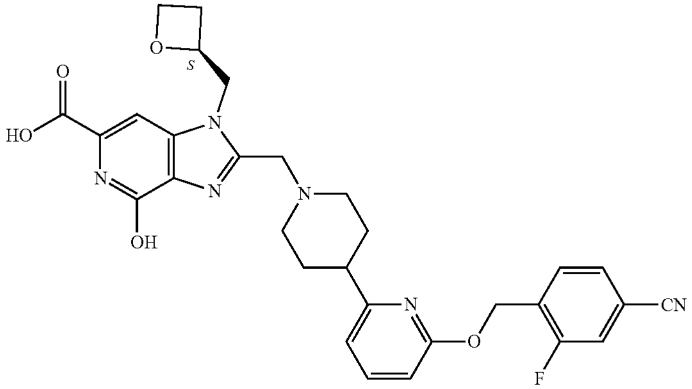 |
| 5-144 | 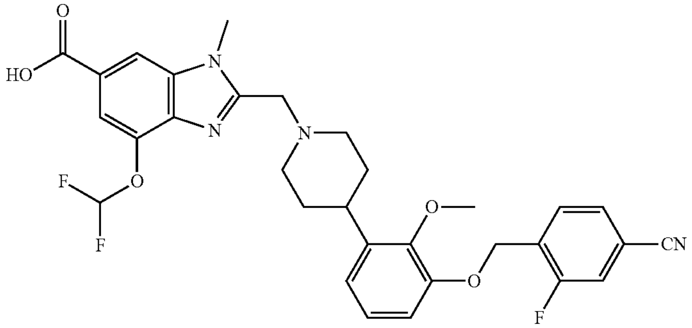 [SMILES: COc1c(OCc2ccc(C#N)cc2F)cccc1C1CCN(Cc2nc3c(OC(F)F)cc(C(=O)O)cc3n2C)CC1] |

TABLE 5-continued
| Compound No. | Structure |
|---|---|
| 5-145 | 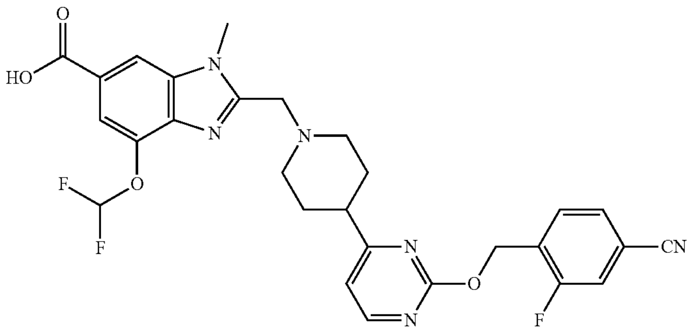 [SMILES: Cn1c(CN2CCC(c3ccnc(OCc4ccc(C#N)cc4F)n3)CC2)nc2c(OC(F)F)cc(C(=O)O)cc21] |
| 5-146 | 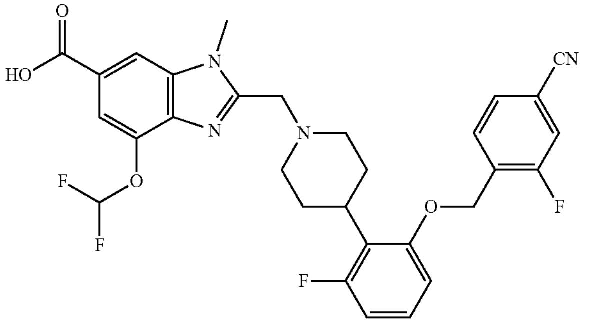 [SMILES: Cn1c(CN2CCC(c3c(F)cccc3OCc3ccc(C#N)cc3F)CC2)nc2c(OC(F)F)cc(C(=O)O)cc21] |
| 5-147 | 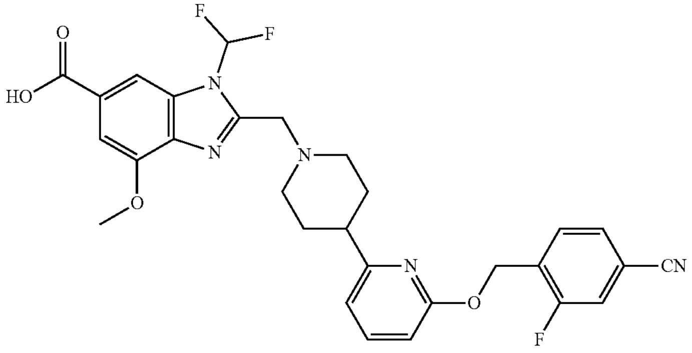 [SMILES: COc1cc(C(=O)O)cc2c1nc(CN1CCC(c3cccc(OCc4ccc(C#N)cc4F)n3)CC1)n2C(F)F] |
| 5-148 | 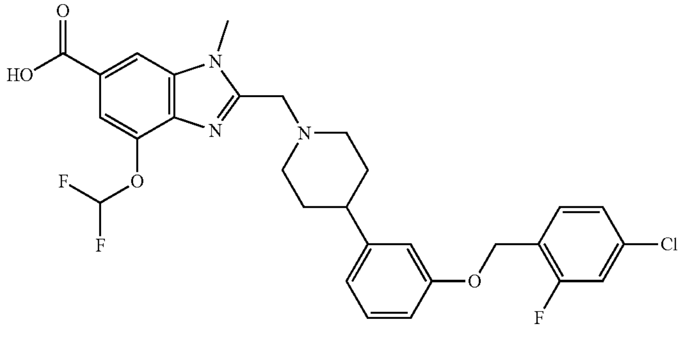 [SMILES: Cn1c(CN2CCC(c3cccc(OCc4ccc(Cl)cc4F)c3)CC2)nc2c(OC(F)F)cc(C(=O)O)cc21] |

TABLE 5-continued
| Compound No. | Structure |
| --- | --- |
| 5-149 | 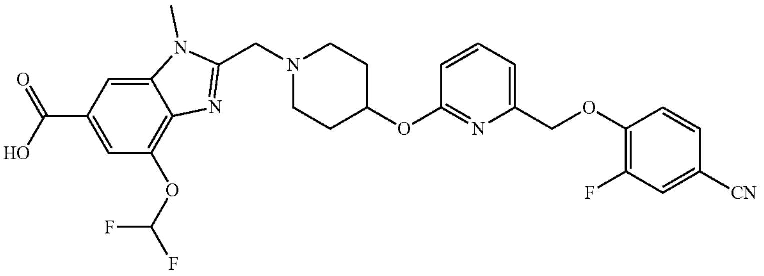 [SMILES: Cn1c(CN2CCC(Oc3cccc(COc4ccc(C#N)cc4F)n3)CC2)nc2c(OC(F)F)cc(C(=O)O)cc21] |
| 5-150 | 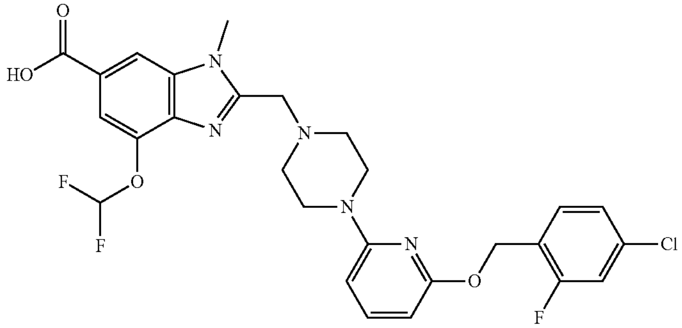 [SMILES: Cn1c(CN2CCN(c3cccc(OCc4ccc(Cl)cc4F)n3)CC2)nc2c(OC(F)F)cc(C(=O)O)cc21] |
| 5-151 | 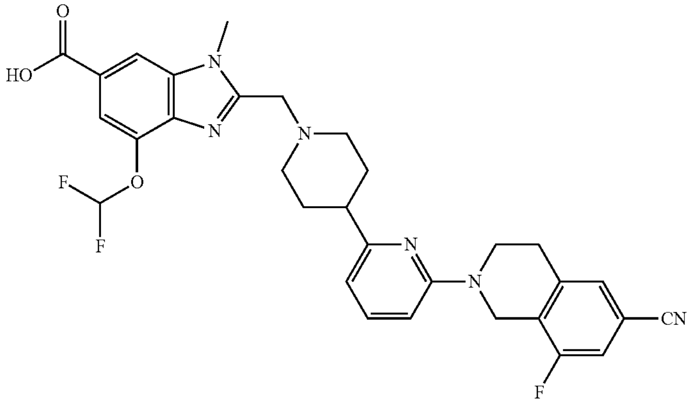 [SMILES: Cn1c(CN2CCC(c3cccc(N4CCc5cc(C#N)cc(F)c5C4)n3)CC2)nc2c(OC(F)F)cc(C(=O)O)cc21] |
| 5-152 | 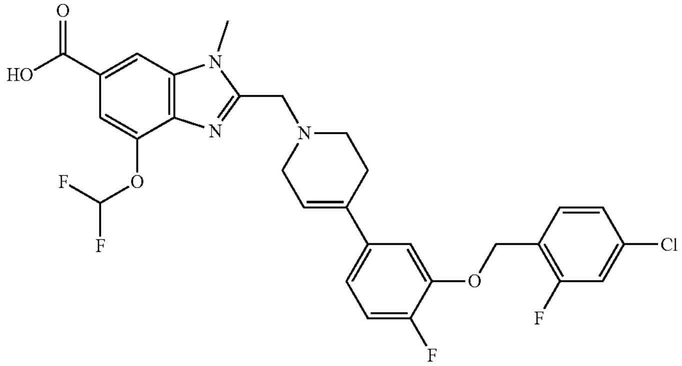 [SMILES: Cn1c(CN2CC=C(c3ccc(F)c(OCc4ccc(Cl)cc4F)c3)CC2)nc2c(OC(F)F)cc(C(=O)O)cc21] |

TABLE 5-continued
| Compound No. | Structure |
| --- | --- |
| 5-153 | 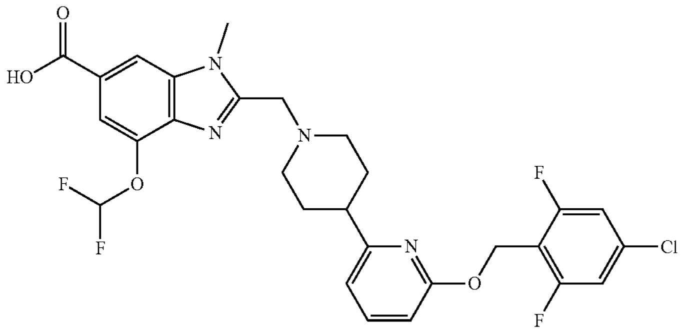 [SMILES: Cn1c(CN2CCC(c3cccc(OCc4c(F)cc(Cl)cc4F)n3)CC2)nc2c(OC(F)F)cc(C(=O)O)cc21] |
| 5-154 | 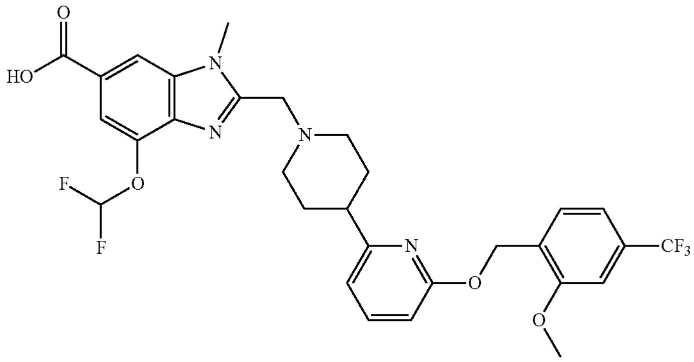 [SMILES: COc1cc(C(F)(F)F)ccc1COc1cccc(C2CCN(Cc3nc4c(OC(F)F)cc(C(=O)O)cc4n3C)CC2)n1] |
| 5-155 | 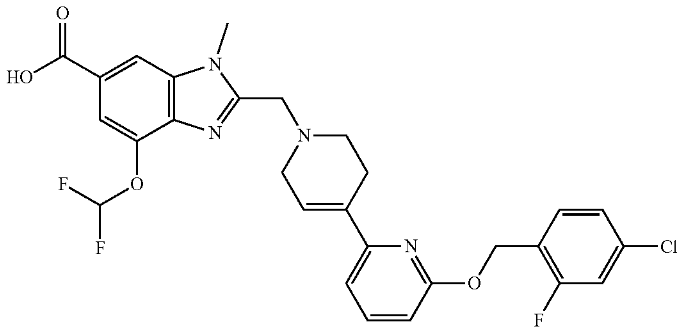 |
| 5-156 | 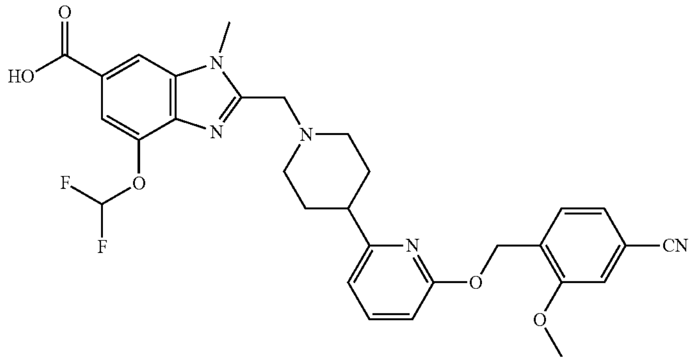 [SMILES: COc1cc(C#N)ccc1COc1cccc(C2CCN(Cc3nc4c(OC(F)F)cc(C(=O)O)cc4n3C)CC2)n1] |

TABLE 5-continued
| Compound No. | Structure |
| --- | --- |
| 5-157 | 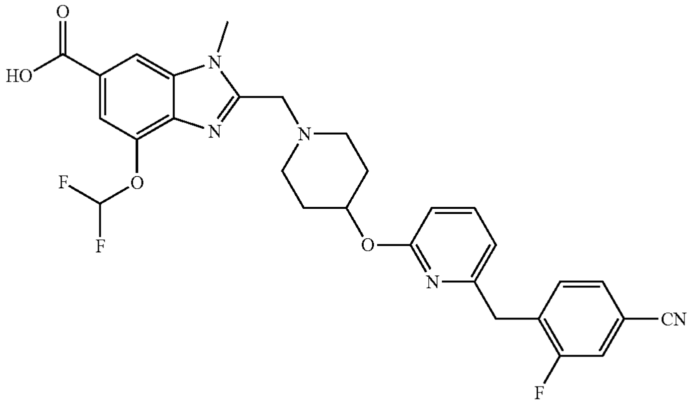 [SMILES: Cn1c(CN2CCC(Oc3cccc(Cc4ccc(C#N)cc4F)n3)CC2)nc2c(OC(F)F)cc(C(=O)O)cc21] |
| 5-158 | 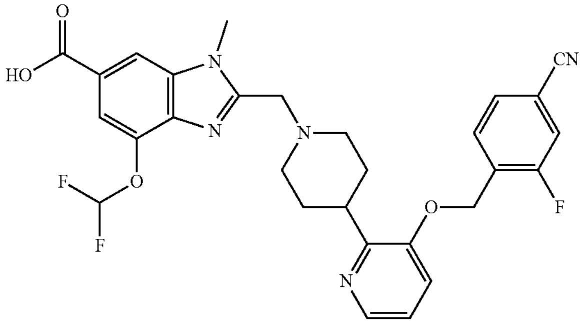 [SMILES: Cn1c(CN2CCC(c3ncccc3OCc3ccc(C#N)cc3F)CC2)nc2c(OC(F)F)cc(C(=O)O)cc21] |
| 5-159 | 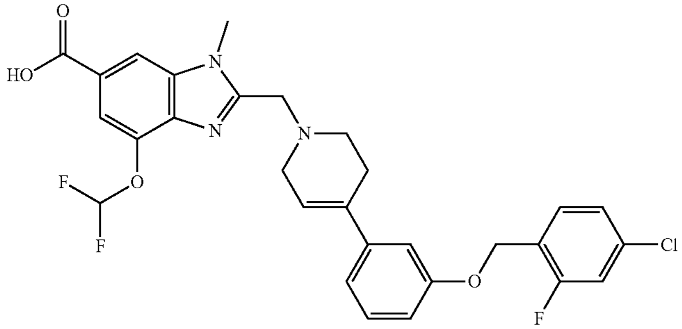 [SMILES: Cn1c(CN2CC=C(c3cccc(OCc4ccc(Cl)cc4F)c3)CC2)nc2c(OC(F)F)cc(C(=O)O)cc21] |
| 5-160 | 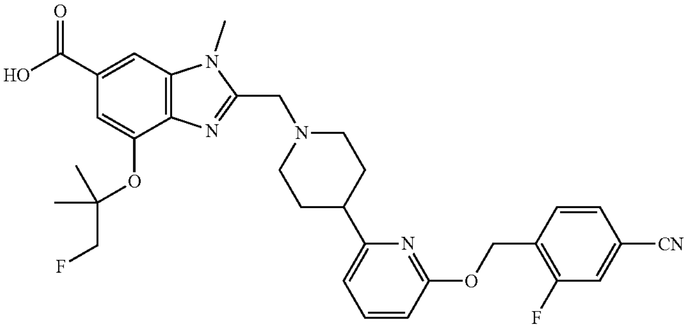 [SMILES: Cn1c(CN2CCC(c3cccc(OCc4ccc(C#N)cc4F)n3)CC2)nc2c(OC(C)(C)CF)cc(C(=O)O)cc21] |

TABLE 5-continued
| Compound No. | Structure |
| --- | --- |
| 5-161 | 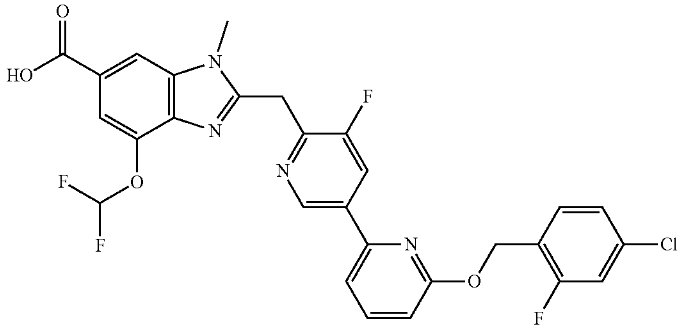 |
| 5-162 | 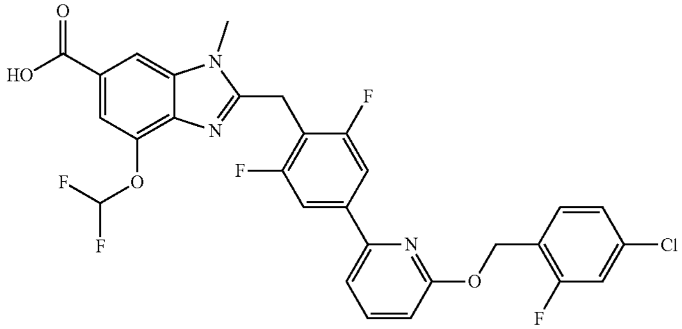 [SMILES: Cn1c(Cc2c(F)cc(-c3cccc(OCc4ccc(Cl)cc4F)n3)cc2F)nc2c(OC(F)F)cc(C(=O)O)cc21] |
| 5-163 | 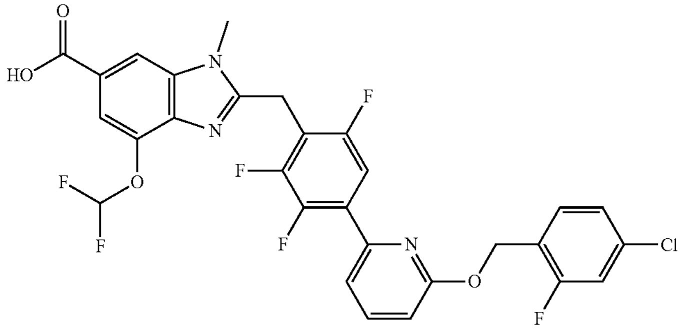 [SMILES: Cn1c(Cc2c(F)cc(-c3cccc(OCc4ccc(Cl)cc4F)n3)c(F)c2F)nc2c(OC(F)F)cc(C(=O)O)cc21] |
| 5-164 | 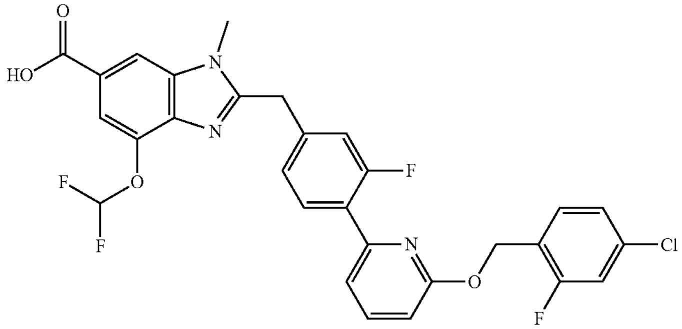 [SMILES: Cn1c(Cc2ccc(-c3cccc(OCc4ccc(Cl)cc4F)n3)c(F)c2)nc2c(OC(F)F)cc(C(=O)O)cc21] |

TABLE 5-continued
| Compound No. | Structure |
|---|---|
| 5-165 | 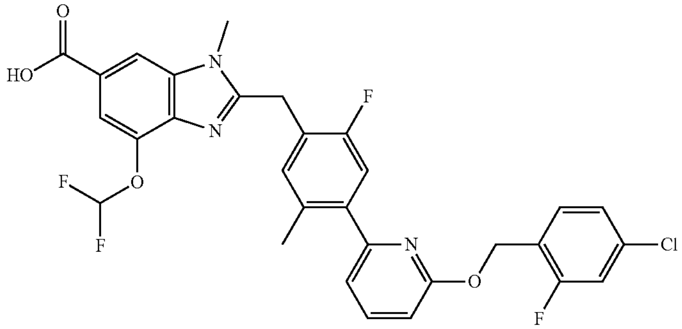 |
| 5-166 | 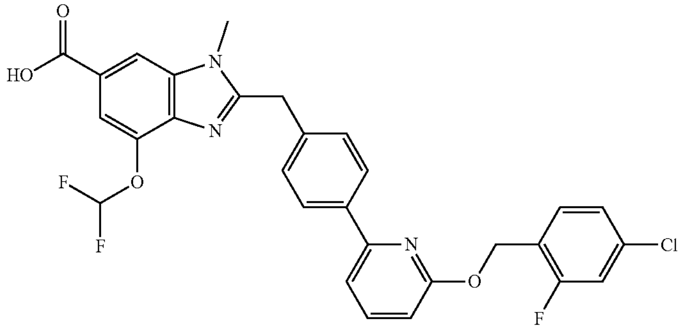 |
| 5-167 | 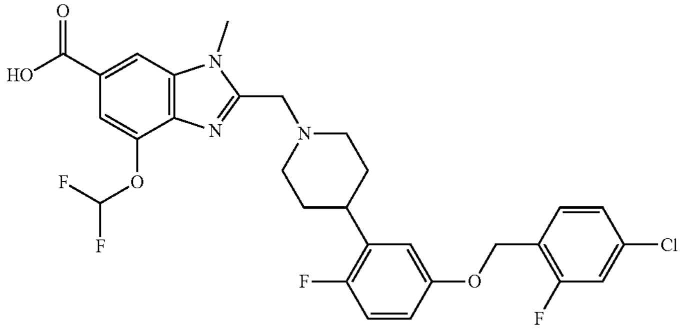 |
| 5-168 | 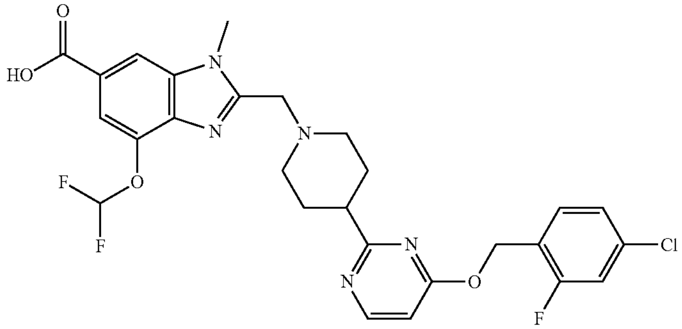 |

TABLE 5-continued
| Compound No. | Structure |
| --- | --- |
| 5-169 | 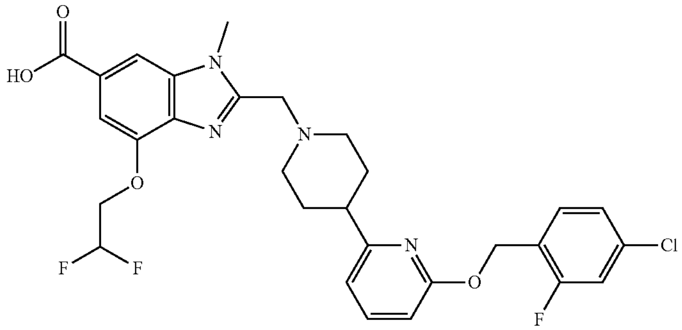 |
| 5-170 | 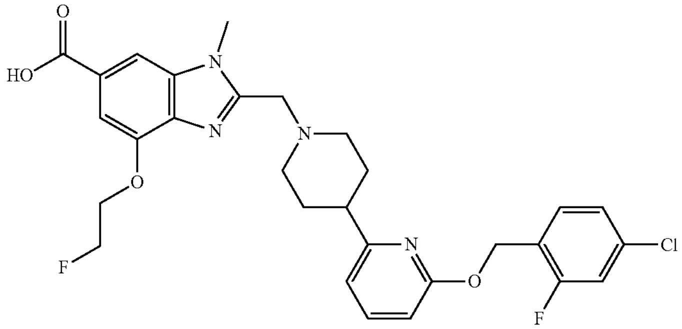 |
| 5-171 | 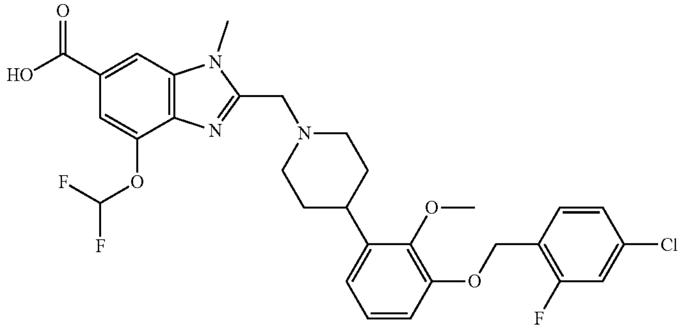 [SMILES: COc1c(OCc2ccc(Cl)cc2F)cccc1C1CCN(Cc2nc3c(OC(F)F)cc(C(=O)O)cc3n2C)CC1] |
| 5-172 | 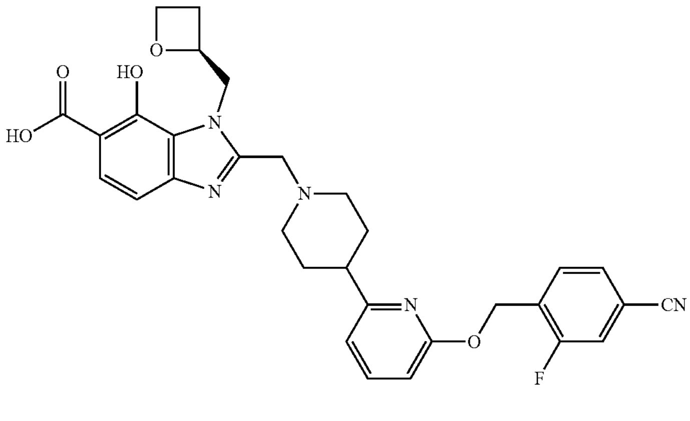 [SMILES: N#Cc1ccc(COc2cccc(C3CCN(Cc4nc5ccc(C(=O)O)c(O)c5n4C[C@@H]4CCO4)CC3)n2)c(F)c1] |

TABLE 5-continued
| Compound No. | Structure |
| --- | --- |
| 5-173 | 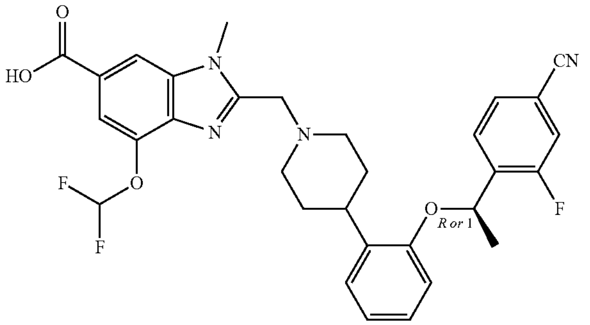 [SMILES: C[C@@H](Oc1ccccc1C1CCN(Cc2nc3c(OC(F)F)cc(C(=O)O)cc3n2C)CC1)c1ccc(C#N)cc1F] |
| 5-174 | 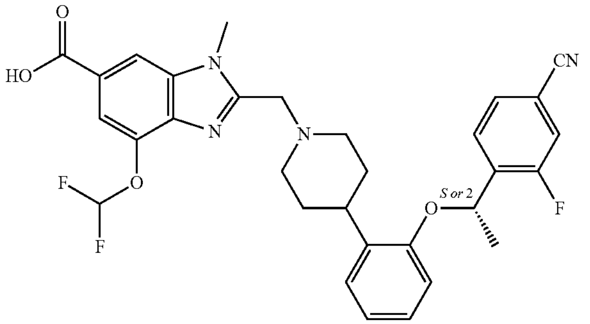 [SMILES: C[C@H](Oc1ccccc1C1CCN(Cc2nc3c(OC(F)F)cc(C(=O)O)cc3n2C)CC1)c1ccc(C#N)cc1F] |
| 5-175 | 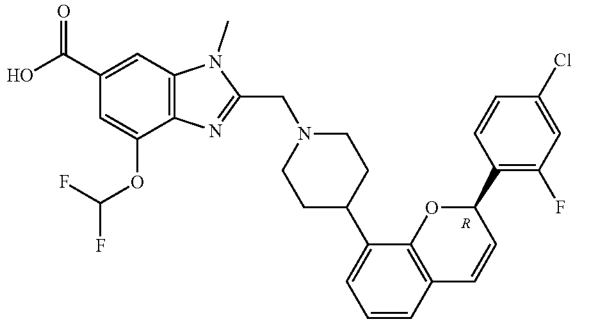 |
| 5-176 | 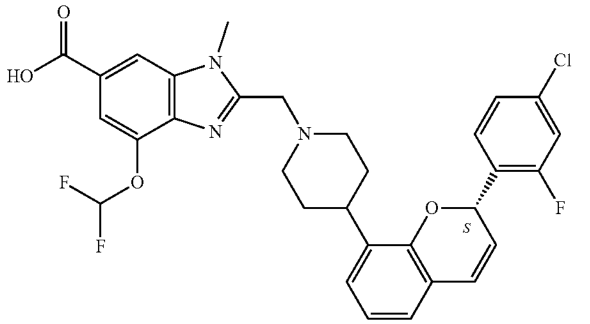 |

TABLE 5-continued
| Compound No. | Structure |
| --- | --- |
| 5-177 | 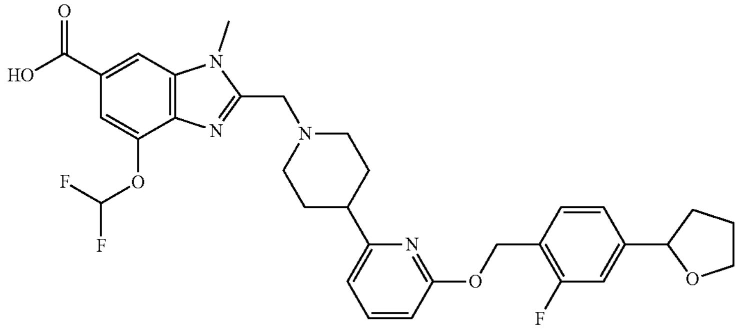 [SMILES: Cn1c(CN2CCC(c3cccc(OCc4ccc(C5CCCO5)cc4F)n3)CC2)nc2c(OC(F)F)cc(C(=O)O)cc21] |
| 5-178 | 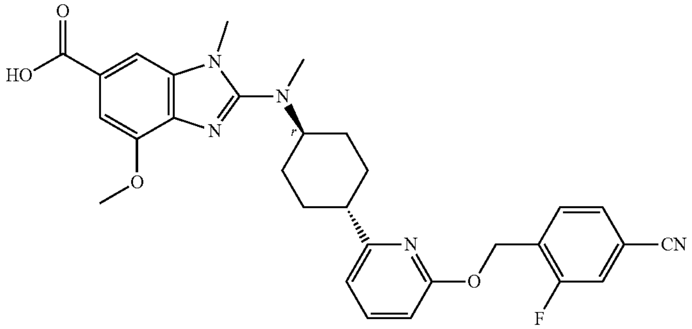 [SMILES: COc1cc(C(=O)O)cc2c1nc(N(C)[C@H]1CC[C@H](c3cccc(OCc4ccc(C#N)cc4F)n3)CC1)n2C] |
| 5-179 | 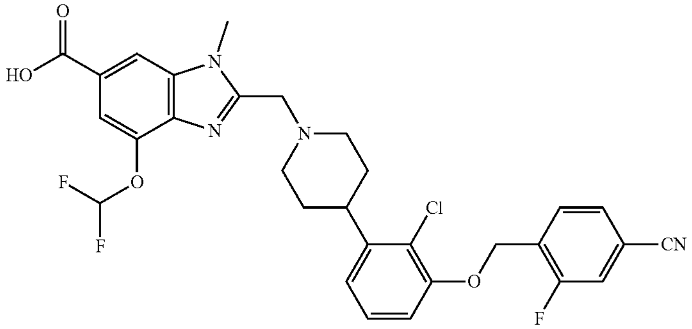 [SMILES: Cn1c(CN2CCC(c3cccc(OCc4ccc(C#N)cc4F)c3Cl)CC2)nc2c(OC(F)F)cc(C(=O)O)cc21] |
| 5-180 | 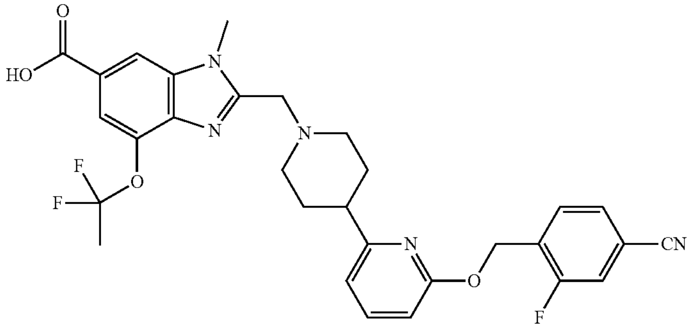 [SMILES: Cn1c(CN2CCC(c3cccc(OCc4ccc(C#N)cc4F)n3)CC2)nc2c(OC(C)(F)F)cc(C(=O)O)cc21] |

TABLE 5-continued
| Compound No. | Structure |
|---|---|
| 5-181 | 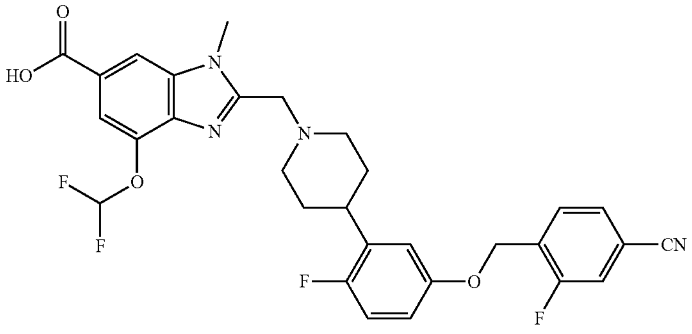 [SMILES: Cn1c(CN2CCC(c3cc(OCc4ccc(C#N)cc4F)ccc3F)CC2)nc2c(OC(F)F)cc(C(=O)O)cc21] |
| 5-182 | 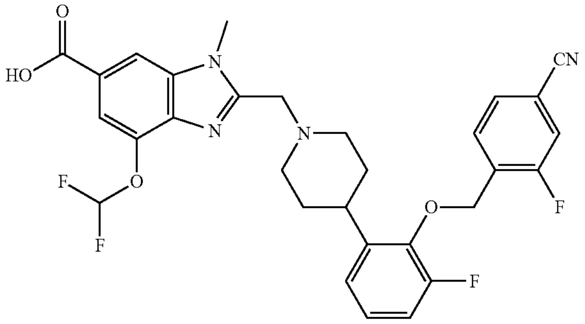 |
| 5-183 | 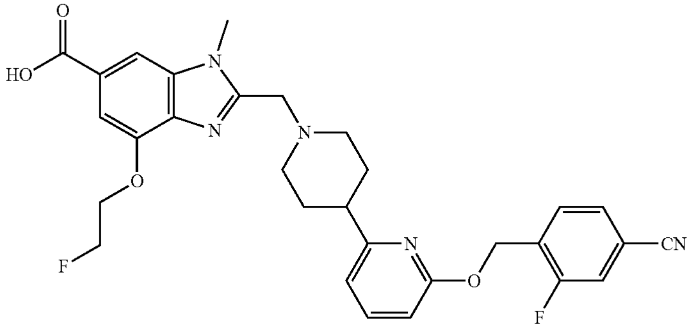 [SMILES: Cn1c(CN2CCC(c3cccc(OCc4ccc(C#N)cc4F)n3)CC2)nc2c(OCCF)cc(C(=O)O)cc21] |
| 5-184 | 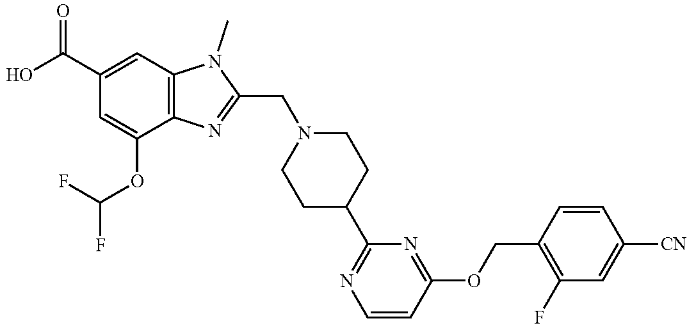 |

TABLE 5-continued
| Compound No. | Structure |
|---|---|
| 5-185 | 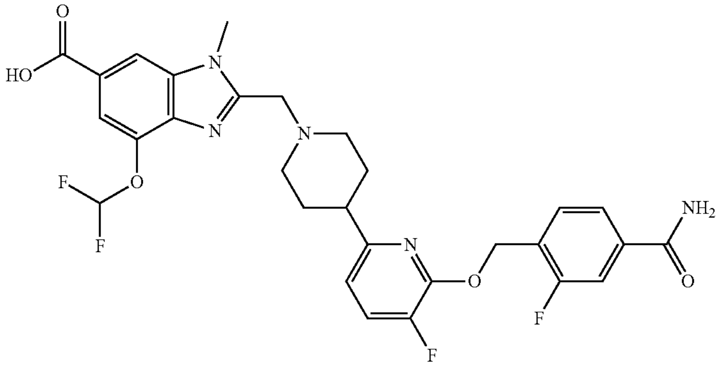 [SMILES: Cn1c(CN2CCC(c3ccc(F)c(OCc4ccc(C(N)=O)cc4F)n3)CC2)nc2c(OC(F)F)cc(C(=O)O)cc21] |
| 5-186 | 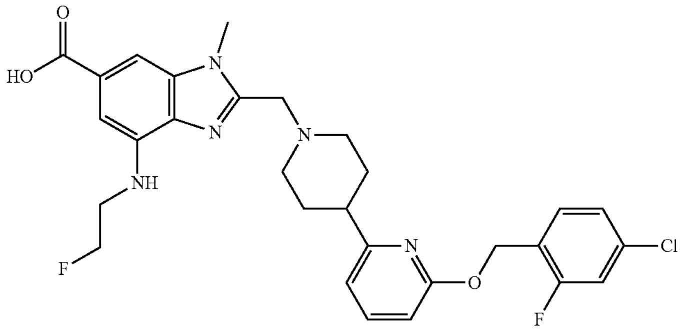 |
| 5-187 | 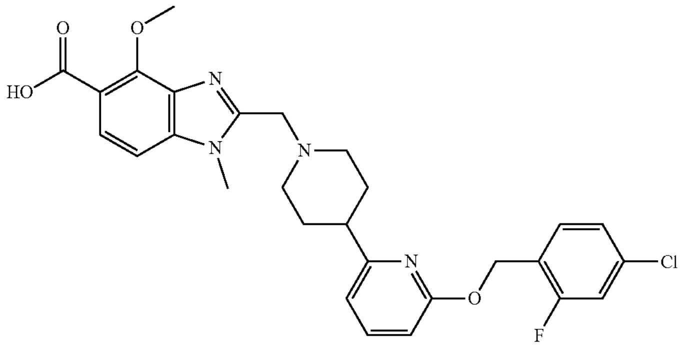 [SMILES: COc1c(C(=O)O)ccc2c1nc(CN1CCC(c3cccc(OCc4ccc(Cl)cc4F)n3)CC1)n2C] |
| 5-188 | 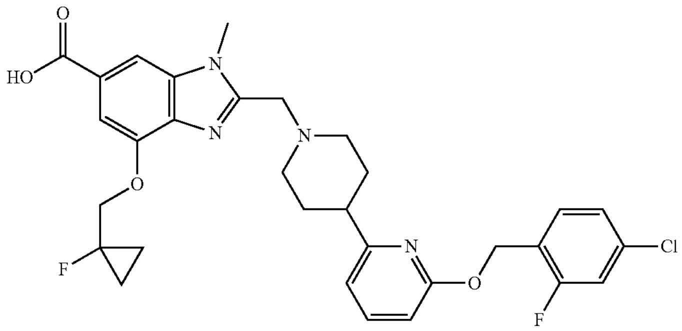 [SMILES: Cn1c(CN2CCC(c3cccc(OCc4ccc(Cl)cc4F)n3)CC2)nc2c(OCC3(F)CC3)cc(C(=O)O)cc21] |

TABLE 5-continued
| Compound No. | Structure |
| --- | --- |
| 5-189 | 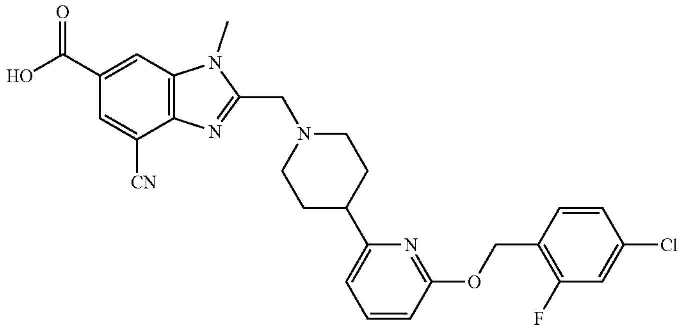 [SMILES: Cn1c(CN2CCC(c3cccc(OCc4ccc(Cl)cc4F)n3)CC2)nc2c(C#N)cc(C(=O)O)cc21] |
| 5-190 | 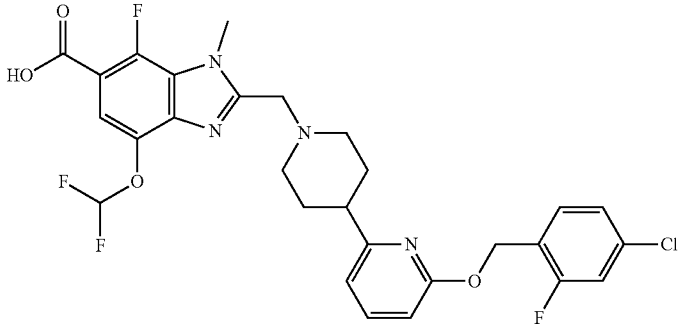 [SMILES: Cn1c(CN2CCC(c3cccc(OCc4ccc(Cl)cc4F)n3)CC2)nc2c(OC(F)F)cc(C(=O)O)c(F)c21] |
| 5-191 | 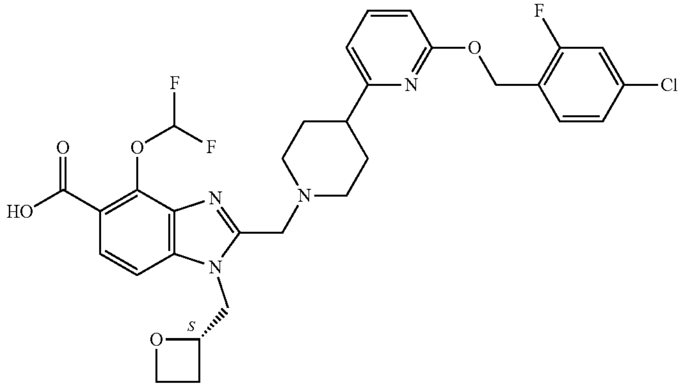 |
| 5-192 | 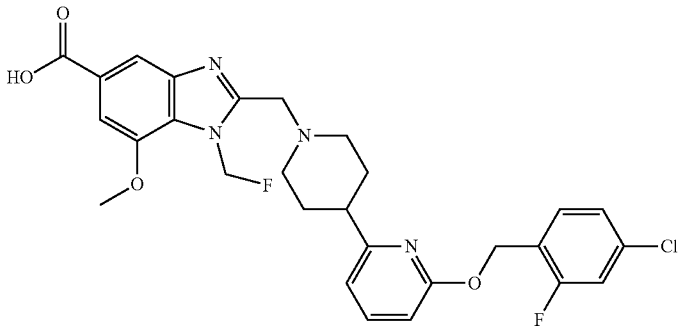 [SMILES: COc1cc(C(=O)O)cc2nc(CN3CCC(c4cccc(OCc5ccc(Cl)cc5F)n4)CC3)n(CF)c12] |

TABLE 5-continued
| Compound No. | Structure |
|---|---|
| 5-193 | 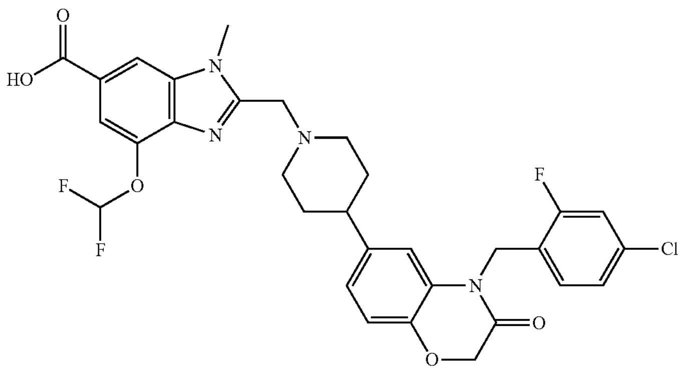 [SMILES: Cn1c(CN2CCC(c3ccc4c(c3)N(Cc3ccc(Cl)cc3F)C(=O)CO4)CC2)nc2c(OC(F)F)cc(C(=O)O)cc21] |
| 5-194 | 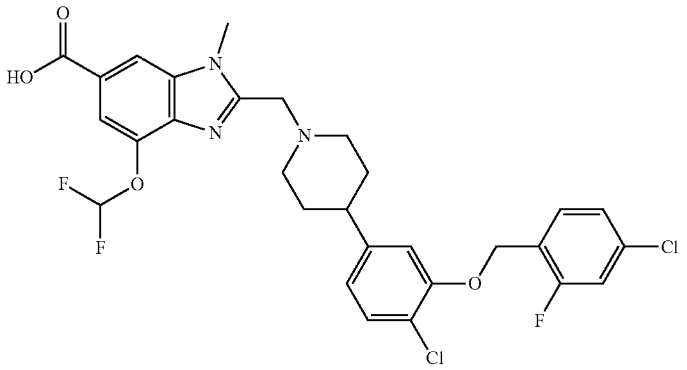 |
| 5-195 | 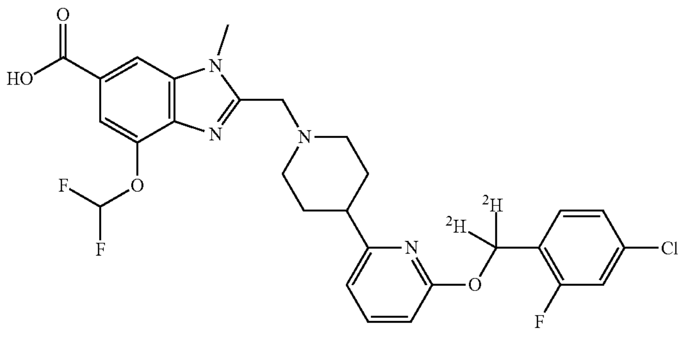 [SMILES: [2H]C([2H])(Oc1cccc(C2CCN(Cc3nc4c(OC(F)F)cc(C(=O)O)cc4n3C)CC2)n1)c1ccc(Cl)cc1F] |
| 5-196 | 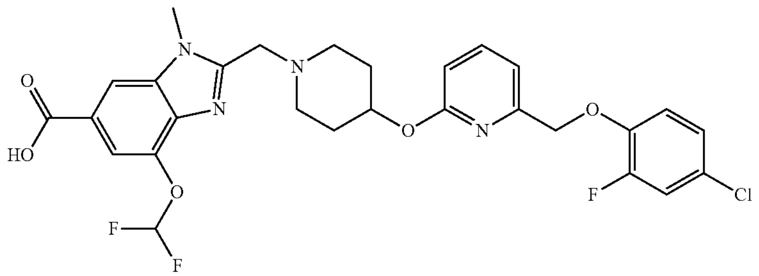 [SMILES: Cn1c(CN2CCC(Oc3cccc(COc4ccc(Cl)cc4F)n3)CC2)nc2c(OC(F)F)cc(C(=O)O)cc21] |

TABLE 5-continued
| Compound No. | Structure |
|---|---|
| 5-197 | 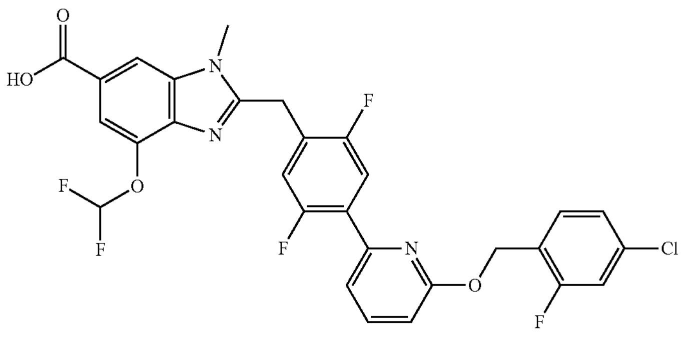 |
| 5-198 | 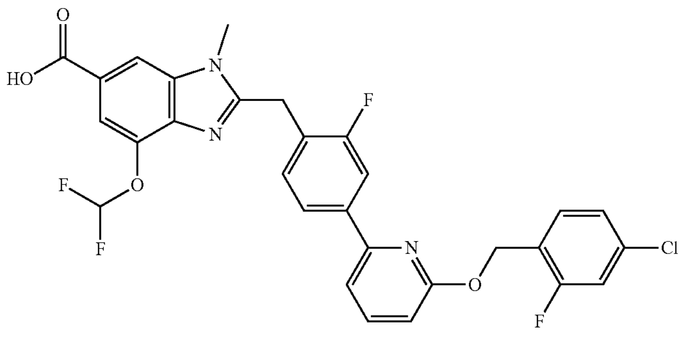 [SMILES: Cn1c(Cc2ccc(-c3cccc(OCc4ccc(Cl)cc4F)n3)cc2F)nc2c(OC(F)F)cc(C(=O)O)cc21] |
| 5-199 | 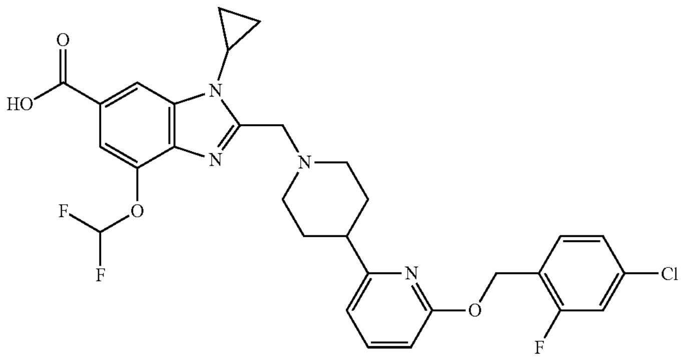 [SMILES: O=C(O)c1cc(OC(F)F)c2nc(CN3CCC(c4cccc(OCc5ccc(Cl)cc5F)n4)CC3)n(C3CC3)c2c1] |
| 5-200 | 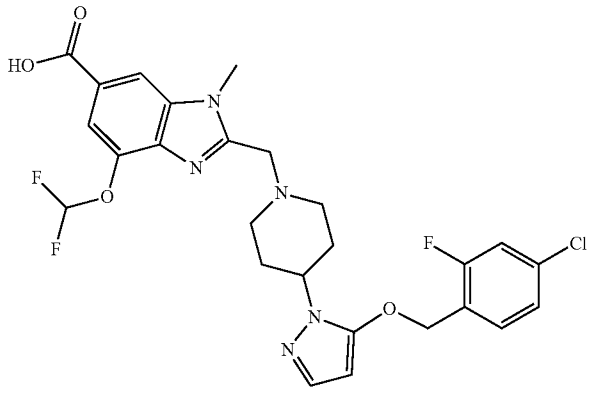 [SMILES: Cn1c(CN2CCC(n3nccc3OCc3ccc(Cl)cc3F)CC2)nc2c(OC(F)F)cc(C(=O)O)cc21] |

TABLE 5-continued
| Compound No. | Structure |
| --- | --- |
| 5-201 | 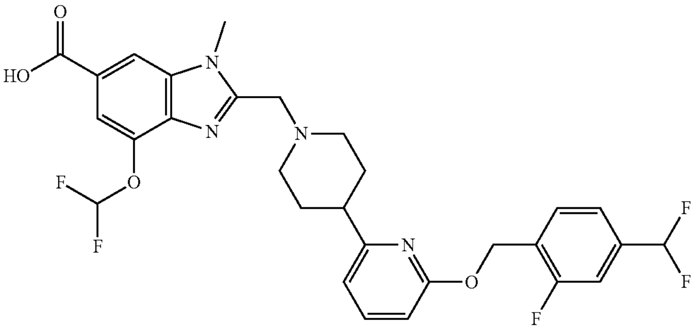 [SMILES: Cn1c(CN2CCC(c3cccc(OCc4ccc(C(F)F)cc4F)n3)CC2)nc2c(OC(F)F)cc(C(=O)O)cc21] |
| 5-202 | 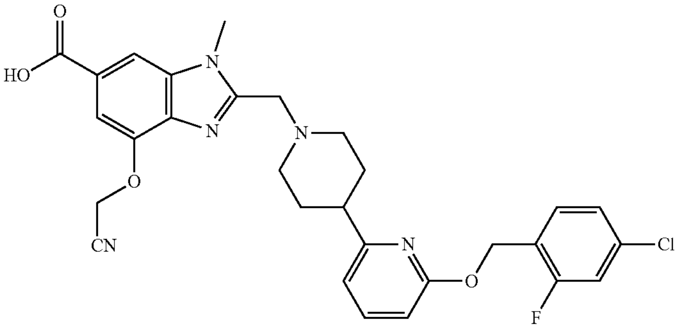 [SMILES: Cn1c(CN2CCC(c3cccc(OCc4ccc(Cl)cc4F)n3)CC2)nc2c(OCC#N)cc(C(=O)O)cc21] |
| 5-203 | 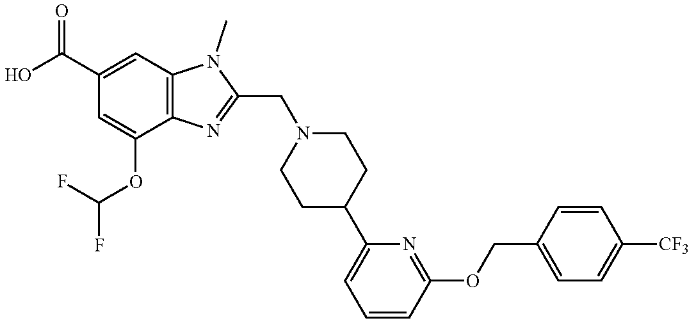 |
| 5-204 | 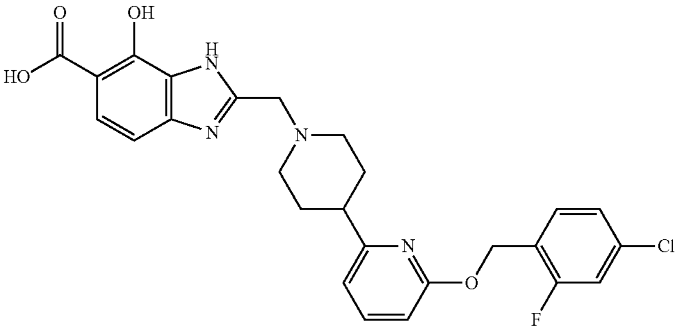 [SMILES: O=C(O)c1ccc2nc(CN3CCC(c4cccc(OCc5ccc(Cl)cc5F)n4)CC3)[nH]c2c1O] |

TABLE 5-continued
| Compound No. | Structure |
| --- | --- |
| 5-205 | 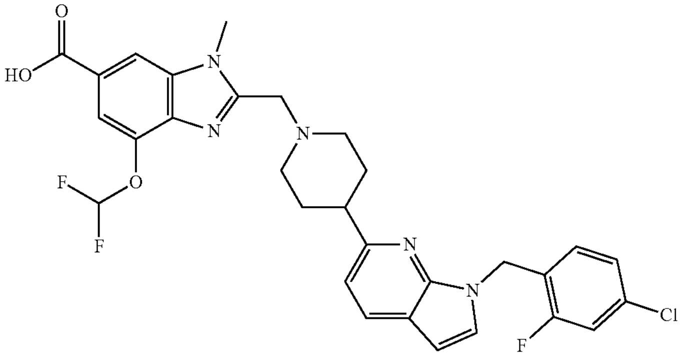 [SMILES: Cn1c(CN2CCC(c3ccc4ccn(Cc5ccc(Cl)cc5F)c4n3)CC2)nc2c(OC(F)F)cc(C(=O)O)cc21] |
| 5-206 | 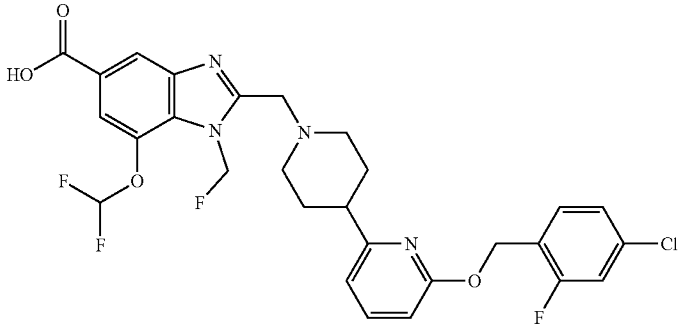 [SMILES: O=C(O)c1cc(OC(F)F)c2c(c1)nc(CN1CCC(c3cccc(OCc4ccc(Cl)cc4F)n3)CC1)n2CF] |
| 5-207 | 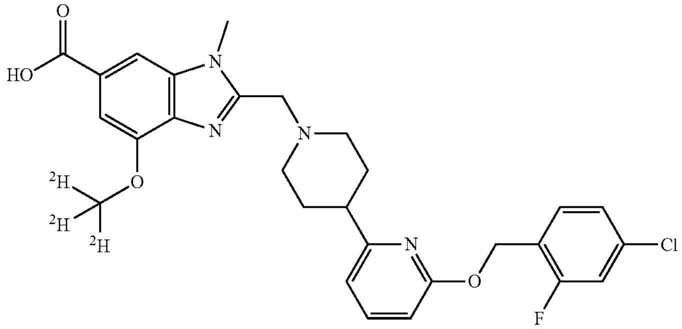 [SMILES: [2H]C([2H])([2H])Oc1cc(C(=O)O)cc2c1nc(CN1CCC(c3cccc(OCc4ccc(Cl)cc4F)n3)CC1)n2C] |
| 5-208 | 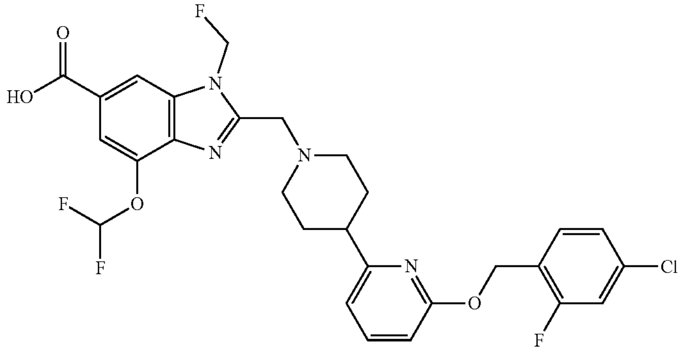 [SMILES: O=C(O)c1cc(OC(F)F)c2nc(CN3CCC(c4cccc(OCc5ccc(Cl)cc5F)n4)CC3)n(CF)c2c1] |

TABLE 5-continued
| Compound No. | Structure |
|---|---|
| 5-209 | 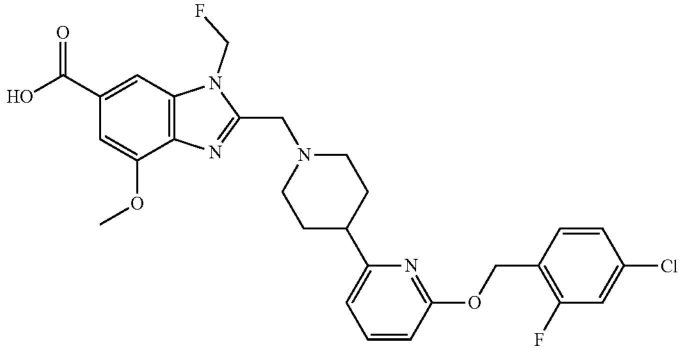 [SMILES: COc1cc(C(=O)O)cc2c1nc(CN1CCC(c3cccc(OCc4ccc(Cl)cc4F)n3)CC1)n2CF] |
| 5-210 | 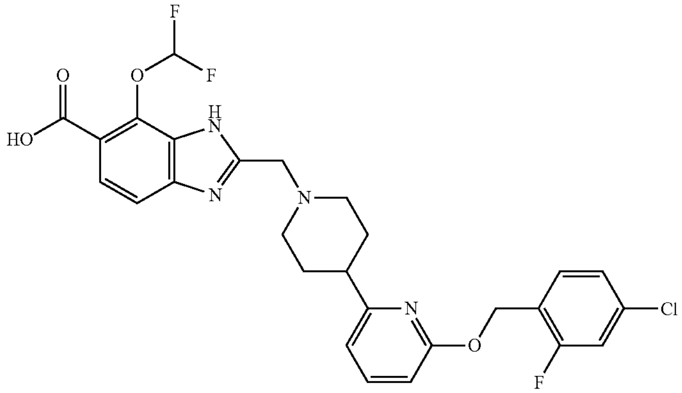 [SMILES: O=C(O)c1ccc2nc(CN3CCC(c4cccc(OCc5ccc(Cl)cc5F)n4)CC3)[nH]c2c1OC(F)F] |
| 5-211 | 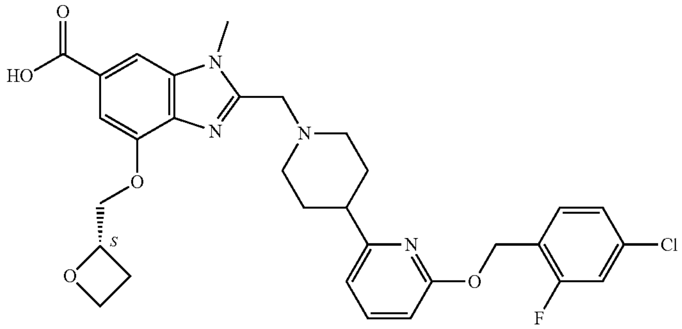 |
| 5-212 | 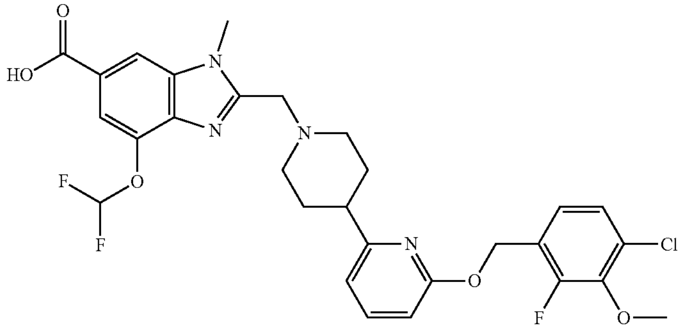 [SMILES: COc1c(Cl)ccc(COc2cccc(C3CCN(Cc4nc5c(OC(F)F)cc(C(=O)O)cc5n4C)CC3)n2)c1F] |

TABLE 5-continued
| Compound No. | Structure |
|---|---|
| 5-213 | 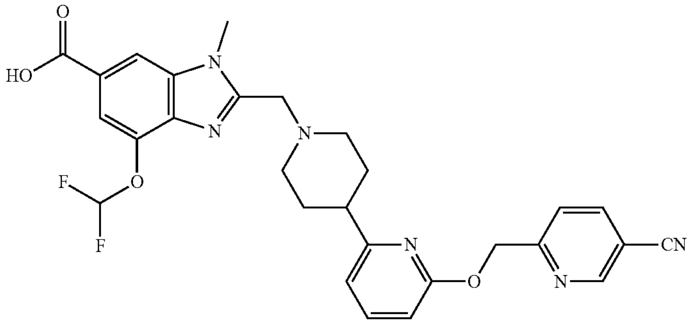 [SMILES: Cn1c(CN2CCC(c3cccc(OCc4ccc(C#N)cn4)n3)CC2)nc2c(OC(F)F)cc(C(=O)O)cc21] |
| 5-214 | 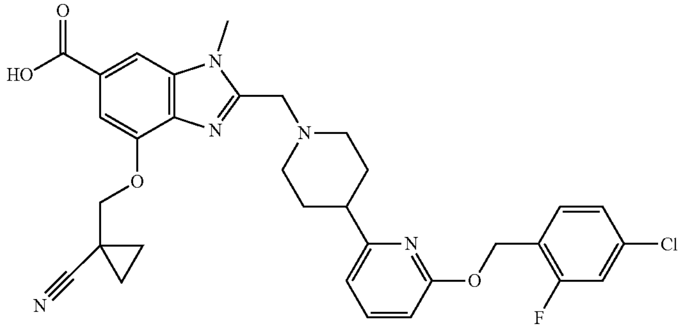 [SMILES: Cn1c(CN2CCC(c3cccc(OCc4ccc(Cl)cc4F)n3)CC2)nc2c(OCC3(C#N)CC3)cc(C(=O)O)cc21] |
| 5-215 | 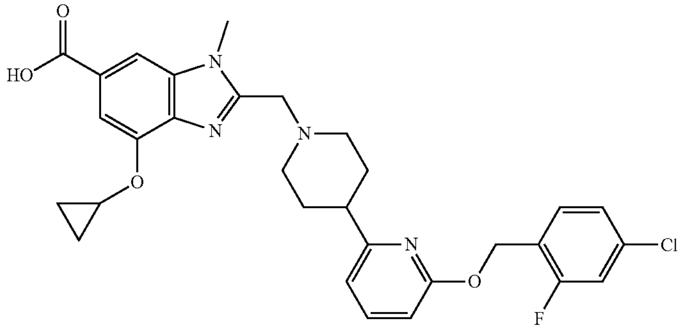 [SMILES: Cn1c(CN2CCC(c3cccc(OCc4ccc(Cl)cc4F)n3)CC2)nc2c(OC3CC3)cc(C(=O)O)cc21] |
| 5-216 | 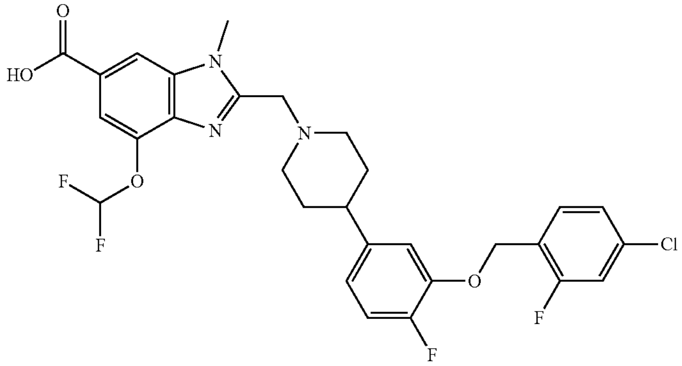 [SMILES: Cn1c(CN2CCC(c3ccc(F)c(OCc4ccc(Cl)cc4F)c3)CC2)nc2c(OC(F)F)cc(C(=O)O)cc21] |

TABLE 5-continued
| Compound No. | Structure |
| --- | --- |
| 5-217 | 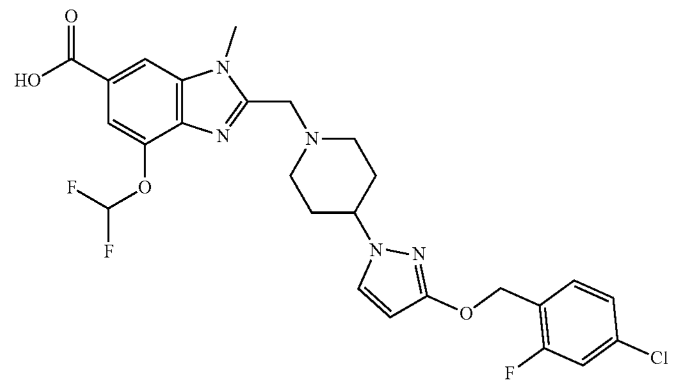 [SMILES: Cn1c(CN2CCC(n3ccc(OCc4ccc(Cl)cc4F)n3)CC2)nc2c(OC(F)F)cc(C(=O)O)cc21] |
| 5-218 | 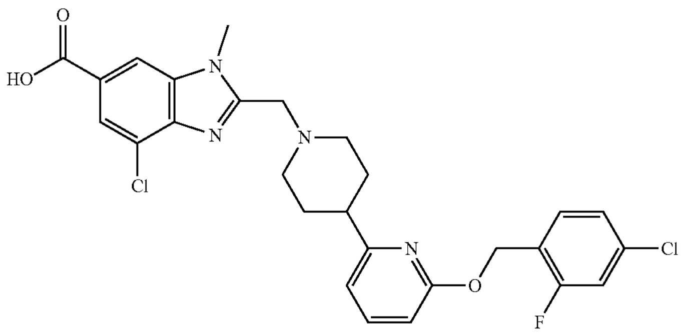 [SMILES: Cn1c(CN2CCC(c3cccc(OCc4ccc(Cl)cc4F)n3)CC2)nc2c(Cl)cc(C(=O)O)cc21] |
| 5-219 | 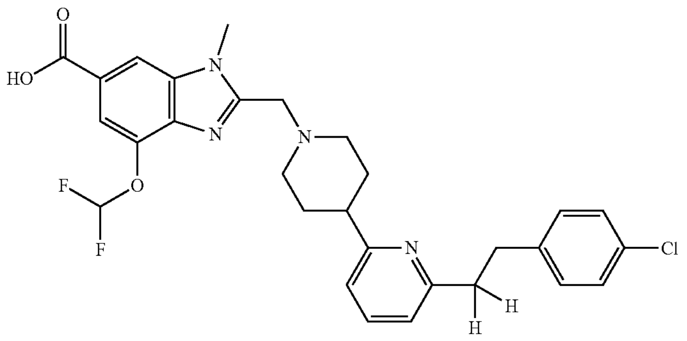 [SMILES: Cn1c(CN2CCC(c3cccc(CCc4ccc(Cl)cc4)n3)CC2)nc2c(OC(F)F)cc(C(=O)O)cc21] |
| 5-220 | 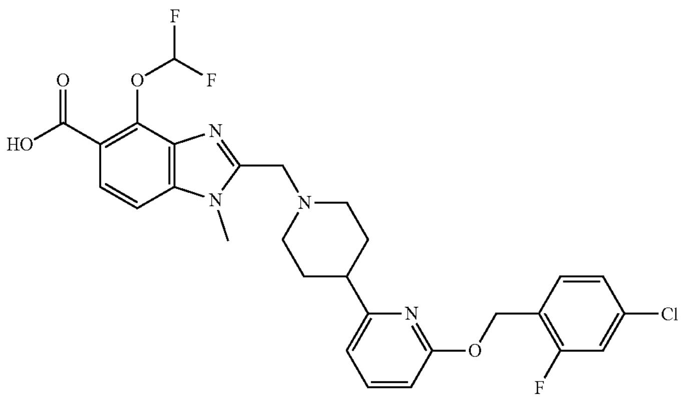 [SMILES: Cn1c(CN2CCC(c3cccc(OCc4ccc(Cl)cc4F)n3)CC2)nc2c(OC(F)F)c(C(=O)O)ccc21] |

TABLE 5-continued
| Compound No. | Structure |
| --- | --- |
| 5-221 | 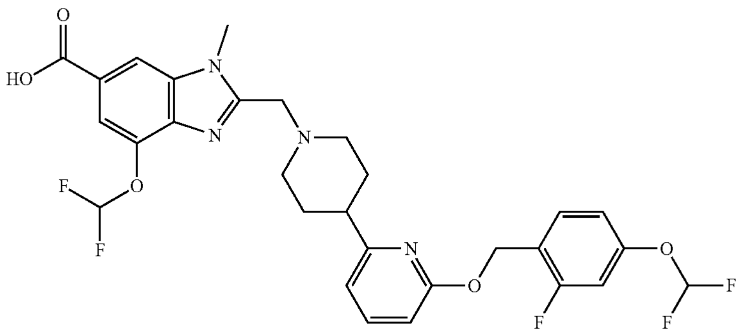 [SMILES: Cn1c(CN2CCC(c3cccc(OCc4ccc(OC(F)F)cc4F)n3)CC2)nc2c(OC(F)F)cc(C(=O)O)cc21] |
| 5-222 | 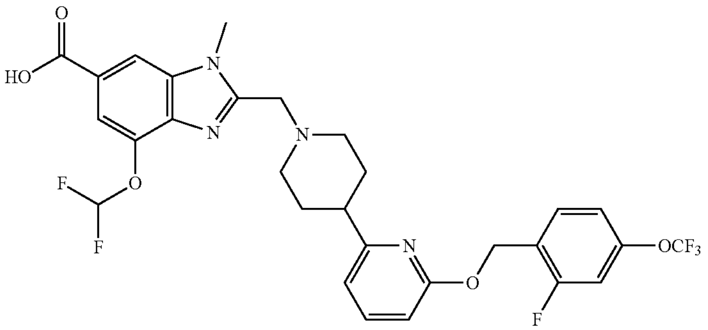 [SMILES: Cn1c(CN2CCC(c3cccc(OCc4ccc(OC(F)(F)F)cc4F)n3)CC2)nc2c(OC(F)F)cc(C(=O)O)cc21] |
| 5-223 | 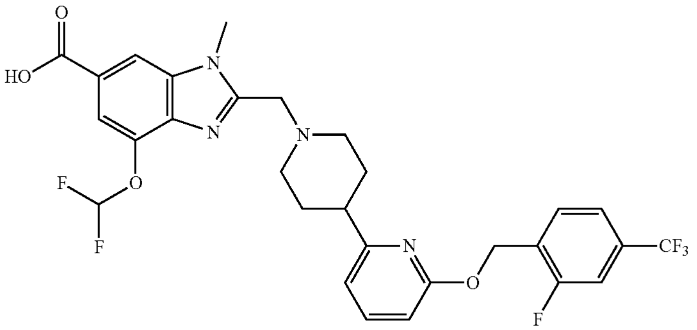 [SMILES: Cn1c(CN2CCC(c3cccc(OCc4ccc(C(F)(F)F)cc4F)n3)CC2)nc2c(OC(F)F)cc(C(=O)O)cc21] |
| 5-224 | 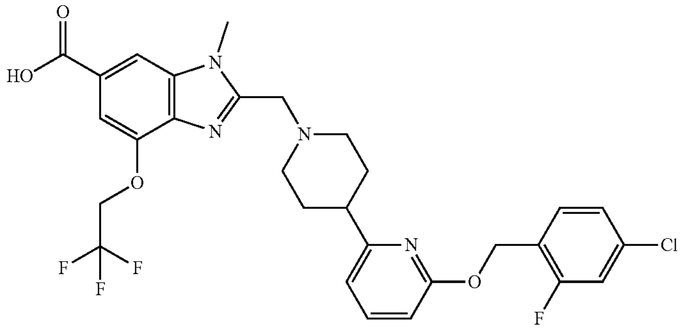 [SMILES: Cn1c(CN2CCC(c3cccc(OCc4ccc(Cl)cc4F)n3)CC2)nc2c(OCC(F)(F)F)cc(C(=O)O)cc21] |

TABLE 5-continued
| Compound No. | Structure |
| --- | --- |
| 5-225 | 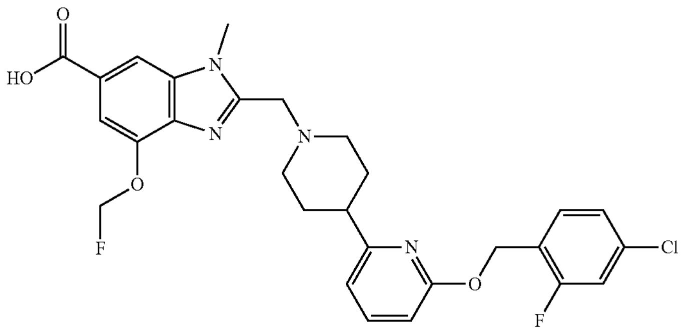 [SMILES: Cn1c(CN2CCC(c3cccc(OCc4ccc(Cl)cc4F)n3)CC2)nc2c(OCF)cc(C(=O)O)cc21] |
| 5-226 | 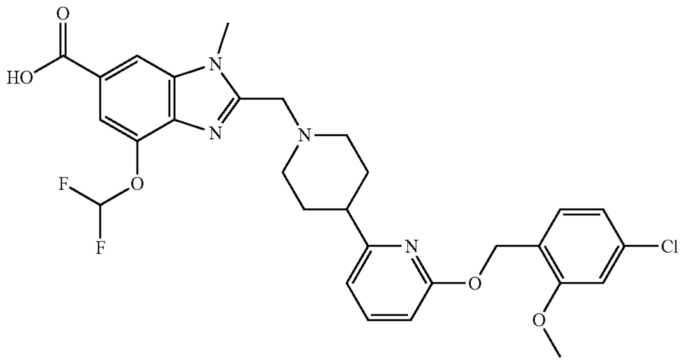 [SMILES: COc1cc(Cl)ccc1COc1cccc(C2CCN(Cc3nc4c(OC(F)F)cc(C(=O)O)cc4n3C)CC2)n1] |
| 5-227 | 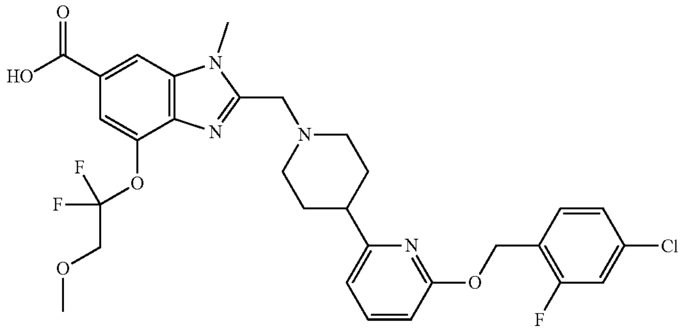 [SMILES: COCC(F)(F)Oc1cc(C(=O)O)cc2c1nc(CN1CCC(c3cccc(OCc4ccc(Cl)cc4F)n3)CC1)n2C] |
| 5-228 | 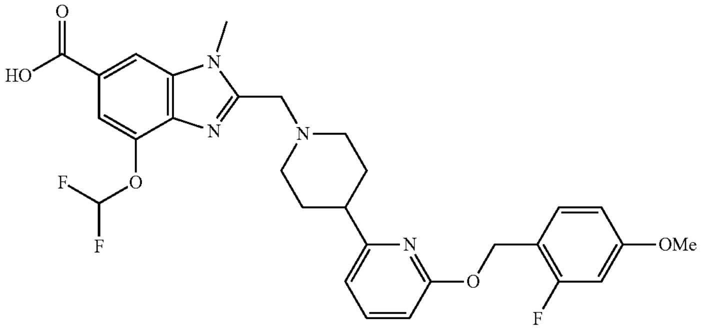 [SMILES: COc1ccc(COc2cccc(C3CCN(Cc4nc5c(OC(F)F)cc(C(=O)O)cc5n4C)CC3)n2)c(F)c1] |

TABLE 5-continued
| Compound No. | Structure |
| --- | --- |
| 5-229 | 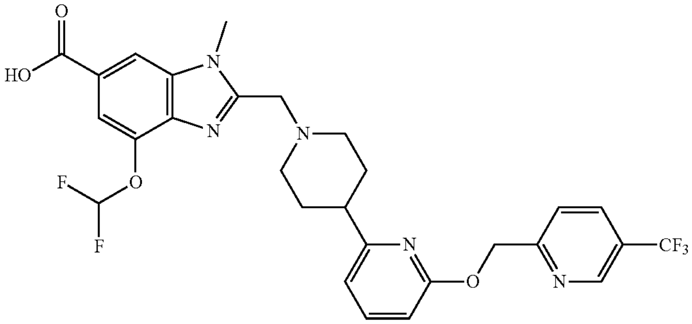 [SMILES: Cn1c(CN2CCC(c3cccc(OCc4ccc(C(F)(F)F)cn4)n3)CC2)nc2c(OC(F)F)cc(C(=O)O)cc21] |
| 5-230 | 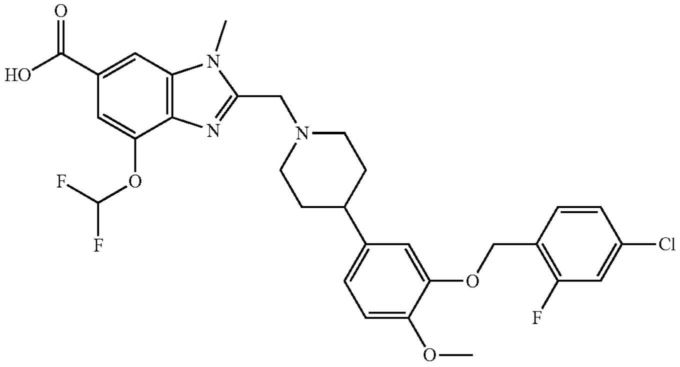 [SMILES: COc1ccc(C2CCN(Cc3nc4c(OC(F)F)cc(C(=O)O)cc4n3C)CC2)cc1OCc1ccc(Cl)cc1F] |
| 5-231 | 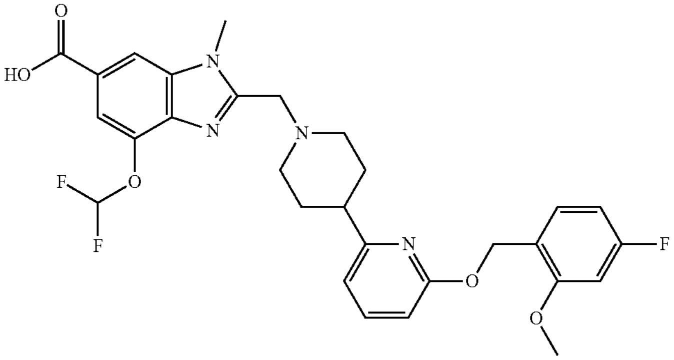 [SMILES: COc1cc(F)ccc1COc1cccc(C2CCN(Cc3nc4c(OC(F)F)cc(C(=O)O)cc4n3C)CC2)n1] |
| 5-232 | 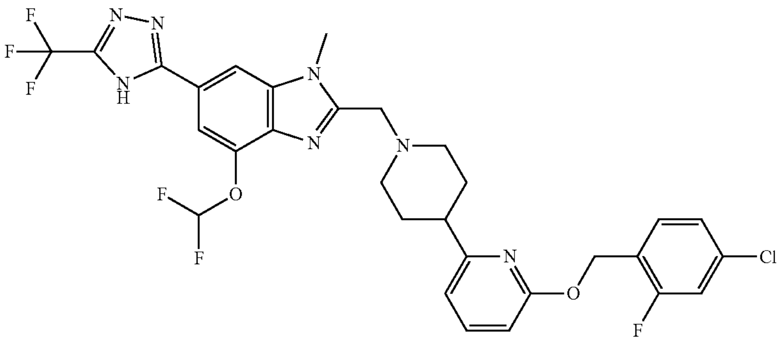 [SMILES: Cn1c(CN2CCC(c3cccc(OCc4ccc(Cl)cc4F)n3)CC2)nc2c(OC(F)F)cc(-c3nnc(C(F)(F)F)[nH]3)cc21] |

TABLE 5-continued
| Compound No. | Structure |
| --- | --- |
| 5-233 | 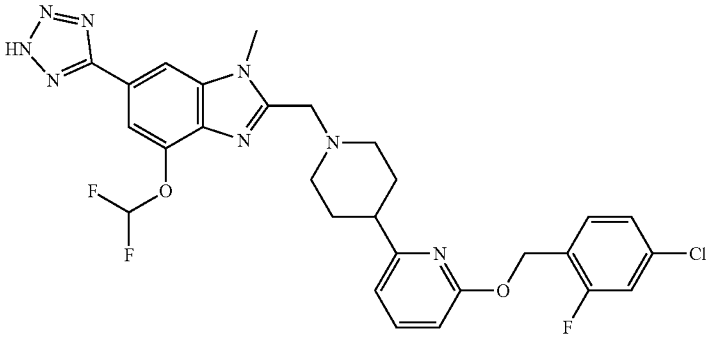 [SMILES: Cn1c(CN2CCC(c3cccc(OCc4ccc(Cl)cc4F)n3)CC2)nc2c(OC(F)F)cc(-c3nn[nH]n3)cc21] |
| 5-234 | 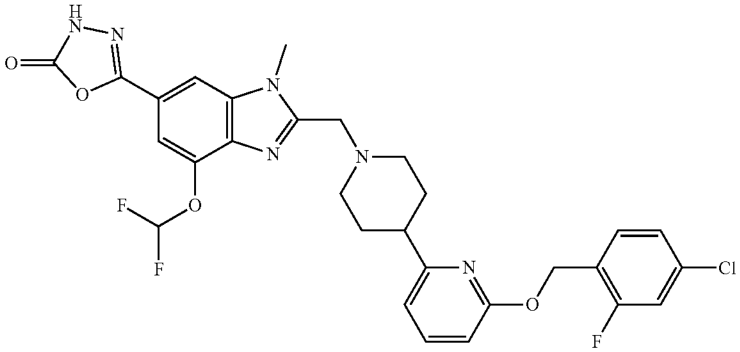 [SMILES: Cn1c(CN2CCC(c3cccc(OCc4ccc(Cl)cc4F)n3)CC2)nc2c(OC(F)F)cc(-c3n[nH]c(=O)o3)cc21] |
| 5-235 | 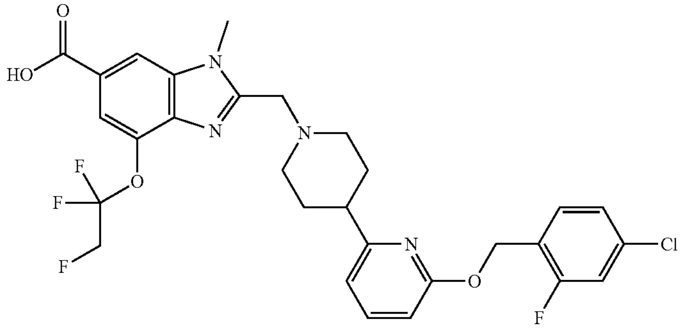 [SMILES: Cn1c(CN2CCC(c3cccc(OCc4ccc(Cl)cc4F)n3)CC2)nc2c(OC(F)(F)CF)cc(C(=O)O)cc21] |
| 5-236 | 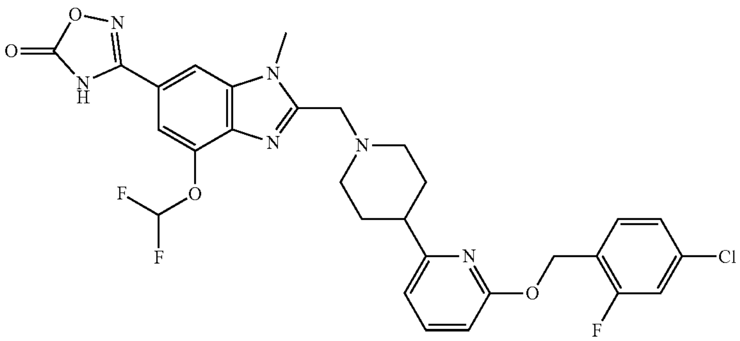 [SMILES: Cn1c(CN2CCC(c3cccc(OCc4ccc(Cl)cc4F)n3)CC2)nc2c(OC(F)F)cc(-c3noc(=O)[nH]3)cc21] |

TABLE 5-continued
| Compound No. | Structure |
| --- | --- |
| 5-237 | 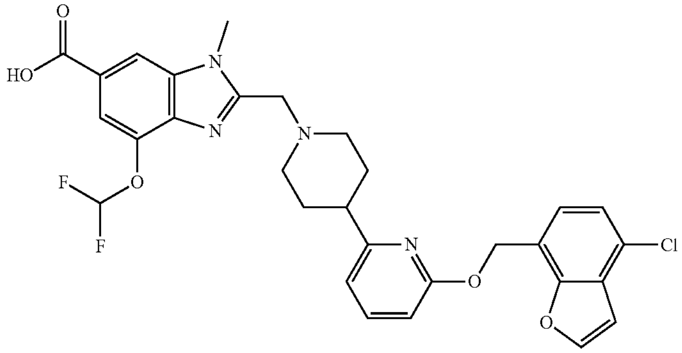 [SMILES: Cn1c(CN2CCC(c3cccc(OCc4ccc(Cl)c5ccoc45)n3)CC2)nc2c(OC(F)F)cc(C(=O)O)cc21] |
| 5-238 | 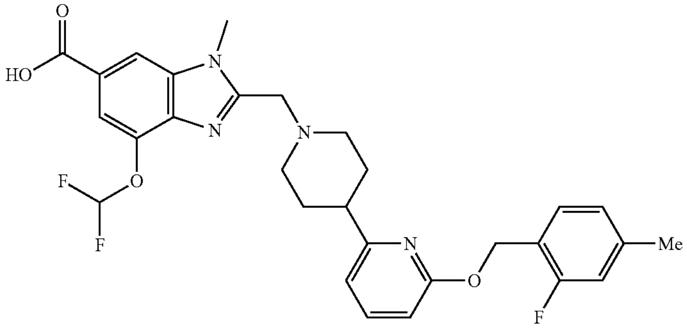 [SMILES: Cc1ccc(COc2cccc(C3CCN(Cc4nc5c(OC(F)F)cc(C(=O)O)cc5n4C)CC3)n2)c(F)c1] |
| 5-239 | 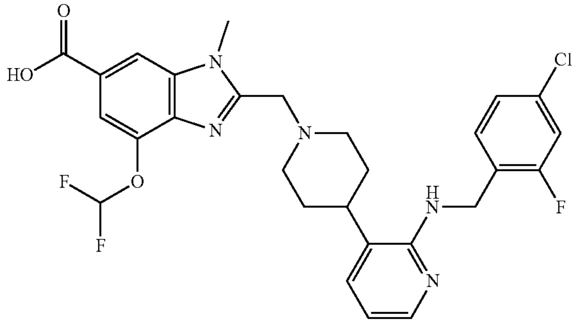 [SMILES: Cn1c(CN2CCC(c3cccnc3NCc3ccc(Cl)cc3F)CC2)nc2c(OC(F)F)cc(C(=O)O)cc21] |
| 5-240 | 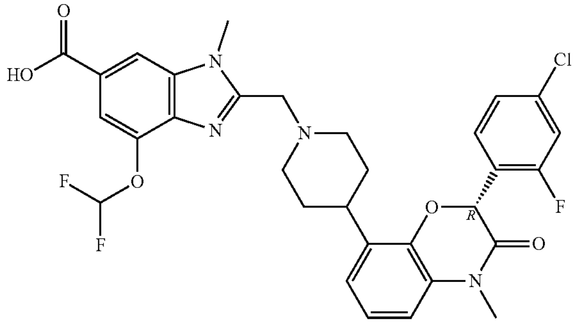 |

TABLE 5-continued
| Compound No. | Structure |
|---|---|
| 5-241 | 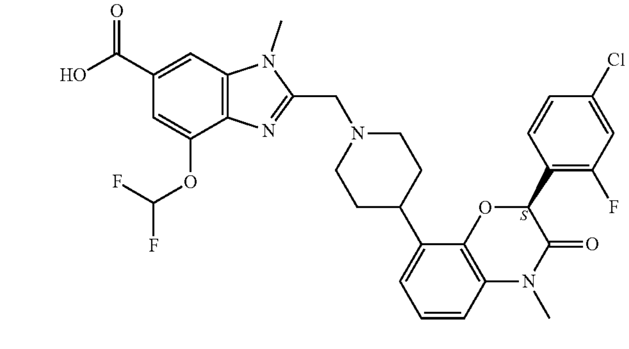 |
| 5-242 | 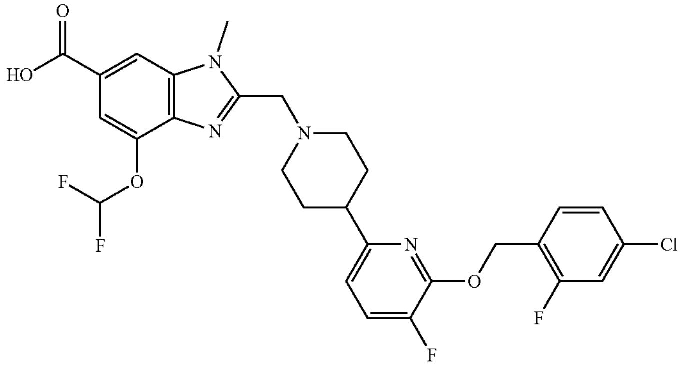 |
| 5-243 | 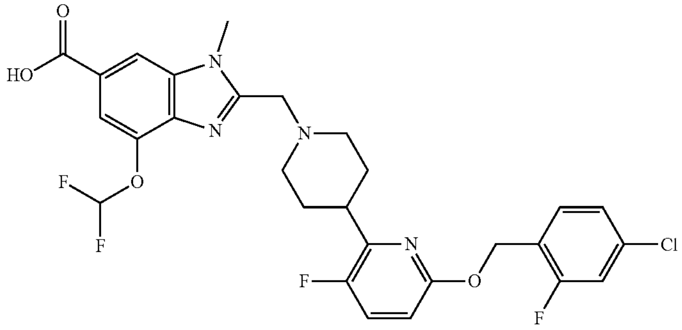 [SMILES: Cn1c(CN2CCC(c3nc(OCc4ccc(Cl)cc4F)ccc3F)CC2)nc2c(OC(F)F)cc(C(=O)O)cc21] |
| 5-244 | 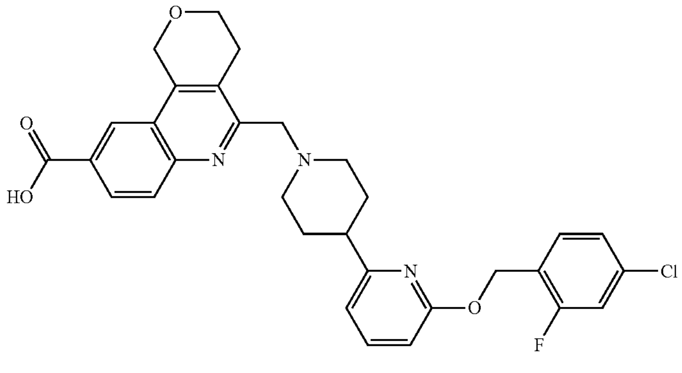 [SMILES: O=C(O)c1ccc2nc(CN3CCC(c4cccc(OCc5ccc(Cl)cc5F)n4)CC3)c3c(c2c1)COCC3] |

TABLE 5-continued
| Compound No. | Structure |
| --- | --- |
| 5-245 | 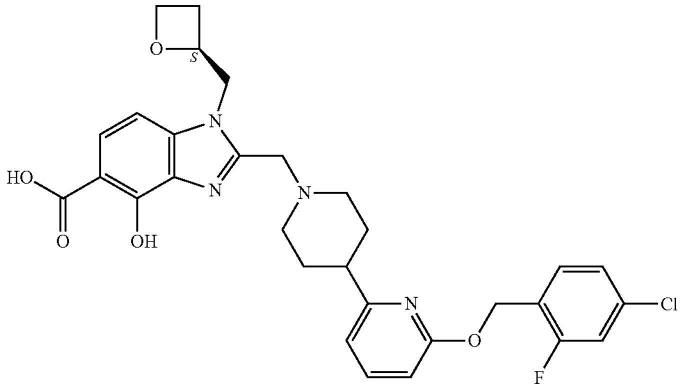 |
| 5-246 | 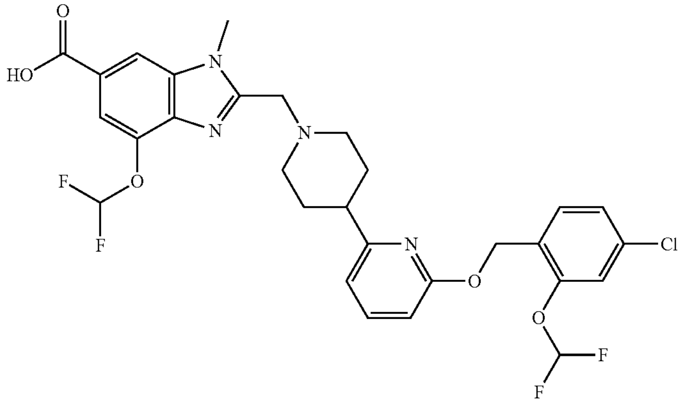 [SMILES: Cn1c(CN2CCC(c3cccc(OCc4ccc(Cl)cc4OC(F)F)n3)CC2)nc2c(OC(F)F)cc(C(=O)O)cc21] |
| 5-247 | 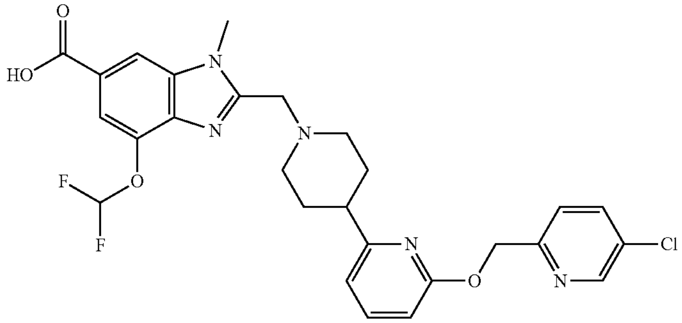 [SMILES: Cn1c(CN2CCC(c3cccc(OCc4ccc(Cl)cn4)n3)CC2)nc2c(OC(F)F)cc(C(=O)O)cc21] |
| 5-248 | 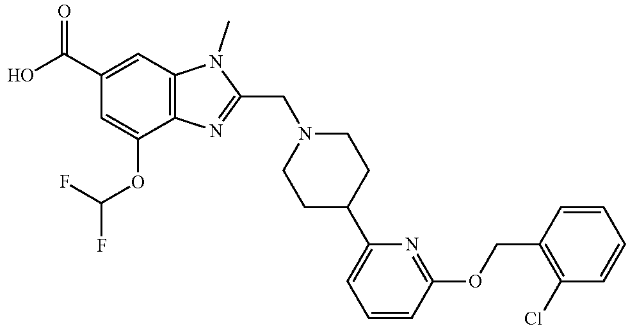 [SMILES: Cn1c(CN2CCC(c3cccc(OCc4ccccc4Cl)n3)CC2)nc2c(OC(F)F)cc(C(=O)O)cc21] |

TABLE 5-continued
| Compound No. | Structure |
|---|---|
| 5-249 | 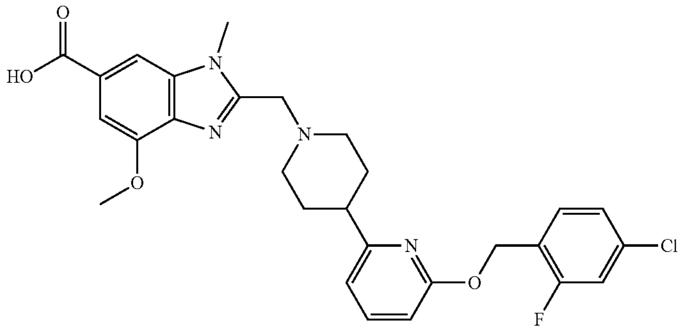 [SMILES: COc1cc(C(=O)O)cc2c1nc(CN1CCC(c3cccc(OCc4ccc(Cl)cc4F)n3)CC1)n2C] |
| 5-250 | 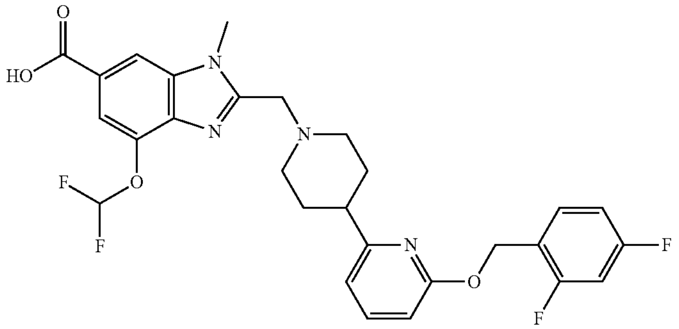 [SMILES: Cn1c(CN2CCC(c3cccc(OCc4ccc(F)cc4F)n3)CC2)nc2c(OC(F)F)cc(C(=O)O)cc21] |
| 5-251 | 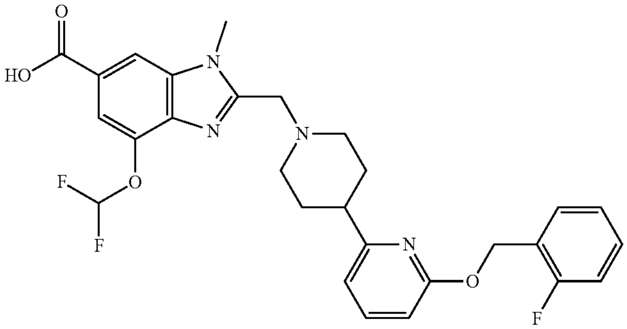 |
| 5-252 | 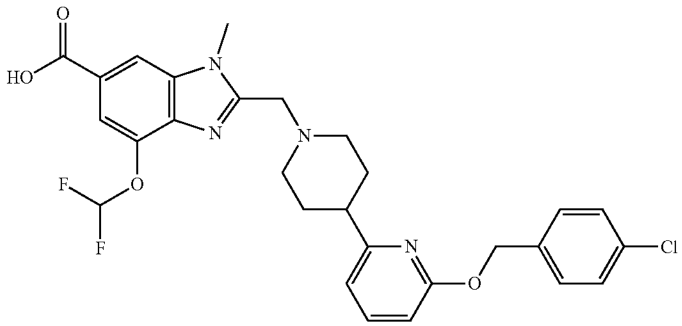 [SMILES: Cn1c(CN2CCC(c3cccc(OCc4ccc(Cl)cc4)n3)CC2)nc2c(OC(F)F)cc(C(=O)O)cc21] |

TABLE 5-continued
| Compound No. | Structure |
|---|---|
| 5-253 | 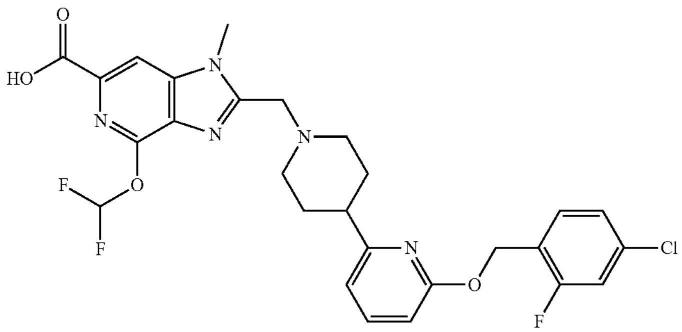 |
| 5-254 | 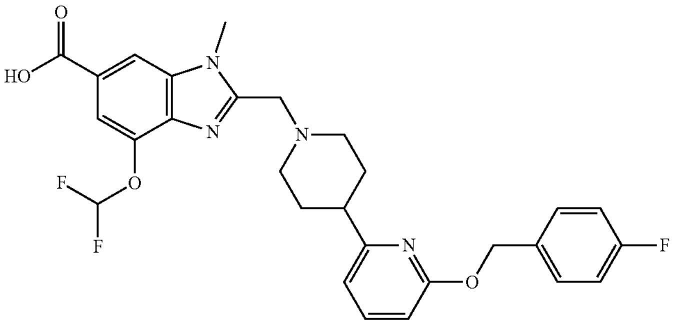 [SMILES: Cn1c(CN2CCC(c3cccc(OCc4ccc(F)cc4)n3)CC2)nc2c(OC(F)F)cc(C(=O)O)cc21] |
In some embodiments, the GLP-1R agonist is selected from those listed in Table 5A below, or a pharmaceutically acceptable salt thereof:
TABLE 5A
| Compound No. | Name | Structure |
|---|---|---|
| 5-255 | (2-((4-(6-((4-chloro-2-fluorobenzyl)oxy)pyridin-2-yl)piperidin-1-yl)methyl)-4-(difluoromethoxy)-1-methyl-1H-benzo[d]imidazol-6-yl)glycine | 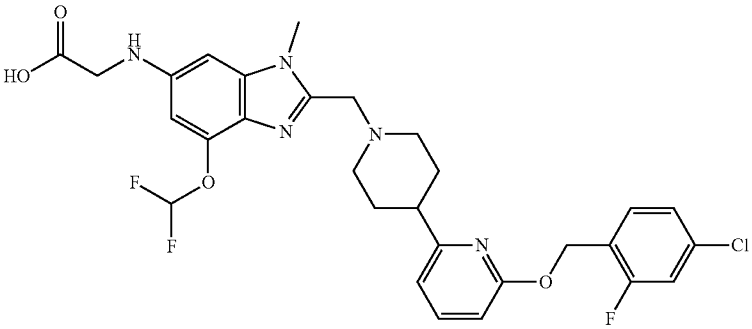 [SMILES: Cn1c(CN2CCC(c3cccc(OCc4ccc(Cl)cc4F)n3)CC2)nc2c(OC(F)F)cc(NCC(=O)O)cc21] |

TABLE 5A-continued

| Compound No. | Name | Structure |
| --- | --- | --- |
| 5-256 | 2-((4-((6-((4-chloro-2-fluorophenoxy)methyl) pyridin-2-yl)oxy)piperidin-1-yl)methyl)-4-ethoxy-1-methyl-1H-benzo[d]imidazole-6-carboxylic acid | 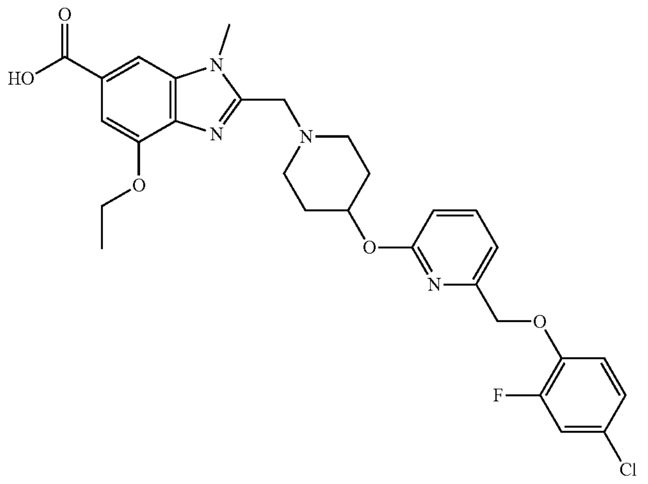 [SMILES: CCOc1cc(C(=O)O)cc2c1nc(CN1CCC(Oc3cccc(COc4ccc(Cl)cc4F)n3)CC1)n2C] |
| 5-257 | (S)-3-(2-((4-(6-((4-Chloro-2-fluorobenzyl)oxy)pyridin-2-yl)piperidin-1-yl)methyl)-4-methoxy-1-(oxetan-2-ylmethyl)-1H-benzo[d]imidazol-6-yl)propiolic acid | 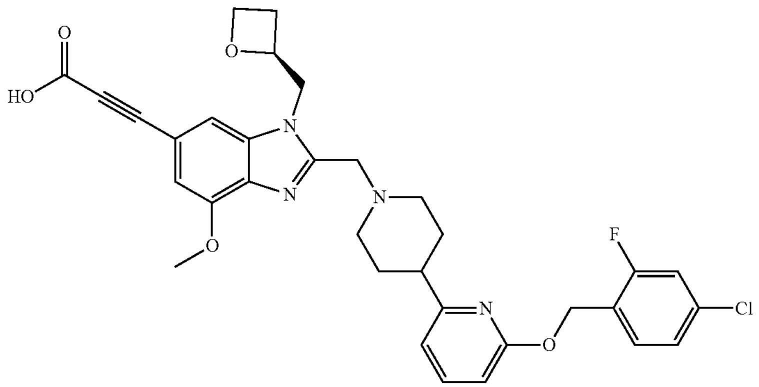 [SMILES: COc1cc(C#CC(=O)O)cc2c1nc(CN1CCC(c3cccc(OCc4ccc(Cl)cc4F)n3)CC1)n2C[C@@H]1CCO1] |
| 5-258 | (S)-2-((4-(2-(4-Chloro-2-fluorophenyl)-2,3-dihydrobenzo[b][1,4]dioxin-5-yl)piperidin-1-yl)methyl)-4-methoxy-1-methyl-1H-benzo[d]imidazole-6-carboxylic acid | 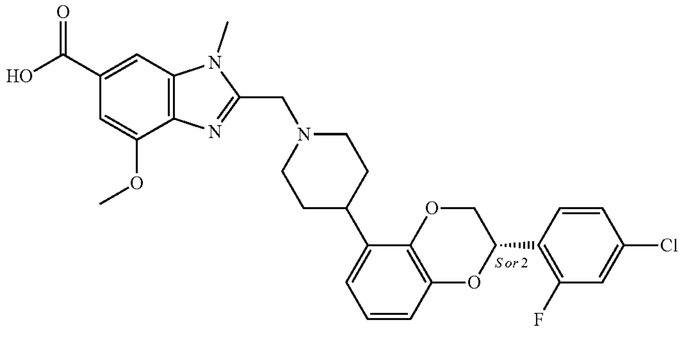 [SMILES: COc1cc(C(=O)O)cc2c1nc(CN1CCC(c3cccc4c3OC[C@H](c3ccc(Cl)cc3F)O4)CC1)n2C] |
| 5-259 | 2-(2-((4-(6-((4-Cyano-2-fluorobenzyl)oxy)pyridin-2-yl)piperidin-1-yl)methyl)-4-ethoxy-1-methyl-1H-benzo[d]imidazol-6-yl)acetic acid | 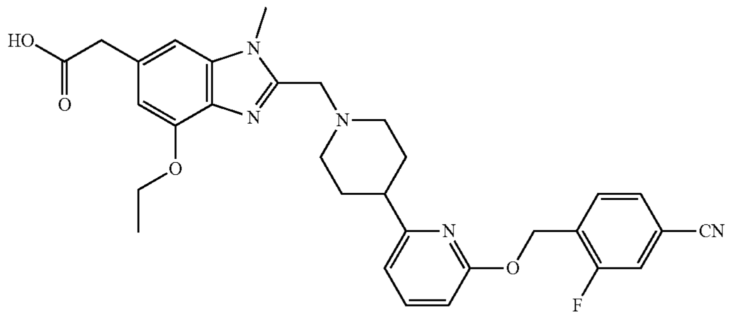 [SMILES: CCOc1cc(CC(=O)O)cc2c1nc(CN1CCC(c3cccc(OCc4ccc(C#N)cc4F)n3)CC1)n2C] |

TABLE 5A-continued

| Compound No. | Name | Structure |
|---|---|---|
| 5-260 | 4-(((6-(1-((4-ethoxy-1-methyl-6-(5-oxo-2,5-dihydro-1,2,4-oxadiazol-3-yl)-1H-benzo[d]imidazol-2-yl)methyl)piperidin-4-yl)pyridin-2-yl)oxy)methyl)-3-fluorobenzonitrile | 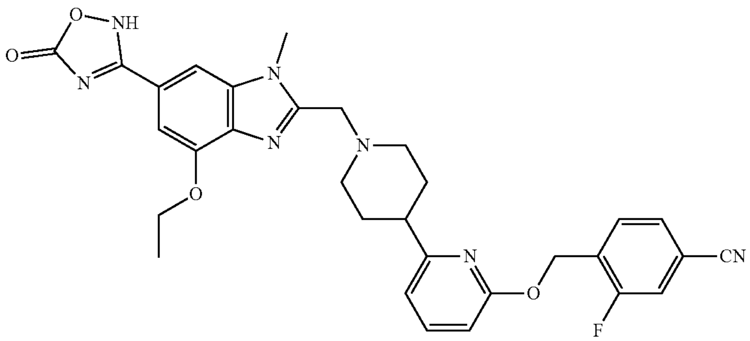 [SMILES: CCOc1cc(-c2nc(=O)o[nH]2)cc2c1nc(CN1CCC(c3cccc(OCc4ccc(C#N)cc4F)n3)CC1)n2C] |
| 5-261 | 2-((4-(6-((4-Cyano-2-fluorobenzyl)oxy)pyridin-2-yl)piperidin-1-yl)methyl)-4-ethoxy-1-methyl-N-(methylsulfonyl)-1H-benzo[d]imidazole-6-carboxamide | 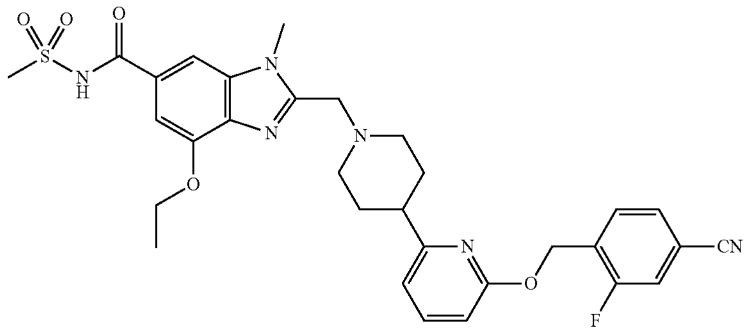 [SMILES: CCOc1cc(C(=O)NS(C)(=O)=O)cc2c1nc(CN1CCC(c3cccc(OCc4ccc(C#N)cc4F)n3)CC1)n2C] |
| 5-262 | rel-(R)-2-((4-(6-((4-Chloro-2-fluorobenzyl)oxy)pyridin-2-yl)piperidin-1-yl)methyl)-4-((1-fluoropropan-2-yl)oxy)-1-methyl-1H-benzo[d]imidazole-6-carboxylic acid | 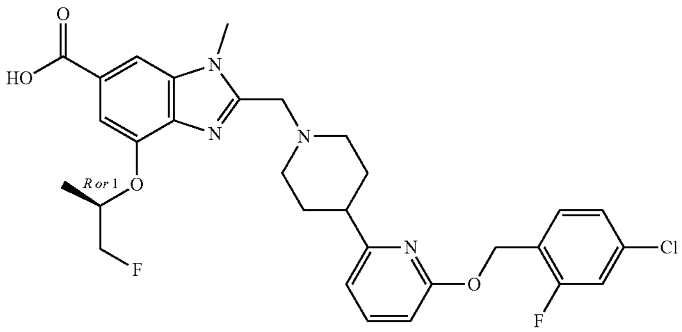 [SMILES: C[C@H](CF)Oc1cc(C(=O)O)cc2c1nc(CN1CCC(c3cccc(OCc4ccc(Cl)cc4F)n3)CC1)n2C] |
| 5-263 | rel-(S)-2-((4-(6-((4-Chloro-2-fluorobenzyl)oxy)pyridin-2-yl)piperidin-1-yl)methyl)-4-((1-fluoropropan-2-yl)oxy)-1-methyl-1H-benzo[d]imidazole-6-carboxylic acid | 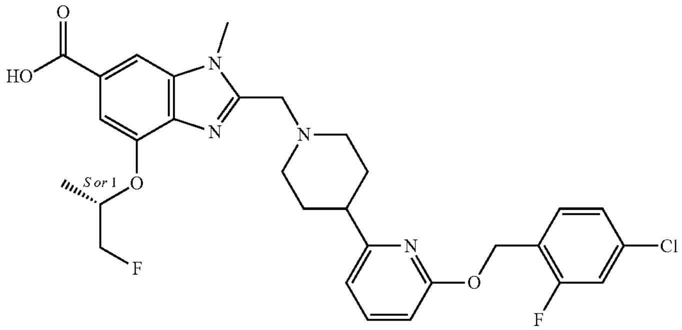 [SMILES: C[C@@H](CF)Oc1cc(C(=O)O)cc2c1nc(CN1CCC(c3cccc(OCc4ccc(Cl)cc4F)n3)CC1)n2C] |

TABLE 5A-continued

| Compound No. | Name | Structure |
| --- | --- | --- |
| 5-264 | (2-((4-(3-((4-chloro-2-fluorobenzyl)oxy)phenyl) piperidin-1-yl)methyl)-4-(difluoromethoxy)-1-methyl-1H-benzo[d]imidazol-6-yl)glycine | 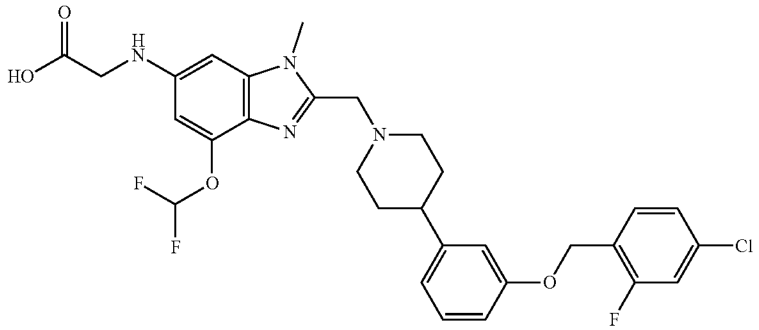 |
| 5-265 | (R)-2-((4-(3-(4-chloro-2-fluorophenyl)-2,3-dihydrobenzo[b][1,4]dioxin-5-yl)piperidin-1-yl)methyl)-4-ethoxy-1-methyl-1H-benzo[d]imidazole-6-carboxylic acid | 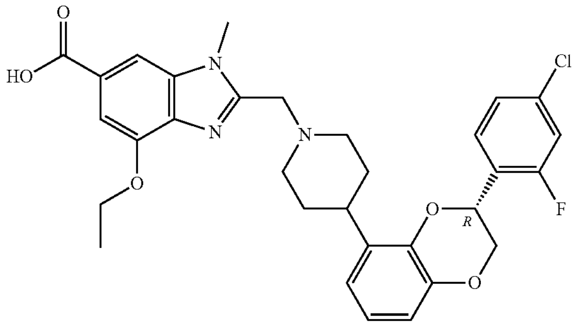 |
| 5-266 | (S)-2-((4-(3-(4-chloro-2-fluorophenyl)-2,3-dihydrobenzo[b][1,4]dioxin-5-yl)piperidin-1-yl)methyl)-4-ethoxy-1-methyl-1H-benzo[d]imidazole-6-carboxylic acid | 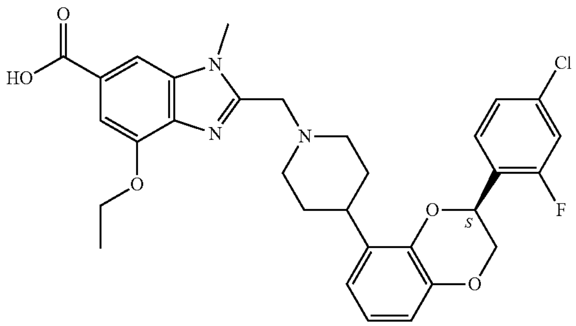 |
| 5-267 | (R)-2-((4-(3-(4-Chloro-2-fluorophenyl)-2,3-dihydrobenzo[b][1,4]dioxin-5-yl)piperidin-1-yl)methyl)-4-methoxy-1-methyl-1H-benzo[d]imidazole-6-carboxylic acid | 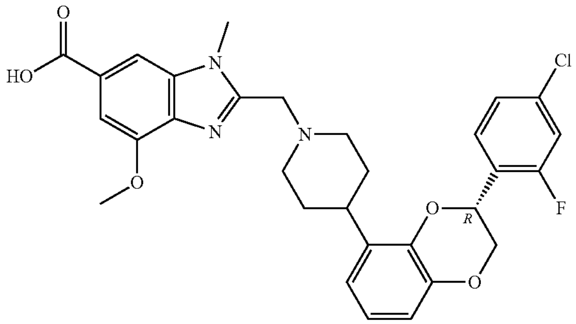 |

TABLE 5A-continued

| Compound No. | Name | Structure |
|---|---|---|
| 5-268 | (S)-2-((4-(3-(4-Chloro-2-fluorophenyl)-2,3-dihydrobenzo[b][1,4]dioxin-5-yl)piperidin-1-yl)methyl)-4-methoxy-1-methyl-1H-benzo[d]imidazole-6-carboxylic acid | 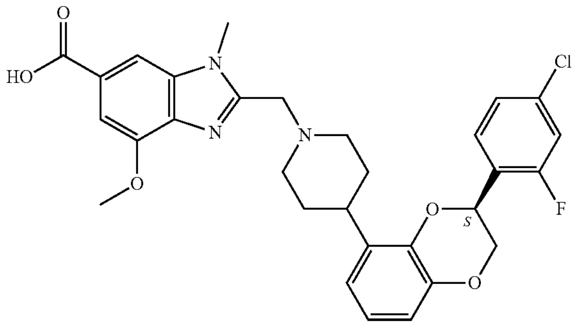 |
| 5-269 | (R)-2-((4-(2-(4-chloro-2-fluorophenyl)-2,3-dihydrobenzo[b][1,4]dioxin-5-yl)piperidin-1-yl)methyl)-4-ethoxy-1-methyl-1H-benzo[d]imidazole-6-carboxylic acid | 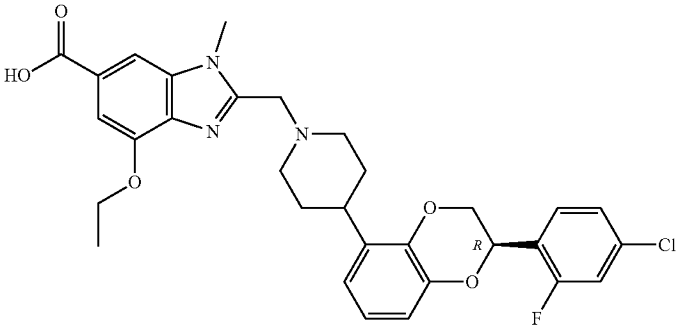 |
| 5-270 | (S)-2-((4-(2-(4-Chloro-2-fluorophenyl)-2,3-dihydrobenzo[b][1,4]dioxin-5-yl)piperidin-1-yl)methyl)-4-ethoxy-1-methyl-1H-benzo[d]imidazole-6-carboxylic acid | 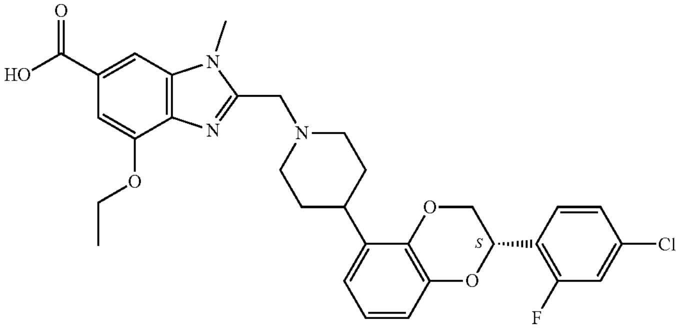 |
| 5-271 | (R)-2-((4-(2-(4-Chloro-2-fluorophenyl)-2,3-dihydrobenzo[b][1,4]dioxin-5-yl)piperidin-1-yl)methyl)-4-methoxy-1-methyl-1H-benzo[d]imidazole-6-carboxylic acid | 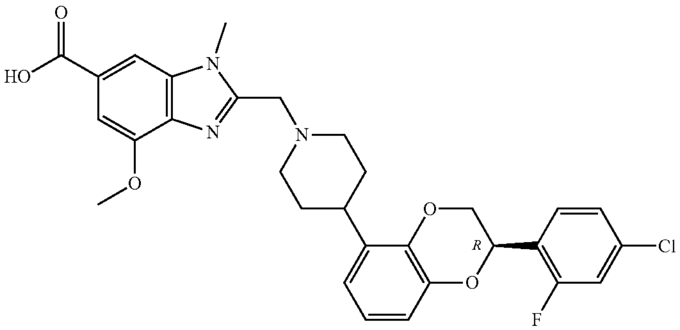 |

TABLE 5A-continued

| Compound No. | Name | Structure |
| --- | --- | --- |
| 5-272 | 2-((4-(6-((4-Chloro-2,5-difluorobenzyl)oxy)pyridin-2-yl)piperidin-1-yl)methyl)-4-methoxy-1-methyl-1H-benzo[d]imidazole-6-carboxylic acid | 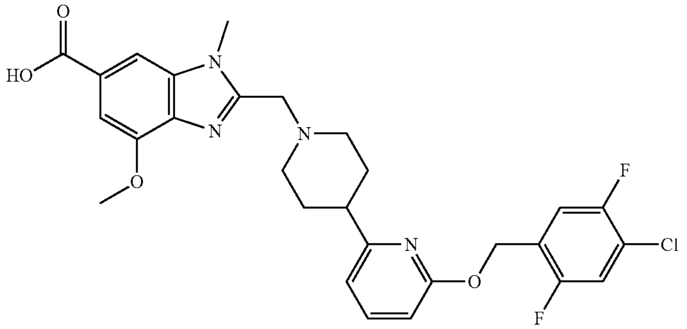 [SMILES: COc1cc(C(=O)O)cc2c1nc(CN1CCC(c3cccc(OCc4cc(F)c(Cl)cc4F)n3)CC1)n2C] |
| 5-273 | 4-(((6-(1-((4-ethoxy-1-methyl-6-(1H-tetrazol-5-yl)-1H-benzo[d]imidazol-2-yl)methyl)piperidin-4-yl)pyridin-2-yl)oxy)methyl)-3-fluorobenzonitrile | 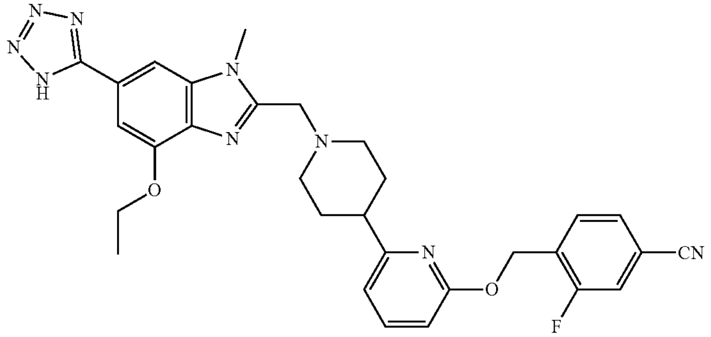 [SMILES: CCOc1cc(-c2nnn[nH]2)cc2c1nc(CN1CCC(c3cccc(OCc4ccc(C#N)cc4F)n3)CC1)n2C] |
| 5-274 | (S)-2-((4-(2-(4-Cyano-2-fluorophenyl)-2,3-dihydrobenzo[b][1,4]dioxin-5-yl)piperidin-1-yl)methyl)-4-methoxy-1-methyl-1H-benzo[d]imidazole-6-carboxylic acid | 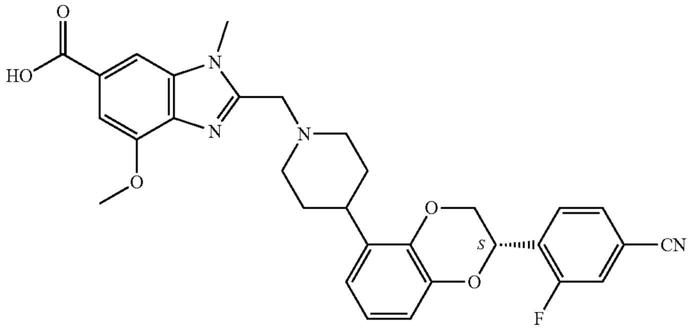 |
| 5-275 | 7-((4-(6-((4-Chloro-2-fluorobenzyl)oxy)pyridin-2-yl)piperidin-1-yl)methyl)-6-methyl-6H-[1,3]dioxolo[4',5':3,4]benzo[1,2-d]imidazole-4-carboxylic acid | 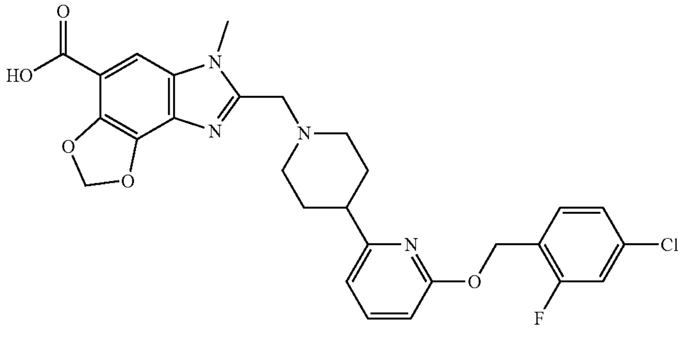 [SMILES: Cn1c(CN2CCC(c3cccc(OCc4ccc(Cl)cc4F)n3)CC2)nc2c3c(c(C(=O)O)cc21)OCO3] |

TABLE 5A-continued

| Compound No. | Name | Structure |
|---|---|---|
| 5-276 | (R)-2-((4-(2-(4-Cyano-2-fluorophenyl)-2,3-dihydrobenzo[b][1,4]dioxin-5-yl)piperidin-1-yl)methyl)-4-ethoxy-1-methyl-1H-benzo[d]imidazole-6-carboxylic acid | 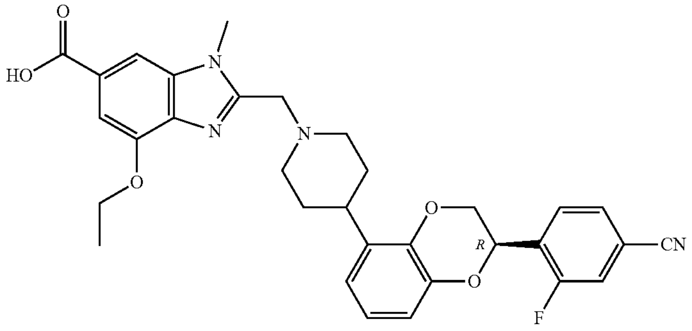 |
| 5-277 | (S)-2-((4-(2-(4-Cyano-2-fluorophenyl)-2,3-dihydrobenzo[b][1,4]dioxin-5-yl)piperidin-1-yl)methyl)-4-ethoxy-1-methyl-1H-benzo[d]imidazole-6-carboxylic acid | 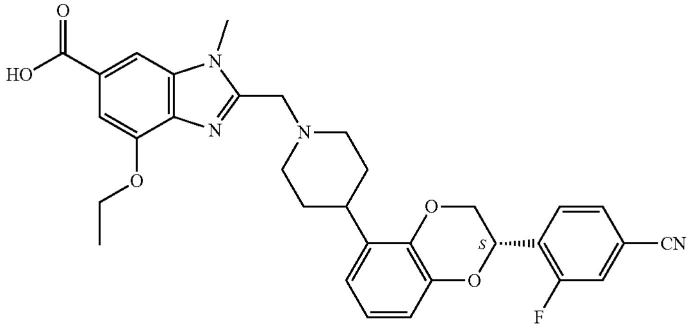 |
| 5-278 | (R)-2-((4-(2-(4-Cyano-2-fluorophenyl)-2,3-dihydrobenzo[b][1,4]dioxin-5-yl)piperidin-1-yl)methyl)-4-methoxy-1-methyl-1H-benzo[d]imidazole-6-carboxylic acid | 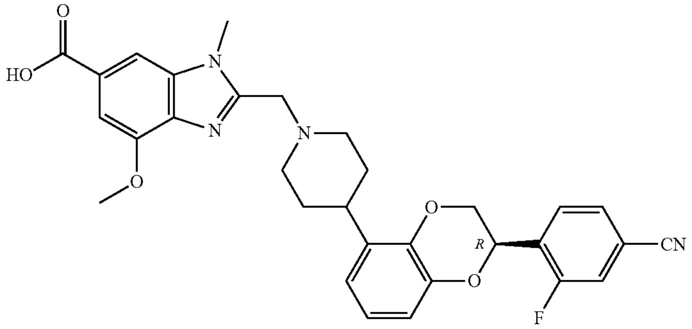 |
| 5-279 | (S)-2-((4-(6-((4-Chloro-2-fluorobenzyl)oxy)pyridin-2-yl)piperidin-1-yl)methyl)-4-methoxy-1-(oxetan-2-ylmethyl)-6-(1H-tetrazol-5-yl)-1H-benzo[d]imidazole | 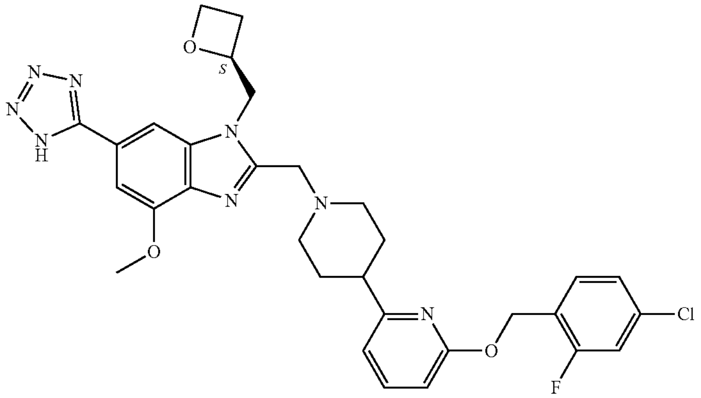 |

TABLE 5A-continued

| Compound No. | Name | Structure |
|---|---|---|
| 5-280 | 2-((4-(6-((4-chloro-2-fluorobenzyl)oxy)pyridin-2-yl)piperidin-1-yl)methyl)-4-methoxy-N,1-dimethyl-1H-benzo[d]imidazole-6-carboxamide | 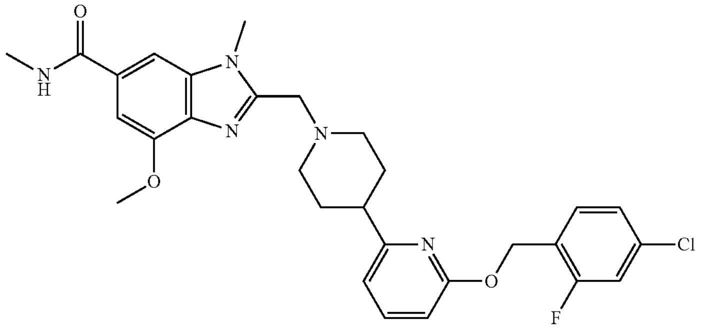 [SMILES: CNC(=O)c1cc(OC)c2nc(CN3CCC(c4cccc(OCc5ccc(Cl)cc5F)n4)CC3)n(C)c2c1] |
| 5-281 | 5-(2-((4-(3-((4-Chloro-2-fluorobenzyl)oxy)phenyl) piperidin-1-yl)methyl)-4-(difluoromethoxy)-1-methyl-1H-benzo[d]imidazol-6-yl)-1,2,5-thiadiazolidin-3-one 1,1-dioxide | 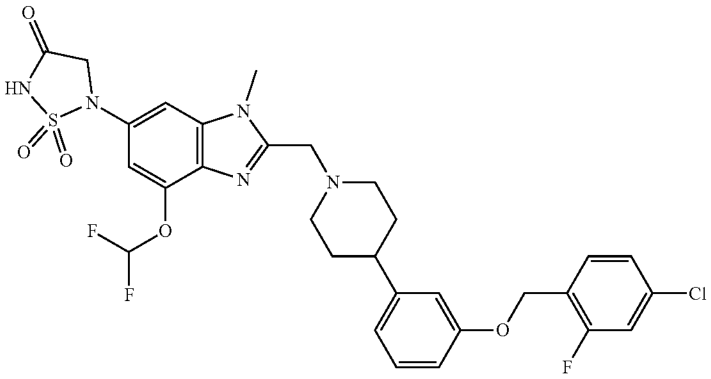 [SMILES: Cn1c(CN2CCC(c3cccc(OCc4ccc(Cl)cc4F)c3)CC2)nc2c(OC(F)F)cc(N3CC(=O)NS3(=O)=O)cc21] |
| 5-282 | 2-(4-(6-((4-Chloro-2-fluorobenzyl)oxy)pyridin-2-yl)-2,5-difluorobenzyl)-4-methoxy-1-methyl-1H-benzo[d]imidazole-6-carboxylic acid | 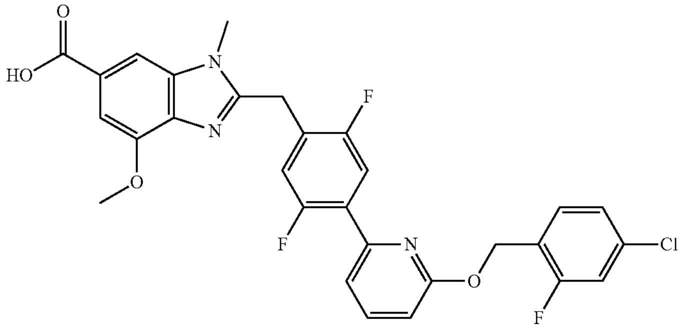 [SMILES: COc1cc(C(=O)O)cc2c1nc(Cc1cc(F)c(-c3cccc(OCc4ccc(Cl)cc4F)n3)cc1F)n2C] |
| 5-283 | 2-((4-(6-((4-Cyano-2,3-dihydrobenzofuran-7-yl)methoxy)pyridin-2-yl)piperidin-1-yl)methyl)-4-methoxy-1-methyl-1H-benzo[d]imidazole-6-carboxylic acid | 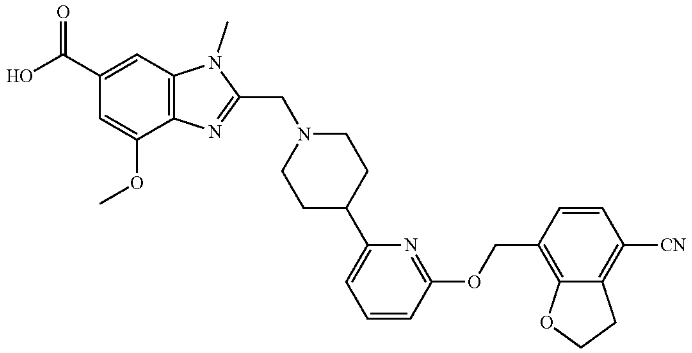 [SMILES: COc1cc(C(=O)O)cc2c1nc(CN1CCC(c3cccc(OCc4ccc(C#N)c5c4OCC5)n3)CC1)n2C] |

TABLE 5A-continued

| Compound No. | Name | Structure |
|---|---|---|
| 5-284 | 2-((4-(3-((4-Chloro-2-fluorobenzyl)oxy)phenyl) piperidin-1-yl)methyl)-4-(ethoxy-1,1-d2)-1-methyl-1H-benzo[d]imidazole-6-carboxylic acid | 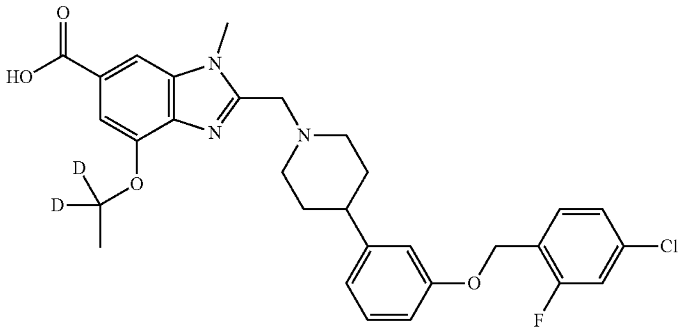 [SMILES: [2H]C([2H])(C)Oc1cc(C(=O)O)cc2c1nc(CN1CCC(c3cccc(OCc4ccc(Cl)cc4F)c3)CC1)n2C] |
| 5-285 | 2-((4-(6-((4-Cyano-2-fluorophenyl)methoxy-d2)pyridin-2-yl)piperidin-1-yl)methyl)-4-(ethoxy-1,1-d2)-1-methyl-1H-benzo[d]imidazole-6-carboxylic acid | 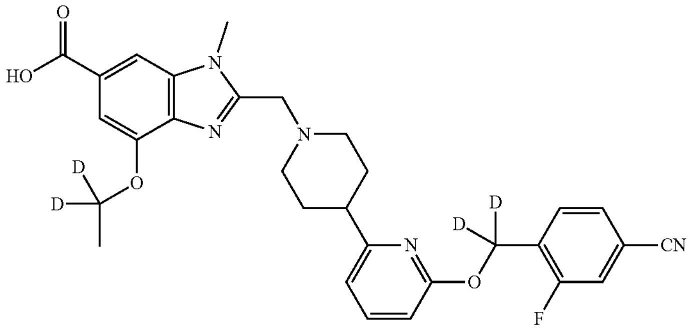 [SMILES: [2H]C([2H])(C)Oc1cc(C(=O)O)cc2c1nc(CN1CCC(c3cccc(OC([2H])([2H])c4ccc(C#N)cc4F)n3)CC1)n2C] |
| 5-286 | 2-((4-(6-((4-Chloro-2-fluorophenyl)methoxy-d2)pyridin-2-yl)piperidin-1-yl)methyl)-4-(ethoxy-1,1-d2)-1-methyl-1H-benzo[d]imidazole-6-carboxylic acid | 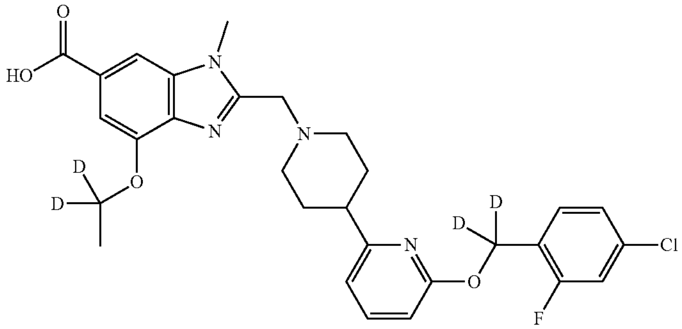 [SMILES: [2H]C([2H])(C)Oc1cc(C(=O)O)cc2c1nc(CN1CCC(c3cccc(OC([2H])([2H])c4ccc(Cl)cc4F)n3)CC1)n2C] |
| 5-287 | (S)-2-((4-(3-(4-Cyano-2-fluorophenyl)-2,3-dihydrobenzo[b][1,4]dioxin-5-yl)piperidin-1-yl)methyl)-4-ethoxy-1-methyl-1H-benzo[d]imidazole-6-carboxylic acid | 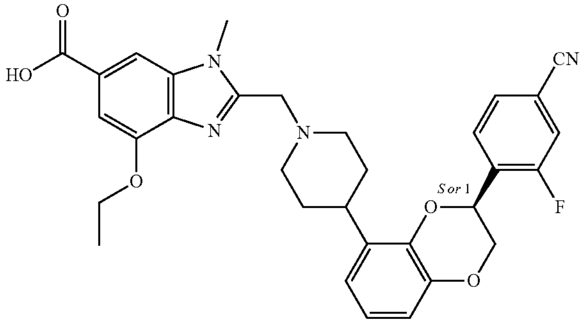 [SMILES: CCOc1cc(C(=O)O)cc2c1nc(CN1CCC(c3cccc4c3O[C@@H](c3ccc(C#N)cc3F)CO4)CC1)n2C] |

TABLE 5A-continued

| Compound No. | Name | Structure |
|---|---|---|
| 5-288 | (R)-2-((4-(3-(4-Cyano-2-fluorophenyl)-2,3-dihydrobenzo[b][1,4]dioxin-5-yl)piperidin-1-yl)methyl)-4-ethoxy-1-methyl-1H-benzo[d]imidazole-6-carboxylic acid | 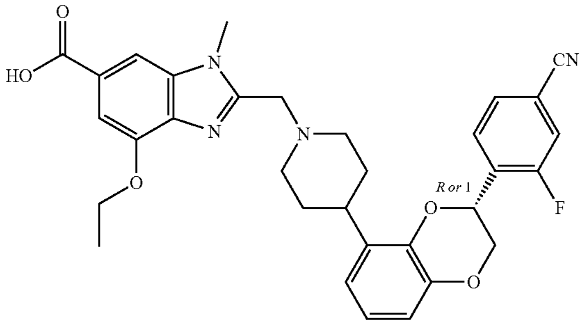 [SMILES: CCOc1cc(C(=O)O)cc2c1nc(CN1CCC(c3cccc4c3O[C@H](c3ccc(C#N)cc3F)CO4)CC1)n2C] |
| 5-289 | 2-((4-(6-((4-Cyano-2-fluorobenzyl)oxy)pyridin-2-yl)piperidin-1-yl)methyl)-3-methyl-7,8-dihydro-3H-[1,4]dioxino[2',3':3,4]benzo[1,2-d]imidazole-5-carboxylic acid | 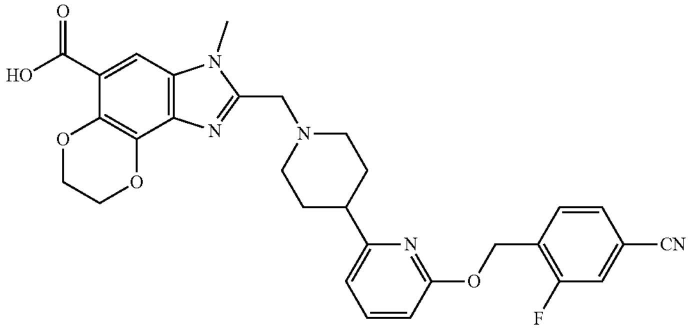 [SMILES: Cn1c(CN2CCC(c3cccc(OCc4ccc(C#N)cc4F)n3)CC2)nc2c3c(c(C(=O)O)cc21)OCCO3] |
| 5-290 | 2-((4-((6-((4-Cyano-2-fluorophenoxy)methyl)pyridin-2-yl)oxy)piperidin-1-yl)methyl)-4-ethoxy-1-methyl-1H-benzo[d]imidazole-6-carboxylic acid | 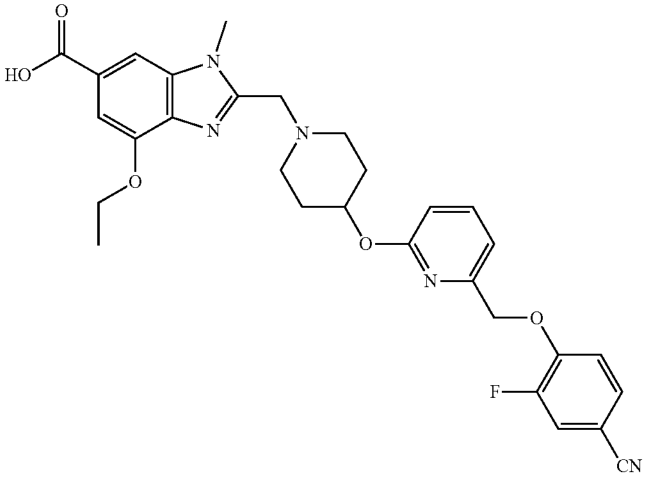 [SMILES: CCOc1cc(C(=O)O)cc2c1nc(CN1CCC(Oc3cccc(COc4ccc(C#N)cc4F)n3)CC1)n2C] |
| 5-291 | 2-((4-(6-((4-Cyano-2-fluorobenzyl)oxy)pyridin-2-yl)piperidin-1-yl)methyl)-4-(2-hydroxyethoxy)-1-methyl-1H-benzo[d]imidazole-6-carboxylic acid | 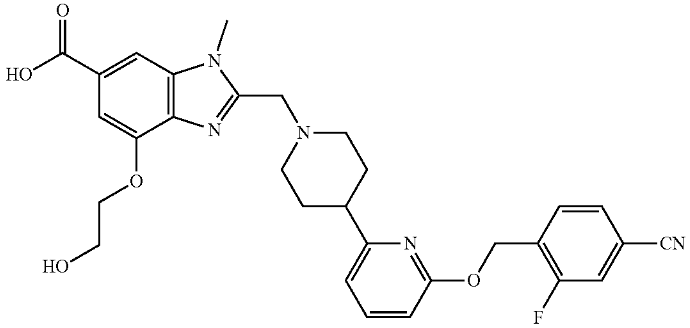 |

TABLE 5A-continued

| Compound No. | Name | Structure |
|---|---|---|
| 5-292 | 2-(4-(6-((4-Chloro-2-fluorobenzyl)oxy)pyridin-2-yl)-2-fluorobenzyl)-4-methoxy-1-methyl-1H-benzo[d]imidazole-6-carboxylic acid | 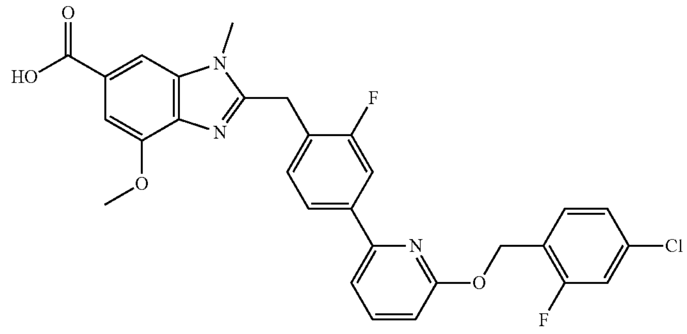 [SMILES: COc1cc(C(=O)O)cc2c1nc(Cc1ccc(-c3cccc(OCc4ccc(Cl)cc4F)n3)cc1F)n2C] |
| 5-293 | 2-(4-(6-((4-Cyano-2-fluorobenzyl)oxy)pyridin-2-yl)-2-fluorobenzyl)-4-ethoxy-1-methyl-1H-benzo[d]imidazole-6-carboxylic acid | 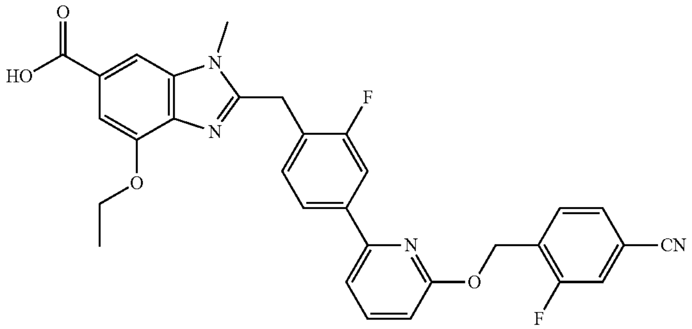 [SMILES: CCOc1cc(C(=O)O)cc2c1nc(Cc1ccc(-c3cccc(OCc4ccc(C#N)cc4F)n3)cc1F)n2C] |
| 5-294 | (S)-2-((4-(3-(4-Cyano-2-fluorophenyl)-2,3-dihydrobenzo[b][1,4]dioxin-5-yl)piperidin-1-yl)methyl)-4-(2-fluoroethoxy)-1-methyl-1H-benzo[d]imidazole-6-carboxylic acid | 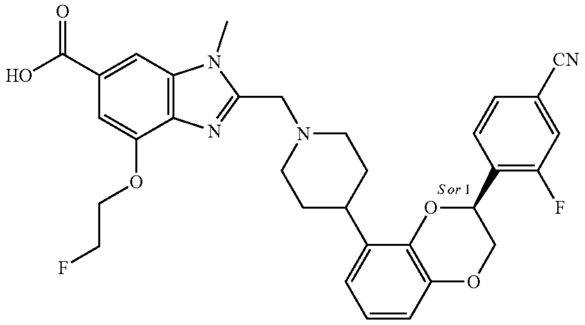 [SMILES: Cn1c(CN2CCC(c3cccc4c3O[C@@H](c3ccc(C#N)cc3F)CO4)CC2)nc2c(OCCF)cc(C(=O)O)cc21] |
| 5-295 | 2-((4-(6-((4-Cyano-2-fluorobenzyl)oxy)pyridin-2-yl)piperidin-1-yl)methyl)-4-(ethoxy-1,1-d2)-1-methyl-1H-benzo[d]imidazole-6-carboxylic acid | 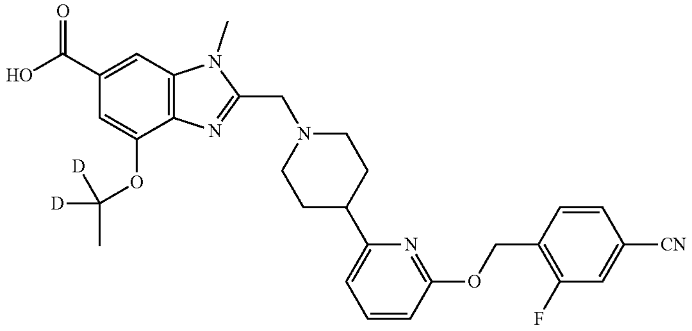 |

TABLE 5A-continued

| Compound No. | Name | Structure |
|---|---|---|
| 5-296 | 2-((4-(6-((4-Chloro-2-fluorobenzyl)oxy)pyridin-2-yl)piperidin-1-yl)methyl)-4-(ethoxy-1,1-d2)-1-methyl-1H-benzo[d]imidazole-6-carboxylic acid | 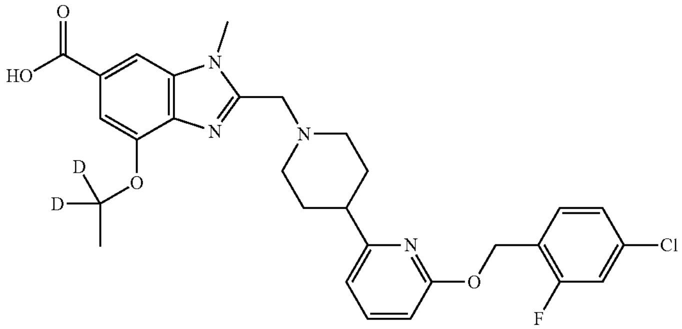 [SMILES: [2H]C([2H])(C)Oc1cc(C(=O)O)cc2c1nc(CN1CCC(c3cccc(OCc4ccc(Cl)cc4F)n3)CC1)n2C] |
| 5-297 | 2-((4-(6-((4-Chloro-2,3-dihydrobenzofuran-7-yl)methoxy)pyridin-2-yl)piperidin-1-yl)methyl)-4-methoxy-1-methyl-1H-benzo[d]imidazole-6-carboxylic acid | 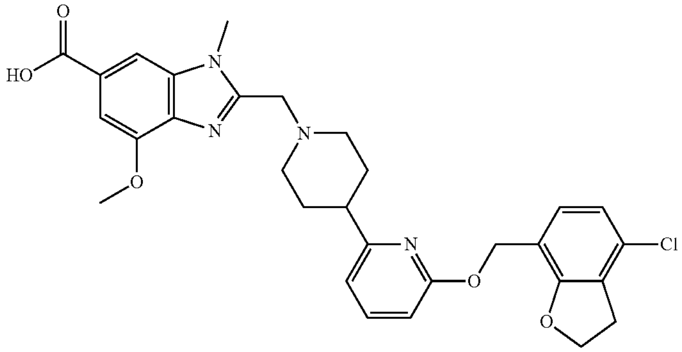 [SMILES: COc1cc(C(=O)O)cc2c1nc(CN1CCC(c3cccc(OCc4ccc(Cl)c5c4OCC5)n3)CC1)n2C] |
| 5-298 | 2-((4-(6-((4-Cyano-2-fluorobenzyl)oxy)pyridin-2-yl)piperidin-1-yl)methyl)-4-ethoxy-1-methyl-1H-benzo[d]imidazole-6-carboxylic acid | 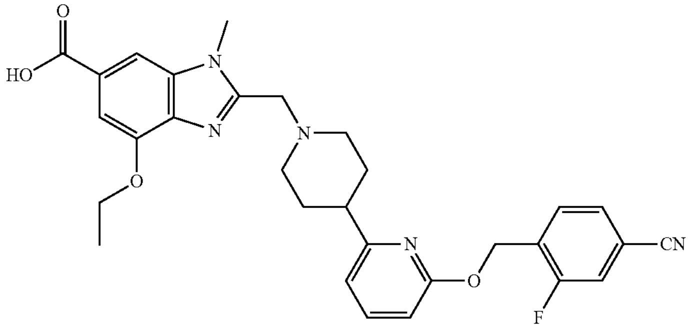 |
| 5-299 | (S)-2-((4-(3-(4-chloro-2-fluorophenyl)-2,3-dihydrobenzo[b][1,4]dioxin-5-yl)piperidin-1-yl)methyl)-4-(2-fluoroethoxy)-1-methyl-1H-benzo[d]imidazole-6-carboxylic acid | 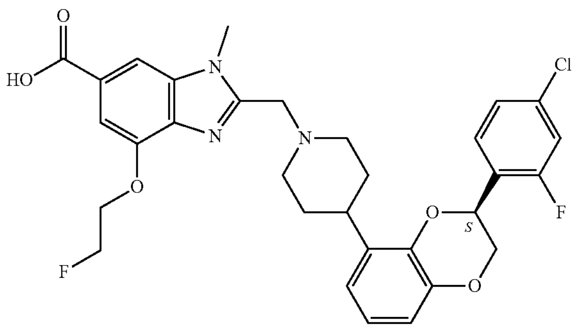 |

TABLE 5A-continued

| Compound No. | Name | Structure |
|---|---|---|
| 5-300 | (R)-2-((4-(2-(4-Cyano-2-fluorophenyl)-2,3-dihydrobenzo[b][1,4]dioxin-5-yl)piperidin-1-yl)methyl)-4-(difluoromethoxy)-1-methyl-1H-benzo[d]imidazole-6-carboxylic acid | 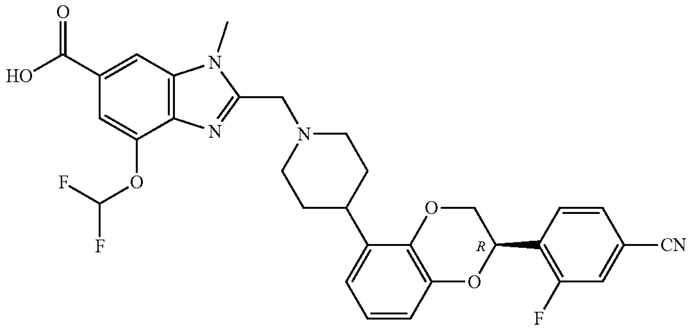 |
| 5-301 | 2-((4-(6-((4-Cyano-2-fluorobenzyl)oxy)pyridin-2-yl)piperidin-1-yl)methyl)-5-fluoro-4-methoxy-1-methyl-1H-benzo[d]imidazole-6-carboxylic acid | 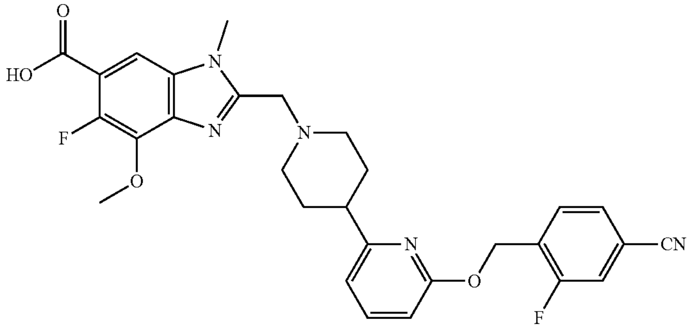 [SMILES: COc1c(F)c(C(=O)O)cc2c1nc(CN1CCC(c3cccc(OCc4ccc(C#N)cc4F)n3)CC1)n2C] |
| 5-302 | 2-((4-(6-((4-Chloro-2-fluorobenzyl)oxy)pyridin-2-yl)piperidin-1-yl)methyl)-7-fluoro-4-methoxy-1-methyl-1H-benzo[d]imidazole-6-carboxylic acid | 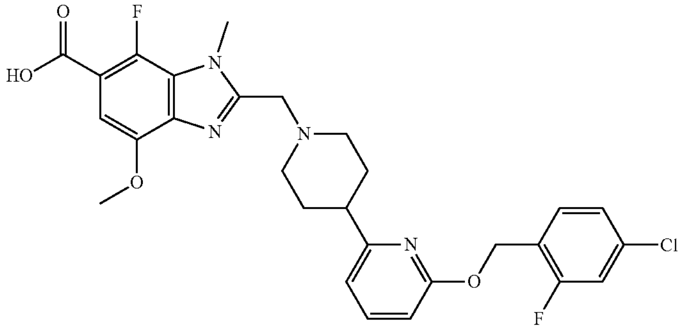 [SMILES: COc1cc(C(=O)O)c(F)c2c1nc(CN1CCC(c3cccc(OCc4ccc(Cl)cc4F)n3)CC1)n2C] |
| 5-303 | 2-((4-(6-((4-Cyano-2-fluorobenzyl)oxy)pyridin-2-yl)piperidin-1-yl)methyl)-7-fluoro-4-methoxy-1-methyl-1H-benzo[d]imidazole-6-carboxylic acid | 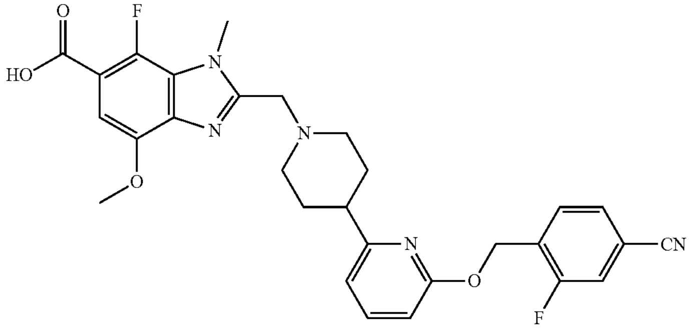 [SMILES: COc1cc(C(=O)O)c(F)c2c1nc(CN1CCC(c3cccc(OCc4ccc(C#N)cc4F)n3)CC1)n2C] |

TABLE 5A-continued

| Compound No. | Name | Structure |
|---|---|---|
| 5-304 | 2-(4-(6-((4-Cyano-2-fluorobenzyl)oxy)pyridin-2-yl)-2,5-difluorobenzyl)-4-methoxy-1-methyl-1H-benzo[d]imidazole-6-carboxylic acid | 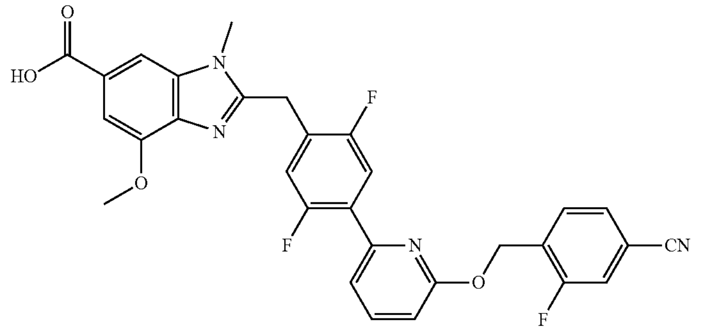 |
| 5-305 | 2-((4-(6-((4-(Difluoromethyl)-2-fluorobenzyl)oxy)pyridin-2-yl)piperidin-1-yl)methyl)-4-methoxy-1-methyl-1H-benzo[d]imidazole-6-carboxylic acid | 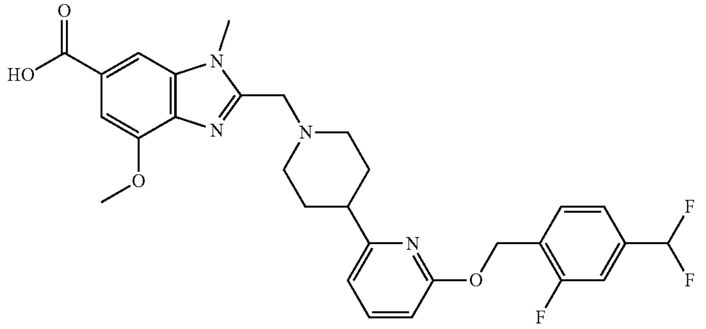 [SMILES: COc1cc(C(=O)O)cc2c1nc(CN1CCC(c3cccc(OCc4ccc(C(F)F)cc4F)n3)CC1)n2C] |
| 5-306 | 4-Methoxy-2-((4-(6-((2-methoxy-4-(trifluoromethyl)benzyl)oxy)pyridin-2-yl)piperidin-1-yl)methyl)-1-methyl-1H-benzo[d]imidazole-6-carboxylic acid | 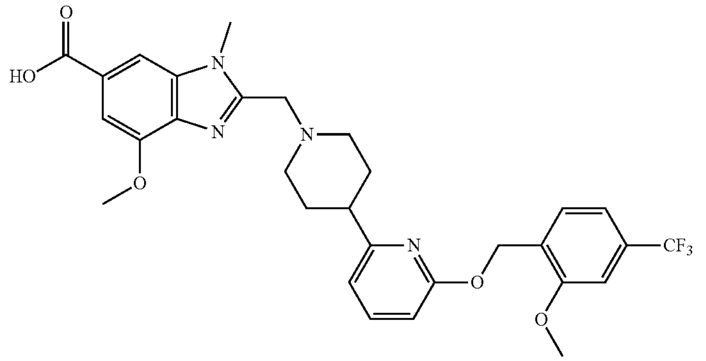 [SMILES: COc1cc(C(F)(F)F)ccc1COc1cccc(C2CCN(Cc3nc4c(OC)cc(C(=O)O)cc4n3C)CC2)n1] |
| 5-307 | 2-((4-(6-((4-Chloro-2-fluorobenzyl)oxy)pyridin-2-yl)piperidin-1-yl)methyl)-4-hydroxy-1-methyl-1H-benzo[d]imidazole-6-carboxylic acid | 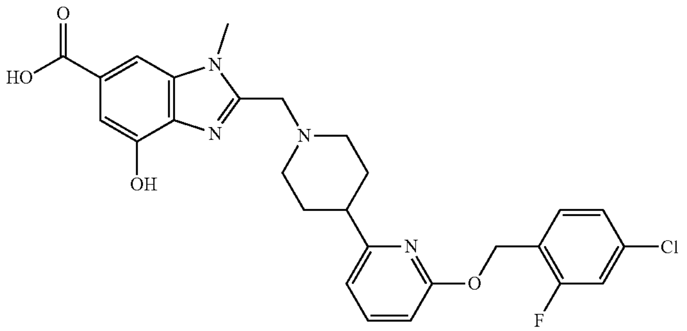 |

TABLE 5A-continued

| Compound No. | Name | Structure |
|---|---|---|
| 5-308 | 2-((4-(6-((4-Cyano-2-fluorobenzyl)oxy)pyridin-2-yl)piperidin-1-yl)methyl)-4-methoxy-1-methyl-1H-benzo[d]imidazole-6-carboxylic acid | 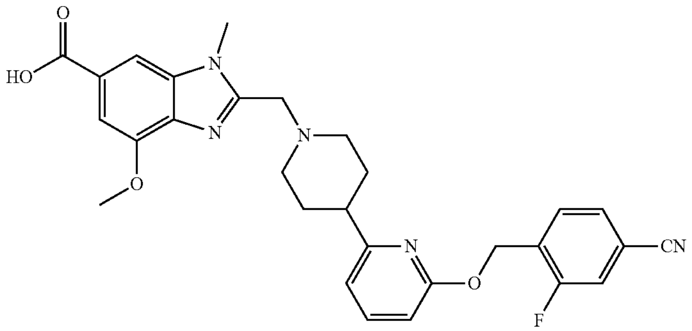 [SMILES: COc1cc(C(=O)O)cc2c1nc(CN1CCC(c3cccc(OCc4ccc(C#N)cc4F)n3)CC1)n2C] |
| 5-309 | (S)-2-((4-(2-(5-Chloropyridin-2-yl)-2-methylbenzo[d][1,3]dioxol-4-yl)piperidin-1-yl)methyl)-4-(2-methoxyethoxy)-1-methyl-1H-benzo[d]imidazole-6-carboxylic acid | 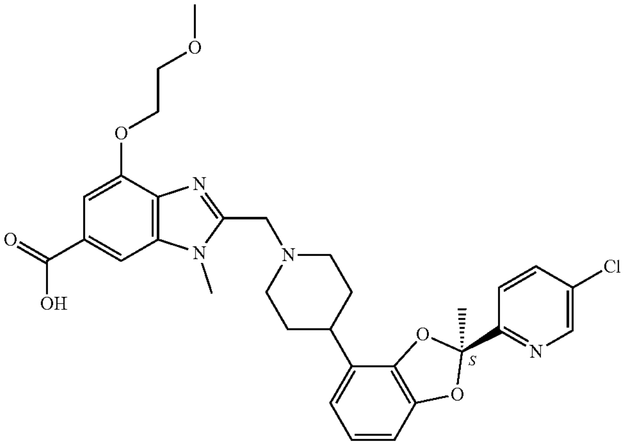 |
| 5-310 | (R)-2-((4-(3-(4-cyano-2-fluorophenyl)-2,3-dihydrobenzo[b][1,4]dioxin-5-yl)piperidin-1-yl)methyl)-4-methoxy-1-methyl-1H-benzo[d]imidazole-6-carboxylic acid | 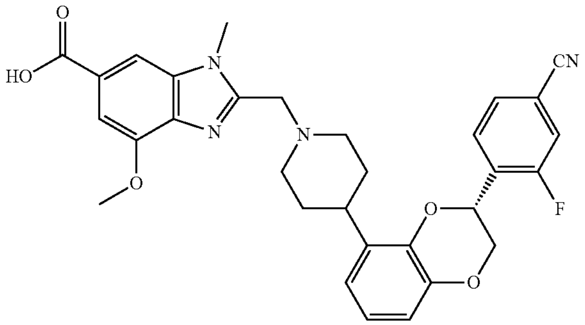 [SMILES: COc1cc(C(=O)O)cc2c1nc(CN1CCC(c3cccc4c3O[C@H](c3ccc(C#N)cc3F)CO4)CC1)n2C] |
| 5-311 | 2-((4-(6-((4-chloro-2-fluorobenzyl)oxy)pyridin-2-yl)piperidin-1-yl)methyl)-3-methyl-7,8-dihydro-3H-[1,4]dioxino[2',3':3,4]benzo[1,2-d]imidazole-5-carboxylic acid | 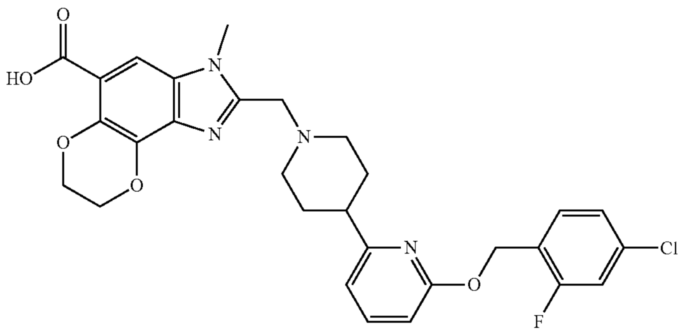 [SMILES: Cn1c(CN2CCC(c3cccc(OCc4ccc(Cl)cc4F)n3)CC2)nc2c3c(c(C(=O)O)cc21)OCCO3] |

TABLE 5A-continued

| Compound No. | Name | Structure |
|---|---|---|
| 5-312 | (R)-2-((4-(6-((4-Cyano-2-fluorobenzyl)oxy)pyridin-2-yl)piperidin-1-yl)methyl)-4-(1-fluoroethoxy)-1-methyl-1H-benzo[d]imidazole-6-carboxylic acid | 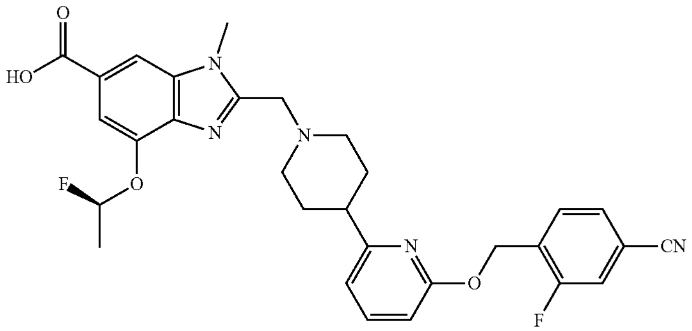 [SMILES: C[C@@H](F)Oc1cc(C(=O)O)cc2c1nc(CN1CCC(c3cccc(OCc4ccc(C#N)cc4F)n3)CC1)n2C] |
| 5-313 | (S)-2-((4-(6-((4-Cyano-2-fluorobenzyl)oxy)pyridin-2-yl)piperidin-1-yl)methyl)-4-(1-fluoroethoxy)-1-methyl-1H-benzo[d]imidazole-6-carboxylic acid | 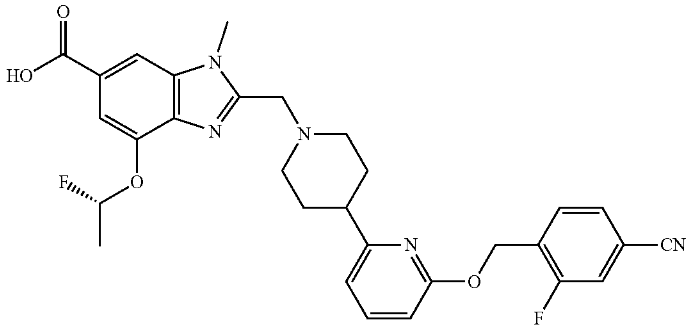 |
| 5-314 | (S)-2-((4-(3-(4-Cyano-2-fluorophenyl)-2,3-dihydrobenzo[b][1,4]dioxin-5-yl)piperidin-1-yl)methyl)-4-methoxy-1-methyl-1H-benzo[d]imidazole-6-carboxylic acid | 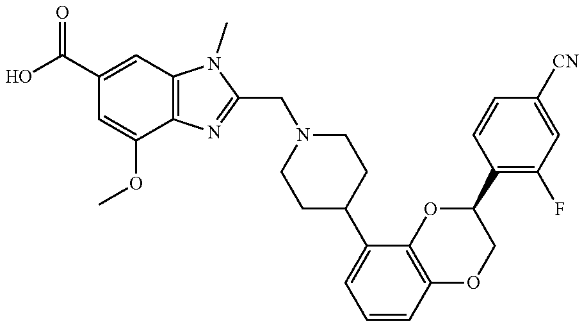 [SMILES: COc1cc(C(=O)O)cc2c1nc(CN1CCC(c3cccc4c3O[C@@H](c3ccc(C#N)cc3F)CO4)CC1)n2C] |
| 5-315 | (R)-2-((4-(3-(4-Cyano-2-fluorophenyl)-2,3-dihydrobenzo[b][1,4]dioxin-5-yl)piperidin-1-yl)methyl)-4-(2-fluoroethoxy)-1-methyl-1H-benzo[d]imidazole-6-carboxylic acid | 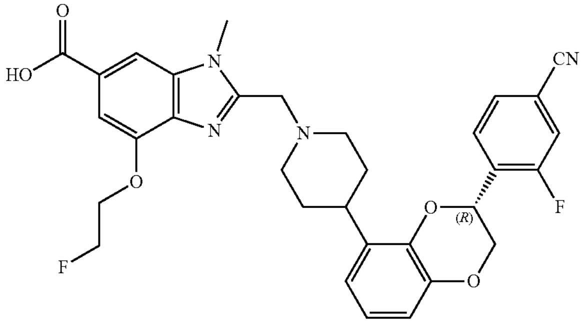 |

TABLE 5A-continued

| Compound No. | Name | Structure |
|---|---|---|
| 5-316 | 5-(2-((4-(6-((4-Chloro-2-fluorobenzyl)oxy)pyridin-2-yl)piperidin-1-yl)methyl)-4-(difluoromethoxy)-1-methyl-1H-benzo[d]imidazol-6-yl)isoxazol-3-ol | 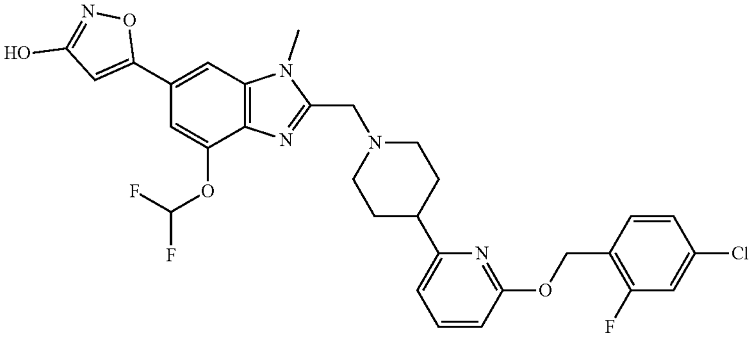 [SMILES: Cn1c(CN2CCC(c3cccc(OCc4ccc(Cl)cc4F)n3)CC2)nc2c(OC(F)F)cc(-c3cc(O)no3)cc21] |
| 5-317 | 2-((4-(6-((4-Cyano-2-fluorobenzyl)oxy)pyridin-2-yl)piperidin-1-yl)methyl)-4-((1r,3r)-3-methoxycyclobutoxy)-1-methyl-1H-benzo[d]imidazole-6-carboxylic acid | 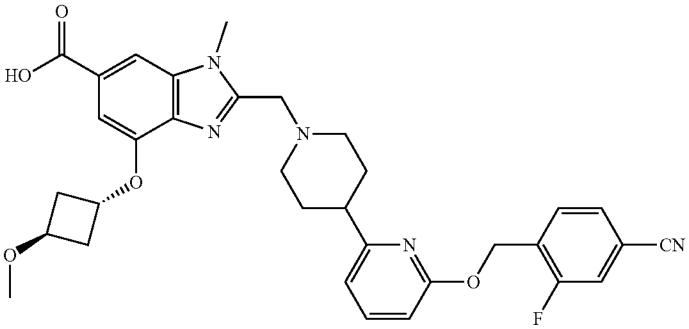 [SMILES: CO[C@H]1C[C@H](Oc2cc(C(=O)O)cc3c2nc(CN2CCC(c4cccc(OCc5ccc(C#N)cc5F)n4)CC2)n3C)C1] |
| 5-318 | 2-((4-(6-((4-Cyano-2-fluorobenzyl)oxy)pyridin-2-yl)piperidin-1-yl)methyl)-4-((1s,3s)-3-methoxycyclobutoxy)-1-methyl-1H-benzo[d]imidazole-6-carboxylic acid | 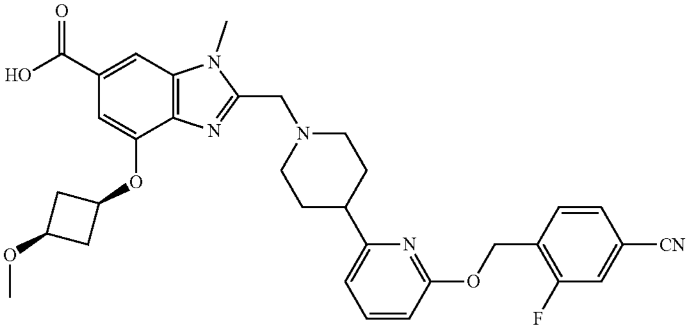 [SMILES: CO[C@H]1C[C@@H](Oc2cc(C(=O)O)cc3c2nc(CN2CCC(c4cccc(OCc5ccc(C#N)cc5F)n4)CC2)n3C)C1] |
| 5-319 | 2-((4-(6-((4-Cyano-2-fluorobenzyl)oxy)pyridin-2-yl)piperidin-1-yl)methyl)-1-methyl-4-propoxy-1H-benzo[d]imidazole-6-carboxylic acid | 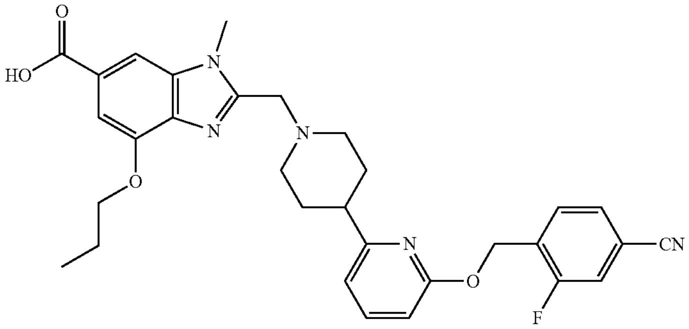 [SMILES: CCCOc1cc(C(=O)O)cc2c1nc(CN1CCC(c3cccc(OCc4ccc(C#N)cc4F)n3)CC1)n2C] |

TABLE 5A-continued

| Compound No. | Name | Structure |
| --- | --- | --- |
| 5-320 | 2-((4-(6-((4-Chloro-2-fluorobenzyl)oxy)pyridin-2-yl)piperidin-1-yl)methyl)-4-((1-hydroxypropan-2-yl)oxy)-1-methyl-1H-benzo[d]imidazole-6-carboxylic acid | 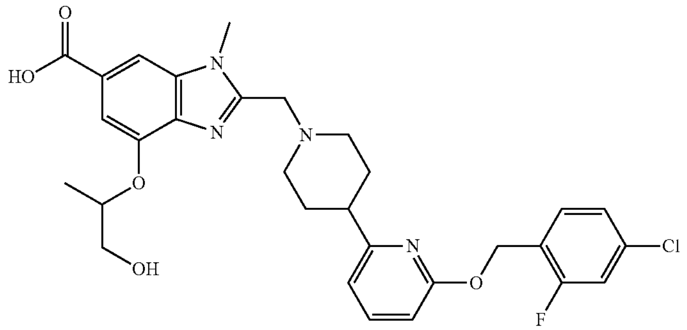 [SMILES: CC(CO)Oc1cc(C(=O)O)cc2c1nc(CN1CCC(c3cccc(OCc4ccc(Cl)cc4F)n3)CC1)n2C] |
| 5-321 | 2-((4-(6-((4-Chloro-2-fluorophenyl)methoxy-d2)pyridin-2-yl)piperidin-1-yl)methyl-d2)-4-(difluoromethoxy)-1-methyl-1H-benzo[d]imidazole-6-carboxylic acid | 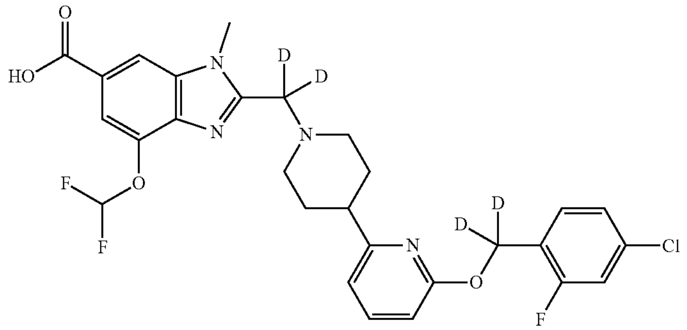 [SMILES: [2H]C([2H])(Oc1cccc(C2CCN(C([2H])([2H])c3nc4c(OC(F)F)cc(C(=O)O)cc4n3C)CC2)n1)c1ccc(Cl)cc1F] |
| 5-322 | 2-((4-(6-((4-chloro-2-fluorobenzyl)oxy)pyridin-2-yl)piperidin-1-yl)methyl)-1-methyl-4-propoxy-1H-benzo[d]imidazole-6-carboxylic acid | 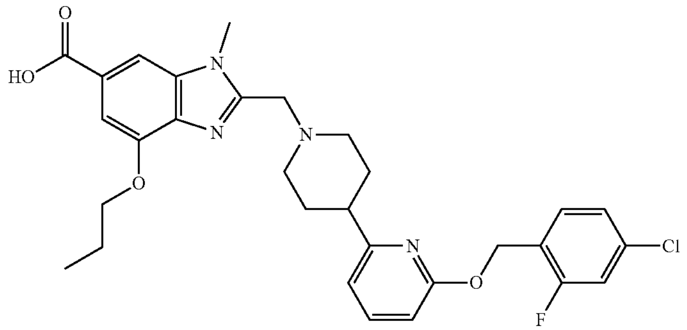 [SMILES: CCCOc1cc(C(=O)O)cc2c1nc(CN1CCC(c3cccc(OCc4ccc(Cl)cc4F)n3)CC1)n2C] |
| 5-323 | 2-((4-(6-((4-Cyano-2-fluorobenzyl)oxy)pyridin-2-yl)piperidin-1-yl)methyl)-7-methoxy-3-methyl-3H-imidazo[4,5-b]pyridine-5-carboxylic acid | 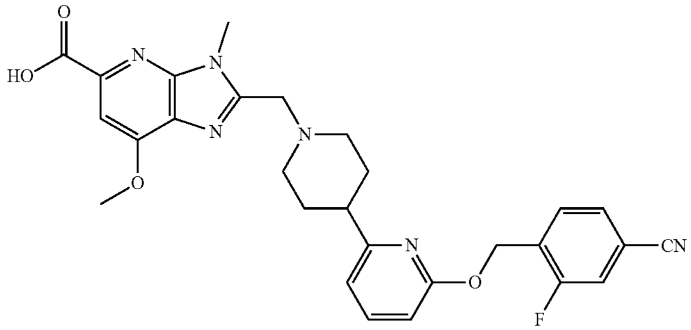 [SMILES: COc1cc(C(=O)O)nc2c1nc(CN1CCC(c3cccc(OCc4ccc(C#N)cc4F)n3)CC1)n2C] |

TABLE 5A-continued

| Compound No. | Name | Structure |
|---|---|---|
| 5-324 | 2-((4-(6-((4-Chloro-2-fluorobenzyl)oxy)pyridin-2-yl)piperidin-1-yl)methyl)-7-methoxy-3-methyl-3H-imidazo[4,5-b]pyridine-5-carboxylic acid | 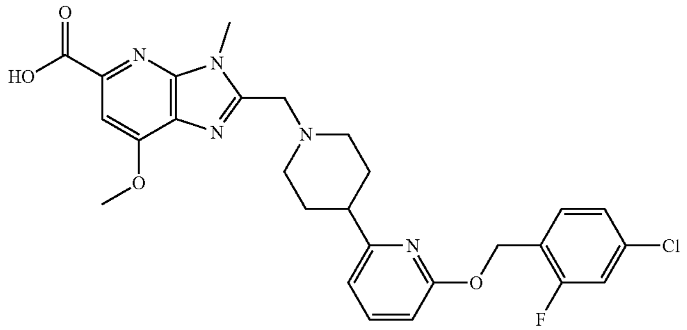 |
| 5-325 | 2-((4-(6-((4-Chloro-2-fluorobenzyl)oxy)pyridin-2-yl)piperidin-1-yl)methyl)-4-((1r,3r)-3-methoxycyclobutoxy)-1-methyl-1H-benzo[d]imidazole-6-carboxylic acid | 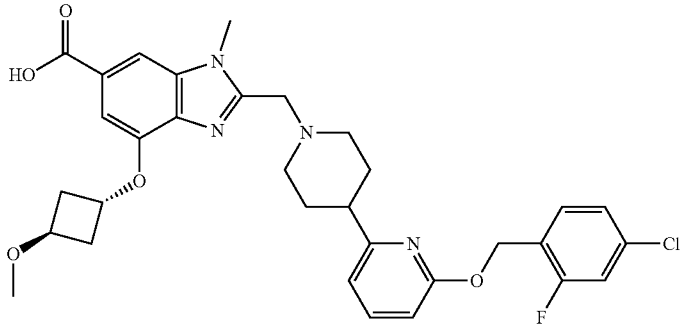 [SMILES: CO[C@H]1C[C@H](Oc2cc(C(=O)O)cc3c2nc(CN2CCC(c4cccc(OCc5ccc(Cl)cc5F)n4)CC2)n3C)C1] |
| 5-326 | (S)-2-((4-(2-(4-Cyano-2-fluorophenyl)-2,3-dihydrobenzo[b][1,4]dioxin-5-yl)piperidin-1-yl)methyl)-4-(difluoromethoxy)-1-methyl-1H-benzo[d]imidazole-6-carboxylic acid | 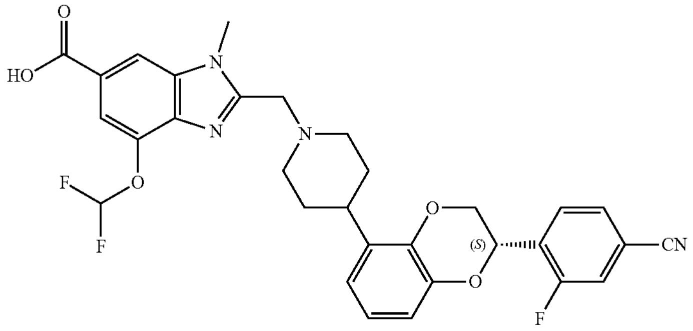 |
| 5-327 | 2-((4-(6-((4-Cyano-2,5-difluorobenzyl)oxy)pyridin-2-yl)piperidin-1-yl)methyl)-4-methoxy-1-methyl-1H-benzo[d]imidazole-6-carboxylic acid | 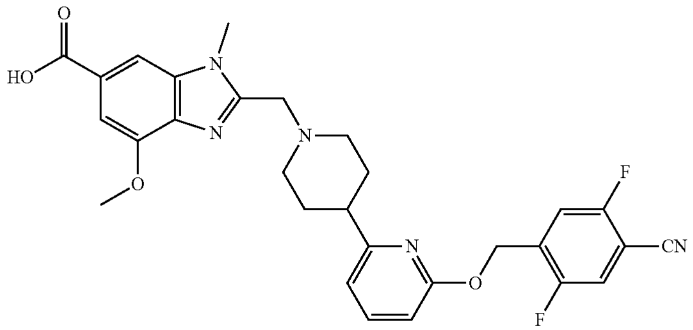 [SMILES: COc1cc(C(=O)O)cc2c1nc(CN1CCC(c3cccc(OCc4cc(F)c(C#N)cc4F)n3)CC1)n2C] |

TABLE 5A-continued

| Compound No. | Name | Structure |
|---|---|---|
| 5-328 | 2-((4-(6-((4-Chloro-2-fluorobenzyl)oxy)pyridin-2-yl)piperidin-1-yl)methyl)-7-(difluoromethoxy)-3-methyl-3H-imidazo[4,5-b]pyridine-5-carboxylic acid | 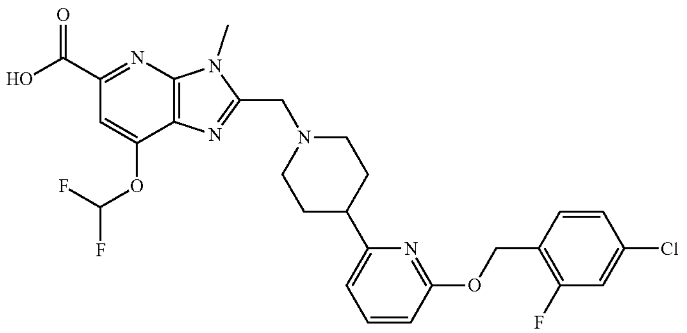 [SMILES: Cn1c(CN2CCC(c3cccc(OCc4ccc(Cl)cc4F)n3)CC2)nc2c(OC(F)F)cc(C(=O)O)nc21] |
| 5-329 | (S)-2-((4-(6-((4-chloro-2-fluorobenzyl)oxy)pyridin-2-yl)piperidin-1-yl)methyl)-4-(1,2-difluoroethoxy)-1-methyl-1H-benzo[d]imidazole-6-carboxylic acid | 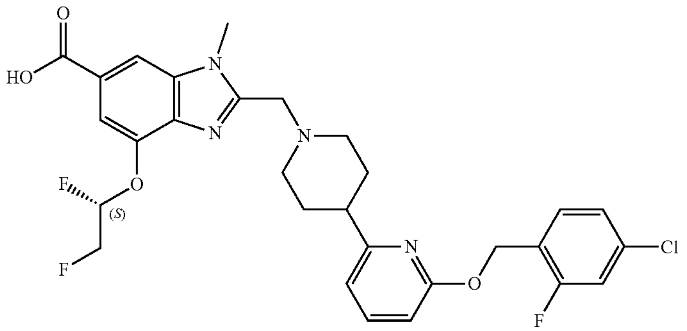 |
| 5-330 | (R)-2-((4-(6-((4-chloro-2-fluorobenzyl)oxy)pyridin-2-yl)piperidin-1-yl)methyl)-4-(1,2-difluoroethoxy)-1-methyl-1H-benzo[d]imidazole-6-carboxylic acid | 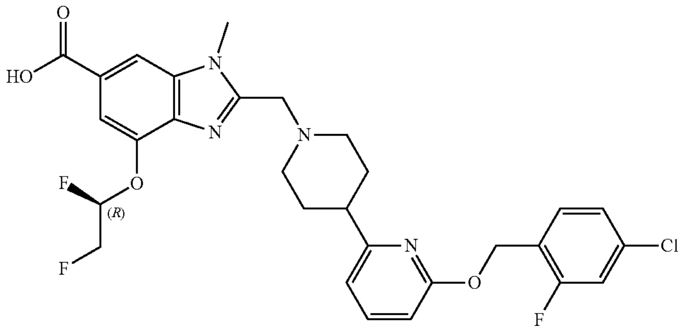 |
| 5-331 | 2-((4-(6-((4-Chloro-2,3-dihydrobenzofuran-7-yl)methoxy)pyridin-2-yl)piperidin-1-yl)methyl)-4-(difluoromethoxy)-1-methyl-1H-benzo[d]imidazole-6-carboxylic acid | 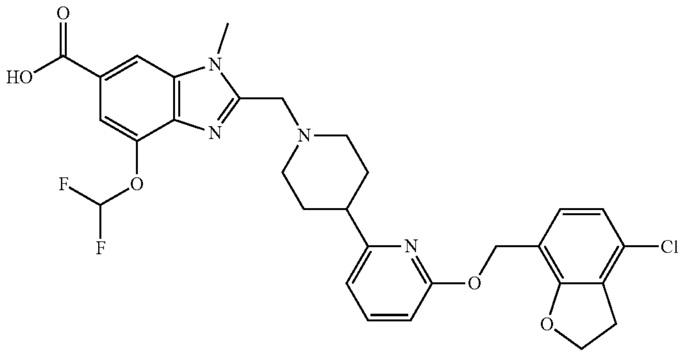 [SMILES: Cn1c(CN2CCC(c3cccc(OCc4ccc(Cl)c5c4OCC5)n3)CC2)nc2c(OC(F)F)cc(C(=O)O)cc21] |

TABLE 5A-continued

| Compound No. | Name | Structure |
|---|---|---|
| 5-332 | (S)-2-((4-(3-(4-chloro-2-fluorophenyl)-2,3-dihydrobenzo[b][1,4]dioxin-5-yl)piperidin-1-yl)methyl)-4-(2-fluoroethoxy)-1-methyl-1H-benzo[d]imidazole-6-carboxylic acid | 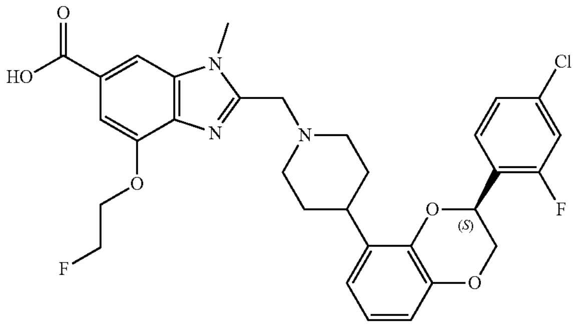 |
| 5-333 | (R)-2-((4-(3-(4-chloro-2-fluorophenyl)-2,3-dihydrobenzo[b][1,4]dioxin-5-yl)piperidin-1-yl)methyl)-4-(2-fluoroethoxy)-1-methyl-1H-benzo[d]imidazole-6-carboxylic acid | 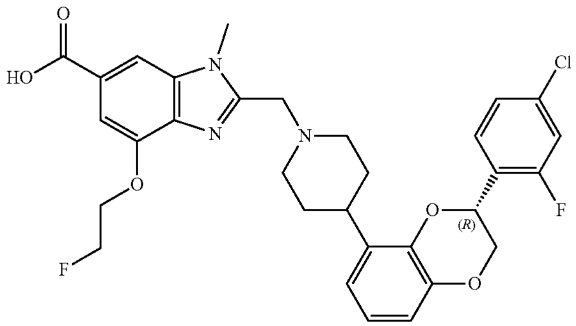 |
| 5-334 | (S)-2-((4-(3-(4-Chloro-2-fluorophenyl)-2,3-dihydrobenzo[b][1,4]dioxin-5-yl)piperidin-1-yl)methyl)-4-(difluoromethoxy)-1-methyl-1H-benzo[d]imidazole-6-carboxylic acid | 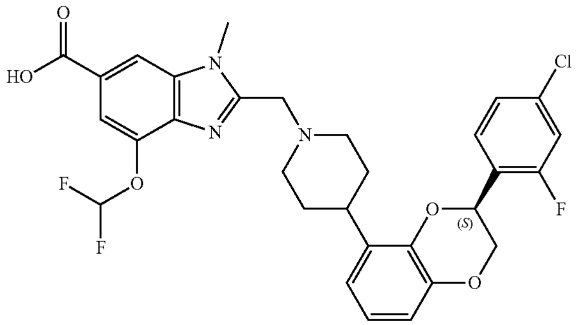 |
| 5-335 | (R)-2-((4-(3-(4-Chloro-2-fluorophenyl)-2,3-dihydrobenzo[b][1,4]dioxin-5-yl)piperidin-1-yl)methyl)-4-(difluoromethoxy)-1-methyl-1H-benzo[d]imidazole-6-carboxylic acid | 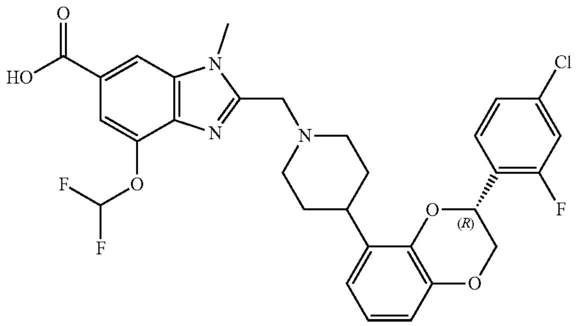 |

TABLE 5A-continued

| Compound No. | Name | Structure |
|---|---|---|
| 5-336 | 2-((4-(6-((4-Cyano-2-fluorobenzyl)oxy)pyridin-2-yl)piperidin-1-yl)methyl)-6-fluoro-7-methoxy-1-methyl-1H-benzo[d]imidazole-5-carboxylic acid | 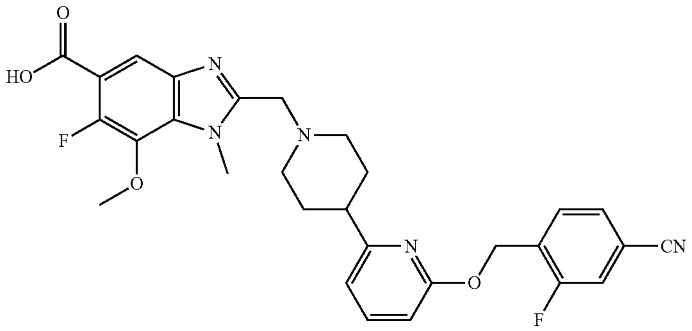 [SMILES: COc1c(F)c(C(=O)O)cc2nc(CN3CCC(c4cccc(OCc5ccc(C#N)cc5F)n4)CC3)n(C)c12] |
| 5-337 | 2-((4-(6-((4-Chloro-2-fluorobenzyl)oxy)pyridin-2-yl)piperidin-1-yl)methyl)-5-fluoro-4-methoxy-1-methyl-1H-benzo[d]imidazole-6-carboxylic acid | 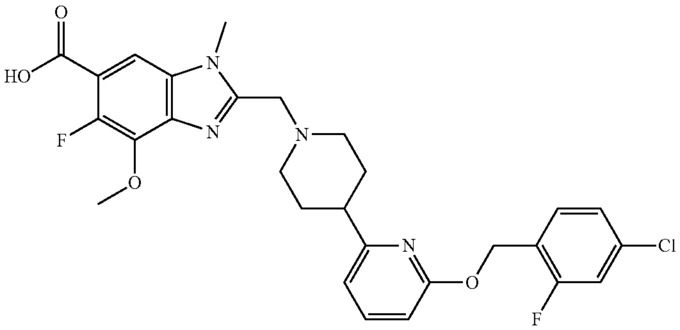 [SMILES: COc1c(F)c(C(=O)O)cc2c1nc(CN1CCC(c3cccc(OCc4ccc(Cl)cc4F)n3)CC1)n2C] |
| 5-338 | 2-((4-(6-((4-chloro-2-fluorobenzyl)oxy)pyridin-2-yl)piperidin-1-yl)methyl)-6-fluoro-7-methoxy-1-methyl-1H-benzo[d]imidazole-5-carboxylic acid | 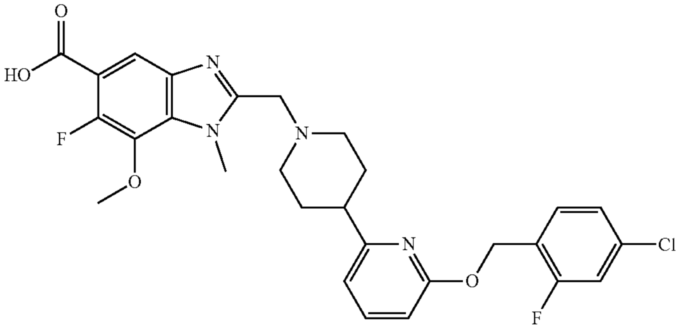 [SMILES: COc1c(F)c(C(=O)O)cc2nc(CN3CCC(c4cccc(OCc5ccc(Cl)cc5F)n4)CC3)n(C)c12] |
| 5-339 | 2-((4-(3-((4-Cyano-2-fluorobenzyl)oxy)-4-fluorophenyl)piperidin-1-yl)methyl)-7-fluoro-4-methoxy-1-methyl-1H-benzo[d]imidazole-6-carboxylic acid | 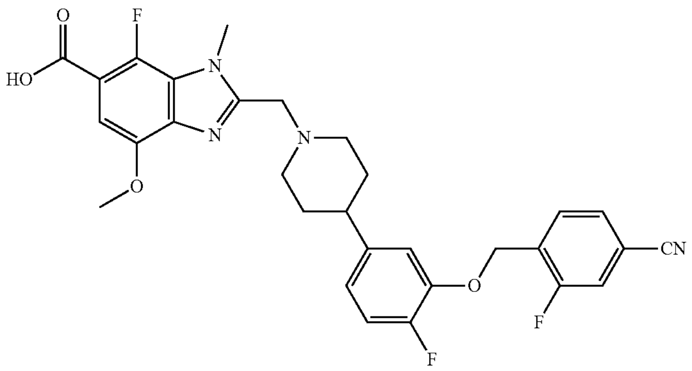 [SMILES: COc1cc(C(=O)O)c(F)c2c1nc(CN1CCC(c3ccc(F)c(OCc4ccc(C#N)cc4F)c3)CC1)n2C] |

TABLE 5A-continued

| Compound No. | Name | Structure |
|---|---|---|
| 5-340 | 2-((4-(3-((4-Chloro-2-fluorobenzyl)oxy)-4-fluorophenyl)piperidin-1-yl)methyl)-7-fluoro-4-methoxy-1-methyl-1H-benzo[d]imidazole-6-carboxylic acid | 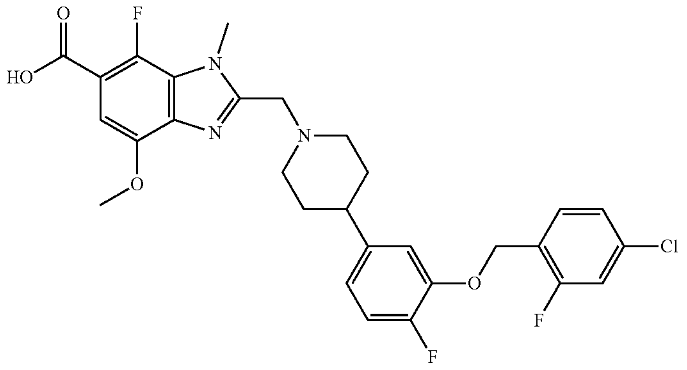 [SMILES: COc1cc(C(=O)O)c(F)c2c1nc(CN1CCC(c3ccc(F)c(OCc4ccc(Cl)cc4F)c3)CC1)n2C] |
| 5-341 | 2-((4-(6-((4-Chloro-2-fluorobenzyl)oxy)pyridin-2-yl)piperidin-1-yl)methyl)-7-hydroxy-1-methyl-1H-benzo[d]imidazole-6-carboxylic acid | 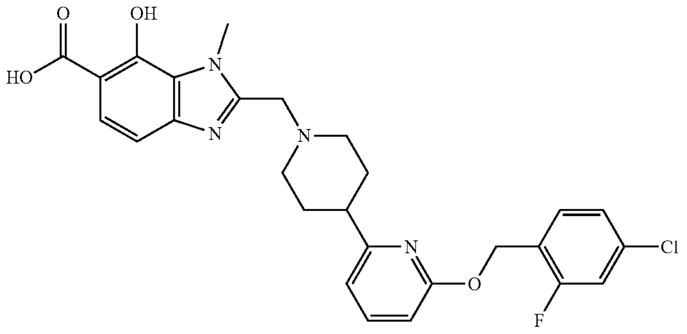 [SMILES: Cn1c(CN2CCC(c3cccc(OCc4ccc(Cl)cc4F)n3)CC2)nc2ccc(C(=O)O)c(O)c21] |
| 5-342 | 2-(4-(6-((4-cyano-2-fluorobenzyl)oxy)pyridin-2-yl)-2-fluorobenzyl)-4-methoxy-1-methyl-1H-benzo[d]imidazole-6-carboxylic acid | 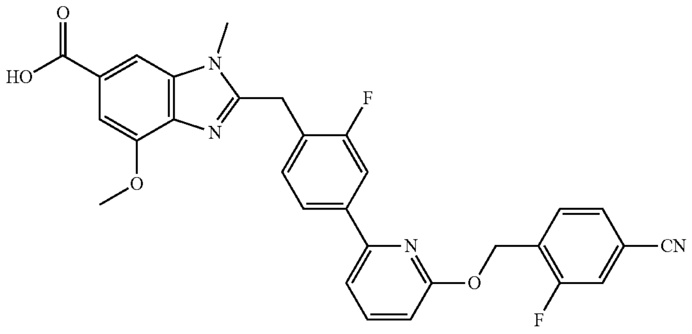 [SMILES: COc1cc(C(=O)O)cc2c1nc(Cc1ccc(-c3cccc(OCc4ccc(C#N)cc4F)n3)cc1F)n2C] |
| 5-343 | 2-((4-(6-((4-Chloro-2-fluorobenzyl)oxy)pyridin-2-yl)piperidin-1-yl)methyl)-4-(2-hydroxyethoxy)-1-methyl-1H-benzo[d]imidazole-6-carboxylic acid | 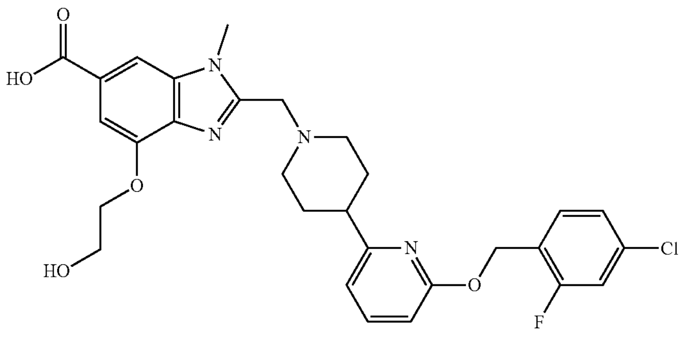 [SMILES: Cn1c(CN2CCC(c3cccc(OCc4ccc(Cl)cc4F)n3)CC2)nc2c(OCCO)cc(C(=O)O)cc21] |

TABLE 5A-continued

| Compound No. | Name | Structure |
|---|---|---|
| 5-344 | 2-((4-(6-((4-Cyano-2-methoxybenzyl)oxy)pyridin-2-yl)piperidin-1-yl)methyl)-4-methoxy-1-methyl-1H-benzo[d]imidazole-6-carboxylic acid | 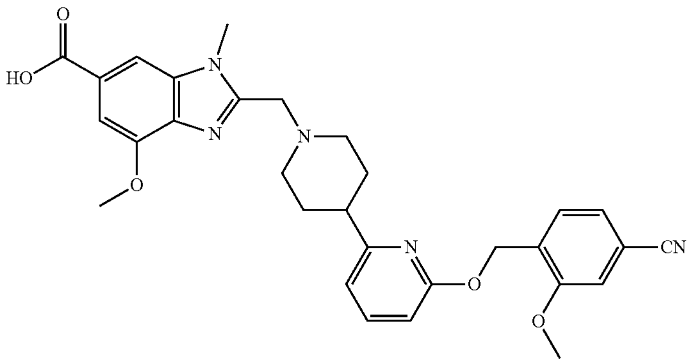 [SMILES: COc1cc(C#N)ccc1COc1cccc(C2CCN(Cc3nc4c(OC)cc(C(=O)O)cc4n3C)CC2)n1] |
| 5-345 | 2-((4-(6-((4-Chloro-2-fluorobenzyl)oxy)pyridin-2-yl)piperidin-1-yl)methyl)-4-hydroxy-1-methyl-1H-benzo[d]imidazole-5-carboxylic acid | 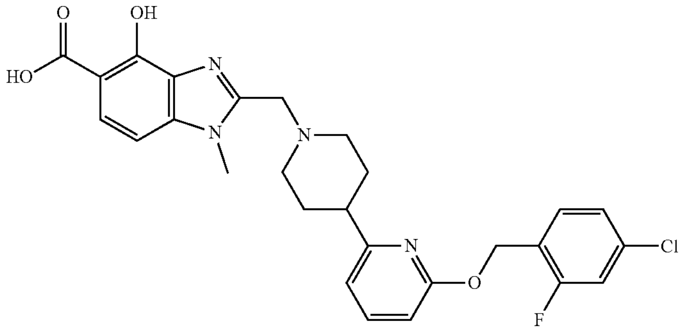 [SMILES: Cn1c(CN2CCC(c3cccc(OCc4ccc(Cl)cc4F)n3)CC2)nc2c(O)c(C(=O)O)ccc21] |
| 5-346 | 2-((4-(6-((4-Chloro-2-fluorobenzyl)oxy)pyridin-2-yl)piperidin-1-yl)methyl)-4-(fluoromethoxy)-1-(fluoromethyl)-1H-benzo[d]imidazole-6-carboxylic acid | 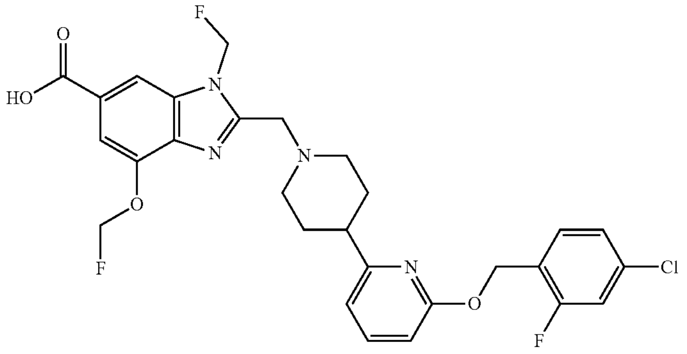 |
| 5-347 | 2-((4-(6-((4-Chloro-2-fluorobenzyl)oxy)pyridin-2-yl)piperidin-1-yl)methyl)-7-(fluoromethoxy)-1-(fluoromethyl)-1H-benzo[d]imidazole-5-carboxylic acid | 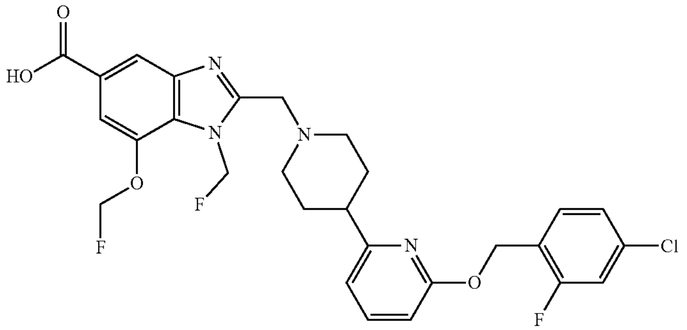 [SMILES: O=C(O)c1cc(OCF)c2c(c1)nc(CN1CCC(c3cccc(OCc4ccc(Cl)cc4F)n3)CC1)n2CF] |

TABLE 5A-continued

| Compound No. | Name | Structure |
|---|---|---|
| 5-348 | 2-((4-(6-((4-Chloro-2-methoxybenzyl)oxy)pyridin-2-yl)piperidin-1-yl)methyl)-4-methoxy-1-methyl-1H-benzo[d]imidazole-6-carboxylic acid | 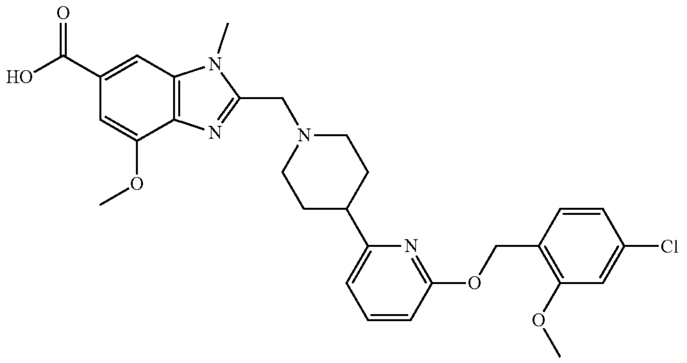 [SMILES: COc1cc(Cl)ccc1COc1cccc(C2CCN(Cc3nc4c(OC)cc(C(=O)O)cc4n3C)CC2)n1] |
| 5-349 | 2-((4-(6-((4-Cyano-2-fluorobenzyl)oxy)pyridin-2-yl)piperidin-1-yl)methyl)-4-(methoxy-d3)-1-methyl-1H-benzo[d]imidazole-6-carboxylic acid | 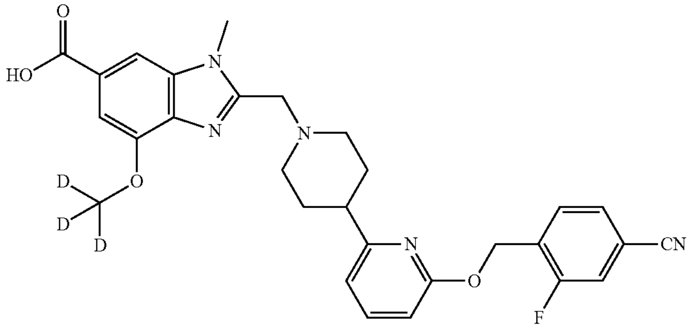 |
| 5-350 | 2-((4-(6-((6-Cyano-4-fluoropyridin-3-yl)methoxy)pyridin-2-yl)piperidin-1-yl)methyl)-4-(difluoromethoxy)-1-methyl-1H-benzo[d]imidazole-6-carboxylic acid | 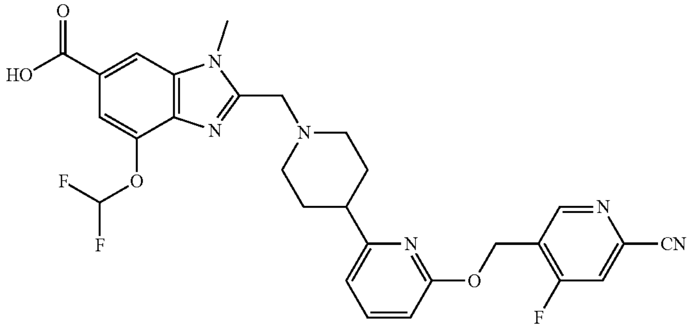 |
| 5-351 | 2-((4-(6-((4-Chloro-2-fluorobenzyl)oxy)pyridin-2-yl)piperidin-1-yl)methyl)-4-(1-fluoropropoxy)-1-methyl-1H-benzo[d]imidazole-6-carboxylic acid | 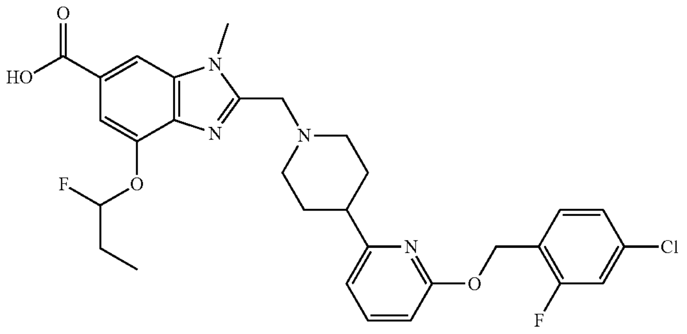 [SMILES: CCC(F)Oc1cc(C(=O)O)cc2c1nc(CN1CCC(c3cccc(OCc4ccc(Cl)cc4F)n3)CC1)n2C] |

TABLE 5A-continued

| Compound No. | Name | Structure |
| --- | --- | --- |
| 5-352 | 2-((4-(6-((4-Cyano-2-fluorobenzyl)oxy)pyridin-2-yl)piperidin-1-yl)methyl)-4-(4-fluorophenoxy)-1-methyl-1H-benzo[d]imidazole-6-carboxylic acid | 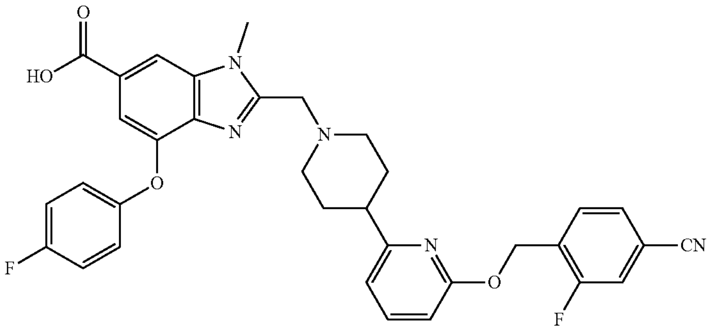 [SMILES: Cn1c(CN2CCC(c3cccc(OCc4ccc(C#N)cc4F)n3)CC2)nc2c(Oc3ccc(F)cc3)cc(C(=O)O)cc21] |
| 5-353 | 2-((4-(6-((4-Chloro-2-fluorobenzyl)oxy)pyridin-2-yl)piperidin-1-yl)methyl)-4-((1r,3r)-3-fluorocyclobutoxy)-1-methyl-1H-benzo[d]imidazole-6-carboxylic acid | 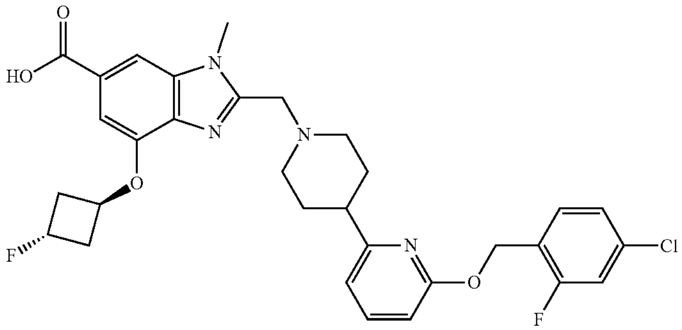 [SMILES: Cn1c(CN2CCC(c3cccc(OCc4ccc(Cl)cc4F)n3)CC2)nc2c(O[C@H]3C[C@H](F)C3)cc(C(=O)O)cc21] |
| 5-354 | 2-((4-(2-((4-Chloro-2-fluorobenzyl)oxy)-5-fluoropyrimidin-4-yl)piperidin-1-yl)methyl)-4-(difluoromethoxy)-1-methyl-1H-benzo[d]imidazole-6-carboxylic acid | 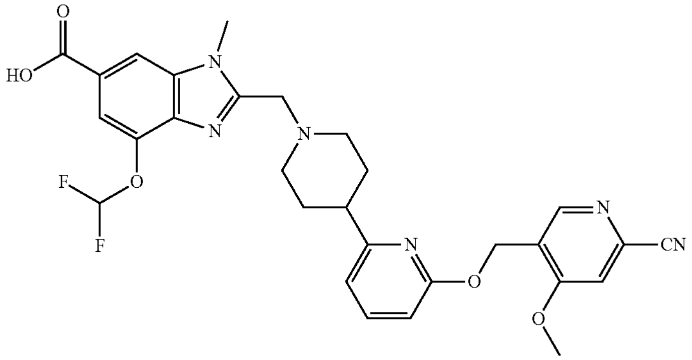 [SMILES: COc1cc(C#N)ncc1COc1cccc(C2CCN(Cc3nc4c(OC(F)F)cc(C(=O)O)cc4n3C)CC2)n1] |
| 5-355 | 2-((4-(3-((4-Chloro-2-fluorobenzyl)oxy)pyridazin-4-yl)piperidin-1-yl)methyl)-4-(difluoromethoxy)-1-methyl-1H-benzo[d]imidazole-6-carboxylic acid | 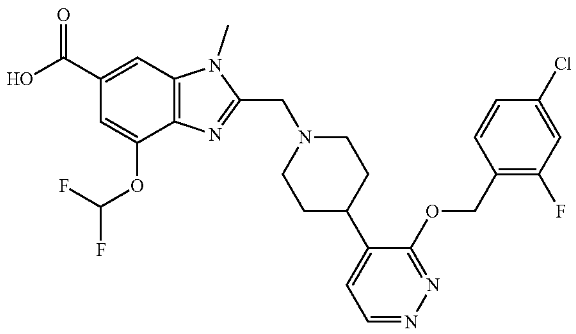 [SMILES: Cn1c(CN2CCC(c3ccnnc3OCc3ccc(Cl)cc3F)CC2)nc2c(OC(F)F)cc(C(=O)O)cc21] |

TABLE 5A-continued

| Compound No. | Name | Structure |
|---|---|---|
| 5-356 | 2-((4-(4-((4-Chloro-2-fluorobenzyl)oxy)-5-fluoropyrimidin-2-yl)piperidin-1-yl)methyl)-4-(difluoromethoxy)-1-methyl-1H-benzo[d]imidazole-6-carboxylic acid | 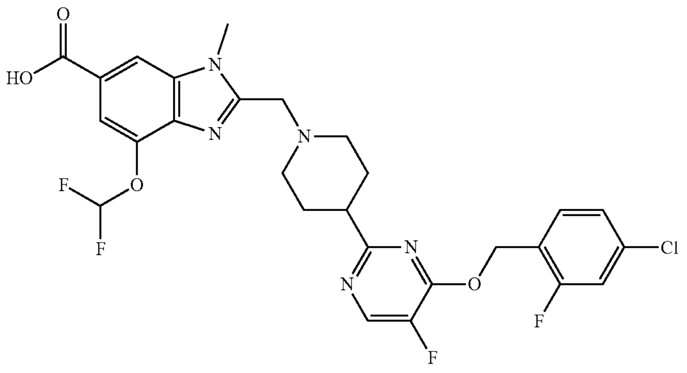 [SMILES: Cn1c(CN2CCC(c3ncc(F)c(OCc4ccc(Cl)cc4F)n3)CC2)nc2c(OC(F)F)cc(C(=O)O)cc21] |
| 5-357 | 2-((4-(6-((4-Chloro-2-fluorobenzyl)oxy)pyridin-2-yl)piperidin-1-yl)methyl)-4-(cyclopropylmethoxy)-1-methyl-1H-benzo[d]imidazole-6-carboxylic acid | 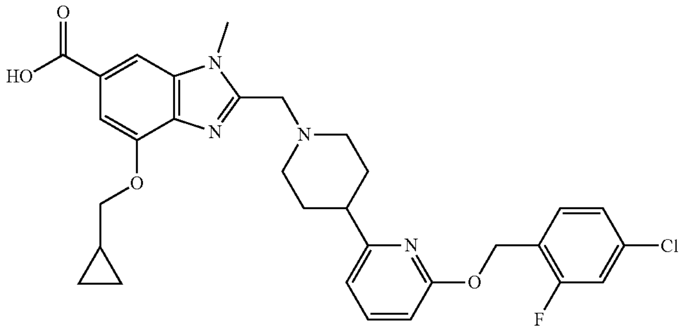 [SMILES: Cn1c(CN2CCC(c3cccc(OCc4ccc(Cl)cc4F)n3)CC2)nc2c(OCC3CC3)cc(C(=O)O)cc21] |
| 5-358 | 2-((4-(6-((4-Chloro-2-fluorobenzyl)oxy)pyridin-2-yl)piperidin-1-yl)methyl)-4-ethoxy-1-methyl-1H-benzo[d]imidazole-6-carboxylic acid | 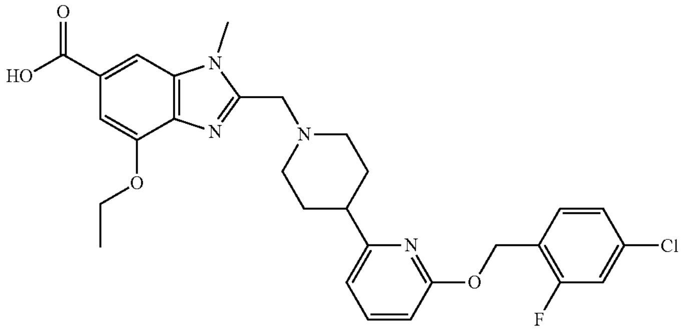 [SMILES: CCOc1cc(C(=O)O)cc2c1nc(CN1CCC(c3cccc(OCc4ccc(Cl)cc4F)n3)CC1)n2C] |
| 5-359 | -((4-(6-((4-Chloro-2-fluorobenzyl)oxy)pyridin-2-yl)piperidin-1-yl)methyl)-4-(1-fluoroethoxy)-1-methyl-1H-benzo[d]imidazole-6-carboxylic acid | 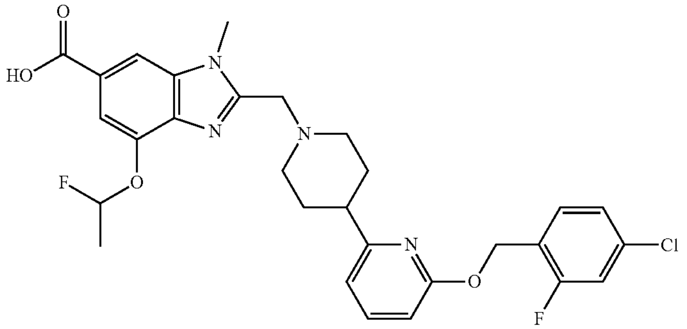 [SMILES: CC(F)Oc1cc(C(=O)O)cc2c1nc(CN1CCC(c3cccc(OCc4ccc(Cl)cc4F)n3)CC1)n2C] |

TABLE 5A-continued

| Compound No. | Name | Structure |
| --- | --- | --- |
| 5-360 | (S)-2-((4-(6-((4-chloro-2-fluorobenzyl)oxy)pyridin-2-yl)piperidin-1-yl)methyl)-4-(1-fluoroethoxy)-1-methyl-1H-benzo[d]imidazole-6-carboxylic acid | 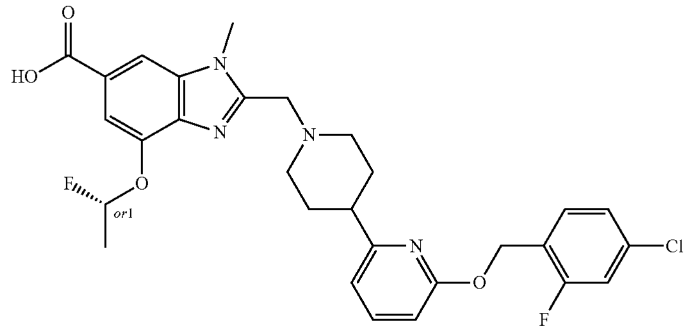 |
| 5-361 | (R)-2-((4-(6-((4-Chloro-2-fluorobenzyl)oxy)pyridin-2-yl)piperidin-1-yl)methyl)-4-(1-fluoroethoxy)-1-methyl-1H-benzo[d]imidazole-6-carboxylic acid | 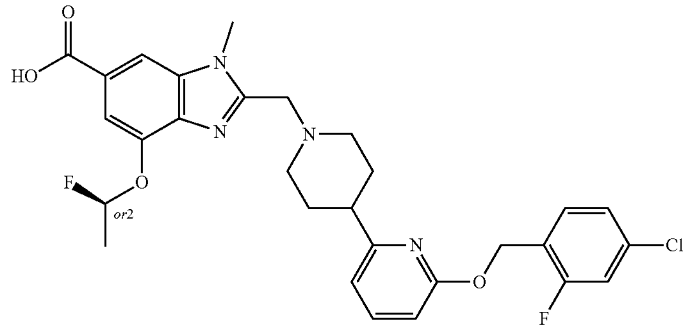 [SMILES: C[C@@H](F)Oc1cc(C(=O)O)cc2c1nc(CN1CCC(c3cccc(OCc4ccc(Cl)cc4F)n3)CC1)n2C] |
| 5-362 | 2-((3-(6-((4-Chloro-2-fluorophenoxy)methyl)pyridin-2-yl)pyrrolidin-1-yl)methyl)-4-(difluoromethoxy)-1-methyl-1H-benzo[d]imidazole-6-carboxylic acid | 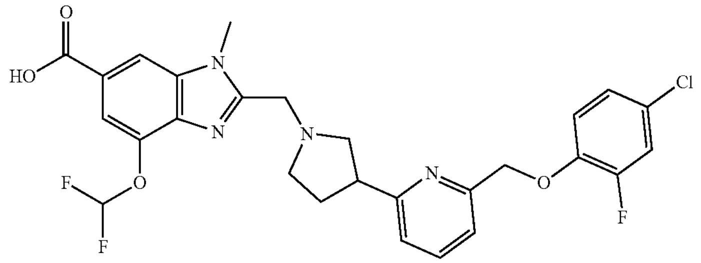 [SMILES: Cn1c(CN2CCC(c3cccc(COc4ccc(Cl)cc4F)n3)C2)nc2c(OC(F)F)cc(C(=O)O)cc21] |
| 5-363 | 2-(((1r,4r)-4-(6-((4-Chloro-2-fluorobenzyl)oxy)pyridin-2-yl)cyclohexyl)(methyl)amino)-4-methoxy-1-methyl-1H-benzo[d]imidazole-6-carboxylic acid | 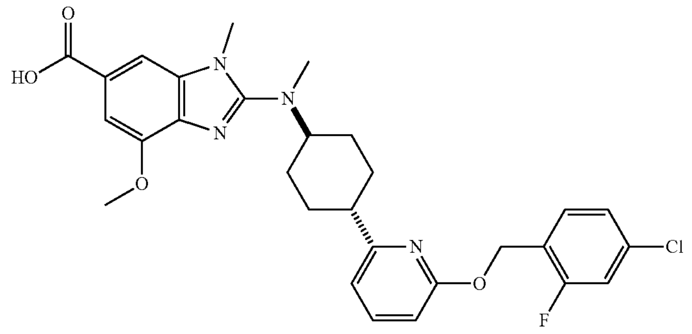 |

TABLE 5A-continued

| Compound No. | Name | Structure |
|---|---|---|
| 5-364 | 2-((4-(2-((4-Chloro-2-fluorobenzyl)oxy)pyridin-3-yl)piperidin-1-yl)methyl)-4-(difluoromethoxy)-1-methyl-1H-benzo[d]imidazole-6-carboxylic acid | 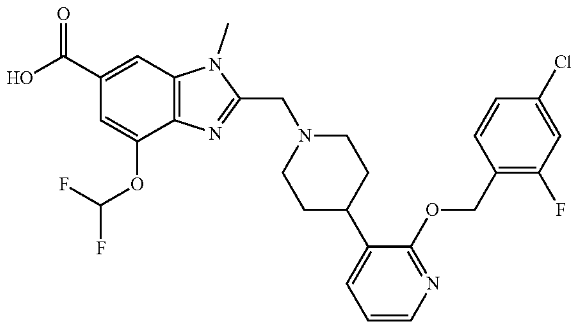 [SMILES: Cn1c(CN2CCC(c3cccnc3OCc3ccc(Cl)cc3F)CC2)nc2c(OC(F)F)cc(C(=O)O)cc21] |
| 5-365 | 2-((4-(6-((4-Cyclopropyl-2-fluorobenzyl)oxy)pyridin-2-yl)piperidin-1-yl)methyl)-4-(difluoromethoxy)-1-methyl-1H-benzo[d]imidazole-6-carboxylic acid | 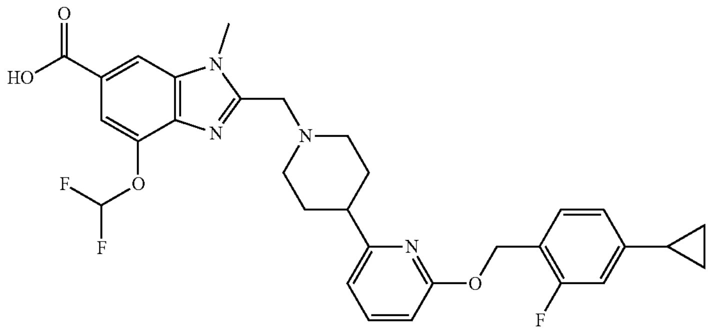 [SMILES: Cn1c(CN2CCC(c3cccc(OCc4ccc(C5CC5)cc4F)n3)CC2)nc2c(OC(F)F)cc(C(=O)O)cc21] |
| 5-366 | 2-((4-(6-((4-Cyano-2,5-difluorobenzyl)oxy)pyridin-2-yl)piperidin-1-yl)methyl)-4-(difluoromethoxy)-1-methyl-1H-benzo[d]imidazole-6-carboxylic acid | 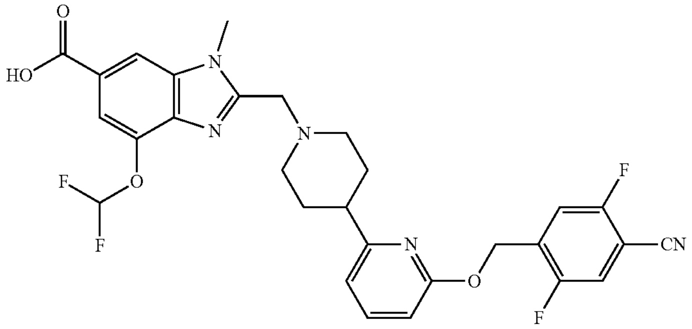 [SMILES: Cn1c(CN2CCC(c3cccc(OCc4cc(F)c(C#N)cc4F)n3)CC2)nc2c(OC(F)F)cc(C(=O)O)cc21] |
| 5-367 | 2-(4-((6-((4-chloro-2-fluorophenoxy)methyl)pyridin-2-yl)oxy)-2-fluorobenzyl)-4-(difluoromethoxy)-1-methyl-1H-benzo[d]imidazole-6-carboxylic acid | 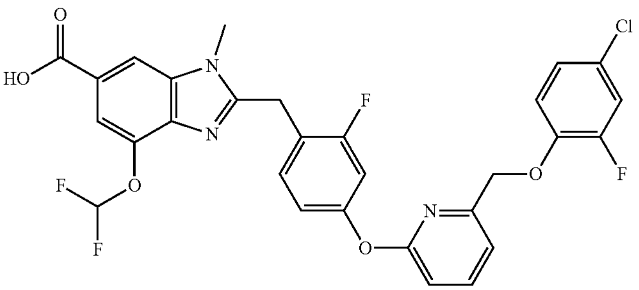 [SMILES: Cn1c(Cc2ccc(Oc3cccc(COc4ccc(Cl)cc4F)n3)cc2F)nc2c(OC(F)F)cc(C(=O)O)cc21] |

TABLE 5A-continued

| Compound No. | Name | Structure |
|---|---|---|
| 5-368 | S)-2-((4-(2-(4-Chloro-2-fluorophenyl)chroman-8-yl)piperidin-1-yl)methyl)-4-(difluoromethoxy)-1-methyl-1H-benzo[d]imidazole-6-carboxylic acid | 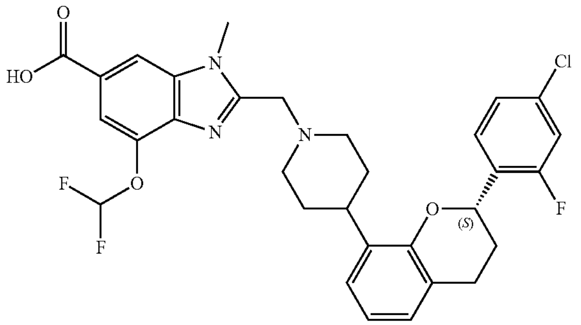 |
| 5-369 | (R)-2-((4-(2-(4-Chloro-2-fluorophenyl)chroman-8-yl)piperidin-1-yl)methyl)-4-(difluoromethoxy)-1-methyl-1H-benzo[d]imidazole-6-carboxylic acid | 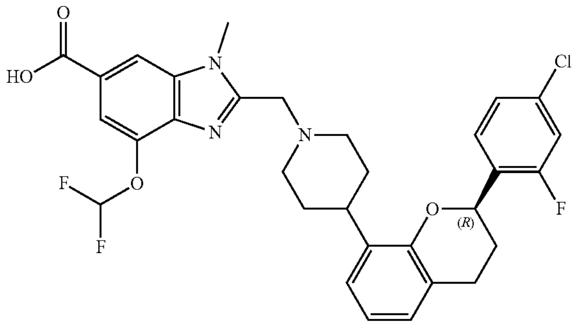 |
| 5-370 | 3-(2-((4-(6-((4-Chloro-2-fluorobenzyl)oxy)pyridin-2-yl)piperidin-1-yl)methyl)-4-(difluoromethoxy)-1-methyl-1H-benzo[d]imidazol-6-yl)-1,2,4-thiadiazol-5(4H)-one | 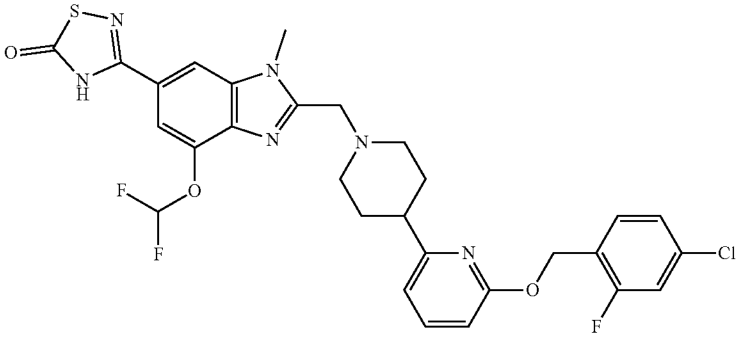 [SMILES: Cn1c(CN2CCC(c3cccc(OCc4ccc(Cl)cc4F)n3)CC2)nc2c(OC(F)F)cc(-c3nsc(=O)[nH]3)cc21] |
| 5-371 | 2-(((1r,4r)-4-(6-((4-Chloro-2-fluorobenzyl)oxy)pyridin-2-yl)cyclohexyl)amino)-4-(difluoromethoxy)-1-methyl-1H-benzo[d]imidazole-6-carboxylic acid | 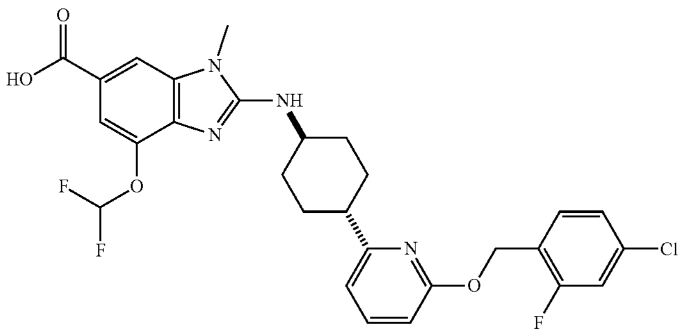 |

TABLE 5A-continued

| Compound No. | Name | Structure |
|---|---|---|
| 5-372 | 2-(((1r,4r)-4-(6-((4-Chloro-2-fluorobenzyl)oyridinedin-2-yl)cyclohexyl)(methyl-d3)amino)-4-(difluoromethoxy)-1-methyl-1H-benzo[d]imidazole-6-carboxylic acid | 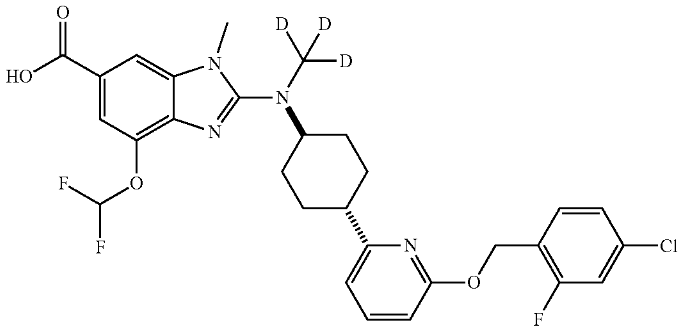 |
| 5-373 | 2-((4-(4-(4-Chloro-2-fluorobenzyl)-3,4-dihydro-2H-benzo[b][1,4]oxazin-6-yl)piperidin-1-yl)methyl)-4-(difluoromethoxy)-1-methyl-1H-benzo[d]imidazole-6-carboxylic acid | 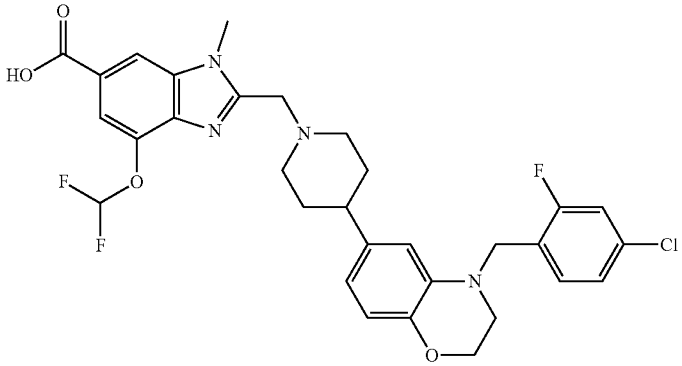 [SMILES: Cn1c(CN2CCC(c3ccc4c(c3)N(Cc3ccc(Cl)cc3F)CCO4)CC2)nc2c(OC(F)F)cc(C(=O)O)cc21] |
| 5-374 | 2-((4-(6-((4-Chloro-2-fluorobenzyl)oxy)pyrazin-2-yl)piperidin-1-yl)methyl)-4-(difluoromethoxy)-1-methyl-1H-benzo[d]imidazole-6-carboxylic acid | 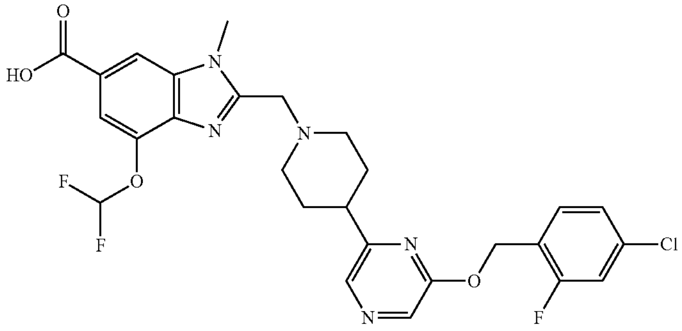 |
| 5-375 | 2-((4-(2-((4-Chloro-2-fluorobenzyl)oxy)-5-fluoropyrimidin-4-yl)piperidin-1-yl)methyl)-4-(difluoromethoxy)-1-methyl-1H-benzo[d]imidazole-6-carboxylic acid | 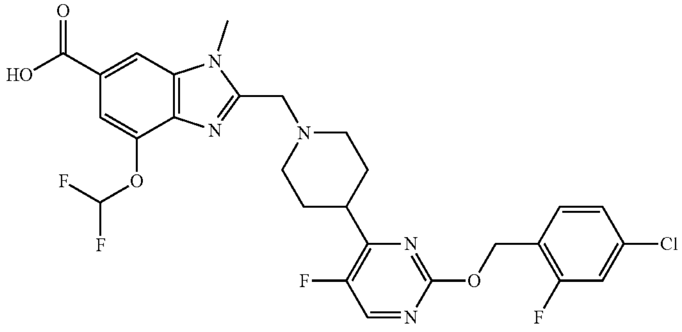 [SMILES: Cn1c(CN2CCC(c3nc(OCc4ccc(Cl)cc4F)ncc3F)CC2)nc2c(OC(F)F)cc(C(=O)O)cc21] |

TABLE 5A-continued

| Compound No. | Name | Structure |
| --- | --- | --- |
| 5-376 | (S)-2-((4-(6-((4-Cyano-2-fluorobenzyl)oxy)pyridin-2-yl)piperidin-1-yl)methyl)-4-hydroxy-1-(oxetan-2-ylmethyl)-1H-benzo[d]imidazole-5-carboxylic acid | 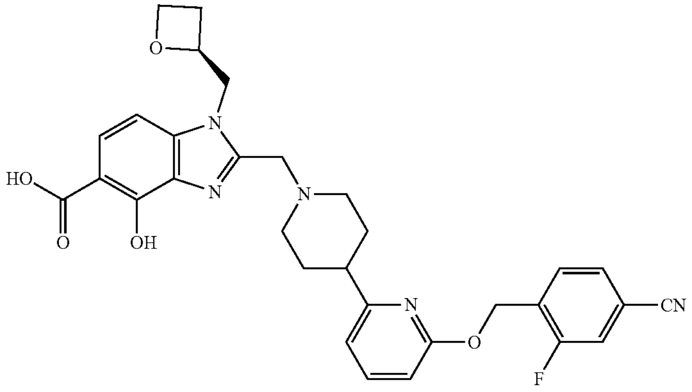 [SMILES: N#Cc1ccc(COc2cccc(C3CCN(Cc4nc5c(O)c(C(=O)O)ccc5n4C[C@@H]4CCO4)CC3)n2)c(F)c1] |
| 5-377 | (S)-2-((4-(6-((4-Cyano-2-fluorobenzyl)oxy)pyridin-2-yl)piperidin-1-yl)methyl)-7-hydroxy-1-(oxetan-2-ylmethyl)-1H-benzo[d]imidazole-6-carboxylic acid | 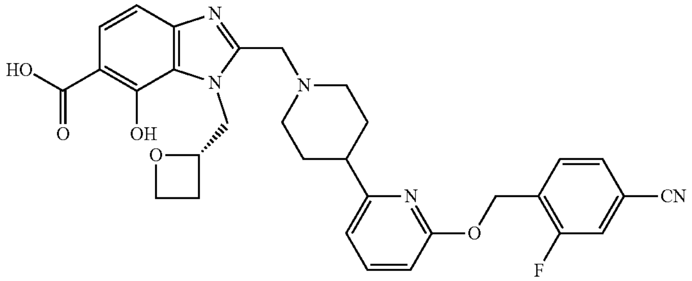 [SMILES: N#Cc1ccc(COc2cccc(C3CCN(Cc4nc5ccc(C(=O)O)c(O)c5n4C[C@@H]4CCO4)CC3)n2)c(F)c1] |
| 5-378 | (S)-2-((4-(6-((4-Cyano-2-fluorobenzyl)oxy)pyridin-2-yl)piperidin-1-yl)methyl)-1-(oxetan-2-ylmethyl)-1H-imidazo[4,5-c]pyridine-6-carboxylic acid | 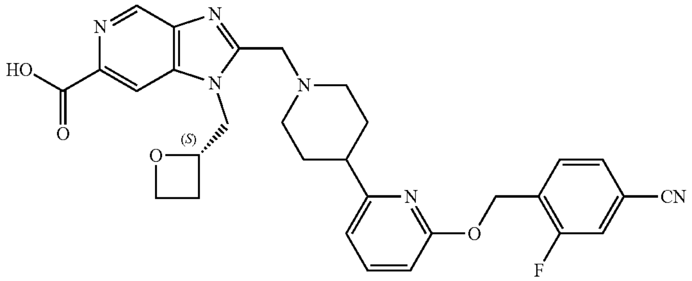 |
| 5-379 | 2-((4-(6-((4-Chloro-2-fluorobenzyl)oxy)pyridin-2-yl)piperidin-1-yl)methyl)-4-((1s,3s)-3-fluorocyclobutoxy)-1-methyl-1H-benzo[d]imidazole-6-carboxylic acid | 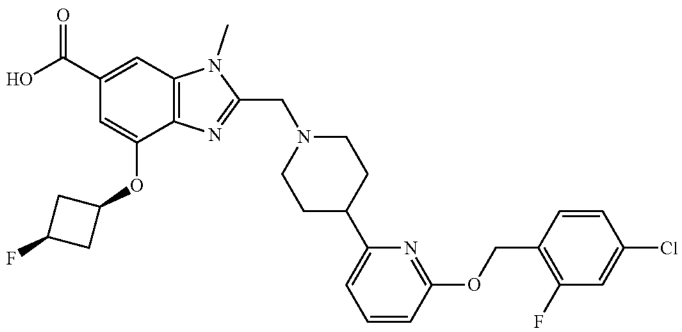 [SMILES: Cn1c(CN2CCC(c3cccc(OCc4ccc(Cl)cc4F)n3)CC2)nc2c(O[C@H]3C[C@@H](F)C3)cc(C(=O)O)cc21] |

TABLE 5A-continued

| Compound No. | Name | Structure |
|---|---|---|
| 5-380 | 2-((4-(6-((4-Chloro-2-fluorobenzyl)oxy)pyridin-2-yl)piperidin-1-yl)methyl)-4-methoxy-1-methyl-1H-imidazo[4,5-c]pyridine-6-carboxylic acid | 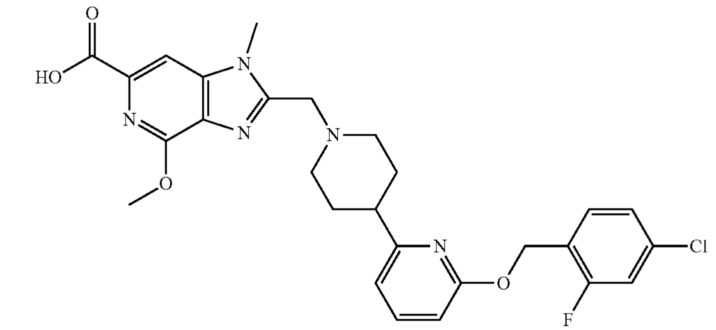 |
| 5-381 | 2-((4-(6-((4-Chloro-2-fluorophenyl)methoxy-d2)pyridin-2-yl)piperidin-1-yl)methyl-d2)-4-(ethoxy-1,1-d2)-1-methyl-1H-benzo[d]imidazole-6-carboxylic acid | 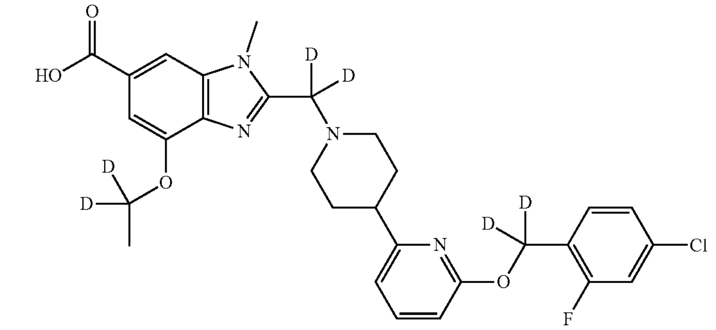 [SMILES: [2H]C([2H])(C)Oc1cc(C(=O)O)cc2c1nc(C([2H])([2H])N1CCC(c3cccc(OC([2H])([2H])c4ccc(Cl)cc4F)n3)CC1)n2C] |
| 5-382 | (S)-5-(2-((4-(6-((4-Chloro-2-fluorobenzyl)oxy)pyridin-2-yl)piperidin-1-yl)methyl)-4-methoxy-1-(oxetan-2-ylmethyl)-1H-benzo[d]imidazol-6-yl)isoxazol-3(2H)-one | 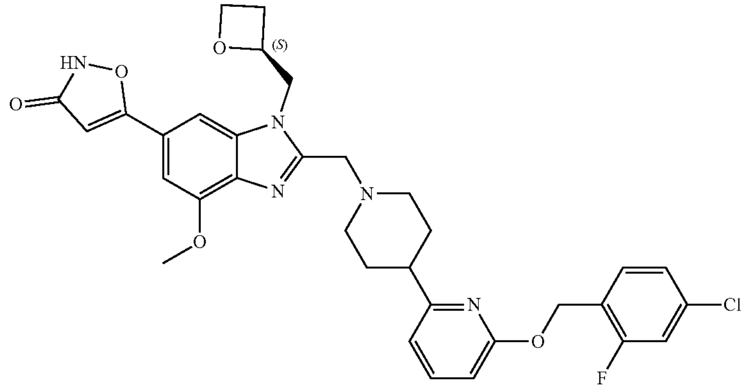 |
| 5-383 | 2-((4-(6-((4-Chloro-2-fluorobenzyl)oxy)pyridin-2-yl)piperazin-1-yl)methyl)-4-methoxy-1-methyl-1H-benzo[d]imidazole-6-carboxylic acid | 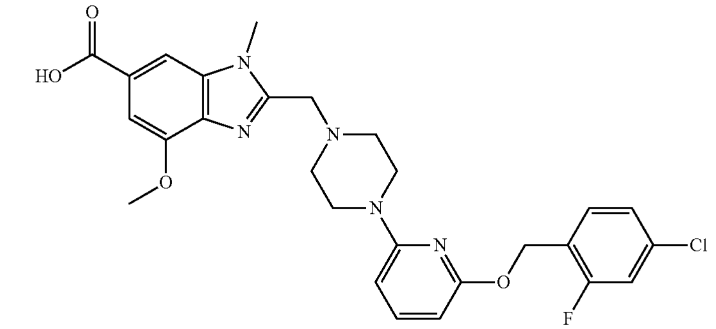 [SMILES: COc1cc(C(=O)O)cc2c1nc(CN1CCN(c3cccc(OCc4ccc(Cl)cc4F)n3)CC1)n2C] |

TABLE 5A-continued

| Compound No. | Name | Structure |
|---|---|---|
| 5-384 | 4-(((6-(1-((4-Ethoxy-1-methyl-6-(3-oxo-2,3-dihydroisoxazol-5-yl)-1H-benzo[d]imidazol-2-yl)methyl)piperidin-4-yl)pyridin-2-yl)oxy)methyl)-3-fluorobenzonitrile | 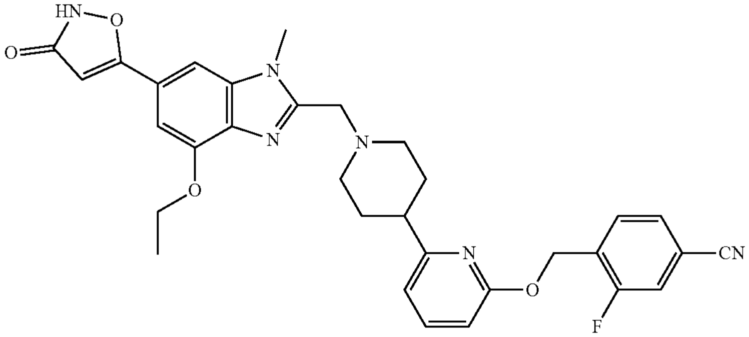 [SMILES: CCOc1cc(-c2cc(=O)[nH]o2)cc2c1nc(CN1CCC(c3cccc(OCc4ccc(C#N)cc4F)n3)CC1)n2C] |
| 5-385 | 4-(Difluoromethoxy)-1-methyl-2-((4-(6-((4-(trifluoromethyl)benzyl)oxy)pyridin-2-yl)piperidin-1-yl)methyl)-1H-benzo[d]imidazole-6-carboxylic acid | 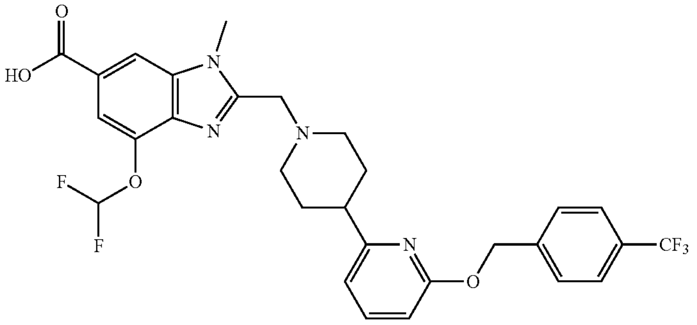 [SMILES: Cn1c(CN2CCC(c3cccc(OCc4ccc(C(F)(F)F)cc4)n3)CC2)nc2c(OC(F)F)cc(C(=O)O)cc21] |
| 5-386 | 2-((4-((S)-2-(5-Chloropyridin-2-yl)-2-methylbenzo[d][1,3]dioxol-4-yl)piperidin-1-yl)methyl)-4-(1,1-difluoroethyl)-1-(((S)-oxetan-2-yl)methyl)-1H-benzo[d]imidazole-6-carboxylic acid | 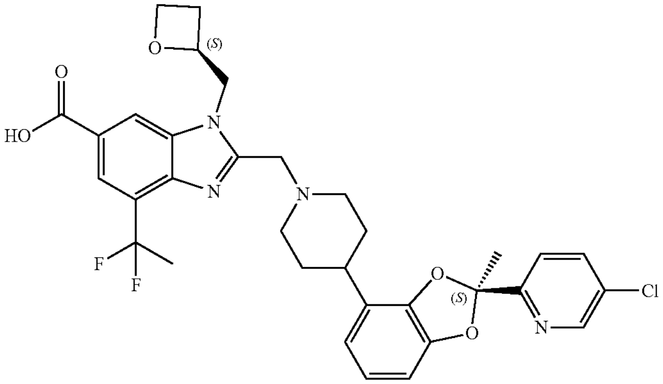 |
| 5-387 | 2-(((1S,5R,6S)-5-(6-((4-cyano-2-fluorobenzyl)oxy)pyridin-2-yl)-2-azabicyclo[4.1.0]heptan-2-yl)methyl)-4-methoxy-1-(((S)-oxetan-2-yl)methyl)-1H-benzo[d]imidazole-6-carboxylic acid | 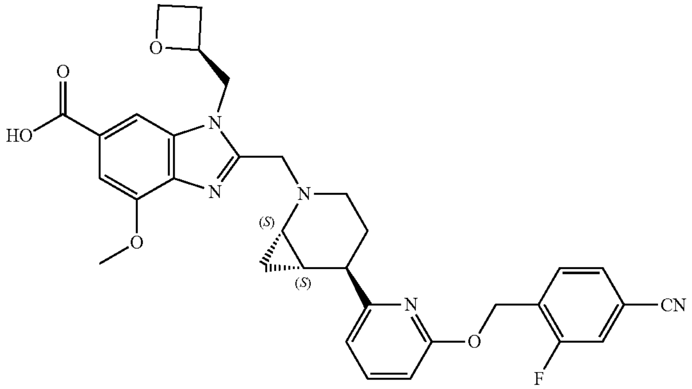 |

THRβ Agonists

In some embodiments, the THRβ agonist administered to the patient in need thereof is resmetirom (MGL-3196, Madrigal Therapeutics). In some embodiments, the THRβ agonist administered to the patient in need thereof is VK2809 (Viking Therapeutics). In some embodiments, the THRβ agonist administered to the patient in need thereof is sobetirome. In some embodiments, the THRβ agonist administered to the patient in need thereof is eprotirome. In some embodiments, the THRβ agonist administered to the patient in need thereof is ALG-055009 (Aligo). In some embodiments, the THRβ agonist administered to the patient in need thereof is CNPT-101 101. In some embodiments, the THRβ agonist administered to the patient in need thereof is CNPT-101207. In some embodiments, the THRβ agonist administered to the patient in need thereof is ASC41 (Ascletis).

Suitable THRβ agonists that can be used in accordance with the methods described herein are also described in, e.g., PCT Pub. Nos. WO/2020/123827, WO/2020/041741, WO/2020/077123, WO/2021/041237, WO/2021/050945, or WO/2022/187403, incorporated herein by reference.

In some embodiments, the THRβ agonist is a compound of Formula (II-1)

(II-1)

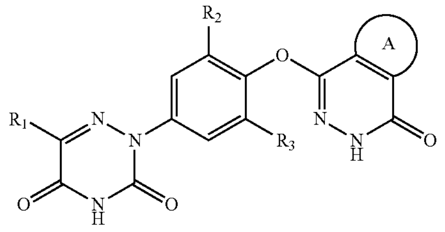

wherein:

- $R^1$ is selected from the group consisting of hydrogen, cyano, substituted or unsubstituted $C_{1-6}$ alkyl, and substituted or unsubstituted $C_{3-6}$ cycloalkyl, the substituent being selected from the group consisting of halogen atoms, hydroxy, and $C_{1-6}$ alkoxy;
- $R^2$ and $R^3$ are each independently selected from the group consisting of halogen atoms and substituted or unsubstituted $C_{1-6}$ alkyl, the substituent being selected from the group consisting of halogen atoms, hydroxy, and $C_{1-6}$ alkoxy;
- ring A is a substituted or unsubstituted saturated or unsaturated $C_{5-10}$ aliphatic ring, or a substituted or unsubstituted $C_{5-10}$ aromatic ring, the substituent being one or more substances selected from the group consisting of hydrogen, halogen atoms, hydroxy, —$OCF_3$, —$NH_2$, —$NHC_{1-4}$ alkyl, —$N(C_{1-4}$ alkyl$)_2$, —$CONH_2$, —$CONHC_{1-4}$ alkyl, —$CON(C_{1-4}$ alkyl$)_2$, —$NHCOC_{1-4}$ alkyl, $C_{1-6}$ alkyl, $C_{1-6}$ alkoxy or $C_{3-6}$ cycloalkyl, and when two substituents are contained, the two substituents can form a ring structure together with the carbon connected thereto; and the halogen atoms are selected from the group consisting of F, Cl and Br, or a pharmaceutically acceptable salt thereof.

In some embodiments, the THRβ agonist administered to the patient in need thereof is a compound of Formula (II-1a)

(II-1a)

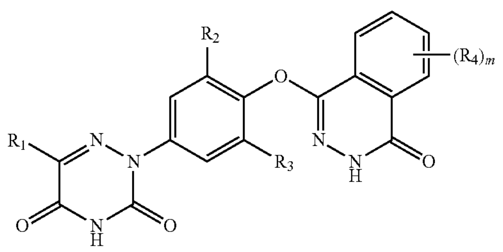

wherein:

- $R^1$ to $R^3$ are defined as detailed herein for Formula (II-1);
- $R^4$ is selected from the group consisting of hydrogen, halogen atoms, hydroxy, —$OCF_3$, —$NH_2$, —$NHC_{1-4}$ alkyl, —$N(C_{1-4}$ alkyl$)_2$, —$CONH_2$, —$CONHC_{1-4}$ alkyl, —$CON(C_{1-4}$ alkyl$)_2$, —$NHCOC_{1-4}$ alkyl, $C_{1-6}$ alkyl, $C_{1-6}$ alkoxy and $C_{3-6}$ cycloalkyl;
- m is an integer from the range 1 to 4; and
- the halogen atoms are selected from the group consisting of F, Cl and Br.
- or a pharmaceutically acceptable salt thereof.

In some embodiments, wherein $R^a$ is selected from the group consisting of hydrogen, halogen atoms, hydroxy, —$OCF_3$, $C_{1-6}$alkyl, $C_{1-6}$ alkoxy and $C_{1-6}$ cycloalkyl; and m is an integer from the range 1 to 3.

In some embodiments, wherein $R^1$ is selected from the group consisting of hydrogen, cyano, and substituted or unsubstituted $C_{1-6}$ alkyl, the substituent being selected from the group consisting of halogen atoms, hydroxy, and $C_1$ alkoxy; and the halogen atoms are selected from the group consisting of F, Cl and Br.

In some embodiments, the THRβ agonist administered to the patient in need thereof is a compound of Formula (II-2)

(II-2)

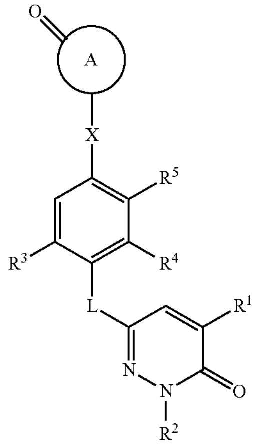

or a pharmaceutically acceptable salt thereof, wherein:

- ring A together with the carbonyl (keto) group within the ring form a 5 membered heterocycle containing 1-3 ring heteroatoms selected from the group consisting of N, O, and S, wherein the heterocycle is optionally substituted with 1-2 $C_1$-$C_3$ alkyl or $C_3$-$C_4$ cycloalkyl groups, and wherein the carbonyl (keto) group is not adjacent to the atom attached to X;
- $R^1$ is $C_1$-$C_4$ alkyl optionally substituted with 1-5 halo or hydroxyl groups, $C_3$-$C_5$ cycloalkyl, $CON(R^{10})_2$, or $NR^{10}COR^{10}$:
- $R^2$ is H or C, —$C_{1-6}$ alkyl;
- L is O, $CH_2$, S, SO, $SO_2$, CO, CHF, $CF_2$, $C(R^{11})CN$, $CHR^{11}$, or $C(R^{11})R^{11}$;
- $R^3$ and $R^4$ are independently $C_1$, Br, methyl, or ethyl;
- $R^5$ is H, halo, $C_1$-$C_4$ alkyl, or $C_1$-$C_4$ cycloalkyl;
- or $R^5$ together with $R^4$ and the intervening atoms form a 5-7 membered cycloalkyl or a 5-7 membered heterocycle containing 1-2 ring heteroatoms;
- X is absent, O, $NR^{12}$, $C(O)NR^{12}$, $NR^{12}C(O)$, $CR^{12}R^{12}$, $OCR^{12}R^{12}$, $CR^{12}R^2O$, $NR^{12}CR^{12}R^{12}$, $CR^{12}R^{12}NR^{12}$, $SO_2NR^{12}$, or $NR^{12}SO_2$;
- each $R^{10}$ is independently $C_1$-$C_3$ alkyl or H;

each $R^{11}$ is independently $C_1$-$C_2$ alkyl optionally substituted with 1-5 halo, or two $R^{11}$ groups together with the carbon atom to which they are attached form a cyclopropyl or cyclobutyl ring; and each $R^{12}$ is independently H or methyl.

In some embodiments, the THRβ agonist administered to the patient in need thereof is a compound of Formula (II-3)

(II-3)

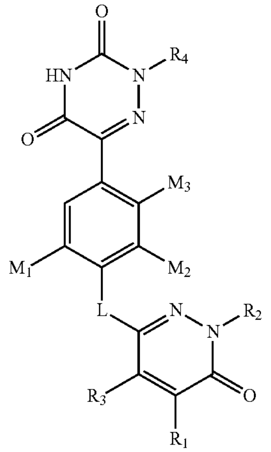

wherein:

$R_1$ is substituted or unsubstituted $C_1$-$C_6$ alkyl, substituted or unsubstituted $C_3$-$C_6$ cycloalkyl, —C(O)N($R_7$)($R_5$), —N($R_9$)C(OX$R_{10}$), or halo;

$R_2$ is H, substituted or unsubstituted $C_1$-$C_6$ alkyl, or substituted or unsubstituted $C_3$-$C_6$ cycloalkyl;

$R_3$ is H or halo;

$R_4$ is H, or substituted or unsubstituted linear $C_1$-$C_3$ alkyl;

L is —O—, —S—, —S(O)—, —S(O)$_2$—, —C(O)—, or —C($R_5$)($R_6$)—;

$R_5$ and $R_5$ are independently H, halo, —CN, or substituted or unsubstituted $C_1$-$C_6$ alkyl, or $R_5$ and $R_6$ are taken together with the carbon atom to which they are attached to form a substituted or unsubstituted $C_3$-$C_6$ cycloalkyl;

$R_7$ and $R_8$ are independently H, or substituted or unsubstituted $C_1$-$C_6$ alkyl, or $R_7$ and $R_8$ are taken together with the nitrogen atom to which they are attached to form a substituted or unsubstituted 3- to 7-membered heterocycloalkyl; $R_9$ is H, substituted or unsubstituted $C_1$-$C_6$ alkyl, or substituted or unsubstituted $C_3$-$C_6$ cycloalkyl;

$R_{10}$ is substituted or unsubstituted $C_1$-$C_6$ alkyl, substituted or unsubstituted $C_3$-$C_6$ cycloalkyl, —N($R_7$)($R_8$), or —O($R_{11}$);

$R_{11}$ is substituted or unsubstituted $C_1$-$C_6$ alkyl, or substituted or unsubstituted $C_3$-$C_6$ cycloalkyl;

$M_1$ and $M_2$ are independently halo, or substituted or unsubstituted $C_1$-$C_6$ alkyl; and $M_3$ is H, halo, or substituted or unsubstituted $C_1$-$C_6$ alkyl, or $M_3$ is taken together with $M_2$ and the carbon atoms to which they are attached to form a 5- to 7-membered ring containing 0, 1, or 2 heteroatoms selected from the group consisting of N, O, and S, or a pharmaceutically acceptable salt thereof.

In some embodiments, the THRβ agonist administered to the patient in need thereof is a compound of Formula (II-4)

(II-4)

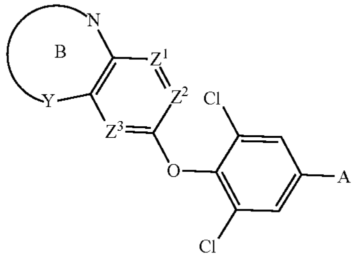

or a tautomer or an N-oxide thereof, or an isotopomer of each thereof, or a stereoisomer of the aforesaid, or a pharmaceutically acceptable salt of each of the foregoing, or a solvate of each of the preceding, wherein:

A is

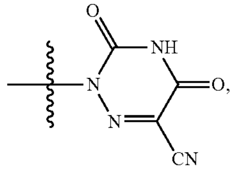 [SMILES: *n1nc(C#N)c(=O)[nH]c1=O] 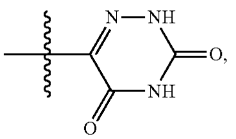 or

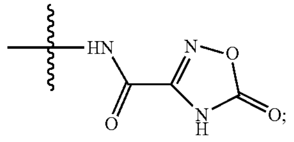 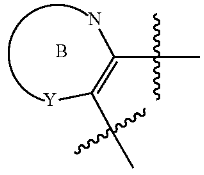

is 5-membered heterocyclyl or 5- to 6-membered heteroaryl, each of which optionally contains 1-2 additional annular heteroatoms selected from the group consisting of N and 0, wherein each heteroatom of the heterocyclyl or heteroaryl is bound to one $R^1$ group if needed to complete the valency of the heteroatom, and wherein each carbon atom of the heterocyclyl or heteroaryl is bound to one $R^2$ group if needed to complete the valency of the carbon atom, provided that no more than one $R^2$ group is needed to complete the valency of each carbon atom;

$Z^1$, $Z^2$, and $Z^3$ are independently N or CH;

Y is N or C;

each $R^1$ is independently H, $C_1$-$C_6$ alkyl, or $C_3$-$C_6$ cycloalkyl, wherein each $C_1$-$C_6$ alkyl or $C_3$-$C_6$ cycloalkyl group is optionally substituted by 1-5 $R^3$ groups;

each $R^2$ is independently H, $C_1$-$C_6$ alkyl, $C_3$-$C_6$ cycloalkyl, —O($C_1$-$C_6$ alkyl), —O($C_3$-$C_6$ cycloalkyl), hydroxyl, or oxo, wherein each $C_1$-$C_6$ alkyl, $C_3$-$C_6$ cycloalkyl, —O($C_1$-$C_6$ alkyl), or —O($C_3$-$C_6$ cycloalkyl) group is optionally substituted by 1-5 $R^3$ groups;

or $R^1$ and $R^2$ are taken together to form a 5- to 6-membered heteroaryl or 5- to 7-membered heterocyclyl;

or two $R^2$ groups are taken together to form a 5- to 6-membered heteroaryl, 5- to 7-membered heterocyclyl, $C_5$-$C_7$ cycloalkyl, or $C_6$ aryl;

each $R^3$ is independently halogen, $C_1$-$C_6$ alkyl, $C_3$-$C_6$ cycloalkyl, $C_1$-$C_6$ haloalkyl, $C_1$-$C_6$ alkyl-OH, —$NH_2$, —CN, or hydroxyl.

In some embodiments, the THRβ agonist administered to the patient in need thereof is a compound of Formula (II-5)

(II-5)

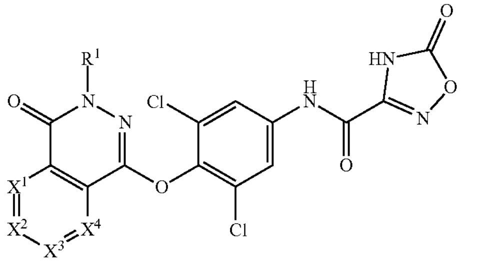

or a tautomer thereof, or a pharmaceutically acceptable salt of any of the foregoing, wherein:

$R^1$ is H or —$CH_3$;

$X^1$, $X^2$, $X^3$, and $X^4$ are each independently $CR^2$ or N, wherein at least two of $X^1$, $X^2$, $X^3$, and $X^4$ are $CR^2$;

each $R^2$ is independently H, halo, $C_1$-$C_6$ alkyl, $C_1$-$C_6$ alkyl-CN, $C_1$-$C_6$ alkyl-OH, $C_1$-$C_6$ haloalkyl, —CN, hydroxyl, —$NH_2$, —NH($C_1$-$C_6$ alkyl), —N($C_1$-$C_6$ alkyl)$_2$, —O($C_1$-$C_6$ alkyl), $C_3$-$C_6$ cycloalkyl, 5-to 6-membered heteroaryl, 5- to 7-membered heterocyclyl, or $C_6$ aryl, wherein each $C_1$-$C_6$ alkyl, —O($C_1$-$C_6$ alkyl), $C_3$-$C_6$ cycloalkyl, 5- to 6-membered heteroaryl, 5- to 7-membered heterocyclyl, or $C_6$ aryl is optionally substituted by 1-5 $R^3$ groups;

or two $R^2$ groups are taken together with the carbon atoms to which they are attached to form a 5-to 6-membered heteroaryl, 5- to 7-membered heterocyclyl, $C_5$-$C_7$ cycloalkyl, or $C_6$ aryl, each of which is optionally substituted by 1-5 $R^3$ groups; and each $R^3$ is independently $C_1$-$C_6$ alkyl, —O($C_1$-$C_6$ alkyl), halo, —CN, hydroxyl, —$NH_2$, —NH($C_1$-$C_6$ alkyl), —N($C_1$-$C_6$ alkyl)$_2$, or $CO_2H$.

In some embodiments, the THRβ agonist administered to the patient in need thereof is a compound of Formula (II-6)

(II-6)

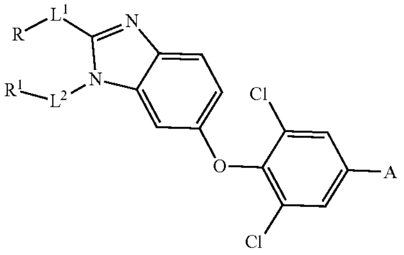

or a tautomer or stereoisomer thereof, or a pharmaceutically acceptable salt of each of the foregoing, wherein:

A is

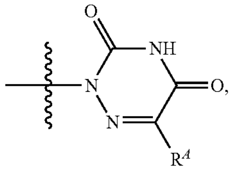

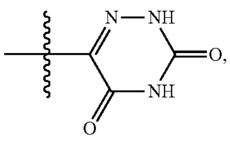

or

-continued

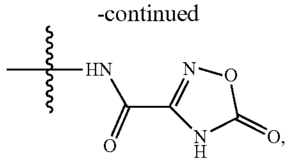

wherein $R^A$ is H or —CN;

$L^1$ is a bond, —NR'—, —O—, —S—, or —S(O)$_2$—, wherein R' is H or $C_1$-$C_6$ alkyl;

$L^2$ is a bond or —S(O)$_2$—;

$R^1$ is H, $C_1$-$C_6$ alkyl, $C_6$-$C_{10}$ aryl, 3-12 membered heterocyclyl, 5-12 membered heteroaryl, or $C_3$-$C_6$ cycloalkyl, wherein the $C_1$-$C_6$ alkyl, $C_6$-$C_{10}$ aryl, 3-12 membered heterocyclyl, 5-12 membered heteroaryl, and $C_3$-$C_6$ cycloalkyl are each independently optionally substituted by 1-5 $R^2$ groups;

R is H, $C_1$-$C_6$ alkyl, $C_6$-$C_{10}$ aryl, 3-12 membered heterocyclyl, 5-12 membered heteroaryl, or $C_3$-$C_6$ cycloalkyl, wherein the $C_1$-$C_6$ alkyl, $C_6$-$C_{10}$ aryl, 3-12 membered heterocyclyl, 5-12 membered heteroaryl, and $C_3$-$C_6$ cycloalkyl are each independently optionally substituted by 1-5 $R^2$ groups; and each $R^2$ is independently halogen, $C_1$-$C_6$ alkyl, $C_3$-$C_6$ cycloalkyl, $C_1$-$C_6$ haloalkyl, $C_1$-$C_6$ alkyl-OH, —$NH_2$, —CN, or hydroxyl, provided that when $L^1$ is a bond and R is H, then A is

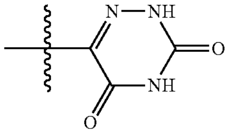

or

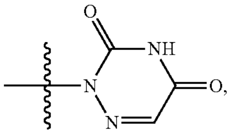

and when $L^1$ is —O—, R is H, and A is

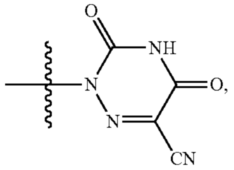

then $R^1$ is $C_2$-$C_6$ alkyl, $C_6$-$C_{10}$ aryl, 3-12 membered heterocyclyl, 5-12 membered heteroaryl, or $C_3$-$C_6$ cycloalkyl, wherein the $C_2$-$C_6$ alkyl, $C_6$-$C_{10}$ aryl, 3-12 membered heterocyclyl, 5-12 membered heteroaryl, and $C_3$-$C_6$ cycloalkyl are each independently optionally substituted by 1-5 $R^2$ groups.

In some embodiments, the THRβ agonist is selected from those listed in Table 6 below, or a pharmaceutically acceptable salt thereof:

TABLE 6
1
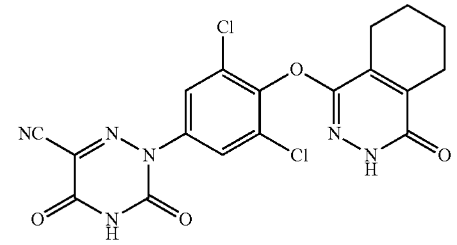 [SMILES: N#Cc1nn(-c2cc(Cl)c(Oc3n[nH]c(=O)c4c3CCCC4)c(Cl)c2)c(=O)[nH]c1=O]
2
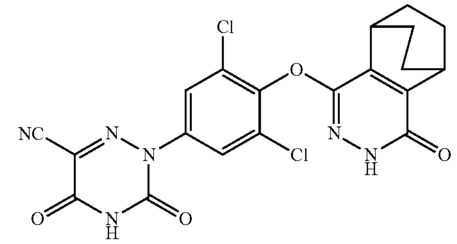 [SMILES: N#Cc1nn(-c2cc(Cl)c(Oc3n[nH]c(=O)c4c3C3CCC4CC3)c(Cl)c2)c(=O)[nH]c1=O]
3
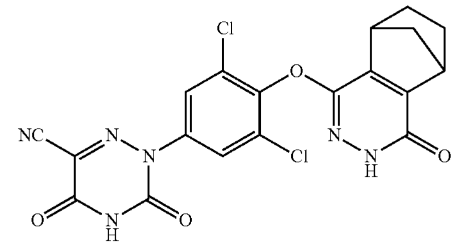 [SMILES: N#Cc1nn(-c2cc(Cl)c(Oc3n[nH]c(=O)c4c3C3CCC4C3)c(Cl)c2)c(=O)[nH]c1=O]
4
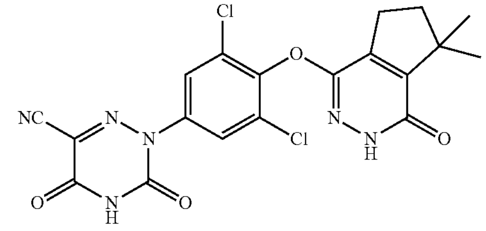 [SMILES: CC1(C)CCc2c(Oc3c(Cl)cc(-n4nc(C#N)c(=O)[nH]c4=O)cc3Cl)n[nH]c(=O)c21]
5
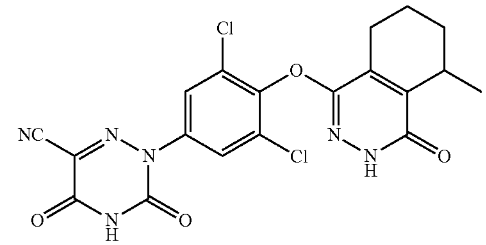 [SMILES: CC1CCCc2c(Oc3c(Cl)cc(-n4nc(C#N)c(=O)[nH]c4=O)cc3Cl)n[nH]c(=O)c21]
6
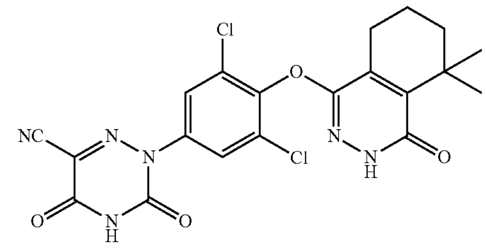 [SMILES: CC1(C)CCCc2c(Oc3c(Cl)cc(-n4nc(C#N)c(=O)[nH]c4=O)cc3Cl)n[nH]c(=O)c21]
TABLE 6-continued
7
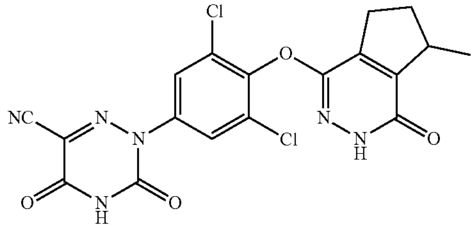 [SMILES: CC1CCc2c(Oc3c(Cl)cc(-n4nc(C#N)c(=O)[nH]c4=O)cc3Cl)n[nH]c(=O)c21]
8
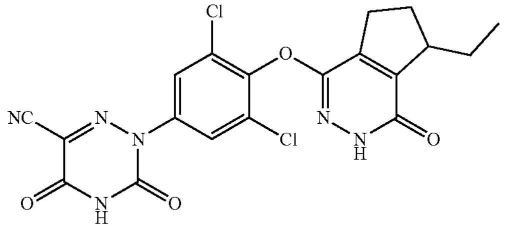 [SMILES: CCC1CCc2c(Oc3c(Cl)cc(-n4nc(C#N)c(=O)[nH]c4=O)cc3Cl)n[nH]c(=O)c21]
9
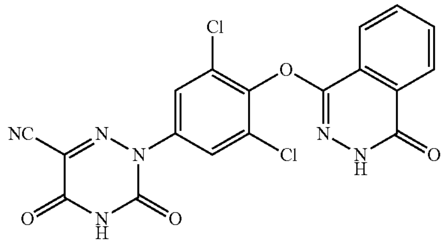 [SMILES: N#Cc1nn(-c2cc(Cl)c(Oc3n[nH]c(=O)c4ccccc34)c(Cl)c2)c(=O)[nH]c1=O]
10
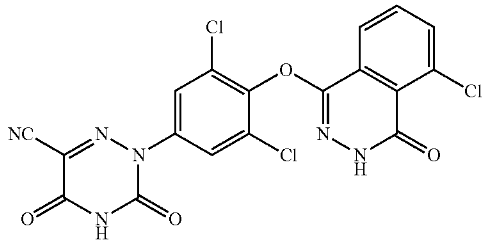 [SMILES: N#Cc1nn(-c2cc(Cl)c(Oc3n[nH]c(=O)c4c(Cl)cccc34)c(Cl)c2)c(=O)[nH]c1=O]
11
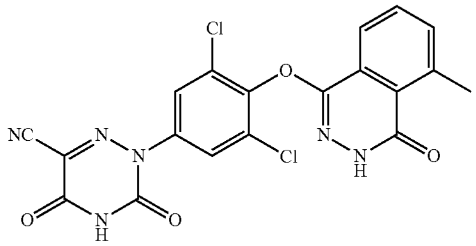 [SMILES: Cc1cccc2c(Oc3c(Cl)cc(-n4nc(C#N)c(=O)[nH]c4=O)cc3Cl)n[nH]c(=O)c12]
12
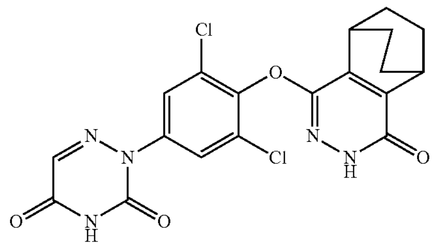 [SMILES: O=c1cnn(-c2cc(Cl)c(Oc3n[nH]c(=O)c4c3C3CCC4CC3)c(Cl)c2)c(=O)[nH]1]

TABLE 6-continued

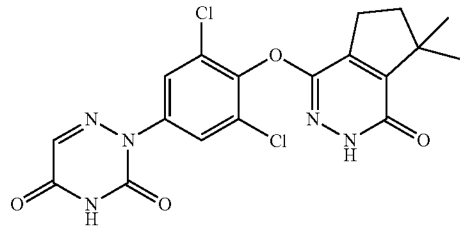 [SMILES: CC1(C)CCc2c(Oc3c(Cl)cc(-n4ncc(=O)[nH]c4=O)cc3Cl)n[nH]c(=O)c21]
13

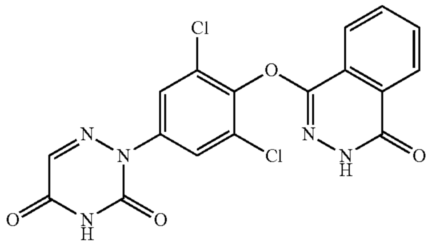 [SMILES: O=c1cnn(-c2cc(Cl)c(Oc3n[nH]c(=O)c4ccccc34)c(Cl)c2)c(=O)[nH]1]
14

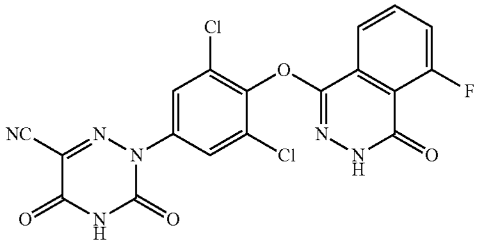 [SMILES: N#Cc1nn(-c2cc(Cl)c(Oc3n[nH]c(=O)c4c(F)cccc34)c(Cl)c2)c(=O)[nH]c1=O]
15

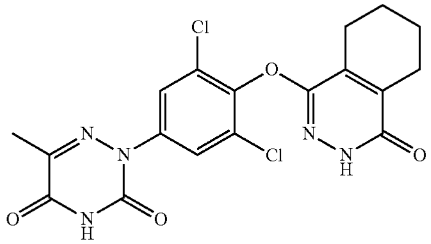 [SMILES: Cc1nn(-c2cc(Cl)c(Oc3n[nH]c(=O)c4c3CCCC4)c(Cl)c2)c(=O)[nH]c1=O]
16

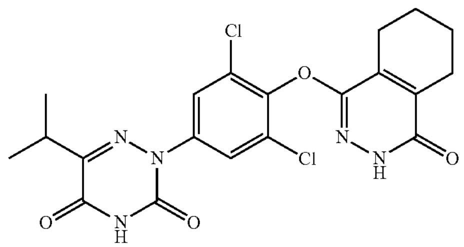 [SMILES: CC(C)c1nn(-c2cc(Cl)c(Oc3n[nH]c(=O)c4c3CCCC4)c(Cl)c2)c(=O)[nH]c1=O]
17

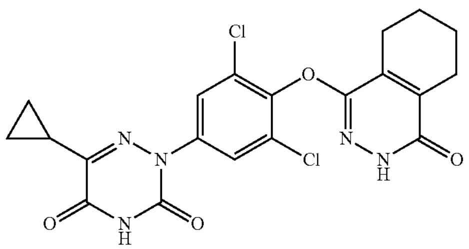 [SMILES: O=c1[nH]c(=O)n(-c2cc(Cl)c(Oc3n[nH]c(=O)c4c3CCCC4)c(Cl)c2)nc1C1CC1]
18

TABLE 6-continued

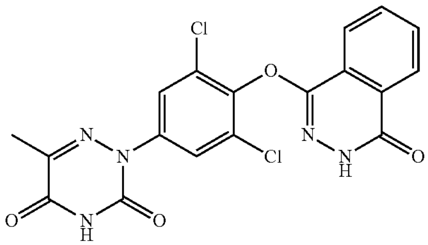 [SMILES: Cc1nn(-c2cc(Cl)c(Oc3n[nH]c(=O)c4ccccc34)c(Cl)c2)c(=O)[nH]c1=O]
19

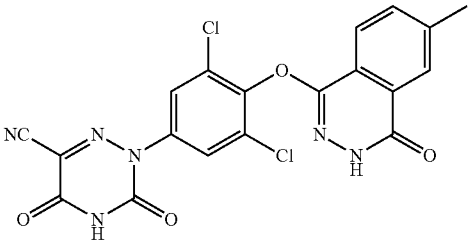 [SMILES: Cc1ccc2c(Oc3c(Cl)cc(-n4nc(C#N)c(=O)[nH]c4=O)cc3Cl)n[nH]c(=O)c2c1]
20

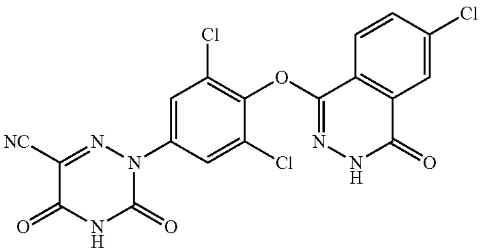 [SMILES: N#Cc1nn(-c2cc(Cl)c(Oc3n[nH]c(=O)c4cc(Cl)ccc34)c(Cl)c2)c(=O)[nH]c1=O]
21

In some embodiments, the THRβ agonist is H (Compound 9)

(Compound 9)

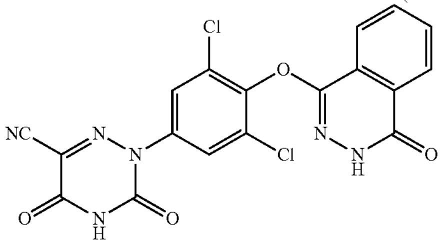

which is 2-(3,5-dichloro-4-((4-oxo-3,4-dihydrophthalazin–1-yl)oxy)phenyl)-3,5-dioxo-2,3,4,5-tetrahydro-1,2,4-triazine-6-carbonitrile, or a pharmaceutically acceptable salt thereof. In some embodiments, the THRβ agonist is 2-(3,5-dichloro-4-((4-oxo-3,4-dihydrophthalazin-1-yl)oxy)phenyl)-3,5-dioxo-2,3,4,5-tetrahydro-1,2,4-triazine-6-carbonitrile potassium salt. In some embodiments, the THRβ agonist is 2-(3,5-dichloro-4-((4-oxo-3,4-dihydrophthalazin-1-yl)oxy)phenyl)-3,5-dioxo-2,3,4,5-tetrahydro-1,2,4-triazine-6-carbonitrile sodium salt.

In some embodiments, the THRβ agonist is selected from those listed in Table 7 below, or a pharmaceutically acceptable salt thereof:

TABLE 7
| Example | Structure |
|---|---|
| 7-1 | 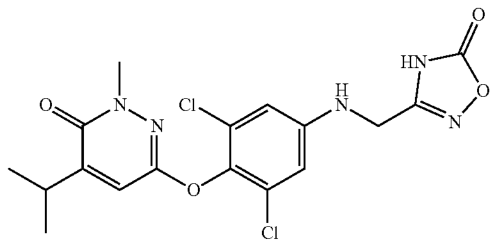 |
| 7-2 | 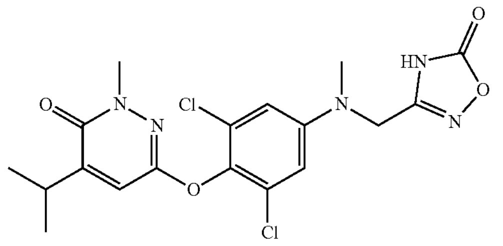 [SMILES: CC(C)c1cc(Oc2c(Cl)cc(N(C)Cc3noc(=O)[nH]3)cc2Cl)nn(C)c1=O] |
| 7-3 | 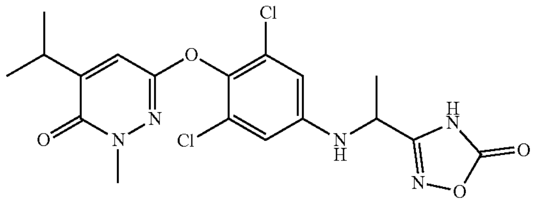 |
| 7-4 | 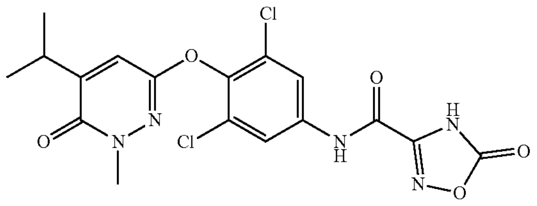 [SMILES: CC(C)c1cc(Oc2c(Cl)cc(NC(C)c3noc(=O)[nH]3)cc2Cl)nn(C)c1=O] |
| 7-5 | 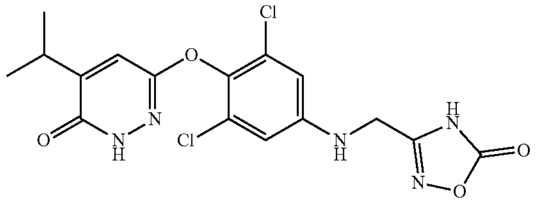 [SMILES: CC(C)c1cc(Oc2c(Cl)cc(NCc3noc(=O)[nH]3)cc2Cl)n[nH]c1=O] |
| 7-6 | 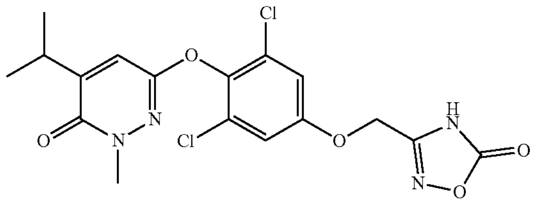 [SMILES: CC(C)c1cc(Oc2c(Cl)cc(OCc3noc(=O)[nH]3)cc2Cl)nn(C)c1=O] |
| 7-7 | 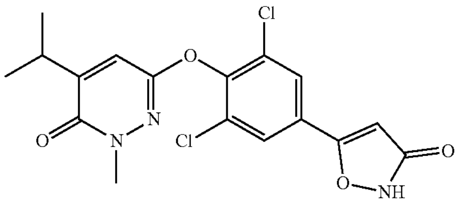 [SMILES: CC(C)c1cc(Oc2c(Cl)cc(-c3cc(=O)[nH]o3)cc2Cl)nn(C)c1=O] |

TABLE 7-continued
| Example | Structure |
|---|---|
| 7-8 | 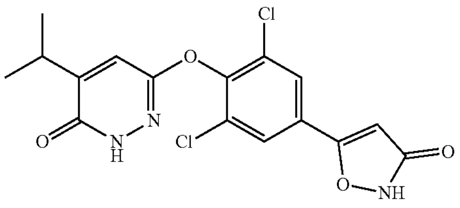 [SMILES: CC(C)c1cc(Oc2c(Cl)cc(-c3cc(=O)[nH]o3)cc2Cl)n[nH]c1=O] |
| 7-9 | 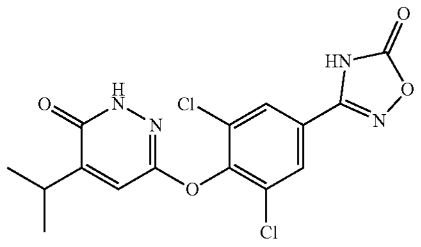 [SMILES: CC(C)c1cc(Oc2c(Cl)cc(-c3noc(=O)[nH]3)cc2Cl)n[nH]c1=O] |
| 7-10 | 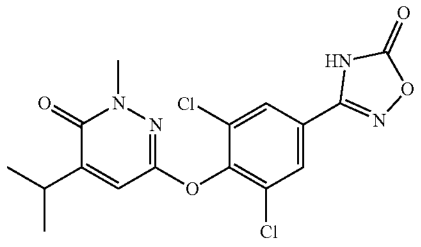 [SMILES: CC(C)c1cc(Oc2c(Cl)cc(-c3noc(=O)[nH]3)cc2Cl)nn(C)c1=O] |
| 7-11 | 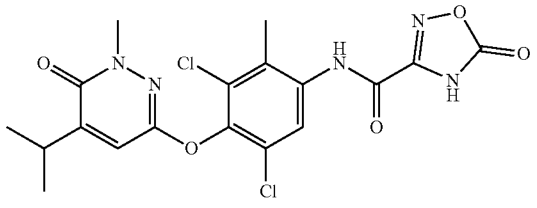 [SMILES: Cc1c(NC(=O)c2noc(=O)[nH]2)cc(Cl)c(Oc2cc(C(C)C)c(=O)n(C)n2)c1Cl] |
| 7-12 | 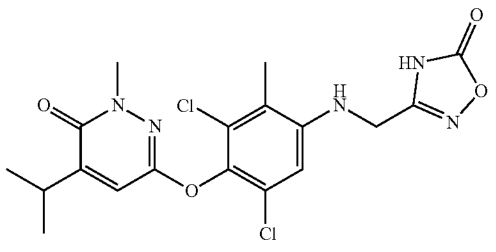 [SMILES: Cc1c(NCc2noc(=O)[nH]2)cc(Cl)c(Oc2cc(C(C)C)c(=O)n(C)n2)c1Cl] |
| 7-13 | 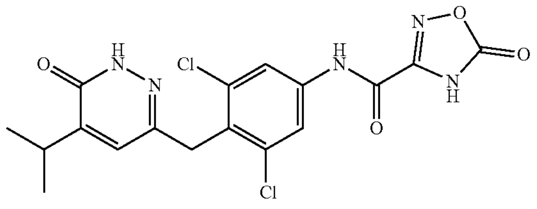 [SMILES: CC(C)c1cc(Cc2c(Cl)cc(NC(=O)c3noc(=O)[nH]3)cc2Cl)n[nH]c1=O] |

TABLE 7-continued
| Example | Structure |
|---|---|
| 7-14 | 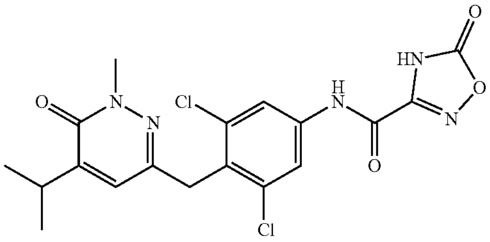 [SMILES: CC(C)c1cc(Cc2c(Cl)cc(NC(=O)c3noc(=O)[nH]3)cc2Cl)nn(C)c1=O] |
| 7-15 | 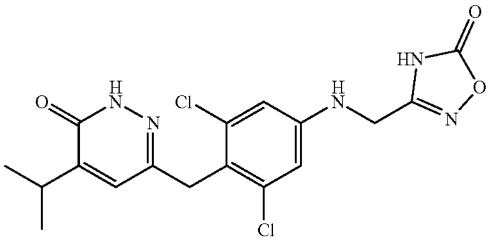 [SMILES: CC(C)c1cc(Cc2c(Cl)cc(NCc3noc(=O)[nH]3)cc2Cl)n[nH]c1=O] |
| 7-16 | 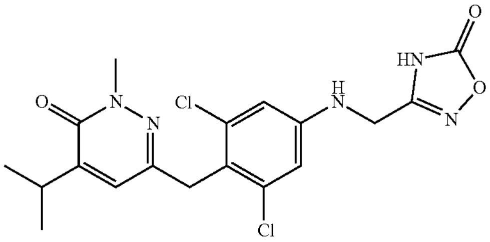 [SMILES: CC(C)c1cc(Cc2c(Cl)cc(NCc3noc(=O)[nH]3)cc2Cl)nn(C)c1=O] |
| 7-17 | 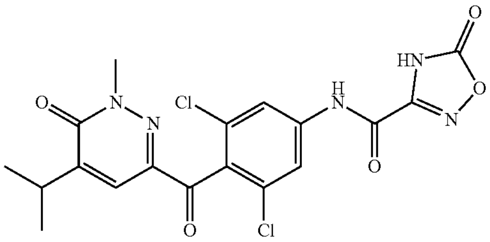 [SMILES: CC(C)c1cc(C(=O)c2c(Cl)cc(NC(=O)c3noc(=O)[nH]3)cc2Cl)nn(C)c1=O] |
| 7-18 | 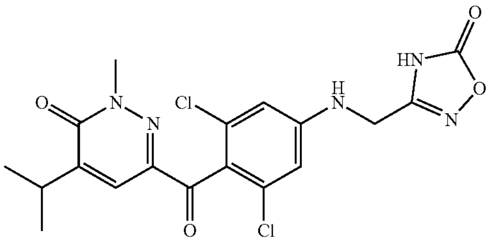 [SMILES: CC(C)c1cc(C(=O)c2c(Cl)cc(NCc3noc(=O)[nH]3)cc2Cl)nn(C)c1=O] |
| 7-19 | 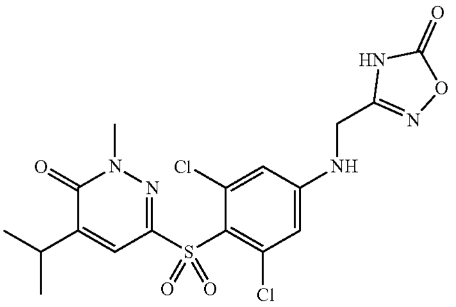 [SMILES: CC(C)c1cc(S(=O)(=O)c2c(Cl)cc(NCc3noc(=O)[nH]3)cc2Cl)nn(C)c1=O] |

TABLE 7-continued
| Example | Structure |
| --- | --- |
| 7-20 | 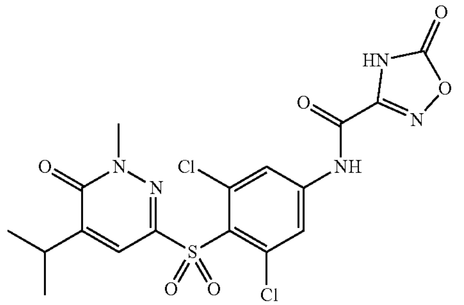 [SMILES: CC(C)c1cc(S(=O)(=O)c2c(Cl)cc(NC(=O)c3noc(=O)[nH]3)cc2Cl)nn(C)c1=O] |
| 7-21 | 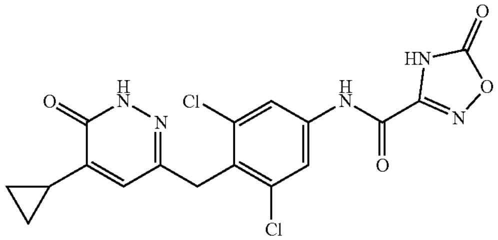 [SMILES: O=C(Nc1cc(Cl)c(Cc2cc(C3CC3)c(=O)[nH]n2)c(Cl)c1)c1noc(=O)[nH]1] |
| 7-22 | 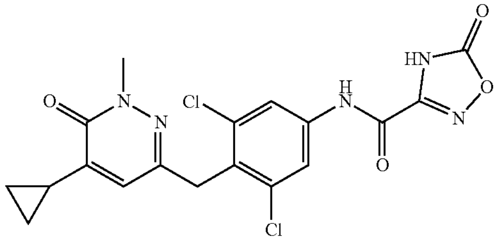 [SMILES: Cn1nc(Cc2c(Cl)cc(NC(=O)c3noc(=O)[nH]3)cc2Cl)cc(C2CC2)c1=O] |
| 7-23 | 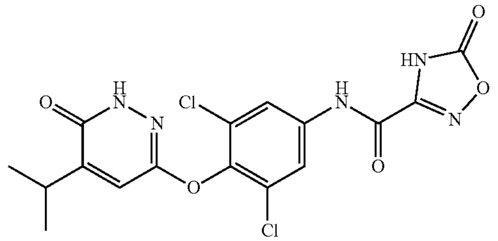 [SMILES: CC(C)c1cc(Oc2c(Cl)cc(NC(=O)c3noc(=O)[nH]3)cc2Cl)n[nH]c1=O] |
| 7-24 | 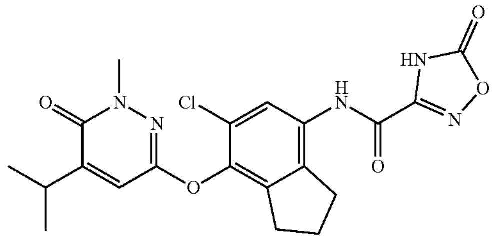 [SMILES: CC(C)c1cc(Oc2c(Cl)cc(NC(=O)c3noc(=O)[nH]3)c3c2CCC3)nn(C)c1=O] |
| 7-25 | 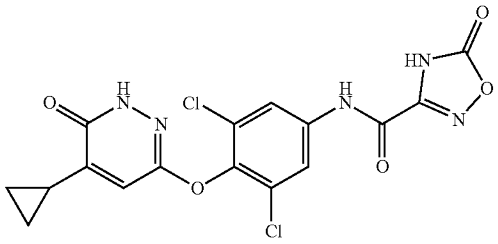 [SMILES: O=C(Nc1cc(Cl)c(Oc2cc(C3CC3)c(=O)[nH]n2)c(Cl)c1)c1noc(=O)[nH]1] |

TABLE 7-continued
| Example | Structure |
|---|---|
| 7-26 | 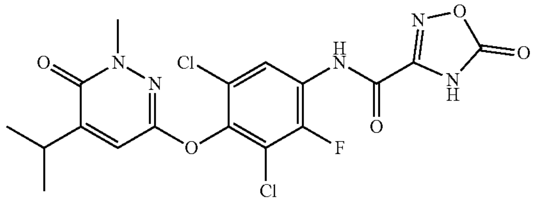 [SMILES: CC(C)c1cc(Oc2c(Cl)cc(NC(=O)c3noc(=O)[nH]3)c(F)c2Cl)nn(C)c1=O] |
| 7-27 | 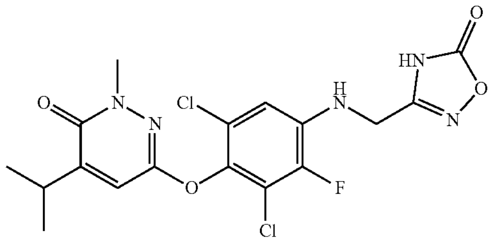 [SMILES: CC(C)c1cc(Oc2c(Cl)cc(NCc3noc(=O)[nH]3)c(F)c2Cl)nn(C)c1=O] |
| 7-28 | 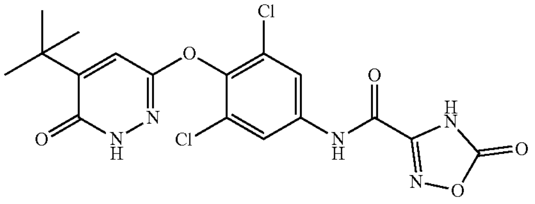 [SMILES: CC(C)(C)c1cc(Oc2c(Cl)cc(NC(=O)c3noc(=O)[nH]3)cc2Cl)n[nH]c1=O] |
| 7-29 | 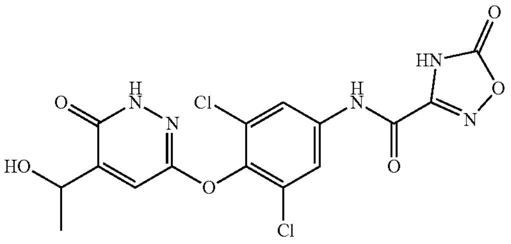 [SMILES: CC(O)c1cc(Oc2c(Cl)cc(NC(=O)c3noc(=O)[nH]3)cc2Cl)n[nH]c1=O] |
| 7-30 | 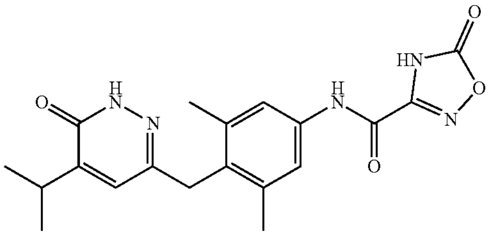 [SMILES: Cc1cc(NC(=O)c2noc(=O)[nH]2)cc(C)c1Cc1cc(C(C)C)c(=O)[nH]n1] |
| 7-31 | 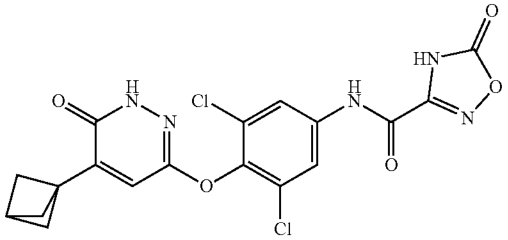 [SMILES: O=C(Nc1cc(Cl)c(Oc2cc(C34CC(C3)C4)c(=O)[nH]n2)c(Cl)c1)c1noc(=O)[nH]1] |

TABLE 7-continued
| Example | Structure |
| --- | --- |
| 7-32 | 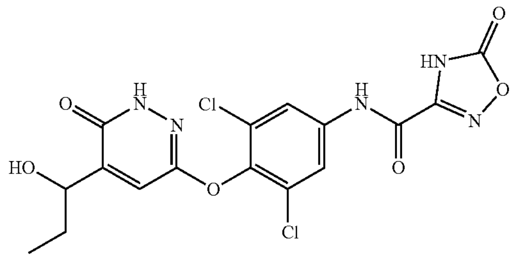 [SMILES: CCC(O)c1cc(Oc2c(Cl)cc(NC(=O)c3noc(=O)[nH]3)cc2Cl)n[nH]c1=O] |
| 7-33 | 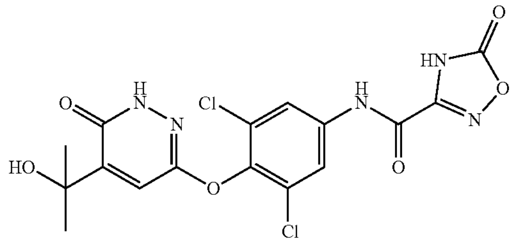 [SMILES: CC(C)(O)c1cc(Oc2c(Cl)cc(NC(=O)c3noc(=O)[nH]3)cc2Cl)n[nH]c1=O] |
| 7-34 | 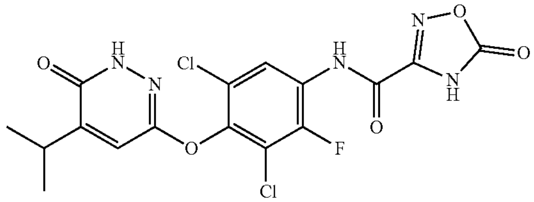 [SMILES: CC(C)c1cc(Oc2c(Cl)cc(NC(=O)c3noc(=O)[nH]3)c(F)c2Cl)n[nH]c1=O] |
| 7-35 | 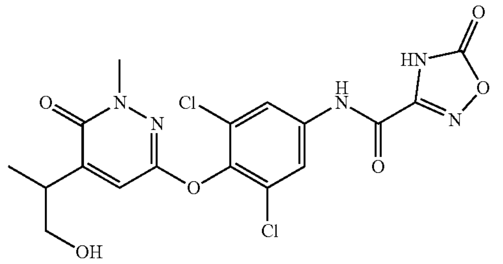 [SMILES: CC(CO)c1cc(Oc2c(Cl)cc(NC(=O)c3noc(=O)[nH]3)cc2Cl)nn(C)c1=O] |
| 7-36 | 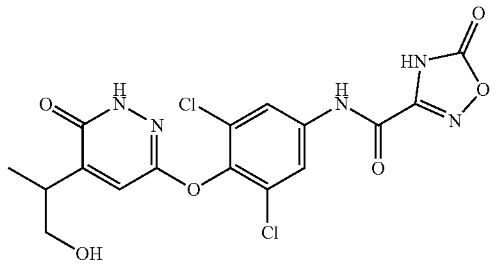 [SMILES: CC(CO)c1cc(Oc2c(Cl)cc(NC(=O)c3noc(=O)[nH]3)cc2Cl)n[nH]c1=O] |
| 7-37 | 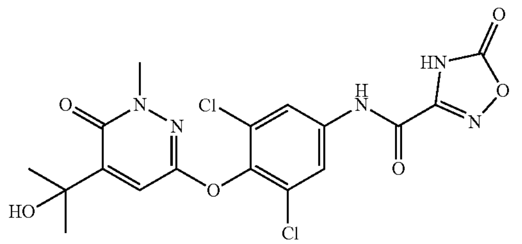 [SMILES: Cn1nc(Oc2c(Cl)cc(NC(=O)c3noc(=O)[nH]3)cc2Cl)cc(C(C)(C)O)c1=O] |

In some embodiments, the THRβ agonist is selected from those listed in Table 8 below, or a pharmaceutically acceptable salt thereof:
TABLE 8
| Compound Structure and Number |
|---|
| 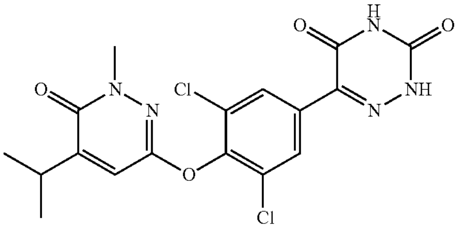 [SMILES: CC(C)c1cc(Oc2c(Cl)cc(-c3n[nH]c(=O)[nH]c3=O)cc2Cl)nn(C)c1=O] 8-1 |
| 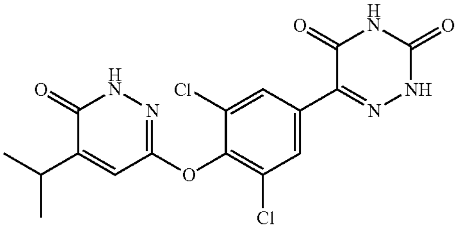 [SMILES: CC(C)c1cc(Oc2c(Cl)cc(-c3n[nH]c(=O)[nH]c3=O)cc2Cl)n[nH]c1=O] 8-2 |
| 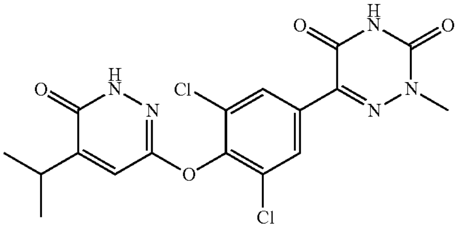 [SMILES: CC(C)c1cc(Oc2c(Cl)cc(-c3nn(C)c(=O)[nH]c3=O)cc2Cl)n[nH]c1=O] 8-3 |
| 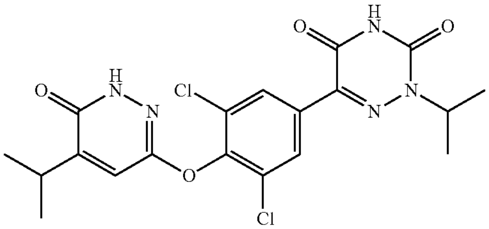 [SMILES: CC(C)c1cc(Oc2c(Cl)cc(-c3nn(C(C)C)c(=O)[nH]c3=O)cc2Cl)n[nH]c1=O] 8-4 |
| 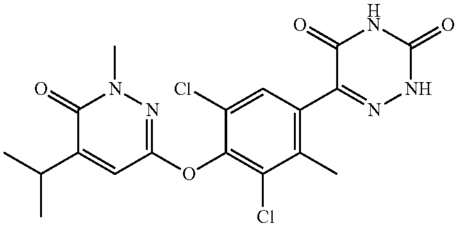 [SMILES: Cc1c(-c2n[nH]c(=O)[nH]c2=O)cc(Cl)c(Oc2cc(C(C)C)c(=O)n(C)n2)c1Cl] 8-5 |
| 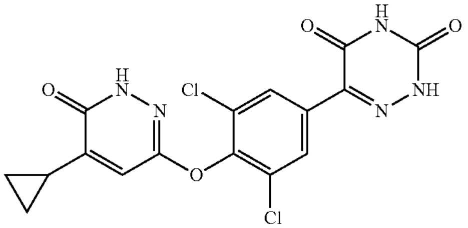 [SMILES: O=c1[nH]nc(-c2cc(Cl)c(Oc3cc(C4CC4)c(=O)[nH]n3)c(Cl)c2)c(=O)[nH]1] 8-6 |
TABLE 8-continued
| Compound Structure and Number |
|---|
| 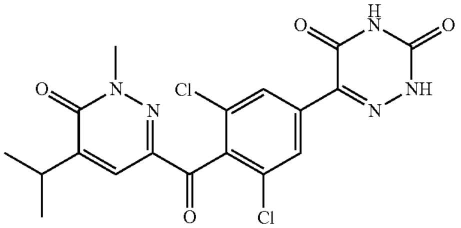 [SMILES: CC(C)c1cc(C(=O)c2c(Cl)cc(-c3n[nH]c(=O)[nH]c3=O)cc2Cl)nn(C)c1=O] 8-7 |
| 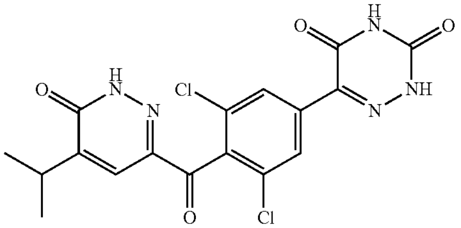 [SMILES: CC(C)c1cc(C(=O)c2c(Cl)cc(-c3n[nH]c(=O)[nH]c3=O)cc2Cl)n[nH]c1=O] 8-8 |
| 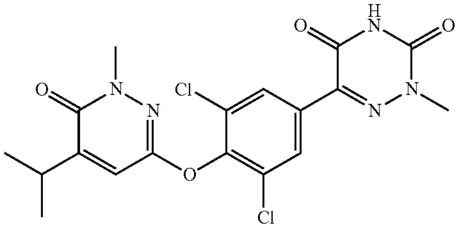 [SMILES: CC(C)c1cc(Oc2c(Cl)cc(-c3nn(C)c(=O)[nH]c3=O)cc2Cl)nn(C)c1=O] 8-9 |
| 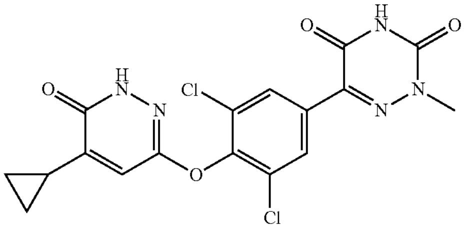 [SMILES: Cn1nc(-c2cc(Cl)c(Oc3cc(C4CC4)c(=O)[nH]n3)c(Cl)c2)c(=O)[nH]c1=O] 8-10 |
| 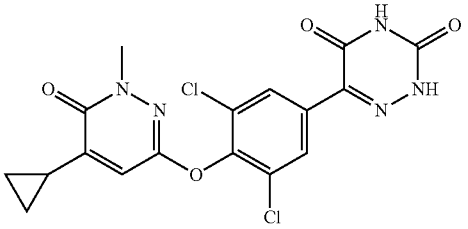 [SMILES: Cn1nc(Oc2c(Cl)cc(-c3n[nH]c(=O)[nH]c3=O)cc2Cl)cc(C2CC2)c1=O] 8-11 |
| 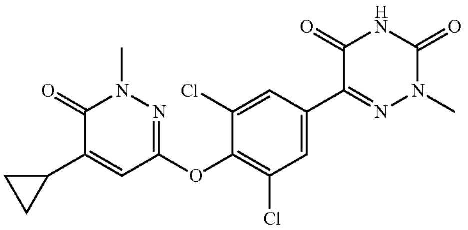 [SMILES: Cn1nc(-c2cc(Cl)c(Oc3cc(C4CC4)c(=O)n(C)n3)c(Cl)c2)c(=O)[nH]c1=O] 8-12 |

TABLE 8-continued
| Compound Structure and Number | |
|---|---|
| 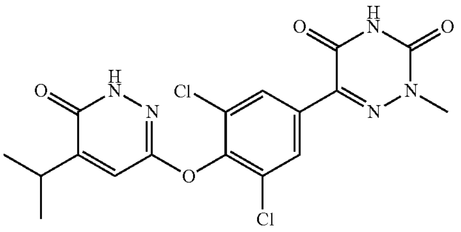 | 8-13 |
| 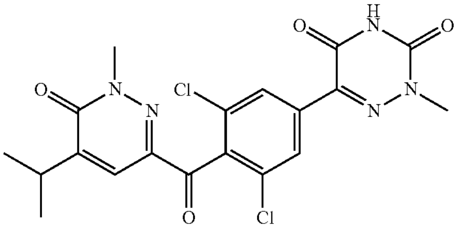 [SMILES: CC(C)c1cc(C(=O)c2c(Cl)cc(-c3nn(C)c(=O)[nH]c3=O)cc2Cl)nn(C)c1=O] | 8-14 |
| 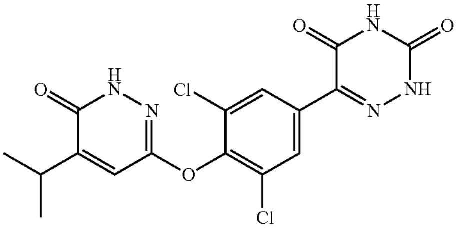 [SMILES: CC(C)c1cc(Oc2c(Cl)cc(-c3n[nH]c(=O)[nH]c3=O)cc2Cl)n[nH]c1=O] | 8-15 |
| 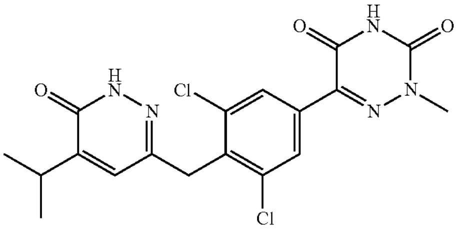 | 8-16 |
| 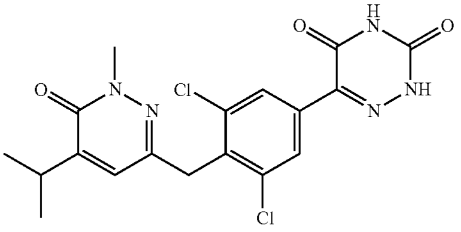 [SMILES: CC(C)c1cc(Cc2c(Cl)cc(-c3n[nH]c(=O)[nH]c3=O)cc2Cl)nn(C)c1=O] | 8-17 |
| 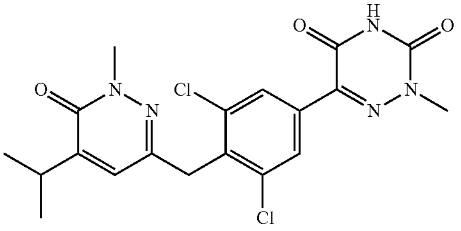 | 8-18 |
TABLE 8-continued
| Compound Structure and Number | |
|---|---|
| 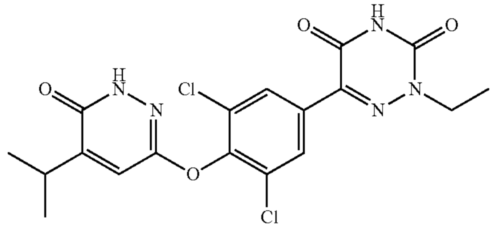 [SMILES: CCn1nc(-c2cc(Cl)c(Oc3cc(C(C)C)c(=O)[nH]n3)c(Cl)c2)c(=O)[nH]c1=O] | 8-19 |
| 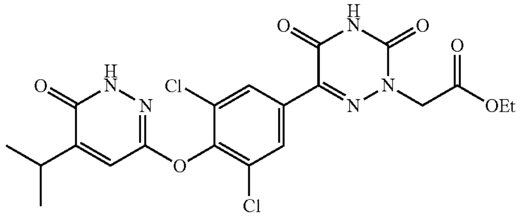 [SMILES: CCOC(=O)Cn1nc(-c2cc(Cl)c(Oc3cc(C(C)C)c(=O)[nH]n3)c(Cl)c2)c(=O)[nH]c1=O] | 8-20 |
| 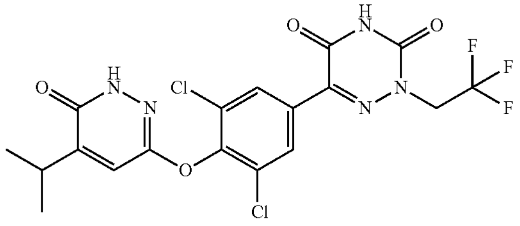 [SMILES: CC(C)c1cc(Oc2c(Cl)cc(-c3nn(CC(F)(F)F)c(=O)[nH]c3=O)cc2Cl)n[nH]c1=O] | 8-21 |
| 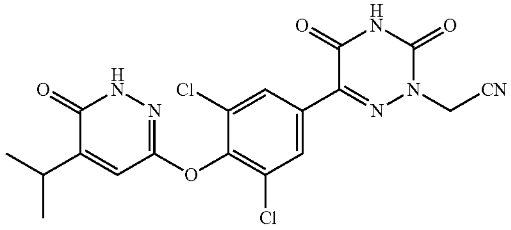 [SMILES: CC(C)c1cc(Oc2c(Cl)cc(-c3nn(CC#N)c(=O)[nH]c3=O)cc2Cl)n[nH]c1=O] | 8-22 |
| 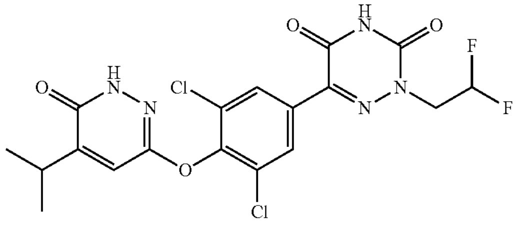 [SMILES: CC(C)c1cc(Oc2c(Cl)cc(-c3nn(CC(F)F)c(=O)[nH]c3=O)cc2Cl)n[nH]c1=O] | 8-23 |
| 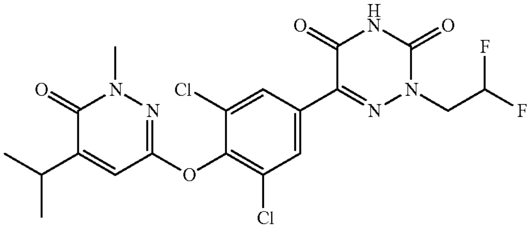 [SMILES: CC(C)c1cc(Oc2c(Cl)cc(-c3nn(CC(F)F)c(=O)[nH]c3=O)cc2Cl)nn(C)c1=O] | 8-24 |

TABLE 8-continued
| Compound Structure and Number |
| --- |
| 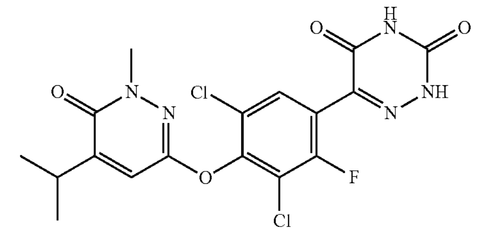 8-25 |
| 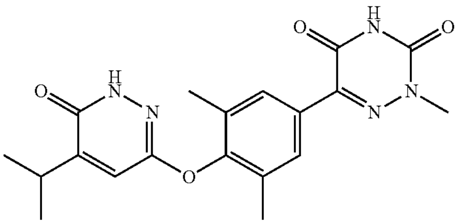 [SMILES: Cc1cc(-c2nn(C)c(=O)[nH]c2=O)cc(C)c1Oc1cc(C(C)C)c(=O)[nH]n1] 8-26 |
| 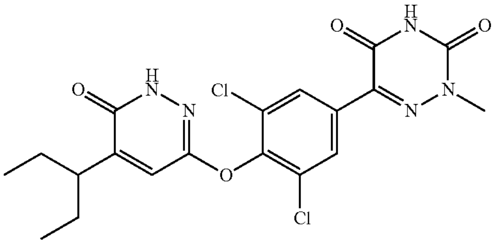 [SMILES: CCC(CC)c1cc(Oc2c(Cl)cc(-c3nn(C)c(=O)[nH]c3=O)cc2Cl)n[nH]c1=O] 8-27 |
| 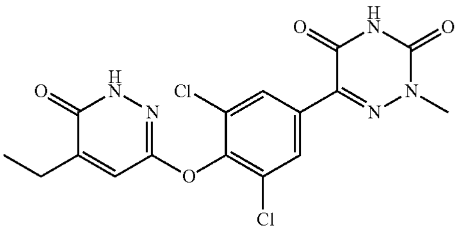 [SMILES: CCc1cc(Oc2c(Cl)cc(-c3nn(C)c(=O)[nH]c3=O)cc2Cl)n[nH]c1=O] 8-28 |
| 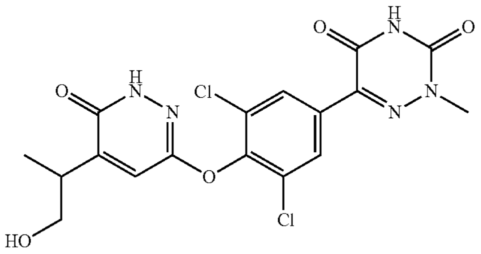 [SMILES: CC(CO)c1cc(Oc2c(Cl)cc(-c3nn(C)c(=O)[nH]c3=O)cc2Cl)n[nH]c1=O] 8-29 |
| 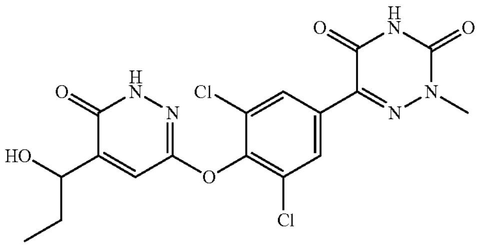 [SMILES: CCC(O)c1cc(Oc2c(Cl)cc(-c3nn(C)c(=O)[nH]c3=O)cc2Cl)n[nH]c1=O] 8-30 |
TABLE 8-continued
| Compound Structure and Number |
| --- |
| 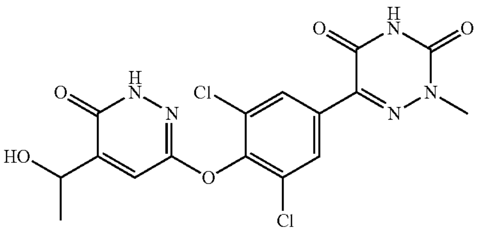 [SMILES: CC(O)c1cc(Oc2c(Cl)cc(-c3nn(C)c(=O)[nH]c3=O)cc2Cl)n[nH]c1=O] 8-31 |
| 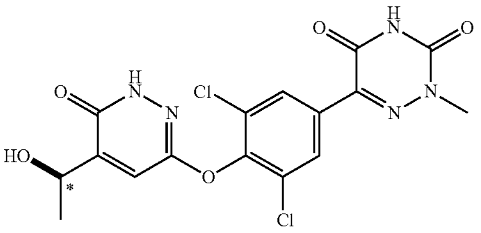 8-31 P1 |
| 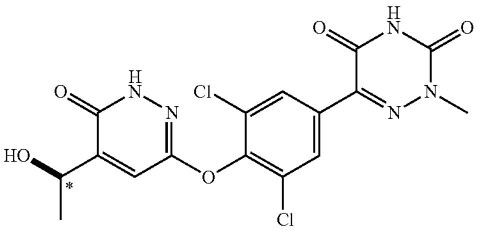 8-31 P2 |
| 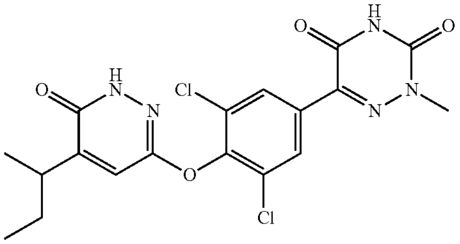 [SMILES: CCC(C)c1cc(Oc2c(Cl)cc(-c3nn(C)c(=O)[nH]c3=O)cc2Cl)n[nH]c1=O] 8-32 |
| 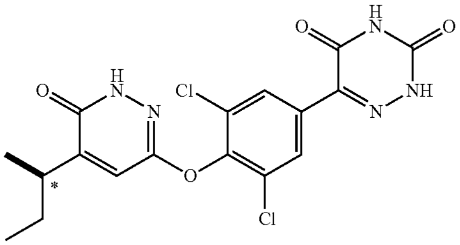 8-33 P1 |

TABLE 8-continued
| Compound Structure and Number | |
|---|---|
| 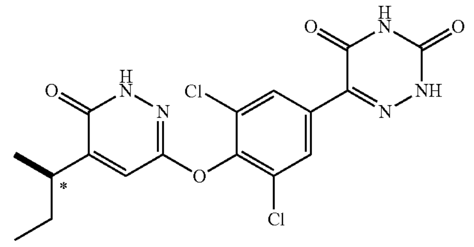 | 8-33 P2 |
| 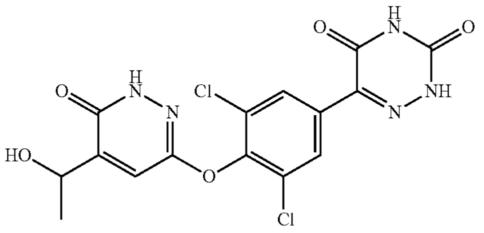 [SMILES: CC(O)c1cc(Oc2c(Cl)cc(-c3n[nH]c(=O)[nH]c3=O)cc2Cl)n[nH]c1=O] | 8-34 |
TABLE 8-continued
| Compound Structure and Number | |
|---|---|
| 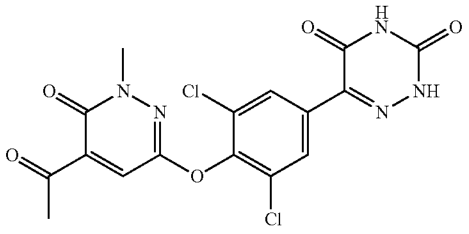 [SMILES: CC(=O)c1cc(Oc2c(Cl)cc(-c3n[nH]c(=O)[nH]c3=O)cc2Cl)nn(C)c1=O] | 8-35 |
In some embodiments, the THRβ agonist is selected from those listed in Table 9 below, or a pharmaceutically acceptable salt thereof:
TABLE 9
| Example | Structure |
|---|---|
| 9-1 | 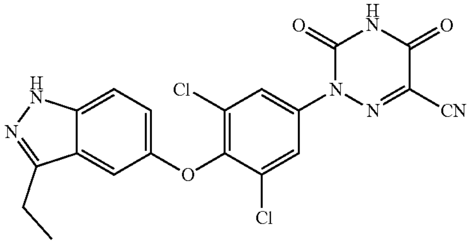 [SMILES: CCc1n[nH]c2ccc(Oc3c(Cl)cc(-n4nc(C#N)c(=O)[nH]c4=O)cc3Cl)cc12] |
| 9-2 | 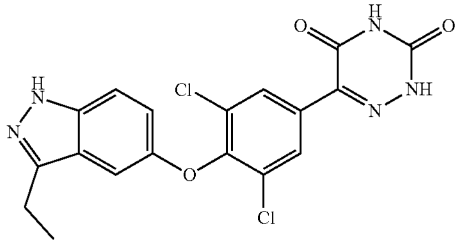 [SMILES: CCc1n[nH]c2ccc(Oc3c(Cl)cc(-c4n[nH]c(=O)[nH]c4=O)cc3Cl)cc12] |
| 9-3 | 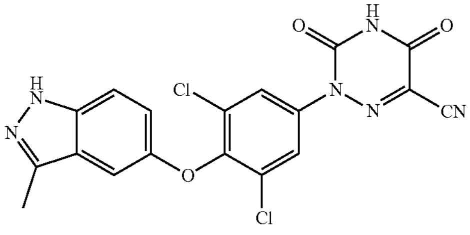 |
| 9-4 | 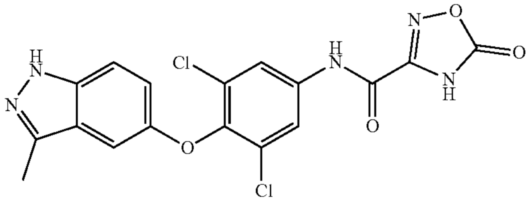 [SMILES: Cc1n[nH]c2ccc(Oc3c(Cl)cc(NC(=O)c4noc(=O)[nH]4)cc3Cl)cc12] |

TABLE 9-continued
| Example | Structure |
|---|---|
| 9-5 | 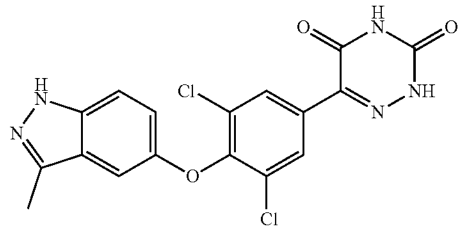 [SMILES: Cc1n[nH]c2ccc(Oc3c(Cl)cc(-c4n[nH]c(=O)[nH]c4=O)cc3Cl)cc12] |
| 9-6 | 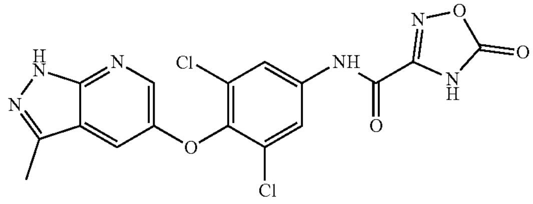 [SMILES: Cc1n[nH]c2ncc(Oc3c(Cl)cc(NC(=O)c4noc(=O)[nH]4)cc3Cl)cc12] |
| 9-7 | 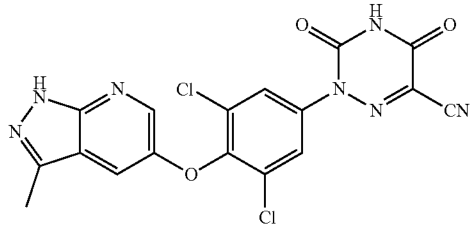 [SMILES: Cc1n[nH]c2ncc(Oc3c(Cl)cc(-n4nc(C#N)c(=O)[nH]c4=O)cc3Cl)cc12] |
| 9-8 | 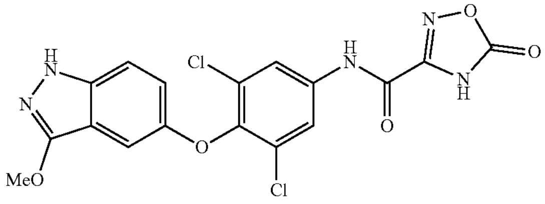 [SMILES: COc1n[nH]c2ccc(Oc3c(Cl)cc(NC(=O)c4noc(=O)[nH]4)cc3Cl)cc12] |
| 9-9 | 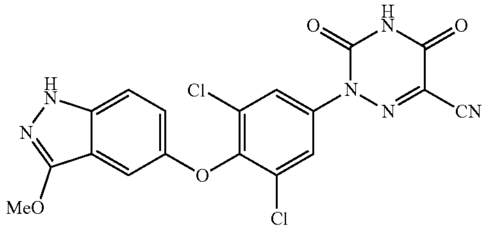 [SMILES: COc1n[nH]c2ccc(Oc3c(Cl)cc(-n4nc(C#N)c(=O)[nH]c4=O)cc3Cl)cc12] |
| 9-10 | 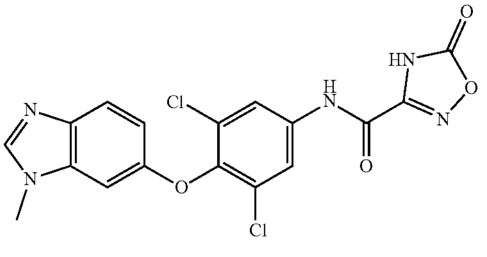 [SMILES: Cn1cnc2ccc(Oc3c(Cl)cc(NC(=O)c4noc(=O)[nH]4)cc3Cl)cc21] |

TABLE 9-continued
| Example | Structure |
| --- | --- |
| 9-11 | 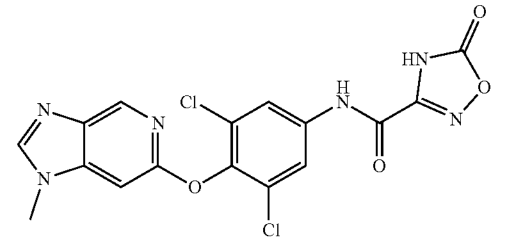 [SMILES: Cn1cnc2cnc(Oc3c(Cl)cc(NC(=O)c4noc(=O)[nH]4)cc3Cl)cc21] |
| 9-12 | 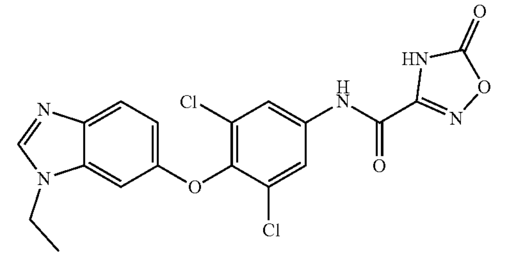 [SMILES: CCn1cnc2ccc(Oc3c(Cl)cc(NC(=O)c4noc(=O)[nH]4)cc3Cl)cc21] |
| 9-13 | 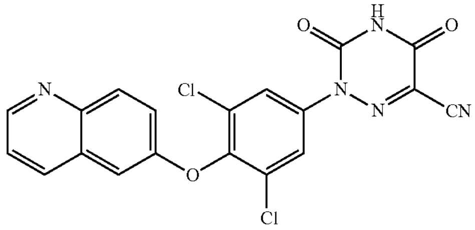 [SMILES: N#Cc1nn(-c2cc(Cl)c(Oc3ccc4ncccc4c3)c(Cl)c2)c(=O)[nH]c1=O] |
| 9-14 | 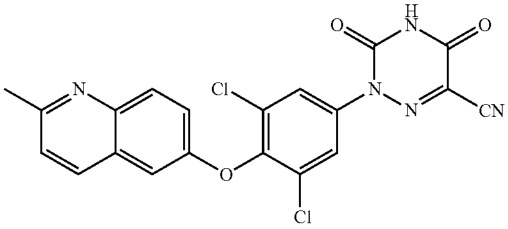 [SMILES: Cc1ccc2cc(Oc3c(Cl)cc(-n4nc(C#N)c(=O)[nH]c4=O)cc3Cl)ccc2n1] |
| 9-15 | 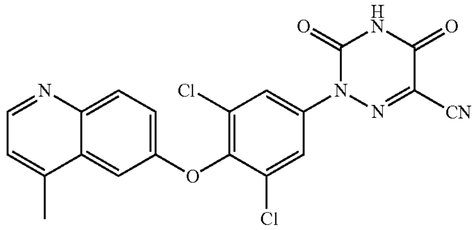 [SMILES: Cc1ccnc2ccc(Oc3c(Cl)cc(-n4nc(C#N)c(=O)[nH]c4=O)cc3Cl)cc12] |
| 9-16 | 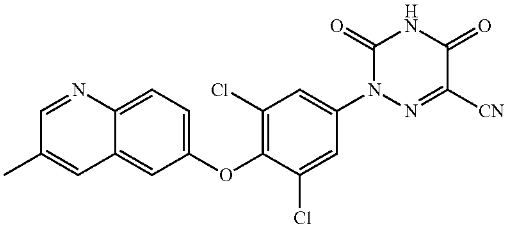 [SMILES: Cc1cnc2ccc(Oc3c(Cl)cc(-n4nc(C#N)c(=O)[nH]c4=O)cc3Cl)cc2c1] |

TABLE 9-continued
| Example | Structure |
| --- | --- |
| 9-17 | 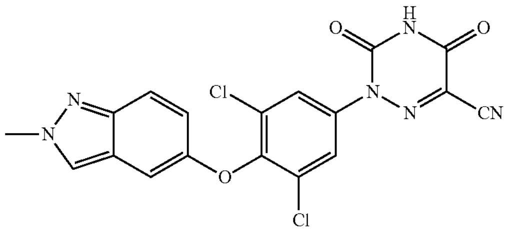 [SMILES: Cn1cc2cc(Oc3c(Cl)cc(-n4nc(C#N)c(=O)[nH]c4=O)cc3Cl)ccc2n1] |
| 9-18 | 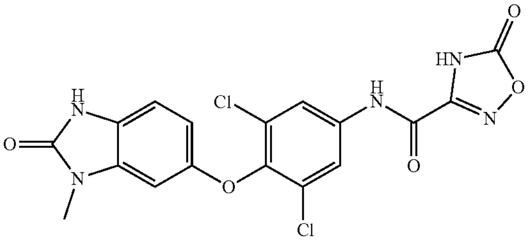 [SMILES: Cn1c(=O)[nH]c2ccc(Oc3c(Cl)cc(NC(=O)c4noc(=O)[nH]4)cc3Cl)cc21] |
| 9-19 | 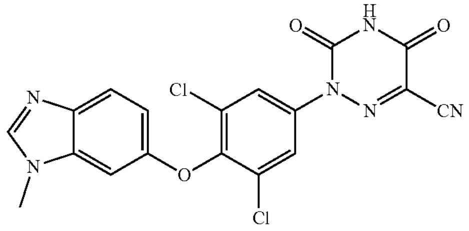 [SMILES: Cn1cnc2ccc(Oc3c(Cl)cc(-n4nc(C#N)c(=O)[nH]c4=O)cc3Cl)cc21] |
| 9-20 | 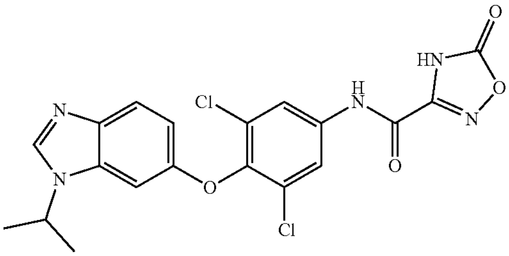 [SMILES: CC(C)n1cnc2ccc(Oc3c(Cl)cc(NC(=O)c4noc(=O)[nH]4)cc3Cl)cc21] |
| 9-21 | 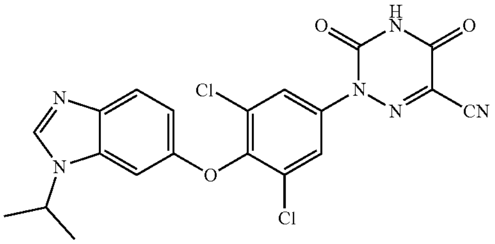 [SMILES: CC(C)n1cnc2ccc(Oc3c(Cl)cc(-n4nc(C#N)c(=O)[nH]c4=O)cc3Cl)cc21] |
| 9-22 | 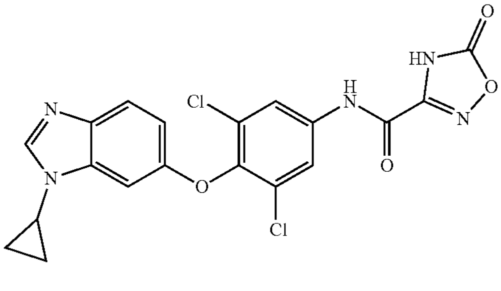 [SMILES: O=C(Nc1cc(Cl)c(Oc2ccc3ncn(C4CC4)c3c2)c(Cl)c1)c1noc(=O)[nH]1] |

TABLE 9-continued
| Example | Structure |
|---|---|
| 9-23 | 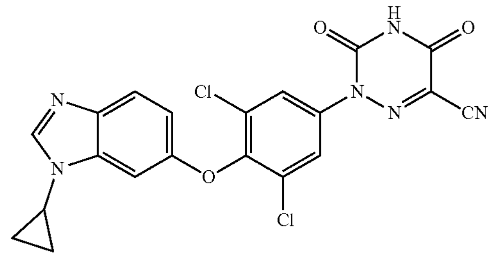 [SMILES: N#Cc1nn(-c2cc(Cl)c(Oc3ccc4ncn(C5CC5)c4c3)c(Cl)c2)c(=O)[nH]c1=O] |
| 9-24 | 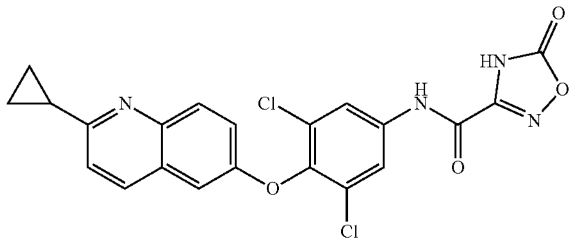 [SMILES: O=C(Nc1cc(Cl)c(Oc2ccc3nc(C4CC4)ccc3c2)c(Cl)c1)c1noc(=O)[nH]1] |
| 9-25 | 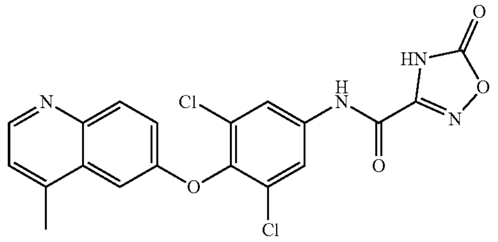 [SMILES: Cc1ccnc2ccc(Oc3c(Cl)cc(NC(=O)c4noc(=O)[nH]4)cc3Cl)cc12] |
| 9-26 | 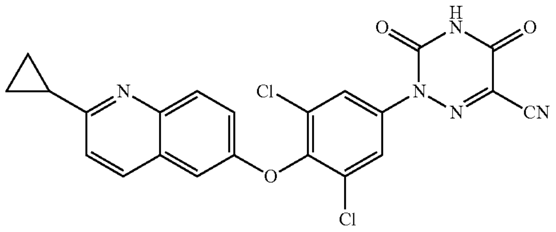 [SMILES: N#Cc1nn(-c2cc(Cl)c(Oc3ccc4nc(C5CC5)ccc4c3)c(Cl)c2)c(=O)[nH]c1=O] |
| 9-27 | 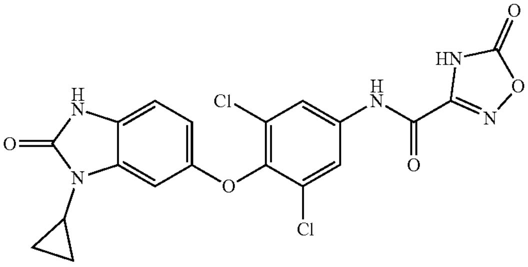 [SMILES: O=C(Nc1cc(Cl)c(Oc2ccc3[nH]c(=O)n(C4CC4)c3c2)c(Cl)c1)c1noc(=O)[nH]1] |
| 9-28 | 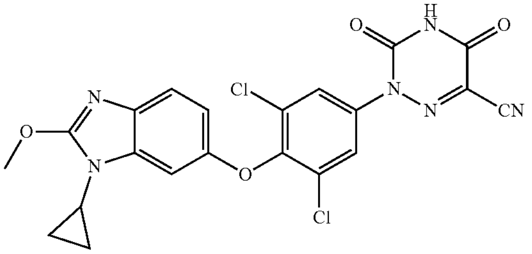 [SMILES: COc1nc2ccc(Oc3c(Cl)cc(-n4nc(C#N)c(=O)[nH]c4=O)cc3Cl)cc2n1C1CC1] |

TABLE 9-continued
| Example | Structure |
| --- | --- |
| 9-29 | 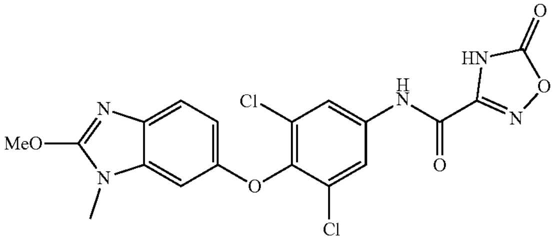 [SMILES: COc1nc2ccc(Oc3c(Cl)cc(NC(=O)c4noc(=O)[nH]4)cc3Cl)cc2n1C] |
| 9-30 | 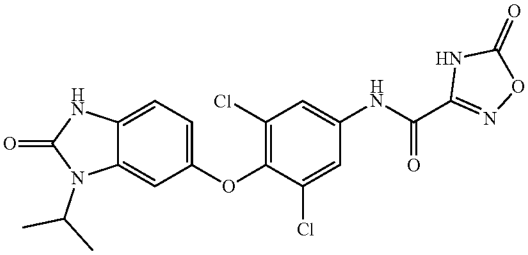 [SMILES: CC(C)n1c(=O)[nH]c2ccc(Oc3c(Cl)cc(NC(=O)c4noc(=O)[nH]4)cc3Cl)cc21] |
| 9-31 | 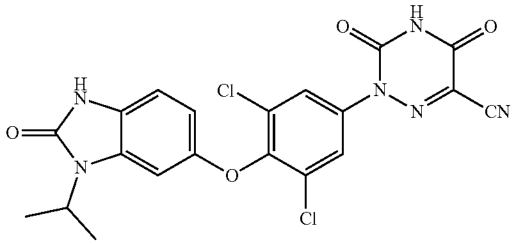 [SMILES: CC(C)n1c(=O)[nH]c2ccc(Oc3c(Cl)cc(-n4nc(C#N)c(=O)[nH]c4=O)cc3Cl)cc21] |
| 9-32 | 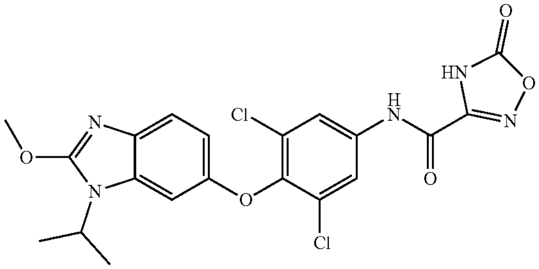 [SMILES: COc1nc2ccc(Oc3c(Cl)cc(NC(=O)c4noc(=O)[nH]4)cc3Cl)cc2n1C(C)C] |
| 9-33 | 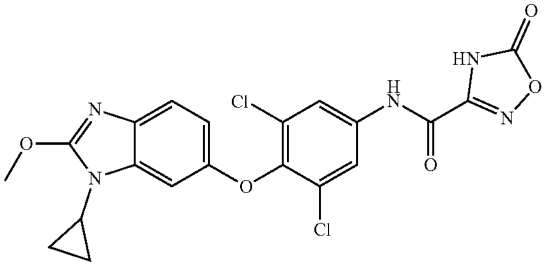 [SMILES: COc1nc2ccc(Oc3c(Cl)cc(NC(=O)c4noc(=O)[nH]4)cc3Cl)cc2n1C1CC1] |
| 9-34 | 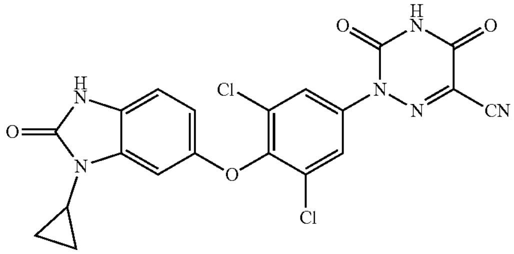 [SMILES: N#Cc1nn(-c2cc(Cl)c(Oc3ccc4[nH]c(=O)n(C5CC5)c4c3)c(Cl)c2)c(=O)[nH]c1=O] |

TABLE 9-continued
| Example | Structure |
| --- | --- |
| 9-35 | 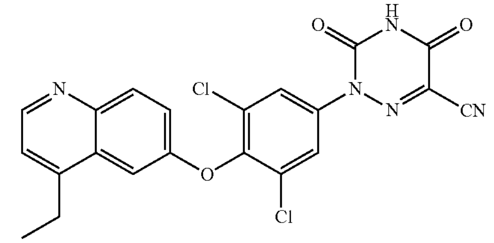 [SMILES: CCc1ccnc2ccc(Oc3c(Cl)cc(-n4nc(C#N)c(=O)[nH]c4=O)cc3Cl)cc12] |
| 9-36 | 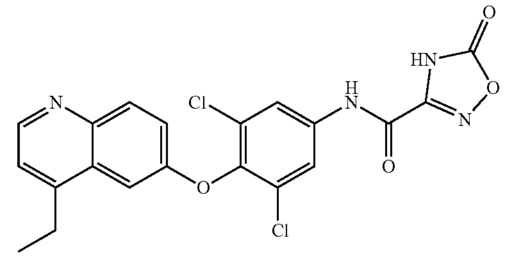 [SMILES: CCc1ccnc2ccc(Oc3c(Cl)cc(NC(=O)c4noc(=O)[nH]4)cc3Cl)cc12] |
| 9-37 | 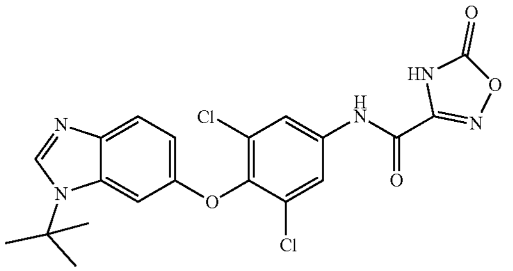 [SMILES: CC(C)(C)n1cnc2ccc(Oc3c(Cl)cc(NC(=O)c4noc(=O)[nH]4)cc3Cl)cc21] |
| 9-38 | 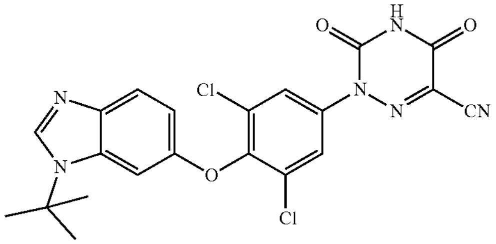 [SMILES: CC(C)(C)n1cnc2ccc(Oc3c(Cl)cc(-n4nc(C#N)c(=O)[nH]c4=O)cc3Cl)cc21] |
| 9-39 | 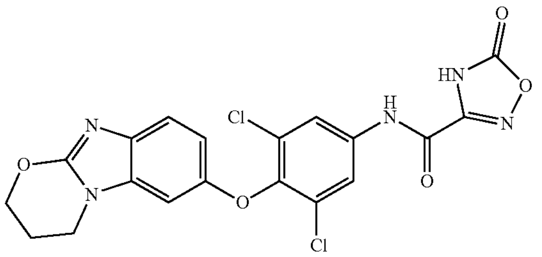 [SMILES: O=C(Nc1cc(Cl)c(Oc2ccc3nc4n(c3c2)CCCO4)c(Cl)c1)c1noc(=O)[nH]1] |
| 9-40 | 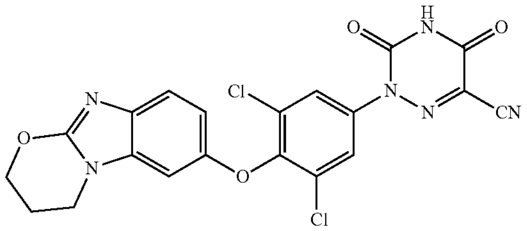 [SMILES: N#Cc1nn(-c2cc(Cl)c(Oc3ccc4nc5n(c4c3)CCCO5)c(Cl)c2)c(=O)[nH]c1=O] |

TABLE 9-continued
| Example | Structure |
|---|---|
| 9-41 | 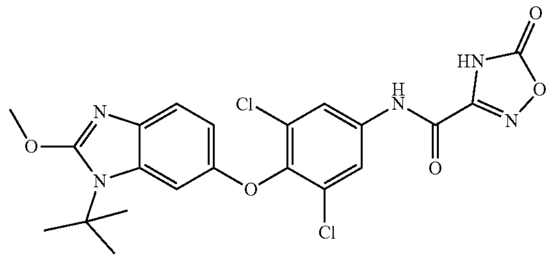 [SMILES: COc1nc2ccc(Oc3c(Cl)cc(NC(=O)c4noc(=O)[nH]4)cc3Cl)cc2n1C(C)(C)C] |
| 9-42 | 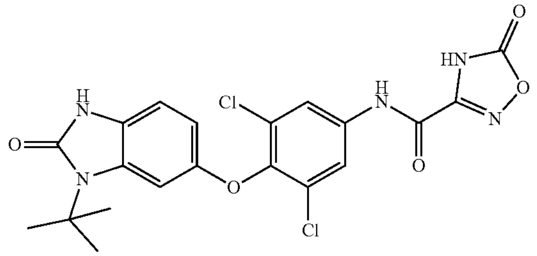 [SMILES: CC(C)(C)n1c(=O)[nH]c2ccc(Oc3c(Cl)cc(NC(=O)c4noc(=O)[nH]4)cc3Cl)cc21] |
| 9-43 | 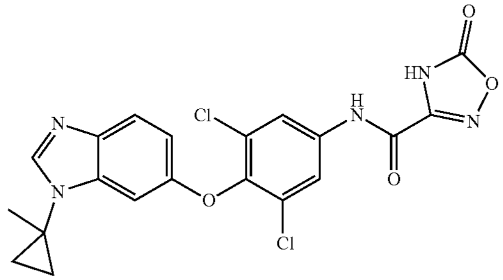 [SMILES: CC1(n2cnc3ccc(Oc4c(Cl)cc(NC(=O)c5noc(=O)[nH]5)cc4Cl)cc32)CC1] |
| 9-44 | 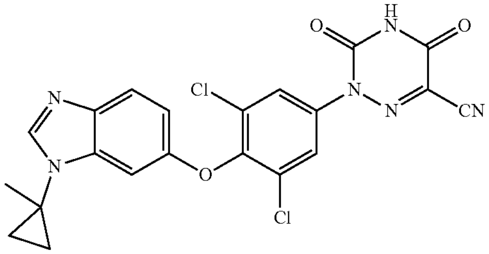 [SMILES: CC1(n2cnc3ccc(Oc4c(Cl)cc(-n5nc(C#N)c(=O)[nH]c5=O)cc4Cl)cc32)CC1] |
| 9-45 | 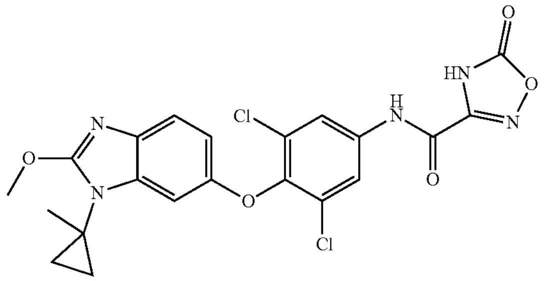 [SMILES: COc1nc2ccc(Oc3c(Cl)cc(NC(=O)c4noc(=O)[nH]4)cc3Cl)cc2n1C1(C)CC1] |

TABLE 9-continued
| Example | Structure |
| --- | --- |
| 9-46 | 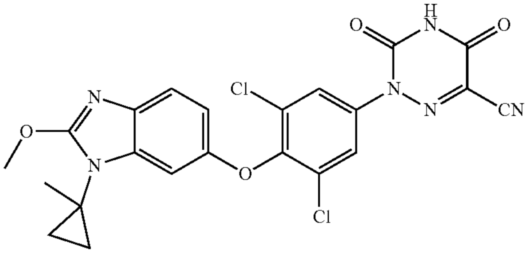 [SMILES: COc1nc2ccc(Oc3c(Cl)cc(-n4nc(C#N)c(=O)[nH]c4=O)cc3Cl)cc2n1C1(C)CC1] |
| 9-47 | 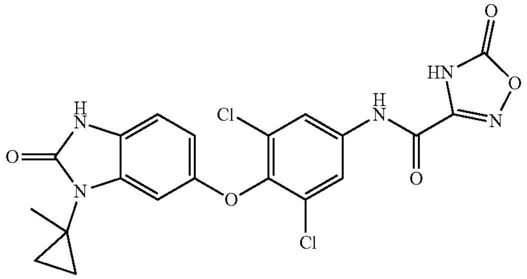 [SMILES: CC1(n2c(=O)[nH]c3ccc(Oc4c(Cl)cc(NC(=O)c5noc(=O)[nH]5)cc4Cl)cc32)CC1] |
| 9-48 | 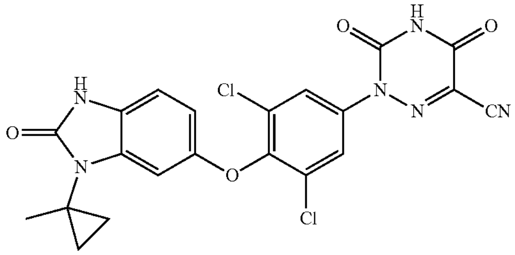 [SMILES: CC1(n2c(=O)[nH]c3ccc(Oc4c(Cl)cc(-n5nc(C#N)c(=O)[nH]c5=O)cc4Cl)cc32)CC1] |
| 9-49 | 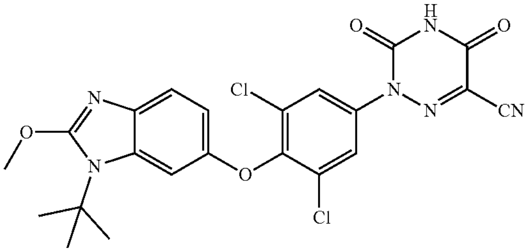 [SMILES: COc1nc2ccc(Oc3c(Cl)cc(-n4nc(C#N)c(=O)[nH]c4=O)cc3Cl)cc2n1C(C)(C)C] |
| 9-50 | 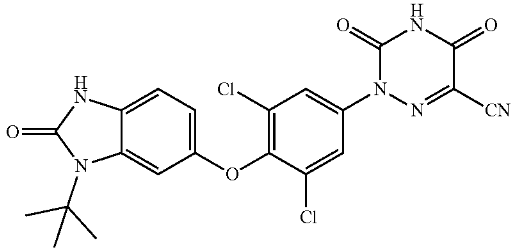 [SMILES: CC(C)(C)n1c(=O)[nH]c2ccc(Oc3c(Cl)cc(-n4nc(C#N)c(=O)[nH]c4=O)cc3Cl)cc21] |
| 9-51 | 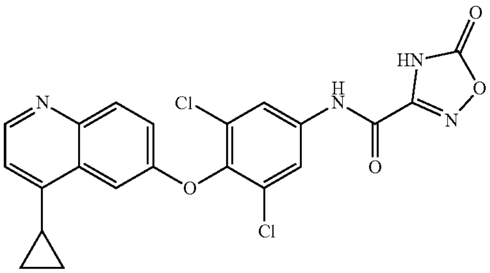 [SMILES: O=C(Nc1cc(Cl)c(Oc2ccc3nccc(C4CC4)c3c2)c(Cl)c1)c1noc(=O)[nH]1] |

TABLE 9-continued
| Example | Structure |
| --- | --- |
| 9-52 | 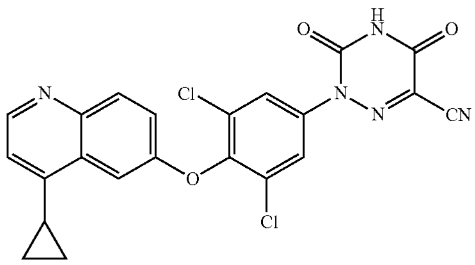 [SMILES: N#Cc1nn(-c2cc(Cl)c(Oc3ccc4nccc(C5CC5)c4c3)c(Cl)c2)c(=O)[nH]c1=O] |
| 9-53 | 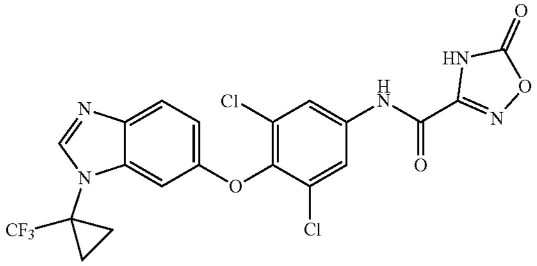 [SMILES: O=C(Nc1cc(Cl)c(Oc2ccc3ncn(C4(C(F)(F)F)CC4)c3c2)c(Cl)c1)c1noc(=O)[nH]1] |
| 9-54 | 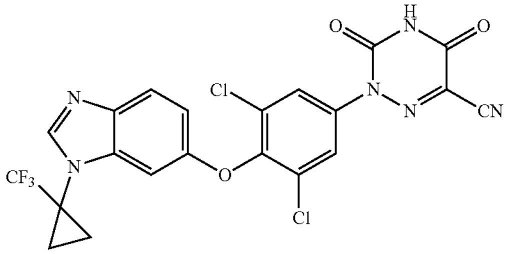 [SMILES: N#Cc1nn(-c2cc(Cl)c(Oc3ccc4ncn(C5(C(F)(F)F)CC5)c4c3)c(Cl)c2)c(=O)[nH]c1=O] |
| 9-55 | 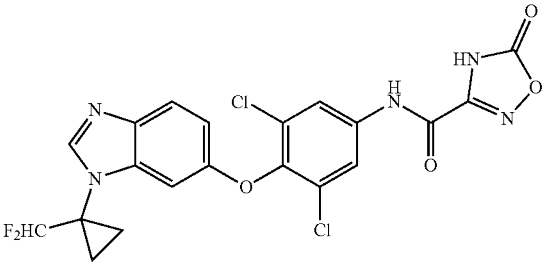 [SMILES: O=C(Nc1cc(Cl)c(Oc2ccc3ncn(C4(C(F)F)CC4)c3c2)c(Cl)c1)c1noc(=O)[nH]1] |
| 9-56 | 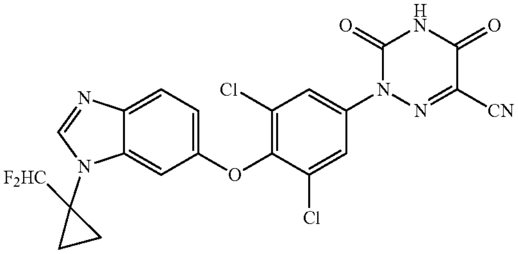 [SMILES: N#Cc1nn(-c2cc(Cl)c(Oc3ccc4ncn(C5(C(F)F)CC5)c4c3)c(Cl)c2)c(=O)[nH]c1=O] |

TABLE 9-continued
| Example | Structure |
| --- | --- |
| 9-57 | 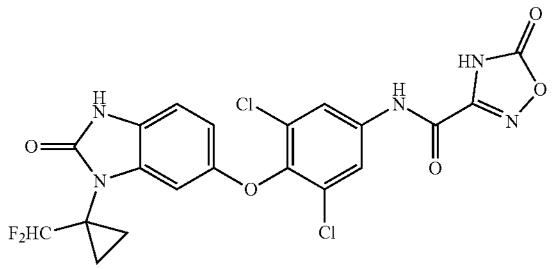 [SMILES: O=C(Nc1cc(Cl)c(Oc2ccc3[nH]c(=O)n(C4(C(F)F)CC4)c3c2)c(Cl)c1)c1noc(=O)[nH]1] |
| 9-58 | 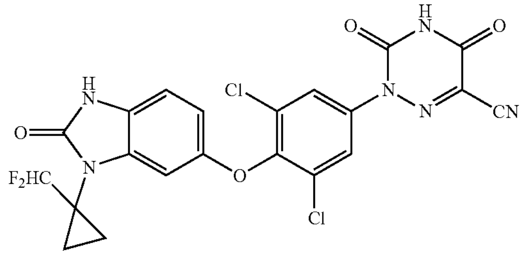 [SMILES: N#Cc1nn(-c2cc(Cl)c(Oc3ccc4[nH]c(=O)n(C5(C(F)F)CC5)c4c3)c(Cl)c2)c(=O)[nH]c1=O] |
| 9-59 | 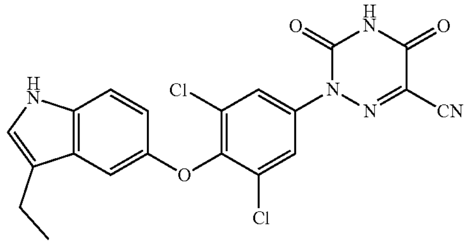 [SMILES: CCc1c[nH]c2ccc(Oc3c(Cl)cc(-n4nc(C#N)c(=O)[nH]c4=O)cc3Cl)cc12] |
In some embodiments, the THRβ agonist is selected from those listed in Table 10 below, or a pharmaceutically acceptable salt thereof:
TABLE 10
| Example | Structure |
| --- | --- |
| 10-1 | 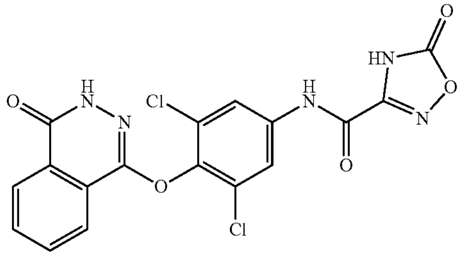 [SMILES: O=C(Nc1cc(Cl)c(Oc2n[nH]c(=O)c3ccccc23)c(Cl)c1)c1noc(=O)[nH]1] |
TABLE 10-continued
| Example | Structure |
| --- | --- |
| 10-2 | 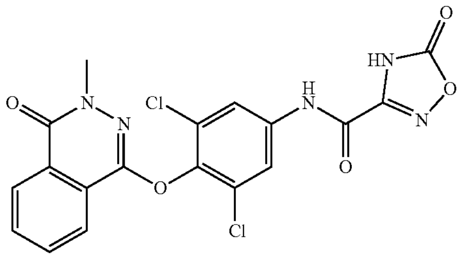 [SMILES: Cn1nc(Oc2c(Cl)cc(NC(=O)c3noc(=O)[nH]3)cc2Cl)c2ccccc2c1=O] |
In some embodiments, the THRβ agonist is selected from those listed in Table 11 below, or a pharmaceutically acceptable salt thereof:

TABLE 11
| Example | Structure |
| --- | --- |
| 11-1 | 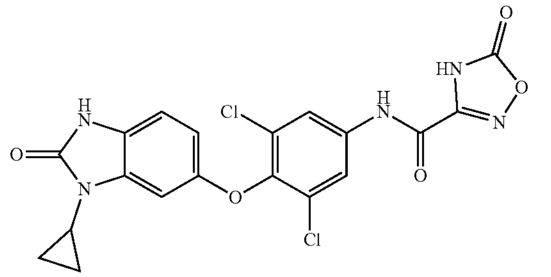 [SMILES: O=C(Nc1cc(Cl)c(Oc2ccc3[nH]c(=O)n(C4CC4)c3c2)c(Cl)c1)c1noc(=O)[nH]1] |
| 11-2 | 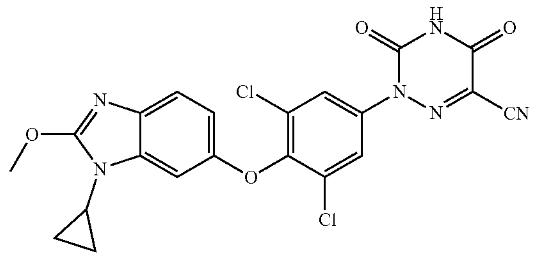 [SMILES: COc1nc2ccc(Oc3c(Cl)cc(-n4nc(C#N)c(=O)[nH]c4=O)cc3Cl)cc2n1C1CC1] |
| 11-3 | 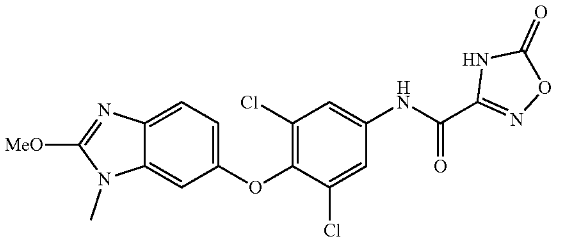 [SMILES: COc1nc2ccc(Oc3c(Cl)cc(NC(=O)c4noc(=O)[nH]4)cc3Cl)cc2n1C] |
| 11-4 | 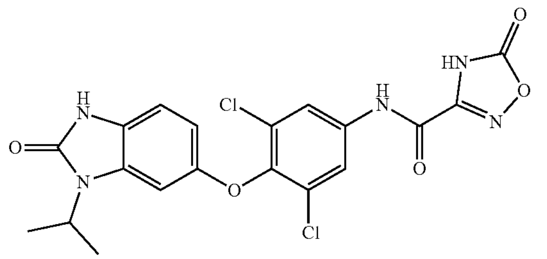 [SMILES: CC(C)n1c(=O)[nH]c2ccc(Oc3c(Cl)cc(NC(=O)c4noc(=O)[nH]4)cc3Cl)cc21] |
| 11-5 | 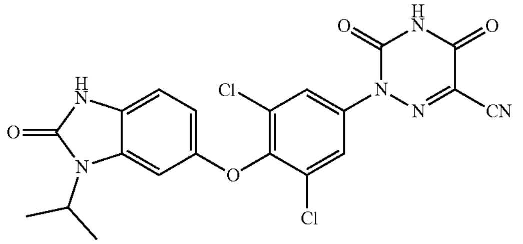 [SMILES: CC(C)n1c(=O)[nH]c2ccc(Oc3c(Cl)cc(-n4nc(C#N)c(=O)[nH]c4=O)cc3Cl)cc21] |
| 11-6 | 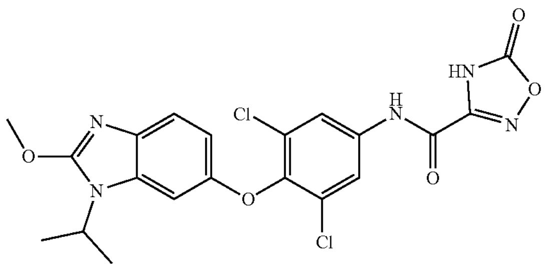 [SMILES: COc1nc2ccc(Oc3c(Cl)cc(NC(=O)c4noc(=O)[nH]4)cc3Cl)cc2n1C(C)C] |

TABLE 11-continued
| Example | Structure |
|---|---|
| 11-7 | 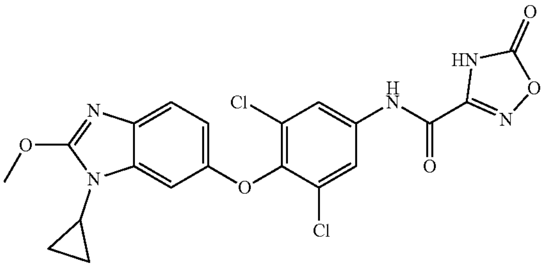 [SMILES: COc1nc2ccc(Oc3c(Cl)cc(NC(=O)c4noc(=O)[nH]4)cc3Cl)cc2n1C1CC1] |
| 11-8 | 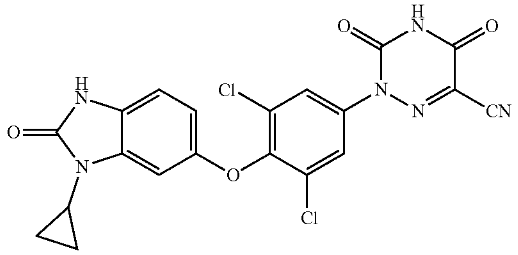 [SMILES: N#Cc1nn(-c2cc(Cl)c(Oc3ccc4[nH]c(=O)n(C5CC5)c4c3)c(Cl)c2)c(=O)[nH]c1=O] |
| 11-9 | 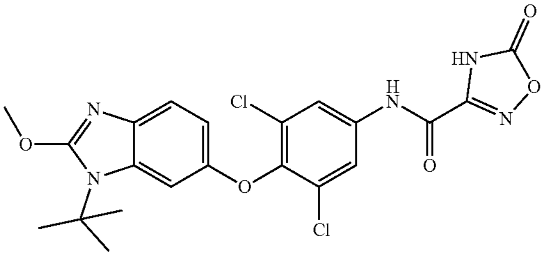 [SMILES: COc1nc2ccc(Oc3c(Cl)cc(NC(=O)c4noc(=O)[nH]4)cc3Cl)cc2n1C(C)(C)C] |
| 11-10 | 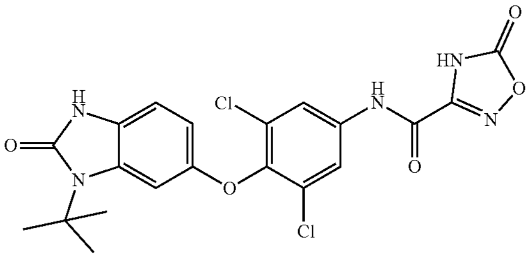 [SMILES: CC(C)(C)n1c(=O)[nH]c2ccc(Oc3c(Cl)cc(NC(=O)c4noc(=O)[nH]4)cc3Cl)cc21] |
| 11-11 | 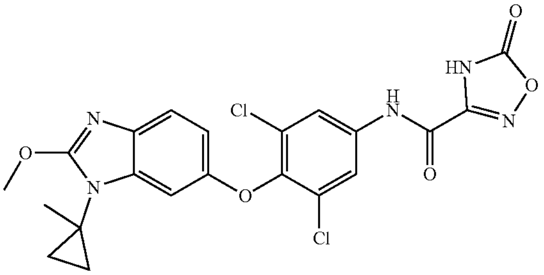 [SMILES: COc1nc2ccc(Oc3c(Cl)cc(NC(=O)c4noc(=O)[nH]4)cc3Cl)cc2n1C1(C)CC1] |
| 11-12 | 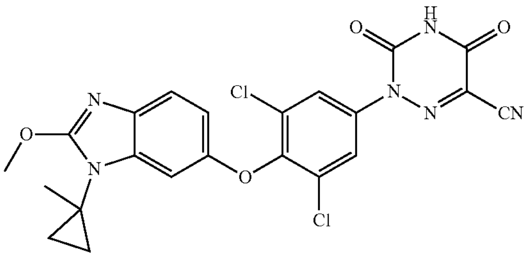 [SMILES: COc1nc2ccc(Oc3c(Cl)cc(-n4nc(C#N)c(=O)[nH]c4=O)cc3Cl)cc2n1C1(C)CC1] |

TABLE 11-continued
| Example | Structure |
| --- | --- |
| 11-13 | 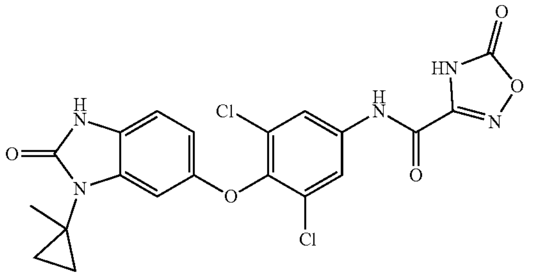 [SMILES: CC1(n2c(=O)[nH]c3ccc(Oc4c(Cl)cc(NC(=O)c5noc(=O)[nH]5)cc4Cl)cc32)CC1] |
| 11-14 | 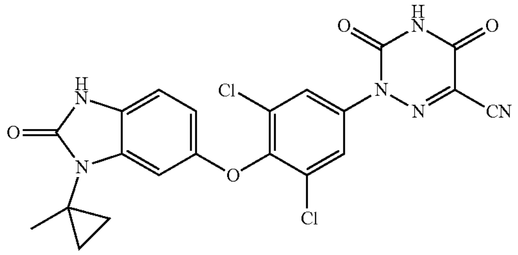 [SMILES: CC1(n2c(=O)[nH]c3ccc(Oc4c(Cl)cc(-n5nc(C#N)c(=O)[nH]c5=O)cc4Cl)cc32)CC1] |
| 11-15 | 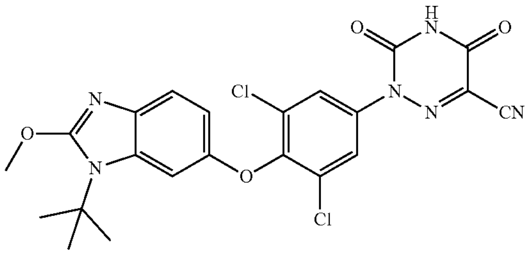 [SMILES: COc1nc2ccc(Oc3c(Cl)cc(-n4nc(C#N)c(=O)[nH]c4=O)cc3Cl)cc2n1C(C)(C)C] |
| 11-16 | 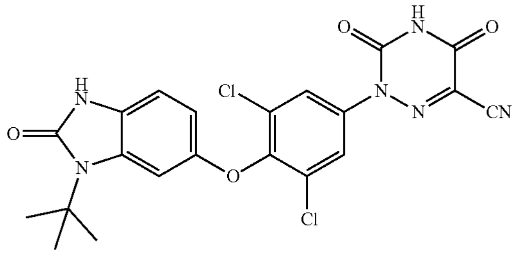 [SMILES: CC(C)(C)n1c(=O)[nH]c2ccc(Oc3c(Cl)cc(-n4nc(C#N)c(=O)[nH]c4=O)cc3Cl)cc21] |
| 11-17 | 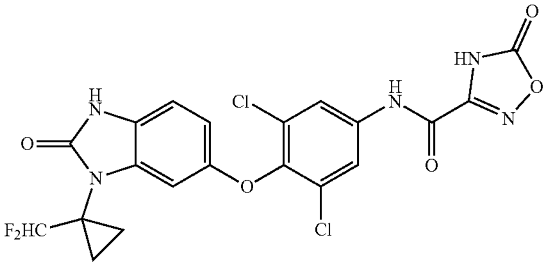 [SMILES: O=C(Nc1cc(Cl)c(Oc2ccc3[nH]c(=O)n(C4(C(F)F)CC4)c3c2)c(Cl)c1)c1noc(=O)[nH]1] |

TABLE 11-continued
| Example | Structure |
| --- | --- |
| 11-18 | 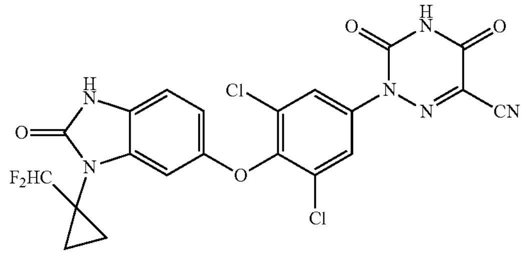 [SMILES: N#Cc1nn(-c2cc(Cl)c(Oc3ccc4[nH]c(=O)n(C5(C(F)F)CC5)c4c3)c(Cl)c2)c(=O)[nH]c1=O] |
| 11-19 | 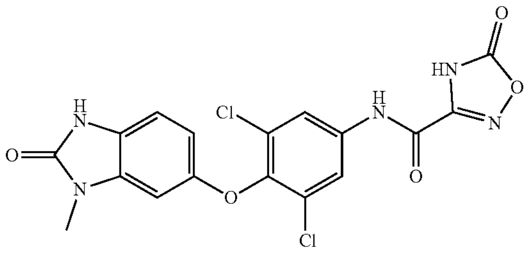 [SMILES: Cn1c(=O)[nH]c2ccc(Oc3c(Cl)cc(NC(=O)c4noc(=O)[nH]4)cc3Cl)cc21] |
| 11-20 | 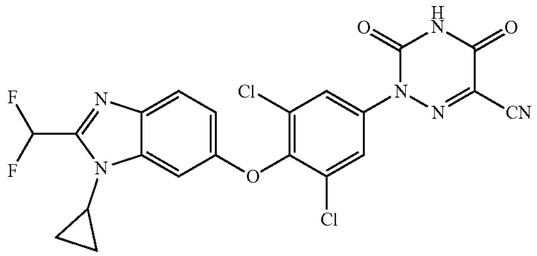 [SMILES: N#Cc1nn(-c2cc(Cl)c(Oc3ccc4nc(C(F)F)n(C5CC5)c4c3)c(Cl)c2)c(=O)[nH]c1=O] |
| 11-21 | 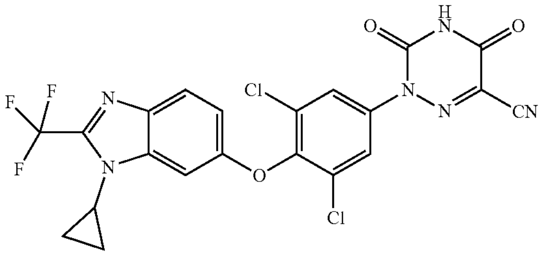 |
| 11-22 | 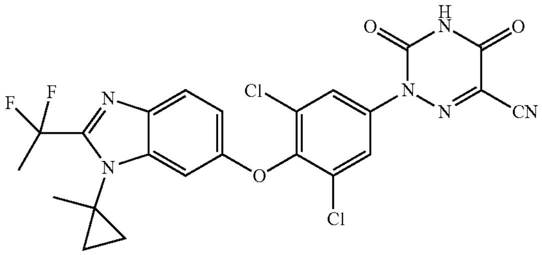 [SMILES: CC(F)(F)c1nc2ccc(Oc3c(Cl)cc(-n4nc(C#N)c(=O)[nH]c4=O)cc3Cl)cc2n1C1(C)CC1] |
| 11-23 | 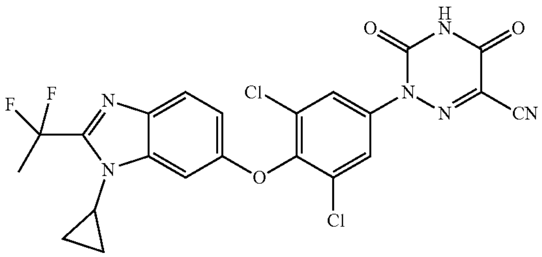 [SMILES: CC(F)(F)c1nc2ccc(Oc3c(Cl)cc(-n4nc(C#N)c(=O)[nH]c4=O)cc3Cl)cc2n1C1CC1] |

TABLE 11-continued
| Example | Structure |
| --- | --- |
| 11-24 | 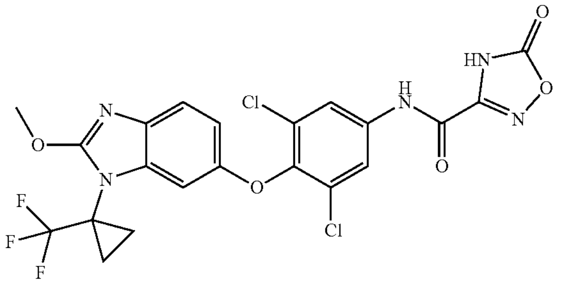 [SMILES: COc1nc2ccc(Oc3c(Cl)cc(NC(=O)c4noc(=O)[nH]4)cc3Cl)cc2n1C1(C(F)(F)F)CC1] |
| 11-25 | 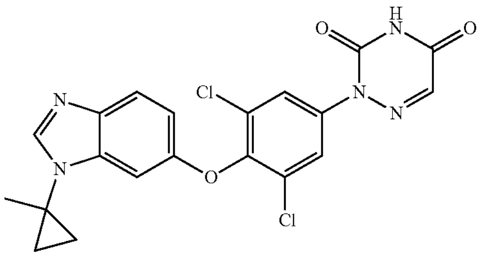 [SMILES: CC1(n2cnc3ccc(Oc4c(Cl)cc(-n5ncc(=O)[nH]c5=O)cc4Cl)cc32)CC1] |
| 11-26 | 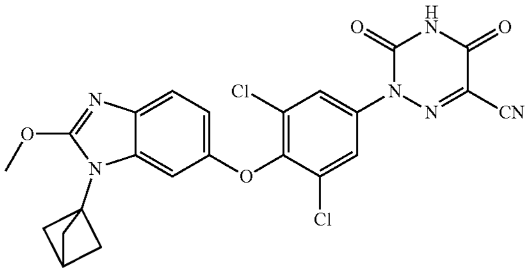 [SMILES: COc1nc2ccc(Oc3c(Cl)cc(-n4nc(C#N)c(=O)[nH]c4=O)cc3Cl)cc2n1C12CC(C1)C2] |
| 11-27 | 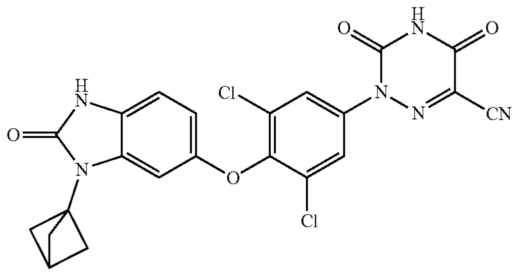 [SMILES: N#Cc1nn(-c2cc(Cl)c(Oc3ccc4[nH]c(=O)n(C56CC(C5)C6)c4c3)c(Cl)c2)c(=O)[nH]c1=O] |
| 11-28 | 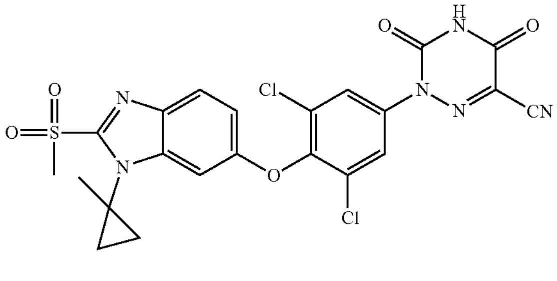 [SMILES: CC1(n2c(S(C)(=O)=O)nc3ccc(Oc4c(Cl)cc(-n5nc(C#N)c(=O)[nH]c5=O)cc4Cl)cc32)CC1] |

TABLE 11-continued
| Example | Structure |
|---|---|
| 11-29 | 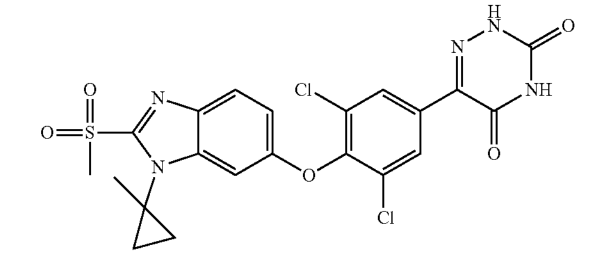 [SMILES: CC1(n2c(S(C)(=O)=O)nc3ccc(Oc4c(Cl)cc(-c5n[nH]c(=O)[nH]c5=O)cc4Cl)cc32)CC1] |
| 11-30 | 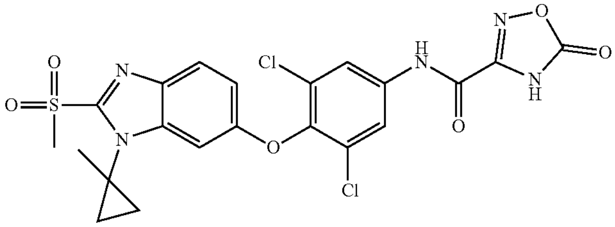 [SMILES: CC1(n2c(S(C)(=O)=O)nc3ccc(Oc4c(Cl)cc(NC(=O)c5noc(=O)[nH]5)cc4Cl)cc32)CC1] |
| 11-31 | 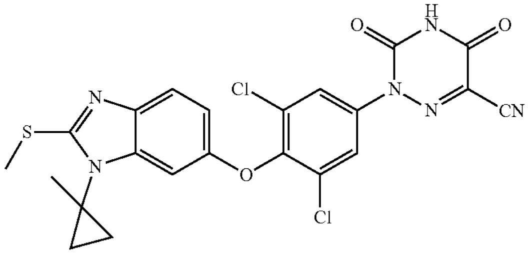 [SMILES: CSc1nc2ccc(Oc3c(Cl)cc(-n4nc(C#N)c(=O)[nH]c4=O)cc3Cl)cc2n1C1(C)CC1] |
| 11-32 | 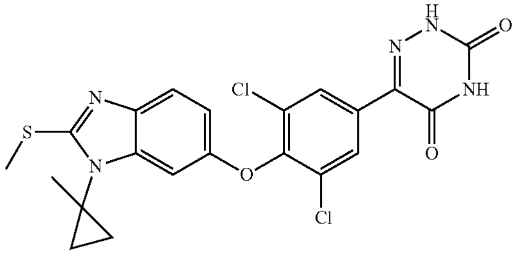 |
| 11-33 | 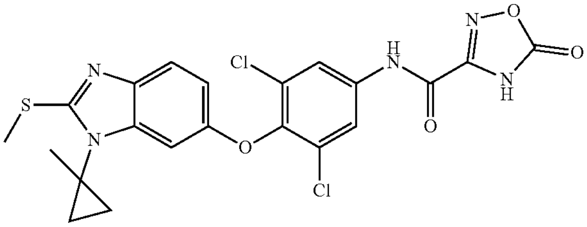 [SMILES: CSc1nc2ccc(Oc3c(Cl)cc(NC(=O)c4noc(=O)[nH]4)cc3Cl)cc2n1C1(C)CC1] |
| 11-34 | 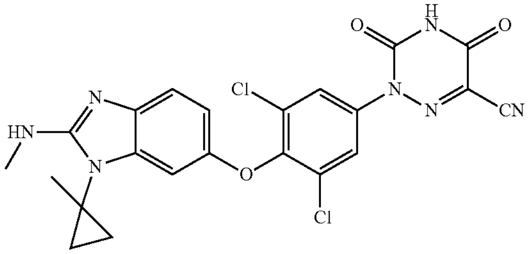 [SMILES: CNc1nc2ccc(Oc3c(Cl)cc(-n4nc(C#N)c(=O)[nH]c4=O)cc3Cl)cc2n1C1(C)CC1] |

TABLE 11-continued
| Example | Structure |
|---|---|
| 11-35 | 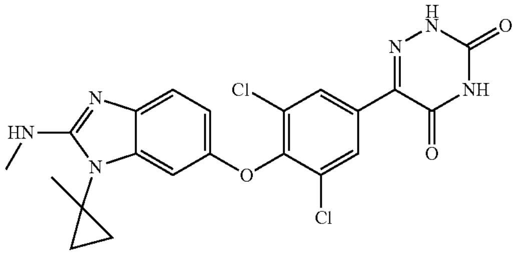 [SMILES: CNc1nc2ccc(Oc3c(Cl)cc(-c4n[nH]c(=O)[nH]c4=O)cc3Cl)cc2n1C1(C)CC1] |
| 11-36 | 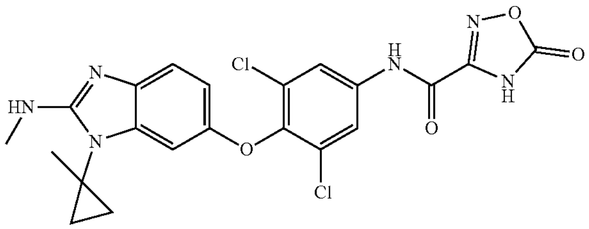 [SMILES: CNc1nc2ccc(Oc3c(Cl)cc(NC(=O)c4noc(=O)[nH]4)cc3Cl)cc2n1C1(C)CC1] |
| 11-37 | 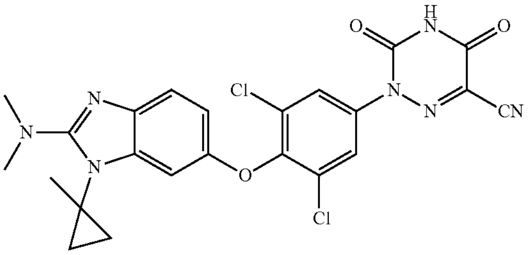 [SMILES: CN(C)c1nc2ccc(Oc3c(Cl)cc(-n4nc(C#N)c(=O)[nH]c4=O)cc3Cl)cc2n1C1(C)CC1] |
| 11-38 | 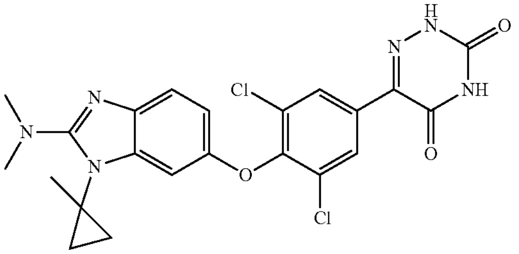 [SMILES: CN(C)c1nc2ccc(Oc3c(Cl)cc(-c4n[nH]c(=O)[nH]c4=O)cc3Cl)cc2n1C1(C)CC1] |
| 11-39 | 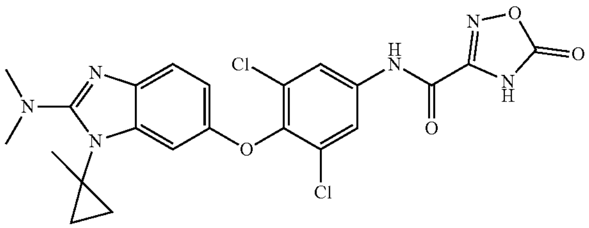 [SMILES: CN(C)c1nc2ccc(Oc3c(Cl)cc(NC(=O)c4noc(=O)[nH]4)cc3Cl)cc2n1C1(C)CC1] |
| 11-40 | 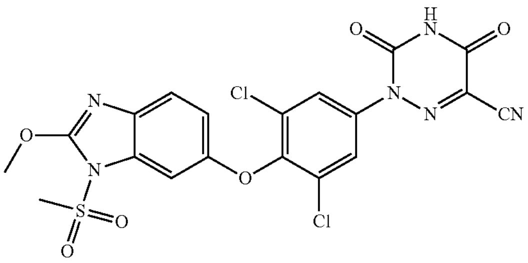 [SMILES: COc1nc2ccc(Oc3c(Cl)cc(-n4nc(C#N)c(=O)[nH]c4=O)cc3Cl)cc2n1S(C)(=O)=O] |

TABLE 11-continued

| Example | Structure |
| --- | --- |
| 11-41 | 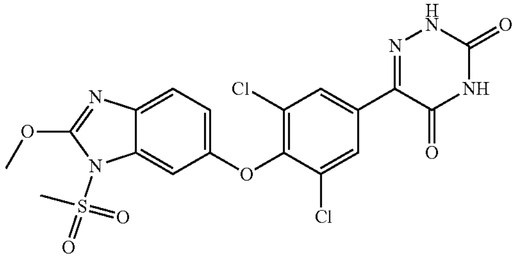 [SMILES: COc1nc2ccc(Oc3c(Cl)cc(-c4n[nH]c(=O)[nH]c4=O)cc3Cl)cc2n1S(C)(=O)=O] |
| 11-42 | 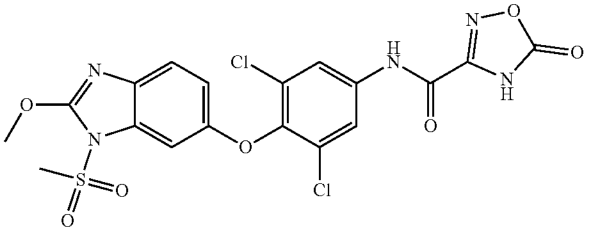 [SMILES: COc1nc2ccc(Oc3c(Cl)cc(NC(=O)c4noc(=O)[nH]4)cc3Cl)cc2n1S(C)(=O)=O] |

Pharmaceutically Acceptable Compositions and Formulations

Pharmaceutically acceptable compositions or simply "pharmaceutical compositions" of any of the compounds detailed herein are embraced by this invention. Thus, the invention includes pharmaceutical compositions comprising an GLP-1R agonist (such as the compound of Formula (I-5j), (I-5k), (I-51), (I-5m), (I-5n), (I-5o), (I-5p), (IQ), (IR), (IS), (IT), (LU), (IX), (IY), (IZ), (IAA), (TAB), (IAC), (TAD), (IAE), (TAG), (IAH), (TAT), (WA), (I**), (I''), (I''',*), (I''',), (I*), (I'), (I), (I-P01), (II**), or (11*), or a pharmaceutically acceptable salt thereof), a THRβ agonist (such as the compounds of Formula (II-1), (II-1a), (II-2), (II-3), (II-4), (II-5), or (II-6), or a pharmaceutically acceptable salt thereof), and a pharmaceutically acceptable carrier or excipient. In some embodiments, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In some embodiments, "substantially pure" intends a composition that contains no more than 35% impurity, wherein the impurity denotes a compound other than the compound comprising the majority of the composition or a salt thereof. For example, a composition of a substantially pure compound intends a composition that contains no more than 35% impurity, wherein the impurity denotes a compound other than the compound or a salt thereof. In some embodiments, a composition of substantially pure compound or a salt thereof is provided wherein the composition contains no more than 25% impurity. In some embodiments, a composition of substantially pure compound or a salt thereof is provided wherein the composition contains or no more than 20% impurity. In some embodiments, a composition of substantially pure compound or a salt thereof is provided wherein the composition contains or no more than 10% impurity. In some embodiments, a composition of substantially pure compound or a salt thereof is provided wherein the composition contains or no more than 5% impurity. In some embodiments, a composition of substantially pure compound or a salt thereof is provided wherein the composition contains or no more than 3% impurity. In some embodiments, a composition of substantially pure compound or a salt thereof is provided wherein the composition contains or no more than 1% impurity. In some embodiments, a composition of substantially pure compound or a salt thereof is provided wherein the composition contains or no more than 0.5% impurity. In some embodiments, a composition of substantially pure compound means that the composition contains no more than 15%, in some embodiments no more than 10%, in some embodiments no more than 5%, in some embodiments no more than 3% and, in some embodiments no more than 1% impurity, which impurity may be the compound in a different stereochemical form.

In some embodiments, the compounds herein are synthetic compounds prepared for administration to a subject such as a human. In some embodiments, compositions are provided containing a compound in substantially pure form. In some embodiments, the invention embraces pharmaceutical compositions comprising a compound detailed herein and a pharmaceutically acceptable carrier or excipient. In some embodiments, methods of administering a compound are provided. The purified forms, pharmaceutical compositions and methods of administering the compounds are suitable for any compound or form thereof detailed herein.

The compounds may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

Compounds described herein can be used in the preparation of a formulation, such as a pharmaceutical formulation, by combining the compounds as active ingredients with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in Remington: The Science and Practice of Pharmacy, Lippincott Williams & Wilkins, 21st ed. (2005), which is incorporated herein by reference.

Compounds as described herein may be administered to a subject (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid polyols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Methods of Use and Uses

The combinations described herein may in some aspects be used in treatment or prevention of liver disorders. In some embodiments, the method of treating or preventing a liver disorder in a patient in need thereof comprises administering to the patient a GLP-1R agonist and administering a THRβ agonist.

Liver disorders include, without limitation, liver inflammation, fibrosis, and steatohepatitis. In some embodiments, the liver disorder is selected from liver inflammation, liver fibrosis, alcohol induced fibrosis, steatosis, alcoholic steatosis, primary sclerosing cholangitis (PSC), primary biliary cirrhosis (PBC), non-alcoholic fatty liver disease (NAFLD), and non-alcoholic steatohepatitis (NASH). In certain embodiments, the liver disorder is selected from: liver fibrosis, alcohol induced fibrosis, steatosis, alcoholic steatosis, NAFLD, and NASH. In one embodiment, the liver disorder is NASH. In another embodiment, the liver disorder is liver inflammation. In another embodiment, the liver disorder is liver fibrosis. In another embodiment, the liver disorder is alcohol induced fibrosis. In another embodiment, the liver disorder is steatosis. In another embodiment, the liver disorder is alcoholic steatosis. In another embodiment, the liver disorder is NAFLD. In one embodiment, the treatment methods provided herein impedes or slows the progression of NAFLD to NASH. In one embodiment, the treatment methods provided herein impedes or slows the progression of NASH. NASH can progress, e.g., to one or more of liver cirrhosis, hepatic cancer, etc. In some embodiments, the liver disorder is NASH. In some embodiments, the patient has had a liver biopsy. In some embodiments, the method further comprising obtaining the results of a liver biopsy.

In some embodiments, the method of treating a liver disorder in a patient in need thereof, wherein the liver disorder is selected from the group consisting of liver inflammation, liver fibrosis, alcohol induced fibrosis, steatosis, alcoholic steatosis, primary sclerosing cholangitis (PSC), primary biliary cirrhosis (PBC), non-alcoholic fatty liver disease (NAFLD), and non-alcoholic steatohepatitis (NASH).

In some embodiments, the disease or condition to be treated and/or prevented is a cardiometabolic disorder, e.g., diabetes (T1 D and/or T2DM, including pre-diabetes), idiopathic T1 D (Type 1 b), latent autoimmune diabetes in adults (IADA), early-onset T2DM (EOD), youth-onset atypical diabetes (YOAD), maturity onset diabetes of the young (MODY), malnutrition-related diabetes, gestational diabetes, hyperglycemia, insulin resistance, hepatic insulin resistance, impaired glucose tolerance, diabetic neuropathy, diabetic nephropathy, kidney disease (e.g., acute kidney disorder, tubular dysfunction, proinflammatory changes to the proximal tubules), diabetic retinopathy, adipocyte dysfunction, visceral adipose deposition, obesity (including hypothalamic obesity and monogenic obesity) and related comorbidities (e.g., osteoarthritis and urine incontinence), overweight without obesity (e.g., BMI between 25 $kg/m^2$ and 30 $kg/m^2$), eating disorders (including binge eating syndrome, bulimia nervosa, and syndromic obesity such as Prader-Willi and Bardet-Biedi syndromes), excessive sugar craving, dyslipidemia (including hyperlipidemia, hypertriglyceridemia, increased total cholesterol, high LDL cholesterol, and low HDL cholesterol), hyperinsulinemia, liver diseases such as NAFLD, steatosis, NASH, fibrosis, cirrhosis, and hepatocellular carcinoma, cardiovascular disease, atherosclerosis (including coronary artery disease), peripheral vascular disease, hypertension, endothelial dysfunction, impaired vascular compliance, congestive heart failure, myocardial infarction (e.g., necrosis and apoptosis), stroke, hemorrhagic stroke, ischemic stroke, pulmonary hypertension, restenosis after angioplasty, intermittent claudication, post-prandial lipemia, metabolic acidosis, ketosis, arthritis, osteoporosis, left ventricular hypertrophy, peripheral arterial disease, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, or hyper apo B lipoproteinemia.

In some embodiments, the disease or condition to be treated includes sleep apnea, weight gain from use of other agents (e.g., from use of steroids and antipsychotics), traumatic brain injury, Parkinson's Disease, macular degeneration, cataract, Alzheimer's Disease, schizophrenia, impaired cognition, inflammatory bowel disease, short bowel syndrome, Crohn's disease, colitis, irritable bowel syndrome Polycystic Ovary Syndrome and addiction (e.g., alcohol and/or drug abuse), prevention or treatment of Polycystic Ovary Syndrome or treatment of addiction (e.g., alcohol and/or drug abuse).

In some embodiments, the present disclosure is directed to co-administration of a GLP-AR agonist and THRβ agonist to a subject resulting in a loss in fat mass in the subject with little or no reduction in lean mass in the subject. In some embodiments, provided herein is a method of treating a cardiometabolic disorder in a subject (e.g., a human patient) in need thereof, comprising administering to the subject a therapeutically effective amount of a compound described herein, or a pharmaceutically acceptable salt thereof.

In one embodiment the methods and combinations of the present disclosure are directed to a) the reduction of HbA1c; b) the prevention or treatment of type 2 diabetes, hyperglycemia, impaired glucose tolerance, or non-insulin dependent diabetes; or c) the prevention or treatment of obesity, for reducing body weight and/or food intake, or for inducing satiety in a subject in need thereof.

In some embodiments, the combinations and methods of the present disclosure are directed to treating or preventing obesity, reducing body fat percentage, increasing lean mass percentage of total weight, or for inducing satiety in a subject in need thereof.

In some embodiments, the combinations and methods of the present disclosure are directed to treating or preventing obesity, reducing body fat percentage, increasing lean mass percentage of total weight, or for inducing satiety in a subject in need thereof.

In some embodiments, the combinations and methods of the present disclosure are directed to treating obesity in a subject in need thereof.

In some embodiments, the combinations and methods of the present disclosure are directed to treating or preventing obesity in a subject in need thereof.

In some embodiments, the combinations and methods of the present disclosure are directed to reducing body fat, increasing lean mass percentage of total weight, or inducing satiety in a subject in need thereof.

In some embodiments, the present disclosure provides methods of treating or preventing obesity, for reducing body fat, and/or for increasing lean mass percentage of total weight, in a subject in need thereof comprising the administration of a THR-B agonist (e.g., Compound 9) and a GLP-1R agonist which results in a synergistic effect compared to the administration of a GLP-1R agonist alone.

In some embodiments, the present disclosure provides methods of treating obesity, for reducing body fat, and/or for increasing lean mass percentage of total weight, in a subject in need thereof comprising the administration of a THR-B agonist (e.g., Compound 9) and a GLP-1R agonist which results in a synergistic effect compared to the administration ofa GLP-1R agonist alone.

In some embodiments, provided herein is a method of treating a liver disorder in a subject (e.g., a human patient) in need thereof, comprising administering to the subject a therapeutically effective amount of a compound described herein, or a pharmaceutically acceptable salt thereof. Exemplary liver disorders include, without limitation, liver inflammation, fibrosis, and steatohepatitis. In some embodiments, the liver disorder is selected from the list consisting of primary biliary cirrhosis (PBC), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, viral hepatitis, alcoholic liver disease, nonalcoholic fatty liver disease (NAFLD), nonalcoholic steatohepatitis (NASH), graft versus host disease, transplant liver regeneration, congenital hepatic fibrosis, choledocholithiasis, granulomatous liver disease, intra- or extrahepatic malignancy, Sjogren's syndrome, sarcoidosis, Wilson's disease, Gaucher's disease, hemochromatosis, and oti-antitrypsin deficiency. In some embodiments, the liver disorder is selected from the list consisting of liver inflammation, liver fibrosis, alcohol induced fibrosis, steatosis, alcoholic steatosis, primary sclerosing cholangitis (PSC), primary biliary cirrhosis (PBC), non-alcoholic fatty liver disease (NAFLD), and non-alcoholic steatohepatitis (NASH). In some embodiments, the liver disorder is selected from the group consisting of liver fibrosis, alcohol induced fibrosis, steatosis, alcoholic steatosis, NAFLD, and NASH. In one embodiment, the liver disorder is NASH. In another embodiment, the liver disorder is liver inflammation. In another embodiment, the liver disorder is liver fibrosis. In another embodiment, the liver disorder is alcohol induced fibrosis. In another embodiment, the liver disorder is steatosis. In another embodiment, the liver disorder is alcoholic steatosis. In another embodiment, the liver disorder is NAFLD. In one embodiment, the treatment methods provided herein impedes or slows the progression of NAFLD to NASH. In one embodiment, the treatment methods provided herein impedes or slows the progression of NASH. NASH can progress, e.g., to one or more of liver cirrhosis, hepatic cancer, etc. In some embodiments, the liver disorder is NASH. In some embodiments, the patient has had a liver biopsy. In some embodiments, the method further comprising obtaining the results of a liver biopsy.

In some embodiments, the present disclosure provides a method of decreasing food intake in a subject in need thereof, the method comprising administering an effective amount of any one of the compounds or pharmaceutical compositions disclosed herein to the subject. In some embodiments, administration of a compound disclosed herein causes the subject's food intake to be reduced at least 10%, e.g., at least 20%, at least 30%, at least 40%, at least 50%, at least 60%, at least 70%, at least 75%, at least 80%, at least 85%, at least 90%, or at least 95% relative to the subject's food intake in the absence of a compound disclosed herein. In some embodiments, the subject's food intake is reduced, e.g., reduced by at least 10%, at least 20%, at least 30%, at least 40%, at least 50%, at least 60%, at least 70%, at least 75%, at least 80%, at least 85%, at least 90%, or at least 95%, for at least 1 hour following administration, e.g., at least 1 hour, at least 2 hours, at least 3 hours, at least 4 hours, at least 5 hours, at least 6 hours, at least 12 hours, at least 1 day, or at least 2 days following administration.

In some embodiments, the present disclosure provides a method of improving glucose tolerance in a subject in need thereof. In some embodiments, following glucose intake, e.g., glucose intake caused by consuming food, and the administration of a compound disclosed herein, the concentration of glucose in the blood of a subject is lower, e.g., 10% lower, 20% lower, 30% lower, 40% lower, 50% lower, 60% lower, 70% lower, 80% lower, 90% lower, 100% lower, 200% lower, 500% lower, 1000% lower, than the blood glucose concentration would have been had the subject not been administered the compound disclosed herein.

In accordance with the present application, a compound described herein, or a pharmaceutically acceptable salt thereof, can be administered by any suitable route in the form of a pharmaceutical composition adapted to such a route, and in a dose effective for the treatment intended. In some embodiments, it is a compound of any embodiment of Formula (I) or selected from the compounds of Table 1, or a pharmaceutically acceptable salt thereof. The compounds and/or compositions described herein may be administered orally, rectally, vaginally, parenterally, or topically.

In some embodiments, the compounds and/or compositions may be administered orally. Oral administration may involve swallowing, so that the compound enters the gastrointestinal tract, or buccal or sublingual administration may be employed by which the compound enters the bloodstream directly from the mouth.

In some embodiments, the compounds and/or compositions may be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In some embodiments, the compounds and/or compositions may be administered topically to the skin or mucosa, that is, dermally or transdermally. In some embodiments, the compounds and/or compositions may be administered intranasally or by inhalation. In some embodiments, the compounds and/or compositions may be administered rectally or vaginally. In some embodiments, the compounds and/or compositions may be administered directly to the eye or ear.

The dosage regimen for the compounds and/or compositions described herein is based on a variety of factors, including the type, age, weight, sex and medical condition of the patient; the severity of the condition; the route of administration; and the activity of the particular compound employed. Thus, the dosage regimen may vary widely. In some embodiments, the total daily dose of the compounds of the present application is typically from about 0.001 to about 100 mg/kg (i.e., mg compound per kg body weight) for the treatment of the indicated conditions discussed herein. In one embodiment, total daily dose of the compounds of the present application is from about 0.01 to about 30 mg/kg, and in another embodiment, from about 0.03 to about 10 mg/kg, and in yet another embodiment, from about 0.1 to about 3. It is not uncommon that the administration of the compounds of the present application will be repeated a plurality of times in a day (typically no greater than 4 times). Multiple doses per day typically may be used to increase the total daily dose, if desired.

Suitable dosages of the THRβ agonists described herein are also described in, e.g., PCT Pub. Nos. WO2021231646, WO2023086561, and WO2023083288, which are each incorporated herein by reference.

In some embodiments, about 0.5 mg to about 100 mg of the THRβ agonist is administered to the subject. In some embodiments, about 0.5 mg to about 90 mg of the compound is administered to the subject. In some embodiments, about 1 mg to about 90 mg of the compound is administered to the subject. In some embodiments, about 3 mg to about 90 mg of the compound is administered to the subject. In some embodiments, about 0.5 mg to about 30 mg of the compound is administered to the subject. In some embodiments, about 1 mg to about 30 mg of the compound is administered to the subject. In some embodiments, about 3 mg to about 90 mg of the compound is administered to the subject. In some embodiments, about 1 mg to about 5 mg of the compound is administered to the subject. In some embodiments about 1 mg to about 3 mg of the compound is administered to the subject. In some embodiments about 5 mg to about 10 mg of the compound is administered to the subject. In some embodiments, about 10 mg to about 15 mg of the compound is administered to the subject. In some embodiments, about 15 mg to about 20 mg of the compound is administered to the subject. In some embodiments, about 20 mg to about 25 mg of the compound is administered to the subject. In some embodiments, about 25 mg to about 30 mg of the compound is administered to the subject. In some embodiments, about 1 mg of the compound is administered to the subject. In some embodiments, about 2 mg of the compound is administered to the subject. In some embodiments, about 3 mg of the compound is administered to the subject. In some embodiments, about 4 mg of the compound is administered to the subject. In some embodiments, about 5 mg of the compound is administered to the subject. In some embodiments, about 6 mg of the compound is administered to the subject. In some embodiments, about 7 mg of the compound is administered to the subject. In some embodiments, about 8 mg of the compound is administered to the subject. In some embodiments, about 9 mg of the compound is administered to the subject. In some embodiments, about 10 mg of the compound is administered to the subject. In some embodiments, about 15 mg of the compound is administered to the subject. In some embodiments, about 20 mg of the compound is administered to the subject. In some embodiments, about 25 mg of the compound is administered to the subject. In some embodiments, about 30 mg of the compound is administered to the subject. In some embodiments, the compound is Compound 9 as described herein.

Combinations

In further embodiments, the pharmaceutical compositions provided herein may be co-formulated with other active ingredients which do not impair the desired therapeutic action, or with substances that supplement the desired action. In some embodiments, the GLP-1R agonist and the THR agonist are administered in temporal proximity (e.g., the GLP-1R agonist and the THRβ agonist can be administered simultaneously). Accordingly, the present disclosure provides a method of treating or preventing a cardiometabolic disorder comprising administering the GLP-1R agonist and the THR agonist in temporal proximity.

In some embodiments, a GLP-1R agonist of Formula (I-1), (I-1a), (I-5) (I**), or (II*), or a pharmaceutically acceptable salt thereof is administered in temporal proximity with a THRβ agonist of Formula (II-1) or (II-1a), or a pharmaceutically acceptable salt thereof.

In some embodiments, a GLP-AR agonist of Formula (I-1), (I-1a), (I-5), (I**), or (II*), or a pharmaceutically acceptable salt thereof is administered in temporal proximity with a THRβ agonist (such as the compounds of Formula (II-1), (II-1a), (II-2), (II-3), (II-4), (II-5), or (II-6), or a pharmaceutically acceptable salt thereof).

some embodiments, a GLP-1R agonist of Formula (II**), or a pharmaceutically acceptable salt thereof is administered in temporal proximity with a THRβ agonist of Formula (II-1) or (II-1a), or a pharmaceutically acceptable salt thereof.

In some embodiments, a GLP-AR agonist of Formula (II**), or a pharmaceutically acceptable salt thereof is administered in temporal proximity with a THRβ agonist (such as the compounds of Formula (II-1), (II-1a), (II-2), (II-3), (II-4), (II-5), or (II-6), or a pharmaceutically acceptable salt thereof).

In some embodiments, a THRβ agonist of Formula (II-1) or (II-1a), or a pharmaceutically acceptable salt thereof, is administered in temporal proximity with a GLP-AR agonist (such as the compound of Formula (I-1), (I-1a), (I-2), (I-3), (I-4), (I-5), (I-5a), (I-5b), (I-5c), (I-5d), (I-5e), (I-5f), (I-5 g), (I-5h), (I-5i), (I-5j), (I-5k), (I-51), (I-5m), (I-5n), (I-5o), (I-5p), (IQ), (IR), (IS), (IT), (IU), (IX), (IY), (IZ), (IAA), (IAB), (IAC), (IAD), (IAE), (IAG), (IAH), (IAI), (IAJ), (I**), (I''), (I'''*), (I'''), (I*), (I'), (I), (I-P0I), (II**), or (II*), or a pharmaceutically acceptable salt thereof).

In some embodiments, "temporal proximity" means that administration of one therapeutic agent occurs within a time period before or after the administration of another therapeutic agent, such that the therapeutic effect of the one therapeutic agent overlaps with the therapeutic effect of the another therapeutic agent. In some embodiments, the therapeutic effect of the one therapeutic agent completely overlaps with the therapeutic effect of the other therapeutic agent. In some embodiments, "temporal proximity" means that administration of one therapeutic agent occurs within a time period before or after the administration of another therapeutic agent, such that there is a synergistic effect between the one therapeutic agent and the another therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

In some embodiments, the THRβ agonist is administered to the patient prior to the GLP-1R agonist. In some embodiments, the THRβ agonist is administered to the patient 0-1 hours, 1-2 hours, 2-3 hours, 3-4 hours, 4-5 hours, or 5-6 hours prior to the GLP-1R agonist. In some embodiments, the THRβ agonist is administered to the patient 0-1 days, 1-2 days, 2-3 days, 3-4 days, 4-5 days, or 5-6 days prior to the GLP-1R agonist. In some embodiments, the THRβ agonist reaches a steady state in a patient prior to the administration of the GLP-1R agonist. In some embodiments, the GLP-1R agonist is administered to the patient prior to the THRβ agonist. In some embodiments, the GLP-1R agonist is administered to the patient 0-1 days, 1-2 days, 2-3 days, 3-4 days, 4-5 days, or 5-6 days prior to the THRβ agonist. In some embodiments, the GLP-1R agonist reaches a steady state in a patient prior to the administration of the THRβ agonist. In some embodiments, the THR-β agonist is administered to the patient at substantially the same time as the GLP-1R agonist.

Articles of Manufacture and Kits

The present disclosure further provides articles of manufacture comprising a compound described herein, or a salt thereof, a composition described herein, or one or more unit dosages described herein in suitable packaging. In certain embodiments, the article of manufacture is for use in any of the methods described herein. Suitable packaging (e.g., containers) is known in the art and includes, for example, vials, vessels, ampules, bottles, jars, flexible packaging and the like. An article of manufacture may further be sterilized and/or sealed.

The present disclosure further provides kits for carrying out the methods of the present disclosure, which comprises at least two compounds described herein, or a pharmaceutically acceptable salt thereof, or a composition comprising a compound described herein, or a pharmaceutically acceptable salt thereof. The kits may employ any of the compounds disclosed herein or a pharmaceutically acceptable salt thereof. In some embodiments, the kit employs an GLP-1R agonist (such as the compound of Formula (I-1), (I-1a), (I-2), (I-3), (I-4), (I-5), (I-5a), (I-5b), (I-5c), (I-5d), (I-5e), (I-5f), (I-5 g), (I-5h), (I-5i), (I-5j), (I-5k), (I-51), (I-5m), (I-5n), (I-5o), (I-5p), (IQ), (IR), (IS), (IT), (IU), (IX), (IY), (IZ), (IAA), (IAB), (IAC), (IAD), (IAE), (IAG), (IAH), (IAI), (IAJ), (I**), (I''), (I''*), (I'''), (I*), (I'), (I), (I-P01), (II**), or (II*), or a pharmaceutically acceptable salt thereof) and a THRβ agonist (such as the compound of (II-1), (II-1a), (II-2), (II-3), (II-4), (II-5), or (II-6), or a pharmaceutically acceptable salt thereof) described herein. The kits may be used for any one or more of the uses described herein, and, accordingly, may contain instructions for the treatment as described herein.

Kits generally comprise suitable packaging. The kits may comprise one or more containers comprising any compound described herein or a pharmaceutically acceptable salt thereof. Each component can be packaged in separate containers or some components can be combined in one container where cross-reactivity and shelf life permit. In some embodiments, the kit includes a container comprising the GLP-1R agonist (such as the compound of Formula (I-1), (I-1a), (I-2), (I-3), (I-4), (I-5), (I-5a), (I-5b), (I-5c), (I-5d), (I-5e), (I-5f), (I-5 g), (I-5h), (I-5i), (I-5j), (I-5k), (I-51), (I-5m), (I-5n), (I-5o), (I-5p), (IQ), (IR), (IS), (IT), (IU), (IX), (IY), (IZ), (IAA), (IAB), (IAC), (IAD), (IAE), (IAG), (IAH), (IAI), (IAJ), (I**), (I''), (I'*), (I'), (1*), (I'), (I), (I-P0I), (II**), or (II*), or a pharmaceutically acceptable salt thereof) and THRβ agonist (such as the compound of (II-1), (II-1a), (II-2), (II-3), (II-4), (II-5), or (II-6), or a pharmaceutically acceptable salt thereof). In other embodiments, the kit includes a first container comprising GLP-1R agonist (such as the compound of Formula (I-1), (I-1a), (I-2), (I-3), (I-4), (I-5), (I-5a), (I-5b), (I-5c), (I-5d), (I-5e), (I-5f), (I-5 g), (I-5h), (I-5i), (I-5j), (I-5k), (I-51), (I-5m), (I-5n), (I-5o), (I-5p), (IQ), (IR), (IS), (IT), (IU), (IX), (IY), (IZ), (IAA), (IAB), (IAC), (IAD), (IAE), (IAG), (IAH), (IAI), (IAJ), (I**), (I''), (I''*), (I'''), (1*), (I'), (I), (I-P0I), (II**), or (11*), or a pharmaceutically acceptable salt thereof) and a second container comprising the THRβ agonist (such as the compound of (II-1), (II-Ia), (II-2), (II-3), (II-4), (II-5), or (II-6), or a pharmaceutically acceptable salt thereof).

The kits may be in unit dosage forms, bulk packages (e.g., multi-dose packages) or sub-unit doses. For example, kits may be provided that contain sufficient dosages of a compound as disclosed herein (e.g., Compound 9), or a pharmaceutically acceptable salt thereof, and/or an additional pharmaceutically active compound useful for a disease detailed herein to provide effective treatment of a subject for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to a subject.

General Biological Protocols

Non-Alcoholic Steatohepatitis (NASH) Mouse Model

This mouse model is fed a high fat diet that results in nonalcoholic steatohepatis (NASH) disease and increased weight.

Liver Biopsy

Mice are anesthetized and a small abdominal incision is made in the midline and the left lateral lobe of the liver is exposed. A cone shaped wedge of liver tissue is excised from the distal portion of the lobe and fixated in 10% neutral buffered formalin for histology. The cut surface of the liver is instantly electrocoagulated using bipolar coagulation.

Blood Sampling and Plasma Preparation

In vivo blood samples: Samples are collected at week 8, 30 minutes post-dose, 1 hour post-dose, 2 hours post-dose, 4 hours post-dose, 6 hours post-dose, and 24 hours post-dose (before the next dose). Tail-vein, tongue or cheek blood is collected in a Microvette tube of appropriate dimensions with anticoagulant and mixed. Blood is centrifuged. The plasma supernatants are transferred to new tubes and immediately frozen on dry ice. Termination blood samples: During anesthesia, the abdominal cavity is opened, and cardiac blood is drawn with a syringe with anticoagulant and mixed. Blood is centrifuged and plasma supernatants are transferred to new tubes and immediately frozen on dry ice.

Tissue sampling

Liver (NASH)

After the animal has been terminated, the liver is collected and weighed.

The liver is divided into left lateral lobe, medial lobe, right lateral lobe, and caudate lobe.

The Post-biopsy piece is cut from the left lateral lobe, 4 mm from the prebiopsy site with an edge. The tissue is collected in paraformaldehyde. The Liver Sponsor piece is dissected from the left medial lobe, put in a tube and placed directly into liquid nitrogen.

The Liver RNA Sequencing (RNAseq) piece is dissected from the center of the left lateral lobe, snap frozen (put directly in liquid nitrogen in Nunc filter) and collected in a pre-cooled tube which is put in liquid nitrogen.

The Liver TG TC piece is dissected from the right medial lobe, with no edges, on the opposite side of the sponsor piece. The samples are weighed individually and collected in tubes before placed in liquid nitrogen.

The Liver Extra piece is dissected from the right lateral lobe and collected in tubes before placed in liquid nitrogen, to have as backup tissue from the study and can be used for re-analysis if necessary.

Biopsy Processing

Microtome Sectioning of Formalin Fixed Paraffin-Embedded (FFPE) Biopsies

FFPE biopsies are placed in 10% neutral buffered formalin then transferred to 70% EtOH. The FFPE biopsies are then placed in the Histokinette to infiltrate prior to embedding in blocks. Biopsy tissues are cut at 3 μm on a microtome and the sections are mounted on Superfrost Plus slides.

NAFLD Activity Score (NAS) and Fibrosis Stage

Liver samples stained with Hematoxylin and Eosin (H&E) or Picro Sirius Red (PSR) are given a score for NAS and fibrosis stage respectively using the clinical criteria outlined by Kleiner et al. 2005. Total NAS represents the sum of scores for steatosis, inflammation, and ballooning, and ranges from 0-8. Adapted from: Design and validation of a histological scoring system for nonalcoholic fatty liver disease, Kleiner et al., Hepatology 41; 2005

Histological staining procedures

Slides with paraffin embedded sections are deparaffinated in xylene and rehydrated in series of graded ethanol.

Hematoxylin & Eosin (H&E) staining: Slides are incubated in Mayer's Hematoxylin (Dako), washed in tap water, stained in Eosin Y solution (Sigma-Aldrich), dehydrated and cover slipped.

Sirius red (PSR) staining: Slides are incubated in Weigert's iron hematoxylin (Sigma-Aldrich), washed in tap water, stained in Picro-sirius red (Sigma-Aldrich) and washed twice in acidified water. Excess water is removed by shaking the slides and the slides are then dehydrated in three changes of 100% ethanol, cleared in xylene and cover slipped.

Immunohistochemistry using single chromogen; IHC is performed using standard procedures. Briefly, after antigen retrieval and blocking of endogenous peroxidase activity, slides are incubated with primary antibody. The primary antibody is detected using a polymeric HRP-linker antibody conjugate. Next, the primary antibody is visualized with DAB as chromogen. Finally, sections are counterstained in hematoxylin and cover slipped. Slides are scanned under a 20X objective in a ScanScope AT slide scanner (Aperio).

Gene expression analysis using RNAseq

RNA isolation: Tissue is collected and snap-frozen in liquid nitrogen. Samples are stored at −70° C. until processing. RNA is isolated using the NucleoSpin® kit (MACHEREY-NAGEL).

Librarypreparation andsequencing: A total of 10 ng-1 μg purified RNA from each sample is used to generate a cDNA library using the NEBNext® Ultra™ II Directional RNA Library Prep Kit for Illumina (New England Biolabs). cDNA libraries are then sequenced on a NextSeq 500 using NextSeq 500/550 High Output Kit V2 (Illumina).

Data analysis: The sequencing data is aligned to the genome of the animal species obtained from the Ensembl database using the Spliced Transcripts Alignment to a Reference (STAR) software. For the bioinformatic analysis, the quality of the data is evaluated using the standard RNA-sequencing quality control parameters, the inter- and intra-group variability is evaluated using principal component analysis and hierarchical clustering and the differentially expressed genes are identified using the R-package DESeq2. Downstream analyses such as pathway analysis or target identification are performed as agreed with the sponsor.

Blood and Plasma Assays

Alanine transaminase (ALT), Aspartate transaminase (AST), Triglycerides (TG) and Total Cholesterol (TC): Blood samples are collected in heparinized tubes and plasma is separated and stored at −70° C. until analysis. Samples are measured using commercial kits.

Cytokeratin 18 (CK18-M30): Blood samples are collected in EDTA tubes and plasma is separated and stored at −70° C. until analysis. CK18 is measured using a commercial ELISA kit.

Insulin: Blood samples are collected in heparinized tubes and plasma is separated and stored at −70° C. until analysis. Insulin is measured using a commercial MSD platform.

TIMP-1: Blood samples are collected in EDTA tubes and plasma is separated and stored at −70° C. until analysis. TIMP-1 is measured using a commercial ELISA kit.

PIIINP: Blood samples are collected in EDTA tubes and plasma is separated and stored at -70° C. until analysis. PIIINP is measured using a commercial ELISA kit. Tissue assays Triglycerides (TG) and Total cholesterol (TC): Liver samples are homogenized and TG and TC is extracted. The samples are centrifuged and the TG and TC content is measured in the supernatant using commercial kits.

Oral Glucose Tolerance Test (OGTT)

On the day of the OGTT, random blood glucose and body weight of the mice are measured, mice are dosed with corresponding compounds or vehicle in the morning before fasting, then the mice are fasted for 6 hours, basal fasting glucose is measured by tail vein nick thereafter. Glucose is orally gavaged with 2 g/kg at a dose volume of 5 mL/kg. Blood glucose levels are measured at 0 (pre-dose), 15-, 30-, 60-, and 120-min post glucose dosing. The second dose is administrated after OGTT treatment.

Terminal Plasma and Tissue Collection

The body weight and food intake of all mice is measured and then fasted for 6 hours, all mice are euthanized with $CO_2$ and bled via cardiac puncture. Blood samples will be processed for serum by centrifugation and stored for TC/TG/LDL/HDL/AST/ALT analysis. Blood samples are mixed with $K_2EDTA$ anticoagulant and processed for plasma by centrifugation stored for insulin and other possible analysis.

The weight of whole liver and epididymal fat are weighed and recorded. Left lobule of liver is fixed in formalin. The remaining liver is flash frozen and stored. Pancreas is collected and fixed in formalin. Brown adipose, subcutaneous white adipose, and epididymal white adipose tissues and the brain hypothalamus region are frozen with liquid nitrogen and preserved and stored for optional qPCR analysis.

Hypothalmus Collection Procedure

The brain tissue is placed in the mold, and the olfactory bulb is placed in the center of the groove. The brain tissue is sliced into 8 coronal sections evenly spaced at 2 mm intervals. The third section (6-8 mm) of the coronal brain tissue is taken out, and the section is cut along the boundary of the purple part with a scalpel to separate the cerebral cortex. The remaining tissue is hypothalamus.

Weight Loss Analysis

Body weight, food and water intake are measured daily. Body composition is measured using EchoMRI. Subcutaneous fat is collected and weighed at study termination. Subcutaneous fat tissue samples are assessed for UCP-1 expression by qPCR and Western blot analyses.

NUMBERED EMBODIMENTS

Embodiments 1-169

1. A combination comprising a THRβ agonist, or a pharmaceutically acceptable salt thereof, and a GLP-1R agonist, or a pharmaceutically acceptable salt thereof, for the treatment of a liver disorder or a cardiometabolic disease in a patient in need thereof.
2. A combination of THRβ agonist, or a pharmaceutically acceptable salt thereof, and a GLP-1R agonist, or a pharmaceutically acceptable salt thereof, for effectuating weight loss in a patient in need thereof.
3. The combination of embodiment 1 or 2, wherein the THR agonist is a compound of Formula (II-1)

(II-1)

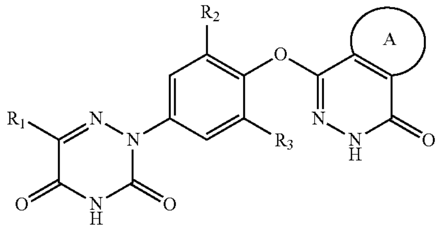

wherein:

$R_1$ is selected from the group consisting of hydrogen, cyano, substituted or unsubstituted $C_{1-6}$ alkyl, and substituted or unsubstituted $C_{3-6}$ cycloalkyl, the substituent being selected from the group consisting of halogen atoms, hydroxy, and $C_{1-6}$ alkoxy;

$R_2$ and $R_1$ are each independently selected from the group consisting of halogen atoms and substituted or unsubstituted $C_{1-6}$ alkyl, the substituent being selected from the group consisting of halogen atoms, hydroxy, and $C_{1-6}$ alkoxy; ring A is a substituted or unsubstituted saturated or unsaturated $C_{5-10}$ aliphatic ring, or a substituted or unsubstituted $C_{5-10}$ aromatic ring, the substituent being one or more substances selected from the group consisting of hydrogen, halogen atoms, hydroxy, —$OCF_3$, —$NH_2$, —$NHC_{1-4}$ alkyl, —$N(C_{1-4}$ alkyl$)_2$, —$CONH_2$, —$CONHC_{1-4}$ alkyl, —$CON(C_{1-4}$ alkyl$)_2$, —$NHCOC_{1-4}$ alkyl, $C_{1-6}$ alkyl, $C_{1-6}$ alkoxy or $C_{3-6}$ cycloalkyl, and when two substituents are contained, the two substituents can form a ring structure together with the carbon connected thereto; and the halogen atoms are selected from the group consisting of F, Cl and Br; or a pharmaceutically acceptable salt thereof.

4. The combination of any one of the preceding embodiments, wherein the THRβ agonist is a compound of Formula (II-Ia)

(II-1a)

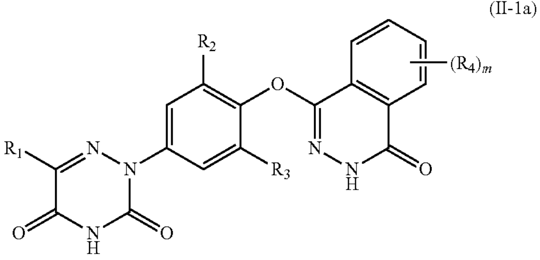

wherein:

$R_1$ to $R_3$ are defined as detailed herein for Formula (II-1);

$R_4$ is selected from the group consisting of hydrogen, halogen atoms, hydroxy, —$OCF_3$, —$NH_2$, —$NHC_{1-4}$ alkyl, —$N(C_{1-4}$ alkyl$)_2$, —$CONH_2$, —$CONHC_{1-4}$ alkyl, —$CON(C_{1-4}$ alkyl$)_2$, —$NHCOC_{1-4}$ alkyl, $C_{1-6}$ alkyl, $C_{1-6}$ alkoxy and $C_{3-6}$ cycloalkyl;

m is an integer from the range 1 to 4; and the halogen atoms are selected from the group consisting of F, Cl and Br.

or a pharmaceutically acceptable salt thereof.

5. The combination of any one of the preceding embodiments, wherein the THRβ agonist is Compound 9:

(9)

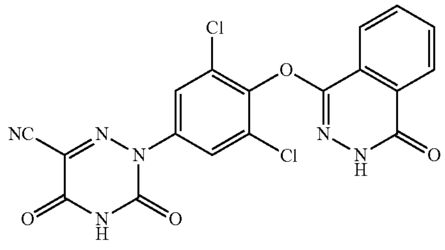

or a pharmaceutically acceptable salt thereof.

6. The combination of any one of the preceding embodiments, wherein the THR agonist is a potassium salt of Compound 9.

7. The combination of any one of the preceding embodiments, wherein the GLP-1R agonist is a compound of Formula (I-1):

(I-1)

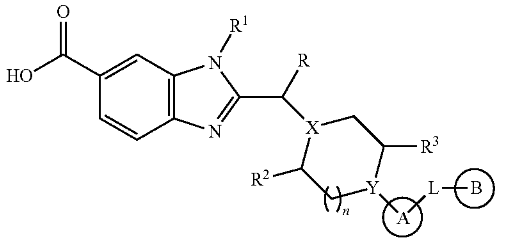

or a pharmaceutically acceptable salt thereof, wherein: X is N or CH;

Y is N or $CR^4$;

n is 0 or 1;

R is hydrogen;

$R^1$ is —$C_1$-$C_6$ alkylene-$R^5$;

$R^2$ is hydrogen, oxo, or $C_1$-$C_6$ alkyl;

$R^3$ is hydrogen, oxo, or $C_1$-$C_6$ alkyl and $R^4$ is hydrogen, OH, or $C_1$-$C_6$ alkyl;

or $R^3$ and $R^4$ are taken together with the carbon atoms to which they are attached to form $C_3$-$C_6$ cycloalkyl optionally substituted by halo or $C_1$-$C_3$ alkyl;

$R^5$ is 5-membered heterocyclyl or 5-membered heteroaryl, each of which comprises 1, 2, or 3 heteroatoms independently selected from O, N, and S, wherein at least one heteroatom of $R^5$ is S, and further wherein $R^5$ is optionally substituted by halo, —O—$C_{1-6}$ alkyl, $C_{1-6}$ alkyl, $C_{1-6}$ alkenyl, or $C_1$-$C_6$ haloalkyl;

Ring A is 5- to 12-membered heterocyclene or 5- to 12-membered heteroarylene, each of which is independently optionally substituted by halo, CN, $C_3$-$C_6$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein

* represents the point of attachment to ring A and ** represents the point of attachment to ring B;

when L is *—O—$C_1$-$C_6$ alkylene-**, the $C_1$-$C_6$ alkylene of L is optionally substituted by $R^L$, wherein each $R^1$ is independently $C_1$-$C_6$ alkyl or halo, or two $R^L$ are taken together with the carbon atom or atoms to which they are attached to form $C_3$-$C_6$ cycloalkyl or 3- to 6-membered heterocyclyl; and when L is $C_1$-$C_6$ alkylene, the $C_1$-$C_6$ alkylene is optionally substituted by $R^{L1}$, wherein each $R^{L1}$ is independently halo, OH, oxo, or $C_1$-$C_6$ alkyl, or two $R^{L1}$ are taken together with the carbon atom or atoms to which they are attached to form $C_3$-$C_6$ cycloalkyl or 3- to 6-membered heterocyclyl;

$R^6$ is hydrogen or $C_1$-$C_6$ alkyl; and

Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

8. The combination of any one of the preceding embodiments, wherein the GLP-1R agonist is a compound of Formula (I-Ia):

(I-Ia)

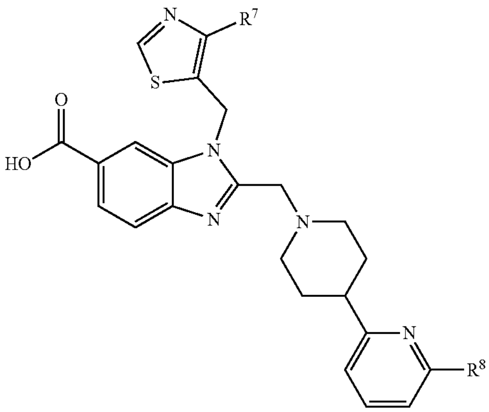

wherein $R^7$ is hydrogen, chloro, bromo, fluoro, methyl, or vinyl; and $R^8$ is

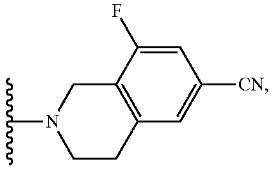

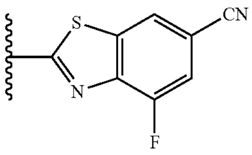

,

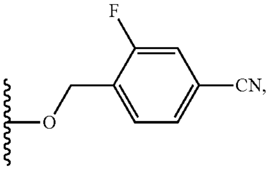

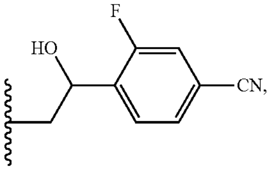

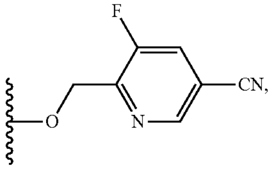

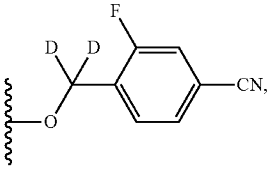

or

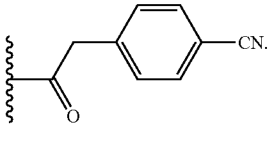

9. The combination of any one of the preceding embodiments, wherein the GLP-1R agonist is a compound of Formula (I**):

(I**)

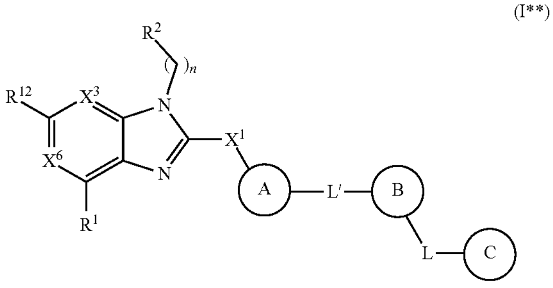

or a pharmaceutically acceptable salt thereof; wherein:

$X^3$ is $CR^6$ or N;

$X^6$ is $CR^4$ or N;

$R^1$ is —$C_{1-6}$ haloalkyl, halogen, —O—$X^4$, or —$NR^8R^9$, or $R^1$ and $R^4$, together with the atoms to which they are attached, combine to form a 5- or 6-membered heterocyclyl;

$X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}—CH_3$, —$(CH_2—CH(—OCH_3)—CH_2—O)_{1-5}—CH_3$, $C_{3-10}$ cycloalkyl, or $C_{6-10}$ aryl, wherein the alkyl, heteroalkyl, alkylene, or haloalkyl group is optionally substituted with one or more deuterium, $C_{1-6}$ alkoxy, hydroxyl, —CN, or oxo, and the cycloalkyl, heterocyclyl, or aryl group is optionally substituted with one or more halogen, $C_{1-6}$ alkoxy, or —CN;

$R^6$ is hydrogen, halogen, or —O—$R^7$; wherein $R^7$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocycyl; wherein the $C_{1-6}$ alkyl is optionally substituted by one or more oxo;

n is 0, 1, 2, 3, 4, 5, or 6;

$R^2$ is:

hydrogen;

$C_{1-6}$ alkyl optionally substituted with deuterium;

$C_{1-6}$ haloalkyl;

—(O)—$C_{1-6}$ alkyl;

—CN;

a $C_{3-10}$ cycloalkyl optionally substituted with one or more —CN, $C_{1-6}$,haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

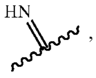, or $C_{1-6}$ alkyl;

a 5-membered heteroaryl, comprising 1 or 2 heteroatoms independently selected from N, and S, wherein at least one heteroatom of $R^5$ is S; or $R^2$ and $R^7$, together with the atoms to which they are attached, combine to form a 5- or 6-membered heterocyclyl;

$R^4$ is halogen, hydrogen, —C(O)OH, or —O—$R^8$, wherein $R^8$ and $R^1$, together with the atoms to which they are attached, combine to form a 6-membered heterocyclyl;

$R^{12}$ is hydrogen, —C(O)OH, —C(O)$NR^{N12}R^{N12\prime}$, —C(O)$NR^{12}S(O)_2R^{12}$, —($C_{2-6}$ alkynylene)-C(O)OH, —($C_{1-6}$ alkylene)-C(O)OH, —$NR^{N12}$—($C_{1-6}$ alkylene)-C(O)OH, 5-10 membered heteroaryl or 5- to 10-membered heterocyclyl optionally substituted with one or more oxo, $C_{1-6}$ alkyl or $C_{1-6}$ haloalkyl;

$R^{N12}$ and $R^{N12}$ independently are H or $C_{1-6}$ alkyl;

$X^1$ is

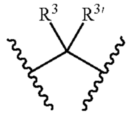

or

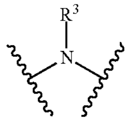, wherein $R^3$ and $R^{3\prime}$ independently are H, D or $C_{1-6}$ alkyl, wherein the $C_{1-6}$ alkyl is optionally substituted with detuerium;

Ring A is

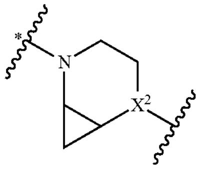

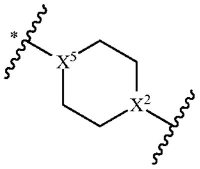,

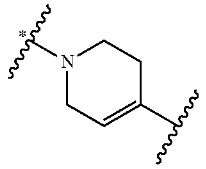, phenylene optionally substituted with one or more halo or $C_{1-6}$ alkyl, or 6-membered heteroarylene optionally substituted with one or more halo or $C_{1-6}$ alkyl;

wherein * indicates attachment to $X^1$, $X^5$ is $CR^3$ or N, and $X^2$ is $CR^3$ or N;

L' is a bond or —O—;

Ring B is a $C_{6-10}$ arylene, a 5-10 membered heteroarylene, or a 3-10 membered heterocycylene, wherein the $C_{6-10}$ arylene, 5-10 membered heteroarylene, or 3-10 membered heterocyclene is optionally substituted with one or more oxo, $C_{1-6}$ alkyl, $C_{1-6}$ alkoxy, or halogen;

L is a bond, *—($C_{1-6}$ alkylene)-, *—$NR^L$—($C_1$i alkylene)-, *—O—($C_{1-6}$ alkylene)-, or *—($C_{1-6}$ alkylene)-O—, wherein * indicates attachment to Ring B and the $C_{1-6}$ alkylene is optionally substituted with deuterium;

wherein $R^L$ is H or $C_{1-6}$ alkyl; and

Ring C is:

a 6-membered aryl optionally substituted with one or more $C_{3-10}$ cycloalkyl, $C_{1-6}$ alkyl, $C_{1-6}$ haloalkyl, 3-10 membered heterocyclyl, halogen, $C_{1-6}$ alkoxy, $C_{1-6}$ haloalkoxy, —CN, $C_{3-10}$ cycloalkyl, or —C(O)$NR^{12}$; wherein $R^1$ is H or $C_{1-6}$ alkyl a 6-membered heteroaryl comprising a nitrogen atom optionally substituted with one or more halogen, —CN, $C_{1-6}$ haloalkyl, —O—$C_{1-6}$ alkyl, $C_{3-10}$ cycloalkyl, —C(═O)—($C_{3-10}$ cycloalkyl),

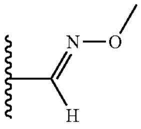
,
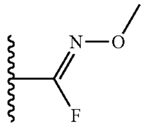
, or
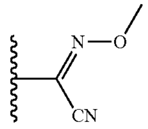
;

or a bicylic 9- or 10-membered heteroaryl or heterocyclyl optionally substituted with one or more $C_{1-6}$ alkyl, halogen, —CN, or oxo.

10. The combination of any one of the preceding embodiments, wherein the GLP-1R agonist is a compound of Formula (I-5)

(I-5)

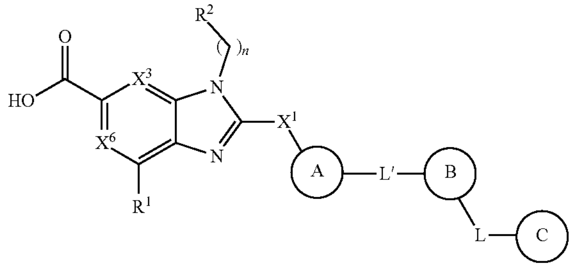

or a pharmaceutically acceptable salt thereof; wherein:

$X^3$ is $CR^6$ or N;

$X^6$ is $CR^4$ or N;

$R^1$ is —$C_{1-6}$ haloalkyl, —O—$X^4$, or —$NR^8R^9$, or $R^1$ and $R^4$, together with the atoms to which they are attached, combine to form a 6-membered heterocyclyl;

$X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}$—$CH_3$, or —$(CH_2—CH(—OCH_3)—CH_2—O)_{1-5}$—$CH_3$, wherein the alkyl, heteroalkyl, alkylene, or haloalkyl group is optionally substituted with one or more deuterium, hydroxyl, —CN, or oxo, and the cycloalkyl or heterocyclyl group is optionally substituted with one or more halogen or —CN;

$R^6$ is hydrogen, halogen, or —O—$R^7$;

wherein $R^7$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocyclyl; wherein the $C_{1-6}$ alkyl is optionally substituted by one or more oxo;

n is 0, 1, 2, 3, 4, 5, or 6;

$R^2$ is:

hydrogen;

branched $C_{1-6}$ alkyl;

$C_{1-6}$ haloalkyl;

—(O)—$C_{1-6}$ alkyl;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

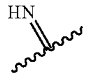
, or $C_{1-6}$ alkyl;

a 5-membered heteroaryl, comprising 1 or 2 heteroatoms independently selected from N, and S, wherein at least one heteroatom of $R^5$ is S; or $R^2$ and $R^7$, together with the atoms to which they are attached, combine to form a 5- or 6-membered heterocyclyl;

$R^4$ is hydrogen or —O—$R^8$, wherein $R^8$ and $R^1$, together with the atoms to which they are attached, combine to form a 6-membered heterocyclyl;

$X^1$ is

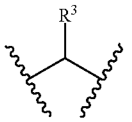
or
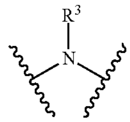
, wherein $R^3$ is H or $C_{1-6}$ alkyl;

Ring A is

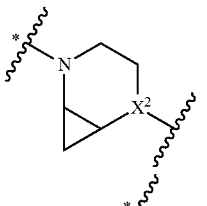
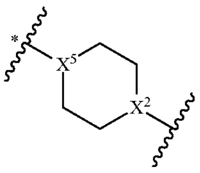
,
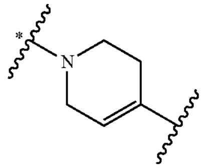
, phenylene optionally substituted with one or more halo or $C_{1-6}$ alkyl, or 6-membered heteroarylene optionally substituted with one or more halo or $C_{1-6}$ alkyl;

wherein * indicates attachment to $X^1$, $X^5$ is $CR^3$ or N, and $X^2$ is $CR^3$ or N;

L' is a bond or —O—;

Ring B is a $C_{6-10}$ arylene, a 6-10 membered heteroarylene, or a 3-10 membered heterocyclene, wherein the $C_{6-10}$ arylene, 6-10 heteroarylene, or 3-10 membered heterocyclene is optionally substituted with one or more $C_{1-6}$ alkyl, $C_{1-6}$ alkoxy, or halogen;

L is a bond, *—$CH_2$—, *—O—($C_{1-6}$ alkylene)-, or *—($C_{1-6}$ alkylene)-O—, wherein * indicates attachment to Ring B and the $C_{1-6}$ alkylene is optionally substituted with deuterium; and Ring C is:

a 6-membered aryl optionally substituted with one or more $C_{1-6}$ alkyl, 3-10 membered heterocyclyl, halogen, —$OCH_3$, —CN, or $C_{3-10}$ cycloalkyl;

a 6-membered heteroaryl comprising a nitrogen atom optionally substituted with one or more halogen, —CN, —O—$C_{1-6}$ alkyl, $C_{3-10}$ cycloalkyl, —C(=O)—($C_{3-10}$ cycloalkyl)

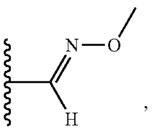 , 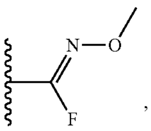 , or 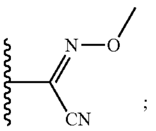 ;

a bicyclic 9- or 10-membered heteroaryl comprising two nitrogen atoms optionally substituted with one or more $C_{1-6}$ alkyl, or oxo.

11. The combination of any one of the preceding embodiments, wherein the GLP-1R agonist is a compound of Formula (II**):

(II**)

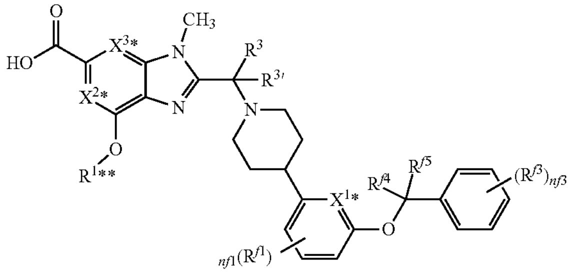

or a pharmaceutically acceptable salt thereof; wherein $R^{f4}$ and $R^a$ are each independently selected from $C_{1-6}$ alkyl, H and D nf1 is 0, 1, 2, 3, or 4;

nf3 is 0, 1, 2, 3, 4, or 5, each $R^{f1}$ is halogen;

$R^3$ and $R^{3'}$ independently are H or D;

$X^{1*}$ is N or $CR^{f1}$;

$X^{2*}$ and $X^{3*}$ independently are CH or CF;

each $R^{f3}$ is independently selected from halogen, —CN, $C_{1-6}$ alkyl, $C_{1-6}$ haloalkyl, $C_{1-6}$ alkoxy, or —C(O)N$(R^{f3'})_2$, each $R^{f3'}$ is indepdendently selected from H or $C_{1-6}$ alkyl; and $R^{1**}$ is H or $C_{1-2}$ alkyl optionally substituted with one or more deuterium or halogen.

12. The combination of any one of the preceding embodiments, wherein the GLP-1R agonist is Compound 1-2:

(1-2)

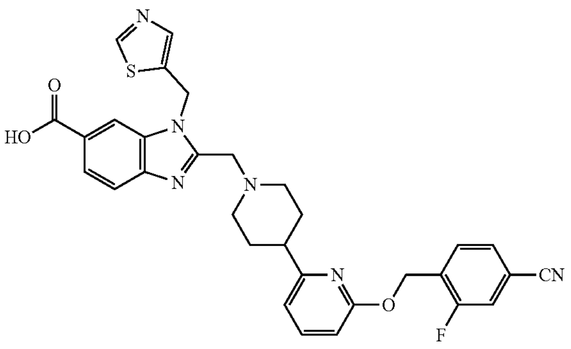

or a pharmaceutically acceptable salt thereof.

13. The combination of any one of the preceding embodiments, wherein the GLP-1R agonist is a meglumine salt of Compound 1-2.

14. The combination of any one of the preceding embodiments, wherein the THRβ agonist is selected from those listed in Tables 6-11.

15. The combination of any one of the preceding embodiments, wherein the GLP-1R agonist is selected from those listed in Tables 1-5.

16. The combination of any one of the preceding embodiments, wherein the GLP-1R agonist is selected from those listed in Table 5A.

17. The combination of any one of the preceding embodiments, wherein the THRβ agonist is compound 9

(9)

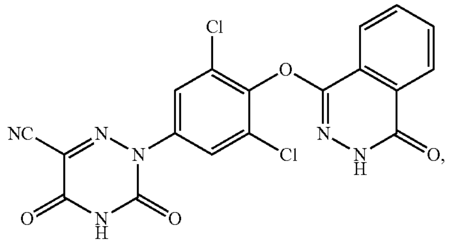

and the GLP-1R agonist is orforglipron, danuglipron, liraglutide, exenatide, dulaglutide, albiglutide, lixisenatide, tirzepatide, or semaglutide, or a pharmaceutically acceptable salt thereof.

17a. The combination of any one of the preceding embodiments, wherein the THRβ agonist is compound 9

(9)

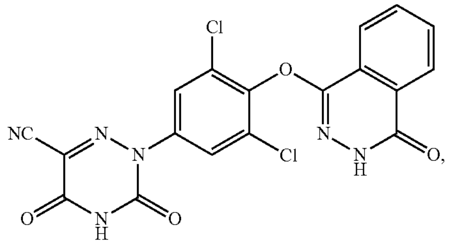

and the GLP-1R agonist is orforglipron or a pharmaceutically acceptable salt thereof.

17b. The combination of any one of the preceding embodiments, wherein the THRβ agonist is compound 9

(9)

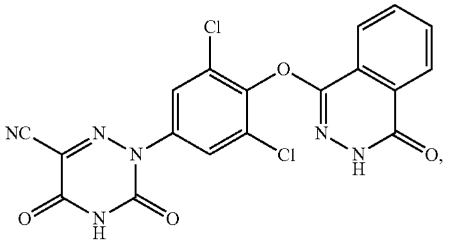

and the GLP-1R agonist is semaglutide or a pharmaceutically acceptable salt thereof.

17c. The combination of any one of the preceding embodiments, wherein the THRβ agonist is compound 9

(9)

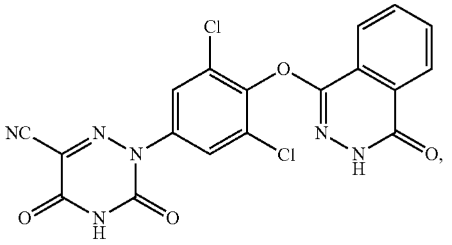

and the GLP-1R agonist is danuglipron or a pharmaceutically acceptable salt thereof.

18. The combination of any one of the preceding embodiments, wherein the THRβ agonist is resmetirom, VK2809, sobetirome, eprotirome, ALG-055009, CNPT-101101, CNPT-101207, ASC41 or a pharmaceutically acceptable salt thereof and the GLP-1R agonist is compound 1-2

(1-2)

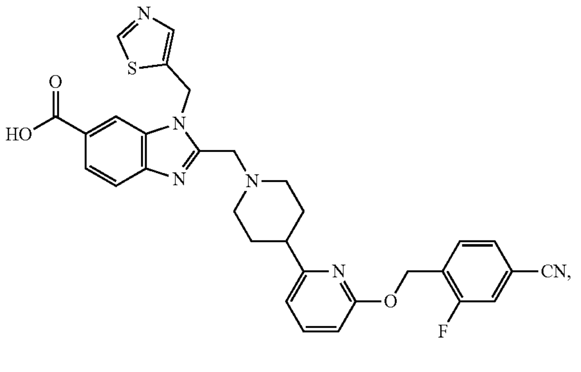

or a pharmaceutically acceptable salt thereof.

19. The combination of any one of the preceding embodiments, wherein the THRβ agonist is compound 9

(9)

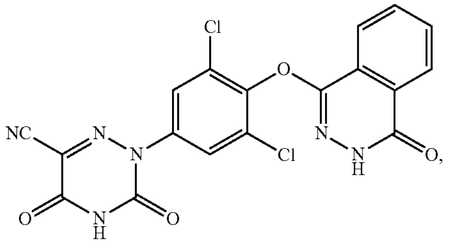

or a pharmaceutically acceptable salt thereof, and the GLP-1R agonist is compound 1-2

(1-2)

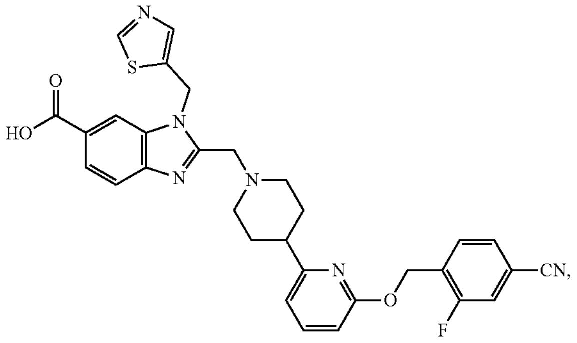

or a pharmaceutically acceptable salt thereof.

20. A method of treating a liver disorder or a cardiometabolic disease in a patient in need thereof, comprising administering to the patient a combination according to any one of the previous embodiments.

21. A method of treating a liver disorder or a cardiometabolic disease in a patient in need thereof, comprising administering to the patient a therapeutically effective amount of the combination according to any one of the previous embodiments.

22. A method of increasing the proportion of lean body mass relative to total body mass in a patient in need thereof, comprising administering to the patient a combination according to any one of the previous embodiments.

23. A method of decreasing the proportion of fat mass relative to total body mass in a patient in need thereof, comprising administering to the patient a combination according to any one of the previous embodiments.

24. A method of effectuating weight loss in a patient in need thereof, comprising administering to the patient a combination according to any one of the previous embodiments.

25. The method of any one of the previous embodiments, wherein the patient has a Body Mass Index (BMI) of 20 $kg/m^2$ to 25 $kg/m^2$.

26. The method of any one of the previous embodiments, wherein the patient has a BMI of 25 $kg/m^2$ to 30 $kg/m^2$.

27. The method of any one of the previous embodiments, wherein the patient has a BMI of 30 $kg/m^2$ or greater.

28. The method of any one of the preceding embodiments, wherein the cardiometabolic disease is obesity.

29. The method of any one of the preceding embodiments, wherein the liver disorder is NASH.

30. The method of any one of the preceding embodiments, wherein the liver disorder is liver fibrosis.
31. The method of any one of the preceding embodiments, wherein the GLP-1R agonist element of the combination is administered to the subject more than once.
32. The method of any one of the preceding embodiments, wherein the THR-β agonist element of the combination is administered to the subject more than once.
33. The method of any one of the preceding embodiments, wherein both the GLP-1R agonist and THRβ agonist elements of the combination are administered to the subject more than once.
34. The method of any one of the preceding embodiments, wherein the THRβ agonist is administered prior to or concurrent with the GLP-1R agonist.
35. The method of any one of the preceding embodiments, wherein the THRβ agonist is administered in temporal proximity to the GLP-1R agonist.
36. The method of any one of the preceding embodiments, wherein the THRβ agonist is administered on the same day as the GLP-1R agonist.
37. The method of any one of the preceding embodiments, wherein the THRβ agonist is administered at substantially the same time as the GLP-1R agonist.
38. The method of any one of the preceding embodiments, wherein the initial dose of THRβ agonist is administered in temporal proximity to the GLP-1R agonist.
39. The method of any one of the preceding embodiments, wherein the initial dose of THRβ agonist is administered on the same day as the GLP-1R agonist.
40. The method of any one of the preceding embodiments, wherein the wherein the initial dose of THRβ agonist is at substantially the same time as the GLP-1R agonist.
41. The method of any one of the preceding embodiments, wherein the initial dose of THRβ agonist is administered prior to the initial dose of GLP-1R agonist.
42. The method of embodiment 40, wherein a subsequent dose of THRβ agonist is administered in temporal proximity to the GLP-1R agonist.
43. The method of embodiment 41 or 42, wherein a subsequent dose of THRβ agonist is administered on the same day as the GLP-1R agonist.
44. The method of any one of embodiments 41 to 43, wherein a subsequent dose of THRβ agonist is administered at substantially the same time as the GLP-1R agonist.
45. A method of improving a patient's response to the administration of a GLP-1R agonist in a patient in need thereof, comprising
(i) administering to the patient compound 9

(9)

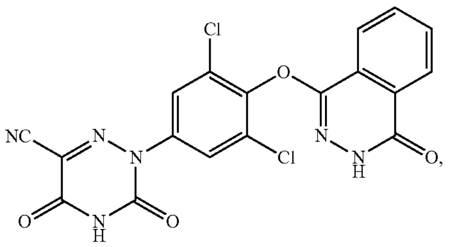

or a pharmaceutically acceptable salt thereof, and
(ii) administering a GLP-1R agonist, or a pharmaceutically acceptable salt thereof.
46. The method of embodiment 45, wherein administering compound 9, or a pharmaceutically acceptable salt thereof, increases fat loss associated with administering the GLP-1R agonist.
47. The method of embodiment 45, wherein administering compound 9, or a pharmaceutically acceptable salt thereof, increases fat loss associated with administering the GLP-1R agonist while maintaining lean mass.
48. The method of embodiment 45, wherein administering compound 9, or a pharmaceutically acceptable salt thereof, is performed prior to or concurrent with the administration of the GLP-1R agonist.
49. The method of embodiment 45, wherein administering compound 9, or a pharmaceutically acceptable salt thereof, is performed prior to the administration of the GLP-1R agonist.
50. The method of any one of the preceding embodiments, wherein the GLP-1R agonist is administered to the subject more than once.
51. The method of any one the preceding embodiments, wherein the THR agonist element is administered to the subject more than once.
52. The method of any one of the preceding embodiments, wherein both the GLP-1R agonist and THR-β agonist are administered to the subject more than once.
53. The method of any one of the preceding embodiments, wherein the THR agonist is administered prior to or concurrent with the GLP-1R agonist.
54. The method of any one of the preceding embodiments, wherein the THRβ agonist is administered in temporal proximity to the GLP-1R agonist.
55. The method of any one of the preceding embodiments, wherein the THRβ agonist is administered on the same day as the GLP-1R agonist.
56. The method of any one of the preceding embodiments, wherein the THRβ agonist is administered at substantially the same time as the GLP-1R agonist.
57. The method of any one of the preceding embodiments, wherein the initial dose of THRβ agonist is administered in temporal proximity to the GLP-1R agonist.
58. The method of any one of the preceding embodiments, wherein the initial dose of THRβ agonist is administered on the same day as the GLP-1R agonist.
59. The method of any one of the preceding embodiments, wherein the initial dose of THRβ agonist is at substantially the same time as the GLP-1R agonist.
60. The method of any one of the preceding embodiments, wherein the initial dose of THRβ agonist is administered prior to the initial dose of GLP-1R agonist.
61. The method of any one of the preceding embodiments, wherein a subsequent dose of THRβ agonist is administered in temporal proximity to the GLP-1R agonist.
62. The method of any one of the preceding embodiments, wherein a subsequent dose of THRβ agonist is administered on the same day as the GLP-1R agonist.
63. The method of any one of the preceding embodiments, wherein a subsequent dose of THRβ agonist is administered at substantially the same time as the GLP-1R agonist.
64. A combinational therapy comprising a THRβ agonist, or a pharmaceutically acceptable salt thereof, and a GLP-1R agonist, or a pharmaceutically acceptable salt thereof, for the treatment of obesity in a patient in need thereof.
65. The combinational therapy of embodiment 64, wherein the THRβ agonist is a compound of Formula (II-1)

(II-1)

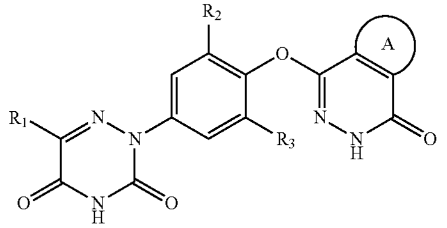

wherein:

$R_1$ is selected from the group consisting of hydrogen, cyano, substituted or unsubstituted $C_{1-6}$ alkyl, and substituted or unsubstituted $C_{3-6}$ cycloalkyl, the substituent being selected from the group consisting of halogen atoms, hydroxy, and $C_{1-6}$ alkoxy;

$R_2$ and $R_3$ are each independently selected from the group consisting of halogen atoms and substituted or unsubstituted $C_{1-6}$ alkyl, the substituent being selected from the group consisting of halogen atoms, hydroxy, and $C_{1-6}$ alkoxy;

ring A is a substituted or unsubstituted saturated or unsaturated $C_{5-10}$ aliphatic ring, or a substituted or unsubstituted $C_{5-10}$ aromatic ring, the substituent being one or more substances selected from the group consisting of hydrogen, halogen atoms, hydroxy, —$OCF_3$, —$NH_2$, —$NHC_{1-4}$ alkyl, —$N(C_{1-4}$ alkyl$)_2$, —$CONH_2$, —$CONHC_{1-4}$ alkyl, —$CON(C_{1-4}$ alkyl$)_2$, —$NHCOC_{1-4}$ alkyl, $C_{1-6}$ alkyl, $C_{1-6}$ alkoxy or $C_{3-6}$ cycloalkyl, and when two substituents are contained, the two substituents can form a ring structure together with the carbon connected thereto; and the halogen atoms are selected from the group consisting of F, Cl and Br, or a pharmaceutically acceptable salt thereof.

66. The combinational therapy of embodiment 64 or 65, wherein the THRβ agonist is a compound of Formula (II-1a)

(II-1a)

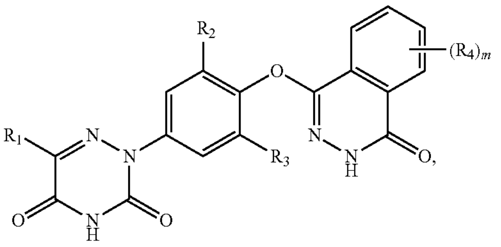

wherein:

$R_1$ to $R_3$ are defined as detailed herein for Formula (II-1);

$R_4$ is selected from the group consisting of hydrogen, halogen atoms, hydroxy, —$OCF_3$, —$NH_2$, —$NHC_{1-4}$ alkyl, —$N(C_{1-4}$ alkyl$)_2$, —$CONH_2$, —$CONHC_{1-4}$ alkyl, —$CON(C_{1-4}$ alkyl$)_2$, —$NHCOC_{1-4}$ alkyl, $C_{1-6}$ alkyl, $C_{1-6}$ alkoxy and $C_{3-6}$ cycloalkyl;

m is an integer from the range 1 to 4; and the halogen atoms are selected from the group consisting of F, Cl and Br.

Or a pharmaceutically acceptable salt thereof.

67. The combinational therapy of any one of the preceding embodiments, wherein the THRβ agonist is compound 9

(9)

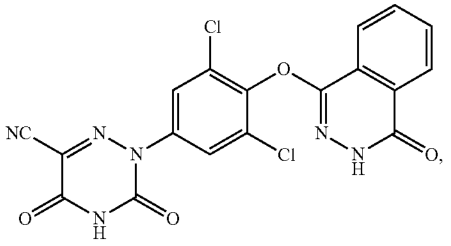

and the GLP-1R agonist is orforglipron, danuglipron, liraglutide, exenatide, dulaglutide, albiglutide, lixisenatide, tirzepatide, or semaglutide, or a pharmaceutically acceptable salt thereof.

67a. The combinational therapy of any one of the preceding embodiments, wherein the THRβ agonist is compound 9

(9)

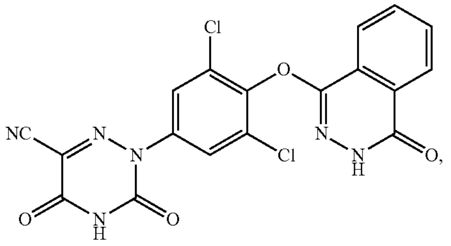

and the GLP-1R agonist is orforglipron or a pharmaceutically acceptable salt thereof.

67b. The combinational therapy of any one of the preceding embodiments, wherein the THRβ agonist is compound 9

(9)

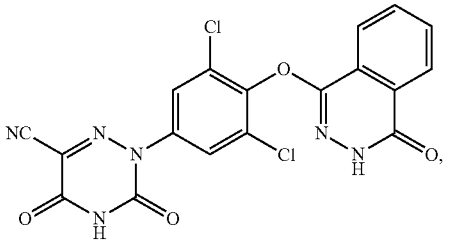

and the GLP-1R agonist is semaglutide or a pharmaceutically acceptable salt thereof.

67c. The combinational therapy of any one of the preceding embodiments, wherein the THRβ agonist is compound 9

(9)

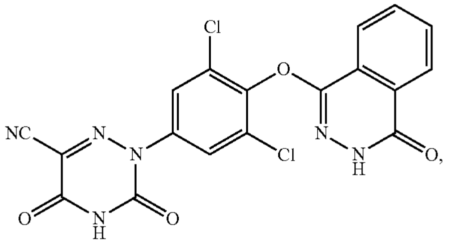

and the GLP-1R agonist is danuglipron or a pharmaceutically acceptable salt thereof.

68. The combinational therapy of any one of the preceding embodiments, wherein the THRβ agonist is a potassium salt of Compound 9.

69. The combinational therapy of any one of the preceding embodiments, wherein the GLP-1R agonist is a compound of Formula (I-1):

(I-1)

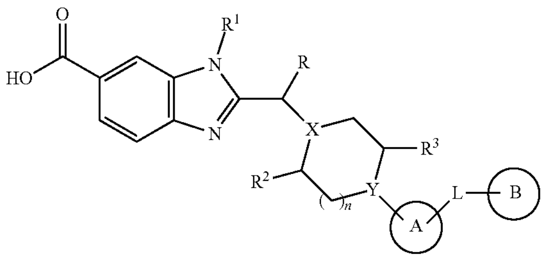

or a pharmaceutically acceptable salt thereof, wherein:

X is N or CH;

Y is N or $CR^4$;

n is 0 or 1;

R is hydrogen;

$R^1$ is —$C_1$-$C_6$ alkylene-$R^5$;

$R^2$ is hydrogen, oxo, or $C_1$-$C_6$ alkyl;

$R^3$ is hydrogen, oxo, or $C_1$-$C_6$ alkyl and $R^4$ is hydrogen, OH, or $C_1$-$C_6$ alkyl; or $R^3$ and $R^4$ are taken together with the carbon atoms to which they are attached to form $C_3$-$C_6$ cycloalkyl optionally substituted by halo or $C_1$-$C_3$ alkyl;

$R^3$ is 5-membered heterocyclyl or 5-membered heteroaryl, each of which comprises 1, 2, or 3 heteroatoms independently selected from O, N, and S, wherein at least one heteroatom of $R^5$ is S, and further wherein $R^5$ is optionally substituted by halo, —O—$C_{1-6}$ alkyl, $C_{1-6}$ alkyl, $C_{1-6}$ alkenyl, or $C_1$-$C_6$ haloalkyl;

Ring A is 5- to 12-membered heterocyclene or 5- to 12-membered heteroarylene, each of which is independently optionally substituted by halo, CN, $C_3$-$C_6$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein

* represents the point of attachment to ring A and ** represents the point of attachment to ring B;

when L is *—O—$C_1$-$C_6$ alkylene-**, the $C_1$-$C_6$ alkylene of L is optionally substituted by $R^L$, wherein each $R^1$ is independently $C_1$-$C_6$ alkyl or halo, or two $R^L$ are taken together with the carbon atom or atoms to which they are attached to form $C_3$-$C_6$ cycloalkyl or 3- to 6-membered heterocyclyl; and when L is $C_1$-$C_6$ alkylene, the $C_1$-$C_6$ alkylene is optionally substituted by $R^{L1}$, wherein each $R^{L1}$ is independently halo, OH, oxo, or $C_1$-$C_6$ alkyl, or two $R^{L1}$ are taken together with the carbon atom or atoms to which they are attached to form $C_3$-$C_6$ cycloalkyl or 3- to 6-membered heterocyclyl;

$R^6$ is hydrogen or $C_1$-$C_6$ alkyl; and

Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

70. The combinational therapy of any one of the preceding embodiments, wherein the GLP-1R agonist is a compound of Formula (I-1a):

(I-1a)

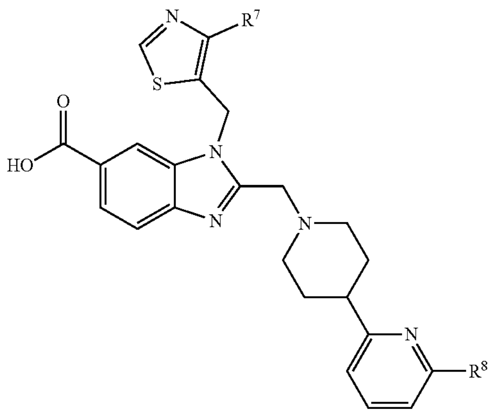

wherein $R^7$ is hydrogen, chloro, bromo fluoro methyl, or vinyl; and $R^8$ is

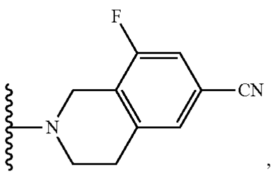
,
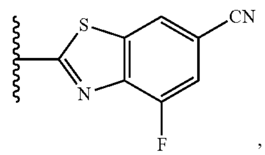
,
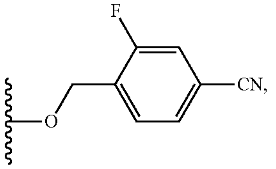

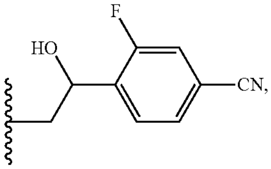

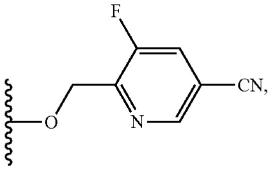

-continued

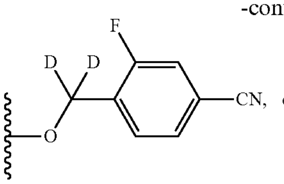

or

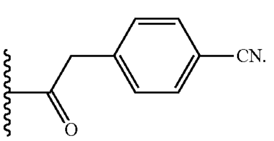

71. The combinational therapy of any one of the preceding embodiments, wherein the GLP-1R agonist is a compound of Formula (I**):

(I**)

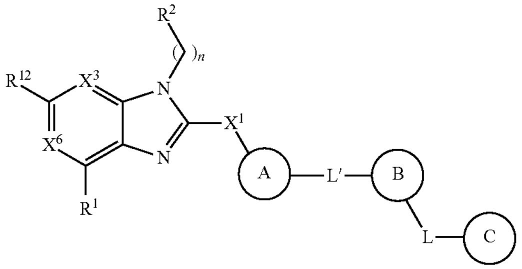

or a pharmaceutically acceptable salt thereof; wherein:

$X^3$ is $CR^6$ or N;

$X^6$ is $CR^4$ or N;

$R^1$ is —$C_{1-6}$ haloalkyl, halogen, —O—$X^4$, or —$NR^8R^9$, or $R^1$ and $R^4$, together with the atoms to which they are attached, combine to form a 5- or 6-membered heterocyclyl;

$X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}$—$CH_3$, —($CH_2$—CH(—$OCH_3$)—$CH_2$—$O)_{1-5}$—$CH_3$, $C_{3-10}$ cycloalkyl, or $C_{6-10}$ aryl, wherein the alkyl, heteroalkyl, alkylene, or haloalkyl group is optionally substituted with one or more deuterium, $C_{1-6}$ alkoxy, hydroxyl, —CN, or oxo, and the cycloalkyl, heterocyclyl, or aryl group is optionally substituted with one or more halogen, $C_{1-6}$ alkoxy, or —CN;

$R^6$ is hydrogen, halogen, or —O—$R^7$;

wherein $R^7$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocycyl; wherein the $C_{1-6}$ alkyl is optionally substituted by one or more oxo;

n is 0, 1, 2, 3, 4, 5, or 6;

$R^2$ is:

hydrogen;

$C_{1-6}$ alkyl optionally substituted with deuterium;

$C_{1-6}$ haloalkyl;

—(O)—$C_{1-6}$ alkyl;

—CN;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

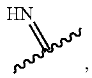, or $C_{1-6}$ alkyl;

a 5-membered heteroaryl, comprising 1 or 2 heteroatoms independently selected from N, and S, wherein at least one heteroatom of $R^5$ is S; or $R^2$ and $R^7$, together with the atoms to which they are attached, combine to form a 5- or 6-membered heterocyclyl;

$R^4$ is halogen, hydrogen, —C(O)OH, or —O—$R^8$, wherein $R^8$ and $R^1$, together with the atoms to which they are attached, combine to form a 6-membered heterocyclyl;

$R^{12}$ is hydrogen, —C(O)OH, —C(O)$NR^{N12}R^{N12'}$, —C(O)$NR^{12}S(O)_2R^{12}$, —($C_{2-6}$ alkynylene)-C(O)OH, —($C_{1-6}$ alkylene)-C(O)OH, —$NR^{N12}$—($C_{1-6}$ alkylene)-C(O)OH, 5-10 membered heteroaryl or 5- to 10-membered heterocyclyl optionally substituted with one or more oxo, $C_{1-6}$ alkyl or $C_{1-6}$ haloalkyl;

$R^{N12}$ and $R^{N12}$ independently are H or $C_{1-6}$ alkyl;

$X^1$ is

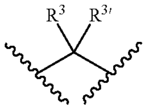

or

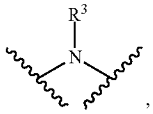, wherein $R^3$ and $R^{3'}$ independently are H, D or $C_{1-6}$ alkyl, wherein the $C_{1-6}$ alkyl is optionally substituted with detuerium;

Ring A is

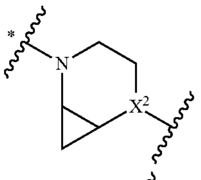

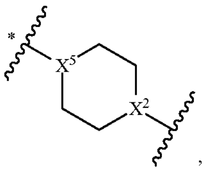,

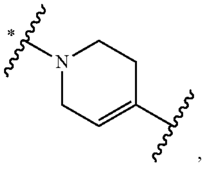, phenylene optionally substituted with one or more halo or $C_{1-6}$ alkyl, or 6-membered heteroarylene optionally substituted with one or more halo or $C_{1-6}$ alkyl;

wherein * indicates attachment to $X^1$, $X^5$ is $CR^3$ or N, and $X^2$ is $CR^3$ or N;

L' is a bond or —O—;

Ring B is a $C_{6-10}$ arylene, a 5-10 membered heteroarylene, or a 3-10 membered heterocycylene, wherein the $C_{6-10}$ arylene, 5-10 membered heteroarylene, or 3-10 membered heterocyclene is optionally substituted with one or more oxo, $C_{1-6}$ alkyl, $C_{1-6}$ alkoxy, or halogen;

L is a bond, *—($C_{1-6}$ alkylene)-, *—$NR^L$—($C_1$i alkylene)-, *—O—($C_{1-6}$ alkylene)-, or *—($C_{1-6}$ alkylene)-O—, wherein * indicates attachment to Ring B and the $C_{1-6}$ alkylene is optionally substituted with deuterium;

wherein $R^L$ is H or $C_{1-6}$ alkyl; and

Ring C is:

a 6-membered aryl optionally substituted with one or more $C_{3-10}$ cycloalkyl, $C_{1-6}$ alkyl, $C_{1-6}$ haloalkyl, 3-10 membered heterocyclyl, halogen, $C_{1-6}$ alkoxy, $C_{1-6}$ haloalkoxy, —CN, $C_{3-10}$ cycloalkyl, or —C(O)NR$^{12}$; wherein $R^1$ is H or $C_{1-6}$ alkyl a 6-membered heteroaryl comprising a nitrogen atom optionally substituted with one or more halogen, —CN, $C_{1-6}$ haloalkyl, —O—$C_{1-6}$ alkyl, $C_{3-10}$ cycloalkyl, —C(=O)—($C_{3-10}$ cycloalkyl),

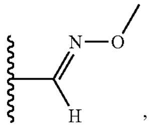
,
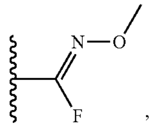
, or
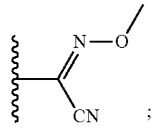
;

or a bicylic 9- or 10-membered heteroaryl or heterocyclyl optionally substituted with one or more $C_{1-6}$ alkyl, halogen, —CN, or oxo.

72. The combinational therapy of any one of the preceding embodiments, wherein the GLP-1R agonist is a compound of Formula (I-5)

(I-5)

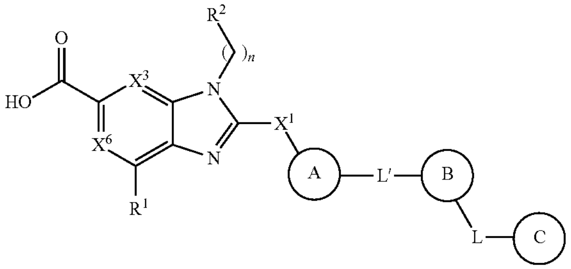

or a pharmaceutically acceptable salt thereof; wherein:

$X^3$ is $CR^6$ or N;

$X^6$ is $CR^4$ or N;

$R^1$ is —$C_{1-6}$ haloalkyl, —O—$X^4$, or —$NR^8R^9$, or $R^1$ and $R^4$, together with the atoms to which they are attached, combine to form a 6-membered heterocyclyl;

$X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or -($C_{1-6}$ alkylene)-(3- to 8-membered heterocyclyl), 3- to 8-membered heterocyclyl, —$(CH_2CH_2—O)_{1-5}$—$CH_3$, or —$(CH_2—CH(—OCH_3)—CH_2—O)_{1-5}$—$CH_3$, wherein the alkyl, heteroalkyl, alkylene, or haloalkyl group is optionally substituted with one or more deuterium, hydroxyl, —CN, or oxo, and the cycloalkyl or heterocyclyl group is optionally substituted with one or more halogen or —CN;

$R^6$ is hydrogen, halogen, or —O—$R^7$;

wherein $R^7$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocyclyl; wherein the $C_{1-6}$ alkyl is optionally substituted by one or more oxo;

n is 0, 1, 2, 3, 4, 5, or 6;

$R^2$ is:

hydrogen;

branched $C_{1-6}$ alkyl;

$C_{1-6}$ haloalkyl;

—(O)—$C_{1-6}$ alkyl;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

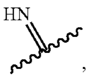
, or $C_{1-6}$ alkyl;

a 5-membered heteroaryl, comprising 1 or 2 heteroatoms independently selected from N, and S, wherein at least one heteroatom of $R^5$ is S; or $R^2$ and $R^7$, together with the atoms to which they are attached, combine to form a 5- or 6-membered heterocyclyl;

$R^4$ is hydrogen or —O—$R^8$, wherein $R^8$ and $R^9$, together with the atoms to which they are attached, combine to form a 6-membered heterocyclyl;

$X^1$ is

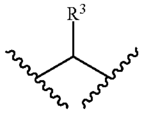
or
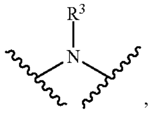
, wherein $R^3$ is H or $C_{1-6}$ alkyl;

Ring A is

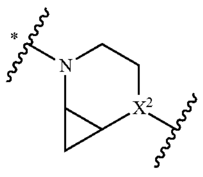
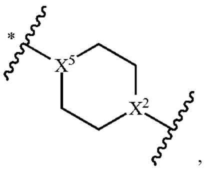
,
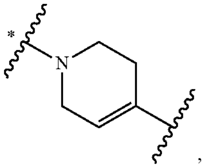
, phenylene optionally substituted with one or more halo or $C_{1-6}$ alkyl, or 6-membered heteroarylene optionally substituted with one or more halo or $C_{1-6}$ alkyl;

wherein * indicates attachment to $X^1$, $X^5$ is $CR^3$ or N, and $X^2$ is $CR^3$ or N;

L' is a bond or —O—;

Ring B is a $C_6$—.o arylene, a 6-10 membered heteroarylene, or a 3-10 membered heterocyclene, wherein the $C_{6-10}$ arylene, 6-10 heteroarylene, or 3-10 membered heterocyclene is optionally substituted with one or more $C_{1-6}$ alkyl, $C_{1-6}$ alkoxy, or halogen;

L is a bond, *—$CH_2$—, *—O—($C_{1-6}$ alkylene)-, or *-($C_{1-6}$ alkylene)-O—, wherein * indicates attachment to Ring B and the $C_{1-6}$ alkylene is optionally substituted with deuterium; and Ring C is:

a 6-membered aryl optionally substituted with one or more $C_{1-6}$ alkyl, 3-10 membered heterocyclyl, halogen, —$OCH_3$, —CN, or $C_{3-10}$ cycloalkyl;

a 6-membered heteroaryl comprising a nitrogen atom optionally substituted with one or more halogen, —CN, —O—$C_{1-6}$ alkyl, $C_{3-10}$ cycloalkyl, —C(═O)—($C_{3-10}$ cycloalkyl),

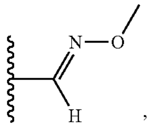 , 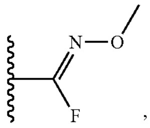 , or 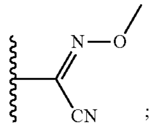 ;

a bicyclic 9- or 10-membered heteroaryl comprising two nitrogen atoms optionally substituted with one or more $C_{1-6}$ alkyl, or oxo.

73. The combinational therapy of any one of the preceding embodiments, wherein the GLP-1R agonist is a compound of Formula (II**):

(II**)

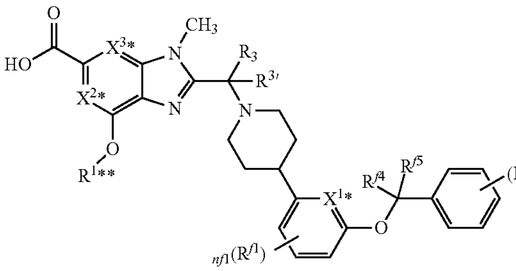

or a pharmaceutically acceptable salt thereof, wherein $R^{f4}$ and $R^{f5}$ are each independently selected from $C_{1-6}$ alkyl, H and D nf1 is 0, 1, 2, 3, or 4;

nf3 is 0, 1, 2, 3, 4, or 5;

each $R^{f1}$ is halogen;

$R^3$ and $R^{3'}$ independently are H or D;

$X^{1*}$ is N or $CR^{f1}$;

$X^{2*}$ and $X^{3*}$ independently are CH or CF;

each $R^{f3}$ is independently selected from halogen, —CN, $C_{1-6}$ alkyl, $C_{1-6}$ haloalkyl, $C_{1-6}$ alkoxy, or —C(O)N$(R^{f3'})_2$, each $R^{1*}$ is indepdendently selected from H or $C_{1-6}$ alkyl; and $R^{1**}$ is H or $C_{1-2}$ alkyl optionally substituted with one or more deuterium or halogen.

74. The combinational therapy of any one of the preceding embodiments, wherein the GLP-1R agonist is Compound 1-2:

(1-2)

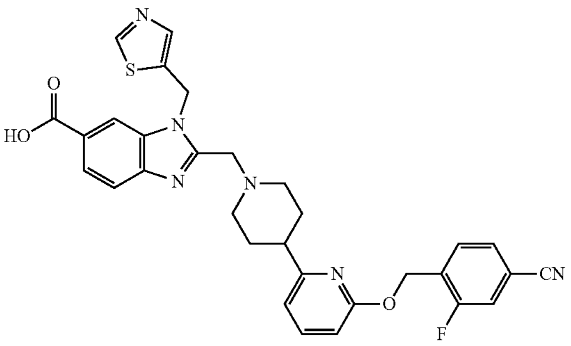

or a pharmaceutically acceptable salt thereof.

75. The combinational therapy of any one of the preceding embodiments, wherein the GLP-1R agonist is a meglumine salt of Compound 1-2.

76. The combinational therapy of any one of the preceding embodiments, wherein the THRβ agonist is selected from those listed in Tables 6-11.

77. The combinational therapy of any one of the preceding embodiments, wherein the GLP-1R agonist is selected from those listed in Tables 1-5.

78. The combinational therapy of any one of the preceding embodiments, wherein the GLP-1R agonist is selected from those listed in Table 5A.

79. The combinational therapy of any one of the preceding embodiments, wherein the THRβ agonist is compound 9

(9)

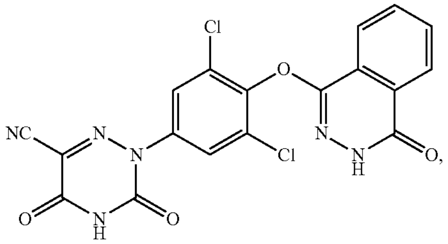

and the GLP-1R agonist is orforglipron, danuglipron, liraglutide, exenatide, dulaglutide, albiglutide, lixisenatide, tirzepatide, or semaglutide, or a pharmaceutically acceptable salt thereof.

79a. The combinational therapy of any one of the preceding embodiments, wherein the THRβ agonist is compound 9

(9)

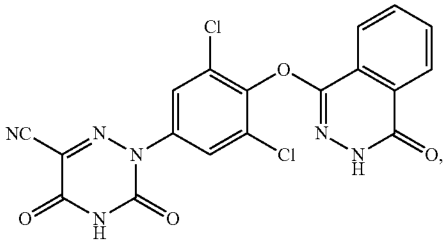

and the GLP-1R agonist is orforglipron or a pharmaceutically acceptable salt thereof.

79b. The combinational therapy of any one of the preceding embodiments, wherein the THRβ agonist is compound 9

(9)

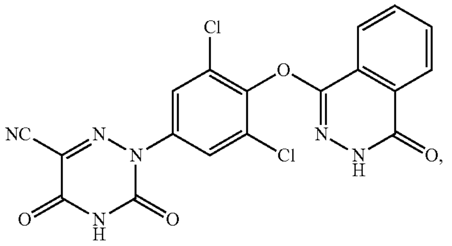

and the GLP-1R agonist is semaglutide or a pharmaceutically acceptable salt thereof.

79c. The combinational therapy of any one of the preceding embodiments, wherein the THRβ agonist is compound 9

(9)

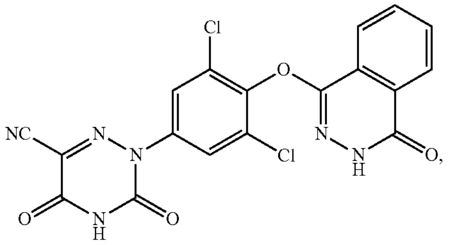

and the GLP-1R agonist is danuglipron or a pharmaceutically acceptable salt thereof.

80. The combinational therapy of any one of the preceding embodiments, wherein the THRβ agonist is resmetirom, VK2809, sobetirome, eprotirome, ALG-055009, CNPT-101101, CNPT-101207, ASC41 or a pharmaceutically acceptable salt thereof and the GLP-1R agonist is compound 1-2

(1-2)

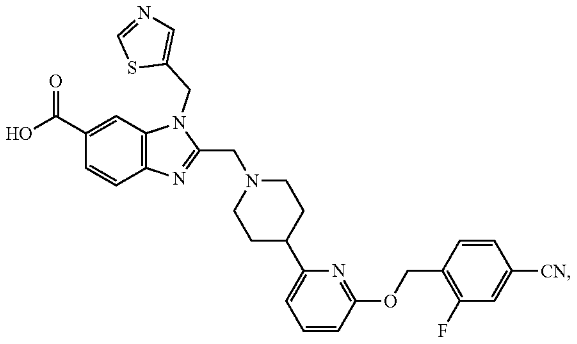

or a pharmaceutically acceptable salt thereof.

81. The combinational therapy of any one of the preceding embodiments, wherein the THRβ agonist is compound 9

(9)

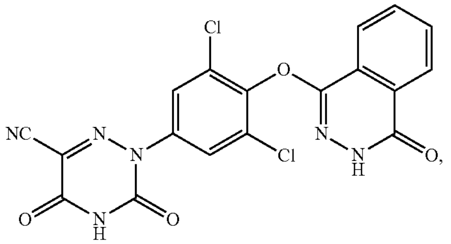

or a pharmaceutically acceptable salt thereof, and the GLP-1R agonist is compound 1-2

(1-2)

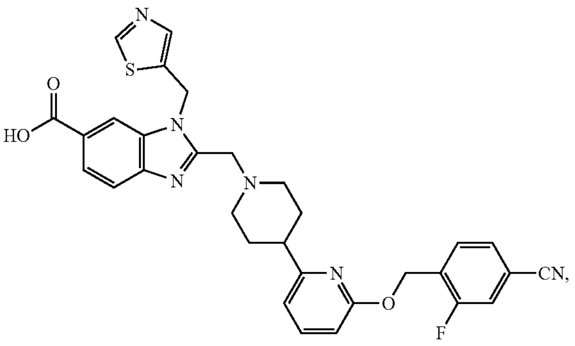

or a pharmaceutically acceptable salt thereof.

82. The combinational therapy of any one of the preceding embodiments, wherein the patient has a body mass index (BMI) of 25 $kg/m^2$ to 30 $kg/m^2$.

83. The combinational therapy of any one of the preceding embodiments, wherein the patient has a BMI of 30 $kg/m^2$ or greater.

84. The combinational therapy of any one of the preceding embodiments, wherein the GLP-1R agonist element of the combinational therapy is administered to the subject more than once.

85. The combinational therapy of any one the preceding embodiments, wherein the THRβ agonist element of the combinational therapy is administered to the subject more than once.

86. The combinational therapy of any one of the preceding embodiments, wherein both the GLP-1R agonist and THR-β agonist elements of the combination therapy are administered to the subject more than once.

87. The combinational therapy of any one of the preceding embodiments, wherein the THRβ agonist is administered prior to or concurrent with the GLP-1R agonist.

88. The combinational therapy of any one of the preceding embodiments, wherein the THRβ agonist is administered in temporal proximity to the GLP-1R agonist.

89. The combinational therapy of any one of the preceding embodiments, wherein the THRβ agonist is administered on the same day as the GLP-1R agonist.

90. The combinational therapy of any one of the preceding embodiments, wherein the THRβ agonist is administered at substantially the same time as the GLP-1R agonist.

91. The combinational therapy of any one of the preceding embodiments, wherein the initial dose of THRβ agonist is administered in temporal proximity to the GLP-1R agonist.

92. The combinational therapy of any one of the preceding embodiments, wherein the initial dose of THRβ agonist is administered on the same day as the GLP-1R agonist.

93. The combinational therapy of any one of the preceding embodiments, wherein the initial dose of THR agonist is at substantially the same time as the GLP-1R agonist.

94. The combinational therapy of any one of the preceding embodiments, wherein the initial dose of THRβ agonist is administered prior to the initial dose of GLP-1R agonist.

95. The combinational therapy of any one of the preceding embodiments, wherein a subsequent dose of THRβ agonist is administered in temporal proximity to the GLP-1R agonist.

96. The combinational therapy of any one of the preceding embodiments, wherein a subsequent dose of THRβ agonist is administered on the same day as the GLP-1R agonist.

97. The combinational therapy of any one of the preceding embodiments, wherein a subsequent dose of THRβ agonist is administered at substantially the same time as the GLP-1R agonist.

98. A THR-β agonist, or a pharmaceutically acceptable salt thereof, and a GLP-1R agonist, or a pharmaceutically acceptable salt thereof, for use in a combinational therapy for the treatment of obesity in a patient in need thereof.

99. The THR-β agonist, or pharmaceutically acceptable salt thereof, and GLP-1R agonist, or pharmaceutically acceptable salt thereof, for use according to embodiment 98, wherein the THRβ agonist is a compound of Formula (II-1)

(II-1)

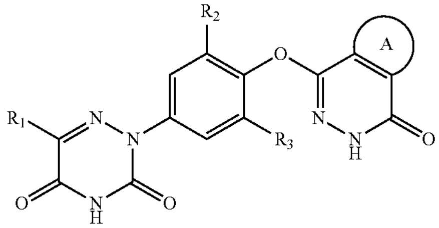

wherein:

$R_1$ is selected from the group consisting of hydrogen, cyano, substituted or unsubstituted $C_{1-6}$ alkyl, and substituted or unsubstituted $C_{3-6}$ cycloalkyl, the substituent being selected from the group consisting of halogen atoms, hydroxy, and $C_{1-6}$ alkoxy;

$R_2$ and $R_3$ are each independently selected from the group consisting of halogen atoms and substituted or unsubstituted $C_{1-6}$ alkyl, the substituent being selected from the group consisting of halogen atoms, hydroxy, and $C_{1-6}$ alkoxy;

ring A is a substituted or unsubstituted saturated or unsaturated $C_{5-10}$ aliphatic ring, or a substituted or unsubstituted $C_{5-10}$ aromatic ring, the substituent being one or more substances selected from the group consisting of hydrogen, halogen atoms, hydroxy, —$OCF_3$, —$NH_2$, —$NHC_{1-4}$ alkyl, —$N(C_{1-4}$ alkyl$)_2$, —$CONH_2$, —$CONHC_{1-4}$ alkyl, —$CON(C_{1-4}$ alkyl$)_2$, —$NHCOC_{1-4}$ alkyl, $C_{1-6}$ alkyl, $C_{1-6}$ alkoxy or $C_{3-6}$ cycloalkyl, and when two substituents are contained, the two substituents can form a ring structure together with the carbon connected thereto; and the halogen atoms are selected from the group consisting of F, Cl and Br, or a pharmaceutically acceptable salt thereof.

100. The THR-β agonist, or pharmaceutically acceptable salt thereof, and GLP-1R agonist, or pharmaceutically acceptable salt thereof, for use according to embodiment 98 or 99, wherein the THRβ agonist is a compound of Formula (II-1a)

(II-1a)

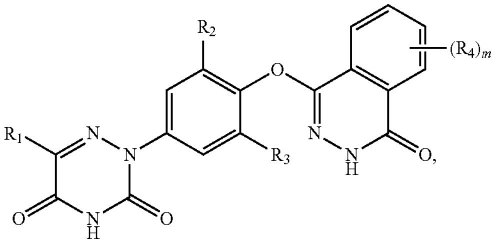

wherein:

$R_1$ to $R_3$ are defined as detailed herein for Formula (II-1);

$R_4$ is selected from the group consisting of hydrogen, halogen atoms, hydroxy, —$OCF_3$, —$NH_2$, —$NHC_{1-4}$ alkyl, —$N(C_{1-4}$ alkyl$)_2$, —$CONH_2$, —$CONHC_{1-4}$ alkyl, —$CON(C_{1-4}$ alkyl$)_2$, —$NHCOC_{1-4}$ alkyl, $C_{1-6}$ alkyl, $C_{1-6}$ alkoxy and $C_{3-6}$ cycloalkyl;

m is an integer from the range 1 to 4; and the halogen atoms are selected from the group consisting of F, Cl and Br.

or a pharmaceutically acceptable salt thereof.

101. The THR-β agonist, or pharmaceutically acceptable salt thereof, and GLP-1R agonist, or pharmaceutically acceptable salt thereof, for use according to any one of the preceding embodiments, wherein the THRβ agonist is compound 9

(9)

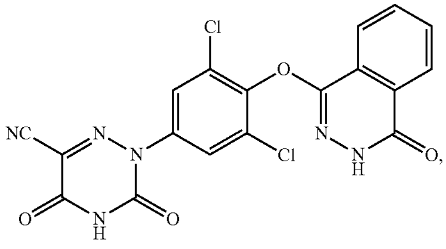

and the GLP-1R agonist is orforglipron, danuglipron, liraglutide, exenatide, dulaglutide, albiglutide, lixisenatide, tirzepatide, or semaglutide, or a pharmaceutically acceptable salt thereof.

101a. The THR-β agonist, or pharmaceutically acceptable salt thereof, and GLP-1R agonist, or pharmaceutically acceptable salt thereof, for use according to any one of the preceding embodiments, wherein the THRβ agonist is compound 9

(9)

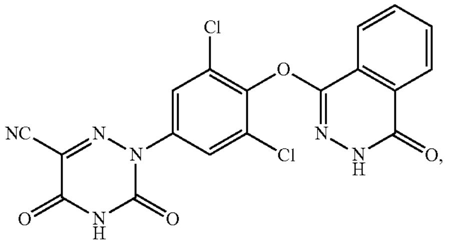

and the GLP-1R agonist is orforglipron or a pharmaceutically acceptable salt thereof.

101b. The THR-β agonist, or pharmaceutically acceptable salt thereof, and GLP-1R agonist, or pharmaceutically acceptable salt thereof, for use according to any one of the preceding embodiments, wherein the THRp agonist is compound 9

(9)

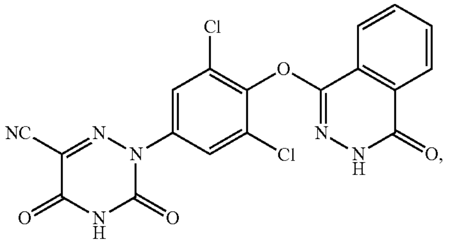

and the GLP-1R agonist is semaglutide or a pharmaceutically acceptable salt thereof.

101c. The THR-β agonist, or pharmaceutically acceptable salt thereof, and GLP-1R agonist, or pharmaceutically acceptable salt thereof, for use according to any one of the preceding embodiments, wherein the THRβ agonist is compound 9

(9)

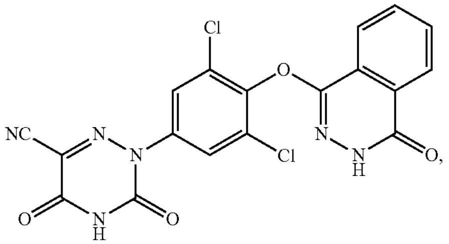

and the GLP-1R agonist is danuglipron or a pharmaceutically acceptable salt thereof.

102. The THR-β agonist, or pharmaceutically acceptable salt thereof, and GLP-1R agonist, or pharmaceutically acceptable salt thereof, for use according to any one of the preceding embodiments, wherein the THR agonist is a potassium salt of Compound 9.

103. The THR-β agonist, or pharmaceutically acceptable salt thereof, and GLP-1R agonist, or pharmaceutically acceptable salt thereof, for use according to any one of the preceding embodiments, wherein the GLP-1R agonist is a compound of Formula (I-1):

(I-1)

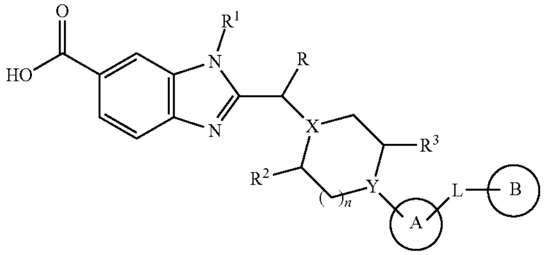

or a pharmaceutically acceptable salt thereof, wherein:

X is N or CH;

Y is N or $CR^4$;

n is 0 or 1;

R is hydrogen;

$R^1$ is —$C_1$-$C_6$ alkylene-$R^5$;

$R^2$ is hydrogen, oxo, or $C_1$-$C_6$ alkyl;

$R^3$ is hydrogen, oxo, or $C_1$-$C_6$ alkyl and $R^4$ is hydrogen, OH, or $C_1$-$C_6$ alkyl;

or $R^3$ and $R^4$ are taken together with the carbon atoms to which they are attached to form $C_3$-$C_6$ cycloalkyl optionally substituted by halo or $C_1$-$C_3$ alkyl;

$R^5$ is 5-membered heterocyclyl or 5-membered heteroaryl, each of which comprises 1, 2, or 3 heteroatoms independently selected from O, N, and S, wherein at least one heteroatom of $R^5$ is S, and further wherein $R^5$ is optionally substituted by halo, —O—$C_{1-6}$ alkyl, $C_{1-6}$ alkyl, $C_{1-6}$ alkenyl, or $C_1$-$C_6$ haloalkyl;

Ring A is 5- to 12-membered heterocyclene or 5- to 12-membered heteroarylene, each of which is independently optionally substituted by halo, CN, $C_3$-$C_6$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein

* represents the point of attachment to ring A and ** represents the point of attachment to ring B;

when L is *—O—$C_1$-$C_6$ alkylene-**, the $C_1$-$C_6$ alkylene of L is optionally substituted by $R^L$, wherein each $R^L$ is independently $C_1$-$C_6$ alkyl or halo, or two $R^{L1}$ are taken together with the carbon atom or atoms to which they are attached to form $C_3$-$C_6$ cycloalkyl or 3- to 6-membered heterocyclyl; and when L is $C_1$-$C_6$ alkylene, the $C_1$-$C_6$ alkylene is optionally substituted by $R^{L1}$, wherein each $R^{L1}$ is independently halo, OH, oxo, or $C_1$-$C_6$ alkyl, or two $R^{L1}$ are taken together with the carbon atom or atoms to which they are attached to form $C_3$-$C_6$ cycloalkyl or 3- to 6-membered heterocyclyl;

$R^6$ is hydrogen or $C_1$-$C_6$ alkyl; and

Ring B is $C_3$-$C_{10}$ cycloalkyl, $C_6$-$C_1$4 aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

104. The THR-β agonist, or pharmaceutically acceptable salt thereof, and GLP-AR agonist, or pharmaceutically acceptable salt thereof, for use according to any one of the preceding embodiments, wherein the GLP-AR agonist is a compound of Formula (I-1a):

(I-1a)

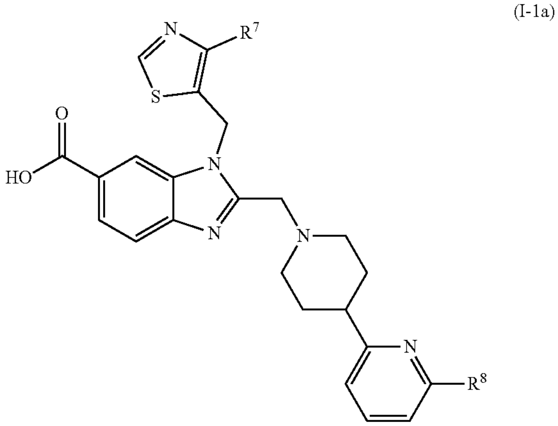

wherein $R^7$ is hydrogen, chloro, bromo, fluoro, methyl, or vinyl; and $R^8$ is

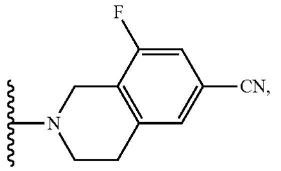 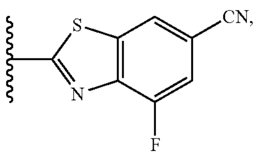

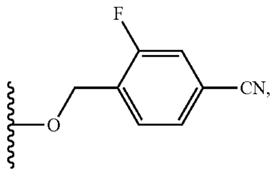 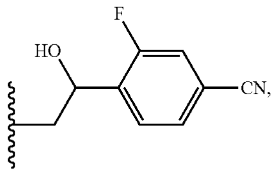

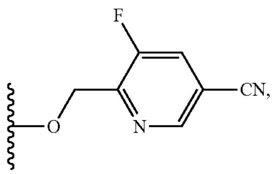 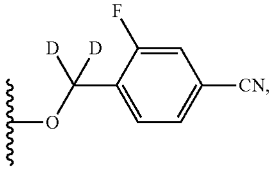 or

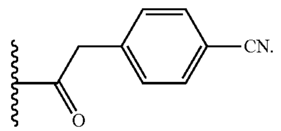

105. The THR-β agonist, or pharmaceutically acceptable salt thereof, and GLP-1R agonist, or pharmaceutically acceptable salt thereof, for use according to any one of the preceding embodiments, wherein the GLP-1R agonist is a compound of Formula (I**):

(I**)

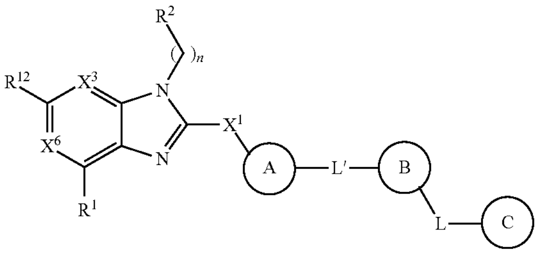

or a pharmaceutically acceptable salt thereof; wherein:

$X^3$ is $CR^6$ or N;

$X^6$ is $CR^4$ or N;

$R^1$ is —$C_{1-6}$ haloalkyl, halogen, —O—$X^4$, or —$NR^8R^9$, or $R^1$ and $R^4$, together with the atoms to which they are attached, combine to form a 5- or 6-membered heterocyclyl;

$X^4$ is hydrogen, $C_{1-6}$ alkyl, $C_{1-6}$ heteroalkyl, $C_{1-4}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}—CH_3$, —$(CH_2—CH(—OCH_3)—CH_2—O)_{1-5}—CR^1$, $C_{3-10}$ cycloalkyl, or $C_{6-10}$ aryl, wherein the alkyl, heteroalkyl, alkylene, or haloalkyl group is optionally substituted with one or more deuterium, $C_{1-6}$ alkoxy, hydroxyl, —CN, or oxo, and the cycloalkyl, heterocyclyl, or aryl group is optionally substituted with one or more halogen, $C_{1-6}$ alkoxy, or —CN;

$R^6$ is hydrogen, halogen, or —O—$R^7$;

wherein $R^7$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocycyl; wherein the $C_{1-6}$ alkyl is optionally substituted by one or more oxo;

n is 0, 1, 2, 3, 4, 5, or 6;

$R^2$ is:

hydrogen;

$C_{1-6}$ alkyl optionally substituted with deuterium;

$C_{1-6}$ haloalkyl;

—(O)—$C_{1-6}$ alkyl;

—CN;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

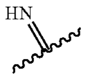, or $C_{1-6}$ alkyl;

a 5-membered heteroaryl, comprising 1 or 2 heteroatoms independently selected from N, and S, wherein at least one heteroatom of $R^5$ is S; or $R^2$ and $R^7$, together with the atoms to which they are attached, combine to form a 5- or 6-membered heterocyclyl;

$R^4$ is halogen, hydrogen, —C(O)OH, or —O—$R^8$, wherein $R^8$ and $R^1$, together with the atoms to which they are attached, combine to form a 6-membered heterocyclyl;

$R^{12}$ is hydrogen, —C(O)OH, —C(O)$NR^{N12}R^{N12'}$, —C(O)$NR^{12}S(O)_2R^{12}$, —($C_{2-6}$ alkynylene)-C(O)OH, —($C_{1-6}$ alkylene)-C(O)OH, —$NR^{N12}$—($C_{1-6}$ alkylene)-C(O)OH, 5-10 membered heteroaryl or 5- to 10-membered heterocyclyl optionally substituted with one or more oxo, $C_{1-6}$ alkyl or $C_{1-6}$ haloalkyl;

$R^{N12}$ and $R^{N12'}$ independently are H or $C_{1-6}$ alkyl;

$X^1$ is

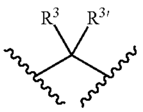
or
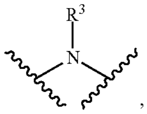
, wherein $R^3$ and $R^{3'}$ independently are H, D or $C_{1-6}$ alkyl, wherein the $C_{1-6}$ alkyl is optionally substituted with detuerium;

Ring A is

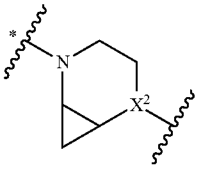
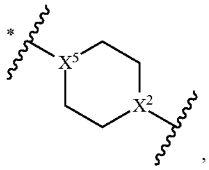
,
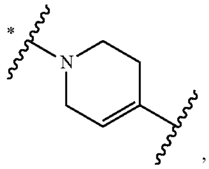
, phenylene optionally substituted with one or more halo or $C_{1-6}$ alkyl, or 6-membered heteroarylene optionally substituted with one or more halo or $C_{1-6}$ alkyl;

wherein * indicates attachment to $X^1$, $X^5$ is $CR^3$ or N, and $X^2$ is $CR^3$ or N;

L' is a bond or —O—;

Ring B is a $C_6$—.o arylene, a 5-10 membered heteroarylene, or a 3-10 membered heterocycylene, wherein the $C_{6-10}$ arylene, 5-10 membered heteroarylene, or 3-10 membered heterocyclene is optionally substituted with one or more oxo, $C_{1-6}$ alkyl, $C_{1-6}$ alkoxy, or halogen;

L is a bond, *—($C_{1-6}$ alkylene)-, *—$NR^L$—($C_{1-6}$ alkylene)-, *—O—($C_{1-6}$ alkylene)-, or *—($C_{1-6}$ alkylene)-O—, wherein * indicates attachment to Ring B and the $C_{1-6}$ alkylene is optionally substituted with deuterium;

wherein $R^L$ is H or $C_{1-6}$ alkyl; and

Ring C is:

a 6-membered aryl optionally substituted with one or more $C_{3-10}$ cycloalkyl, $C_{1-6}$ alkyl, $C_{1-6}$ haloalkyl, 3-10 membered heterocyclyl, halogen, $C_{1-6}$ alkoxy, $C_{1-6}$ haloalkoxy, —CN, $C_{3-10}$ cycloalkyl, or —C(O)$NR^{2'}$; wherein R' is H or $C_{1-6}$ alkyl a 6-membered heteroaryl comprising a nitrogen atom optionally substituted with one or more halogen, —CN, $C_{1-6}$ haloalkyl, —O—$C_{1-6}$ alkyl, $C_{3-10}$ cycloalkyl, —C(═O)—($C_{3-10}$ cycloalkyl),

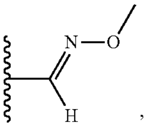
,
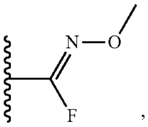
, or
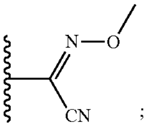
;

a bicylic 9- or 10-membered heteroaryl or heterocyclyl optionally substituted with one or more $C_{1-6}$ alkyl, halogen, —CN, or oxo.

106. The THR-β agonist, or pharmaceutically acceptable salt thereof, and GLP-1R agonist, or pharmaceutically acceptable salt thereof, for use according to any one of the preceding embodiments, wherein the GLP-1R agonist is a compound of Formula (I-5)

(I-5)

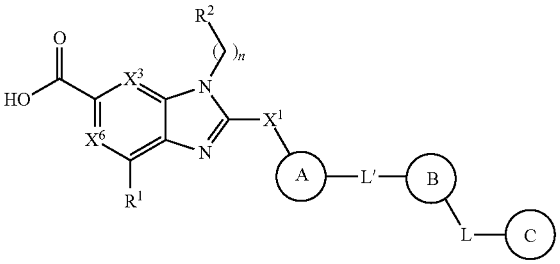

or a pharmaceutically acceptable salt thereof; wherein:

$X^3$ is $CR^6$ or N;

$X^6$ is $CR^4$ or N;

$R^1$ is —$C_{1-6}$ haloalkyl, —O—$X^4$, or —$NR^R$?, or $R^1$ and $R^4$, together with the atoms to which they are attached, combine to form a 6-membered heterocyclyl;

$X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_1$-5-$CH_3$, or —$(CH_2—CH(—OCH_3)—CH_2—O)_{1-5}—CH_3$, wherein the alkyl, heteroalkyl, alkylene, or haloalkyl group is optionally substituted with one or more deuterium, hydroxyl, —CN, or oxo, and the cycloalkyl or heterocyclyl group is optionally substituted with one or more halogen or —CN;

$R^6$ is hydrogen, halogen, or —O—$R^7$;

wherein $R^7$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocyclyl; wherein the $C_{1-6}$ alkyl is optionally substituted by one or more oxo;

n is 0, 1, 2, 3, 4, 5, or 6;

$R^2$ is:

hydrogen;

branched $C_{1-6}$ alkyl;

$C_{1-6}$ haloalkyl;

—(O)—$C_{1-6}$ alkyl;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

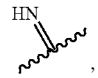

, or $C_{1-6}$ alkyl;

a 5-membered heteroaryl, comprising 1 or 2 heteroatoms independently selected from N, and S, wherein at least one heteroatom of $R^5$ is S; or $R^2$ and $R^7$, together with the atoms to which they are attached, combine to form a 5- or 6-membered heterocyclyl;

$R^4$ is hydrogen or —O—$R^8$, wherein $R^8$ and $R^1$, together with the atoms to which they are attached, combine to form a 6-membered heterocyclyl;

$X^1$ is

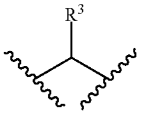 or 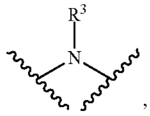, wherein $R^3$ is H or $C_{1-6}$ alkyl;

Ring A is

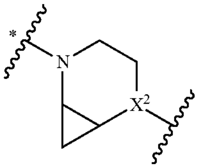

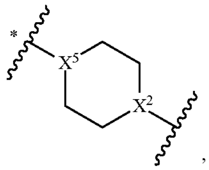,

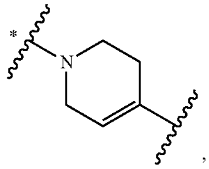, phenylene optionally substituted with one or more halo or $C_{1-6}$ alkyl, or 6-membered heteroarylene optionally substituted with one or more halo or $C_{1-6}$ alkyl;

wherein * indicates attachment to $X^1$, $X^5$ is $CR^3$ or N, and $X^2$ is $CR^3$ or N;

L' is a bond or —O—;

Ring B is a $C_{6-10}$ arylene, a 6-10 membered heteroarylene, or a 3-10 membered heterocyclene, wherein the $C_{6-10}$ arylene, 6-10 heteroarylene, or 3-10 membered heterocyclene is optionally substituted with one or more $C_{1-6}$ alkyl, $C_{1-6}$ alkoxy, or halogen;

L is a bond, *—$CH_2$—, *—O—($C_{1-6}$ alkylene)-, or *-($C_{1-6}$ alkylene)-O—, wherein * indicates attachment to Ring B and the $C_{1-6}$ alkylene is optionally substituted with deuterium; and Ring C is:

a 6-membered aryl optionally substituted with one or more $C_{1-6}$ alkyl, 3-10 membered heterocyclyl, halogen, —$OCH_3$, —CN, or $C_{3-10}$ cycloalkyl;

a 6-membered heteroaryl comprising a nitrogen atom optionally substituted with one or more halogen, —CN, —O—$C_{1-6}$ alkyl, $C_{3-10}$ cycloalkyl, —C(═O)—($C_{3-10}$ cycloalkyl),

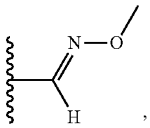, 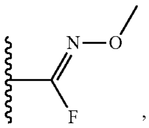, or 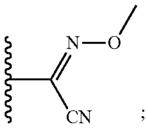;

a bicyclic 9- or 10-membered heteroaryl comprising two nitrogen atoms optionally substituted with one or more $C_{1-6}$ alkyl, or oxo.

107. The THR-β agonist, or pharmaceutically acceptable salt thereof, and GLP-1R agonist, or pharmaceutically acceptable salt thereof, for use according to any one of the preceding embodiments, wherein the GLP-1R agonist is a compound of Formula (II**):

(II**)

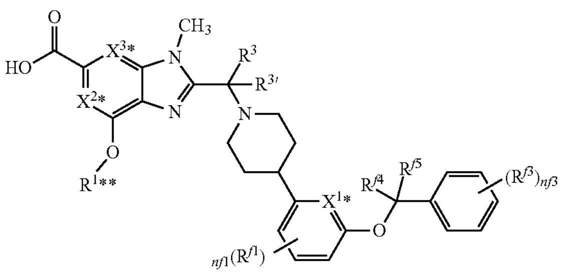

or a pharmaceutically acceptable salt thereof; wherein $R^{f4}$ and $R^{f5}$ are each independently selected from $C_{1-6}$ alkyl, H and D nf1 is 0, 1, 2, 3, or 4;

nf3 is 0, 1, 2, 3, 4, or 5;

each $R^{f1}$ is halogen;

$R^3$ and $R^{3'}$ independently are H or D;

$X^1$* is N or $CR^{f1}$;

$X^2$* and $X^3$* independently are CH or CF;

each $R^{f3}$ is independently selected from halogen, —CN, $C_{1-6}$ alkyl, $C_{1-6}$ haloalkyl, $C_{1-6}$ alkoxy, or —C(O)N$(R^{3f'})_2$, each $R^{f3'}$ is indepdendently selected from H or $C_{1-6}$ alkyl; and $R^{1**}$ is H or $C_{1-2}$ alkyl optionally substituted with one or more deuterium or halogen.

108. The THR-β agonist, or pharmaceutically acceptable salt thereof, and GLP-1R agonist, or pharmaceutically acceptable salt thereof, for use according to any one of the preceding embodiments, wherein the GLP-1R agonist is Compound 1-2:

(1-2)

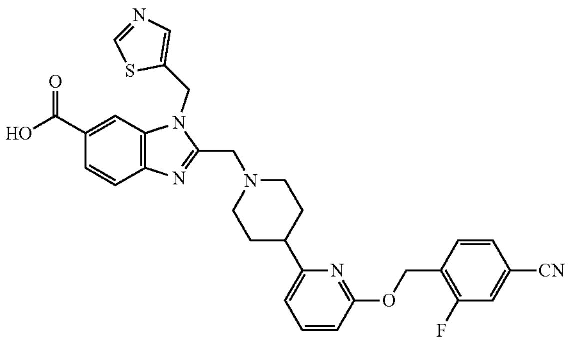

or a pharmaceutically acceptable salt thereof.

109. The THR-β agonist, or pharmaceutically acceptable salt thereof, and GLP-1R agonist, or pharmaceutically acceptable salt thereof, for use according to any one of the preceding embodiments, wherein the GLP-1R agonist is a meglumine salt of Compound 1-2.

110. The THR-β agonist, or pharmaceutically acceptable salt thereof, and GLP-1R agonist, or pharmaceutically acceptable salt thereof, for use according to any one of the preceding embodiments, wherein the THRβ agonist is selected from those listed in Tables 6-11.

111. The THR-β agonist, or pharmaceutically acceptable salt thereof, and GLP-1R agonist, or pharmaceutically acceptable salt thereof, for use according to any one of the preceding embodiments, wherein the GLP-1R agonist is selected from those listed in Tables 1-5.

112. The THR-β agonist, or pharmaceutically acceptable salt thereof, and GLP-1R agonist, or pharmaceutically acceptable salt thereof, for use according to any one of the preceding embodiments, wherein the GLP-1R agonist is selected from those listed in Table 5A.

113. The THR-β agonist, or pharmaceutically acceptable salt thereof, and GLP-1R agonist, or pharmaceutically acceptable salt thereof, for use according to any one of the preceding embodiments, wherein the THRβ agonist is Compound 9

(9)

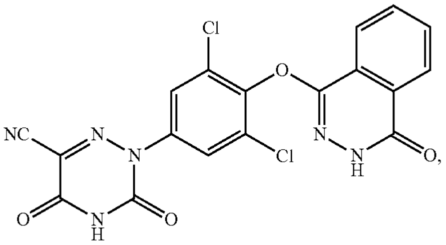

and the GLP-1R agonist is orforglipron, danuglipron, liraglutide, exenatide, dulaglutide, albiglutide, lixisenatide, tirzepatide, or semaglutide, or a pharmaceutically acceptable salt thereof.

113a. The THR-β agonist, or pharmaceutically acceptable salt thereof, and GLP-1R agonist, or pharmaceutically acceptable salt thereof, for use according to any one of the preceding embodiments, wherein the THRβ agonist is compound 9

(9)

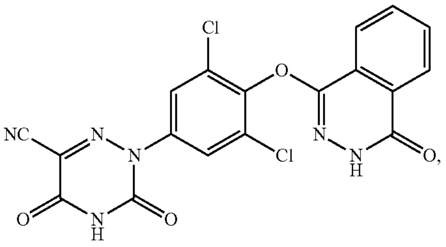

and the GLP-1R agonist is orforglipron or a pharmaceutically acceptable salt thereof.

113b. The THR-β agonist, or pharmaceutically acceptable salt thereof, and GLP-1R agonist, or pharmaceutically acceptable salt thereof, for use according to any one of the preceding embodiments, wherein the THRβ agonist is compound 9

(9)

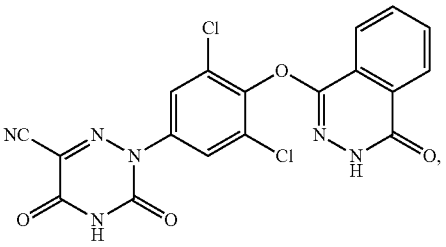

and the GLP-1R agonist is semaglutide or a pharmaceutically acceptable salt thereof.

113c. The THR-β agonist, or pharmaceutically acceptable salt thereof, and GLP-AR agonist, or pharmaceutically acceptable salt thereof, for use according to any one of the preceding embodiments, wherein the THRβ agonist is compound 9

(9)

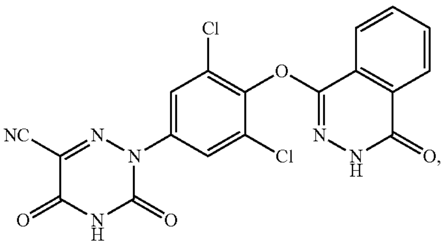

and the GLP-AR agonist is danuglipron or a pharmaceutically acceptable salt thereof.

114. The THR-β agonist, or pharmaceutically acceptable salt thereof, and GLP-AR agonist, or pharmaceutically acceptable salt thereof, for use according to any one of the preceding embodiments, wherein the THRβ agonist is resmetirom, VK2809, sobetirome, eprotirome, ALG-055009, CNPT-101101, CNPT-101207, ASC41 or a pharmaceutically acceptable salt thereof and the GLP-AR agonist is Compound 1-2

(1-2)

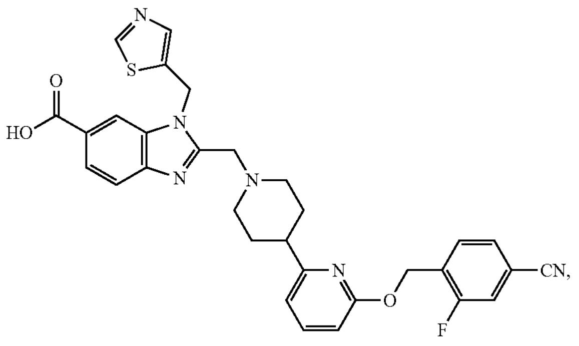

or a pharmaceutically acceptable salt thereof.

115. The THR-β agonist, or pharmaceutically acceptable salt thereof, and GLP-AR agonist, or pharmaceutically acceptable salt thereof, for use according to any one of the preceding embodiments, wherein the THRβ agonist is compound 9

(9)

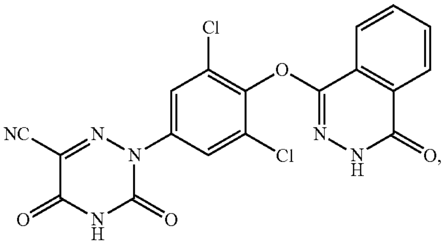

or a pharmaceutically acceptable salt thereof, and the GLP-AR agonist is Compound 1-2

(1-2)

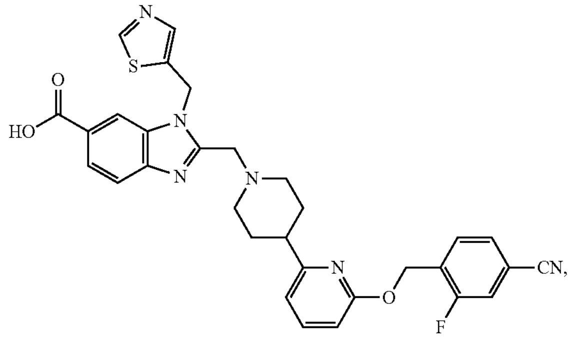

or a pharmaceutically acceptable salt thereof.

116. The THR-β agonist, or pharmaceutically acceptable salt thereof, and GLP-1R agonist, or pharmaceutically acceptable salt thereof, for use according to any one of the preceding embodiments, wherein the patient has a body mass index (BMI) of 25 kg/$m^2$ to 30 kg/$m^2$.

117a. The THR-β agonist, or pharmaceutically acceptable salt thereof, and GLP-1R agonist, or pharmaceutically acceptable salt thereof, for use according to any one of the preceding embodiments, wherein the patient has a BMI of 27 kg/$m^2$ or greater.

117b. The THR-β agonist, or pharmaceutically acceptable salt thereof, and GLP-1R agonist, or pharmaceutically acceptable salt thereof, for use according to any one of the preceding embodiments, wherein the patient has a BMI of 30 kg/$m^2$ or greater.

118. The THR-β agonist, or pharmaceutically acceptable salt thereof, and GLP-1R agonist, or pharmaceutically acceptable salt thereof, for use according to any one of the preceding embodiments, wherein the GLP-1R agonist is administered to the subject more than once.

119. The THR-β agonist, or pharmaceutically acceptable salt thereof, and GLP-1R agonist, or pharmaceutically acceptable salt thereof, for use according to any one the preceding embodiments, wherein the THRβ agonist is administered to the subject more than once.

120. The THR-β agonist, or pharmaceutically acceptable salt thereof, and GLP-1R agonist, or pharmaceutically acceptable salt thereof, for use according to any one of the preceding embodiments, wherein both the GLP-1R agonist and THR-β agonist are administered to the subject more than once.

121. The THR-β agonist, or pharmaceutically acceptable salt thereof, and GLP-1R agonist, or pharmaceutically acceptable salt thereof, for use according to any one of the preceding embodiments, wherein the THRβ agonist is administered prior to or concurrent with the GLP-1R agonist.

122. The THR-β agonist, or pharmaceutically acceptable salt thereof, and GLP-1R agonist, or pharmaceutically acceptable salt thereof, for use according to any one of the preceding embodiments, wherein the THRβ agonist is administered in temporal proximity to the GLP-1R agonist.

123. The THR-β agonist, or pharmaceutically acceptable salt thereof, and GLP-1R agonist, or pharmaceutically acceptable salt thereof, for use according to any one of the preceding embodiments, wherein the THRβ agonist is administered on the same day as the GLP-1R agonist.

124. The THR-β agonist, or pharmaceutically acceptable salt thereof, and GLP-1R agonist, or pharmaceutically acceptable salt thereof, for use according to any one of the preceding embodiments, wherein the THRβ agonist is administered at substantially the same time as the GLP-1R agonist.

125. The THR-β agonist, or pharmaceutically acceptable salt thereof, and GLP-1R agonist, or pharmaceutically acceptable salt thereof, for use according to any one of the preceding embodiments, wherein the initial dose of THRβ agonist is administered in temporal proximity to the GLP-1R agonist.

126. The THR-β agonist, or pharmaceutically acceptable salt thereof, and GLP-1R agonist, or pharmaceutically acceptable salt thereof, for use according to any one of the preceding embodiments, wherein the initial dose of THRβ agonist is administered on the same day as the GLP-1R agonist.

127. The THR-β agonist, or pharmaceutically acceptable salt thereof, and GLP-AR agonist, or pharmaceutically acceptable salt thereof, for use according to any one of the preceding embodiments, wherein the initial dose of THRβ agonist is at substantially the same time as the GLP-AR agonist.

128. The THR-β agonist, or pharmaceutically acceptable salt thereof, and GLP-AR agonist, or pharmaceutically acceptable salt thereof, for use according to any one of the preceding embodiments, wherein the initial dose of THRβ agonist is administered prior to the initial dose of GLP-1R agonist.

129. The THR-β agonist, or pharmaceutically acceptable salt thereof, and GLP-1R agonist, or pharmaceutically acceptable salt thereof, for use according to any one of the preceding embodiments, wherein a subsequent dose of THRβ agonist is administered in temporal proximity to the GLP-1R agonist.

130. The THR-β agonist, or pharmaceutically acceptable salt thereof, and GLP-AR agonist, or pharmaceutically acceptable salt thereof, for use according to any one of the preceding embodiments, wherein a subsequent dose of THRβ agonist is administered on the same day as the GLP-AR agonist.

131. The THR-β agonist, or pharmaceutically acceptable salt thereof, and GLP-1R agonist, or pharmaceutically acceptable salt thereof, for use according to any one of the preceding embodiments, wherein a subsequent dose of THRβ agonist is administered at substantially the same time as the GLP-AR agonist.

132. A method of treating obesity in a patient in need thereof, the method comprising administering a THRβ agonist, or a pharmaceutically acceptable salt thereof, and a GLP-1R agonist, or a pharmaceutically acceptable salt thereof, to the patient.

133. The method of embodiment 132, wherein the THRβ agonist is a compound of Formula (II-1)

(II-1)

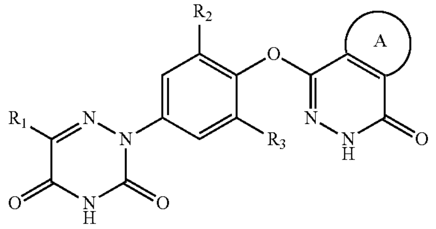

wherein:

$R_1$ is selected from the group consisting of hydrogen, cyano, substituted or unsubstituted $C_{1-6}$ alkyl, and substituted or unsubstituted $C_{3-6}$ cycloalkyl, the substituent being selected from the group consisting of halogen atoms, hydroxy, and $C_{1-6}$ alkoxy;

$R_2$ and $R_3$ are each independently selected from the group consisting of halogen atoms and substituted or unsubstituted $C_{1-6}$ alkyl, the substituent being selected from the group consisting of halogen atoms, hydroxy, and $C_{1-6}$ alkoxy; ring A is a substituted or unsubstituted saturated or unsaturated $C_{5-10}$ aliphatic ring, or a substituted or unsubstituted $C_{5-10}$ aromatic ring, the substituent being one or more substances selected from the group consisting of hydrogen, halogen atoms, hydroxy, —$OCF_3$, —$NH_2$, —$NHC_{1-6}$ alkyl, —$N(C_{1-4}$ alkyl$)_2$, —$CONH_2$, —$CONHC_{1-4}$ alkyl, —$CON(C_{1-4}$ alkyl$)_2$, —$NHCOC_{1-4}$ alkyl, $C_{1-6}$ alkyl, $C_{1-6}$ alkoxy or $C_{3-6}$ cycloalkyl, and when two substituents are contained, the two substituents can form a ring structure together with the carbon connected thereto; and the halogen atoms are selected from the group consisting of F, Cl and Br, or a pharmaceutically acceptable salt thereof.

134. The method of embodiment 132 or 133, wherein the THRβ agonist is a compound of Formula (II-1a)

(II-1a)

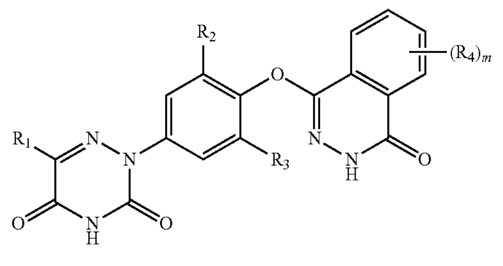

wherein:

$R_1$ to $R_3$ are defined as detailed herein for Formula (II-1);

$R_4$ is selected from the group consisting of hydrogen, halogen atoms, hydroxy, —$OCF_3$, —$NH_2$, —$NHC_{1-4}$ alkyl, —$N(C_{1-4}$ alkyl$)_2$, —$CONH_2$, —$CONHC_{1-4}$ alkyl, —$CON(C_{1-4}$ alkyl$)_2$, —$NHCOC_{1-4}$ alkyl, $C_{1-6}$ alkyl, $C_{1-6}$ alkoxy and $C_{3-6}$ cycloalkyl;

m is an integer from the range 1 to 4; and the halogen atoms are selected from the group consisting of F, Cl and Br.

or a pharmaceutically acceptable salt thereof.

135. The method of any one of the preceding embodiments, wherein the THRβ agonist is compound 9

(9)

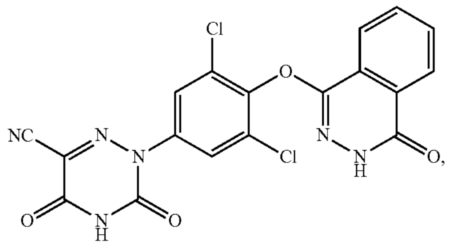

and the GLP-1R agonist is orforglipron, danuglipron, liraglutide, exenatide, dulaglutide, albiglutide, lixisenatide, tirzepatide, or semaglutide, or a pharmaceutically acceptable salt thereof.

135a. The method of any one of the preceding embodiments, wherein the THRp agonist is compound 9

(9)

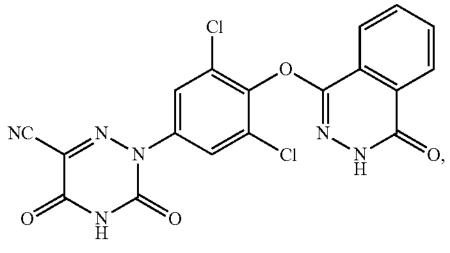

and the GLP-1R agonist is orforglipron or a pharmaceutically acceptable salt thereof 135b. The method of any one of the preceding embodiments, wherein the THRβ agonist is compound 9

(9)

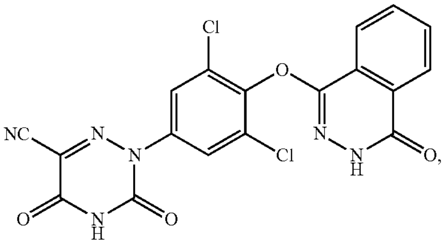

and the GLP-1R agonist is semaglutide or a pharmaceutically acceptable salt thereof.

135c. The method of any one of the preceding embodiments, wherein the THRβ agonist is compound 9

(9)

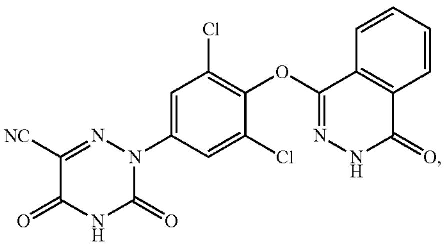

and the GLP-1R agonist is danuglipron or a pharmaceutically acceptable salt thereof.

136. The method of any one of the preceding embodiments, wherein the THRβ agonist is a potassium salt of Compound 9.

137. The method of any one of the preceding embodiments, wherein the GLP-1R agonist is a compound of Formula (I-1):

(I-1)

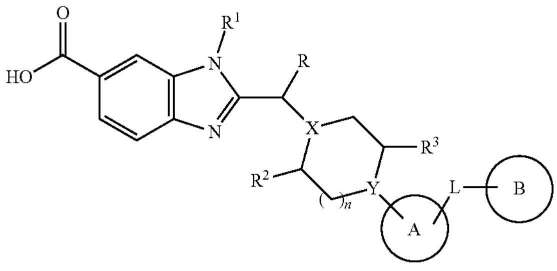

or a pharmaceutically acceptable salt thereof, wherein:

X is N or CH;

Y is N or $CR^4$;

n is 0 or 1;

R is hydrogen;

$R^1$ is —$C_1$-$C_6$ alkylene-$R^5$;

$R^2$ is hydrogen, oxo, or $C_1$-$C_6$ alkyl;

$R^3$ is hydrogen, oxo, or $C_1$-$C_6$ alkyl and $R^4$ is hydrogen, OH, or $C_1$-$C_6$ alkyl;

or $R^3$ and $R^4$ are taken together with the carbon atoms to which they are attached to form $C_3$-$C_6$ cycloalkyl optionally substituted by halo or $C_1$-$C_3$ alkyl;

$R^5$ is 5-membered heterocyclyl or 5-membered heteroaryl, each of which comprises 1, 2, or 3 heteroatoms independently selected from O, N, and S, wherein at least one heteroatom of $R^5$ is S, and further wherein $R^5$ is optionally substituted by halo, —O—$C_{1-6}$ alkyl, $C_{1-6}$ alkyl, $C_{1-6}$ alkenyl, or $C_1$-$C_6$ haloalkyl;

Ring A is 5- to 12-membered heterocyclene or 5- to 12-membered heteroarylene, each of which is independently optionally substituted by halo, CN, $C_3$-$C_6$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *—$C_1$-$C_6$ alkylene-O—**, or *—$NR^6$—$C_1$-$C_6$ alkylene-**, wherein

* represents the point of attachment to ring A and ** represents the point of attachment to ring B;

when L is *—O—$C_1$-$C_6$ alkylene-**, the $C_1$-$C_6$ alkylene of L is optionally substituted by $R^L$, wherein each $R^L$ is independently $C_1$-$C_6$ alkyl or halo, or two $R^{L1}$ are taken together with the carbon atom or atoms to which they are attached to form $C_3$-$C_6$ cycloalkyl or 3- to 6-membered heterocyclyl; and when L is $C_1$-$C_6$ alkylene, the $C_1$-$C_6$ alkylene is optionally substituted by $R^{L1}$, wherein each $R^{L1}$ is independently halo, OH, oxo, or $C_1$-$C_6$ alkyl, or two $R^{L1}$ are taken together with the carbon atom or atoms to which they are attached to form $C_3$-$C_6$ cycloalkyl or 3- to 6-membered heterocyclyl;

$R^6$ is hydrogen or $C_1$-$C_6$ alkyl; and

Ring B is $C_3$-$C_{10}$ cycloalkyl, $C_6$-$C_14$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

138. The method of any one of the preceding embodiments, wherein the GLP-1R agonist is a compound of Formula (I-1a):

(I-Ia)

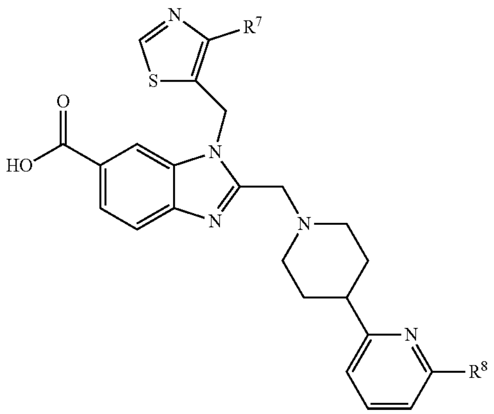

wherein $R^7$ is hydrogen, chloro, bromo, fluoro, methyl, or vinyl; and

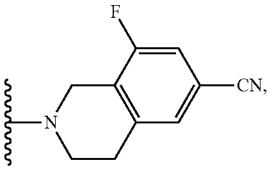

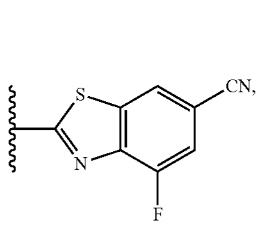

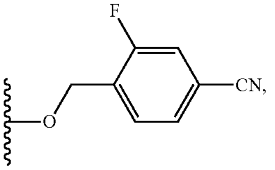

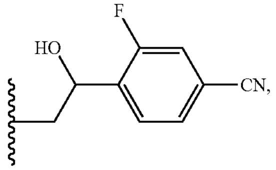

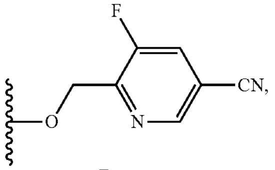

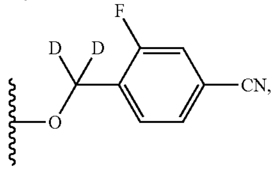

or

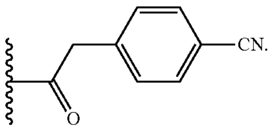

139. The method of any one of the preceding embodiments, wherein the GLP-1R agonist is a compound of Formula (I**):

(I**)

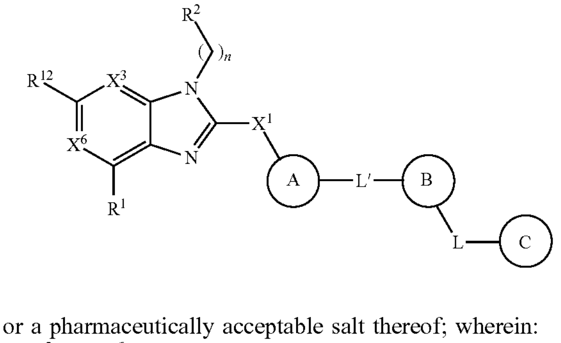

or a pharmaceutically acceptable salt thereof; wherein:

$X^3$ is $CR^6$ or N;

$X^6$ is $CR^4$ or N;

$R^1$ is —$C_{1-6}$ haloalkyl, halogen, —O—$X^4$, or —$NR^8R^9$, or $R^1$ and $R^4$, together with the atoms to which they are attached, combine to form a 5- or 6-membered heterocyclyl;

$X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}$—$CH_3$, —($CH_2$—CH(—$OCH_3$)—$CH_2$—O$)_{1-5}$—$CH_3$, $C_{3-10}$ cycloalkyl, or $C_{6-10}$ aryl, wherein the alkyl, heteroalkyl, alkylene, or haloalkyl group is optionally substituted with one or more deuterium, $C_{1-6}$ alkoxy, hydroxyl, —CN, or oxo, and the cycloalkyl, heterocyclyl, or aryl group is optionally substituted with one or more halogen, $C_{1-6}$ alkoxy, or —CN;

$R^6$ is hydrogen, halogen, or —O—$R^7$;

wherein $R^7$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocycyl; wherein the $C_{1-6}$ alkyl is optionally substituted by one or more oxo;

n is 0, 1, 2, 3, 4, 5, or 6;

$R^2$ is:

hydrogen;

$C_{1-6}$ alkyl optionally substituted with deuterium;

$C_{1-6}$ haloalkyl;

—(O)—$C_{1-6}$ alkyl;

—CN;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

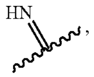, or $C_{1-6}$ alkyl;

a 5-membered heteroaryl, comprising 1 or 2 heteroatoms independently selected from N, and S, wherein at least one heteroatom of $R^5$ is S; or $R^2$ and $R^7$, together with the atoms to which they are attached, combine to form a 5- or 6-membered heterocyclyl;

$R^4$ is halogen, hydrogen, —C(O)OH, or —O—$R^8$, wherein $R^8$ and $R^1$, together with the atoms to which they are attached, combine to form a 6-membered heterocyclyl;

$R^{12}$ is hydrogen, —C(O)OH, —C(O)$NRN^{12}R^{N12}$, —C(O)$NR^{12}S(O)_2R^{12}$, —($C_{2-6}$ alkynylene)-C(O)OH, —($C_{1-6}$ alkylene)-C(O)OH, —$NR^{N12}$—($C_{1-6}$ alkylene)-C(O)OH, 5-10 membered heteroaryl or 5- to 10-membered heterocyclyl optionally substituted with one or more oxo, $C_{1-6}$ alkyl or $C_{1-6}$ haloalkyl;

$R^{N12}$ and $R^{N12}$ independently are H or $C_{1-6}$ alkyl;

$X^1$ is

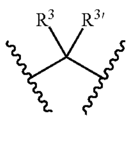 or 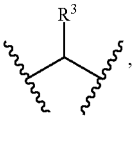, wherein $R^3$ and $R^{3\prime}$ independently are H, D or $C_{1-6}$ alkyl, wherein the $C_{1-6}$ alkyl is optionally substituted with detuerium;

Ring A is

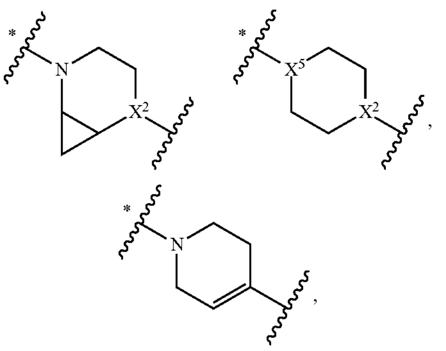

phenylene optionally substituted with one or more halo or $C_{1-6}$ alkyl, or 6-membered heteroarylene optionally substituted with one or more halo or $C_{1-6}$ alkyl;

wherein * indicates attachment to $X^1$, $X^5$ is $CR^3$ or N, and $X^2$ is $CR^3$ or N;

L' is a bond or —O—;

Ring B is a $C_{6-10}$ arylene, a 5-10 membered heteroarylene, or a 3-10 membered heterocycylene, wherein the $C_{6-10}$ arylene, 5-10 membered heteroarylene, or 3-10 membered heterocyclene is optionally substituted with one or more oxo, $C_{1-6}$ alkyl, $C_{1-6}$ alkoxy, or halogen;

L is a bond, *—($C_{1-6}$ alkylene)-, *—$NR^L$—($C_{1-6}$ alkylene)-, *—O—($C_{1-6}$ alkylene)-, or *—($C_{1-6}$ alkylene)-O—, wherein * indicates attachment to Ring B and the $C_{1-6}$ alkylene is optionally substituted with deuterium;

wherein $R^L$ is H or $C_{1-6}$ alkyl; and

Ring C is:

a 6-membered aryl optionally substituted with one or more $C_{3-10}$ cycloalkyl, $C_{1-6}$ alkyl, $C_{1-6}$ haloalkyl, 3-10 membered heterocyclyl, halogen, $C_{1-6}$ alkoxy, $C_{1-6}$ haloalkoxy, —CN, $C_{3-10}$ cycloalkyl, or —C(O)$NR^{2}$';

wherein R' is H or $C_{1-6}$ alkyl a 6-membered heteroaryl comprising a nitrogen atom optionally substituted with one or more halogen, —CN, $C_{1-6}$ haloalkyl, —O—$C_{1-6}$ alkyl, $C_{3-10}$ cycloalkyl, —C(=O)—($C_{3-10}$ cycloalkyl),

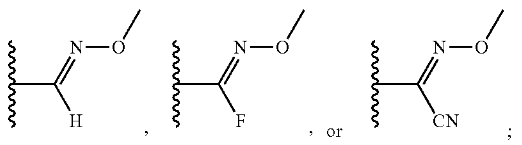

a bicylic 9- or 10-membered heteroaryl or heterocyclyl optionally substituted with one or more $C_{1-6}$ alkyl, halogen, —CN, or oxo.

140. The method of any one of the preceding embodiments, wherein the GLP-1R agonist is a compound of Formula (I-5)

(I-5)

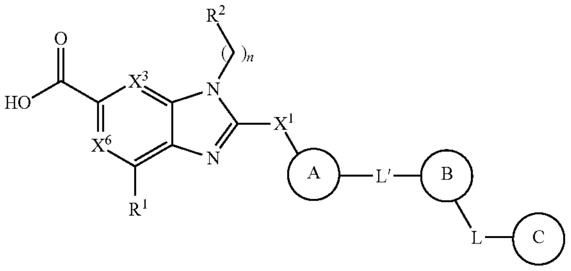

or a pharmaceutically acceptable salt thereof; wherein:

$X^3$ is $CR^6$ or N;

$X^6$ is $CR^4$ or N;

$R^1$ is —$C_{1-6}$ haloalkyl, —O—$X^4$, or —$NR^8R^9$, or $R^1$ and $R^4$, together with the atoms to which they are attached, combine to form a 6-membered heterocyclyl;

$X^4$ is hydrogen, $C_{1-6}$ alkyl, $C_{1-6}$ heteroalkyl, $C_{1-6}$ haloalkyl, —($C_{1-6}$ alkylene)-($C_{3-10}$ cycloalkyl), or —($C_{1-6}$ alkylene)-(3- to 8-membered heterocyclyl), 3- to 8-membered heterocyclyl, —$(CH_2CH_2—O)_{1-5}$—$CH_3$, or —($CH_2$—CH(—$OCH_3$)—$CH_2$—O$)_{1-5}$—$CH_3$, wherein the alkyl, heteroalkyl, alkylene, or haloalkyl group is optionally substituted with one or more deuterium, hydroxyl, —CN, or oxo, and the cycloalkyl or heterocyclyl group is optionally substituted with one or more halogen or —CN;

$R^6$ is hydrogen, halogen, or —O—$R^7$;

wherein $R^7$ and $R^2$, together with the atoms to which they are attached, combine to form a 6-membered heterocyclyl;

$R^8$ and $R^9$ each independently are selected from hydrogen, $C_{1-6}$ alkyl, or —$S(O)_2$—$C_{1-6}$ alkyl, or $R^8$ and $R^9$, together with the atoms to which they are attached, combine to form a 6-membered heterocyclyl; wherein the $C_{1-6}$ alkyl is optionally substituted by one or more oxo;

n is 0, 1, 2, 3, 4, 5, or 6;

$R^2$ is:

hydrogen;

branched $C_{1-6}$ alkyl;

$C_{1-6}$ haloalkyl;

—(O)—$C_{1-6}$ alkyl;

a $C_{3-10}$ cycloalkyl optionally substituted with one or more —CN, $C_{1-6}$ haloalkyl, or $C_{1-6}$ alkyl optionally substituted with one or more —CN;

a 4 or 5-membered heterocyclyl comprising at least one oxygen or at least one sulfur atom, wherein the 4- or 5-membered heterocyclyl is optionally substituted with one or more oxo,

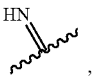

or $C_{1-6}$ alkyl;

a 5-membered heteroaryl, comprising 1 or 2 heteroatoms independently selected from N, and S, wherein at least one heteroatom of $R^5$ is S; or $R^2$ and $R^7$, together with the atoms to which they are attached, combine to form a 5- or 6-membered heterocyclyl;

$R^4$ is hydrogen or —O—$R^8$, wherein $R^8$ and $R^1$, together with the atoms to which they are attached, combine to form a 6-membered heterocyclyl;

$X^1$ is

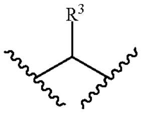 or 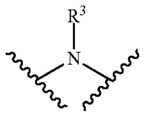, wherein $R^3$ is H or $C_{1-6}$ alkyl;

Ring A is

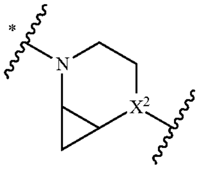 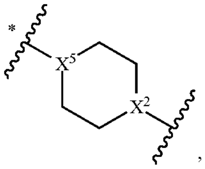, 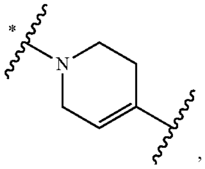, phenylene optionally substituted with one or more halo or $C_{1-6}$ alkyl, or 6-membered heteroarylene optionally substituted with one or more halo or $C_{1-6}$ alkyl;

wherein * indicates attachment to $X^1$, $X^5$ is $CR^3$ or N, and $X^2$ is $CR^3$ or N;

L' is a bond or —O—;

Ring B is a $C_{6-10}$ arylene, a 6-10 membered heteroarylene, or a 3-10 membered heterocyclene, wherein the $C_{6-10}$ arylene, 6-10 heteroarylene, or 3-10 membered heterocyclene is optionally substituted with one or more $C_{1-6}$ alkyl, $C_{1-6}$ alkoxy, or halogen;

L is a bond, *—$CH_2$—, *—O—($C_{1-6}$ alkylene)-, or *—($C_{1-6}$ alkylene)-O—, wherein * indicates attachment to Ring B and the $C_{1-6}$ alkylene is optionally substituted with deuterium; and Ring C is:

a 6-membered aryl optionally substituted with one or more $C_{1-6}$ alkyl, 3-10 membered heterocyclyl, halogen, —$OCH_3$, —CN, or $C_{3-10}$ cycloalkyl;

a 6-membered heteroaryl comprising a nitrogen atom optionally substituted with one or more halogen, —CN, —O—$C_{1-6}$ alkyl, $C_{3-10}$ cycloalkyl, —C(═O)—($C_{3-10}$ cycloalkyl),

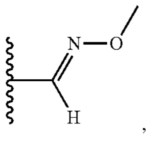, 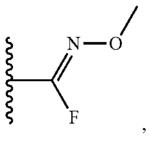, or 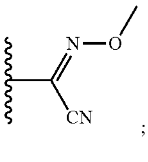;

or a bicyclic 9- or 10-membered heteroaryl comprising two nitrogen atoms optionally substituted with one or more $C_{1-6}$ alkyl, or oxo.

141. The method of any one of the preceding embodiments, wherein the GLP-1R agonist is a compound of Formula (II**):

(II**)

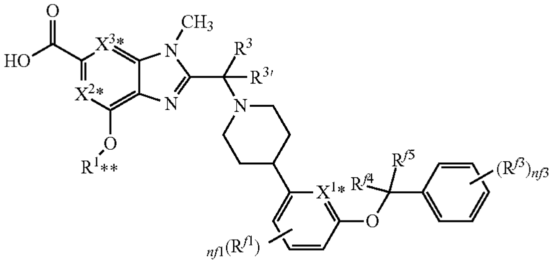

or a pharmaceutically acceptable salt thereof; wherein $R^{f4}$ and $R^{f5}$ are each independently selected from $C_{1-6}$ alkyl, H and D nf1 is 0, 1, 2, 3, or 4;

nf3 is 0, 1, 2, 3, 4, or 5;

each $R^{f1}$ is halogen;

$R^3$ and $R^{3'}$ independently are H or D;

$X^{1*}$ is N or $CR^{f1}$;

$X^{2*}$ and $X^{3*}$ independently are CH or CF;

each $R^{f3}$ is independently selected from halogen, —CN, $C_{1-6}$ alkyl, $C_{1-6}$ haloalkyl, $C_{1-6}$ alkoxy, or —C(O)N$(R^{f3'})_2$, each $R^{3'}$ is indepdendently selected from H or $C_{1-6}$ alkyl; and $R^{1**}$ is H or $C_{1-2}$ alkyl optionally substituted with one or more deuterium or halogen.

142. The method of any one of the preceding embodiments, wherein the GLP-1R agonist is Compound 1-2:

(1-2)

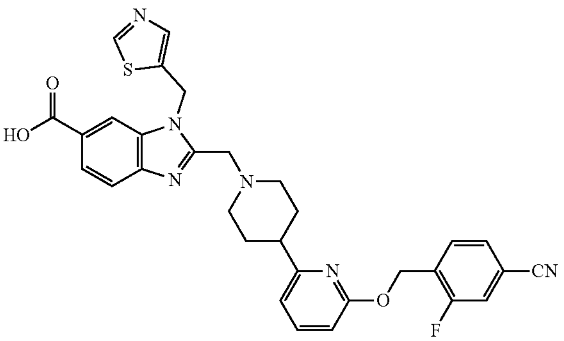

or a pharmaceutically acceptable salt thereof.

143. The method of any one of the preceding embodiments, wherein the GLP-1R agonist is a meglumine salt of Compound 1-2.

144. The method of any one of the preceding embodiments, wherein the THRβ agonist is selected from those listed in Tables 6-11.

145. The method of any one of the preceding embodiments, wherein the GLP-1R agonist is selected from those listed in Tables 1-5.

146. The method of any one of the preceding embodiments, wherein the GLP-1R agonist is selected from those listed in Table 5A.

147. The method of any one of the preceding embodiments, wherein the THRβ agonist is compound 9

(9)

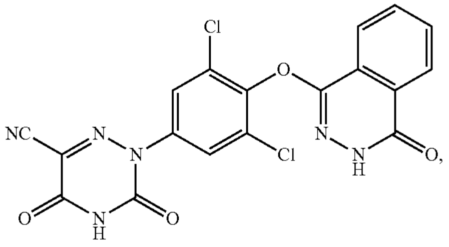

and the GLP-1R agonist is orforglipron, danuglipron, liraglutide, exenatide, dulaglutide, albiglutide, lixisenatide, tirzepatide, or semaglutide, or a pharmaceutically acceptable salt thereof.

147a. The method of any one of the preceding embodiments, wherein the THRβ agonist is compound 9

(9)

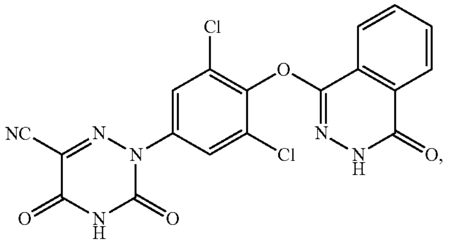

and the GLP-1R agonist is orforglipron or a pharmaceutically acceptable salt thereof.

147b. The method of any one of the preceding embodiments, wherein the THRβ agonist is compound 9

(9)

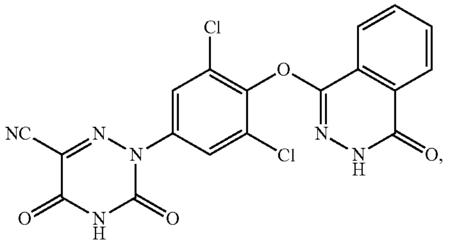

and the GLP-1R agonist is semaglutide or a pharmaceutically acceptable salt thereof.

147c. The method of any one of the preceding embodiments, wherein the THRβ agonist is compound 9

(9)

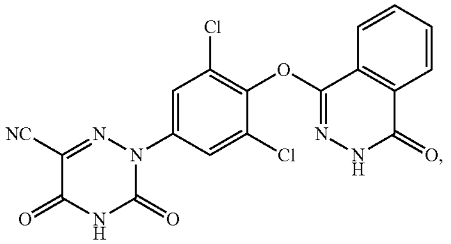

and the GLP-1R agonist is danuglipron or a pharmaceutically acceptable salt thereof.

148. The method of any one of the preceding embodiments, wherein the THRβ agonist is resmetirom, VK2809, sobetirome, eprotirome, ALG-055009, CNPT-101101, CNPT-101207, ASC41 or a pharmaceutically acceptable salt thereof and the GLP-1R agonist is compound 1-2

(1-2)

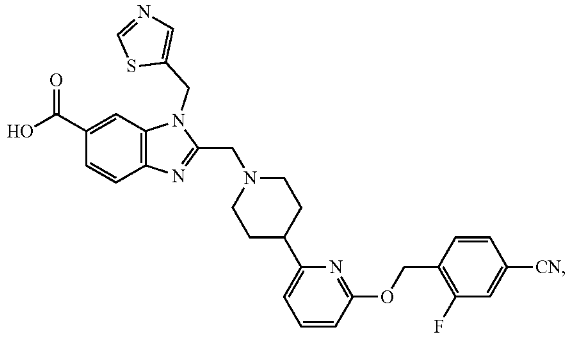

or a pharmaceutically acceptable salt thereof.

149. The method of any one of the preceding embodiments, wherein the THRβ agonist is compound 9

(9)

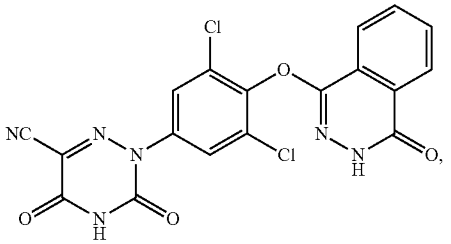

or a pharmaceutically acceptable salt thereof, and the GLP-1R agonist is compound 1-2

(1-2)

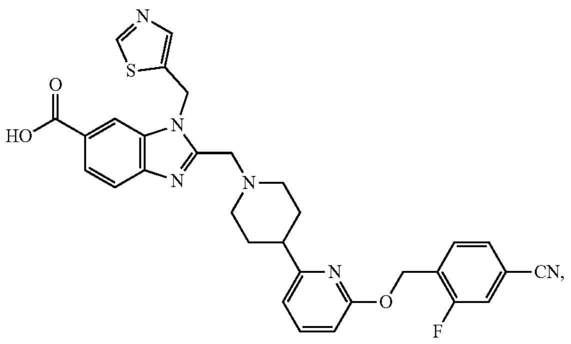

or a pharmaceutically acceptable salt thereof.

150. The method of any one of the preceding embodiments, wherein the patient has a body mass index (BMI) of 25 $kg/m^2$ to 30 $kg/m^2$.

151. The method of any one of the preceding embodiments, wherein the patient has a BMI of 30 $kg/m^2$ or greater.

152. The method of any one of the preceding embodiments, wherein the GLP-1R agonist is administered to the subject more than once.

153. The method of any one the preceding embodiments, wherein the THRβ agonist is administered to the subject more than once.

154. The method of any one of the preceding embodiments, wherein both the GLP-1R agonist and THR-β agonist are administered to the subject more than once.

155. The method of any one of the preceding embodiments, wherein the THRβ agonist is administered prior to or concurrent with the GLP-1R agonist.

156. The method of any one of the preceding embodiments, wherein the THRβ agonist is administered in temporal proximity to the GLP-1R agonist.

157. The method of any one of the preceding embodiments, wherein the THR agonist is administered on the same day as the GLP-1R agonist.

158. The method of any one of the preceding embodiments, wherein the THRβ agonist is administered at substantially the same time as the GLP-1R agonist.

159. The method of any one of the preceding embodiments, wherein the initial dose of THRα agonist is administered in temporal proximity to the GLP-1R agonist.

160. The method of any one of the preceding embodiments, wherein the initial dose of THRβ agonist is administered on the same day as the GLP-1R agonist.

161. The method of any one of the preceding embodiments, wherein the initial dose of THRβ agonist is at substantially the same time as the GLP-1R agonist.

162. The method of any one of the preceding embodiments, wherein the initial dose of THRβ agonist is administered prior to the initial dose of GLP-1R agonist.

163. The method of any one of the preceding embodiments, wherein a subsequent dose of THRβ agonist is administered in temporal proximity to the GLP-1R agonist.

164. The method of any one of the preceding embodiments, wherein a subsequent dose of THRβ agonist is administered on the same day as the GLP-1R agonist.

165. The method of any one of the preceding embodiments, wherein a subsequent dose of THRβ agonist is administered at substantially the same time as the GLP-1R agonist.

166. The combination of any one of the preceding embodiments, wherein the THRβ agonist is compound 9

(9)

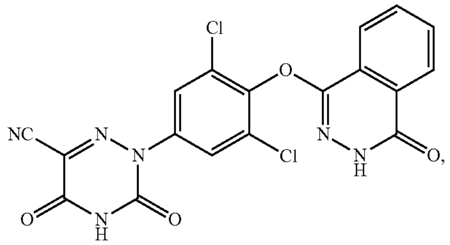

and the GLP-1R agonist is orforglipron, or a pharmaceutically acceptable salt thereof.

167. The combinational therapy of any one of the preceding embodiments, wherein the THRα agonist is compound 9

(9)

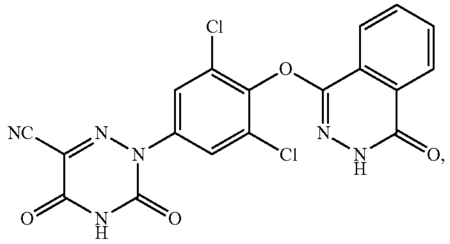

and the GLP-1R agonist is orforglipron, or a pharmaceutically acceptable salt thereof.

168. The THR-β agonist, or pharmaceutically acceptable salt thereof, and GLP-1R agonist, or pharmaceutically acceptable salt thereof, for use according to any one of the preceding embodiments, wherein the THRβ agonist is compound 9

(9)

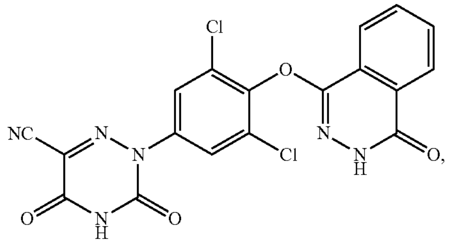

and the GLP-1R agonist is orforglipron, or a pharmaceutically acceptable salt thereof.

169. The method of any one of the preceding embodiments, wherein the GLP-1R agonist is orforglipron, or a pharmaceutically acceptable salt thereof.

Embodiments A1-A48

A1. A combination comprising a THRβ agonist, or a pharmaceutically acceptable salt thereof, and a GLP-1R agonist, or a pharmaceutically acceptable salt thereof.

A2. The combination of embodiment A1, wherein the THRβ agonist is a compound of Formula (II-1)

(II-1)

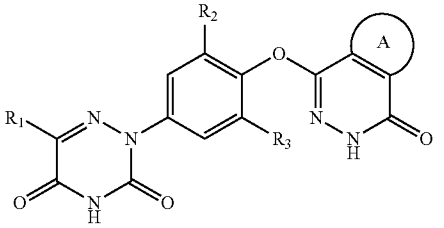

wherein:

$R_1$ is selected from the group consisting of hydrogen, cyano, substituted or unsubstituted $C_{1-6}$ alkyl, and substituted or unsubstituted $C_{3-6}$ cycloalkyl, the substituent being selected from the group consisting of halogen atoms, hydroxy, and $C_{1-6}$ alkoxy;

$R_2$ and $R_3$ are each independently selected from the group consisting of halogen atoms and substituted or unsubstituted $C_{1-6}$ alkyl, the substituent being selected from the group consisting of halogen atoms, hydroxy, and $C_{1-6}$ alkoxy; ring A is a substituted or unsubstituted saturated or unsaturated $C_{5-10}$ aliphatic ring, or a substituted or unsubstituted $C_{5-10}$ aromatic ring, the substituent being one or more substances selected from the group consisting of hydrogen, halogen atoms, hydroxy, $—OCF_3$, $—NH_2$, $—NHC_{1-4}$ alkyl, $—N(C_{1-4}$ alkyl$)_2$, $—CONH_2$, $—CONHC_{1-4}$ alkyl, $—CON(C_{1-4}$ alkyl$)_2$, $—NHCOC_{1-4}$ alkyl, $C_{1-6}$ alkyl, $C_{1-6}$ alkoxy or $C_{3-6}$ cycloalkyl, and when two substituents are contained, the two substituents can form a ring structure together with the carbon connected thereto; and the halogen atoms are selected from the group consisting of F, Cl and Br; or a pharmaceutically acceptable salt thereof.

A3. The combination of embodiment A1 or A2, wherein the THRβ agonist is a compound of Formula (II-1a)

(II-1a)

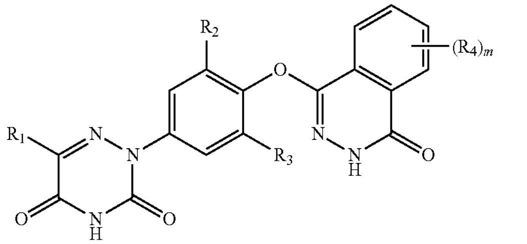

wherein:

$R_1$ to $R_3$ are defined as detailed herein for Formula (II-1);

$R_4$ is selected from the group consisting of hydrogen, halogen atoms, hydroxy, $—OCF_3$, $—NH_2$, $—NHC_{1-4}$ alkyl, $—N(C_{1-4}$ alkyl$)_2$, $—CONH_2$, $—CONHC_{1-4}$ alkyl, $—CON(C_{1-4}$ alkyl$)_2$, $—NHCOC_{1-4}$ alkyl, $C_{1-6}$ alkyl, $C_{1-6}$ alkoxy and $C_{3-6}$ cycloalkyl;

m is an integer from the range 1 to 4; and the halogen atoms are selected from the group consisting of F, Cl and Br.

or a pharmaceutically acceptable salt thereof.

A4. The combination of any one of the preceding embodiments, wherein the THRβ agonist is Compound 9:

(9)

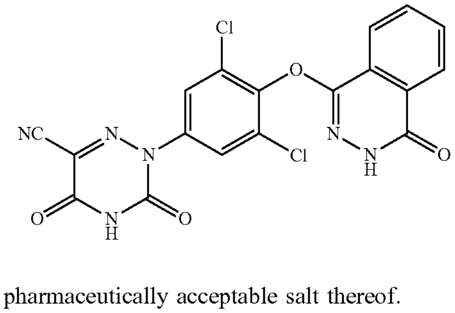

or a pharmaceutically acceptable salt thereof.

A5. The combination of any one of the preceding embodiments, wherein the THRβ agonist is a potassium salt of Compound 9.

A6. The combination of any one of the preceding embodiments, wherein the GLP-1R agonist is a compound of Formula (I-1):

(I-1)

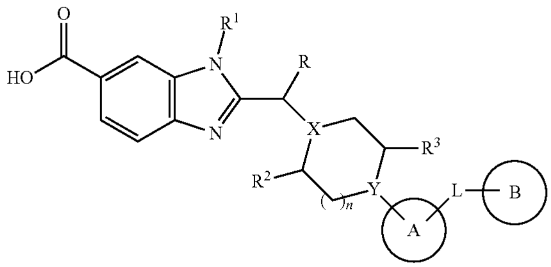

or a pharmaceutically acceptable salt thereof, wherein:

X is N or CH;

Y is N or $CR^4$;

n is 0 or 1;

R is hydrogen;

$R^1$ is $—C_1$-$C_6$ alkylene-$R^5$;

$R^2$ is hydrogen, oxo, or $C_1$-$C_6$ alkyl;

$R^3$ is hydrogen, oxo, or $C_1$-$C_6$ alkyl and $R^4$ is hydrogen, OH, or $C_1$-$C_6$ alkyl;

or $R^3$ and $R^4$ are taken together with the carbon atoms to which they are attached to form $C_3$-$C_6$ cycloalkyl optionally substituted by halo or $C_1$-$C_3$ alkyl;

$R^5$ is 5-membered heterocyclyl or 5-membered heteroaryl, each of which comprises 1, 2, or 3 heteroatoms independently selected from O, N, and S, wherein at least one heteroatom of $R^5$. is S, and further wherein $R^5$ is optionally substituted by halo, $—O—C_{1-6}$ alkyl, $C_{1-6}$ alkyl, $C_{1-6}$ alkenyl, or $C_1$-$C_6$ haloalkyl;

Ring A is 5- to 12-membered heterocyclene or 5- to 12-membered heteroarylene, each of which is independently optionally substituted by halo, CN, $C_3$-$C_6$ cycloalkyl, or $C_1$-$C_6$ alkyl optionally substituted by halo or OH;

L is a bond, —O—, $C_1$-$C_6$ alkylene, $*—O—C_1$-$C_6$ alkylene-$**$, $*—C_1$-$C_6$ alkylene-O—$**$, or $*—NR^6—C_1$-$C_6$ alkylene-$**$, wherein

* represents the point of attachment to ring A and ** represents the point of attachment to ring B;

when L is *—O—$C_1$-$C_6$ alkylene-**, the $C_1$-$C_6$ alkylene of L is optionally substituted by $R^L$, wherein each $R^L$ is independently $C_1$-$C_6$ alkyl or halo, or two $R^L$ are taken together with the carbon atom or atoms to which they are attached to form $C_3$-$C_6$ cycloalkyl or 3- to 6-membered heterocyclyl; and when L is $C_1$-$C_6$ alkylene, the $C_1$-$C_6$ alkylene is optionally substituted by $R^L$i, wherein each $R^L$ is independently halo, OH, oxo, or $C_1$-$C_6$ alkyl, or two $R^{L1}$ are taken together with the carbon atom or atoms to which they are attached to form $C_3$-$C_6$ cycloalkyl or 3- to 6-membered heterocyclyl;

$R^6$ is hydrogen or $C_1$-$C_6$ alkyl; and

Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

A7. The combination of any one of the preceding embodiments, wherein the GLP-1R agonist is a compound of Formula I-1a):

(I-1a)

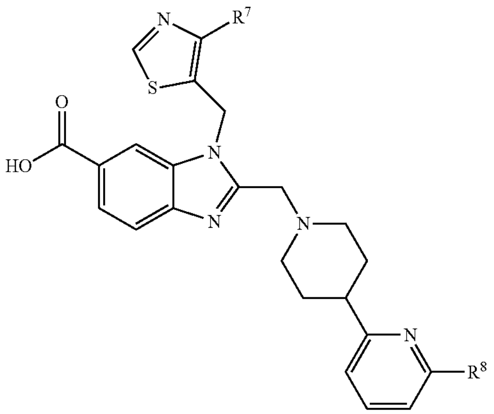

wherein $R^7$ is hydrogen, chloro, bromo, fluoro, methyl, or vinyl; and $R^8$ is

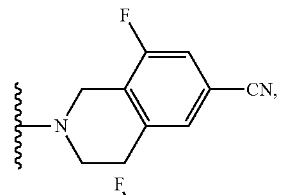

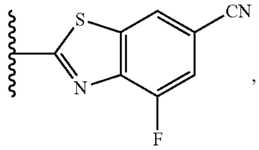

,

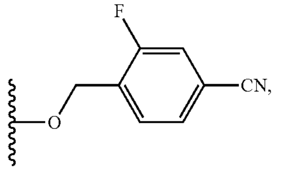

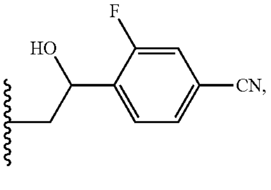

-continued

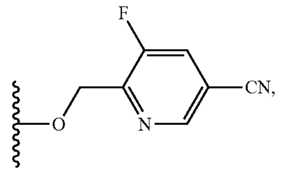

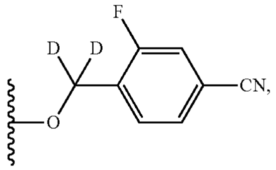

or

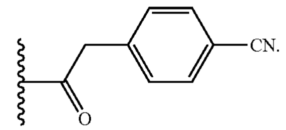

A8. The combination of any one of the preceding embodiments, wherein the GLP-1R agonist is a compound of Formula (II**):

(II**)

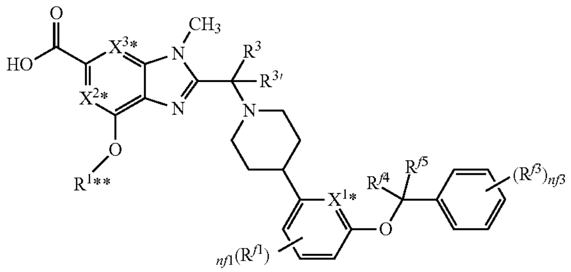

or a pharmaceutically acceptable salt thereof; wherein $R^{f4}$ and $R^{f5}$ are each independently selected from $C_{1-6}$ alkyl, H and D nf1 is 0, 1, 2, 3, or 4;

nf3 is 0, 1, 2, 3, 4, or 5;

each $R^{f1}$ is halogen;

$R^3$ and $R^{3'}$ independently are H or D;

$X^1$* is N or CRP;

$X^2$* and $X^3$* independently are CH or CF;

each $R^{f3}$ is independently selected from halogen, —CN, $C_{1-6}$ alkyl, $C_{1-6}$ haloalkyl, $C_{1-6}$ alkoxy, or —C(O)N$(R^{3'})_2$, each $R^{f3'}$ is indepdendently selected from H or $C_{1-6}$ alkyl; and $R^{1**}$ is H or $C_{1-2}$ alkyl optionally substituted with one or more deuterium or halogen.

A9. The combination of any one of the preceding embodiments, wherein the GLP-1R agonist is Compound 1-2:

(1-2)

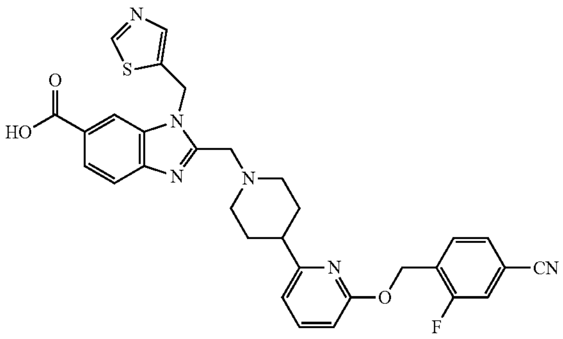

or a pharmaceutically acceptable salt thereof.

A10. The combination of any one of the preceding embodiments, wherein the GLP-1R agonist is a meglumine salt of Compound 1-2.

A11. The combination of any one of the preceding embodiments, wherein the THRβ agonist is selected from those listed in Tables 6-11, or a pharmaceutically acceptable salt thereof.

A12. The combination of any one of the preceding embodiments, wherein the GLP-1R agonist is selected from those listed in Tables 1-5, or a pharmaceutically acceptable salt thereof.

A13. The combination of any one of the preceding embodiments, wherein the GLP-1R agonist is selected from those listed in Table 5A, or a pharmaceutically acceptable salt thereof.

A14. The combination of any one of the preceding embodiments, wherein the THRβ agonist is compound 9

(9)

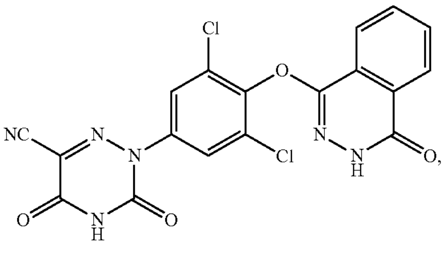

and the GLP-1R agonist is orforglipron, danuglipron, liraglutide, exenatide, dulaglutide, albiglutide, lixisenatide, tirzepatide, or semaglutide, or a pharmaceutically acceptable salt thereof.

A15. The combination of any one of the preceding embodiments, wherein the THRβ agonist is compound 9

(9)

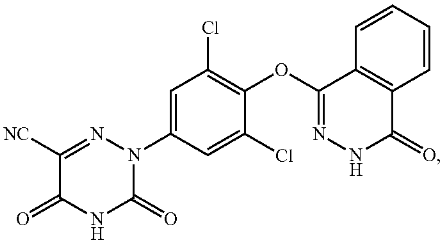

and the GLP-1R agonist is orforglipron, danuglipron, or semaglutide, or a pharmaceutically acceptable salt thereof.

A16. The combination of any one of the preceding embodiments, wherein the THRβ agonist is resmetirom, VK2809, sobetirome, eprotirome, ALG-055009, CNPT-101101, CNPT-101207, ASC41 or a pharmaceutically acceptable salt thereof and the GLP-1R agonist is compound 1-2

(1-2)

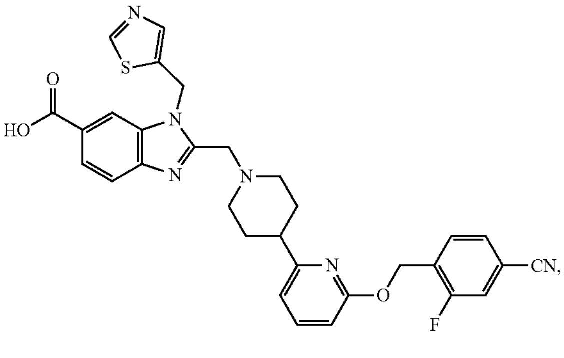

or a pharmaceutically acceptable salt thereof.

A17. The combination of any one of the preceding embodiments, wherein the THRβ agonist is compound 9

(9)

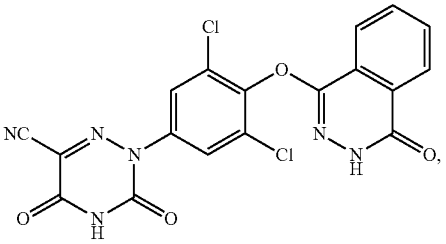

or a pharmaceutically acceptable salt thereof, and the GLP-1R agonist is compound 1-2

(1-2)

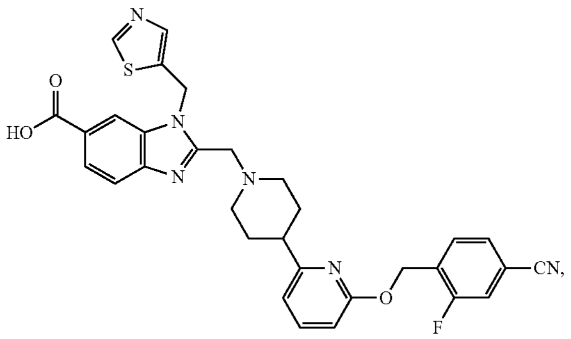

or a pharmaceutically acceptable salt thereof.

A18. The combination of any one of the preceding embodiments, wherein the amount of the THRβ agonist is from about 0.5 mg to about 25 mg.

A19. The combination of any one of the preceding embodiments, wherein the amount of the THRβ agonist is from about 1 mg to about 15 mg.

A20. The combination of any one of the preceding embodiments, wherein the amount of the THRβ agonist is from about 2 mg to about 10 mg.

A21. The combination of any one of the preceding embodiments, wherein the amount of the THRβ agonist is about 1 mg.

A22. The combination of any one of the preceding embodiments, wherein the amount of the THRβ agonist is about 3 mg.

A23. The combination of any one of the preceding embodiments, wherein the amount of the THRβ agonist is about 6 mg.

A24. The combination of any one of the preceding embodiments, wherein the amount of the THRβ agonist is about 10 mg.

A25. The combination of any one of the preceding embodiments for use in the treatment of a liver disorder or a cardiometabolic disease in a patient in need thereof.

A26. The combination of any one of the preceding embodiments for use in effectuating weight loss in a patient in need thereof.

A27. The combination of any one of the preceding embodiments for use in a combinational therapy for the treatment of obesity in a patient in need thereof.

A28. A method of treating a liver disorder or a cardiometabolic disease in a patient in need thereof, comprising administering to the patient a combination according to any one of the preceding embodiments.

A29. A method of treating a liver disorder or a cardiometabolic disease in a patient in need thereof, comprising administering to the patient a therapeutically effective amount of the combination according to any one of the preceding embodiments.

A30. A method of increasing the proportion of lean body mass relative to total body mass in a patient in need thereof, comprising administering to the patient a combination according to any one of the preceding embodiments.

A31. A method of decreasing the proportion of fat mass relative to total body mass in a patient in need thereof, comprising administering to the patient a combination according to any one of the preceding embodiments.

A32. A method of effectuating weight loss in a patient in need thereof, comprising administering to the patient a combination according to any one of the preceding embodiments.

A33. The method of any one of the preceding embodiments, wherein the patient has a Body Mass Index (BMI) of 27 $kg/m^2$ or greater.

A34. The method of any one of the preceding embodiments, wherein the patient has a BMI of 30 $kg/m^2$ or greater.

A35. The method of any one of the preceding embodiments, wherein the administration of the THR agonist allows for administration of a reduced dose of the GLP-1R agonist while maintaining equivalent weight loss.

A36. The method of any one of the preceding embodiments, wherein the administration of the THRβ agonist increases weight loss compared to administration of a GLP-1R agonist at an equivalent dose.

A37. The method of any one of the preceding embodiments, wherein the cardiometabolic disease is obesity or an obesity-associated condition.

A38. The method of any one of the preceding embodiments, wherein the cardiometabolic disease is diabetes.

A39. The method of any one of the preceding embodiments, wherein the combination or method improves glycemic control in adults with type 2 diabetes mellitus.

A40. A method of treating obesity or effectuating weight loss in a patient in need thereof, the method comprising (i) administering to the patient compound 9

(9)

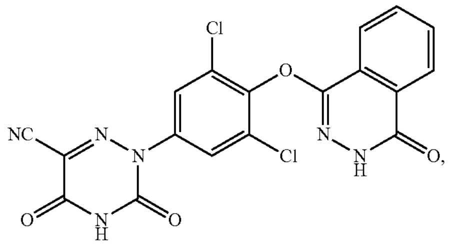

or a pharmaceutically acceptable salt thereof, and (ii) administering to the patient a GLP-1R agonist, or a pharmaceutically acceptable salt thereof;

wherein administering to the patient compound 9, or a pharmaceutically acceptable salt thereof, improves the patient's response to the GLP-1R agonist or a pharmaceutically acceptable salt thereof.

A41. The combination or method of any one of the preceding embodiments, wherein the THRβ agonist is administered once daily or twice daily.

A42. The combination or method of any one of the preceding embodiments, wherein the THRβ agonist is administered orally.

A43. The combination or method of any one of the preceding embodiments, wherein the GLP-1R agonist is administered orally.

A44. The method of embodiment A40, wherein the GLP-1R agonist comprises compound 1-2, orforglipron, semaglutide, tirzepatide, or danuglipron.

A45. The method of any one of the preceding embodiments, wherein administering compound 9, or a pharmaceutically acceptable salt thereof, increases fat loss associated with administering the GLP-1R agonist.

A46. The method of any one of the preceding embodiments, wherein administering compound 9, or a pharmaceutically acceptable salt thereof, increases fat loss associated with administering the GLP-1R agonist while maintaining lean mass.

A47. The combination of any one of embodiments A1-A27 for the preparation of a medicament for the use in a method according to any one of embodiments A28-A46.

A48. Use of the combination of any one of embodiments A1-A27 in a method according to any one of embodiments A28-A46.

EXAMPLES

The combination treatment provided herein can be tested by administering the combination of the agents to a well-known mouse model and evaluating the results. Methods of such testing can be adapted from those known.

Example 1. Evaluating THR-B Agonist Compound 9 in Combination with a GLP-1R Agonist (e.g., Semaglutide)

To evaluate the effect of 12 weeks of treatment with Compound 9 alone and in combination with semaglutide on metabolic parameters, hepatic pathology and NAFLD Activity Score including Fibrosis Stage in male biopsy-confirmed GAN DIO-NASH mice are determined.

Sample Formulation

| Compound | Frequency of preparation | Dosing solution Stored at 4° C. Conc. | Storage [temp] | pH | Detailed instruction on compound preparation |
|---|---|---|---|---|---|
| Vehicle (Compound 9) | Weekly | NA | 4° C. | 8 | 1% HP-β-CD (Cyclodextrin) and 90% 50 mM Tris buffer in reverse osmosis water (pH 8.0 ± 0.2 with NaOH or HCl) |
| Vehicle (Semaglutide) | Weekly | NA | 4° C. | 7.4 | PBS + 0.1% BSA |
| Compound 9 | Daily | Gr. 3 and 6: 1.2 mg/ml Gr. 4 and 7: 0.6 mg/ml | 4° C. | 8 | Weigh out compound in amber colored vial, add vehicle and pH adjust to 8.0 with NaOH or HCL; stir and sonicate (if needed) for ~20 minutes. Solution may be slightly opaque. Dilute with vehicle to achieve the low concentration. Always protect from light. |
| Semaglutide | Weekly | 6 nmol/ml* | 4° C. | 7.4 | Dilute in PBS + 0.1% BSA |

*Titration: 0.12 nmol/ml day 1; 0.24 nmol/ml day 2; 0.48 nmol/ml day 3: 0.96 nmol/ml day 4; 2.4 nmol/ml day 5, 6 nmol/ml day 6

Groups of the Study

| Group # | Group Name | Compound | n | Model | Dosing conc. | Dosing 5 ml/kg, QD, AM Route |
|---|---|---|---|---|---|---|
| 1 | Lean-chow Vehicle | Vehicle (Compound 9) | 10 | Lean chow | NA | PO |
| | | Vehicle (Semaglutide) | | | NA | SC |
| 2 | DIO-NASH Vehicle | Vehicle (Compound 9) | 18 | DIO-NASH | NA | PO |
| | | Vehicle (Semaglutide) | | | NA | SC |
| 3 | Compound 9 (6 mg/kg) | Compound 9 | 18 | DIO-NASH | 6 mg/kg | PO |
| | | Vehicle (Semaglutide) | | | NA | SC |
| 4 | Compound 9 (3 mg/kg) | Compound 9 | 18 | DIO-NASH | 3 mg/kg | PO |
| | | Vehicle (Semaglutide) | | | NA | SC |
| 5 | Semaglutide | Semaglutide* | 18 | DIO-NASH | 30 nmol/kg | SC |
| | | Vehicle (Compound 9) | | | NA | PO |
| 6 | Compound 9 (6 mg/kg) + Semaglutide | Compound 9 | 18 | DIO-NASH | 6 mg/kg | PO |
| | | Semaglutide* | | | 30 nmol/kg | SC |
| 7 | Compound 9 (3 mg/kg) + Semaglutide | Compound 9 | 18 | DIO-NASH | 3 mg/kg | PO |
| | | Semaglutide* | | | 30 nmol/kg | SC |

*Titration: 0.6 nmol/kg day 1; 1.2 nmol/kg day 2; 2.4 nmol/kg day 3: 4.8 nmol/kg day 4; 12 nmol/kg day 5, 30 nmol/kg day 6.

Measurements (In Vivo Pharmacology)

| Measurement Name | Groups | Sample Name | Periods or frequency | Comments |
|---|---|---|---|---|
| Body weight | All | NA | QD from day −3 to day 85/86 | NA |
| Food intake | All | NA | QW from week 1 to week 12 | NA |
| Fasting BG | All | 4 h Fasting blood glucose | Week 10 | NA |
| EchoMRI | All | NA | Week 12 | Whole body lean/fat tissue mass |
| Liver weight | All | Liver weight | Termination | NA |

Measurements (Histology)

| Measurement Name | Sample Name | Comments |
|---|---|---|
| Fibrosis quantification for randomization | Liver pre-biopsy Liver post biopsy | PSR staining |
| NAFLD Activity Score | Liver pre-biopsy Liver post biopsy | HE staining |
| Fibrosis stage | Liver pre-biopsy Liver post biopsy | PSR staining |
| Steatosis quantification | Liver post biopsy | HE staining |
| Fibrosis (PSR) quantification | Liver post biopsy | PSR staining |
| Gal-3 quantification | Liver post biopsy | IHC staining |
| Col1a1 quantification | Liver post biopsy | IHC staining |
| α-SMA quantification | Liver post biopsy | IHC staining |

Measurements (Assays)

| Measurement | Sample Type |
|---|---|
| Plasma insulin | 4 h Fasting plasma insulin |
| Plasma ALT | Plasma ALT/AST/TG/TC |
| Plasma AST | Plasma ALT/AST/TG/TC |
| Plasma TG | Plasma ALT/AST/TG/TC |
| Plasma TC | Plasma ALT/AST/TG/TC |
| Plasma TIMP-1 | Plasma TIMP-1 |
| Plasma PIIINP | Plasma PIIINP |
| Plasma CK18-M30 | Plasma CK18- M30 |
| Liver TG | Liver TG/TC |
| Liver TC | Liver TG/TC |
| Liver RNAseq | Liver RNAseq n = 10 |

Non-Alcoholic Steatohepatitis (NASH) Mouse Model

This mouse model is fed a high fat diet that results in nonalcoholic steatohepatis (NASH) disease. The NASH mice are based on male C57BL/6JRj mice fed a 40% fat, 22% fructose and 2% cholesterol diet (D09100310, SSNIFF, Germany) for at least 28 weeks, respectively, prior to experiment.

Liver Biopsy

Mice are anesthetized by inhalation anesthesia using isoflurane (2-3%). A small abdominal incision is made in the midline and the left lateral lobe of the liver is exposed. A cone shaped wedge of liver tissue (approximately 50 mg) is excised from the distal portion of the lobe and fixated in 10% neutral buffered formalin (10% NBF) for histology. The cut surface of the liver is instantly electrocoagulated using bipolar coagulation (ERBE VIO 100 electrosurgical unit). The liver is returned to the abdominal cavity, the abdominal wall is sutured and the skin is closed with staplers. For post-operative recovery mice receive carprofen (5 mg/kg) administered subcutaneously on OP day and post-OP day 1 and 2.

Blood Sampling and Plasma Preparation

In vivo blood samples: Samples are collected at week 8, 30 minutes post-dose, 1 hour post-dose, 2 hours post-dose, 4 hours post-dose, 6 hours post-dose, and 24 hours post-dose (before the next dose). Tail-vein, tongue or cheek blood is collected in a Microvette tube of appropriate dimensions with anticoagulant and mixed by inversion 5 times. Blood is placed at 4° C. until it is centrifuged at 3000 g for 10 minutes. The plasma supernatants are transferred to new tubes and immediately frozen on dry ice. The samples are stored at −70° C.

Termination blood samples: During anesthesia with isoflurane, the abdominal cavity is opened, and cardiac blood is drawn with a syringe into a Microvette/Vacuette of appropriate dimensions with anticoagulant and mixed by inversion 5 times. Blood is placed at 4° C. until it is centrifuged at 3000 g for 10 minutes. The plasma supernatants are transferred to new tubes and immediately frozen on dry ice. The samples are stored at −70° C.

Tissue Sampling

Liver (NASH)

After the animal has been terminated by heart puncture, the liver is collected and weighed. Specific liver samples and biopsies are dissected and processed as specified in table “Termination samples” and further described below.

The liver is divided into left lateral lobe, medial lobe, right lateral lobe, and caudate lobe. The remaining lobes are not used unless specified in the protocol.

The Post-biopsy piece (−200 mg, less than 0.7×0.5 cm) is cut from the left lateral lobe, 4 mm from the prebiopsy site with an edge. The tissue is collected in paraformaldehyde.

The Liver Sponsor piece (−150 mg) is dissected from the left medial lobe, put in a tube and placed directly into liquid nitrogen. The samples are stored at −70° C. Please note that the size of the sponsor piece varies according to the size of the left medial lobe.

The Liver RNA Sequencing (RNAseq) piece (20±10 mg) is dissected from the center of the left lateral lobe, snap frozen (put directly in liquid nitrogen in Nunc filter) and collected in a pre-cooled tube which is put in liquid nitrogen. The samples are stored at −70° C.

The Liver TG TC piece (25±5 mg) is dissected from the right medial lobe, with no edges, on the opposite side of the sponsor piece. The samples are weighed individually and collected in tubes before placed in liquid nitrogen. The samples are stored at −70° C.

The Liver Extra piece (~100-300 mg) is dissected from the right lateral lobe and collected in tubes before placed in liquid nitrogen, to have as backup tissue from the study and can be used for re-analysis if necessary. The samples are stored at −70° C.

Biopsy Processing

Microtome Sectioning of Formalin Fixed Paraffin-Embedded (FFPE) Biopsies

FFPE biopsies are placed in 10% neutral buffered formalin (10% NBF) for approximately 24 h and then transferred to 70% EtOH and stored at 4° C. The FFPE biopsies are then placed in the Histokinette to infiltrate prior to embedding in blocks. Biopsy tissues are cut at 3 μm on a microtome and the sections are mounted on Superfrost Plus slides and stored at 4° C.

NAFLD Activity Score (NAS) and Fibrosis Stage

Liver samples stained with Hematoxylin and Eosin (H&E) or Picro Sirius Red (PSR) are given a score for NAS and fibrosis stage respectively using the clinical criteria outlined by Kleiner et al. 2005. Total NAS represents the sum of scores for steatosis, inflammation, and ballooning, and ranges from 0-8. Adapted from: Design and validation of a histological scoring system for nonalcoholic fatty liver disease, Kleiner et al., Hepatology 41; 2005

Histological Staining Procedures

In brief, slides with paraffin embedded sections are deparaffinated in xylene and rehydrated in series of graded ethanol.

Hematoxylin & Eosin (H&E) staining: Slides are incubated in Mayer’s Hematoxylin (Dako), washed in tap water, stained in Eosin Y solution (Sigma-Aldrich), dehydrated and cover slipped.

Sirius red (PSR) staining: Slides are incubated in Weigert’s iron hematoxylin (Sigma-Aldrich), washed in tap water, stained in Picro-sirius red (Sigma-Aldrich) and washed twice in acidified water. Excess water is removed by shaking the slides and the slides are then dehydrated in three changes of 100% ethanol, cleared in xylene and cover slipped.

Immunohistochemistry using single chromogen; IHC is performed using standard procedures. Briefly, after antigen retrieval and blocking of endogenous peroxidase activity, slides are incubated with primary antibody. The primary antibody is detected using a polymeric HRP-linker antibody conjugate. Next, the primary antibody is visualized with DAB as chromogen. Finally, sections are counterstained in hematoxylin and cover slipped. Slides are scanned under a 20X objective in a ScanScope AT slide scanner (Aperio).

Gene Expression Analysis Using RNAseq

RNA isolation: Tissue is collected and snap-frozen in liquid nitrogen. Samples are stored at −70° C. until processing. RNA is isolated using the NucleoSpin@kit (MACHEREY-NAGEL).

Library preparation and sequencing: A total of 10 ng-1 μg purified RNA from each sample is used to generate a cDNA library using the NEBNext® Ultram II Directional RNA Library Prep Kit for Illumina (New England Biolabs). cDNA libraries are then sequenced on a NextSeq 500 using NextSeq 500/550 High Output Kit V2 (Illumina).

Data analysis: The sequencing data is aligned to the genome of the animal species obtained from the Ensembl database using the Spliced Transcripts Alignment to a Reference (STAR) software. For the bioinformatic analysis, the quality of the data is evaluated using the standard RNA-sequencing quality control parameters, the inter- and intra-group variability is evaluated using principal component analysis and hierarchical clustering and the differentially expressed genes are identified using the R-package DESeq2. Downstream analyses such as pathway analysis or target identification are performed as agreed with the sponsor.

Blood and Plasma Assays

Alanine transaminase (ALT), Aspartate transaminase (AST), Triglycerides (TG) and Total Cholesterol (TC): Blood samples are collected in heparinized tubes and plasma is separated and stored at −70° C. until analysis. Samples are measured using commercial kits (Roche Diagnostics), on the cobas c 501 autoanalyzer.

Cytokeratin 18 (CK18-M30): Blood samples are collected in EDTA tubes and plasma is separated and stored at −70° C. until analysis. CK18 is measured using a commercial ELISA kit (Cusabio).

Insulin: Blood samples are collected in heparinized tubes and plasma is separated and stored at −70° C. until analysis. Insulin is measured using the commercial MSD platform (Meso Scale Diagnostics).

TIMP-1: Blood samples are collected in EDTA tubes and plasma is separated and stored at −70° C. until analysis. TIMP-1 is measured using a commercial ELISA kit (R&D Systems).

PIIINP: Blood samples are collected in EDTA tubes and plasma is separated and stored at -70° C. until analysis. PIIINP is measured using a commercial ELISA kit (Cusabio).

Tissue Assays

Triglycerides (TG) and Total cholesterol (TC): Liver samples are homogenized and TG and TC is extracted in 5% NP-40 by heating twice to 90° C. The samples are centrifuged and the TG and TC content is measured in the supernatant using commercial kits (Roche Diagnostics) on the cobas c 501 autoanalyzer.

Example 2: In Vivo Efficacy of Compound (I-2) Alone and in Combination with Compound 9 on Weight Loss in a High Fat Diet-Induced Obesity Model in hGLP1R-C57BL/6J Mice hGLP1R-C57BL/6J mice on >20 weeks high fat diet to induce obesity are administered Compound (1-2) alone or in combination with Compound 9. Other groups are administered alternative GLP-1R agonists, e.g., semaglutide. Body weight and food-intake are measured daily.

Animal Use

| | |
|---|---|
| Species | C57BL6/J-h-GLP1-r |
| Level | SPF |
| Weight | ~45 g |
| Age (Order) | 6-7 weeks |
| Age (Start) | 23-24 weeks |
| Sex | Male |
| Method of Identification | The mice are singly housed per cage with a unique cage |
| Animal Number | 127 |
| Animal Number (used) | 88 |

Mouse Generation 118 h-GLP1R-C57BL/6J mice at 6-7 weeks age old are fed a high fat diet (HFD, Research Diets D12492i 60% kcal) for ~20 weeks to obtain a diet induced obese (DIO) phenotype, while n=10 h-GLP IR-C57BL/6J mice are fed regular chow diet to serve as lean controls. All animals have ad libitum access to diet and water. The animal room environment is controlled (target conditions: temperature 20 to 24° C., relative humidity 30 to 70%). Temperature and relative humidity are monitored daily. An electronic time-controlled lighting system is used to provide a 12-hour light/12-hour dark cycle. 2-3 mice are housed per plastic cage, which is in accordance with the National Research Council "Guide for the Care and Use of Laboratory Animals." Enrichment toys are provided. Before the formal experiment, the animals are housed in a single cage and adapted to the environment for at least one week. Weight is measured once a week during modeling.

Study Procedure

Group Design

| Group ID | Treatment | Number | Dose level (mg/kg) | Dose volume (mL/kg) | Dose Method | Dose Frequency[1] Study Days | Start Dosing time |
|---|---|---|---|---|---|---|---|
| 1 | Vehicle (Lean) | 8 | — | 5 | PO | BID * 30 | 9:30 am, 17:30 pm |
| 2 | Vehicle (DIO) | 10 | — | 5 | PO | BID * 30 | 9:30 am, 17:30 pm |
| 3 | Danuglipron | 10 | 10 | 5 | PO | BID * 30 | 9:30 am, 17:30 pm |
| 4 | Compound (1-2) High | 10 | 10 | 5 | PO | BID * 30 | 9:30 am, 17:30 pm |

-continued

| Group ID | Treatment | Number | Dose level (mg/kg) | Dose volume (mL/kg) | Dose Method | Dose Frequency[1] Study Days | Start Dosing time |
|---|---|---|---|---|---|---|---|
| 5 | Compound (1-2) Low | 10 | 3 | 5 | PO | BID * 30 | 9:30 am, 17:30 pm |
| 6 | Compound 9 | 10 | 3 | 5 | PO | QD * 30 | 9:30 am |
| | Vehicle | 10 | — | 5 | PO | QD * 30 | 17:30 pm |
| 7 | Compound (1-2) High + Compound 9 | 10 | 10 + 3 | 5 | PO | QD * 30 | 9:30 am |
| | Compound (1-2) High + Vehicle | 10 | 10 | 5 | PO | QD * 30 | 17:30 pm |
| 8 | Compound (1-2) Low + Compound 9 | 10 | 3 + 3 | 5 | PO | QD * 30 | 9:30 am |
| | Compound (1-2) Low + Vehicle | 10 | 3 | 5 | PO | QD * 30 | 17:30 pm |
| 9 | Semaglutide | 10 | 10 nmol/kg | 2 | SC | QD * 30 | 9:30 am |
| | Saline | 10 | — | 2 | SC | QD * 30 | 17:30 pm |

[1]Test article is administered in the morning (9:30 to 10:30 am) for the Groups 6 and 9, and then administered a dose of vehicle (10% Solutol HS15: 90% sterile water, [v/v]) or saline (semaglutide vehicle) in the evening (17:30 to 18:30 pm) to balance treatment. For combination groups (7 and 8), Compound (1-2) and Compound 9 are administered in the morning (9:30 to 10:30 am), and then administered Compound (1-2) and vehicle in the evening (17:30 to 18:30 pm).
SC = subcutaneous injection.

Acclimation

Minus Day-14 to Day-1: After ~16 weeks of modeling to achieve an average model weight ~42 g, the mice are orally dosed with vehicle (10% Solutol HS15:90% sterile water, [v/v]) twice daily for 1-2 weeks to ensure a smooth dosing operation and to acclimate the mice to repeat dosing. Mice with body weights that have not stabilized by the end of the dosing acclimation are removed from the study.

Grouping

All animals on HFD are assigned into 8 groups based on baseline body weight, 3 day's food intake and body composition (Day-4).

Dose and Food Intake

Day 1-30: Body weight and food intake are recorded daily before dosing in the morning.

BID dosing: Dosing time is 9:30 am-10:30 am and 17:30 pm-18:30 pm.

QD dosing (For group 6 and 9): The dosing time of Compound 9 (3 mg/kg, PO), or semaglutide (10 nmol/kg, SC) is between 9:30 am-10:30 am, while vehicle (10% Solutol HS15:90% sterile water, [v/v]) or saline (semaglutide vehicle) is dosed between 17:30 pm-18:30 pm.

Body Composition

Baseline (Day-4), Day 24: Lean and fat mass are measured by Body composition analyzer (Bruker's minispec-LF90) in the morning.

Oral Glucose Tolerance Test (OGTT)

On day 28, random blood glucose and body weight of the mice are measured, mice are dosed with corresponding compounds or vehicle in the morning before fasting, then the mice are placed in new cages at 9:00 am and fasted for 6 hours, basal fasting glucose is measured by tail vein nick thereafter. Glucose is orally gavaged with 2 g/kg at a dose volume of 5 mL/kg. Blood glucose levels are measured at 0 (pre-dose), 15-, 30-, 60-, and 120-min post glucose dosing. The second dose is administrated after OGTT treatment.

Terminal Plasma and Tissue Collection

Day 31: The body weight and food intake of all mice is measured and then fasted for 6 hours, all mice are euthanized with $CO_2$ and bled via cardiac puncture. 500 μL blood samples will be processed for serum by centrifugation at 4° C., 3200×g for 10 min and stored at −80° C. for TC/TG/LDL/HDL/AST/ALT analysis (Analyzed by Biochemical analyzer: Beckman AU480/Hitachi 7180). 200 μL -300 μL blood samples are mixed with $K_2$EDTA anticoagulant and processed for plasma by centrifugation at 4° C., 3200×g for 10 min and stored at −80° C. for insulin and other possible analysis.

The weight of whole liver and epididymal fat are weighed and recorded. Left lobule of liver is fixed in formalin. The remaining liver is flash frozen and stored at −80° C. Pancreas is collected and fixed in formalin. Brown adipose, subcutaneous white adipose, and epididymal white adipose tissues and the brain hypothalamus region are frozen with liquid nitrogen and preserved and stored at −80° C. for optional qPCR analysis.

Hypothalmus Collection Procedure

The brain tissue is placed in the mold, and the olfactory bulb is placed in the center of the groove. The brain tissue is sliced into 8 coronal sections evenly spaced at 2 mm intervals. The third section (6-8 mm) of the coronal brain tissue is taken out, and the section is cut along the boundary of the purple part with a scalpel to separate the cerebral cortex. The remaining tissue is hypothalamus.

Blood Collection

Day 21: Animals in all groups are divided into 3 subgroups respectively. All mice for PK sampling, except for the pre-dose mice, receive the first dose of corresponding compound in the morning between 9:30 am to 10:30 am, 60 μL blood is collected from mice under the jaw into pre-chilled tubes containing 1.2 μL $K_2$ EDTA, and placed on ice. For the evening dose, the 8-hour post-1$^{st}$-dose samples are collected before the second dose of the day. Blood samples are processed to plasma within 1 hour of collection by centrifugation at 4° C., 3200×g for 10 min. About 30 μL of plasma is collected and stored at −80° C. for further analysis.

Data Processing and Analysis

The significances of the differences among groups and within groups are evaluated by one-way or two-way ANOVA using Graph Pad statistic software. A p-value of less than 0.05 are considered statistically significant.

Example 3. Effects of 4 Weeks of Treatment with Semaglutide Alone and in Combination with Compound 9 on Body Weight Regulation and Composition in Male DIO Mice at Thermoneutrality Methods Male C57BL/6JRj mice (n=48), 5 weeks of age were fed a high fat diet (HFD) for 24 weeks before treatment starts. Mice were randomized during week -1 into 7 groups (n=12 each group) based on body weight and fat tissue mass. The DIO mice were dosed once a day per oral (PO) and subcutaneous (SC) for 28 days.

Figure 3:
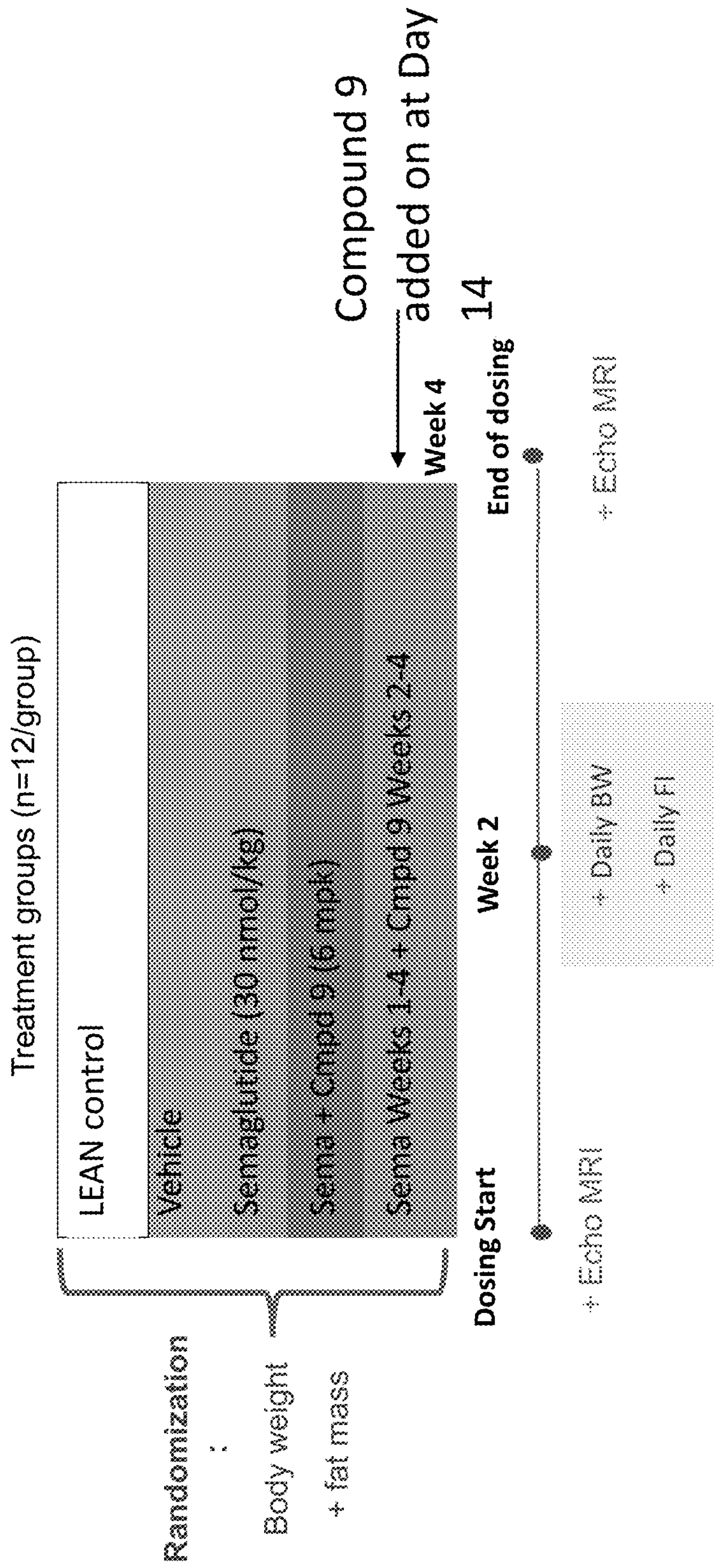
FIG. 3 depicts the study design for useage of a THRβ agonist (Compound 9) and a GLP-1R agonist (semaglutide) in combination for chronic weight management.

Group 1 received Vehicle (PO+SC),

Group 2 Semaglutide (30 nmol/kg, SC)+Vehicle (PO),

Group 3 Semaglutide (30 nmol/kg, SC)+Compound 9 (6 mg/kg, PO),

Group 4 Semaglutide (30 nmol/kg, SC) Wk1-4+Compound 9 Wk2-4 (6 mg/kg, PO). See FIG. 3.

Body weight, food intake and water intake were measured daily, EchoMRI was performed during week -1 and at week 4, and plasma samples were collected for sponsor at termination.

Results

Figure 4A:
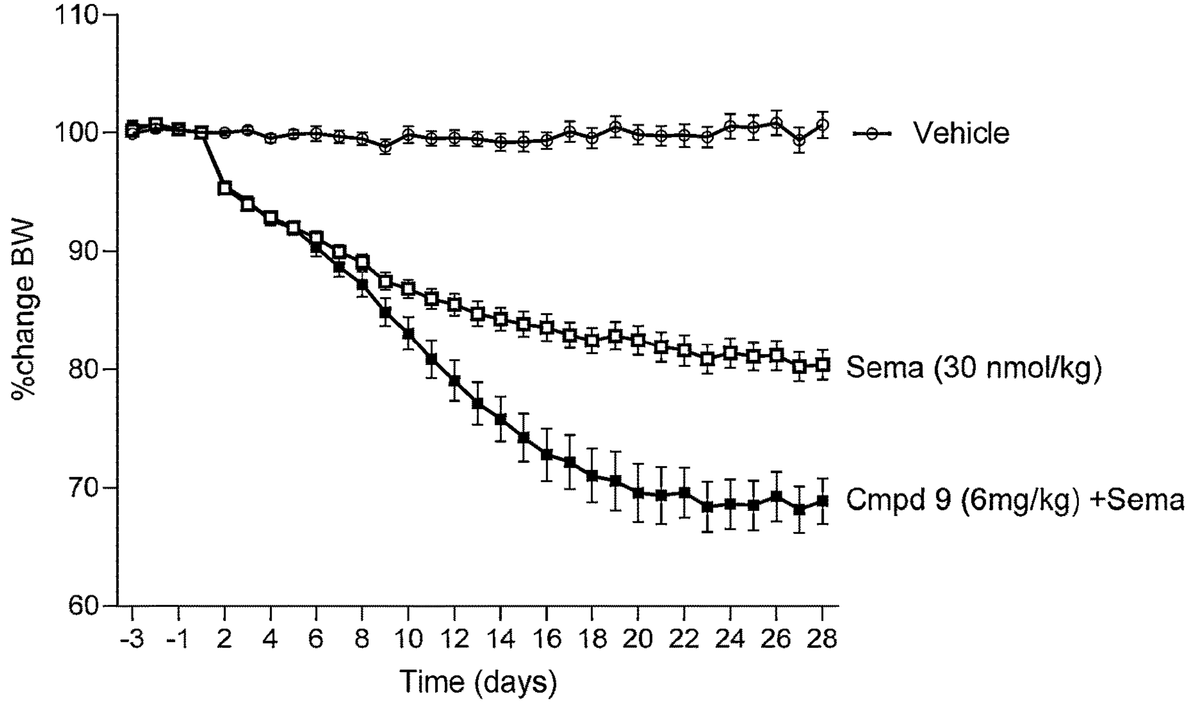
FIG. 4A depicts a graph showing the change in weight loss in Diet Induced Obese (DIO) mice over days of treatment with semaglutide alone or in combination with Compound 9.
Figure 4B:
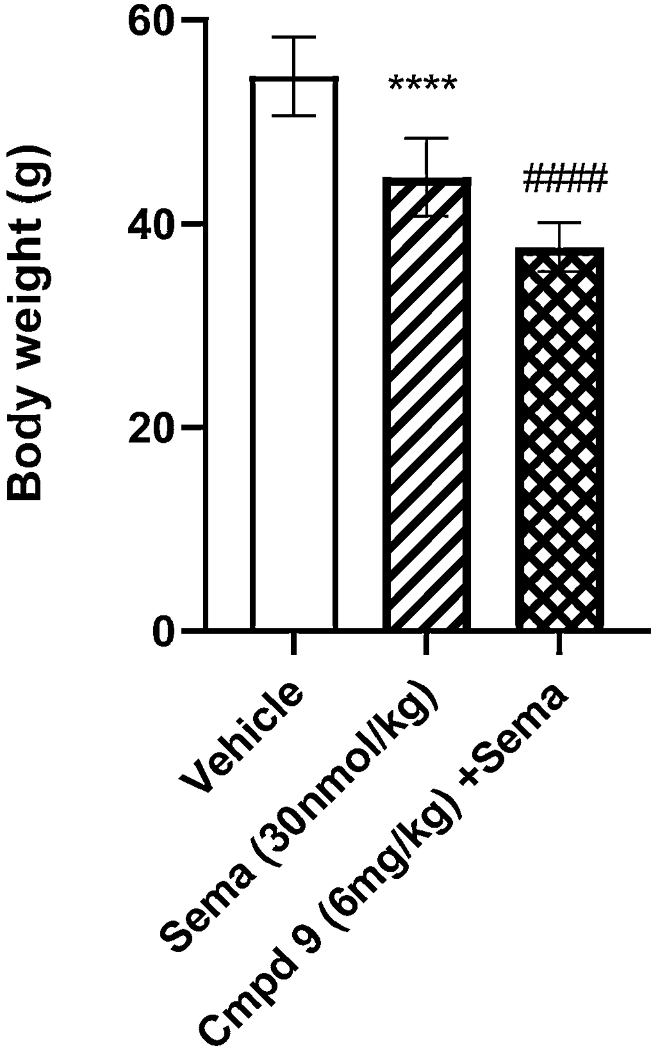
FIG. 4B depicts a graph showing the change in weight loss in DIO mice following treatment with semaglutide alone or in combination with Compound 9.
Figure 5A:
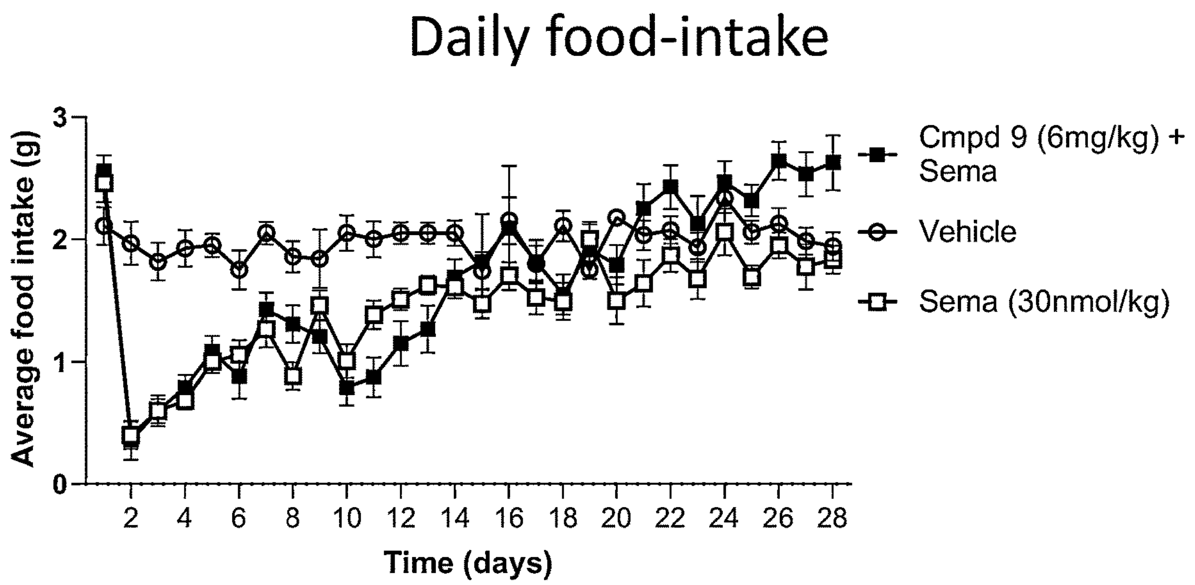
FIG. 5A depicts a graph showing the daily food intake in DIO mice over days of treatment with semaglutide alone or in combination with Compound 9.
Figure 5B:
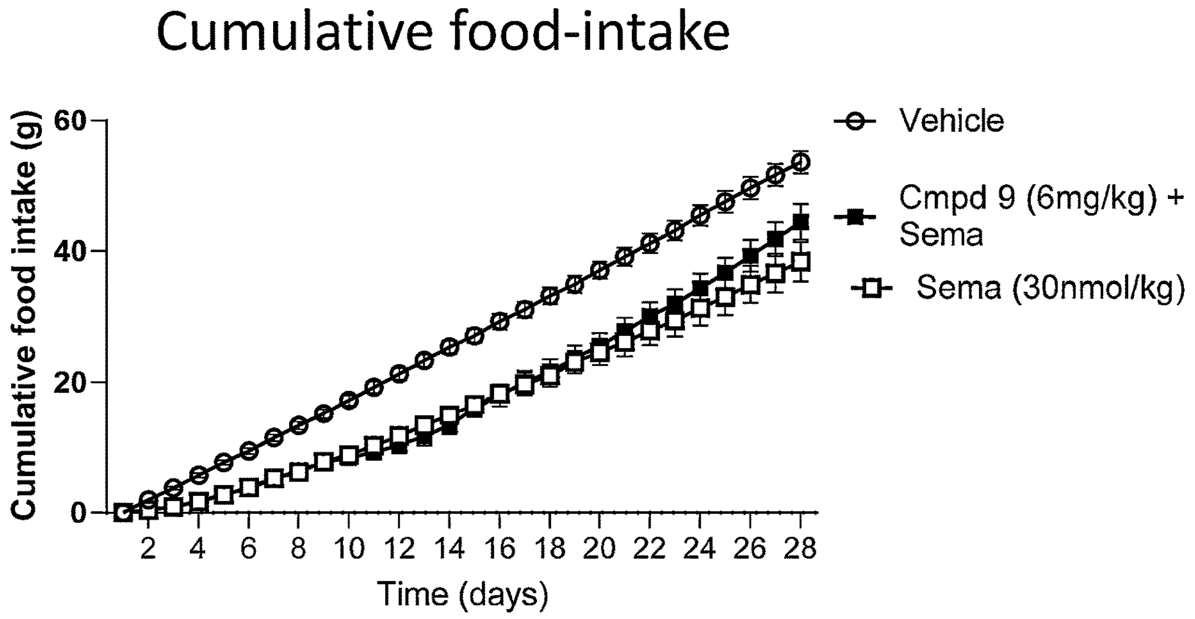
FIG. 5B depicts a graph showing the cumulative food intake in DIG mice over days of treatment with semaglutide alone or in combination with Compound 9.
Figure 6A:
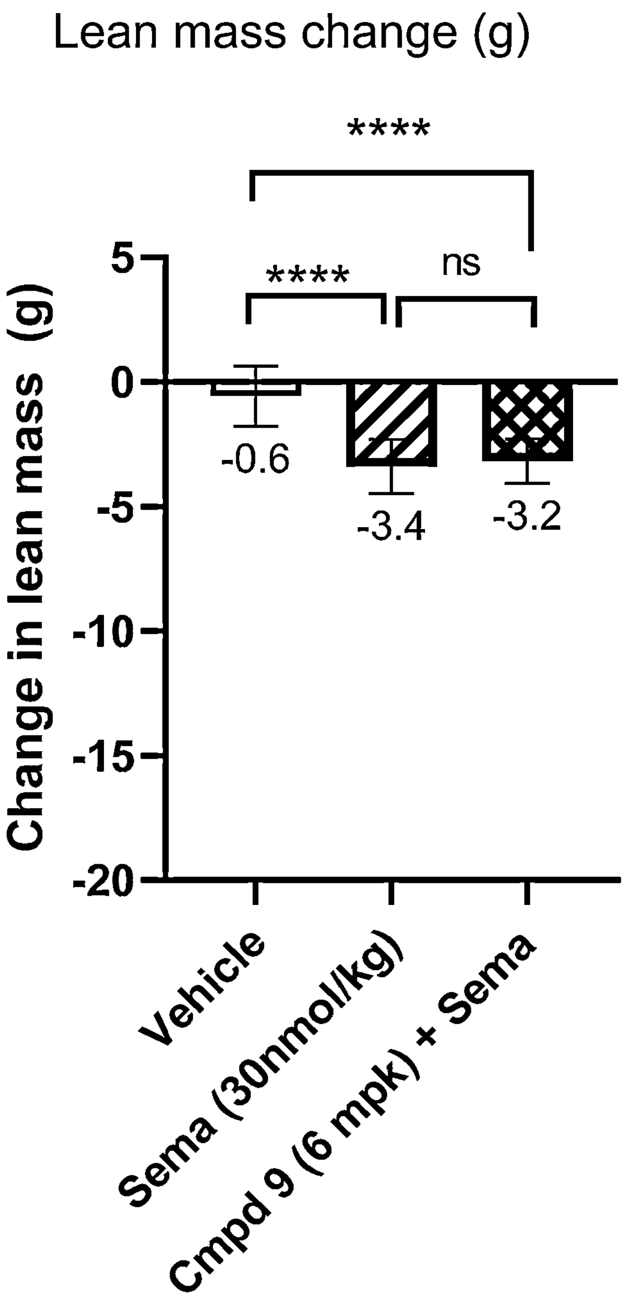
FIG. 6A depicts a graph showing the change in lean mass in DIG mice following treatment with semaglutide alone or in combination with Compound 9. ** Indicates p-value<0.0001 vs. Vehicle
Figure 6B:
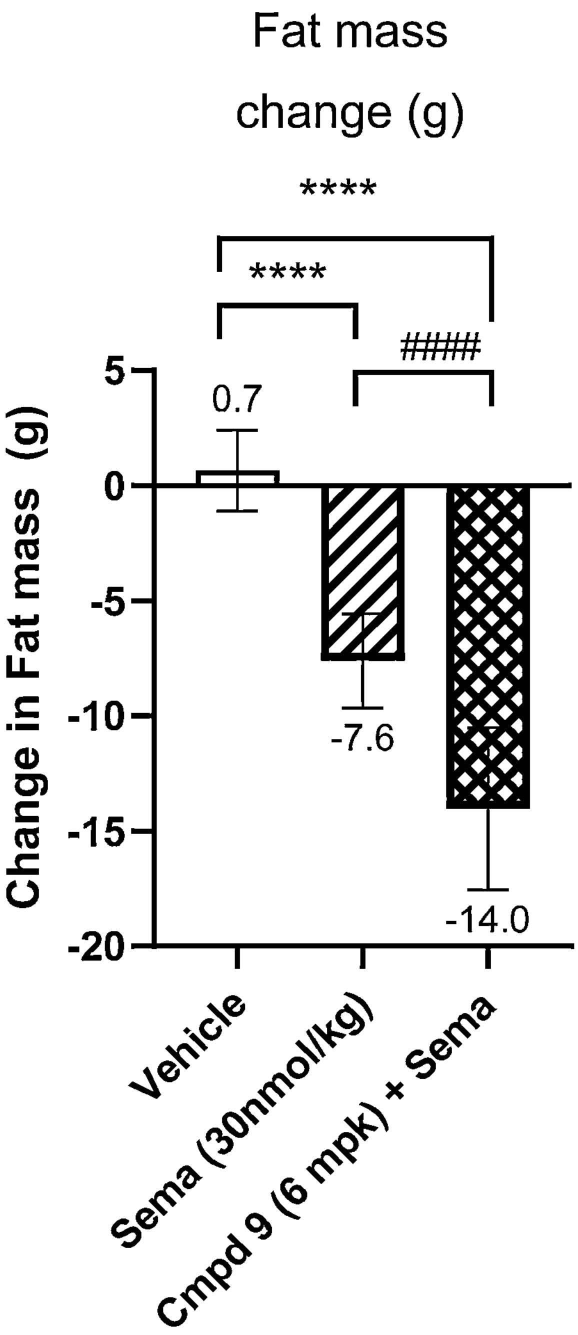
FIG. 6B depicts a graph showing the change in fat mass in DIO mice following treatment with semaglutide alone or in combination with Compound 9.  Indicates p-value<0.0001 vs. Vehicle; ** indicates p-value<0.001 vs. Semaglutide.
Figure 7A:
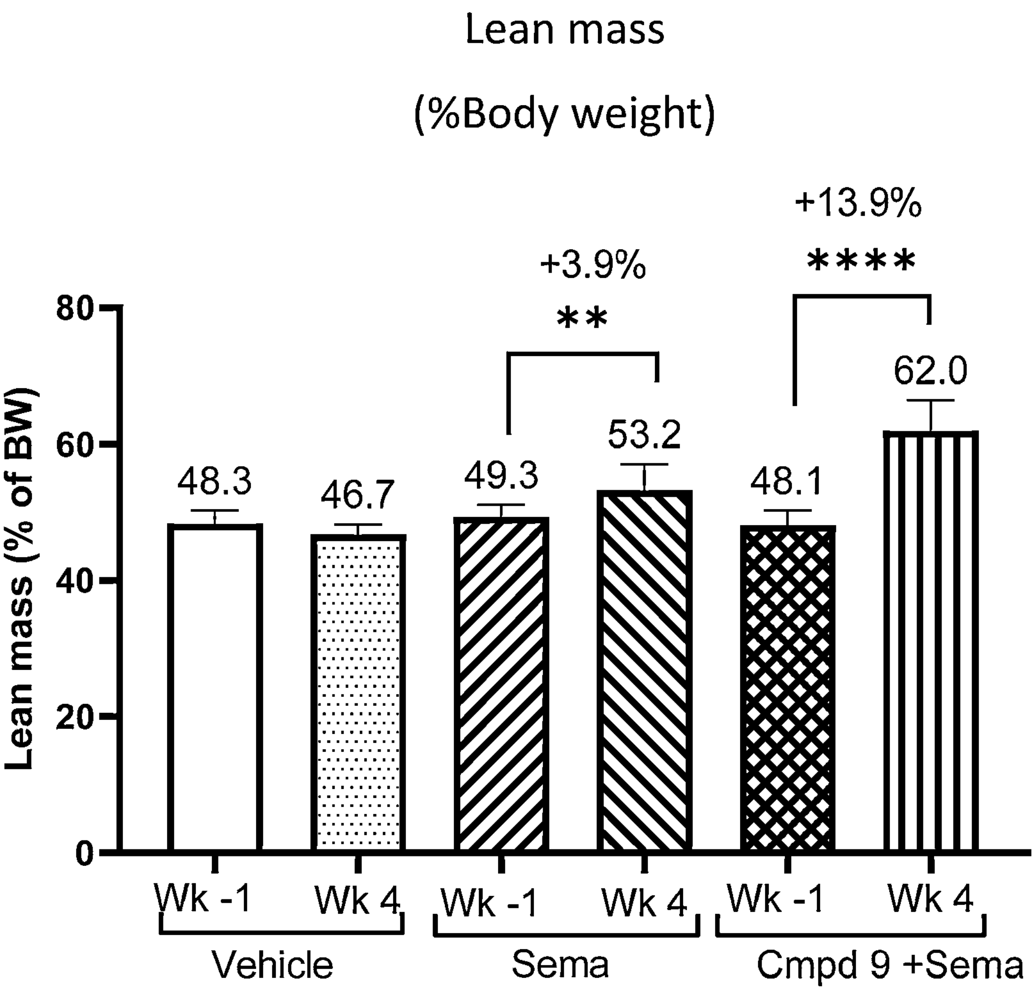
FIG. 7A depicts a graph showing the change in lean mass as a percent of bodyweight in DIG mice following treatment with semaglutide alone or in combination with Compound 9. The proportion of lean mass to total body mass increased by 3.9% following treatment by semaglutide alone and by 13.9% following treatment by semaglutide in combination with Compound 9.  indicates p-value of 0.0028 and ** indicates p-value<0.0001.
Figure 7B:
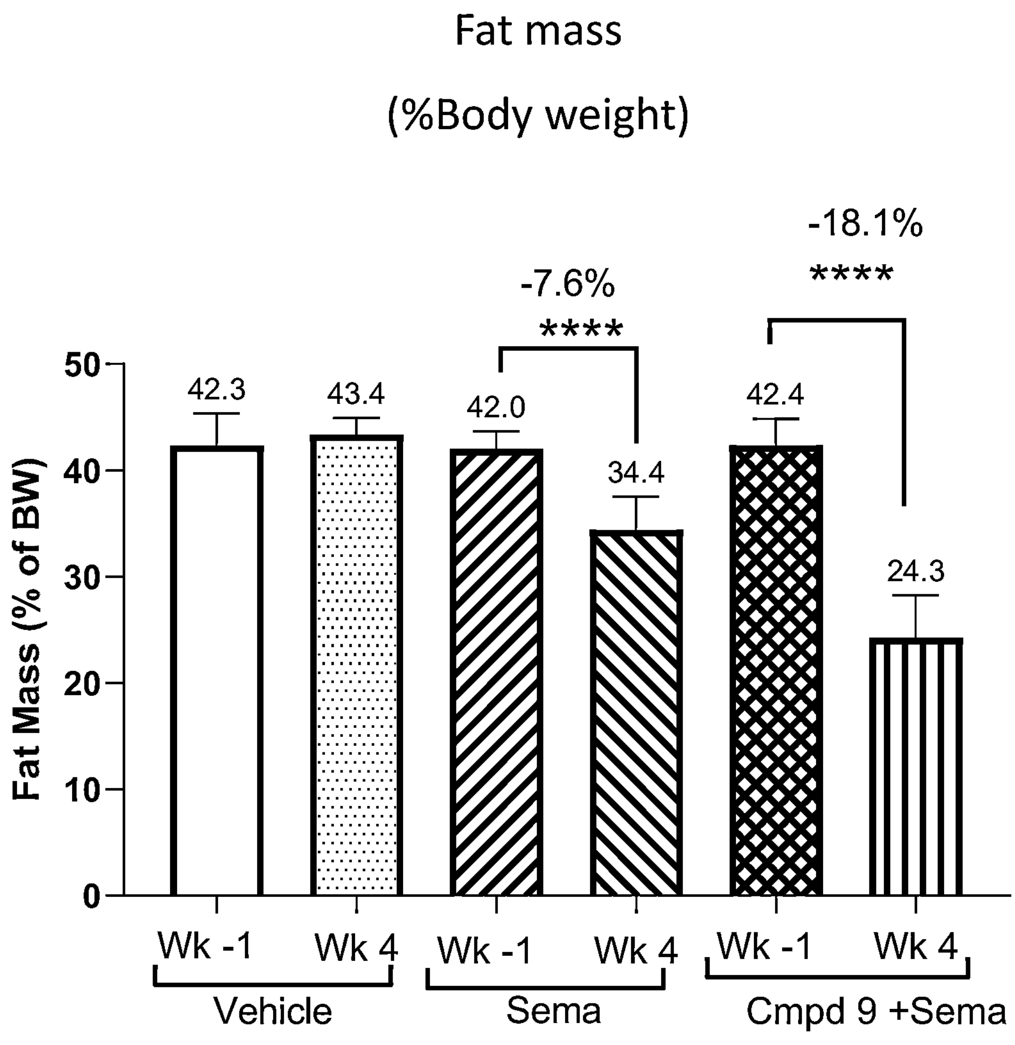
FIG. 7B depicts a graph showing the change in fat mass as a percent of bodyweight in DIO mice following treatment with semaglutide alone or in combination with Compound 9.
Figure 8:
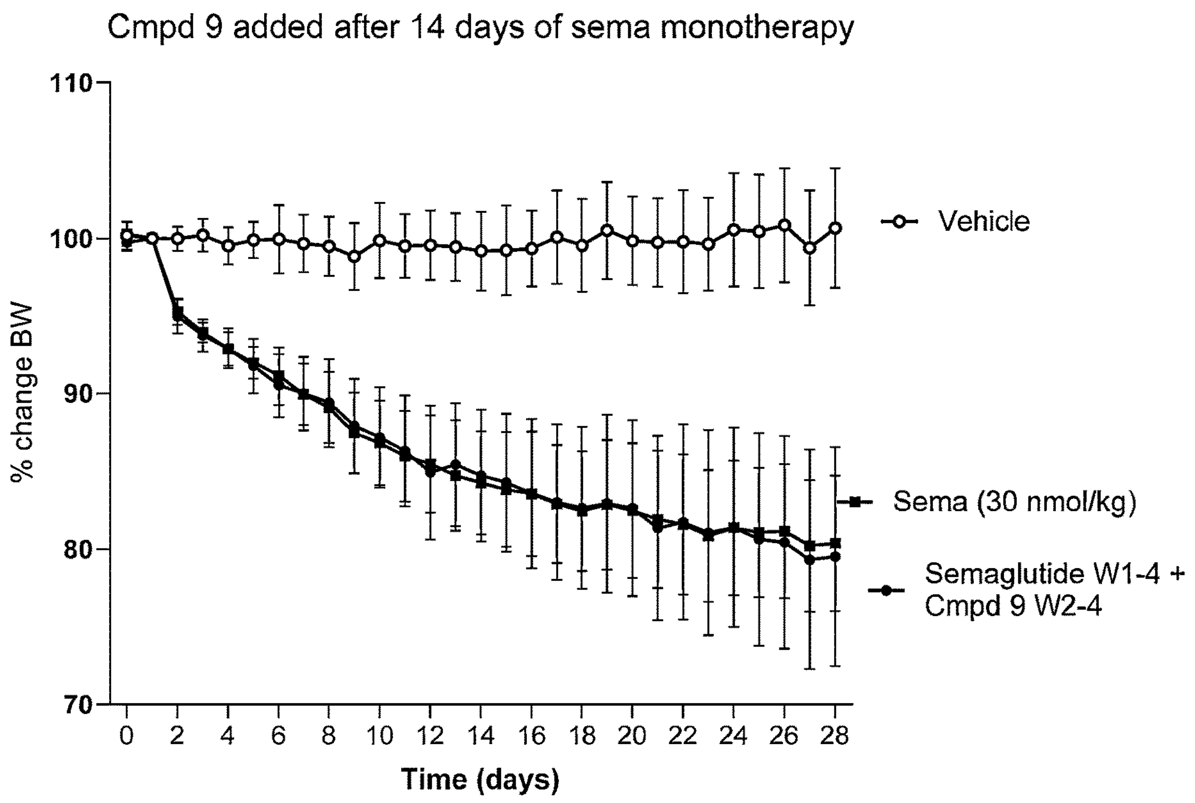
FIG. 8 depicts a graph showing the percent change from baseline in bodyweight in DIO mice following treatment with semaglutide alone or in combination with Compound 9, wherein Compound 9 is added after 14 days of semaglutide monotherapy.
Figure 9A:
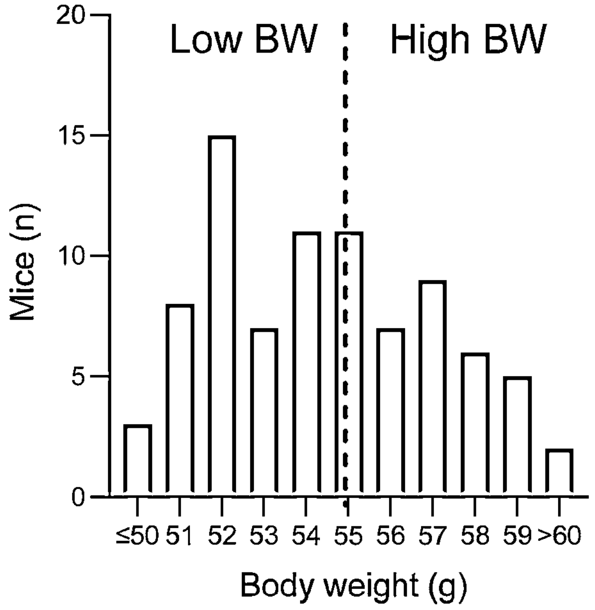
FIGS. 9A-C depict a graph showing the percent change from baseline in bodyweight (BW) in DIO mice following treatment with semaglutide alone or semaglutide in combination with Compound 9. In a Post hoc analysis mice were divided into two subgroups based on their initial starting body weight (FIG. 9A). Body weights ranged from 50-54.9 g (Low BW) and 55-60 g (High BW). Compound 9+Semaglutide has greater efficacy in mice with higher initial body weight (FIG. 9C) compared to those with lower initial body weight (FIG. 9B).
Figure 9B:
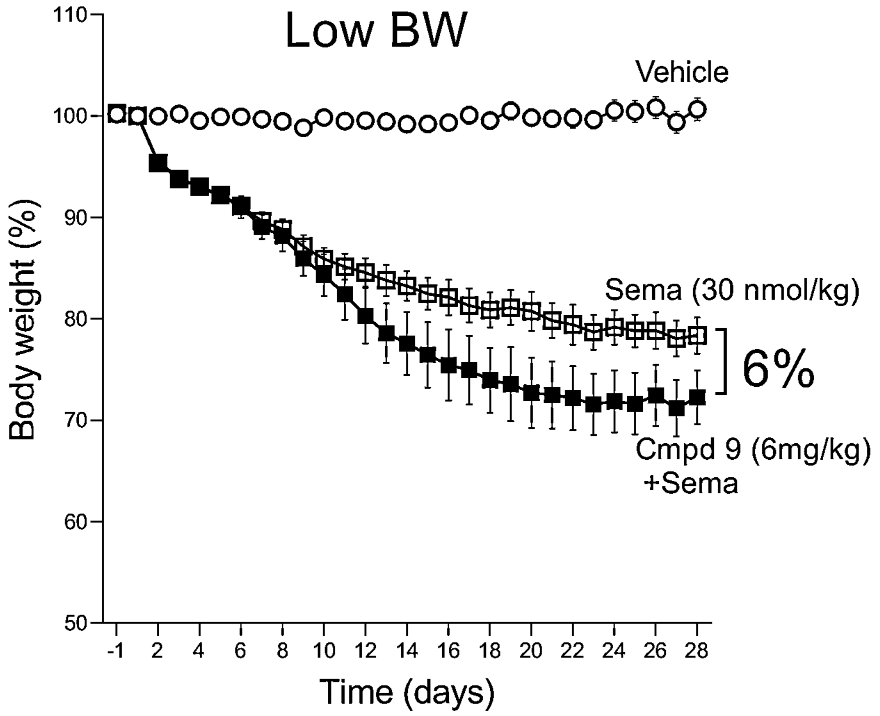
Figure 9C:
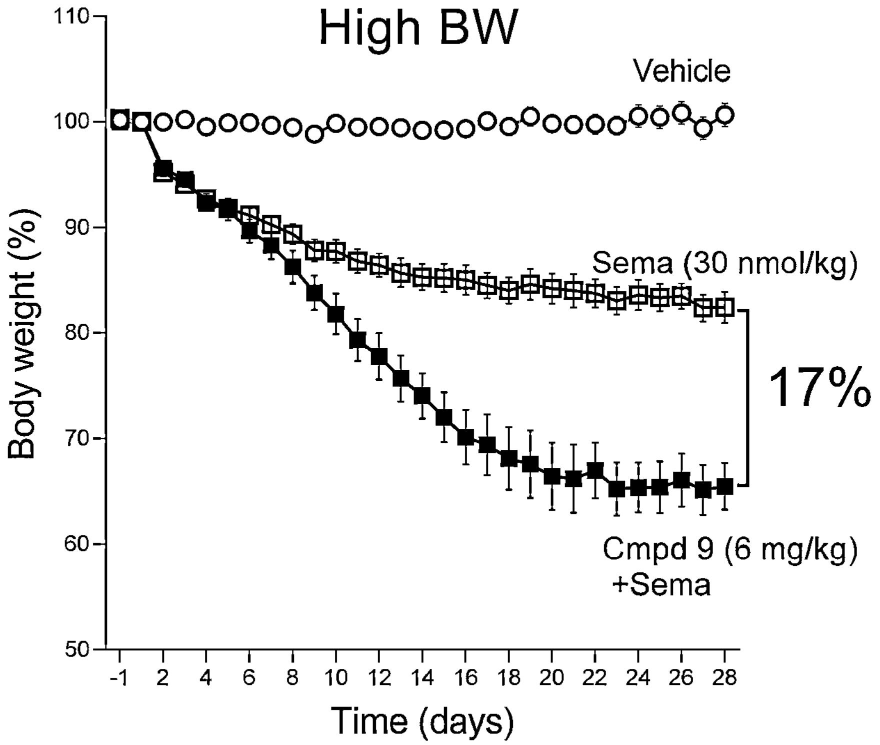

Treatment with Compound 9 in combination with Semaglutide (Semaglutide+Compound 9), induced a reduction of absolute and relative body weight, compared Semaglutide alone. See FIGS. 4-5.

Semaglutide+Compound 9 potentiated semaglutide-induced weight loss and led to a specific loss of fat mass without additional lean mass loss. See FIGS. 6-9.

Figure 10:
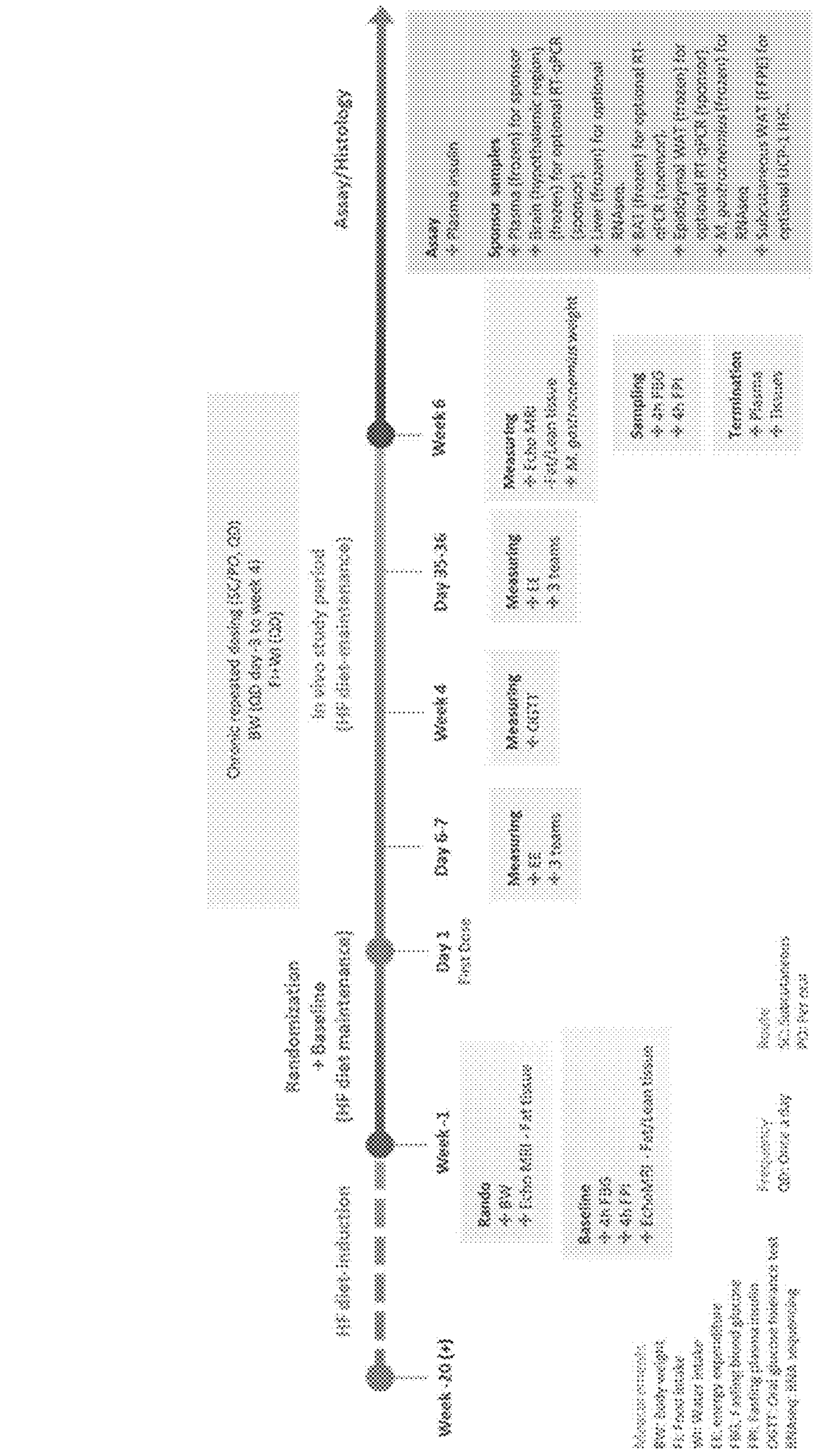
FIG. 10 depicts the design of a study to evaluate the effects of 6 weeks treatment with Compound 9 alone and in combination with Semaglutide on metabolic parameters, energy expenditure and glycemic control in male DIO mice at thermoneutrality.
Figure 11:
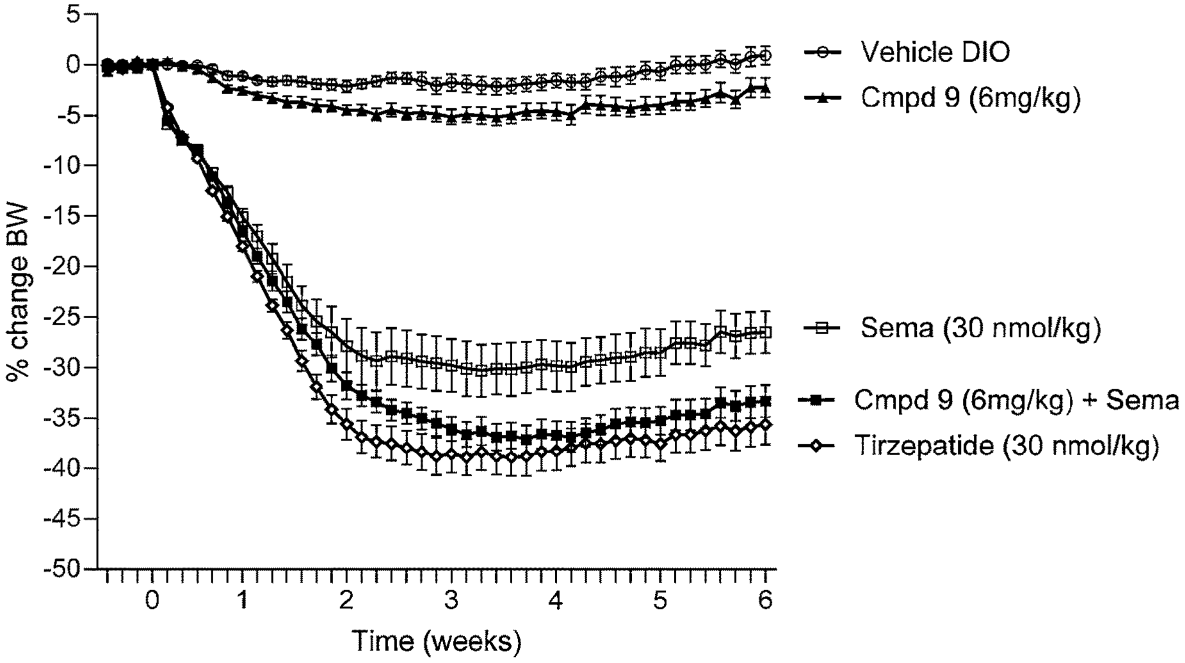
FIG. 11 depicts a graph showing the percent change from baseline in body weight in DIO mice following treatment with semaglutide alone, Compound 9 alone, semaglutide in combination with Compound 9, or tirzepatide alone. After 6 weeks of treatment, Compound 9+Semaglutide induced additional weight loss that was comparable to tirzepatide.****p-value<0.0001;*p-value<0.05.
Figure 12:
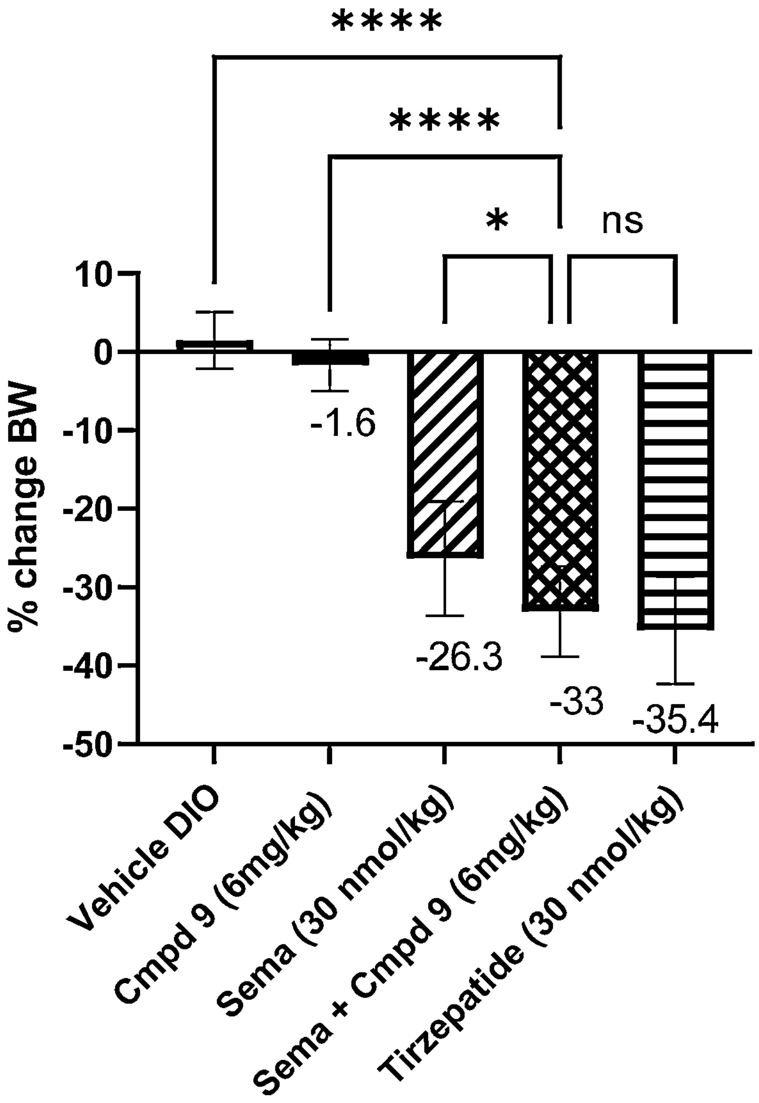
FIG. 12 depicts a graph showing the percent change from baseline in body weight in DIO mice following treatment with semaglutide alone, Compound 9 alone, semaglutide in combination with Compound 9, or tirzepatide alone. Compound 9+Semaglutide induced an additional −7% weight loss compared with semaglutide treatment alone.
Figure 13:
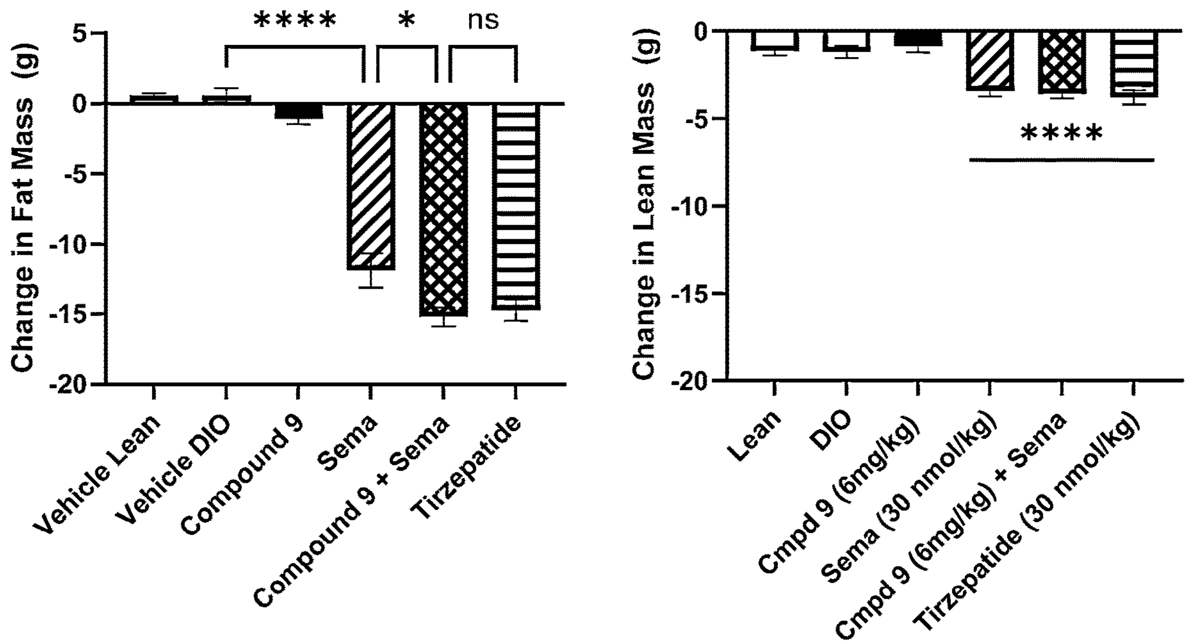
FIG. 13 depicts a pair of graphs showing the percent change in fat mass and lean mass following treatment with semaglutide alone, Compound 9 alone, semaglutide in combination with Compound 9, or tirzepatide. The body composition of mice was assessed on weeks 1 and 6 of the study using an EchoMRI 3-1 Body composition analyzer. Compound 9+Semaglutide enhanced fat loss compared with Semaglutide treatment alone while lean mass loss was similar between semaglutide alone and the combination of Compound 9+Semaglutide. ****p-value<0.0001;*p-value<0.05.
Figure 14:
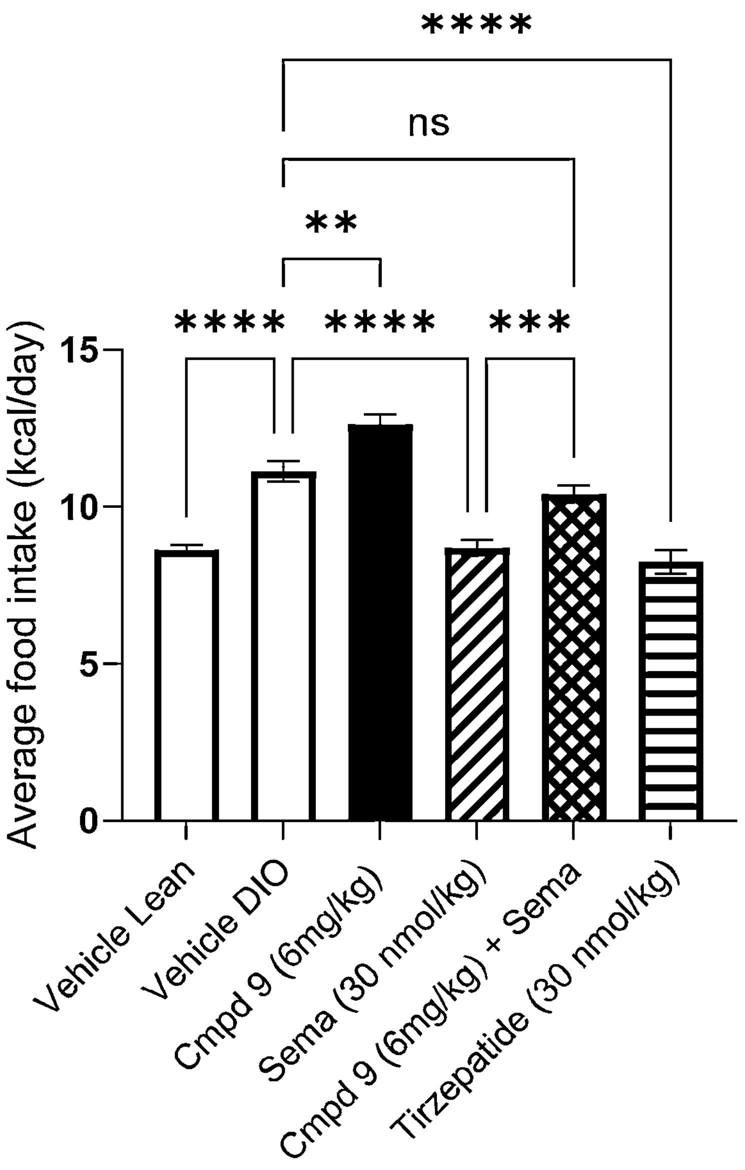
FIG. 14 depicts a graph showing the average food intake in DIO mice following treatment with semaglutide alone, Compound 9 alone, semaglutide in combination with Compound 9, or tirzepatide. Compound 9 normalized semaglutide-induced reduction in food intake. **p-value<0.0001;*p-value<0.001; **p-value<0.01.
Figure 15:
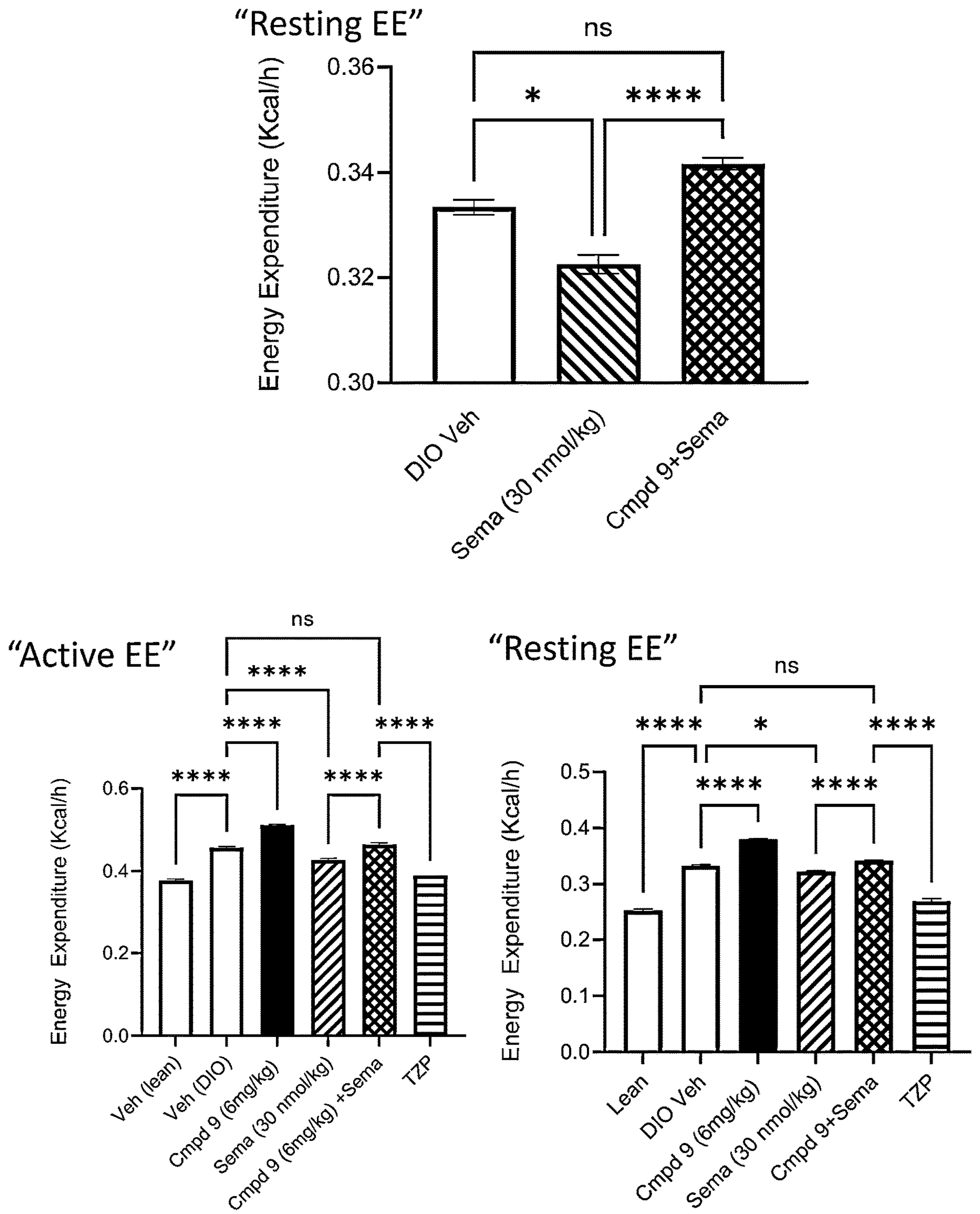
FIG. 15 depicts three graphs showing the energy expenditure (EE) assessed after week 4 in DIO mice following treatment with semaglutide alone, Compound 9 alone, semaglutide in combination with Compound 9, or tirzepatide. Compound 9+semaglutide prevented lowering of energy expenditure (EE) induced by weight Loss. Compound 9 restored energy expenditure to normal (DIO Veh) levels when combined with semaglutide. ****p-value<0.0001;*p-value<0.05.
Figure 16:
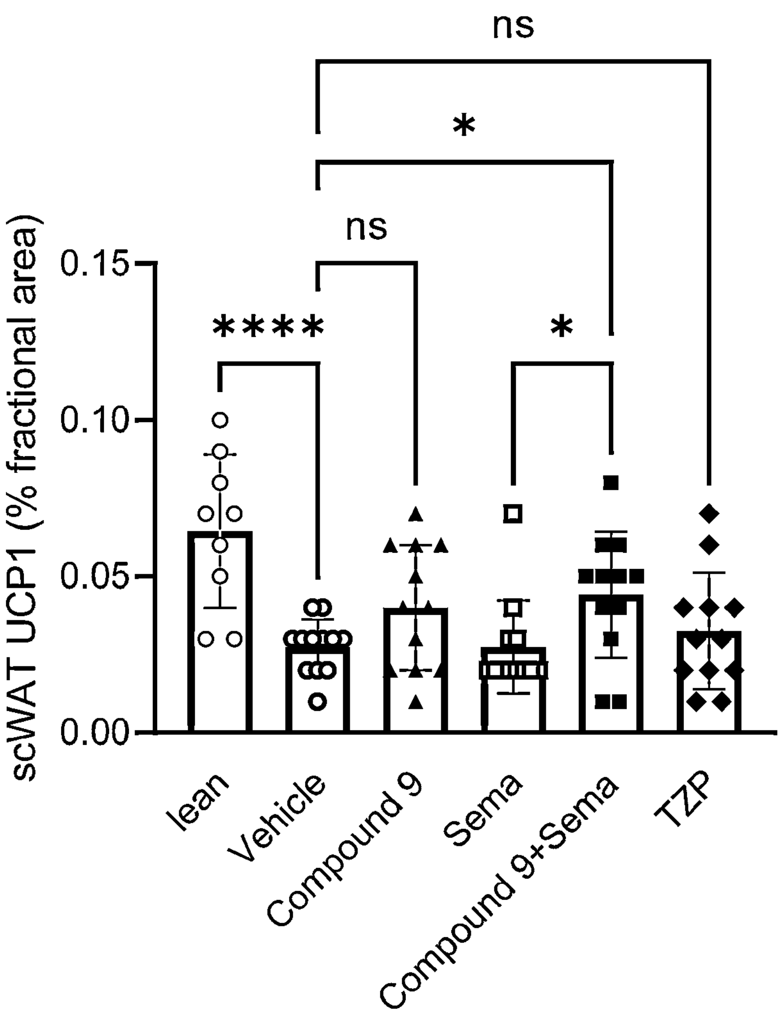
FIG. 16 depicts a graph showing uncoupling protein 1 (UCP-1) expression in DIO mice following treatment with semaglutide alone, Compound 9 alone, semaglutide in combination with Compound 9, or tirzepatide. Obesity lowered uncoupling protein 1 (UCP-1) expression in subcutaneous adipose tissue. Compound 9 partially restored the obesity induced lowering of UCP-1. *p<0.05, one way ANOVA followed by Fisher's LSD test.
Figure 17:
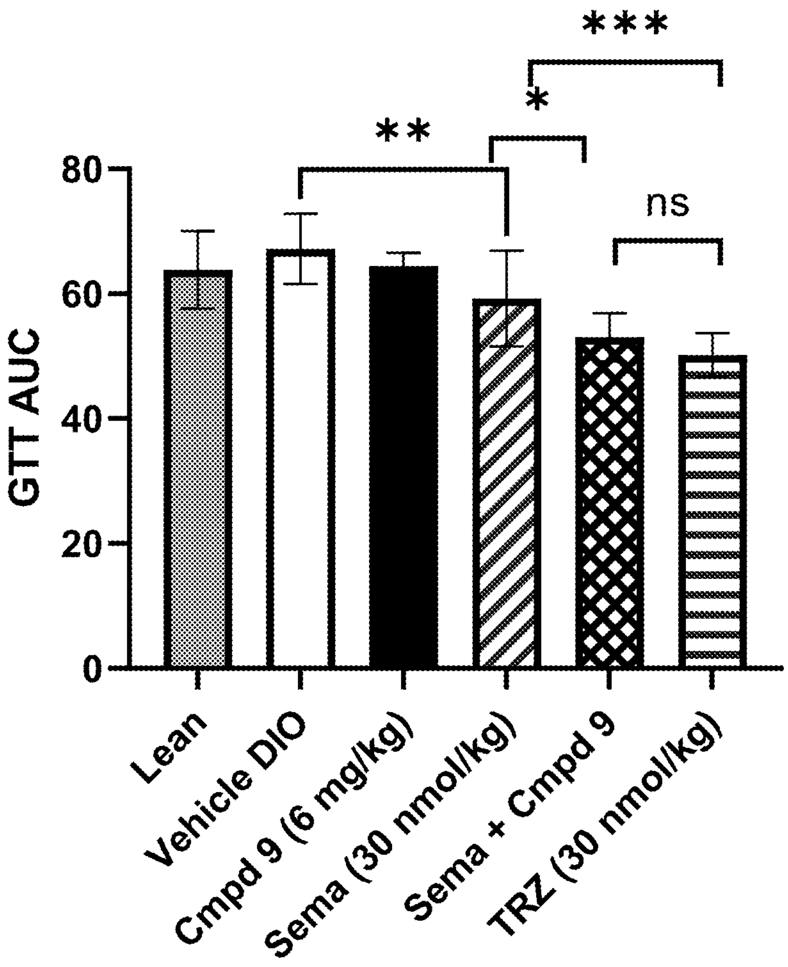
FIG. 17 depicts a graph showing the results of a glucose tolerance test (GTT) administered at week 4 to DIO mice following treatment with semaglutide alone, Compound 9 alone, semaglutide in combination with Compound 9, or tirzepatide. Compound 9+semaglutide further enhanced glucose tolerance compared with semaglutide treatment alone. *p-value<0.001; p-value<0.01; *p-value<0.05.

Example 4: Effect of 6 Weeks of Treatment with Compound 9 Alone and in Combination with Semaglutide on Metabolic Parameters, Energy Expenditure and Glycemic Control in Male DIO Mice at Thermoneutrality Methods Male C57BL/6JRj mice (5 weeks of age, n=70) were fed a high fat diet (n=60, 60% HFD, D12492, Ssniff) for 24 weeks, or a lean-chow diet (n=10, Altromin 1324) before treatment start. HFD animals were randomized during week -1 based on body weight, glucose levels and fat tissue mass into 5 treatments groups. Lean mice (group 1) were treated with vehicle (QD+QD, PO+SC) and DIO mice were treated (QD+QD, PO+SC) as follow: group 2 received vehicle (PO+SC), group 3 received Compound 9 6 mg/kg, PO+vehicle (SC), group 4 received Semaglutide (30 nmol/kg, SC)+vehicle (PO), group 5 received Compound 9 (6 mg/kg, PO)+Semaglutide (30 nmol/kg, SC) and group 6 received Tirzepatide (30 nmol/kg, SC)+vehicle (PO). Body weight, food and water intake were measured daily from day -3, body composition (EchoMRI) was measured during week -1 and week 6; energy expenditure was assessed at study day 5-7 and at study day 34-36. Fasting blood glucose and insulin levels were measured at baseline and termination, while an oral glucose tolerance test was performed at week 4. At termination, the M gastrocnemius muscle was weighted and collected for RNAseq analysis, while plasma, brain, liver, BAT, epidydimal and subcutaneous WAT depots were collected for sponsor. See FIG. 10

TABLE 4-1

Study Groups

| # | Group name | n in group | Animal model | Dose | Route of administration | Dosing frequency |
|---|---|---|---|---|---|---|
| 1 | Vehicle Lean | 9 | Lean mice | NA | PO + SC | QD + QD |
| 2 | Vehicle DIO | 12 | DIO mice | NA | PO + SC | QD + QD |
| 3 | Compound 9 + Vehicle | 12 | DIO mice | 6 mg/kg + NA | PO + SC | QD + QD |
| 4 | Semaglutide + Vehicle | 12 | DIO mice | 30 nmol/kg + NA | SC + PO | QD + QD |
| 5 | Compound 9 + Semaglutide | 12 | DIO mice | 6 mg/kg + 30 nmol/kg | PO + SC | QD + QD |
| 6 | Tirzepatide + Vehicle | 12 | DIO mice | 30 nmol/kg + NA | SC + PO | QD + QD |

Results (See FIGS. 11-17)

At week 1, compared to vehicle, Compound 9 in combination with Semaglutide reduced absolute and relative body weight, together with Semaglutide and Tirzepatide alone. Heat production was increased by Compound 9+Semaglutide treatment in the light phase, together with Semaglutide and Tirzepatide alone, while the RER was reduced compared to vehicle during both dark and light phase in these three treatment groups. Compound 9 in combination with Semaglutide increased oxygen consumption both during dark and light phase.

The OGTT test indicated an increased glucose disposal for the Compound 9+Semaglutide treated group, as well as Semaglutide and Tirzepatide alone, after 4 weeks of treatment, the combination of Compound 9 and Semaglutide reduced absolute and relative fat tissue mass compared to the vehicle-treated group, while absolute lean tissue mass was decreased and relative tissue mass was increased, and the same changes were observed for the Semaglutide and Tirzepatide treatment alone.

The energy expenditure measurement showed that after 5 weeks of treatment, Compound 9 alone increased both dark and light-phase heat production. Moreover, the oxygen consumption was significantly higher for the Compound 9+Semaglutide group during both dark and light phase, while only higher in the light phase for Semaglutide and Tirzepatide alone. Plasma insulin level was increased at week 6 upon Compound 9 treatment, while significantly lower in combination with Semaglutide, Semaglutide and Tirzepatide alone.

Example 5. Evaluating THR-B Agonist Compound 9 in Combination with a GLP-1R Agonist (e.g., Orforglipron)

Background

GLP-1R regulates post prandial blood glucose and satiety. The later effect can induce weight loss but efficacy is limited by metabolic adaptation, a compensatory process that lowers energy expenditure (EE). Moreover, the higher dose levels of GLP-1R needed to achieve clinical meaningful weight loss, are associated with more severe and frequent GI-related side effects including nausea and emesis, which can negatively impact patient compliance. Mechanisms to improve the effectiveness of GLP-1 based therapies at lower doses, could mitigate GI-related side effects and improve patient compliance and outcomes. In addition, combining these mechanisms in an all-oral medication could further improve patient compliance over injectable medications Thyroid hormone receptor beta (THR) plays a central role in regulating energy metabolism. Compound 9 is an orally bioavailable, highly selective, thyroid receptor beta agonist. In preclinical models of obesity, Compound 9 enhances the weight loss efficacy of the injectable peptide GLP-1R agonist semaglutide by mitigating the lowering of EE associated with weight loss and increasing fat mass loss, while preserving relative lean mean loss. In this example, Compound 9 was tested in combination with orforglipron, an orally bioavailable GLP-R agonist in late-stage clinical development for the treatment of type II diabetes myelitis (T2DM) and obesity. Specifically, the combination of Compound 9 with a low dose of orforglipron was tested to see if it could achieve a similar weight loss efficacy as a 10-fold higher dose of orforglipron in monotherapy. Like other small molecule GLP-1R agonists, orforglipron is inactive on rodent GLP-1R. Therefore, for the current study, diet-induced obese (DIO) transgenic mice expressing human GLP-1R (hGLP-1R) were used to assess in vivo efficacy Compound 9 in combination with orforglipron.

Methods

DIO hGLP-1R mice were housed at room temperature (21-25° C.) with a relative humidity of 40-70%. Temperature and relative humidity were monitored and recorded twice daily. An electronic time-controlled lighting system was used to provide a 12 h light/12 h dark cycle, 19:00 pm-7:00 am, lights out and enrichment toys were provided. The mice were fed high fat diet (HFD, Research Diets 12492, 60% kca, 1% fat) for >50 weeks to induce obesity. Mice were acclimated to once-daily (QD) oral dosing (per os, PO) for 1 week with body weight and food intake measured on consecutive 4 days prior to dosing start (Day 1). Body mass composition was measured by EchoMRI (Bruker Minispec LF90II) on Day 0 and mice were randomized to treatment groups (Table 5-1) based on baseline body weight, food intake, and body composition.

Test compounds were formulated in vehicle (10% [v/v] Solutol HS15+90% [v/v]saline) and mice were treated QD PO for 21 days with vehicle, Compound 9 (3 mg/kg), orforglipron (0.2 and 2 mg/kg), and Compound 9 (3 mg/kg) in combination with orforglipron (0.2 mg/kg). Body weight and food intake were measured daily, and mice were maintained on HFD throughout the study period. On Day 20 of the study, plasma samples were collected at predose (O), 2-, 4-, 8-, and 24-hours postdose for pharmacokinetic analyses of Compound 9, orforglipron, and combination treatment groups. Body mass composition was assessed on Day 19. Liver was collected and weighed at study termination and portions were preserved for steatosis assessment by histology. Subcutaneous fat was collected and weighed at study termination. A sample of subcutaneous fat tissue was assessed for UCP-1 expression by qPCR and Western blot analyses.

TABLE 5-1

| Treatment groups | | | | | | |
|---|---|---|---|---|---|---|
| Group ID | Treatment | n | Dose (mg/kg) | Dose volume (mL/kg) | Dose Method | Dose Frequency |
| 1 | Vehicle | 6 | — | 5 | PO | QD * 21 days |
| 2 | Compound 9 | 6 | 3 | 5 | PO | QD * 21 days |
| 3 | Orforglipron | 7 | 2 | 5 | PO | QD * 21 days |
| 4 | Orforglipron | 7 | 0.2 | 5 | PO | QD * 21 days |
| 5 | Compound 9 + Orforglipron | 7 | 0.2 + 3 | 5 | PO | QD * 21 days |

Results

Figure 18:
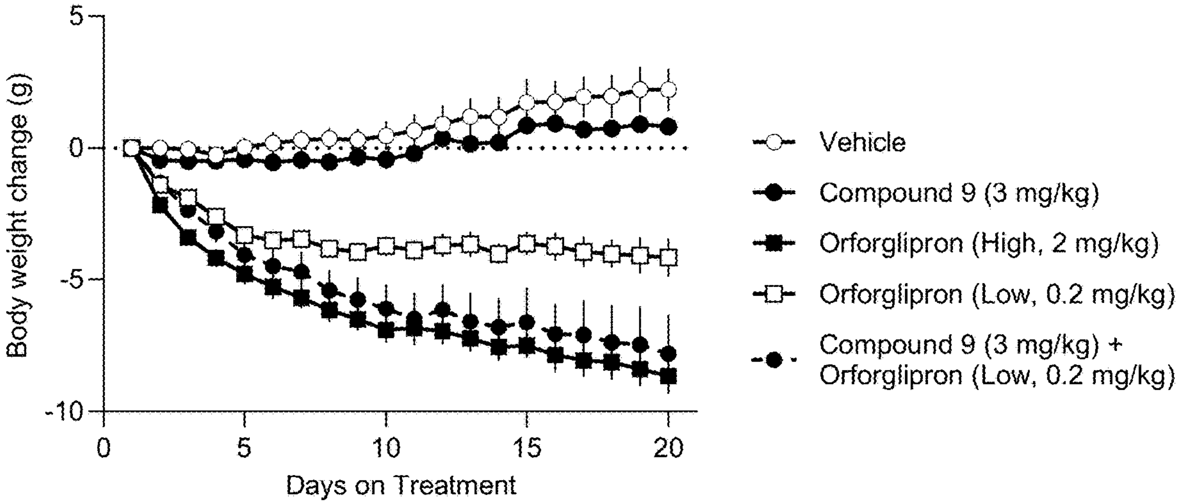
FIG. 18 depicts a graph showing body weight changes from baseline over time in DIO hGLP-1R mice following treatment with Compound 9 alone, orforglipron alone, or orforglipron in combination with Compound 9. Daily change from baseline in body weight (g) shown as mean (SE) with n=6-7 mice per group. Vehicle, Compound 9 (3 mg/kg), and orforglipron (0.2 mg/kg and 2 mg/kg) were dosed once daily by oral gavage.
Figure 19:
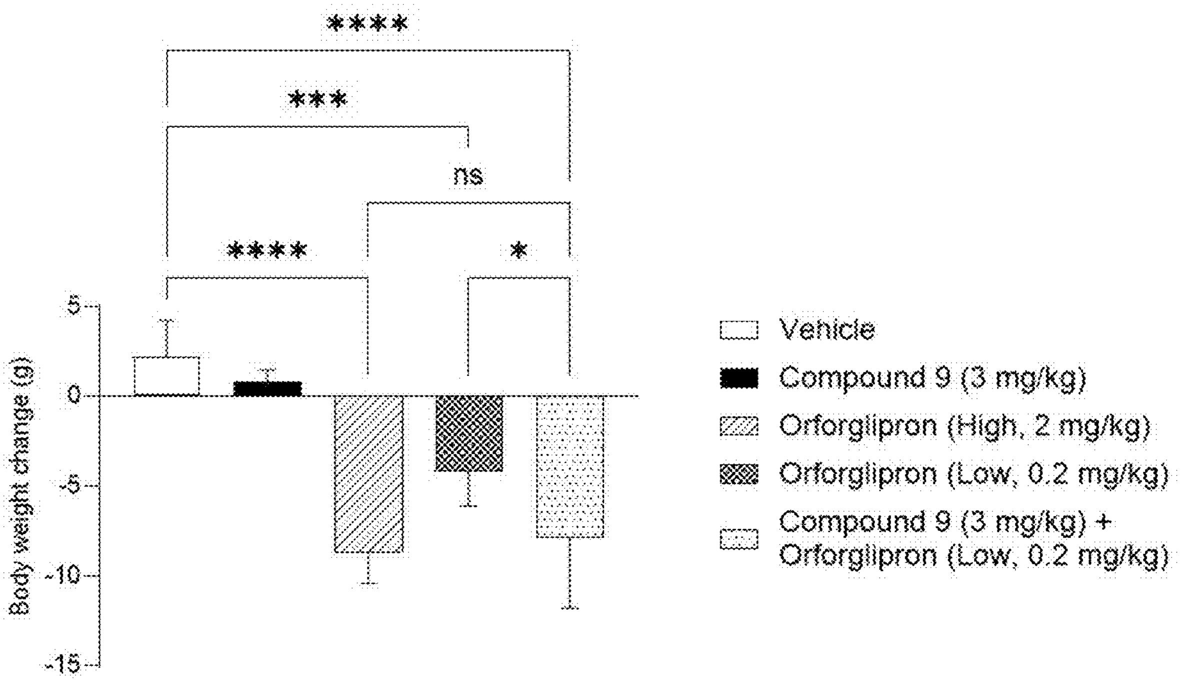
FIG. 19 depicts a graph showing body weight change from baseline in DIO hGLP-1R mice following treatment with Compound 9 alone, orforglipron alone, or orforglipron in combination with Compound 9. Change from baseline at 20 day in body weight (g) shown as mean (SD) with n=6-7 mice per group. Statistical significance determined by ordinary one-way ANOVA with correction for multiple comparisons. *p-value<0.05, *p-value<0.001, **p-value<0.0001. ns=not significant.
Figure 20:
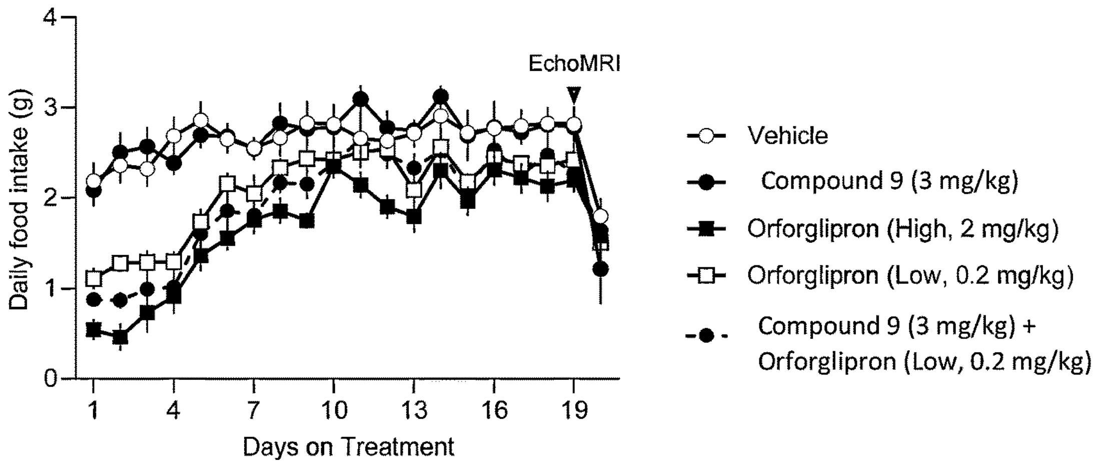
FIG. 20 depicts a graph showing daily food intake over time in DIO hGLP-1R mice following treatment with Compound 9 alone, orforglipron alone, or orforglipron in combination with Compound 9. Daily food intake (g) shown as mean (SE) with n=6-7 mice per group. Measurement of body mass composition on Day 19 leading to acute food intake decrease is denoted.

Treatment with orforglipron (0.2 mg/kg and 2 mg/kg PO QD) resulted in dose-dependent body weight decreases over time (FIG. 18), while body weights in mice treated with vehicle (PO QD) or Compound 9 (3 mg/kg PO QD) alone remained relatively unchanged during the study period. In contrast, mice treated with the combination of Compound 9 (3 mg/kg PO QD) and orforglipron (0.2 mg/kg PO QD) showed comparable weight loss to the high dose of orforglipron (2 mg/kg PO QD) monotherapy. On Day 20 decreases in body weight were significant for mice treated with orforglipron (0.2 and 2 mg/kg) and Compound 9 in combination with orforglipron (0.2 mg/kg) (FIG. 19). Moreover, treatment with the combination resulted in significantly greater weight loss compared with the low dose of orforglipron (0.2 mg/kg) monotherapy. Daily food intake was profoundly reduced in a dose-dependent manner during the first few days in mice treated with orforglipron before steadily increasing towards vehicle control levels (FIG. 20). Daily food intake was similar between mice treated with low dose orforglipron (0.2 mg/kg PO QD) and those treated with Compound 9 (3 mg/kg PO QD) in combination with orforglipron (0.2 mg/kg PO QD). Daily food intake was similar in mice treated with vehicle and Compound 9 (3 mg/kg PO QD). All treatment groups showed acute decreases in food intake following body mass composition measurements on Day 19, suggestive of animal handling induced stress response.

Figure 21A:
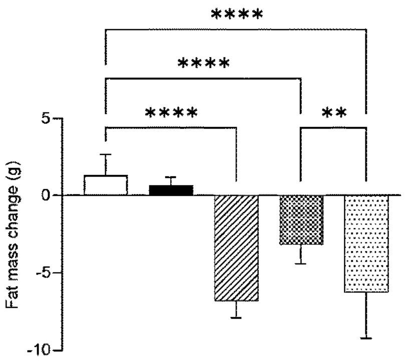
FIG. 21A and FIG. 21B depict two graphs showing body mass composition change from baseline in DIO hGLP-1R mice following treatment with Compound 9 alone, orforglipron alone, or orforglipron in combination with Compound 9. Day 19 change from baseline in fat (FIG. 21A) and lean (FIG. 21B) mass (g) shown as mean (SD) with n=6-7 mice per group. Statistical significance determined by ordinary one-way ANOVA with correction for multiple comparisons. *p-value<0.05, p-value<0.01, *p-value<0.001, ****p-value<0.0001. ns=not significant.
Figure 21B:
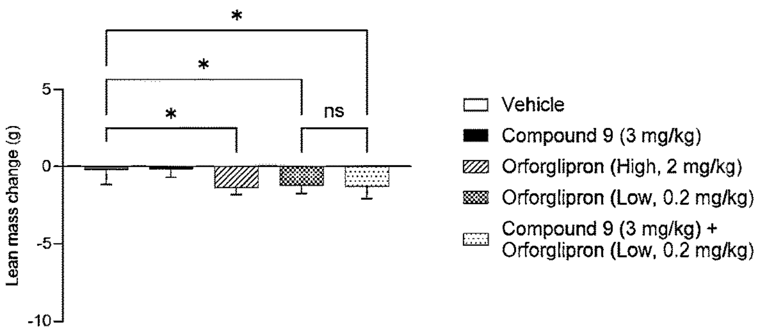

Treatment with orforglipron (0.2 mg/kg and 2 mg/kg PO QD) resulted in a dose-dependent decrease in fat mass (FIG. 21A), while fat mass remained relatively unchanged in mice treated with vehicle (PO QD) or Compound 9 (3 mg/kg PO QD). In contrast, the mice treated with the combination of Compound 9 (3 mg/kg PO QD) and orforglipron (0.2 mg/kg PO QD) showed comparable fat mass loss to the high dose of orforglipron (2 mg/kg PO QD) monotherapy. Lean mass loss was statistically significant in mice treated with orforglipron (0.2 mg/kg and 2 mg/kg PO QD) compared to vehicle treatment (FIG. 21B). Mice treated Compound 9 in combination with orforglipron (0.2 mg/kg PO QD) showed a similar mean decrease in lean mass, which was not statistically significant relative to orforglipron (0.2 mg/kg PO QD) monotherapy. Lean mass loss was negligible in mice treated with vehicle or Compound 9 (3 mg/kg PO QD).

Figure 22:
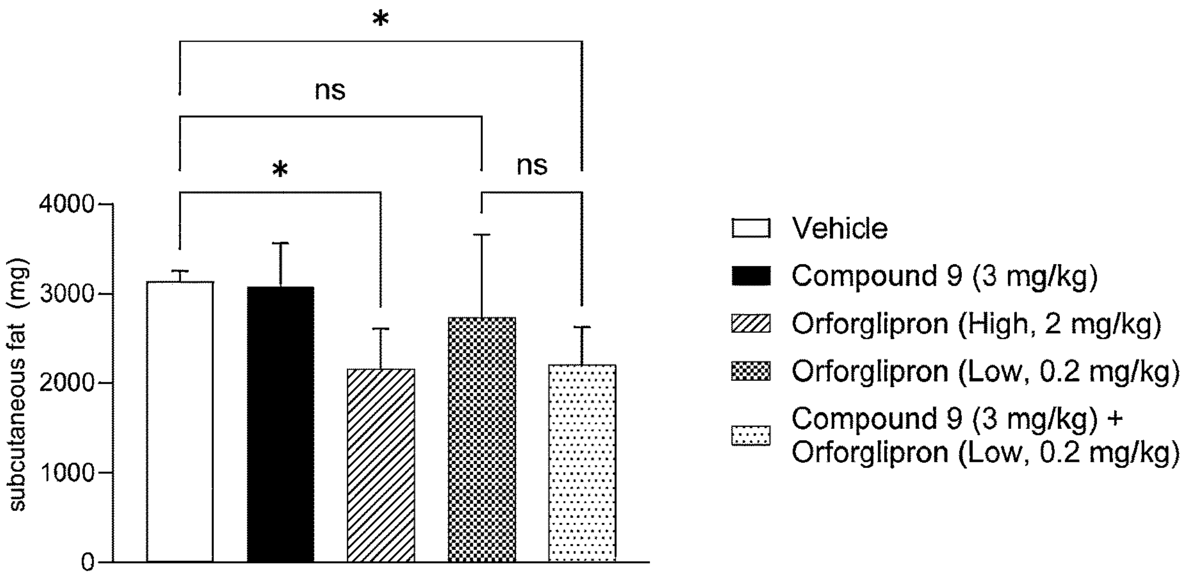
FIG. 22 depicts a graph showing terminal subcutaneous fat in DIO hGLP-1R mice following treatment with Compound 9 alone, orforglipron alone, or orforglipron in combination with Compound 9. Data represents mean (SD) subcutaneous fat (mg) collected at study termination with n=6-7 mice per group. Statistical significance determined by ordinary one-way ANOVA with correction for multiple comparisons. *p-value<0.05. ns=not significant.

Treatment with orforglipron (0.2 mg/kg and 2 mg/kg PO QD) resulted in a dose-dependent decrease in subcutaneous fat, although only the high dose was significantly different from vehicle treatment (FIG. 22. Treatment with the combination of Compound 9 (3 mg/kg PO QD) and orforglipron (0.2 mg/kg PO QD) showed similar levels of subcutaneous fat compared to the high dose of orforglipron (2 mg/kg PO QD). The subcutaneous fat levels in mice treated Compound 9 (3 mg/kg PO QD) alone were not significantly different from mice treated with vehicle.

Figure 23:
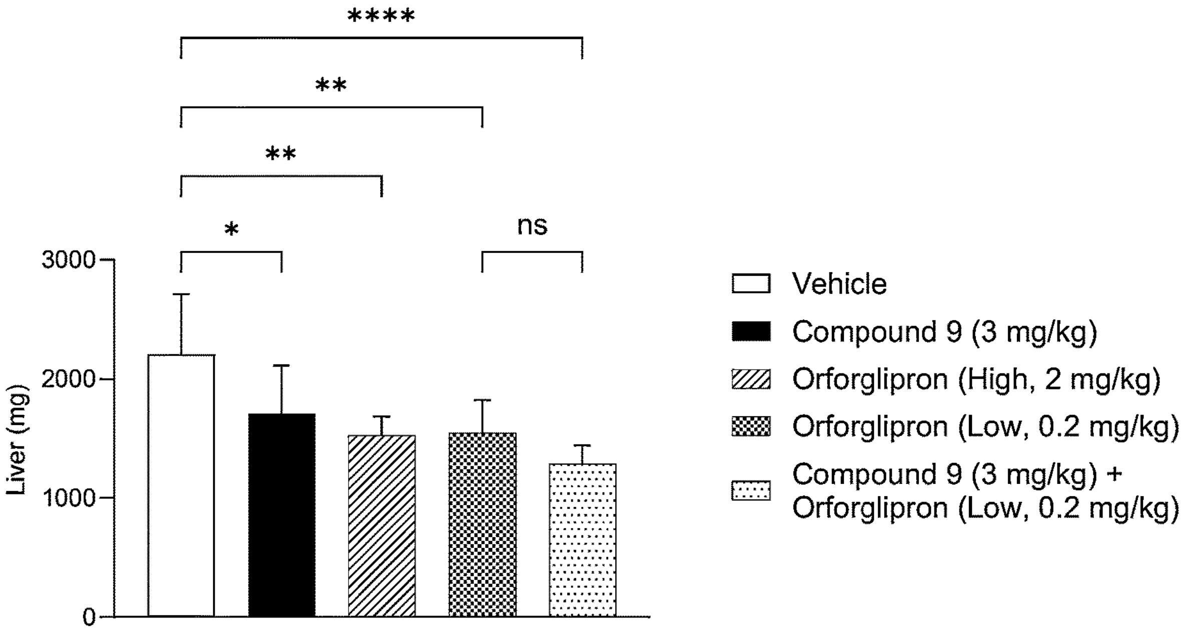
FIG. 23 depicts a graph showing terminal liver weights in DIO hGLP-1R mice following treatment with Compound 9 alone, orforglipron alone, or orforglipron in combination with Compound 9. Data represents mean (SD) liver weight (mg) collected at study termination with n =6-7 mice per group. Statistical significance determined by ordinary one-way ANOVA with correction for multiple comparisons. *p-value<0.05, p-value<0.01, p-value<0.01, ****p-value<0.0001. ns=not significant.

All treatment groups showed significantly lower liver weights at the end of study compared to vehicle control (FIG. 23). Mice treated with Compound 9 (3 mg/kg PO QD) in combination with orforglipron (0.2 mg/kg PO QD) showed trends towards further reductions in liver weight compared to mice treated with the low dose of orforglipron (0.2 mg/kg PO QD).

Figure 24A:
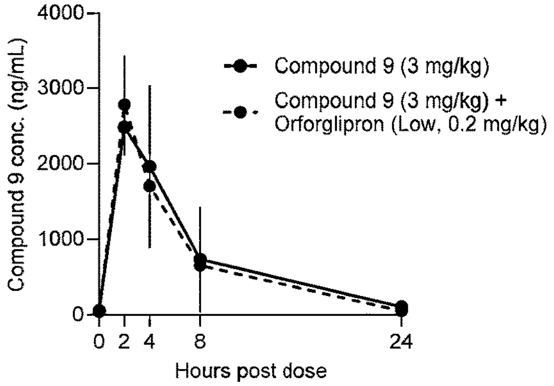
FIG. 24A and FIG. 24B depict two graphs showing concentration-time profiles of Compound 9 and orforglipron in DIO hGLP-1R mice. Compound concentration shown as mean (SD) over time for Compound 9 (FIG. 24A) or orforglipron (FIG. 24B) alone and in combination. Data represent sparse sampling across each treatment cohort as follows: predose (0-hour post dose), n=3; 2-hour post dose, n=3; 4-hour post dose, n=4; 8-hour post dose, n=4; 24-hour post dose, n=7. Nominal doses and times are shown.
Figure 24B:
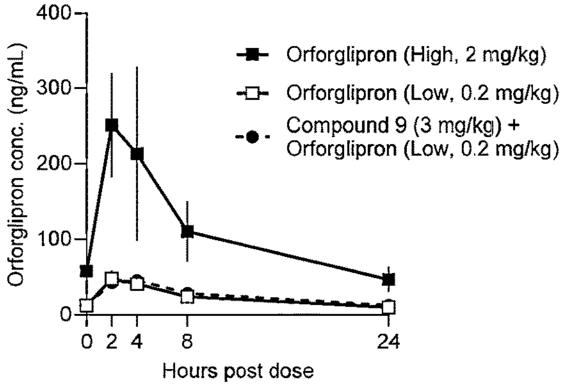

Concentration-time profiles of Compound 9 and orforglipron are shown in FIG. 24A and FIG. 24B, respectively, alone or in combination. Select derived pharmacokinetic parameters are shown in Table 5-2. Orforglipron exposure increased in a less than dose-proportional manner and exposure was largely unaffected when dosed in combination with Compound 9. Similarly, exposure to Compound 9 was unaffected when dosed in combination with orforglipron.

TABLE 5-2

| Derived pharmacokinetic parameters | | | |
|---|---|---|---|
| Analyte | Treatment group | $AUC_{0\text{-}last}$ (h * ng/mL) | $C_{max}$ (ng/mL) |
| Compound 9 | Compound 9 (3 mg/kg) | 19,000 (5310) | 2480 (220) |
| | Compound 9 (3 mg/kg) + orforglipron (0.2 mg/kg) | 17,600 (1810) | 2780 (379) |
| Orforglipron | Orforglipron (0.2 mg/kg) | 543 (34.8) | 47.4 (6.47) |
| | Orforglipron (2 mg/kg) | 2670 (428) | 251 (39.8) |
| | Compound 9 (3 mg/kg) + orforglipron (0.2 mg/kg) | 607 (23.7) | 45.1 (3.45) |

Abbreviations:
$AUC_{0\text{-}last}$ = area under the plasma concentration time curve from time 0 to time of the last measurable concentration;
$C_{max}$ = maximum observed concentration Summary Compound 9 enhanced the weight loss efficacy of a low dose of orforglipron to a level comparable to a 10-fold higher dose of orforglipron as monotherapy.

Daily doses of orforglipron at 0.2 mg/kg in mice provided equivalent unbound exposures ($AUC_{24h,u}$ ~0.300 h.ng/mL) following daily doses of 6 mg/day in humans, while 2 mg/kg in mice provided equivalent unbound exposures ($AUC_{24h,u}$ ~1.60 h.ng/mL) following daily doses of 45 mg/day in humans (Pratt et, al (2023). The daily dose of 45 mg orforglipron in humans is associated with the highest change in body weight at week 26 compared to 12, 24, or 36 mg/day doses, however compared to placebo, the occurrence of total adverse events was significantly higher with orforglipron 12 mg [OR 2.49 (95% CI: 1.25, 4.98), p=0.01, $I^2$=12%], 24 mg [OR 2.23 (95% CI: 1.13, 4.43), p=0.02, $I^2$=10%], 36 mg [OR 2.04 (95% CI: 1,08,3.84),p=0.03, $1^2$=0%]and 45 mg [OR 2.96 (95% CI: 1.41, 6.21), p=0.004, $1^2$=17%]daily doses; the highest rates seen with orforglipron 45 mg. (Frias et al., *Lancet.* 2023; 402(10400):472-483, Wharton et al., *N Engl J Med.* 2023; 389(10):877-888, Pratt et al, *Diabetes Obes Metabol.* 2023; 25:2642-2649).

The enhanced weight loss observed did not appear to be driven by changes in food intake. The enhanced weight loss effects of Compound 9 in combination with orforglipron were driven by larger reductions in fat mass, including subcutaneous fat, without additional decreases in lean mass. Lastly, liver weights were reduced by the combination of Compound 9 and orforglipron, suggesting enhanced anti-steatotic effects with the combination. The ability of Compound 9 to substantially enhance the efficacy of a low dose of GLP-1R agonist may ultimately translate to improved GI tolerability, leading to improved patient compliance and better outcomes.

Example 6. Evaluating THR-B Agonist Compound 9 in Combination with a GLP-1R Agonist (e.g., Compound 1-2)

Figure 25:
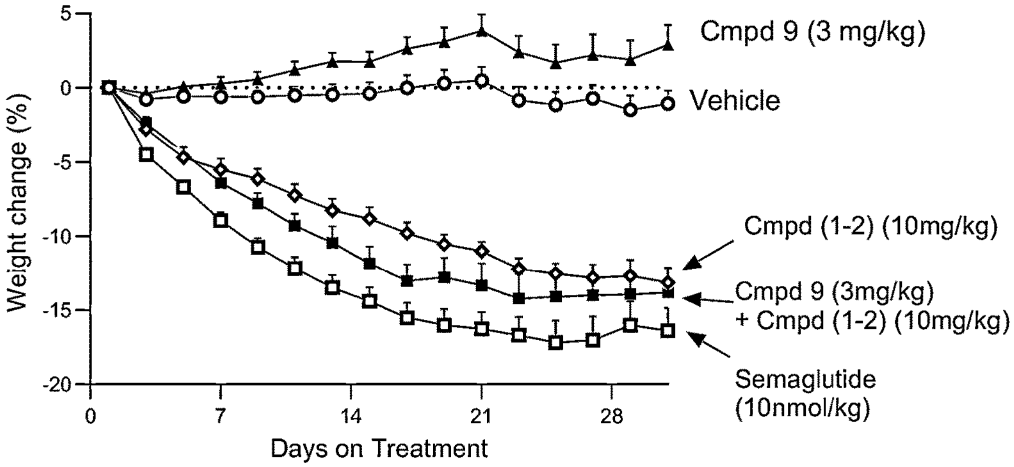
FIG. 25 depicts a graph showing weight loss induced by combination treatment of Compound 9+Compound (I-2) compared to monotherapy in diet induced obese transgenic hGLP1R mice.
Figure 26:
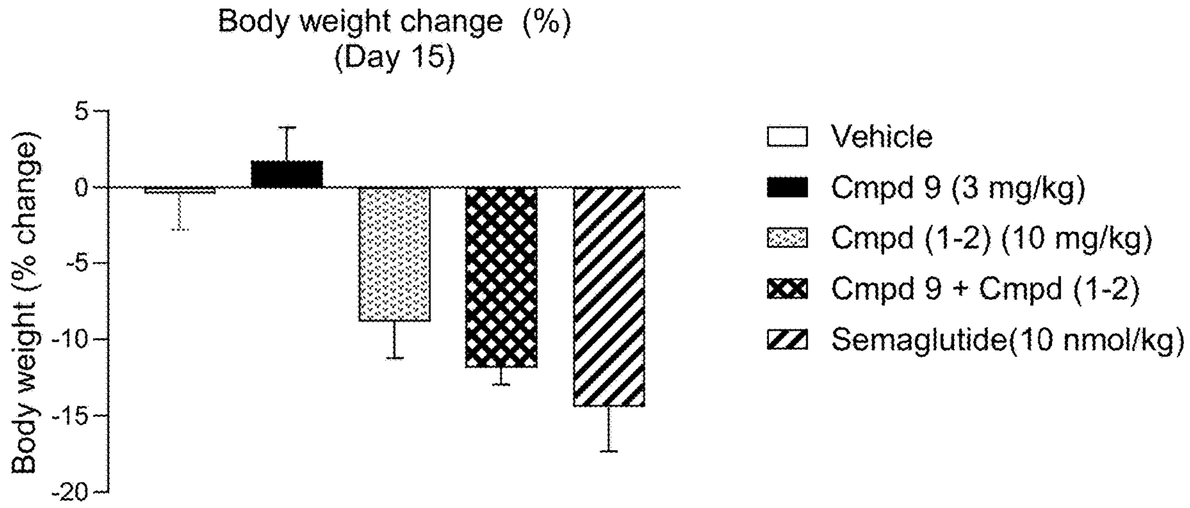
FIG. 26 depicts a graph showing the weight loss induced by combination treatment of Compound 9+Compound (I-2) compared to monotherapy in diet induced obese transgenic hGLP1R mice. Percent change in body weight after 15 days of treatment.

Transgenic C57/BL6J male mice expressing the human glucagon-like peptide-1 receptor (hGLP-1R) were fed a high fat diet (HFD, Research Diets D12492i $60^0$/kcal) for 17 weeks to obtain a diet induced obese (DIO) phenotype. Mice were randomly divided into groups (n=8-10 per group) based on baseline body weight. Mice were treated for 30 days with Compound 9 [3 mpk, PO, once daily], Compound (I-2) [10 mpk PO, twice daily], Compound 9 [3 mpk PO, once daily]+Compound (I-2) [10 mpk, twice daily], Semaglutide [10 nmol/kg SQ, once daily]or vehicle: 10% Solutol HS15:90% sterile water, (v/v). Body weight was measured daily and the mean percent change from baseline was calculated for each treatment group (FIGS. 25 and 26). The combination of Compound 9+Compound (I-2) exerted a greater effect on reducing body weight compared to mice treated with either Compound 9 or Compound (I-2) alone.

EQUIVALENTS

All publications, including patents, patent applications, and scientific articles, mentioned in this specification are herein incorporated by reference in their entirety for all purposes to the same extent as if each individual publication, including patent, patent application, or scientific article, were specifically and individually indicated to be incorporated by reference.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

What is claimed is:

1. A combination comprising:

(i) a THRβ agonist which is:

(Compound 9)

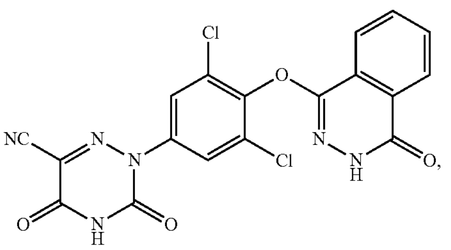

(resmetirom)

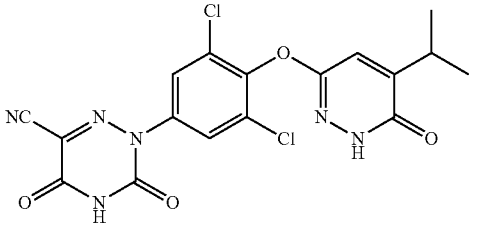

, or (Compound 7)

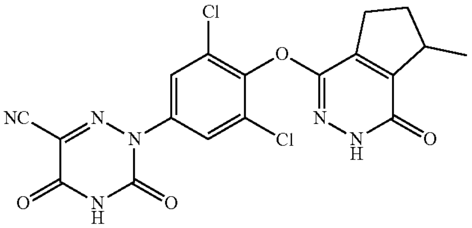

, or a pharmaceutically acceptable salt thereof; and (ii) a GLP-1R agonist which is a GLP-1R agonist listed in Tables 1-4, orforglipron, danuglipron, liraglutide, exenatide, dulaglutide, albiglutide, lixisenatide, tirzepatide, semaglutide, mazdutide, efpeglenatide, or a compound of Formula (I-1):

(I-1)

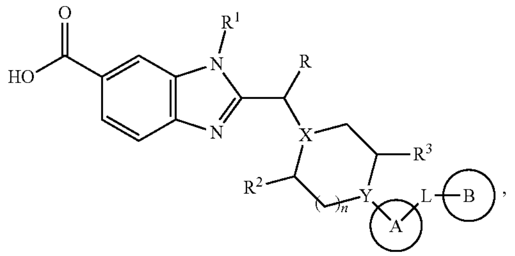

or a pharmaceutically acceptable salt of any of the foregoing, wherein:

X is N or CH;

Y is N or $CR^4$;

n is 0 or 1;

R is hydrogen;

$R^1$ is -$C_1$-$C_6$ alkylene-$R^5$;

$R^2$ is hydrogen, oxo, or $C_1$-$C_6$ alkyl;

$R^3$ is hydrogen, oxo, or $C_1$-$C_6$ alkyl and $R^4$ is hydrogen, OH, or $C_1$-$C_6$ alkyl;

or $R^3$ and $R^4$ are taken together with the carbon atoms to which they are attached to form $C_3$-$C_6$ cycloalkyl optionally substituted by halo or $C_1$-$C_3$ alkyl;

$R^5$ is 5-membered heterocyclyl or 5-membered heteroaryl, each of which comprises 1, 2, or 3 heteroatoms independently selected from O, N, and S, wherein at least one heteroatom of $R^5$ is S, and further wherein $R^5$ is optionally substituted by halo, —O—$C_{1\neq}$alkyl, $C_{1\neq}$alkyl, $C_{1\neq}$alkenyl, or $C_1$-$C_6$ haloalkyl;

Ring A is 5- to 12-membered heterocyclene or 5- to 12-membered heteroarylene, each of which is independently optionally substituted by halo, CN, $C_3$-$C_6$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *-$C_1$-$C_6$ alkylene-O—**, or *—$NR^6$-$C_1$-$C_6$ alkylene-**, wherein

* represents the point of attachment to ring A and ** represents the point of attachment to ring B;

when L is *—O—$C_1$-$C_6$ alkylene-**, the $C_1$-$C_6$ alkylene of L is optionally substituted by $R^L$, wherein each $R^L$ is independently $C_1$-$C_6$ alkyl or halo, or two $R^L$ are taken together with the carbon atom or atoms to which they are attached to form $C_3$-$C_6$ cycloalkyl or 3- to 6-membered heterocyclyl; and when L is $C_1$-$C_6$ alkylene, the $C_1$-$C_6$ alkylene is optionally substituted by $R^{L1}$, wherein each $R^L$1 is independently halo, OH, oxo, or $C_1$-$C_6$ alkyl, or two $R^L$1 are taken together with the carbon atom or atoms to which they are attached to form $C_3$-$C_6$ cycloalkyl or 3- to 6-membered heterocyclyl;

$R^6$ is hydrogen or $C_1$-$C_6$ alkyl; and

Ring B is $C_5$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl, $C_1$-$C_6$ haloalkyl, —$COCH_3$, —$CONH_2$, —$S(O)_2CH_3$, and phenyl.

2. The combination of claim 1, wherein the THRβ agonist is resmetirom, or a pharmaceutically acceptable salt thereof.

3. The combination of claim 1, wherein the THRβ agonist is Compound 9, or a pharmaceutically acceptable salt thereof.

4. The combination of claim 1, wherein the GLP-1R agonist is a compound of Formula (1-1), or a pharmaceutically acceptable salt thereof.

5. The combination of claim 1, wherein the GLP-1R agonist is Compound 1-2:

(Compound 1-2)

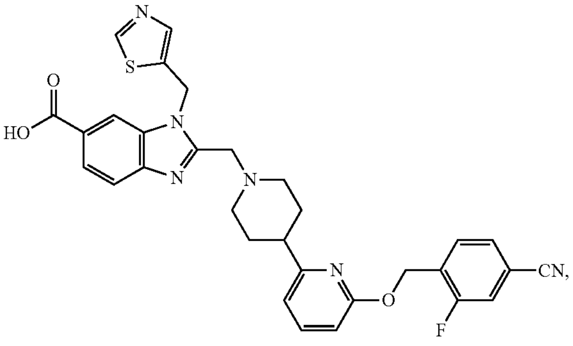

or a pharmaceutically acceptable salt thereof.

6. The combination of claim 1, wherein the GLP-1R agonist is selected from those listed in Table 1, Table 2, Table 3, or Table 4, or a pharmaceutically acceptable salt thereof.

7. The combination of claim 1, wherein the GLP-1R agonist is orforglipron, danuglipron, liraglutide, exenatide, dulaglutide, albiglutide, lixisenatide, tirzepatide, or semaglutide, or a pharmaceutically acceptable salt thereof.

8. The combination of claim 7, wherein the GLP-1R agonist is orforglipron, tirzepatide, or semaglutide, or a pharmaceutically acceptable salt thereof.

9. The combination of claim 1, wherein the THRβ agonist is Compound 9, or a pharmaceutically acceptable salt thereof, and the GLP-1R agonist is Compound 1-2:

(Compound 1-2)

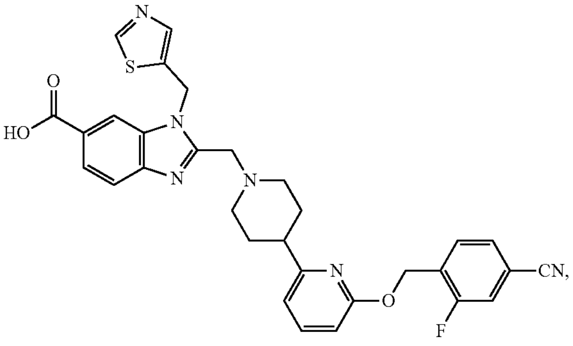

or a pharmaceutically acceptable salt thereof.

10. A method of treating obesity or effectuating weight loss in a patient in need thereof, comprising administering to the patient:

(i) a THRβ agonist which is:

(Compound 9)

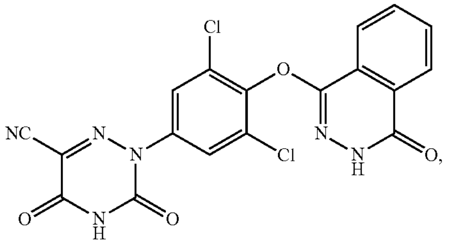

(resmetirom)

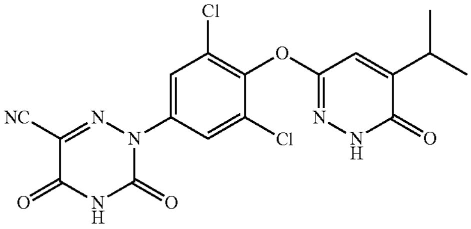

, or (Compound 7)

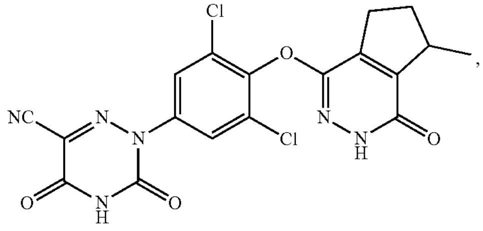

, or a pharmaceutically acceptable salt thereof; and (ii) a GLP-1R agonist which is a GLP-1R agonist listed in Tables 1-4, orforglipron, danuglipron, liraglutide, exenatide, dulaglutide, albiglutide, lixisenatide, tirzepatide, semaglutide, mazdutide, efpeglenatide, or a compound of Formula (I-1):

(I-1)

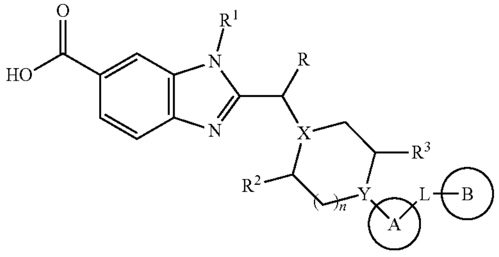

, or a pharmaceutically acceptable salt of any of the foregoing, wherein:

X is N or CH;

Y is N or $CR^4$;

n is 0 or 1;

R is hydrogen;

$R^1$ is-$C_1$-$C_6$ alkylene-$R^5$;

$R^2$ is hydrogen, oxo, or $C_1$-$C_6$ alkyl;

$R^3$ is hydrogen, oxo, or $C_1$-$C_6$ alkyl and $R^4$ is hydrogen, OH, or $C_1$-$C_6$ alkyl;

or $R^3$ and $R^4$ are taken together with the carbon atoms to which they are attached to form $C_3$-$C_6$ cycloalkyl optionally substituted by halo or $C_1$-$C_3$ alkyl;

$R^5$ is 5-membered heterocyclyl or 5-membered heteroaryl, each of which comprises 1, 2, or 3 heteroatoms independently selected from O, N, and S, wherein at least one heteroatom of $R^5$ is S, and further wherein $R^5$ is optionally substituted by halo, —O—$C_{1\neq}$alkyl, $C_{1\neq}$alkyl, $C_{1\neq}$alkenyl, or $C_1$-$C_6$ haloalkyl;

Ring A is 5- to 12-membered heterocyclene or 5- to 12-membered heteroarylene, each of which is independently optionally substituted by halo, CN, $C_8$-$C_6$ cycloalkyl, or $C_1$-$C_6$ alkyl optionally substituted by halo or OH;

L is a bond, —O—, $C_1$-$C_6$ alkylene, *—O—$C_1$-$C_6$ alkylene-**, *-$C_1$-$C_6$ alkylene-O—**, or *—$NR^6$-$C_1$-$C_6$ alkylene-**, wherein

* represents the point of attachment to ring A and ** represents the point of attachment to ring B;

when L is *—O—$C_1$-$C_6$ alkylene-**, the $C_1$-$C_6$ alkylene of Lis optionally substituted by $R^L$, wherein each $R^L$ is independently $C_1$-$C_6$ alkyl or halo, or two $R^L$ are taken together with the carbon atom or atoms to which they are attached to form $C_5$-$C_6$ cycloalkyl or 3- to 6-membered heterocyclyl; and when L is $C_1$-$C_6$ alkylene, the $C_1$-$C_6$ alkylene is optionally substituted by $R^L$1, wherein each $R^L$1 is independently halo, OH, oxo, or $C_1$-$C_6$ alkyl, or two $R^L$1 are taken together with the carbon atom or atoms to which they are attached to form $C_3$-$C_6$ cycloalkyl or 3- to 6-membered heterocyclyl;

$R^6$ is hydrogen or $C_1$-$C_6$ alkyl; and

Ring B is $C_3$-$C_{10}$ cycloalkyl, $C_6$-$C_{14}$ aryl, 4- to 12-membered heterocyclyl, or 5- to 12-membered heteroaryl, each of which is independently optionally substituted by one to three substituents independently selected from the group consisting of halo, CN, oxo, $C_1$-$C_6$ alkyl, $C_1$-$C_6$ haloalkyl, -$COCH_3$, -$CONH_2$, —S(O)$2CH_3$, and phenyl.

11. The method of claim 10, wherein the patient has a Body Mass Index (BMI) of 25 kg/m$^2$ to 30 kg/m$^2$.

12. The method of claim 10, wherein the administration of the THRβ agonist and the GLP-1R agonist:

(i) allows for administration of a reduced dose of the GLP-1R agonist while maintaining equivalent weight loss;

(ii) increases weight loss compared to administration of the GLP-1R agonist at an equivalent dose;

increases fat loss associated with administering the GLP-1R agonist; and/or (iv) increases fat loss associated with administering the GLP-1R agonist while maintaining lean mass.

13. The method of claim 10, wherein the GLP-1R agonist is selected from orforglipron, danuglipron, liraglutide, exenatide, dulaglutide, albiglutide, lixisenatide, tirzepatide, semaglutide, mazdutide, or efpeglenatide, or a pharmaceutically acceptable salt thereof.

14. The method of claim 10, wherein the THRβ agonist is Compound 9, or a pharmaceutically acceptable salt thereof.

15. The method of claim 10, wherein the THRβ agonist is resmetirom, or a pharmaceutically acceptable salt thereof.

16. The method of claim 10, wherein the THRβ agonist is Compound 9, or a pharmaceutically acceptable salt thereof, and the GLP-1R agonist is orforglipron, tirzepatide, or semaglutide, or a pharmaceutically acceptable salt thereof.

17. The method of claim 10, wherein the THRβ agonist and the GLP-1R agonist are formulated in separate pharmaceutically acceptable compositions.

18. The method of claim 10, wherein the THRβ agonist and the GLP-1R agonist are formulated in a single pharmaceutically acceptable composition.

19. The method of claim 10, wherein the proportion of lean body mass relative to total body mass in the patient increases compared to administration of the GLP-1R agonist alone.

20. The method of claim 10, wherein the THRβ agonist is administered once daily or twice daily.

21. The method of claim 10, wherein the THRβ agonist is administered orally.

22. The method of claim 10, wherein the GLP-1R agonist is orforglipron, or a pharmaceutically acceptable salt thereof.

23. The method of claim 10, wherein the patient has a Body Mass Index (BMI) of 30 $kg/m^2$ or greater.

24. The method of claim 10, wherein the GLP-1R agonist is semaglutide, or a pharmaceutically acceptable salt thereof.

25. The method of claim 10, wherein the GLP-1R agonist is Compound 1-2:

(Compound 1-2)

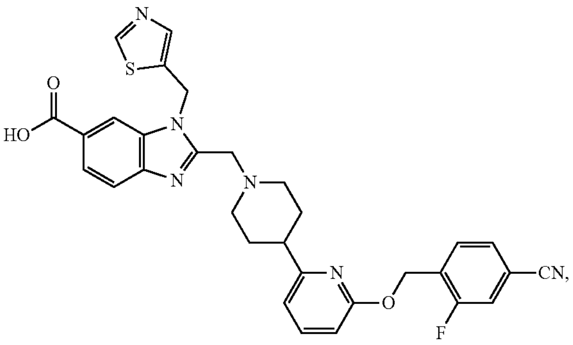

or a pharmaceutically acceptable salt thereof.

26. The method of claim 10, wherein the patient is administered each of the THRβ agonist and the GLP-1R agonist over a period of at least 8 weeks.

27. The method of claim 15, wherein the GLP-1R agonist is semaglutide or orforglipron, or a pharmaceutically acceptable salt thereof.

28. The method of claim 10, wherein the GLP-1R agonist is selected from orforglipron, danuglipron, liraglutide, exenatide, dulaglutide, albiglutide, lixisenatide, tirzepatide, semaglutide, mazdutide, or efpeglenatide, or a pharmaceutically acceptable salt thereof, and wherein the patient is administered each of the THRβ agonist and the GLP-1R agonist over a period of at least 8 weeks, and wherein the proportion of lean body mass relative to total body mass in the patient increases compared to administration of the GLP-1R agonist alone.

29. The method of claim 10, wherein the patient is not in need of treatment for a liver disorder.

30. The method of claim 10, wherein the patient is not in need of treatment for non-alcoholic steatohepatitis.

* * * * *